United States Patent
Yamamoto et al.

(10) Patent No.: US 9,834,520 B2
(45) Date of Patent: Dec. 5, 2017

(54) HETEROCYCLIC COMPOUND

(71) Applicant: TAKEDA PHARMACEUTICAL COMPANY LIMITED, Osaka-shi, Osaka (JP)

(72) Inventors: Satoshi Yamamoto, Fujisawa (JP); Junya Shirai, Fujisawa (JP); Yoshiyuki Fukase, Fujisawa (JP); Ayumu Sato, Fujisawa (JP); Mitsunori Kouno, Fujisawa (JP); Yoshihide Tomata, Fujisawa (JP); Atsuko Ochida, Fujisawa (JP); Kazuko Yonemori, Fujisawa (JP); Tsuneo Oda, Fujisawa (JP); Tomoya Yukawa, Fujisawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/775,514

(22) PCT Filed: Mar. 13, 2014

(86) PCT No.: PCT/JP2014/056721
§ 371 (c)(1),
(2) Date: Sep. 11, 2015

(87) PCT Pub. No.: WO2014/142255
PCT Pub. Date: Sep. 18, 2014

(65) Prior Publication Data
US 2016/0229814 A1 Aug. 11, 2016

(30) Foreign Application Priority Data

Mar. 14, 2013 (JP) .................................. 2013-051867

(51) Int. Cl.
| | | |
|---|---|---|
| A61K 31/517 | (2006.01) |
| C07D 239/72 | (2006.01) |
| C07D 239/96 | (2006.01) |
| C07D 403/12 | (2006.01) |
| C07D 401/12 | (2006.01) |
| C07D 409/12 | (2006.01) |
| C07D 239/80 | (2006.01) |
| C07D 413/12 | (2006.01) |
| C07D 417/12 | (2006.01) |
| C07D 471/04 | (2006.01) |
| C07D 265/36 | (2006.01) |
| C07D 217/24 | (2006.01) |
| C07D 405/06 | (2006.01) |
| C07D 475/04 | (2006.01) |
| C07F 7/08 | (2006.01) |

(52) U.S. Cl.
CPC ......... *C07D 239/96* (2013.01); *C07D 217/24* (2013.01); *C07D 239/80* (2013.01); *C07D 265/36* (2013.01); *C07D 401/12* (2013.01); *C07D 403/12* (2013.01); *C07D 405/06* (2013.01); *C07D 409/12* (2013.01); *C07D 413/12* (2013.01); *C07D 417/12* (2013.01); *C07D 471/04* (2013.01); *C07D 475/04* (2013.01); *C07F 7/0812* (2013.01)

(58) Field of Classification Search
CPC ............................ C07D 239/80; C07D 239/88
USPC ................................ 544/285, 286; 514/266.3
See application file for complete search history.

(56) References Cited

U.S. PATENT DOCUMENTS

| | | |
|---|---|---|
| 5,389,631 A | 2/1995 | Claremon et al. |
| 6,066,649 A | 5/2000 | Podzuweit |
| 6,245,746 B1 | 6/2001 | Chamberland et al. |
| 7,135,498 B1 | 11/2006 | Chopp |
| 9,187,453 B2 | 11/2015 | Tsukamoto |
| 2002/0032203 A1 | 3/2002 | Swope |
| 2002/0119978 A1 | 8/2002 | Swope |
| 2002/0132754 A1 | 9/2002 | Boss |
| 2002/0155173 A1 | 10/2002 | Chopp |
| 2002/0198377 A1 | 12/2002 | Niewohner et al. |
| 2004/0127538 A1 | 7/2004 | Oinuma |
| 2005/0143388 A1 | 6/2005 | Chopp |
| 2005/0282880 A1 | 12/2005 | Oinuma |
| 2006/0106037 A1 | 5/2006 | Baer |

(Continued)

FOREIGN PATENT DOCUMENTS

| | | |
|---|---|---|
| EP | 1341035 | 9/2003 |
| EP | 2873669 | 5/2015 |

(Continued)

OTHER PUBLICATIONS

Hardman et al. "Goodman & Gilman's The Pharmaceutical Basis of Therapeutics," 9th Ed. 1996, pp. 51 and 57-58.*
European Patent Office Supplementary Search Report for Application No. 14762328.4 dated Nov. 3, 2016.
Fauber, B. P et al., "Modulators of the Nuclear Receptor Retinoic Acid Receptor-Related Orphan Receptor-γ (RORγ or RORc)," Journal of Medicinal Chemistry, 2014, vol. 57, No. 14, pp. 5871-5892.
Akdis, M. et al., "Interleukins, from 1 to 37, and interferon-γ: Receptors, functions, and roles in diseases," Journal of Allergy and Clinical Immunology, 2011, 127, 3,701-721.e70.
Banerjee, B. et al., "Second-generation DBFOX ligands for the synthesis of beta-substituted alpha-amino acids via enantioselective radical conjugate additions," J. Org. Chem. (2008) 73:8973-8978.

(Continued)

*Primary Examiner* — Shengjun Wang
(74) *Attorney, Agent, or Firm* — Lisa V. Mueller; Michael Best & Friedrich LLP

(57) ABSTRACT

The present invention provides a heterocyclic compound having an RORγt inhibitory action.
The present invention relates to a compound represented by the formula (I):

(I)

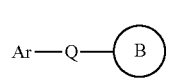

wherein
Ar is a the partial structure (1) to the partial structure (5),
Q is a bivalent group selected from the group consisting of (Ia)-(If), and
B is a ring optionally having substituent(s),
or a salt thereof.

15 Claims, No Drawings

(56) References Cited

U.S. PATENT DOCUMENTS

| | | |
|---|---|---|
| 2006/0128695 A1 | 6/2006 | Bourguignon |
| 2006/0135557 A1 | 6/2006 | Nan et al. |
| 2006/0148802 A1 | 7/2006 | Niewohner et al. |
| 2007/0135457 A1 | 6/2007 | Beyer |
| 2007/0299079 A1 | 12/2007 | Norbert et al. |
| 2008/0027064 A1 | 1/2008 | Hofgen et al. |
| 2008/0280907 A1 | 11/2008 | Schmidt et al. |
| 2008/0312225 A1 | 12/2008 | Schmidt et al. |
| 2009/0163552 A1 | 6/2009 | Benson et al. |
| 2009/0203691 A1 | 8/2009 | Oinuma |
| 2009/0239874 A1 | 9/2009 | Hofgen et al. |
| 2010/0035882 A1 | 2/2010 | Ellinghaus |
| 2010/0063063 A1 | 3/2010 | Benbow et al. |
| 2010/0120762 A1 | 5/2010 | Stange |
| 2010/0120763 A1 | 5/2010 | Stange |
| 2010/0150839 A1 | 6/2010 | Kelleher |
| 2011/0071168 A1 | 3/2011 | Chopp |
| 2011/0136803 A1 | 6/2011 | Schmidt et al. |
| 2011/0144153 A1 | 6/2011 | Nozawa |
| 2012/0009152 A1 | 1/2012 | Chopp |
| 2012/0136012 A1 | 5/2012 | Breslin et al. |
| 2012/0136064 A1 | 5/2012 | Nixon |
| 2012/0252780 A1 | 10/2012 | Ng |
| 2013/0115194 A1 | 5/2013 | Long et al. |
| 2013/0115404 A1 | 5/2013 | Goehlich |
| 2014/0088080 A1 | 3/2014 | Koga |
| 2015/0105373 A1 | 4/2015 | Mikami et al. |
| 2015/0158863 A1 | 6/2015 | Nakamura |

FOREIGN PATENT DOCUMENTS

| | | |
|---|---|---|
| FR | 2860793 | 4/2005 |
| GB | 2404658 | 2/2005 |
| JP | S57-209281 | 12/1982 |
| JP | H06-145169 | 5/1994 |
| JP | H09-221423 | 8/1997 |
| JP | H11-292877 | 10/1999 |
| JP | 2001-512137 | 8/2001 |
| JP | 2004-525098 | 8/2004 |
| JP | 2005-145840 | 6/2005 |
| JP | 2006-519243 | 8/2006 |
| JP | 2007-513996 | 5/2007 |
| JP | 2008-526716 | 7/2008 |
| JP | 2008-526717 | 7/2008 |
| JP | 2009-538853 | 11/2009 |
| WO | WO 92/01938 | 2/1992 |
| WO | WO 99/06435 | 2/1999 |
| WO | WO 99/37667 | 7/1999 |
| WO | WO 00/23091 | 4/2000 |
| WO | WO 00/32575 | 6/2000 |
| WO | WO 01/09125 | 2/2001 |
| WO | WO 01/44228 | 6/2001 |
| WO | WO 01/44266 | 6/2001 |
| WO | WO 01/55106 | 8/2001 |
| WO | WO 02/50078 | 6/2002 |
| WO | WO 02/064094 | 8/2002 |
| WO | WO 03/000682 | 1/2003 |
| WO | WO 2004/037784 | 5/2004 |
| WO | WO 2004/044234 | 5/2004 |
| WO | WO 2004/056823 | 7/2004 |
| WO | WO 2004/060872 | 7/2004 |
| WO | WO 2004/108892 | 12/2004 |
| WO | WO 2005/035534 | 4/2005 |
| WO | WO 2005/037839 | 4/2005 |
| WO | WO 2005/058892 | 6/2005 |
| WO | WO 2005/120497 | 12/2005 |
| WO | WO 2006/015159 | 2/2006 |
| WO | WO 2006/064286 | 6/2006 |
| WO | WO 2006/128129 | 11/2006 |
| WO | WO 2006/128172 | 11/2006 |
| WO | WO 2007/020521 | 2/2007 |
| WO | WO 2007/125405 | 11/2007 |
| WO | WO 2007/137819 | 12/2007 |
| WO | WO 2007/146230 | 12/2007 |
| WO | WO 2008/016659 | 2/2008 |
| WO | WO 2008/043461 | 4/2008 |
| WO | WO 2008/044700 | 4/2008 |
| WO | WO 2008/085302 | 7/2008 |
| WO | WO 2008/121602 | 10/2008 |
| WO | WO 2009/019508 | 2/2009 |
| WO | WO 2009/026276 | 2/2009 |
| WO | WO 2009/095324 | 8/2009 |
| WO | WO 2009/138338 | 11/2009 |
| WO | WO 2010/013161 | 2/2010 |
| WO | WO 2010/054253 | 5/2010 |
| WO | WO 2010/054260 | 5/2010 |
| WO | WO 2010/090290 | 8/2010 |
| WO | WO 2010/097410 | 9/2010 |
| WO | WO 2010/119284 | 10/2010 |
| WO | WO 2010/142752 | 12/2010 |
| WO | WO 2011/022213 | 2/2011 |
| WO | WO 2011/044157 | 4/2011 |
| WO | WO 2011/059839 | 5/2011 |
| WO | WO 2012/042541 | 4/2012 |
| WO | WO 2012/051036 | 4/2012 |
| WO | WO 2012/087861 | 6/2012 |
| WO | 2012/100734 | 8/2012 |
| WO | WO 2012/165399 | 12/2012 |
| WO | WO 2012/178124 | 12/2012 |
| WO | 2013/019682 | 2/2013 |
| WO | WO 2013/018695 | 2/2013 |
| WO | WO 2013/042782 | 3/2013 |
| WO | WO 2013/055984 | 4/2013 |
| WO | WO 2013/100027 | 7/2013 |
| WO | WO 2013/146963 | 10/2013 |
| WO | WO 2013/161913 | 10/2013 |
| WO | WO 2014/142255 | 9/2014 |
| WO | WO 2015/002230 | 1/2015 |
| WO | WO 2015/002231 | 1/2015 |
| WO | WO 2015/012328 | 1/2015 |
| WO | WO 2015/016206 | 2/2015 |

OTHER PUBLICATIONS

Beavo, J.A. et al., "Stimulation of adenosine 3',5'-monophosphate hydrolysis by guanosine 3',5'-monophosphate," J. Biol. Chem. (1971) 246(12):3841-3846.

Bender, A.T. et al., "Differentiation of human monocytes in vitro with granulocyte-macrophage colony-stimulating factor and macrophage colony-stimulating factor produces distinct changes in cGMP phosphodiesterase expression," Cell. Signalling (2004) 16:365-374.

Benton, H.P., "Cytokines and their receptors," Curr Opin Cell Biol. 1991, 3(2):171-5.

Blanco, P. et al., "Dendritic cells and cytokines in human inflammatory and autoimmune diseases," Cytokine Growth Factor Rev., Feb. 2008, 19(1):41-52.

Boess, F.G. et al., "Inhibition of phosphodiesterase 2 increases neuronal cGMP, synaptic plasticity and memory performance," Neuropharmacology (2004) 47:1081-1092.

Chemical Abstracts 1422576-26-8, Imidazo[1,2-a]pyridine-2-carboxamide, N-[2-methoxy-1-(2-pyridinyl)ethyl]-6-methyl-, (2016) ChemBridge Corporation.

Chemical Abstracts 1422628-80-5, "Imidazo[1,2-a]pyridine-6-carboxamide, N-[1-(3,5-dichlorophenyl)-2-hydroxyethyl]-" (2013) ChemBridge Corporation.

Chen, Y. et al., "Design, Synthesis, and Biological Evaluation of Isoquinoline-1, 3, 4-trione Derivatives as Potent Caspase-3 Inhibitors," Journal of Medicinal Chemistry, 2006, vol. 49, No. 5, p. 1613-1623.

Chi, W. et al., "Upregulated IL-23 and IL-17 in Behçet patients with active uveitis," Invest Ophthalmol Vis Sci., 2008, 49(7):3058-64.

Domek-Lopacinska, K.U. et al., "Cyclic GMP and nitric oxide synthase in aging and Alzheimer's disease," Mol. Neurobiol. (2010) 41:129-137.

Dorwald, F.Z., Side Reactions in Organic Synthesis. A Guide to Successful Synthesis Design, (2005) Wiley-VCH Verlag, Weinheim, 6 pages.

Du, J. et al., "Isoquinoline-1, 3, 4-trione Derivates Inactivate Caspase-3 by Generation of Reactive Oxygen Species," Journal of Biological Chemistry, 2008, vol. 283, No. 44, p. 30205-30215.

(56) References Cited

OTHER PUBLICATIONS

Ghoreschi, K. et al., "Selective and therapeutic inhibition of kinases: to be or not to be?," Nat Immunol. Apr. 2009, 10(4):356-360.
Harada, S. et al., "Inclusion Compounds of Lankacidin-Group Antibiotics with Cyclodextrins," The Journal of Antibiotics, 1985, vol. 38, No. 7, pp. 877-885.
Houslay, M.D. et al., "cAMP-specific phosphodiesterase-4 enzymes in the cardiovascular system—A molecular toolbox for generating compartmentalized cAMP signaling," Cir. Res. (2007) 100:950-966.
Imramovsky, A. et al., "Synthetic Route for the Preparation of 2-Hydroxy-N-[1-(2-hydroxyphenylamino)-1-oxoalkan-2-yl] benzamides," J. Comb. Chem., 2010, 12, 414-416.
Jaeger, R. et al., "Activation of PDE2 and PDE5 by specific GAF ligands: delayed activation of PDE5," British J. Pharmacol. (2010) 161:1645-1660.
Jiang, Z. et al., "IL-23R gene confers susceptibility to Behcet's disease in a Chinese Han population," Ann Rheum Dis, 2010, 69(7):1325-8.
Jones, G. H., "Inhibitors of cyclic AMP phosphodiesterase. 1. Analogues of Cilostamide and Anagrelide," Journal of Medicinal Chemistry, 1987, vol. 30, No. 2, p. 295-303.
Jordan, V.C., "Tamoxifen: a most unlikely pioneering medicine," Nature Rev. Drug Disc. (2003) 2:205-213.
Juilfs, D.M. et al., "Cyclic GMP as substrate and regulator of cyclic nucleotide phosphodiesterases (PDEs)," in Rev. Physiol. Biochem. Pharmacol. (1999) 135:67-104.
Klimkowski, V.J. et al., "D-phenylglycinol-derived non-covalent factor Xa inhibitors: effect of non-peptidic S4 linkage elements on affinity and anticoagulant activity," Biorg. Med. Chem. Lett (2007) 17:5801-5805.
Lakics, V. et al., "Quantitative comparison of phosphodiesterase mRNA distribution in human brain and peripheral tissues," Neuropharmacology (2010) 59:367-374.
Martinez, S.E. et al., "The two GAF domains in phosphodiesterase 2A have distinct roles in dimerization and in cGMP binding," Proc. Natl. Acad. Sci. (2002) 99(20):13260-13265.
Martins, T.J. et al., "Purification and characterization of a cyclic GMP-stimulated cyclic nucleotide phosphodiesterase from Bovine Tissues," J. Biol. Chem. (1982) 257(4):1973-1979.
Masood, A. et al., "Anxiolytic effects of phosphodiesterase-2 inhibitors associated with increased cGMP signaling," J. Pharmacology and Exp. Ther. (2009) 331(2):690-699.
Masood, A. et al., "Reversal of oxidative stress-induced anxiety by inhibition of phosphodiesterase-2 in mice," J. Pharm. Exp. Thera. (2008) 326(2):369-379.
Menniti, F.S. et al., "Phosphodiesterases in the CNS: targets for drug development," Nature Rev. Drug Discov. (2006) 5:660-670.
Minegishi, Y. et al., "Molecular mechanisms of the immunological abnormalities in hyper-IgE syndrome," New York Academy of Science, 2011, 1246:34-40.
Pfefferkorn, J.A. et al., "Pyridones as glucokinase activators: Identification of a unique metabolic liability of the 4-sulfonyl-2-pyridone heterocycle," Bioorganic & Medicinal Chemistry Letters 19, 2009, 3247-3252.
Rodefer, J.S. et al., "Selective phosphodiesterase inhibitors improve performance on the ED/ID cognitive task in rats," Neuropharmacology (2012) 62:1182-1190.
Russell, T.R. et al., "Separate phosphodiesterases for the hydrolysis of cyclic adenosine 3',5'-monophosphate and cyclic guanosine 3',5'-monophosphate in rat liver," J. Biol. Chem. (1973) 248(4):1334-1340.
Sheridan, J., "The Most Common Chemical Replacements in Drug-Like Compounds," Chem Inf. Comput. Sci., 2002, 42, 103-108.
Shen, H.C. et al., "Discovery of pyrazolopyrimidines as the first class of allosteric agonists for the high affinity nicotinic acid receptor GPR109A," Bioorg. Med. Chem. Lett. (2008) 18:4948-4951.
Stephenson, D.T. et al., "Immunohistochemical localization of phosphodiesterase 2A in multiple mammalian species," J. Histochem. Cytochem. (2009) 57(10):933-949.
Strobl, B. et al., "Tyrosine kinase 2 (TYK2) in cytokine signalling and host immunity," Front Biosci, 2011, 16:3214-32.
Tenor, H. et al., "2. Analysis of PDE isoenzyme profiles in cells and tissues by pharmacological methods," in Phosphodiesterase Inhibitors (1996) Academic Press Limited, pp. 21-40.
Toguchi, H. et al., "Gastro-Intestinal Absorption of Ethyl 2-Chloro-3-[4-(2-methyl-2-phenylpropyloxy)phenyl]propionate from Different Dosage Forms in Rats and Dogs," Chemical and Pharmaceutical Bulletin, 1990, vol. 38, No. 10, pp. 2792-2796.
Venuti, M.C. et al., "Inhibitors of cyclic AMP phosphodiesterase. 4. Synthesis and evaluation of potential prodrugs of lixazinone (N-cyclohexyl-N-methyl-4-[(1, 2, 3, 5-tetrahydro-2-oxoimidazo[2,1-b] quinazolin-7-yl)oxy] butyramide, RS-82856)," Journal of Medicinal Chemistry, 1988, vol. 31, No. 11, p. 2145-2152.
Wong, J.C. et al., "Application of p21 and klf2 reporter gene assays to identify selective histone deacetylase inhibitors for cancer therapy," Bioorganic & Medicinal Chemistry Letters, 2011, 21(1), 110-116.
Wong, J.C. et al., "Pharmacokinetic Optimization of Class-Selective Histone Deacetylase Inhibitors and Identification of Associated Candidate Predictive Biomarkers of Hepatocellular Carcinoma Tumor Response," Journal of Medicinal Chemistry, 2012, 55(20), 8903-8925.
Wu, A.Y. et al., "Molecular determinants for cyclic nucleotide binding to the regulatory domains of phosphodiesterase 2A," J. Biol. Chem. (2004) 279(36):37928-37938.
Yamagata, K. et al., "Synthesis of 1-acyl-2-oxo-3-pyrrolidinecarbonitriles by the reaction of 2-acylamino-4,5-dihydro-3-furancarbonitriles with sodium iodide," Journal of Heterocyclic Chemistry, 2005, vol. 42, Issue 4, pp. 543-549.
Yamamoto, T. et al., "Purification and characterization of cyclic GMP-stimulated cyclic nucleotide phosphodiesterase from calf liver. Effects of divalent cations on activity," J. Biol. Chem. (1983) 258(20):12526-12533.
International Search Report for Application No. PCT/JP2014/056721 dated May 27, 2014.
Written Opinion for Application No. PCT/JP2014/056721 dated May 27, 2014.
International Search Report for Application No. PCT/JP2014/067650 dated Aug. 19, 2014.
Written Opinion for Application No. PCT/JP2014/067650 dated Aug. 19, 2014.
International Search Report for Application No. PCT/JP2014/067649 dated Sep. 30, 2014.
Written Opinion for Application No. PCT/JP2014/067649 dated Sep. 30, 2014.
International Search Report for Application No. PCT/JP2014/069907 dated Aug. 26, 2014.
Written Opinion for Application No. PCT/JP2014/069907 dated Aug. 26, 2014.
International Search Report for Application No. PCT/JP2014/069494 dated Sep. 24, 2014.
Written Opinion for Application No. PCT/JP2014/069494 dated Sep. 24, 2014.
U.S. Appl. No. 14/909,427 dated Oct. 20, 2016.
Shi et al., "Design and Synthesis of α-Aryloxyphenylacetic Acid Derivatives: A Novel Class of PPARα/γ Dual Agonists with Potent Antihyperglycemic and Lipid Modulating Activity," Journal of Medicinal Chemistry (2005), 48(13), 4457-4468.
Iakovou et al., "Synthesis of oxypropanolamine derivatives of 3,4-dihydro-2H-1,4-benzoxazine, beta-adrenergic affinity, inotropic, chronotropic and coronary vasodilating activities," European Journal of Medicinal Chemistry, 1999, 34(11):903-917.
CAS Registry No. 1356671-41-4 (2012).
CAS Registry No. 1320639-61-9 (2011).
CAS Registry No. 1317037-61-8 (2011).
CAS Registry No. 1302670-75-2 (2011).
CAS Registry No. 1302670-47-8 (2011).
CAS Registry No. 1301474-87-2 (2011).
CAS Registry No. 1295985-33-9 (2011).

(56) References Cited

OTHER PUBLICATIONS

CAS Registry No. 1295387-85-7 (2011).
CAS Registry No. 1294064-89-3 (2011).
CAS Registry No. 1289804-05-2 (2011).
CAS Registry No. 1030687-63-8 (2008).
CAS Registry No. 1011953-64-2 (2008).
CAS Registry No. 1011937-27-1 (2008).
CAS Registry No. 1011937-22-6 (2008).
CAS Registry No. 1011931-02-4 (2008).
CAS Registry No. 1011930-22-5 (2008).
CAS Registry No. 1011915-00-6 (2008).
CAS Registry No. 1011914-96-7 (2008).
CAS Registry No. 1011914-92-3 (2008).
CAS Registry No. 1011912-77-8 (2008).
CAS Registry No. 1011905-19-3 (2008).
CAS Registry No. 1011901-04-4 (2008).
CAS Registry No. 1011901-00-0 (2008).
CAS Registry No. 1011886-55-7 (2008).
CAS Registry No. 1011886-51-3 (2008).
CAS Registry No. 1011886-47-7 (2008).
CAS Registry No. 1011886-13-7 (2008).
CAS Registry No. 1011886-09-1 (2008).
CAS Registry No. 1011886-05-7 (2008).
CAS Registry No. 1011861-19-0 (2008).
CAS Registry No. 1011852-51-9 (2008).
CAS Registry No. 1011852-47-3 (2008).
CAS Registry No. 1011837-53-8 (2008).
CAS Registry No. 1011837-32-3 (2008).
CAS Registry No. 1011837-28-7 (2008).
CAS Registry No. 1011836-65-9 (2008).
CAS Registry No. 1011836-61-5 (2008).
CAS Registry No. 1011836-56-8 (2008).
CAS Registry No. 1011700-86-9 (2008).
CAS Registry No. 1011683-95-6 (2008).
CAS Registry No. 1011683-90-1 (2008).
CAS Registry No. 1011683-85-4 (2008).
CAS Registry No. 1011682-41-9 (2008).
CAS Registry No. 1011682-36-2 (2008).
CAS Registry No. 1011682-31-7 (2008).
CAS Registry No. 1011675-33-4 (2008).
CAS Registry No. 1011674-37-5 (2008).
CAS Registry No. 1011674-32-0 (2008).
CAS Registry No. 1011658-35-7 (2008).
CAS Registry No. 1011652-26-8 (2008).
CAS Registry No. 1320754-70-8 (2011).
CAS Registry No. 1318731-84-8 (2011).
CAS Registry No. 1318731-56-4 (2011).
CAS Registry No. 1317000-55-7 (2011).
CAS Registry No. 1316552-50-7 (2011).
CAS Registry No. 1316383-82-0 (2011).
CAS Registry No. 1302161-96-1 (2011).
CAS Registry No. 1302161-59-6 (2011).
CAS Registry No. 1302159-86-9 (2011).
CAS Registry No. 1300710-88-6 (2011).
CAS Registry No. 1300302-27-5 (2011).
CAS Registry No. 1300301-66-9 (2011).
CAS Registry No. 1299763-52-2 (2011).
CAS Registry No. 1298782-67-8 (2011).
CAS Registry No. 1298612-78-8 (2011).
CAS Registry No. 1296168-85-8 (2011).
CAS Registry No. 1295976-18-9 (2011).
CAS Registry No. 1290479-13-8 (2011).
CAS Registry No. 1290366-31-2 (2011).
CAS Registry No. 1289416-69-8 (2011).
CAS Registry No. 1288899-09-1 (2011).
CAS Registry No. 1288591-07-0 (2011).
CAS Registry No. 1288156-65-9 (2011).
CAS Registry No. 1288050-68-9 (2011).
CAS Registry No. 1287987-42-1 (2011).
CAS Registry No. 1279309-74-8 (2011).
CAS Registry No. 1278242-07-1 (2011).
CAS Registry No. 1208781-17-2 (2010).
CAS Registry No. 1197950-55-2 (2009).
CAS Registry No. 1090785-29-7 (2008).
CAS Registry No. 162749-22-6 (1995).
CAS Registry No. 1332599-63-9 (2011).
CAS Registry No. 1328133-76-1 (2011).
CAS Registry No. 1326629-60-0 (2011).
CAS Registry No. 1322370-33-1 (2011).
CAS Registry No. 1320044-27-6 (2011).
CAS Registry No. 1319987-07-9 (2011).
CAS Registry No. 1319939-45-1 (2011).
CAS Registry No. 1319920-28-9 (2011).
CAS Registry No. 1319169-72-6 (2011).
CAS Registry No. 1318076-93-5 (2011).
CAS Registry No. 1317135-13-9 (2011).
CAS Registry No. 1316619-41-6 (2011).
CAS Registry No. 1316576-74-5 (2011).
CAS Registry No. 1316507-54-6 (2011).
CAS Registry No. 1216923-58-8 (2010).
CAS Registry No. 1216648-71-3 (2010).
CAS Registry No. 1216504-30-1 (2010).
CAS Registry No. 1215771-69-9 (2010).
CAS Registry No. 1214608-02-2 (2010).
CAS Registry No. 1190530-13-2 (2009).
CAS Registry No. 1180459-26-0 (2009).
CAS Registry No. 1180393-45-6 (2009).
CAS Registry No. 1172855-31-0 (2009).
CAS Registry No. 1172432-82-4 (2009).
Cas Registry No. 1172416-42-0 (2009).
CAS Registry No. 1171756-24-3 (2009).
CAS Registry No. 1169979-26-3 (2009).
CAS Registry No. 1111450-42-0 (2009).
CAS Registry No. 1099884-83-9 (2009).
CAS Registry No. 1061171-50-3 (2008).
CAS Registry No. 1043103-17-8 (2008).
CAS Registry No. 1031502-51-8 (2008).
CAS Registry No. 1031041-15-2 (2008).
CAS Registry No. 1016406-11-3 (2008).
CAS Registry No. 1016098-26-2 (2008).
CAS Registry No. 1016032-68-0 (2008).
CAS Registry No. 1014203-51-0 (2008).
CAS Registry No. 1011953-59-5 (2008).
CAS Registry No. 1011953-55-1 (2008).
CAS Registry No. 1011953-51-7 (2008).
CAS Registry No. 1011938-73-0 (2008).
CAS Registry No. 1011937-17-9 (2008).
CAS Registry No. 1011937-12-4 (2008).
CAS Registry No. 1011937-08-8 (2008).
CAS Registry No. 1011937-04-4 (2008).
CAS Registry No. 1011937-00-0 (2008).
CAS Registry No. 1011930-26-9 (2008).
CAS Registry No. 1011914-88-7 (2008).
CAS Registry No. 1011914-84-3 (2008).
CAS Registry No. 1011914-80-9 (2008).
CAS Registry No. 1011905-99-9 (2008).
CAS Registry No. 1011900-96-1 (2008).
CAS Registry No. 1011900-92-7 (2008).
CAS Registry No. 1011900-88-1 (2008).
CAS Registry No. 1011886-59-1 (2008).
CAS Registry No. 1011886-43-3 (2008).
CAS Registry No. 1011886-39-7 (2008).
CAS Registry No. 1011886-01-3 (2008).
CAS Registry No. 1011885-97-4 (2008).
CAS Registry No. 1011885-93-0 (2008).
CAS Registry No. 1011852-43-9 (2008).
CAS Registry No. 1011852-39-3 (2008).
CAS Registry No. 1011837-36-7 (2008).
CAS Registry No. 1011837-24-3 (2008).
CAS Registry No. 1011837-20-9 (2008).
CAS Registry No. 1011837-16-3 (2008).
CAS Registry No. 1011836-51-3 (2008).
CAS Registry No. 1011836-46-6 (2008).

(56) References Cited

OTHER PUBLICATIONS

CAS Registry No. 1011683-80-9 (2008).
CAS Registry No. 1011683-75-2 (2008).
CAS Registry No. 1011683-49-0 (2008).
CAS Registry No. 1011682-26-0 (2008).
CAS Registry No. 1011682-21-5 (2008).
CAS Registry No. 1011652-21-3 (2008).
CAS Registry No. 1011652-16-6 (2008).
CAS Registry No. 1011652-11-1 (2008).
CAS Registry No. 1010279-45-4 (2008).
CAS Registry No. 1010190-73-4 (2008).
CAS Registry No. 1010016-94-0 (2008).
CAS Registry No. 1009883-46-8 (2008).
CAS Registry No. 958716-96-6 (2007).
CAS Registry No. 958716-47-7 (2007).
CAS Registry No. 958699-92-8 (2007).
CAS Registry No. 958694-99-0 (2007).
CAS Registry No. 949218-20-6 (2007).
CAS Registry No. 924064-18-6 (2007).
CAS Registry No. 924038-95-9 (2007).
CAS Registry No. 923891-38-7 (2007).
CAS Registry No. 920728-62-7 (2007).
CAS Registry No. 878570-68-4 (2006).
CAS Registry No. 877958-64-0 (2006).
CAS Registry No. 868232-89-7 (2005).
CAS Registry No. 258525-30-3 (2000).

\* cited by examiner

```
SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: Synthesized

<400> SEQUENCE: 1

Cys Leu Thr Ala Arg His Lys Ile Leu His Arg Leu Leu Gln Glu Gly
1               5                   10                  15

Ser Pro Ser Asp
            20
```

HETEROCYCLIC COMPOUND

CROSS-REFERENCE TO RELATED APPLICATIONS

This is a U.S. national stage entry of International Patent Application No. PCT/JP2014/056721, filed on Mar. 13, 2014, which claims priority to Japanese Patent Application No. 2013-051867, filed on Mar. 14, 2013, the entire contents of all of which are fully incorporated herein by reference.

TECHNICAL FIELD

The present invention relates to a heterocyclic compound having an RORγt inhibitory action, a medicament containing the compound, and the like.

BACKGROUND OF THE INVENTION

Th17 cell and inflammatory cytokine (IL-17A, IL-17F, etc.) produced thereby cause a decrease in QOL as a severe etiology cell and factor accompanying enhancement of a systemic new immune response, in various autoimmune disease such as inflammatory bowel disease (IBD), rheumatoid arthritis, multiple sclerosis or psoriasis. However, the existing therapeutic drugs show only limited effects, and therefore, the earliest possible development of a novel therapeutic drug has been desired.

Involvement of T cells, inter alia, Th17 cell and inflammatory cytokines (IL-17A, IL-17F, etc.) produced thereby, in the pathology of these immune disease has been drawing attention in recent years.

Moreover, it has been recently clarified that a Retinoid-related Orphan Receptor (ROR) γt, which is one of the orphan nuclear receptors, plays an important role in the differentiation of Th17 cells and production of IL-17A/IL-17F. That is, it has been reported that RORγt is mainly expressed in Th17 cells and functions as a transcription factor of IL-17A and IL-17F, as well as a master regulator of Th17 cell differentiation.

Therefore, a medicament that inhibits the action of RORγt is expected to show a treatment effect on various immune diseases by suppressing differentiation and activation of Th17 cells.

As a compound having a nitrogen-containing fused heterocyclic structure, for example, the following benzoxazine compounds are reported.

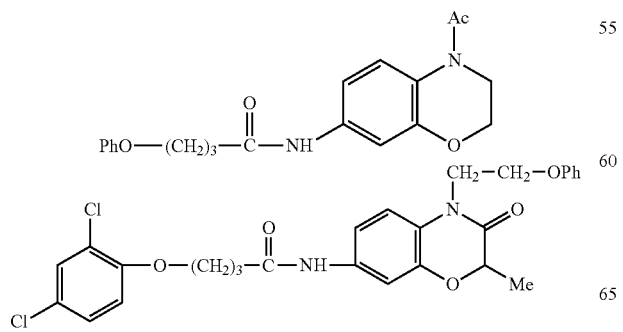

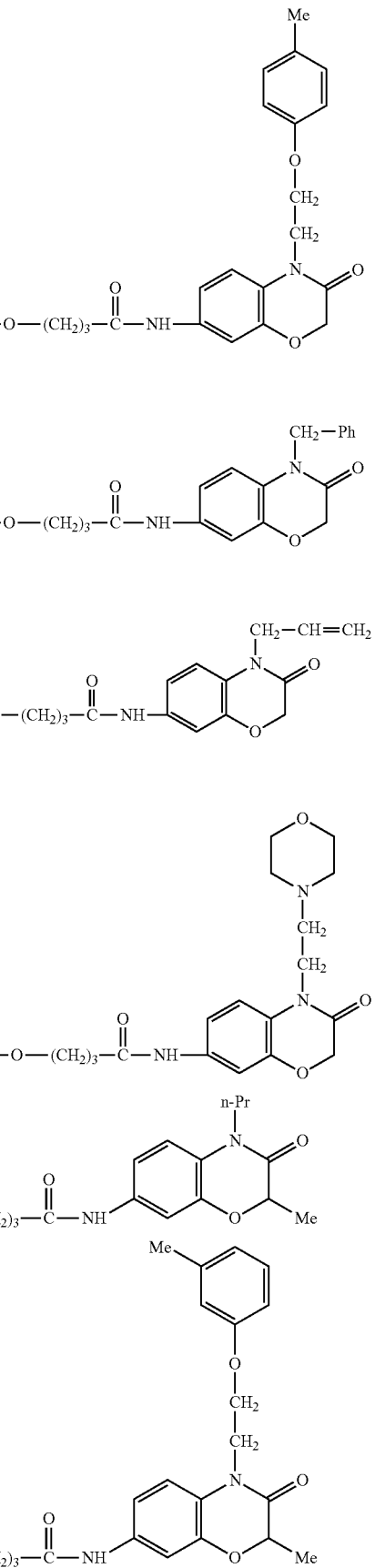

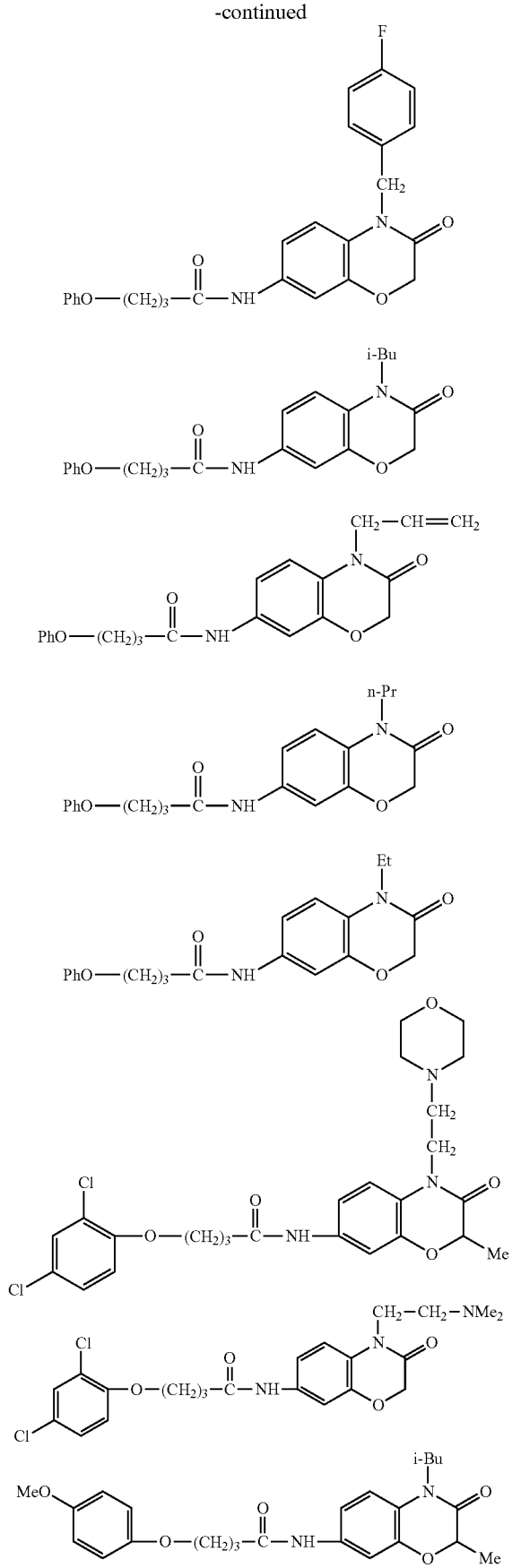
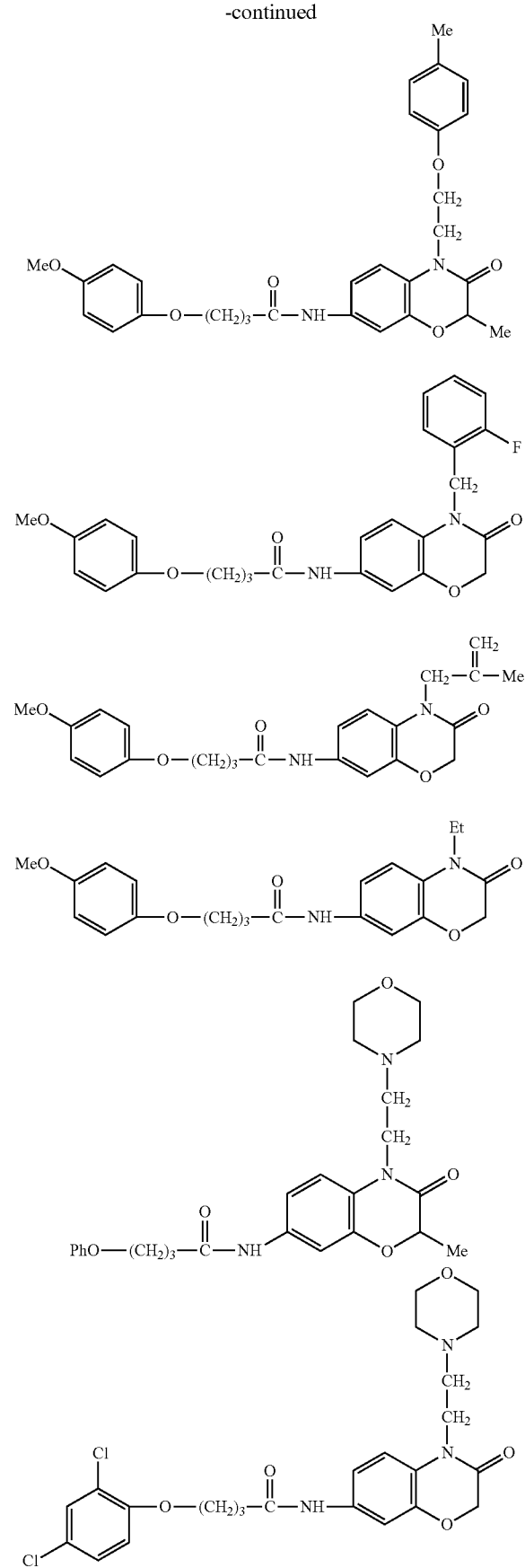

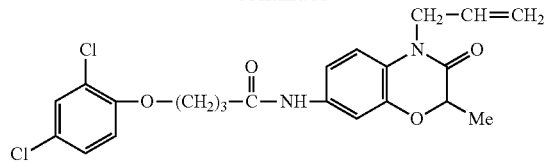
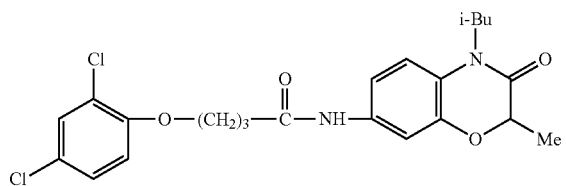
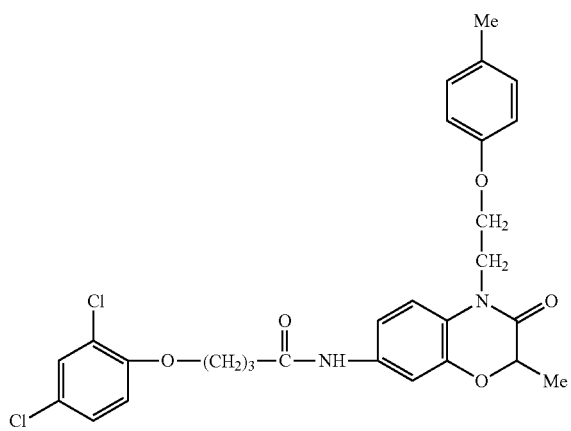
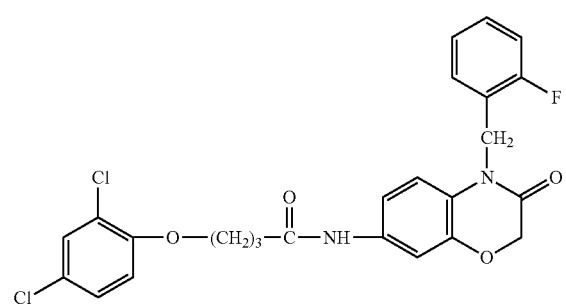
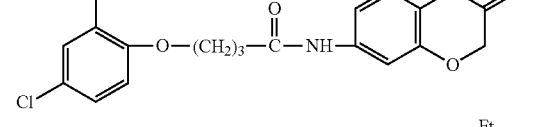
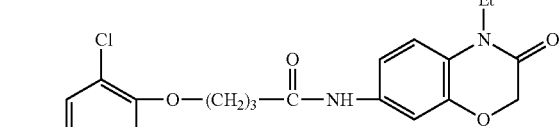
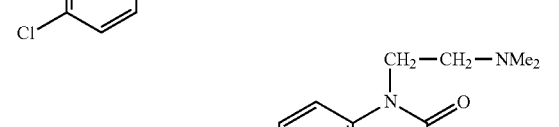
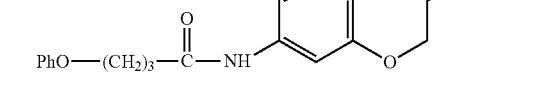
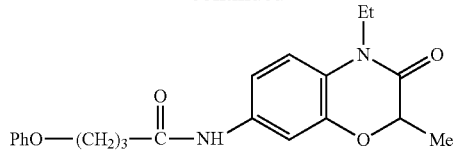
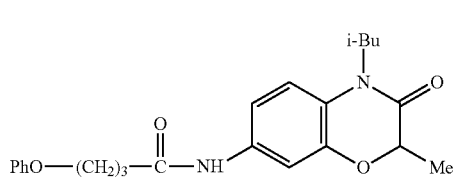
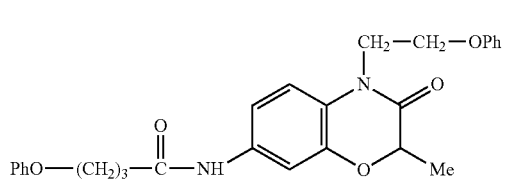
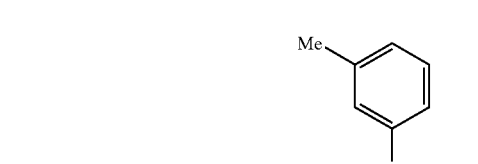
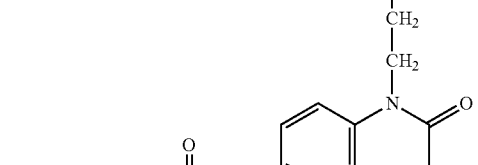
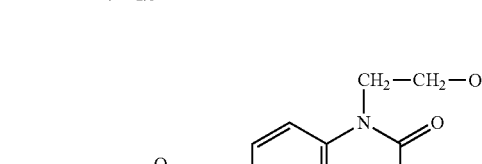
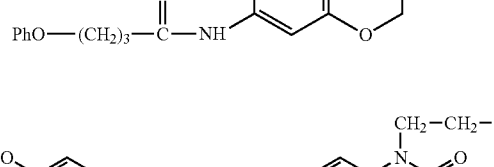
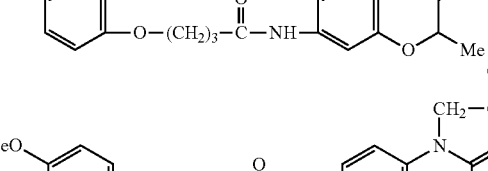
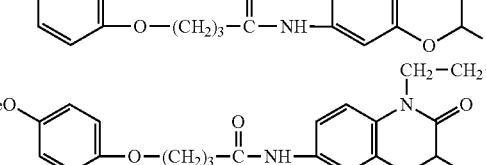

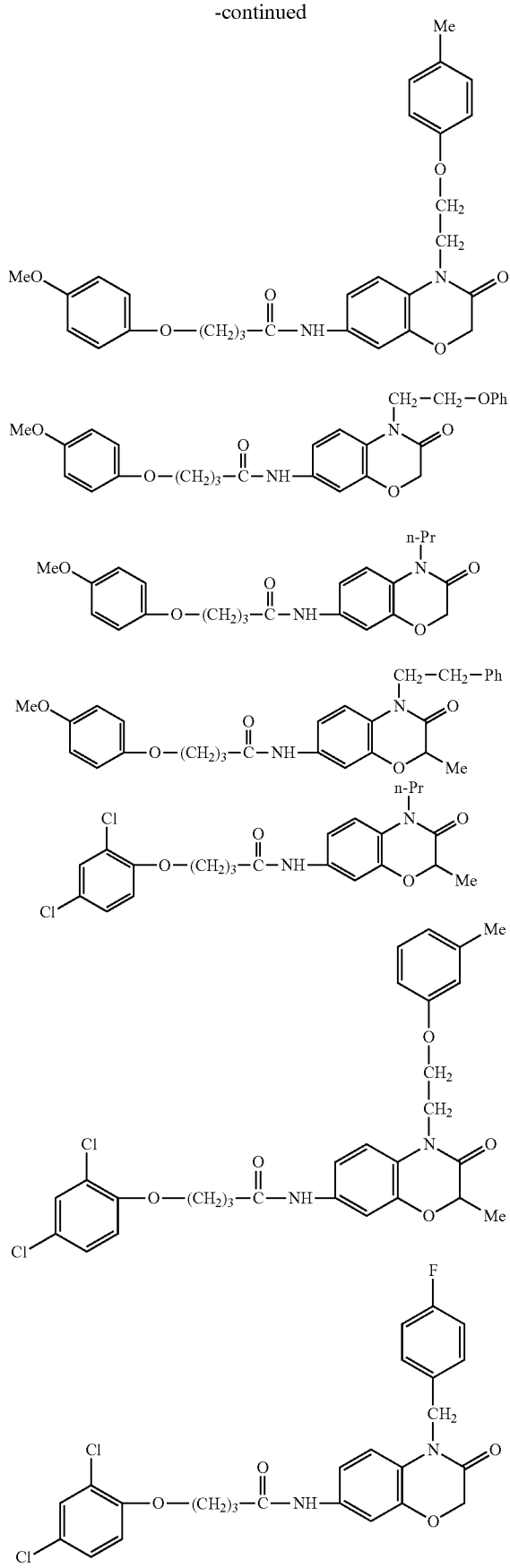
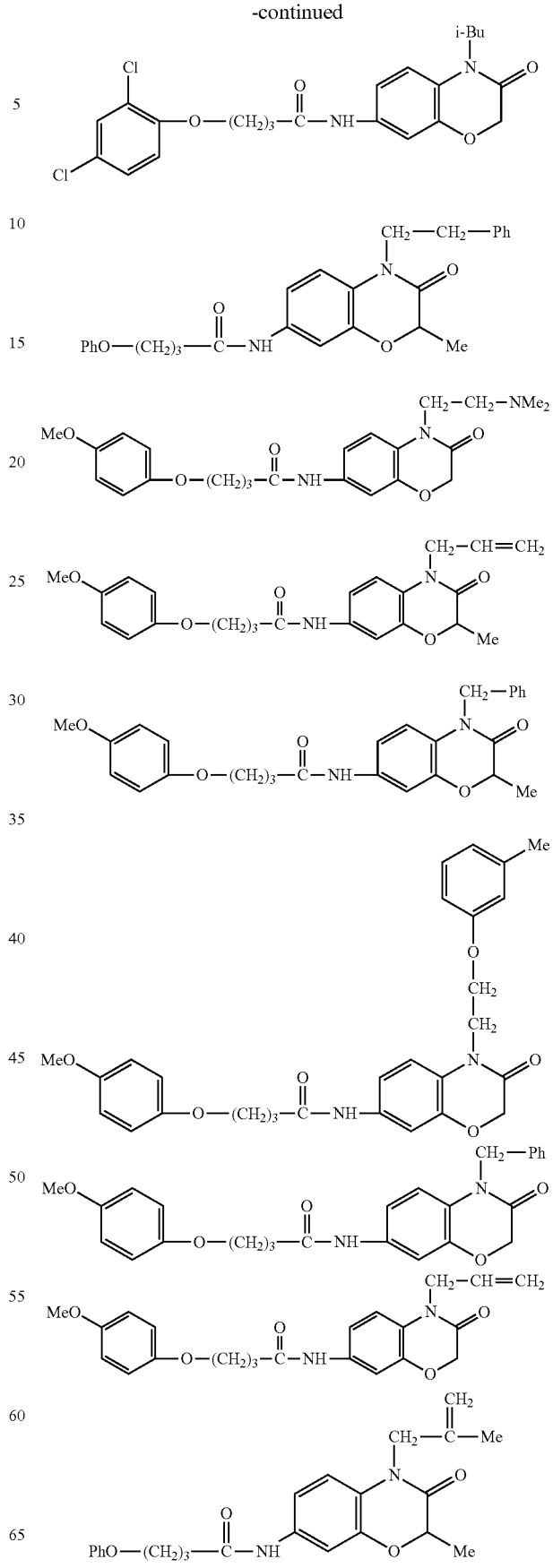

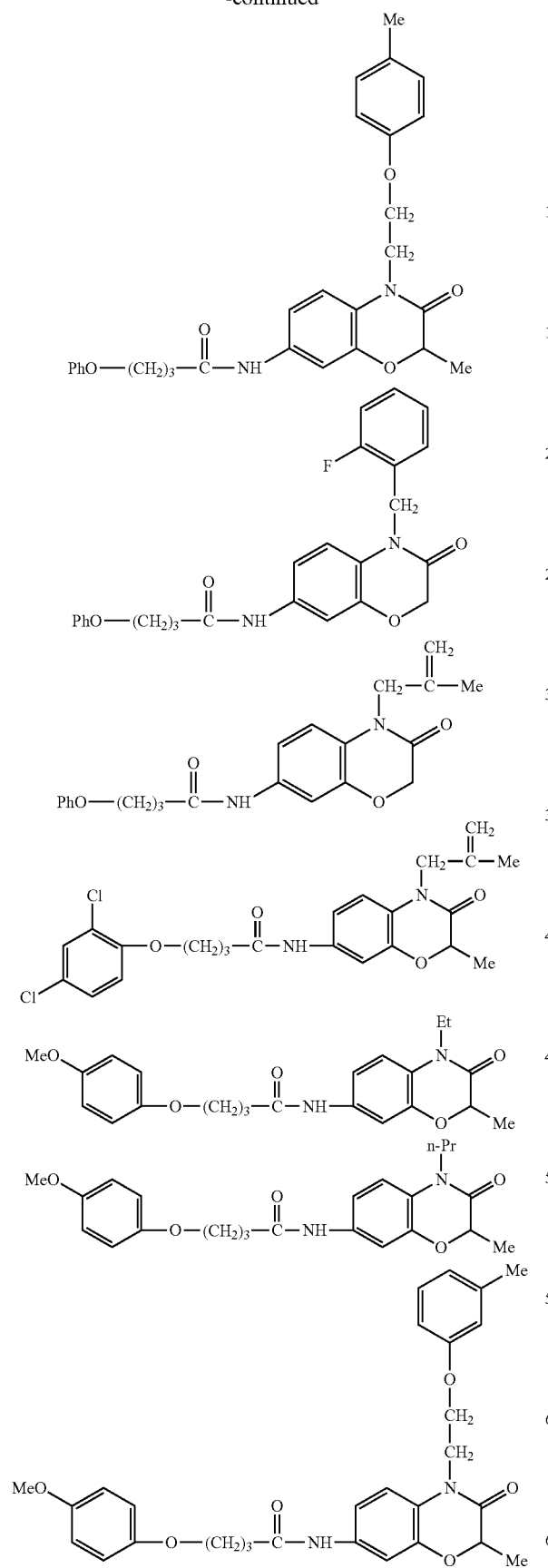
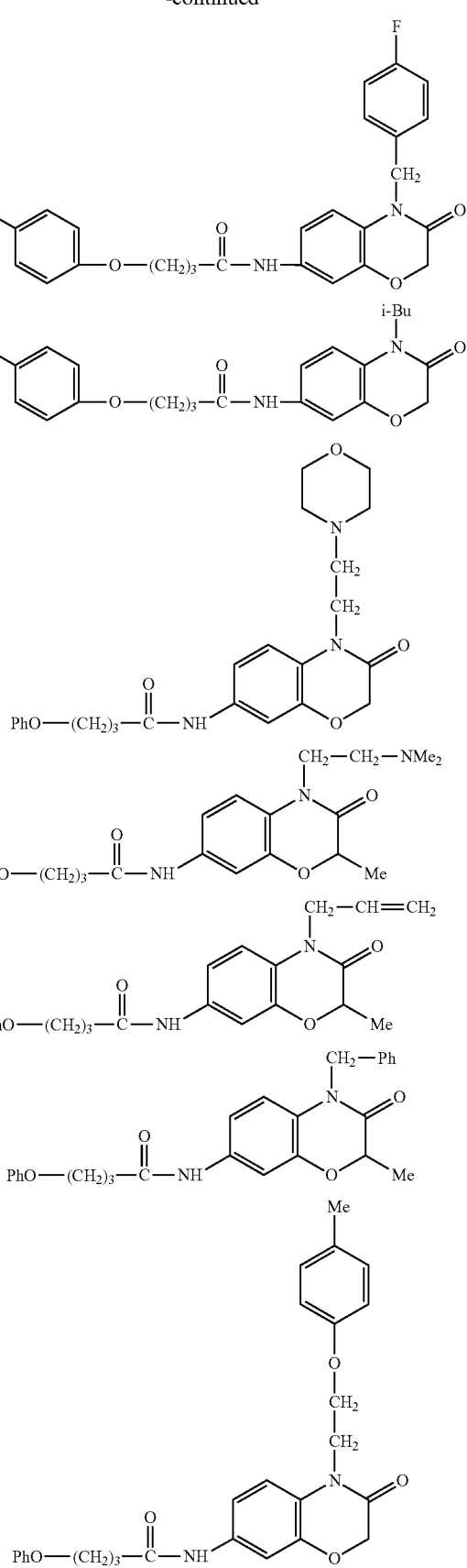

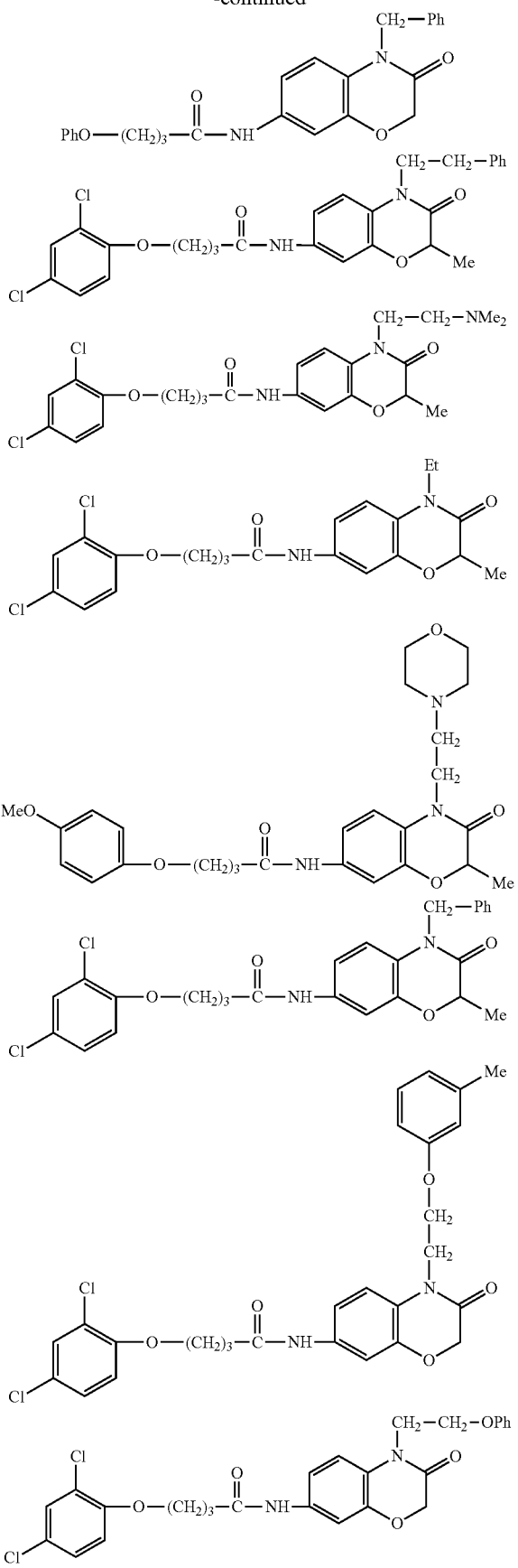

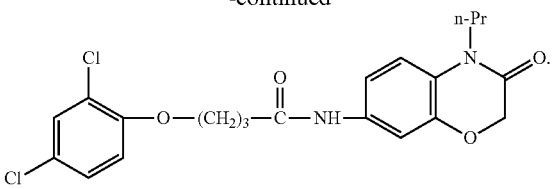

Patent Document 1 reports a compound represented by the formula (I):

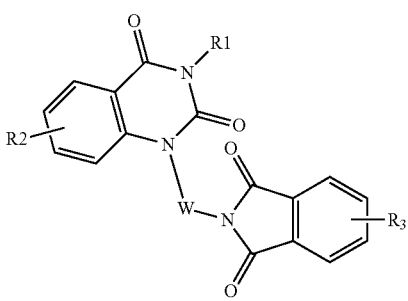

wherein
$R^1$ is $C_{1-6}$ alkyl, $C_{2-6}$ alkynyl, $C_{3-6}$ cycloalkyl, hydroxy-$C_{1-6}$ alkyl or $C_{1-3}$ alkoxy-$C_{1-6}$ alkyl;
$R^2$ is $NR_8R_9$, —O—$C_{1-6}$-alkylene-$NR_4R_5$, —O—$C_{1-6}$ alkylene-$CONR_4R_5$, —O—$C_{1-6}$ alkylene-$CO_2R_6$ or the like; and
W is $C_{1-3}$ alkylene or $C_{2-3}$ alkynylene.

In addition, as a pyrido[2,3-d]pyrimidine compound, the following compounds are known.

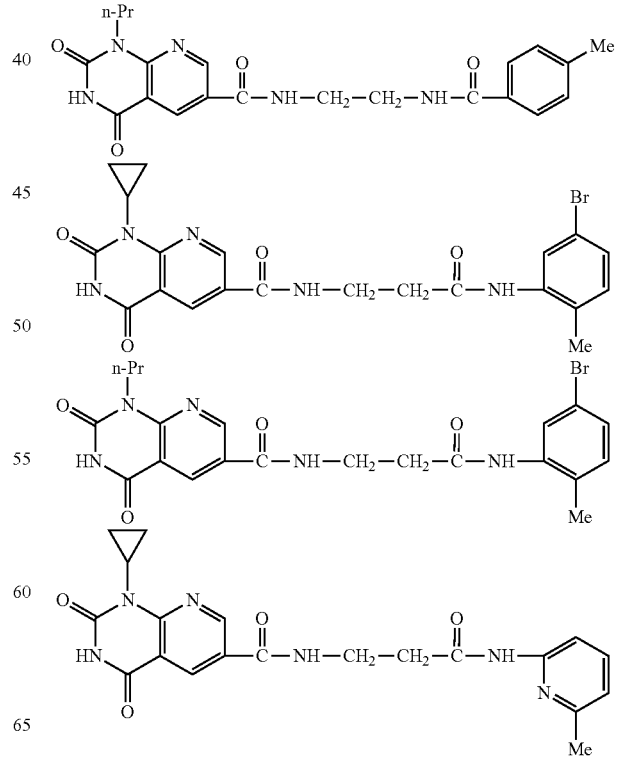

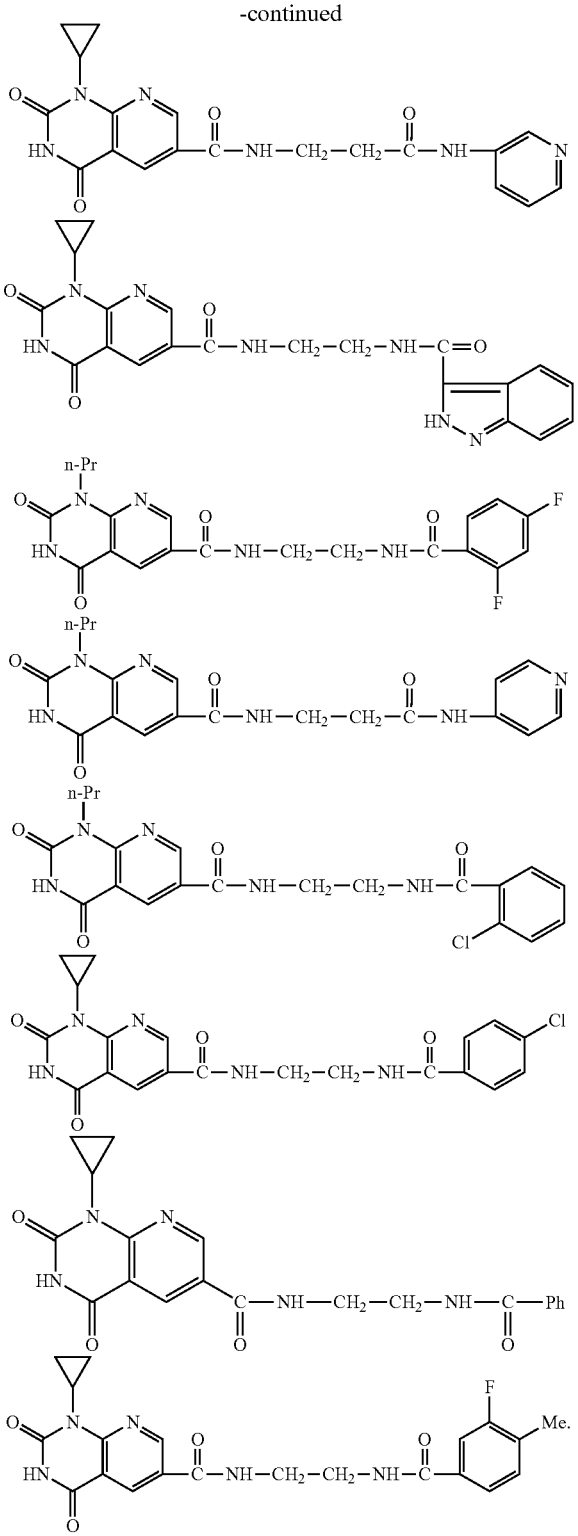

DOCUMENT LIST

Patent Document

[Patent Document 1] WO 01/44228

SUMMARY OF THE INVENTION

Problems to be Solved by the Invention

The present invention aims to provide a compound having a superior RORγt inhibitory action, and useful as an agent for the prophylaxis or treatment of inflammatory bowel disease (IBD), ulcerative colitis (UC), Crohn's disease (CD), rheumatoid arthritis, multiple sclerosis, psoriasis and the like.

Means of Solving the Problems

The present inventors have found that a compound represented by the following formula (I) or a salt thereof has a superior RORγt inhibitory action based on the specific chemical structure thereof and affords superior efficacy as an agent for the prophylaxis or treatment of inflammatory bowel disease (IBD), ulcerative colitis (UC), Crohn's disease (CD), rheumatoid arthritis, multiple sclerosis, psoriasis and the like. The present inventors have conducted intensive studies based on the finding and completed the present invention.

Accordingly, the present invention relates to the followings.

[1] A compound represented by the formula (I):

wherein
Ar is the partial structure (1):

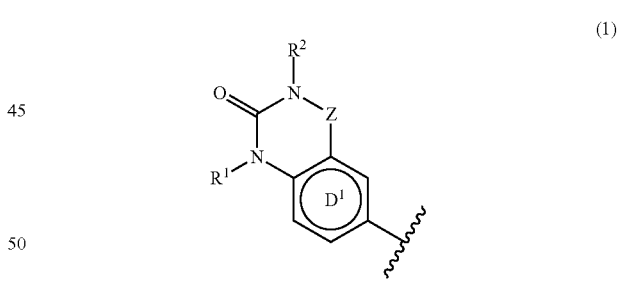

wherein in the partial structure (1),

Z is a carbonyl group or a methylene group, $R^1$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group (excluding a $C_{1-12}$ alkyl group, a $C_{2-12}$ alkenyl group or a $C_{2-12}$ alkynyl group, each substituted by optionally substi- tuted

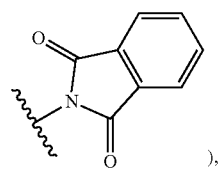 [SMILES: *N1C(=O)c2ccccc2C1=O]

R² is an optionally substituted C_{1-12} alkyl group, an optionally substituted C_{2-12} alkenyl group, an optionally substituted C_{2-12} alkynyl group, an optionally substituted C_{3-12} cycloalkyl group, an optionally substituted C_{3-12} cycloalkenyl group, an optionally substituted C_{6-14} aryl group, an optionally substituted C_{7-16} aralkyl group, an acyl group or a cyano group, and D¹ is an optionally further substituted 6-membered aromatic ring, the partial structure (2):

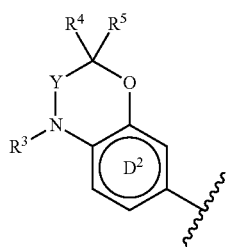

wherein in the partial structure (2),

R³ is a C_{2-12} alkyl group, a substituted C_{1-12} alkyl group, an optionally substituted C_{2-12} alkenyl group, an optionally substituted C_{2-12} alkynyl group, an optionally substituted C_{3-12} cycloalkyl group, an optionally substituted C_{3-12} cycloalkenyl group, an optionally substituted C_{6-14} aryl group, an optionally substituted C_{7-16} aralkyl group, an acyl group or a cyano group, Y is an optionally substituted methylene group, R⁴ is a C_{2-12} alkyl group, a substituted C_{1-12} alkyl group, an optionally substituted C_{2-12} alkenyl group, an optionally substituted C_{2-12} alkynyl group, an optionally substituted C_{3-12} cycloalkyl group, an optionally substituted C_{3-12} cycloalkenyl group, an optionally substituted C_{6-14} aryl group, an optionally substituted C_{7-16} aralkyl group or an acyl group, R⁵ is a hydrogen atom or a substituent, or R⁴ and R⁵ are both methyl groups, or R⁴ and R⁵ in combination optionally form, together with the carbon atom which they are bonded to, an optionally substituted ring, and D² is an optionally further substituted 6-membered aromatic ring, or the partial structure (3):

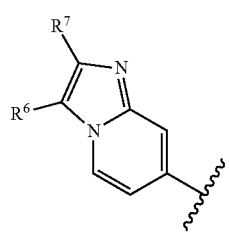

wherein in the partial structure (3),

R⁶ is a C_{2-12} alkyl group, a substituted C_{1-12} alkyl group, an optionally substituted C_{2-12} alkenyl group, an optionally substituted C_{2-12} alkynyl group, an optionally substituted C_{3-12} cycloalkyl group, an optionally substituted C_{3-12} cycloalkenyl group, an optionally substituted C_{6-14} aryl group or an optionally substituted C_{7-16} aralkyl group, and R⁷ is an optionally substituted C_{1-12} alkyl group, an optionally substituted C_{2-12} alkenyl group, an optionally substituted C_{2-12} alkynyl group, an optionally substituted C_{3-12} cycloalkyl group, an optionally substituted C_{3-12} cycloalkenyl group, an optionally substituted C_{6-14} aryl group or an optionally substituted C_{7-16} aralkyl group, Q is a bivalent group selected from the group consisting of the following (Ia)-(Ie):

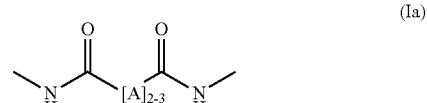

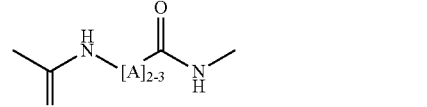

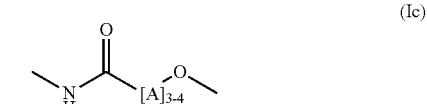

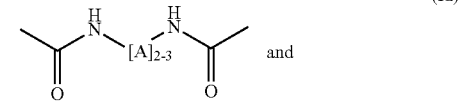

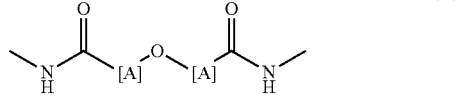

wherein

[A] are the same or different and each is a methylene group optionally substituted by substituent(s) selected from a hydroxy group, an optionally substituted C_{1-6} alkyl group and a C_{6-14} aryl group, and B is an optionally substituted ring, provided that 1,2,3,4-tetrahydro-N-[2-[(4-methoxybenzoyl)amino]ethyl]-2,4-dioxo-1-propyl-pyrido[2,3-d]pyrimidine-6-carboxamide, N-[3-[(5-bromo-2-methylphenyl)amino]-3-oxopropyl]-1-cyclopropyl-1,2,3,4-tetrahydro-2,4-dioxo-pyrido[2,3-d]pyrimidine-6-carboxamide, N-[3-[(5-bromo-2-methylphenyl)amino]-3-oxopropyl]-1,2,3,4-tetrahydro-2,4-dioxo-1-propyl-pyrido[2,3-d]pyrimidine-6-carboxamide, 1-cyclopropyl-1,2,3,4-tetrahydro-N-[3-[(6-methyl-2-pyridyl)amino]-3-oxopropyl]-2,4-dioxo-pyrido[2,3-d]pyrimidine-6-carboxamide, 1-cyclopropyl-1,2,3,4-tetrahydro-2,4-dioxo-N-[3-oxo-3-(3-pyridylamino)propyl]-pyrido[2,3-d]pyrimidine-6-carboxamide, 1-cyclopropyl-1,2,3,4-tetrahydro-N-[2-[(2H-indazol-3-ylcarbonyl)amino]ethyl]-2,4-dioxo-pyrido[2,3-d]pyrimidine-6-carboxamide, N-[2-[(2,4-difluorobenzoyl)amino]ethyl]-1,2,3,4-tetra-hydro-2,4-dioxo-1-propyl-pyrido[2,3-d]pyrimidine-6-carboxamide, 1,2,3,4-tetrahydro-2,4-dioxo-N-[3-oxo-3-(4-pyridylamino)propyl]-1-propyl-pyrido[2,3-d]pyrimidine-6-carboxamide, N-[2-[(2-chlorobenzoyl)amino]ethyl]-1,2,3,4-tetrahydro-2,4-dioxo-1-propyl-pyrido[2,3-d]pyrimidine-6-carboxamide, N-(2-[(4-chlorobenzoyl)amino]ethyl)-1-cyclopropyl-2,4-dioxo-1,2,3,4-tetrahydropyrido[2,3-d]pyrimidine-6-carboxamide, N-[2-(benzoylamino)ethyl]-1-cyclopropyl-2,4-dioxo-1,2,3,4-tetrahydropyrido[2,3-d]pyrimidine-6-carboxamide, and 1-cyclopropyl-N-[2-[(3-fluoro-4-methylbenzoyl)amino]ethyl]-1,2,3,4-tetrahydro-2,4-dioxo-pyrido[2,3-d]pyrimidine-6-carboxamide are excluded, or a salt thereof (hereinafter sometimes to be referred to as compound (I)).

[2] A medicament comprising the compound or salt of the above-mentioned [1].

[3] The medicament of the above-mentioned [2], which is a RORγt inhibitor.

[4] The medicament of the above-mentioned [3], which is an agent for the prophylaxis or treatment of inflammatory disease or autoimmune disease.

[5] The medicament of the above-mentioned [3], which is an agent for the prophylaxis or treatment of inflammatory bowel disease (IBD), ulcerative colitis (UC), Crohn's disease (CD), rheumatoid arthritis, multiple sclerosis or psoriasis.

In another embodiment,

[1] A compound represented by the formula (I):

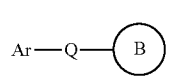
(I)

wherein
Ar is
the partial structure (1):

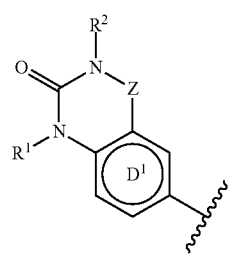
(1)

wherein in the partial structure (1),

Z is a carbonyl group or a methylene group, $R^1$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group (excluding a $C_{1-12}$ alkyl group, a $C_{2-12}$ alkenyl group or a $C_{2-12}$ alkynyl group, each substituted by optionally substituted

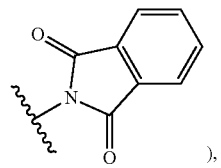 [SMILES: *N1C(=O)c2ccccc2C1=O]
), $R^2$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group, and $D^1$ is an optionally further substituted 6-membered aromatic ring, the partial structure (2):

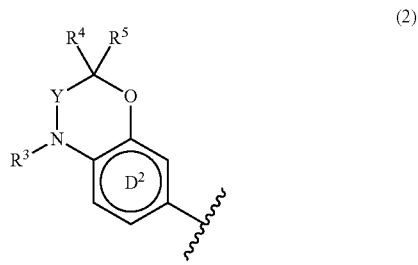
(2)

wherein in the partial structure (2), $R^3$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group, Y is an optionally substituted methylene group, $R^4$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group or an acyl group, $R^5$ is a hydrogen atom or a substituent, or $R^4$ and $R^5$ are both methyl groups, or $R^4$ and $R^5$ in combination optionally form, together with the carbon atom which they are bonded to, an optionally substituted ring, and $D^2$ is an optionally further substituted 6-membered aromatic ring, the partial structure (3):

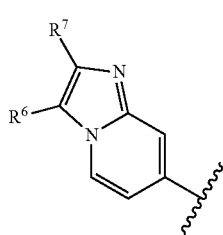
(3)

wherein in the partial structure (3), $R^6$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group or an optionally substituted $C_{7-16}$ aralkyl group, and $R^7$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group or an optionally substituted $C_{7-16}$ aralkyl group, the partial structure (4):

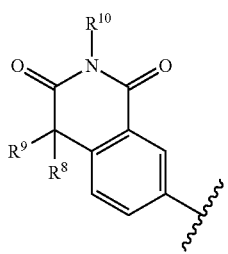
(4)

wherein in the partial structure (4), $R^8$ and $R^9$ are each a hydrogen atom, a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group, or $R^8$ and $R^9$ in combination optionally form, together with the carbon atom which they are bonded to, an optionally substituted ring, and $R^{10}$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group, or the partial structure (5):

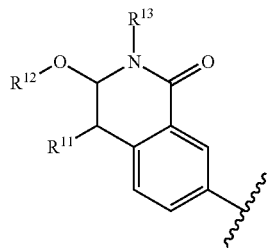
(5)

wherein in the partial structure (5), $R^{11}$, $R^{12}$ and $R^{13}$ are each a substituent, Q is a bivalent group selected from the group consisting of the following (Ia)-(If):

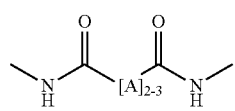
(Ia)

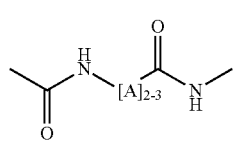
(Ib)

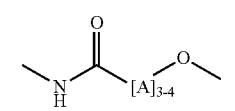
(Ic)

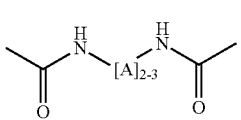
(Id)

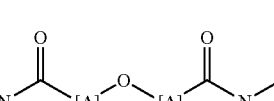
(Ie)
and

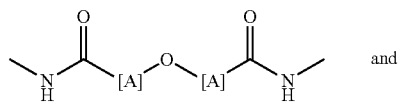
(If)

wherein

[A] are the same or different and each is a methylene group optionally substituted by substituent(s) selected from a hydroxy group, an optionally substituted $C_{1-6}$ alkyl group and a $C_{6-14}$ aryl group, and B is an optionally substituted ring, or a salt thereof.

[2] The compound or salt of the above-mentioned [1], wherein Ar is the partial structure (1).

[3] The compound or salt of the above-mentioned [2], wherein $R^1$ is a $C_{2-6}$ alkyl group or a substituted $C_{1-12}$ alkyl group.

[4] The compound or salt of the above-mentioned [1], wherein Ar is the partial structure (4).

[5] The compound or salt of the above-mentioned [4], wherein $R^8$ and $R^9$ in combination form, together with the carbon atom which they are bonded to, an optionally substituted $C_{3-12}$ cycloalkane.

[6] The compound or salt of the above-mentioned [1], wherein Q is (Ia) wherein [A] are each a methylene group optionally substituted by substituent(s) selected from a hydroxy group and a $C_{1-6}$ alkyl group.

[7] The compound or salt of the above-mentioned [1], wherein B is a $C_{6-14}$ aryl group substituted by cyano group(s) wherein the aryl group is optionally further substituted.

[8] N-[1,3-Bis(cyclopropylmethyl)-2,4-dioxo-1,2,3,4-tetrahydroquinazolin-6-yl]-N'-(3-chloro-4-cyanophenyl)-3-methylpentanediamide.

[9] N-(3-Chloro-4-cyanophenyl)-N'-[3-(cyclopropylmethyl)-1-isopropyl-2,4-dioxo-1,2,3,4-tetrahydroquinazolin-6-yl]-3-hydroxy-3-methylpentanediamide or a salt thereof.

[10] N-(3-Chloro-4-cyanophenyl)-N'-[3-(cyclopropylmethyl)-1-isopropyl-2,4-dioxo-1,2,3,4-tetrahydroquinazolin-6-yl]-3-methylpentanediamide.

[11] N-(3-Chloro-4-cyanophenyl)-N'-[2'-(cyclopropylmethyl)-1',3'-dioxo-2',3'-dihydro-1'H-spiro(cyclopentane-1,4'-isoquinoline)-7'-yl]-3-methylpentanediamide.

[12] A medicament comprising the compound or salt of the above-mentioned [1].

[13] The medicament of the above-mentioned [12], which is a RORγt inhibitor.

[14] The medicament of the above-mentioned [13], which is an agent for the prophylaxis or treatment of inflammatory disease or autoimmune disease.

[15] The medicament of the above-mentioned [13], which is an agent for the prophylaxis or treatment of inflammatory bowel disease (IBD), ulcerative colitis (UC), Crohn's disease (CD), rheumatoid arthritis, multiple sclerosis, psoriasis, bronchial asthma, chronic obstructive pulmonary diseases, ankylopoietic spondylarthritis, Sjogren's syndrome nephritis, systemic lupus erythematosus, Behcet's disease, scleroderma, idiopathic interstitial pneumonia, type I diabetes, atopic dermatitis, graft versus host disease, uveitis, cystic fibrosis or non-alcoholic steatohepatitis.

[16] A method of inhibiting RORγt, which comprises administering an effective amount of the compound or salt of the above-mentioned [1] to a mammal.

[17] A method for the prophylaxis or treatment of inflammatory disease or autoimmune disease, which comprises administering an effective amount of the compound or salt of the above-mentioned [1] to a mammal.

[18] Use of the compound or salt of the above-mentioned [1] for the production of an agent for the prophylaxis or treatment of inflammatory disease or autoimmune disease.

[19] The compound or salt of the above-mentioned [1] for use in the prophylaxis or treatment of inflammatory disease or autoimmune disease.

Effect of the Invention

The compound of the present invention has a superior RORγt inhibitory action, and useful as an agent for the prophylaxis or treatment of inflammatory bowel disease (IBD), ulcerative colitis (UC), Crohn's disease (CD), rheumatoid arthritis, multiple sclerosis or psoriasis and the like.

DETAILED DESCRIPTION OF THE INVENTION

The present invention is explained in detail in the following.

The definition of each substituent used in the present specification is described in detail in the following.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylsulfanyl group" include methylsulfanyl, ethylsulfanyl, propylsulfanyl, isopropylsulfanyl, butylsulfanyl, sec-butylsulfanyl, tert-butylsulfanyl, pentylsulfanyl and hexylsulfanyl.

In the present specification, examples of the "optionally halogenated $C_{1-6}$ alkylsulfanyl group" include a $C_{1-6}$ alkylsulfanyl group optionally having 1 to 7, preferably 1 to 5, halogen atoms. Specific examples thereof include methylsulfanyl, difluoromethylsulfanyl, trifluoromethylsulfanyl, ethylsulfanyl, propylsulfanyl, isopropylsulfanyl, butylsulfanyl, 4,4,4-trifluorobutylsulfanyl, pentylsulfanyl and hexylsulfanyl.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylsulfanyl group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,

(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) an amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-3-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkyl-phosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) an amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) an amino group (e.g., methylcarbamoylamino), a (mono- or di-$C_{7-16}$ aralkyl-carbamoyl) an amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) an amino group (e.g., N-acetyl-N-methylamino) and a ($C_{1-6}$ alkyl) ($C_{6-14}$ aryl-carbonyl) an amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl group, a $C_{1-6}$ alkylsulfanyl group, a $C_{2-6}$ alkenylsulfanyl group (e.g., allylsulfanyl, 2-butenylsulfanyl, 2-pentenylsulfanyl, 3-hexenylsulfanyl), a $C_{3-10}$ cycloalkylsulfanyl group (e.g., cyclohexylsulfanyl), a $C_{6-14}$ arylsulfanyl group (e.g., phenylsulfanyl, naphthylsulfanyl), a $C_{7-16}$ aralkylsulfanyl group (e.g., benzylsulfanyl, phenethylsulfanyl), a $C_{1-6}$ alkyl-carbonylsulfanyl group (e.g., acetylsulfanyl, propionylsulfanyl, butyrylsulfanyl, isobutyrylsulfanyl, pivaloylsulfanyl), a $C_{6-14}$ aryl-carbonylsulfanyl group (e.g., benzoylsulfanyl), a 5- to 14-membered aromatic heterocyclylsulfanyl group (e.g., pyridylsulfanyl) and a halogenated sulfanyl group (e.g., pentafluorosulfanyl).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, unless otherwise specified, examples of the "$C_{1-12}$ alkyl" include, methyl, ethyl, propyl, isopropyl, butyl, isobutyl, sec-butyl, tert-butyl, pentyl, isopentyl, neo-pentyl, 1-ethylpropyl, hexyl, isohexyl, 1,1-dimethylbutyl, 2,2-dimethylbutyl, 3,3-dimethylbutyl, 2-ethylbutyl, heptyl, octyl, nonyl, decyl, undecyl, dodecyl and the like. Examples of the "$C_{2-12}$ alkyl" include ones having 2 to 12 carbon atoms, from among the above-mentioned "$C_{1-12}$ alkyl". In the present specification, examples of the "$C_{1-10}$ alkyl" include ones having 1 to 10 carbon atoms, from among the above-mentioned "$C_{1-12}$ alkyl". In the present specification, examples of the "$C_{2-6}$ alkyl" include ones having 2 to 6 carbon atoms, from among the above-mentioned "$C_{1-12}$ alkyl". In the present specification, examples of the "$C_{1-3}$ alkyl" include ones having 1 to 3 carbon atoms, from among the above-mentioned "$C_{1-12}$ alkyl".

In the present specification, examples of the "$C_{2-12}$ alkenyl" include, unless otherwise specified, ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, 5-hexenyl and the like. In the present specification, examples of the "$C_{2-10}$ alkenyl" include ones having 2 to 10 carbon atoms, from among the above-mentioned "$C_{2-12}$ alkenyl".

In the present specification, examples of the "$C_{2-12}$ alkynyl" include, unless otherwise specified, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 4-methyl-2-pentynyl and the like. In the present specification, examples of the "$C_{2-10}$ alkynyl" include ones having 2 to 10 carbon atoms, from among the above-mentioned "$C_{2-12}$ alkynyl".

In the present specification, examples of the "$C_{3-12}$ cycloalkyl" include, unless otherwise specified, cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, adamantyl and the like. In the present specification, examples of the "$C_{3-8}$ cycloalkyl" include ones having 3 to 8 carbon atoms, from among the above-mentioned "$C_{3-12}$ cycloalkyl".

In the present specification, examples of the "$C_{3-12}$ cycloalkane" include a ring corresponding to the above-mentioned "$C_{3-12}$ cycloalkyl". In the present specification, examples of the "$C_{3-8}$ cycloalkane" include ones having 3 to 8 carbon atoms, from among the above-mentioned "$C_{3-12}$ cycloalkane". The "$C_{3-12}$ cycloalkane" is optionally fused with benzene or the following "$C_{3-12}$ cycloalkene".

In the present specification, examples of the "$C_{3-12}$ cycloalkenyl" include, unless otherwise specified, cyclopropenyl (e.g., 2-cyclopropen-1-yl), cyclobutenyl (e.g., 2-cyclobuten-1-yl), cyclopentenyl (e.g., 1-cyclopenten-1-yl, 2-cyclopenten-1-yl, 3-cyclopenten-1-yl), cyclohexenyl (e.g., 1-cyclohexen-1-yl, 2-cyclohexen-1-yl, 3-cyclohexen-1-yl), cycloheptenyl, cyclooctenyl and the like. In the present specification, examples of the "$C_{3-8}$ cycloalkenyl" include ones having 3 to 8 carbon atoms, from among the above-mentioned "$C_{3-12}$ cycloalkenyl".

In the present specification, examples of the "$C_{3-12}$ cycloalkene" include a ring corresponding to the above-mentioned "$C_{3-12}$ cycloalkenyl". In the present specification, examples of the "$C_{3-8}$ cycloalkene" include ones having 3 to 8 carbon atoms, from among the above-mentioned "$C_{3-12}$ cycloalkene". The "$C_{3-12}$ cycloalkene" is optionally fused with benzene or the above-mentioned "$C_{3-12}$ cycloalkane".

In the present specification, examples of the "$C_{6-10}$ aryl" include ones having 6 to 10 carbon atoms, from among the above-mentioned "$C_{6-14}$ aryl group". The $C_{6-14}$ aryl is optionally fused with the above-mentioned "$C_{3-12}$ cycloalkane" or "$C_{3-12}$ cycloalkene", and examples thereof include tetrahydronaphthyl and the like.

In the present specification, examples of the "$C_{7-12}$ aralkyl" include ones having 7 to 12 carbon atoms, from among the above-mentioned "$C_{7-16}$ aralkyl group".

In the present specification, examples of the "optionally substituted ring" include, unless otherwise specified, "optionally substituted $C_{6-14}$ aromatic hydrocarbon", "optionally substituted $C_{3-12}$ cycloalkane", "optionally substituted $C_{3-12}$ cycloalkene", "optionally substituted heterocycle" and the like.

In the present specification, examples of the "6-membered aromatic ring" include, unless otherwise specified, benzene, pyridine, pyrimidine, pyridazine and pyrazine.

In the present specification, examples of the "$C_{6-14}$ aromatic hydrocarbon" include, unless otherwise specified, a ring corresponding to the above-defined "$C_{6-14}$ aryl group". In the present specification, examples of the "$C_{6-10}$ aromatic hydrocarbon" include ones having 6 to 10 carbon atoms, from among the above-mentioned "$C_{6-14}$ aromatic hydrocarbon".

In the present specification, examples of the "$C_{1-12}$ alkoxy" include, unless otherwise specified, methoxy, ethoxy, propoxy, isopropoxy, butoxy, isobutoxy, sec-butoxy, tert-butoxy, pentyloxy, hexyloxy and the like. In the present specification, examples of the "$C_{1-10}$ alkoxy" include ones having 1 to 10 carbon atoms, from among the above-mentioned "$C_{1-12}$ alkoxy".

In the present specification, examples of the "$C_{2-12}$ alkenyloxy" include, unless otherwise specified, vinyloxy, 2-propynyloxy, 1-methylethenyloxy, 2-methyl-1-propenyloxy and the like. In the present specification, examples of the "$C_{2-6}$ alkenyloxy" include ones wherein the alkenyl moiety has 2 to 6 carbon atoms, from among the above-mentioned "$C_{2-12}$ alkenyloxy".

In the present specification, examples of the "$C_{2-12}$ alkynyloxy" include, unless otherwise specified, 2-butynyloxy, 2-pentynyloxy, 5-hexynyloxy and the like. In the present specification, examples of the "$C_{2-6}$ alkynyloxy" include ones wherein the alkynyl moiety has 2 to 6 carbon atoms, from among the above-mentioned "$C_{2-12}$ alkynyloxy".

In the present specification, examples of the "$C_{3-12}$ cycloalkyloxy" include, unless otherwise specified, cyclopropyloxy, cyclobutyloxy, cyclopentyloxy, cyclohexyloxy, cycloheptyloxy, cyclooctyloxy and the like. In the present specification, examples of the "$C_{3-8}$ cycloalkyloxy" include ones wherein the cycloalkyl moiety has 3 to 8 carbon atoms, from among the above-mentioned "$C_{3-12}$ cycloalkyloxy".

In the present specification, examples of the "$C_{3-12}$ cycloalkenyloxy" include, unless otherwise specified, cyclopropenyloxy (e.g., 2-cyclopropenyloxy), cyclobutenyloxy (e.g., 2-cyclobutenyloxy), cyclopentenyloxy (e.g., 1-cyclopentenyloxy, 2-cyclopentenyloxy, 3-cyclopentenyloxy), cyclohexenyloxy (e.g., 1-cyclohexenyloxy, 2-cyclohexenyloxy, 3-cyclohexenyloxy) and the like. In the present specification, examples of the "$C_{3-8}$ cycloalkenyloxy" include ones wherein the cycloalkenyl moiety has 3 to 8 carbon atoms, from among the above-mentioned "$C_{3-12}$ cycloalkenyloxy".

In the present specification, examples of the "$C_{6-14}$ aryloxy" include, unless otherwise specified, $C_{6-14}$ aryloxy wherein the $C_{6-14}$ aryl moiety is the above-defined "$C_{6-14}$ aryl", and specific examples thereof include phenoxy, 1-naphthyloxy, 2-naphthyloxy and the like. In the present specification, examples of the "$C_{6-10}$ aryloxy" include ones wherein the aryl moiety has 6 to 10 carbon atoms, from among the above-mentioned "$C_{6-14}$ aryloxy".

In the present specification, examples of the "$C_{7-16}$ aralkyloxy" include, unless otherwise specified, $C_{7-16}$ aralkyloxy wherein the $C_{7-16}$ aralkyl moiety is the above-defined "$C_{7-16}$ aralkyl", and specific examples thereof include benzyloxy, phenethyloxy and the like. In the present specification, examples of the "$C_{7-12}$ aralkyloxy" include ones wherein the aralkyl moiety has 7 to 12 carbon atoms, from among the above-mentioned "$C_{7-16}$ aralkyloxy".

In the present specification, examples of the "heterocyclyl-oxy" include, unless otherwise specified, heterocyclyloxy wherein the heterocyclyl moiety is the above-defined "heterocyclic group".

In the present specification, examples of the "tri-$C_{1-12}$ alkylsilyl" include, unless otherwise specified, trimethylsilyl, triethylsilyl, tert-butyldimethylsilyl and the like. In the present specification, examples of the "tri-$C_{1-6}$ alkylsilyl" include ones wherein the alkyl moiety has 1 to 6 carbon atoms, from among the above-mentioned "tri-$C_{1-12}$ alkylsilyl".

In the present specification, examples of the "$C_{1-12}$ alkylsulfanyl" include, unless otherwise specified, methylsulfanyl, ethylsulfanyl, propylsulfanyl, isopropylsulfanyl, butylsulfanyl, isobutylsulfanyl, tert-butylsulfanyl, pentylsulfanyl, hexylsulfanyl and the like.

In the present specification, examples of the "$C_{2-12}$ alkenylsulfanyl" include, unless otherwise specified, vinylsulfanyl, 2-propynylsulfanyl, 1-methylethenylsulfanyl, 2-methyl-1-propenylsulfanyl and the like. In the present specification, examples of the "$C_{2-6}$ alkenylsulfanyl" include ones wherein the alkenyl moiety has 2 to 6 carbon atoms, from among the above-mentioned "$C_{2-12}$ alkenylsulfanyl".

In the present specification, examples of the "$C_{2-12}$ alkynylsulfanyl" include, unless otherwise specified, 2-butynylsulfanyl, 2-pentynylsulfanyl, 5-hexynylsulfanyl and the like. In the present specification, examples of the "$C_{2-6}$ alkynylsulfanyl" include ones wherein the alkynyl moiety has 2 to 6 carbon atoms, from among the above-mentioned "$C_{2-12}$ alkynylsulfanyl".

In the present specification, examples of the "$C_{3-12}$ cycloalkylsulfanyl" include, unless otherwise specified, cyclopropylsulfanyl, cyclobutylsulfanyl, cyclopentylsulfanyl, cyclohexylsulfanyl, cycloheptylsulfanyl, cyclooctylsulfanyl and the like. In the present specification, examples of the "$C_{3-8}$ cycloalkylsulfanyl" include ones wherein the cycloalkyl moiety has 3 to 8 carbon atoms, from among the above-mentioned "$C_{3-12}$ cycloalkylsulfanyl".

In the present specification, examples of the "$C_{3-12}$ cycloalkenylsulfanyl" include, unless otherwise specified, cyclopropenylsulfanyl (e.g., 2-cyclopropenylsulfanyl), cyclobutenylsulfanyl (e.g., 2-cyclobutenylsulfanyl), cyclopentenylsulfanyl (e.g., 1-cyclopentenylsulfanyl, 2-cyclopentenylsulfanyl, 3-cyclopentenylsulfanyl), cyclohexenylsulfanyl (e.g., 1-cyclohexenylsulfanyl, 2-cyclohexenylsulfanyl, 3-cyclohexenylsulfanyl) and the like. In the present specification, examples of the "$C_{3-8}$ cycloalkenylsulfanyl" include ones wherein the cycloalkenyl moiety has 3 to 8 carbon atoms, from among the above-mentioned "$C_{3-12}$ cycloalkenylsulfanyl".

In the present specification, examples of the "$C_{6-14}$ arylsulfanyl" include, unless otherwise specified, $C_{6-14}$ arylsulfanyl wherein the $C_{6-14}$ aryl moiety is the above-defined "$C_{6-14}$ aryl", and specific examples thereof include phenylsulfanyl, 1-naphthylsulfanyl, 2-naphthylsulfanyl and the like. In the present specification, examples of the "$C_{6-10}$ arylsulfanyl" include ones wherein the aryl moiety has 6 to 10 carbon atoms, from among the above-mentioned "$C_{6-14}$ arylsulfanyl".

In the present specification, examples of the "$C_{7-16}$ aralkylsulfanyl" include, unless otherwise specified, $C_{7-16}$ aralkylsulfanyl wherein the $C_{7-16}$ aralkyl moiety is the above-defined "$C_{7-16}$ aralkyl", and specific examples thereof include benzylsulfanyl, phenethylsulfanyl and the like. In the present specification, examples of the "$C_{7-12}$ aralkylsulfanyl" include ones wherein the aralkyl moiety has 7 to 12 carbon atoms, from among the above-mentioned "$C_{7-16}$ aralkylsulfanyl".

In the present specification, examples of the "heterocyclyl-sulfanyl" include, unless otherwise specified, heterocyclyl-sulfanyl wherein the heterocyclyl moiety is the above-defined "heterocyclic group".

In the present specification, examples of the "$C_{1-12}$ alkyl-carbonyl" include, unless otherwise specified, $C_{1-12}$ alkyl-carbonyl wherein the $C_{1-12}$ alkyl moiety is the above-defined "$C_{1-12}$ alkyl", and specific examples thereof include acetyl, propanoyl, butanoyl, 2-methylpropanoyl, pentanoyl, 3-methylbutanoyl, 2-methylbutanoyl, 2,2-dimethylpropanoyl, hexanoyl, heptanoyl and the like. In the present specification, examples of the "$C_{1-10}$ alkyl-carbonyl" include ones wherein the alkyl moiety has 1 to 10 carbon atoms, from among the above-mentioned "$C_{1-12}$ alkyl-carbonyl".

In the present specification, examples of the "$C_{2-12}$ alkenyl-carbonyl" include, unless otherwise specified, $C_{2-12}$ alkenyl-carbonyl wherein the $C_{2-12}$ alkenyl moiety is the above-defined "$C_{2-12}$ alkenyl", and specific examples thereof include ethenylcarbonyl, 2-propynylcarbonyl, 1-methylethenylcarbonyl, 2-methyl-1-propenylcarbonyl and the like. In the present specification, examples of the "$C_{2-6}$ alkenyl-carbonyl" include ones wherein the alkenyl moiety has 2 to 6 carbon atoms, from among the above-mentioned "$C_{2-12}$ alkenyl-carbonyl".

In the present specification, examples of the "$C_{2-12}$ alkynyl-carbonyl" include, unless otherwise specified, $C_{2-12}$ alkynyl-carbonyl wherein the $C_{2-12}$ alkynyl moiety is the above-defined "$C_{2-12}$ alkynyl", and specific examples thereof include 2-butynylcarbonyl, 2-pentynylcarbonyl, 5-hexynylcarbonyl and the like. In the present specification, examples of the "$C_{2-6}$ alkynyl-carbonyl" include ones wherein the alkynyl moiety has 2 to 6 carbon atoms, from among the above-mentioned "$C_{2-12}$ alkynyl-carbonyl".

In the present specification, examples of the "$C_{3-12}$ cycloalkyl-carbonyl" include, unless otherwise specified, $C_{3-12}$ cycloalkyl-carbonyl wherein the $C_{3-12}$ cycloalkyl moiety is the above-defined "$C_{3-12}$ cycloalkyl", and specific examples thereof include cyclopentylcarbonyl, cyclohexylcarbonyl and the like. In the present specification, examples of the "$C_{3-8}$ cycloalkyl-carbonyl" include ones wherein the cycloalkyl moiety has 3 to 8 carbon atoms, from among the above-mentioned "$C_{3-12}$ cycloalkyl-carbonyl".

In the present specification, examples of the "$C_{3-12}$ cycloalkenyl-carbonyl" include, unless otherwise specified, $C_{3-12}$ cycloalkenyl-carbonyl wherein the $C_{3-12}$ cycloalkenyl moiety is the above-defined "$C_{3-12}$ cycloalkenyl", and specific examples thereof include cyclopropenylcarbonyl, cyclopentenylcarbonyl, cyclohexenylcarbonyl and the like. In the present specification, examples of the "$C_{3-8}$ cycloalkenyl-carbonyl" include ones wherein the cycloalkenyl moiety has 3 to 8 carbon atoms, from among the above-mentioned "$C_{3-12}$ cycloalkenyl-carbonyl".

In the present specification, examples of the "$C_{6-10}$ aryl-carbonyl" include ones wherein the aryl moiety has 6 to 10 carbon atoms, from among the above-mentioned "$C_{6-14}$ aryl-carbonyl".

In the present specification, examples of the "$C_{7-16}$ aralkyl-carbonyl" include, unless otherwise specified, $C_{7-16}$ aralkyl-carbonyl wherein the $C_{7-16}$ aralkyl moiety is the above-defined "$C_{7-16}$ aralkyl", and specific examples thereof include phenylacetyl, phenylpropanoyl, phenylbutanoyl, naphthyl acetyl, naphthyl propanoyl and the like. In the present specification, examples of the "$C_{7-12}$ aralkyl-carbonyl" include ones wherein the aralkyl moiety has 7 to 12 carbon atoms, from among the above-mentioned "$C_{7-16}$ aralkyl-carbonyl".

In the present specification, examples of the "heterocyclyl-carbonyl" include, unless otherwise specified, heterocyclyl-carbonyl wherein the heterocyclyl moiety is the above-defined "heterocyclic group".

In the present specification, examples of the "$C_{1-12}$ alkoxy-carbonyl" include, unless otherwise specified, $C_{1-12}$ alkoxy-carbonyl wherein the $C_{1-12}$ alkoxy moiety is the above-defined "$C_{1-12}$ alkoxy", and specific examples thereof include methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl and the like. Examples of the "$C_{1-10}$ alkoxy-carbonyl" include ones wherein the alkoxy moiety has 1 to 10 carbon atoms, from among the above-mentioned "$C_{1-12}$ alkoxy-carbonyl".

In the present specification, examples of the "$C_{2-12}$ alkenyloxy-carbonyl" include, unless otherwise specified, $C_{2-12}$ alkenyloxy-carbonyl wherein the $C_{2-12}$ alkenyloxy moiety is the above-defined "$C_{2-12}$ alkenyloxy", and specific examples thereof include vinyloxycarbonyl, 2-propynyloxycarbonyl, 1-methylethenyloxycarbonyl, 2-methyl-1-propenyloxycarbonyl and the like. In the present specification, examples of the "$C_{2-6}$ alkenyloxy-carbonyl" include ones wherein the alkenyloxy moiety has 2 to 6 carbon atoms, from among the above-mentioned "$C_{2-12}$ alkenyloxy-carbonyl".

In the present specification, examples of the "$C_{2-12}$ alkynyloxy-carbonyl" include, unless otherwise specified, $C_{2-12}$ alkynyloxy-carbonyl wherein the $C_{2-12}$ alkynyloxy moiety is the above-defined "$C_{2-12}$ alkynyloxy", and specific examples thereof include 2-butynyloxycarbonyl, 2-pentynyloxycarbonyl, 5-hexynyloxycarbonyl and the like. In the present specification, examples of the "$C_{2-6}$ alkynyloxy-carbonyl" include ones wherein the alkynyloxy moiety has 2 to 6 carbon atoms, from among the above-mentioned "$C_{2-12}$ alkynyloxy-carbonyl".

In the present specification, examples of the "$C_{3-12}$ cycloalkyloxy-carbonyl" include, unless otherwise specified, $C_{3-12}$ cycloalkyloxy-carbonyl wherein the $C_{3-12}$ cycloalkyloxy moiety is the above-defined "$C_{3-12}$ cycloalkyloxy", and specific examples thereof include cyclopentyloxycarbonyl, cyclohexyloxycarbonyl and the like. In the present specification, examples of the "$C_{3-8}$ cycloalkyloxy-carbonyl" include ones wherein the cycloalkyloxy moiety has 3 to 8 carbon atoms, from among the above-mentioned "$C_{3-12}$ cycloalkyloxy-carbonyl".

In the present specification, examples of the "$C_{3-12}$ cycloalkenyloxy-carbonyl" include, unless otherwise specified, $C_{3-12}$ cycloalkenyl-carbonyl wherein the $C_{3-12}$ cycloalkenyloxy moiety is the above-defined "$C_{3-12}$ cycloalkenyloxy", and specific examples thereof include cyclopropenyloxycarbonyl (e.g., 2-cyclopropenyloxycarbonyl), cyclobutenyloxycarbonyl (e.g., 2-cyclobutenyloxycarbonyl), cyclopentenyloxycarbonyl (e.g., 1-cyclopentenyloxycarbonyl, 2-cyclopentenyloxycarbonyl, 3-cyclopentenyloxycarbonyl), cyclohexenyloxycarbonyl (e.g., 1-cyclohexenyloxycarbonyl, 2-cyclohexenyloxycarbonyl, 3-cyclohexenyloxycarbonyl) and the like. In the present specification, examples of the "$C_{3-8}$ cycloalkenyloxy-carbonyl" include ones wherein the cycloalkenyloxy moiety has 3 to 8 carbon atoms, from among the above-mentioned "$C_{3-12}$ cycloalkenyloxy-carbonyl".

In the present specification, examples of the "$C_{6-14}$ aryloxy-carbonyl" include, unless otherwise specified, $C_{6-14}$ aryloxy-carbonyl wherein the $C_{6-14}$ aryloxy moiety is the above-defined "$C_{6-14}$ aryloxy", and specific examples thereof include phenoxycarbonyl, 1-naphthyloxycarbonyl, 2-naphthyloxycarbonyl and the like. In the present specification, examples of the "$C_{6-10}$ aryloxy-carbonyl" include ones wherein the aryloxy moiety has 6 to 10 carbon atoms, from among the above-mentioned "$C_{6-14}$ aryloxy-carbonyl".

In the present specification, examples of the "$C_{7-16}$ aralkyloxy-carbonyl" include, unless otherwise specified, $C_{7-16}$ aralkyloxy-carbonyl wherein the $C_{7-16}$ aralkyloxy moiety is the above-defined "$C_{7-16}$ aralkyloxy", and specific examples thereof include benzyloxycarbonyl, phenethyloxycarbonyl and the like. In the present specification, examples of the "$C_{7-12}$ aralkyloxy-carbonyl" include ones wherein the aralkyloxy moiety has 7 to 12 carbon atoms, from among the above-mentioned "$C_{7-16}$ aralkyloxy-carbonyl".

In the present specification, examples of the "heterocyclyloxy-carbonyl" include, unless otherwise specified, heterocyclyloxy-carbonyl wherein the heterocyclyl moiety is the above-defined "heterocyclic group", and specific examples thereof include 2-pyridyloxycarbonyl and the like.

In the present specification, examples of the "$C_{1-12}$ alkylsulfonyl" include, unless otherwise specified, $C_{1-12}$ alkylsulfonyl wherein the $C_{1-12}$ alkyl moiety is the above-defined "$C_{1-12}$ alkyl", and specific examples thereof include methylsulfonyl, ethylsulfonyl, propylsulfonyl, isopropylsulfonyl, butylsulfonyl, isobutylsulfonyl, tert-butylsulfonyl and the like. In the present specification, examples of the "$C_{1-10}$ alkylsulfonyl" include ones wherein the alkyl moiety has 1 to 10 carbon atoms, from among the above-mentioned "$C_{1-12}$ alkylsulfonyl".

In the present specification, examples of the "$C_{2-12}$ alkenylsulfonyl" include, unless otherwise specified, $C_{2-12}$ alkenylsulfonyl wherein the $C_{2-12}$ alkenyl moiety is the above-defined "$C_{2-12}$ alkenyl", and specific examples thereof include vinylsulfonyl, propenylsulfonyl, isopropenylsulfonyl, 2-butenylsulfonyl, 4-pentenylsulfonyl, 5-hexenylsulfonyl and the like. In the present specification, examples of the "$C_{2-6}$ alkenylsulfonyl" include ones wherein the alkenyl moiety has 2 to 6 carbon atoms, from among the above-mentioned "$C_{2-12}$ alkenylsulfonyl".

In the present specification, examples of the "$C_{2-12}$ alkynylsulfonyl" include, unless otherwise specified, $C_{2-12}$ alkynylsulfonyl wherein the $C_{2-12}$ alkynyl moiety is the above-defined "$C_{2-12}$ alkynyl", and specific examples thereof include 2-butynylsulfonyl, 4-pentynylsulfonyl, 5-hexynylsulfonyl and the like. In the present specification, examples of the "$C_{2-6}$ alkynylsulfonyl" include ones wherein the alkynyl moiety has 2 to 6 carbon atoms, from among the above-mentioned "$C_{2-12}$ alkynylsulfonyl".

In the present specification, examples of the "$C_{3-12}$ cycloalkylsulfonyl" include, unless otherwise specified, $C_{3-12}$ cycloalkylsulfonyl wherein the $C_{3-12}$ cycloalkyl moiety is the above-defined "$C_{3-12}$ cycloalkyl", and specific examples thereof include cyclopropylsulfonyl, cyclobutyl-sulfonyl, cyclopentylsulfonyl, cyclohexylsulfonyl, cycloheptylsulfonyl and the like. In the present specification, examples of the "$C_{3-8}$ cycloalkylsulfonyl" include ones wherein the cycloalkyl moiety has 3 to 8 carbon atoms, from among the above-mentioned "$C_{3-12}$ cycloalkylsulfonyl".

In the present specification, examples of the "$C_{3-12}$ cycloalkenylsulfonyl" include, unless otherwise specified, $C_{3-12}$ cycloalkenylsulfonyl wherein the $C_{3-12}$ cycloalkenyl moiety is the above-defined "$C_{3-12}$ cycloalkenyl", and specific examples thereof include cyclopropenylsulfonyl (e.g., 2-cyclopropenylsulfonyl), cyclobutenylsulfonyl (e.g., 2-cyclobutenylsulfonyl), cyclopentenylsulfonyl (e.g., 1-cyclopentenylsulfonyl, 2-cyclopentenylsulfonyl, 3-cyclopentenylsulfonyl), cyclohexenylsulfonyl (e.g., 1-cyclohexenylsulfonyl, 2-cyclohexenylsulfonyl, 3-cyclohexenylsulfonyl) and the like. In the present specification, examples of the "$C_{3-8}$ cycloalkenylsulfonyl" include ones wherein the cycloalkenyl moiety has 3 to 8 carbon atoms, from among the above-mentioned "$C_{3-12}$ cycloalkenylsulfonyl".

In the present specification, examples of the "$C_{7-16}$ aralkylsulfonyl" include, unless otherwise specified, $C_{7-16}$ aralkylsulfonyl wherein the $C_{7-16}$ aralkyl moiety is the above-defined "$C_{7-16}$ aralkyl", and specific examples thereof include benzylsulfonyl, phenethylsulfonyl and the like. In the present specification, examples of the "$C_{7-12}$ aralkylsulfonyl" include ones wherein the aralkyl moiety has 7 to 12 carbon atoms, from among the above-mentioned "$C_{7-16}$ aralkylsulfonyl".

In the present specification, examples of the "$C_{6-10}$ arylsulfonyl" include ones wherein the aryl moiety has 6 to 10 carbon atoms, from among the above-mentioned "$C_{6-14}$ arylsulfonyl".

In the present specification, examples of the "heterocyclyl-sulfonyl" include, unless otherwise specified, heterocyclyl-sulfonyl wherein the heterocyclyl moiety is the above-defined "heterocyclic group".

In the present specification, examples of the "$C_{1-12}$ alkylsulfinyl" include, unless otherwise specified, $C_{1-12}$ alkylsulfinyl wherein the $C_{1-12}$ alkyl moiety is the above-defined "$C_{1-12}$ alkyl", and specific examples thereof include methylsulfinyl, ethylsulfinyl, propylsulfinyl, isopropylsulfinyl, butylsulfinyl, isobutylsulfinyl, tert-butylsulfinyl and the like. In the present specification, examples of the "$C_{1-10}$ alkylsulfinyl" include ones wherein the alkyl moiety has 1 to 10 carbon atoms, from among the above-mentioned "$C_{1-12}$ alkylsulfinyl". In the present specification, examples of the "$C_{1-6}$ alkylsulfinyl" include ones wherein the alkyl moiety has 1 to 6 carbon atoms, from among the above-mentioned "$C_{1-12}$ alkylsulfinyl".

In the present specification, examples of the "$C_{2-12}$ alkenylsulfinyl" include, unless otherwise specified, $C_{2-12}$ alkenylsulfinyl wherein the $C_{2-12}$ alkenyl moiety is the above-defined "$C_{2-12}$ alkenyl", and specific examples thereof include vinyl sulfinyl, propenylsulfinyl, isopropenylsulfinyl, 2-butenylsulfinyl, 4-pentenylsulfinyl, 5-hexenylsulfinyl and the like. In the present specification, examples of the "$C_{2-6}$ alkenylsulfinyl" include ones wherein the alkenyl moiety has 2 to 6 carbon atoms, from among the above-mentioned "$C_{2-12}$ alkenylsulfinyl".

In the present specification, examples of the "$C_{2-12}$ alkynylsulfinyl" include, unless otherwise specified, $C_{2-12}$ alkynylsulfinyl wherein the $C_{2-12}$ alkynyl moiety is the above-defined "$C_{2-12}$ alkynyl", and specific examples thereof include 2-butynyl sulfinyl, 4-pentynylsulfinyl, 5-hexynylsulfinyl and the like. In the present specification, examples of the "$C_{2-6}$ alkynylsulfinyl" include ones wherein the alkynyl moiety has 2 to 6 carbon atoms, from among the above-mentioned "$C_{2-12}$ alkynylsulfinyl".

In the present specification, examples of the "$C_{3-12}$ cycloalkylsulfinyl" include, unless otherwise specified, $C_{3-12}$ cycloalkylsulfinyl wherein the $C_{3-12}$ cycloalkyl moiety is the above-defined "$C_{3-12}$ cycloalkyl", and specific examples thereof include cyclopropylsulfinyl, cyclobutylsulfinyl, cyclopentylsulfinyl, cyclohexylsulfinyl, cycloheptylsulfinyl and the like. In the present specification, examples of the "$C_{3-8}$ cycloalkylsulfinyl" include ones wherein the cycloalkyl moiety has 3 to 8 carbon atoms, from among the above-mentioned "$C_{3-12}$ cycloalkylsulfinyl".

In the present specification, examples of the "$C_{3-12}$ cycloalkenylsulfinyl" include, unless otherwise specified, $C_{3-12}$ cycloalkenylsulfinyl wherein the $C_{3-12}$ cycloalkenyl moiety is the above-defined "$C_{3-12}$ cycloalkenyl", and specific examples thereof include cyclopropenylsulfinyl (e.g., 2-cyclopropenylsulfinyl), cyclobutenylsulfinyl (e.g., 2-cyclobutenylsulfinyl), cyclopentenylsulfinyl (e.g., 1-cyclopentenylsulfinyl, 2-cyclopentenylsulfinyl, 3-cyclopentenylsulfinyl), cyclohexenylsulfinyl (e.g., 1-cyclohexenylsulfinyl, 2-cyclohexenylsulfinyl, 3-cyclohexenylsulfinyl) and the like. In the present specification, examples of the "$C_{3-8}$ cycloalkenylsulfinyl" include ones wherein the cycloalkenyl moiety has 3 to 8 carbon atoms, from among the above-mentioned "$C_{3-12}$ cycloalkenylsulfinyl".

In the present specification, examples of the "$C_{7-16}$ aralkylsulfinyl" include, unless otherwise specified, $C_{7-16}$ aralkylsulfinyl wherein the $C_{7-16}$ aralkyl moiety is the above-defined "$C_{7-16}$ aralkyl", and specific examples thereof include benzyl sulfinyl, phenethylsulfinyl and the like. In the present specification, examples of the "$C_{7-12}$ aralkylsulfinyl" include ones wherein the aralkyl moiety has 7 to 12 carbon atoms, from among the above-mentioned "$C_{7-16}$ aralkylsulfinyl".

In the present specification, examples of the "$C_{6-14}$ arylsulfinyl" include, unless otherwise specified, $C_{6-14}$ arylsulfinyl wherein the $C_{6-14}$ aryl moiety is the above-defined "$C_{6-14}$ aryl", and specific examples thereof include for example, phenylsulfinyl, 1-naphthyl sulfinyl, 2-naphthyl sulfinyl and the like. In the present specification, examples of the "$C_{6-10}$ arylsulfinyl" include ones wherein the aryl moiety has 6 to 10 carbon atoms, from among the above-mentioned "$C_{6-14}$ arylsulfinyl".

In the present specification, examples of the "heterocyclyl-sulfinyl" include, unless otherwise specified, heterocyclyl-sulfinyl wherein the heterocyclyl moiety is the above-defined "heterocyclic group".

In the present specification, examples of the "mono- or di-$C_{1-12}$ alkyl-carbamoyl" include, unless otherwise specified, mono- or di-$C_{1-12}$ alkyl-carbamoyl wherein the $C_{1-12}$ alkyl moiety is the above-defined "$C_{1-12}$ alkyl", and specific examples thereof include methylcarbamoyl, dimethylcarbamoyl and the like.

In the present specification, examples of the "mono- or di-$C_{2-12}$ alkenyl-carbamoyl" include, unless otherwise specified, mono- or di-$C_{2-12}$ alkenyl-carbamoyl wherein the $C_{2-12}$ alkenyl moiety is the above-defined "$C_{2-12}$ alkenyl", and specific examples thereof include ethenylcarbamoyl, diethenylcarbamoyl and the like.

In the present specification, examples of the "mono- or di-$C_{2-12}$ alkynyl-carbamoyl" include, unless otherwise specified, mono- or di-$C_{2-12}$ alkynyl-carbamoyl wherein the $C_{2-12}$ alkynyl moiety is the above-defined "$C_{2-12}$ alkynyl", and specific examples thereof include 2-butynylcarbamoyl, 2-pentynylcarbamoyl and the like.

In the present specification, examples of the "mono- or di-$C_{3-12}$ cycloalkyl-carbamoyl" include, unless otherwise specified, mono- or di-$C_{3-12}$ cycloalkyl-carbamoyl wherein the $C_{3-12}$ cycloalkyl moiety is the above-defined "$C_{3-12}$ cycloalkyl", and specific examples thereof include cyclopentylcarbamoyl, cyclohexylcarbamoyl and the like. In the present specification, examples of the "mono- or di-$C_{3-8}$ cycloalkyl-carbamoyl" include ones wherein the cycloalkyl moiety has 3 to 8 carbon atoms, from among the above-mentioned "mono- or di-$C_{3-12}$ cycloalkyl-carbamoyl".

In the present specification, examples of the "mono- or di-$C_{3-12}$ cycloalkenyl-carbamoyl" include, unless otherwise specified, mono- or di-$C_{3-12}$ cycloalkenyl-carbamoyl wherein the $C_{3-12}$ cycloalkenyl moiety is the above-defined "$C_{3-12}$ cycloalkenyl", and specific examples thereof include cyclopropenylcarbamoyl, cyclopentenylcarbamoyl and the like.

In the present specification, examples of the "mono- or di-$C_{6-14}$ aryl-carbamoyl" include, unless otherwise specified, mono- or di-$C_{6-14}$ aryl-carbamoyl wherein the $C_{6-14}$ aryl moiety is the above-defined "$C_{6-14}$ aryl", and specific examples thereof include phenylcarbamoyl, diphenylcarbamoyl and the like. In the present specification, examples of the "mono- or di-$C_{6-10}$ aryl-carbamoyl" include ones wherein the aryl moiety has 6 to 10 carbon atoms, from among the above-mentioned "mono- or di-$C_{6-14}$ aryl-carbamoyl".

In the present specification, examples of the "mono- or di-heterocyclyl-carbamoyl" include, unless otherwise specified, mono- or di-heterocyclyl-carbamoyl wherein the heterocyclyl moiety is the above-defined "heterocyclic group".

In the present specification, examples of the "substituent" for the "optionally substituted" or "substituted" include substituents selected from the above-mentioned substituent group A. The number of the substituents is not limited as long as it is substitutable number, and it is 1 to 5, preferably 1 to 3. When the number of the substituents is plural, the respective substituents may be the same or different.

The definition of each symbol in the formula (I) is explained in detail in the following.

Ar is the following partial structure (1), partial structure (2) or partial structure (3).

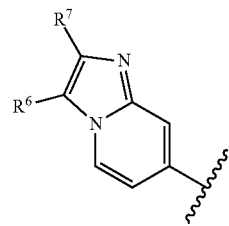

(1)

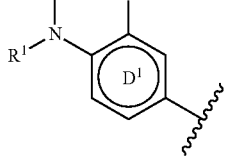

(2)

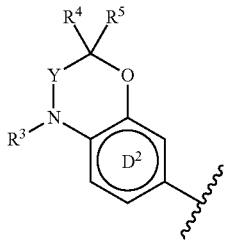

(3)

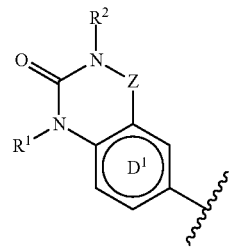

In another embodiment, Ar is the following the partial structure (1), partial structure (2), partial structure (3), partial structure (4) or partial structure (5)

(1)

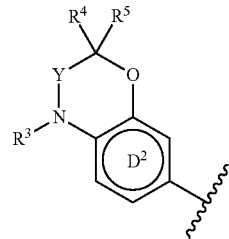

(2)

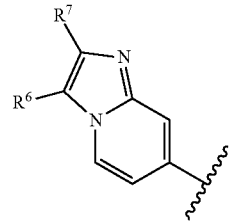

(3)

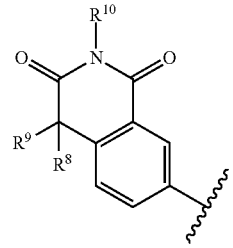

(4)

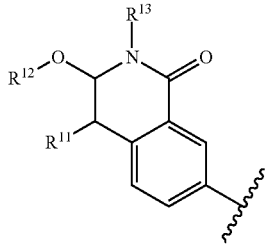

(5)

Z is a carbonyl group or a methylene group. Z is preferably a carbonyl group, and the partial structure (1) is preferably the following partial structure (1'):

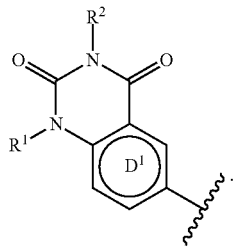

(1')

$R^1$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group (excluding a $C_{1-12}$ alkyl group, a $C_{2-12}$ alkenyl group or a $C_{2-12}$ alkynyl group, each substituted by optionally substituted

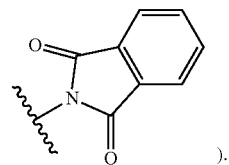 [SMILES: *N1C(=O)c2ccccc2C1=O]

).

$R^1$ is preferably
(1) a $C_{2-12}$ alkyl group,
(2) a substituted $C_{1-12}$ alkyl group, or
(3) an optionally substituted $C_{3-12}$ cycloalkyl group.
$R^1$ is more preferably
(1) a $C_{2-6}$ alkyl group,
(2) a substituted $C_{1-6}$ alkyl group, or
(3) an optionally substituted $C_{3-8}$ cycloalkyl group.
$R^1$ is particularly preferably
(1) a $C_{2-6}$ alkyl group (e.g., ethyl),
(2) a $C_{1-6}$ alkyl group (e.g., methyl, ethyl, propyl) substituted by 1 to 3 substituents selected from
    (a) a $C_{3-8}$ cycloalkyl group (e.g., cyclopropyl),
    (b) a $C_{1-6}$ alkoxy group (e.g., methoxy),
    (c) a $C_{1-6}$ alkylsulfanyl group (e.g., methylsulfanyl), and
    (d) a hydroxy group, or
(3) a $C_{3-8}$ cycloalkyl group (e.g., cyclopropyl).
In another embodiment, $R^1$ is preferably
(1) a $C_{2-12}$ alkyl group,
(2) a substituted $C_{1-12}$ alkyl group,
(3) an optionally substituted $C_{3-12}$ cycloalkyl group, or
(4) an optionally substituted $C_{2-12}$ alkynyl group.
In another embodiment, $R^1$ is more preferably
(1) a $C_{2-6}$ alkyl group,
(2) a substituted $C_{1-6}$ alkyl group,
(3) an optionally substituted $C_{3-6}$ cycloalkyl group, or
(4) an optionally substituted $C_{2-6}$ alkynyl group.
In another embodiment, $R^1$ is further more preferably
(1) a $C_{2-6}$ alkyl group (e.g., ethyl, isopropyl),
(2) a $C_{1-6}$ alkyl group (e.g., methyl, ethyl, propyl) substituted by 1 to 3 substituents selected from
    (a) a $C_{3-8}$ cycloalkyl group (e.g., cyclopropyl),
    (b) a $C_{1-6}$ alkoxy group (e.g., methoxy),
    (c) a $C_{1-6}$ alkylsulfanyl group (e.g., methylsulfanyl),
    (d) a hydroxy group,
    (e) a tri-$C_{1-6}$ alkylsilyl group (e.g., trimethylsilyl), and
    (f) a cyano group,
(3) a $C_{3-8}$ cycloalkyl group (e.g., cyclopropyl), or
(4) a $C_{2-6}$ alkynyl group (e.g., 2-propynyl).
In another embodiment, $R^1$ is still more preferably
(1) a $C_{2-6}$ alkyl group (e.g., ethyl, isopropyl), or
(2) a $C_{1-6}$ alkyl group (e.g., methyl) substituted by 1 to 3 substituents selected from
    (a) a $C_{1-6}$ alkylsulfanyl group (e.g., methylsulfanyl), and
    (c) a tri-$C_{1-6}$ alkylsilyl group (e.g., trimethylsilyl).
$R^1$ is particularly preferably a $C_{2-6}$ alkyl group (e.g., ethyl, isopropyl) or a substituted $C_{1-12}$ alkyl group (e.g., cyclopropylmethyl).

$R^2$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group.
$R^2$ is preferably
(1) an optionally substituted $C_{1-12}$ alkyl group,
(2) an optionally substituted $C_{2-12}$ alkynyl group, or
(3) an optionally substituted $C_{3-12}$ cycloalkyl group.
$R^2$ is more preferably
(1) an optionally substituted $C_{1-6}$ alkyl group,
(2) an optionally substituted $C_{2-6}$ alkynyl group, or
(3) an optionally substituted $C_{3-8}$ cycloalkyl group.
$R^2$ is particularly preferably
(1) a $C_{1-6}$ alkyl group (e.g., methyl, ethyl, propyl) optionally substituted by 1 to 3 substituents selected from
    (a) a cyano group,
    (b) a hydroxy group,
    (c) a $C_{3-8}$ cycloalkyl group (e.g., cyclopropyl),
    (d) a $C_{1-6}$ alkoxy group (e.g., methoxy),
    (e) a $C_{1-6}$ alkylsulfanyl group (e.g., methylsulfanyl),
    (f) a $C_{1-6}$ alkylsulfonyl group (e.g., methylsulfonyl),
    (g) a carbamoyl group optionally mono- or di-substituted by $C_{1-6}$ alkyl group(s) (e.g., methyl), and
    (h) a tri-$C_{1-6}$ alkylsilyl group (e.g., trimethylsilyl),
(2) a $C_{2-6}$ alkynyl group (e.g., 2-propynyl), or
(3) a $C_{3-8}$ cycloalkyl group (e.g., cyclopropyl).
In another embodiment, $R^2$ is more preferably
(1) a $C_{1-6}$ alkyl group (e.g., methyl, ethyl, propyl) optionally substituted by 1 to 3 substituents selected from
    (a) a cyano group,
    (b) a hydroxy group,
    (c) a $C_{3-8}$ cycloalkyl group (e.g., cyclopropyl),
    (d) a $C_{1-6}$ alkoxy group (e.g., methoxy),
    (e) a $C_{1-6}$ alkylsulfanyl group (e.g., methylsulfanyl),
    (f) a $C_{1-6}$ alkylsulfonyl group (e.g., methylsulfonyl),
    (g) a carbamoyl group optionally mono- or di-substituted by $C_{1-6}$ alkyl group(s) (e.g., methyl),
    (h) a tri-$C_{1-6}$ alkylsilyl group (e.g., trimethylsilyl), and
    (i) a non-aromatic heterocyclic group (e.g., oxetanyl),
(2) a $C_{3-8}$ cycloalkyl group (e.g., cyclopropyl), or
(3) a $C_{2-6}$ alkynyl group (e.g., 2-propynyl).
In another embodiment, $R^2$ is still more preferably
(1) a $C_{1-6}$ alkyl group (e.g., methyl, ethyl, propyl) optionally substituted by 1 to 3 substituents selected from
    (a) a $C_{3-8}$ cycloalkyl group (e.g., cyclopropyl),
    (b) a $C_{1-6}$ alkoxy group (e.g., methoxy),
    (c) a $C_{1-6}$ alkylsulfanyl group (e.g., methylsulfanyl), and
    (d) a tri-$C_{1-6}$ alkylsilyl group (e.g., trimethylsilyl),
(2) a $C_{2-6}$ alkynyl group (e.g., 2-propynyl), or
(3) a $C_{3-8}$ cycloalkyl group (e.g., cyclopropyl).

$D^1$ is an optionally further substituted 6-membered aromatic ring.

$D^1$ is preferably benzene or pyridine, each optionally substituted, more preferably benzene or pyridine.

In another embodiment, $D^1$ is preferably benzene, pyridine or pyrazine, each optionally substituted, more preferably benzene, pyridine or pyrazine.

In another embodiment, $D^1$ is more preferably benzene, pyridine or pyrazine, each optionally substituted by halogen atom(s) (e.g., a fluorine atom).

In another embodiment, $D^1$ is still more preferably benzene or pyridine, each optionally substituted by halogen atom(s) (e.g., a fluorine atom).

Specific examples of the partial structure (1) include

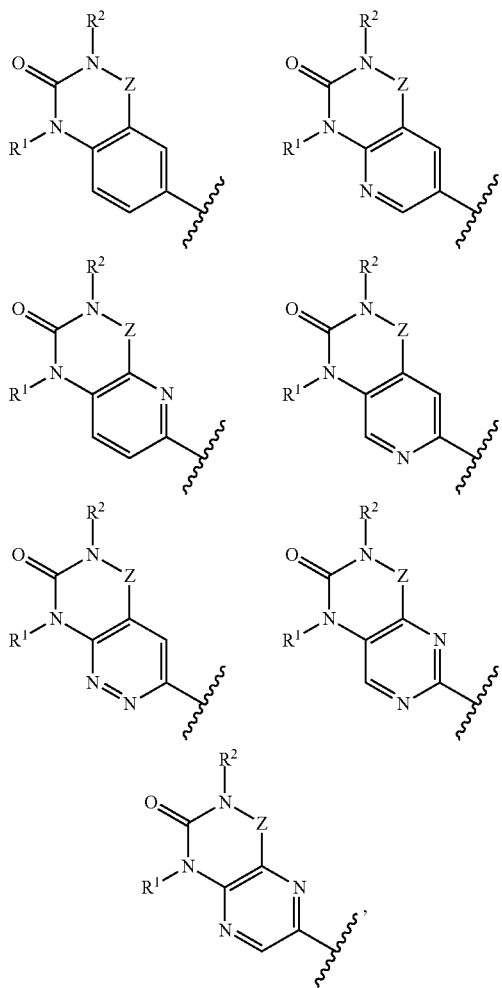

each optionally further substituted.

$R^3$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group.

$R^3$ is preferably a $C_{2-12}$ alkyl group (e.g., ethyl) or a substituted $C_{1-12}$ alkyl group, more preferably a $C_{2-12}$ alkyl group (e.g., ethyl), particularly preferably a $C_{2-6}$ alkyl group (e.g., ethyl).

Y is an optionally substituted methylene group.

Y is preferably a methylene group optionally substituted by oxo (e.g., —C(=O)—).

$R^4$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group or an acyl group.

$R^4$ is preferably a $C_{2-12}$ alkyl group, a substituted $C_{1-12}$ alkyl group or an optionally substituted $C_{6-14}$ aryl group, more preferably a $C_{2-6}$ alkyl group, a substituted $C_{1-6}$ alkyl group or an optionally substituted $C_{6-10}$ aryl group.

$R^4$ is particularly preferably
(1) a $C_{2-6}$ alkyl group (e.g., ethyl, isopropyl),
(2) a $C_{1-6}$ alkyl group (e.g., methyl, ethyl) substituted by 1 to 3 substituents selected from
    (a) hydroxy,
    (b) $C_{1-6}$ alkoxy (e.g., methoxy),
    (c) $C_{1-6}$ alkoxy-carbonyl (e.g., ethoxycarbonyl), and
    (d) $C_{6-10}$ aryl (e.g., phenyl), or
(3) a $C_{6-10}$ aryl group (e.g., phenyl).

$R^5$ is a hydrogen atom or a substituent, or $R^4$ and $R^5$ are both methyl groups, or $R^4$ and $R^5$ in combination optionally form, together with the carbon atom which they are bonded to, an optionally substituted ring. The ring formed by $R^4$ and $R^5$ in combination, together with the carbon atom which they are bonded to, is an optionally substituted $C_{3-12}$ cycloalkane, an optionally substituted $C_{3-12}$ cycloalkene or an optionally substituted non-aromatic heterocycle.

$R^5$ is preferably a hydrogen atom, or $R^4$ and $R^5$ are both methyl groups, or $R^4$ and $R^5$ in combination form, together with the carbon atom which they are bonded to, an optionally substituted $C_{3-12}$ cycloalkane (e.g., cyclopropane, cyclobutane), more preferably a hydrogen atom, or $R^4$ and $R^5$ are both methyl groups, or $R^4$ and $R^5$ in combination form, together with the carbon atom which they are bonded to, an optionally substituted $C_{3-8}$ cycloalkane (e.g., cyclopropane, cyclobutane).

$R^5$ is particularly preferably a hydrogen atom, or $R^4$ and $R^5$ are both methyl groups, or $R^4$ and $R^5$ in combination form, together with the carbon atom which they are bonded to, a $C_{3-8}$ cycloalkane (e.g., cyclopropane, cyclobutane).

$D^2$ is an optionally further substituted 6-membered aromatic ring.

$D^2$ is preferably optionally substituted benzene, more preferably benzene.

Specific examples of the partial structure (2) include

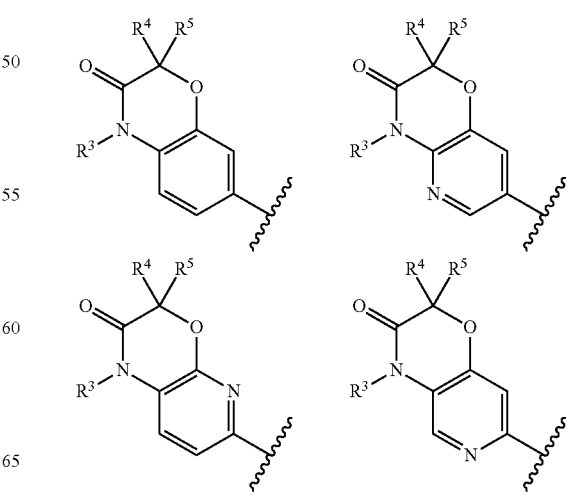

-continued

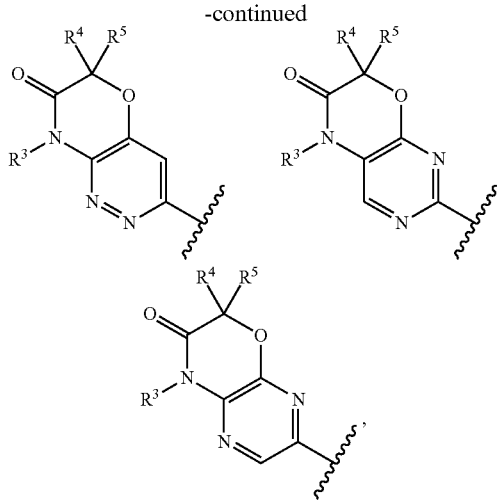

each optionally further substituted.

$R^6$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group or an optionally substituted $C_{7-16}$ aralkyl group.

$R^6$ is preferably $C_{2-12}$ alkyl (e.g., ethyl), substituted $C_{1-12}$ alkyl, more preferably $C_{2-12}$ alkyl (e.g., ethyl), particularly preferably $C_{2-6}$ alkyl (e.g., ethyl).

$R^7$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group or an optionally substituted $C_{7-16}$ aralkyl group.

$R^7$ is preferably optionally substituted $C_{1-12}$ alkyl (e.g., propyl), more preferably $C_{1-12}$ alkyl (e.g., propyl), particularly preferably $C_{1-6}$ alkyl (e.g., propyl).

$R^8$ and $R^9$ are each a hydrogen atom, a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group, or $R^8$ and $R^9$ in combination optionally form, together with the carbon atom which they are bonded to, an optionally substituted ring.

Preferably, the one of $R^8$ and $R^9$ is a substituent other than a hydrogen atom, or $R^8$ and $R^9$ in combination optionally form, together with the carbon atom which they are bonded to, an optionally substituted $C_{3-12}$ cycloalkane (e.g., cyclopropane, cyclobutane, cyclopentane). More preferably, $R^8$ and $R^9$ in combination form, together with the carbon atom which they are bonded to, a $C_{3-12}$ cycloalkane (e.g., cyclopentane).

$R^{10}$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group.

$R^{10}$ is preferably an optionally substituted $C_{1-12}$ alkyl group (e.g., methyl), more preferably a $C_{1-12}$ alkyl group (e.g., methyl) optionally substituted by 1 to 3 $C_{3-8}$ cycloalkyl groups (e.g., cyclopropyl), particularly preferably a $C_{1-6}$ alkyl group (e.g., methyl) optionally substituted by one $C_{3-8}$ cycloalkyl group (e.g., cyclopropyl).

$R^{11}$, $R^{12}$ and $R^{13}$ are each a substituent.

$R^{11}$, $R^{12}$ and $R^{13}$ are preferably each an optionally substituted $C_{1-12}$ alkyl group (e.g., methyl, ethyl).

Ar is preferably the following the partial structure (1)

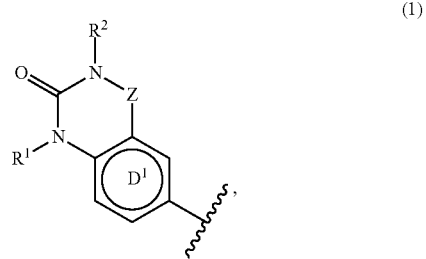

(1)

more preferably the partial structure (1) wherein Z is a carbonyl group, i.e., the following partial structure (1')

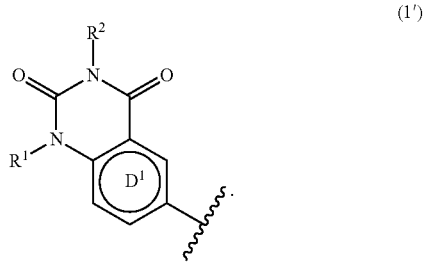

(1')

Q is a bivalent group selected from the group consisting of the following (Ia)-(Ie), and the two bond in Q may be bonded to any of Ar and B.

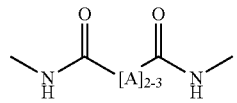

(Ia)

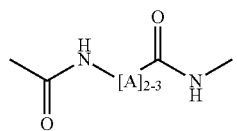

(Ib)

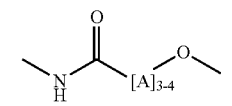

(Ic)

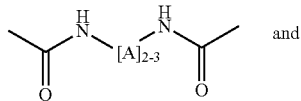 and (Id)

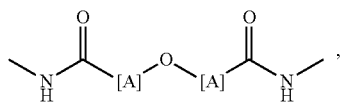
(Ie)

wherein [A] is as defined above.

In another embodiment, Q is a bivalent group selected from the group consisting of the following (Ia)-(If), and the two bond in Q may be bonded to any of Ar and B.

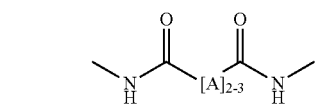
(Ia)

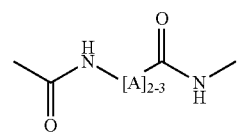
(Ib)

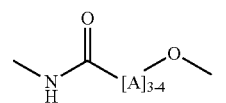
(Ic)

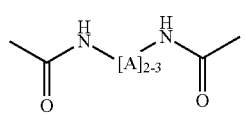
(Id)

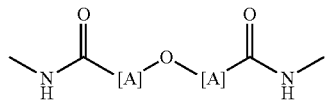
(Ie)
and

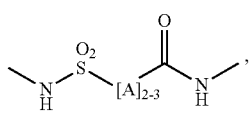
(If)

wherein [A] is as defined above.

Q is preferably a bivalent group selected from the group consisting of the above-mentioned (Ia)-(Ic), more preferably a bivalent group represented by the above-mentioned (Ia) or (Ib), particularly preferably a bivalent group represented by the above-mentioned (Ia).

In another embodiment, Q is preferably a bivalent group selected from the group consisting of the above-mentioned (Ia)-(Ie).

[A] are each preferably a methylene group optionally substituted by substituent(s) selected from hydroxy and a methyl group.

(a) when Q is (Ia), A are preferably the same or different and each is a methylene group optionally substituted by substituent(s) selected from hydroxy and a $C_{1-6}$ alkyl group (e.g., methyl), more preferably the same or different and each is a methylene group optionally substituted by substituent(s) selected from hydroxy and a $C_{1-3}$ alkyl group (e.g., methyl), particularly preferably the same or different and each is a methylene group optionally substituted by substituent(s) selected from hydroxy and a methyl group.

(b) when Q is (Ib), A are preferably the same or different and each is a methylene group optionally substituted by substituent(s) selected from hydroxy, a $C_{1-6}$ alkyl group (e.g., methyl, isopropyl) and a $C_{6-14}$ aryl group (e.g., phenyl), more preferably the same or different and each is a methylene group optionally substituted by substituent(s) selected from hydroxy and a $C_{1-6}$ alkyl group (e.g., methyl, isopropyl), still more preferably the same or different and each is a methylene group optionally substituted by substituent(s) selected from hydroxy and a $C_{1-3}$ alkyl group (e.g., methyl, isopropyl), particularly preferably the same or different and each is a methylene group optionally substituted by substituent(s) selected from a $C_{1-3}$ alkyl group (e.g., methyl, isopropyl).

(c) when Q is (Ic), A are preferably the same or different and each is a methylene group optionally substituted by substituent(s) selected from hydroxy and a $C_{1-6}$ alkyl group (e.g., methyl), more preferably the same or different and each is a methylene group optionally substituted by substituent(s) selected from hydroxy and a $C_{1-3}$ alkyl group (e.g., methyl), particularly preferably the same or different and each is a methylene group optionally substituted by substituent(s) selected from a $C_{1-3}$ alkyl group (e.g., methyl).

(d) when Q is (Id), A are preferably the same or different and each is a methylene group optionally substituted by substituent(s) selected from hydroxy and a $C_{1-6}$ alkyl group (e.g., methyl), more preferably the same or different and each is a methylene group optionally substituted by substituent(s) selected from hydroxy and a $C_{1-3}$ alkyl group (e.g., methyl), particularly preferably the same or different and each is a methylene group optionally substituted by substituent(s) selected from a $C_{1-3}$ alkyl group (e.g., methyl).

(e) when Q is (Ie), A are preferably the same or different and each is a methylene group optionally substituted by substituent(s) selected from hydroxy and a $C_{1-6}$ alkyl group, more preferably the same or different and each is a methylene group optionally substituted by substituent(s) selected from hydroxy and a $C_{1-3}$ alkyl group, particularly preferably a methylene group.

(f) when Q is (If), A are preferably the same or different and each is a methylene group optionally substituted by substituent(s) selected from hydroxy and a $C_{1-6}$ alkyl group, more preferably the same or different and each is a methylene group optionally substituted by substituent(s) selected from hydroxy and a $C_{1-3}$ alkyl group, still more preferably a methylene group.

The bivalent group represented by the above-mentioned (Ia) is particularly preferably

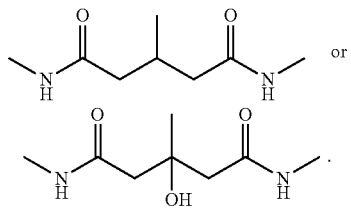

B is an optionally substituted ring.

The "ring" of the "optionally substituted ring" represented by B is optionally fused, for example, with a $C_{6-14}$ aromatic hydrocarbon, a $C_{3-12}$ cycloalkane, a $C_{3-12}$ cycloalkene, heterocycle and the like.

The "ring" of the "optionally substituted ring" represented by B is preferably a $C_{6-14}$ aromatic hydrocarbon, a 5- to 10-membered aromatic heterocycle, a fused ring formed by a $C_{6-14}$ aromatic hydrocarbon and a $C_{3-12}$ cycloalkane, or a fused ring formed by a $C_{6-14}$ aromatic hydrocarbon and a heterocycle, more preferably a $C_{6-10}$ aromatic hydrocarbon, a fused ring formed by a benzene ring and a $C_{3-8}$ cycloalkane, a 5- or 6-membered aromatic heterocycle, or a fused ring formed by a benzene ring and a heterocycle, still more preferably benzene, indane, pyridine, pyrrole, thiadiazole, thiazole, thiophene, benzothiazole, 2,3-dihydrobenzothiazole or 2,3-dihydrobenzoxazole, particularly preferably benzene.

B is preferably a $C_{6-14}$ aromatic hydrocarbon, a 5- to 10-membered aromatic heterocycle, a fused ring formed by a $C_{6-14}$ aromatic hydrocarbon and a $C_{3-12}$ cycloalkane, or a fused ring formed by a $C_{6-14}$ aromatic hydrocarbon and a heterocycle, each optionally substituted.

B is more preferably a $C_{6-14}$ aromatic hydrocarbon, a 5- to 10-membered aromatic heterocycle, a fused ring formed by a $C_{6-14}$ aromatic hydrocarbon and a $C_{3-8}$ cycloalkane, or a fused ring formed by a $C_{6-14}$ aromatic hydrocarbon and a heterocycle (preferably a $C_{6-10}$ aromatic hydrocarbon, a fused ring formed by a benzene ring and a $C_{3-8}$ cycloalkane, a 5- or 6-membered aromatic heterocycle, or a fused ring formed by a benzene ring and a heterocycle, more preferably benzene, indane, pyridine, pyrrole, thiadiazole, thiazole, thiophene, benzothiazole, 2,3-dihydrobenzothiazole or 2,3-dihydrobenzoxazole, particularly preferably benzene), each optionally substituted by 1 to 3 substituents selected from
  (1) a halogen atom (e.g., a fluorine atom, a chlorine atom, a bromine atom),
  (2) cyano,
  (3) hydroxy,
  (4) $C_{1-6}$ alkyl (e.g., methyl) optionally substituted by 1 to 3 substituents selected from
    (i) a halogen atom (e.g., a fluorine atom), and
    (ii) cyano,
  (4) $C_{1-6}$ alkoxy (e.g., methoxy) optionally substituted by 1 to 3 cyano groups,
  (5) $C_{2-6}$ alkynyl (e.g., ethynyl),
  (6) $C_{1-6}$ alkylsulfanyl (e.g., methylsulfanyl),
  (7) optionally halogenated sulfanyl (preferably sulfanyl optionally substituted by 1 to 5 halogen atoms (e.g., a fluorine atom)) (e.g., pentafluorosulfanyl),
  (8) $C_{1-6}$ alkyl-carbonyl (e.g., acetyl),
  (9) a non-aromatic heterocyclic group (e.g., morpholino), and
  (10) oxo.

In another embodiment, B is preferably a $C_{6-10}$ aryl group substituted by cyano group(s) wherein the aryl group is optionally further substituted by 1 to 3 substituents (e.g., halogen atom, $C_{1-6}$ alkoxy), more preferably the aryl group is optionally further substituted by one halogen atom (e.g., a chlorine atom) (e.g., 3-chloro-4-cyanophenyl).

Preferable examples of the ring, group, substituent and the like explained in the present specification are more preferably used in combination.

Preferable examples of compound (I) include the following compounds.
[Compound A]
The compound wherein
Ar is the following partial structure (1), partial structure (2) or partial structure (3);

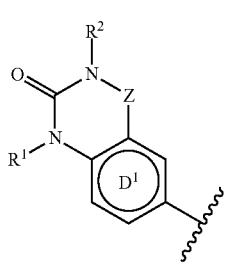

(1)

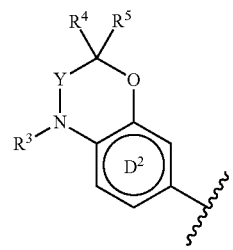

(2)

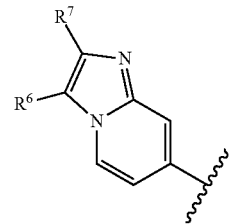

(3)

$R^1$ is
(1) a $C_{2-12}$ alkyl group,
(2) a substituted $C_{1-12}$ alkyl group, or
(3) an optionally substituted $C_{3-12}$ cycloalkyl group;
$R^2$ is
(1) an optionally substituted $C_{1-12}$ alkyl group, or
(2) an optionally substituted $C_{2-12}$ alkynyl group, or
(3) an optionally substituted $C_{3-12}$ cycloalkyl group;
Z is a carbonyl group or a methylene group;
$R^3$ is a $C_{2-12}$ alkyl group (e.g., ethyl) or a substituted $C_{1-12}$ alkyl group;
Y is a methylene group optionally substituted by oxo (e.g., —C(=O)—);
$R^4$ is a $C_{2-12}$ alkyl group, a substituted $C_{1-12}$ alkyl group or an optionally substituted $C_{6-14}$ aryl group;
$R^5$ is a hydrogen atom, or
$R^4$ and $R^5$ are both methyl groups, or
$R^4$ and $R^5$ in combination form, together with the carbon atom which they are bonded to, an optionally substituted $C_{3-12}$ cycloalkane (e.g., cyclopropane, cyclobutane);
$R^6$ is $C_{2-12}$ alkyl (e.g., ethyl) or substituted $C_{1-12}$ alkyl;
$R^7$ is optionally substituted $C_{1-12}$ alkyl (e.g., propyl);
$D^1$ is benzene or pyridine, each optionally substituted;
$D^2$ is optionally substituted benzene;
Q is
(a) when Q is (Ia), A are the same or different and each is a methylene group optionally substituted by substituent(s) selected from hydroxy and a $C_{1-6}$ alkyl group (e.g., methyl),
(b) when Q is (Ib), A are the same or different and each is a methylene group optionally substituted by substituent(s) selected from hydroxy, a $C_{1-6}$ alkyl group (e.g., methyl, isopropyl) and a $C_{6-14}$ aryl group (e.g., phenyl),
(c) when Q is (Ic), A are the same or different and each is a methylene group optionally substituted by substituent(s) selected from hydroxy and a $C_{1-6}$ alkyl group (e.g., methyl),
(d) when Q is (Id), A are the same or different and each is a methylene group optionally substituted by substituent(s) selected from hydroxy and a $C_{1-6}$ alkyl group (e.g., methyl), and
(e) when Q is (Ie), A are the same or different and each is a methylene group optionally substituted by substituent(s) selected from hydroxy and a $C_{1-6}$ alkyl group, and the two bond in Q may be bonded to any of Ar and B; and
B is a $C_{6-14}$ aromatic hydrocarbon, a 5- to 10-membered aromatic heterocycle, a fused ring formed by a $C_{6-14}$ aromatic hydrocarbon and a $C_{3-12}$ cycloalkane, or a fused ring formed by a $C_{6-14}$ aromatic hydrocarbon and a heterocycle, each optionally substituted.

[Compound AA]

The compound wherein

Ar is the following partial structure (1), partial structure (2), partial structure (3), partial structure (4) or partial structure (5);

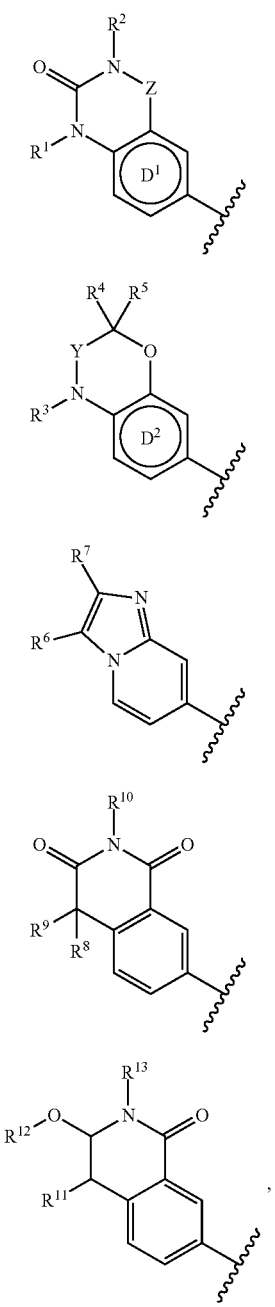

$R^1$ is
(1) a $C_{2-12}$ alkyl group,
(2) a substituted $C_{1-12}$ alkyl group,
(3) an optionally substituted $C_{3-12}$ cycloalkyl group, or
(4) an optionally substituted $C_{2-12}$ alkynyl group;

$R^2$ is
(1) an optionally substituted $C_{1-12}$ alkyl group,
(2) an optionally substituted $C_{2-12}$ alkynyl group, or
(3) an optionally substituted $C_{3-12}$ cycloalkyl group;

Z is a carbonyl group or a methylene group;

$R^3$ is a $C_{2-12}$ alkyl group (e.g., ethyl) or a substituted $C_{1-12}$ alkyl group;

Y is a methylene group optionally substituted by oxo (e.g., —C(=O)—);

$R^4$ is a $C_{2-12}$ alkyl group, a substituted $C_{1-12}$ alkyl group or an optionally substituted $C_{6-14}$ aryl group;

$R^5$ is a hydrogen atom, or $R^4$ and $R^5$ are both methyl groups, or $R^4$ and $R^5$ in combination form, together with the carbon atom which they are bonded to, an optionally substituted $C_{3-12}$ cycloalkane (e.g., cyclopropane, cyclobutane);

$R^6$ is $C_{2-12}$ alkyl (e.g., ethyl) or substituted $C_{1-12}$ alkyl;

$R^7$ is optionally substituted $C_{1-12}$ alkyl (e.g., propyl);

$R^8$ and $R^9$ in combination form, together with the carbon atom which they are bonded to, an optionally substituted $C_{3-12}$ cycloalkane (e.g., cyclopentane);

$R^{10}$ is an optionally substituted $C_{1-12}$ alkyl group;

$R^{11}$, $R^{12}$ and $R^{13}$ are each an optionally substituted $C_{1-12}$ alkyl group;

$D^1$ is benzene, pyridine or pyrazine, each optionally substituted;

$D^2$ is optionally substituted benzene;

Q is (a) when Q is (Ia), A are the same or different and each is a methylene group optionally substituted by substituent(s) selected from hydroxy and a $C_{1-6}$ alkyl group (e.g., methyl),
(b) when Q is (Ib), A are the same or different and each is a methylene group optionally substituted by substituent(s) selected from hydroxy, a $C_{1-6}$ alkyl group (e.g., methyl, isopropyl) and a $C_{6-14}$ aryl group (e.g., phenyl),
(c) when Q is (Ic), A are the same or different and each is a methylene group optionally substituted by substituent(s) selected from hydroxy and a $C_{1-6}$ alkyl group (e.g., methyl),
(d) when Q is (Id), A are the same or different and each is a methylene group optionally substituted by substituent(s) selected from hydroxy and a $C_{1-6}$ alkyl group (e.g., methyl),
(e) when Q is (Ie), A are the same or different and each is a methylene group optionally substituted by substituent(s) selected from hydroxy and a $C_{1-6}$ alkyl group, and
(f) when Q is (If), A are the same or different and each is a methylene group optionally substituted by substituent(s) selected from hydroxy and a $C_{1-6}$ alkyl group, and the two bond in Q may be bonded to any of Ar and B; and B is a $C_{6-14}$ aromatic hydrocarbon, a 5- to 10-membered aromatic heterocycle, a fused ring formed by a $C_{6-14}$ aromatic hydrocarbon and a $C_{3-12}$ cycloalkane, or a fused ring formed by a $C_{6-14}$ aromatic hydrocarbon and a heterocycle, each optionally substituted.

[Compound A-1]

The compound wherein

Ar is the partial structure (1);

$R^1$ is
(1) a $C_{2-12}$ alkyl group,
(2) a substituted $C_{1-12}$ alkyl group, or
(3) an optionally substituted $C_{3-12}$ cycloalkyl group;

$R^2$ is
(1) an optionally substituted $C_{1-12}$ alkyl group,
(2) an optionally substituted $C_{2-12}$ alkynyl group, or
(3) an optionally substituted $C_{3-12}$ cycloalkyl group;

Z is a carbonyl group or a methylene group;

$D^1$ is benzene or pyridine, each optionally substituted;

Q is (a) when Q is (Ia), A are the same or different and each is a methylene group optionally substituted by substituent(s) selected from hydroxy and a $C_{1-6}$ alkyl group (e.g., methyl), (b) when Q is (Ib), A are the same or different and each is a methylene group optionally substituted by substituent(s) selected from hydroxy, a $C_{1-6}$ alkyl group (e.g., methyl, isopropyl) and a $C_{6-14}$ aryl group (e.g., phenyl), (c) when Q is (Ic), A are the same or different and each is a methylene group optionally substituted by substituent(s) selected from hydroxy and a $C_{1-6}$ alkyl group (e.g., methyl), (d) when Q is (Id), A are the same or different and each is a methylene group optionally substituted by substituent(s) selected from hydroxy and a $C_{1-6}$ alkyl group (e.g., methyl), and (e) when Q is (Ie), A are the same or different and each is a methylene group optionally substituted by substituent(s) selected from hydroxy and a $C_{1-6}$ alkyl group, and the two bond in Q may be bonded to any of Ar and B; and B is a $C_{6-14}$ aromatic hydrocarbon, a 5- to 10-membered aromatic heterocycle, a fused ring formed by a $C_{6-14}$ aromatic hydrocarbon and a $C_{3-12}$ cycloalkane, or a fused ring formed by a $C_{6-14}$ aromatic hydrocarbon and a heterocycle, each optionally substituted.

[Compound AA-1]

The compound wherein

Ar is the partial structure (1);

$R^1$ is (1) a $C_{2-12}$ alkyl group, (2) a substituted $C_{1-12}$ alkyl group, (3) an optionally substituted $C_{3-12}$ cycloalkyl group, or (4) an optionally substituted $C_{2-12}$ alkynyl group;

$R^2$ is (1) an optionally substituted $C_{1-12}$ alkyl group, (2) an optionally substituted $C_{2-12}$ alkynyl group, or (3) an optionally substituted $C_{3-12}$ cycloalkyl group;

Z is a carbonyl group or a methylene group;

$D^1$ is benzene, pyridine or pyrazine, each optionally substituted;

Q is (a) when Q is (Ia), A are the same or different and each is a methylene group optionally substituted by substituent(s) selected from hydroxy and a $C_{1-6}$ alkyl group (e.g., methyl), (b) when Q is (Ib), A are the same or different and each is a methylene group optionally substituted by substituent(s) selected from hydroxy, a $C_{1-6}$ alkyl group (e.g., methyl, isopropyl) and a $C_{6-14}$ aryl group (e.g., phenyl), (c) when Q is (Ic), A are the same or different and each is a methylene group optionally substituted by substituent(s) selected from hydroxy and a $C_{1-6}$ alkyl group (e.g., methyl), (d) when Q is (Id), A are the same or different and each is a methylene group optionally substituted by substituent(s) selected from hydroxy and a $C_{1-6}$ alkyl group (e.g., methyl), (e) when Q is (Ie), A are the same or different and each is a methylene group optionally substituted by substituent(s) selected from hydroxy and a $C_{1-6}$ alkyl group, and (f) when Q is (If), A are the same or different and each is a methylene group optionally substituted by substituent(s) selected from hydroxy and a $C_{1-6}$ alkyl group, and the two bond in Q may be bonded to any of Ar and B; and B is a $C_{6-14}$ aromatic hydrocarbon, a 5- to 10-membered aromatic heterocycle, a fused ring formed by a $C_{6-14}$ aromatic hydrocarbon and a $C_{3-12}$ cycloalkane, or a fused ring formed by a $C_{6-14}$ aromatic hydrocarbon and a heterocycle, each optionally substituted.

[Compound A-2]

The compound wherein

Ar is the partial structure (2);

$R^3$ is a $C_{2-12}$ alkyl group (e.g., ethyl) or a substituted $C_{1-12}$ alkyl group;

Y is a methylene group optionally substituted by oxo (e.g., —C(=O)—);

$R^4$ is a $C_{2-12}$ alkyl group, a substituted $C_{1-12}$ alkyl group or an optionally substituted $C_{6-14}$ aryl group;

$R^5$ is a hydrogen atom, or $R^4$ and $R^5$ are both methyl groups, or $R^4$ and $R^5$ in combination form, together with the carbon atom which they are bonded to, an optionally substituted $C_{3-12}$ cycloalkane (e.g., cyclopropane, cyclobutane);

$D^2$ is optionally substituted benzene;

Q is (Ia) wherein A are the same or different and each is a methylene group optionally substituted by substituent(s) selected from hydroxy and a $C_{1-6}$ alkyl group (e.g., methyl), and the two bond in Q may be bonded to any of Ar and B; and B is an optionally substituted $C_{6-14}$ aromatic hydrocarbon (e.g., benzene).

[Compound A-3]

The compound wherein

Ar is the partial structure (3);

$R^6$ is $C_{2-12}$ alkyl (e.g., ethyl) or substituted $C_{1-12}$ alkyl;

$R^7$ is optionally substituted $C_{1-12}$ alkyl (e.g., propyl);

Q is (a) when Q is (Ia), A are the same or different and each is a methylene group optionally substituted by substituent(s) selected from hydroxy and a $C_{1-6}$ alkyl group (e.g., methyl), and (b) when Q is (Ib), A are the same or different and each is a methylene group optionally substituted by substituent(s) selected from hydroxy and a $C_{1-6}$ alkyl group (e.g., methyl, isopropyl), and the two bond in Q may be bonded to any of Ar and B; and B is an optionally substituted $C_{6-14}$ aromatic hydrocarbon (e.g., benzene).

[Compound AA-4]

The compound wherein

Ar is the partial structure (4);

$R^8$ and $R^9$ in combination form, together with the carbon atom which they are bonded to, an optionally substituted $C_{3-12}$ cycloalkane (e.g., cyclopentyl);

$R^{10}$ is an optionally substituted $C_{1-12}$ alkyl group (e.g., methyl);

Q is (Ia) wherein A are the same or different and each is a methylene group optionally substituted by substituent(s) selected from hydroxy and a $C_{1-6}$ alkyl group (e.g., methyl), and the two bond in Q may be bonded to any of Ar and B; and B is an optionally substituted $C_{6-14}$ aromatic hydrocarbon (e.g., benzene).

[Compound AA-5]

The compound wherein

Ar is the partial structure (5);

$R^{11}$, $R^{12}$ and $R^{13}$ are each an optionally substituted $C_{1-12}$ alkyl group (e.g., methyl, ethyl);

Q is (Ia) wherein A are the same or different and each is a methylene group optionally substituted by substituent(s) selected from hydroxy and a $C_{1-6}$ alkyl group (e.g., methyl), and the two bond in Q may be bonded to any of Ar and B; and B is an optionally substituted $C_{6-14}$ aromatic hydrocarbon (e.g., benzene).

[Compound B]
The compound wherein
Ar is the following partial structure (1), partial structure (2) or partial structure (3);

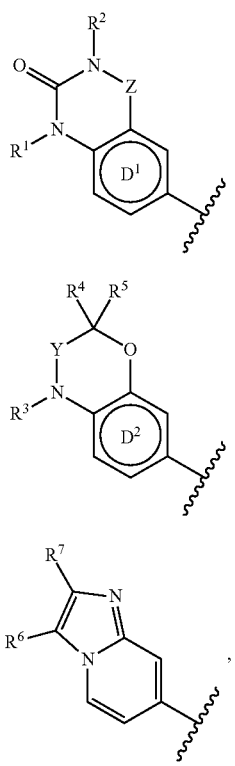

R¹ is
(1) a methyl group substituted by 1 to 3 substituents selected from
  (a) a $C_{3-8}$ cycloalkyl group (e.g., cyclopropyl),
  (b) a $C_{1-6}$ alkoxy group (e.g., methoxy), and
  (c) a $C_{1-6}$ alkylsulfanyl group (e.g., methylsulfanyl),
(2) a $C_{2-6}$ alkyl group (e.g., ethyl, propyl) optionally substituted by 1 to 3 substituents selected from
  (a) a hydroxy group, and
  (b) a $C_{1-6}$ alkoxy group (e.g., methoxy), or
(3) a $C_{3-8}$ cycloalkyl group (e.g., cyclopropyl);
R² is
(1) a $C_{1-6}$ alkyl group (e.g., methyl, ethyl, propyl) optionally substituted by 1 to 3 substituents selected from
  (a) a cyano group,
  (b) a hydroxy group,
  (c) a $C_{3-8}$ cycloalkyl group (e.g., cyclopropyl),
  (d) a $C_{1-6}$ alkoxy group (e.g., methoxy),
  (e) a $C_{1-6}$ alkylsulfanyl group (e.g., methylsulfanyl),
  (f) a $C_{1-6}$ alkylsulfonyl group (e.g., methylsulfonyl),
  (g) a carbamoyl group optionally mono- or di-substituted by $C_{1-6}$ alkyl group(s) (e.g., methyl), and
  (h) a tri-$C_{1-6}$ alkylsilyl group (e.g., trimethylsilyl),
(2) a $C_{3-8}$ cycloalkyl group (e.g., cyclopropyl), or
(3) a $C_{2-6}$ alkynyl group (e.g., 2-propynyl);
Z is a carbonyl group or a methylene group;
R³ is a $C_{2-6}$ alkyl group (e.g., ethyl);
Y is a methylene group optionally substituted by oxo (e.g., —C(=O)—);
R⁴ is
(1) a $C_{2-6}$ alkyl group (e.g., ethyl, isopropyl),
(2) a $C_{1-6}$ alkyl group (e.g., methyl, ethyl) substituted by 1 to 3 substituents selected from
  (a) hydroxy,
  (b) $C_{1-6}$ alkoxy (e.g., methoxy),
  (c) $C_{1-6}$ alkoxy-carbonyl (e.g., ethoxycarbonyl), and
  (d) $C_{6-10}$ aryl (e.g., phenyl), or
(3) a $C_{6-10}$ aryl group (e.g., phenyl);
R⁵ is a hydrogen atom, or
R⁴ and R⁵ are both methyl groups, or
R⁴ and R⁵ in combination form, together with the carbon atom which they are bonded to, a $C_{3-8}$ cycloalkane (e.g., cyclopropane, cyclobutane);
R⁶ is $C_{2-6}$ alkyl (e.g., ethyl);
R⁷ is $C_{1-6}$ alkyl (e.g., propyl);
D¹ is benzene or pyridine;
D² is benzene;
Q is
(a) when Q is (Ia), A are the same or different and each is a methylene group optionally substituted by substituent(s) selected from hydroxy and a methyl group,
(b) when Q is (Ib), A are the same or different and each is a methylene group optionally substituted by substituent(s) selected from a $C_{1-3}$ alkyl group (e.g., methyl, isopropyl) and a $C_{6-14}$ aryl group (e.g., phenyl),
(c) when Q is (Ic), A are the same or different and each is a methylene group optionally substituted by substituent(s) selected from a $C_{1-3}$ alkyl group (e.g., methyl),
(d) when Q is (Id), A are the same or different and each is a methylene group optionally substituted by substituent(s) selected from a $C_{1-3}$ alkyl group (e.g., methyl), and
(e) when Q is (Ie), A are each a methylene group, and the two bond in Q may be bonded to any of Ar and B; and
B is a $C_{6-14}$ aromatic hydrocarbon, a 5- to 10-membered aromatic heterocycle, a fused ring formed by a $C_{6-14}$ aromatic hydrocarbon and a $C_{3-8}$ cycloalkane, or a fused ring formed by a $C_{6-14}$ aromatic hydrocarbon and a heterocycle (preferably a $C_{6-10}$ aromatic hydrocarbon, a fused ring formed by a benzene ring and a $C_{3-8}$ cycloalkane, a 5- or 6-membered aromatic heterocycle, or a fused ring formed by a benzene ring and a heterocycle, more preferably benzene, indane, pyridine, pyrrole, thiadiazole, thiazole, thiophene, benzothiazole, 2,3-dihydrobenzothiazole, 2,3-dihydrobenzoxazole, particularly preferably benzene), each optionally substituted by 1 to 3 substituents selected from
  (1) a halogen atom (e.g., a fluorine atom, a chlorine atom, a bromine atom),
  (2) cyano,
  (3) hydroxy,
  (4) $C_{1-6}$ alkyl (e.g., methyl) optionally substituted by 1 to 3 substituents selected from
    (i) a halogen atom (e.g., a fluorine atom), and
    (ii) cyano,
  (5) $C_{1-6}$ alkoxy (e.g., methoxy) optionally substituted by 1 to 3 cyano groups,
  (6) $C_{2-6}$ alkynyl (e.g., ethynyl),
  (7) $C_{1-6}$ alkylsulfanyl (e.g., methylsulfanyl),
  (8) optionally halogenated sulfanyl (preferably sulfanyl optionally substituted by 1 to 5 halogen atoms (e.g., a fluorine atom)) (e.g., pentafluorosulfanyl),
  (9) $C_{1-6}$ alkyl-carbonyl (e.g., acetyl),
  (10) a non-aromatic heterocyclic group (e.g., morpholino), and
  (11) oxo.

[Compound BB]

The compound wherein

Ar is the following partial structure (1), partial structure (2), partial structure (3), partial structure (4) or partial structure (5);

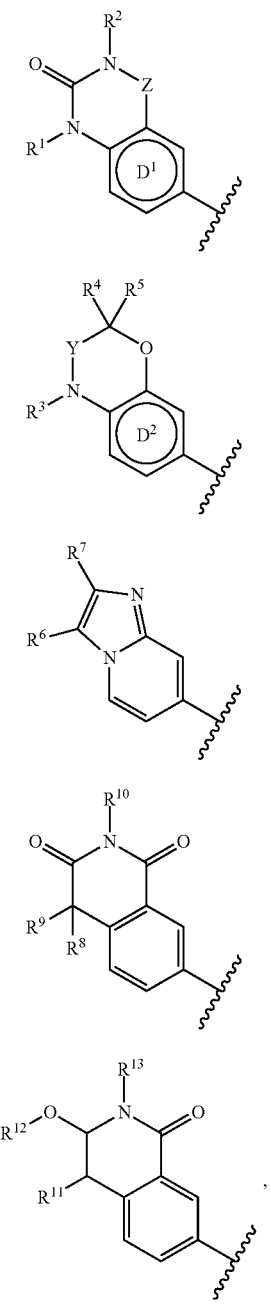

$R^1$ is
(1) a $C_{2-6}$ alkyl group (e.g., ethyl, isopropyl),
(2) a $C_{1-6}$ alkyl group (e.g., methyl, ethyl, propyl) substituted by 1 to 3 substituents selected from
  (a) a $C_{3-8}$ cycloalkyl group (e.g., cyclopropyl),
  (b) a $C_{1-6}$ alkoxy group (e.g., methoxy),
  (c) a $C_{1-6}$ alkylsulfanyl group (e.g., methylsulfanyl)
  (d) a hydroxy group,
  (e) a tri-$C_{1-6}$ alkylsilyl group (e.g., trimethylsilyl), and
  (f) a cyano group,
(3) a $C_{3-8}$ cycloalkyl group (e.g., cyclopropyl), or
(4) a $C_{2-6}$ alkynyl group (e.g., 2-propynyl);

$R^2$ is
(1) a $C_{1-6}$ alkyl group (e.g., methyl, ethyl, propyl) optionally substituted by 1 to 3 substituents selected from
  (a) a cyano group,
  (b) a hydroxy group,
  (c) a $C_{3-8}$ cycloalkyl group (e.g., cyclopropyl),
  (d) a $C_{1-6}$ alkoxy group (e.g., methoxy),
  (e) a $C_{1-6}$ alkylsulfanyl group (e.g., methylsulfanyl),
  (f) a $C_{1-6}$ alkylsulfonyl group (e.g., methylsulfonyl),
  (g) a carbamoyl group optionally mono- or di-substituted by $C_{1-6}$ alkyl group(s) (e.g., methyl),
  (h) a tri-$C_{1-6}$ alkylsilyl group (e.g., trimethylsilyl), and
  (i) a non-aromatic heterocyclic group (e.g., oxetanyl),
(2) a $C_{3-8}$ cycloalkyl group (e.g., cyclopropyl), or
(3) a $C_{2-6}$ alkynyl group (e.g., 2-propynyl);

Z is a carbonyl group or a methylene group;

$R^3$ is a $C_{2-6}$ alkyl group (e.g., ethyl);

Y is a methylene group optionally substituted by oxo (e.g., —C(=O)—);

$R^4$ is
(1) a $C_{2-6}$ alkyl group (e.g., ethyl, isopropyl),
(2) a $C_{1-6}$ alkyl group (e.g., methyl, ethyl) substituted by 1 to 3 substituents selected from
  (a) hydroxy,
  (b) $C_{1-6}$ alkoxy (e.g., methoxy),
  (c) $C_{1-6}$ alkoxy-carbonyl (e.g., ethoxycarbonyl), and
  (d) $C_{6-10}$ aryl (e.g., phenyl), or
(3) a $C_{6-10}$ aryl group (e.g., phenyl);

$R^5$ is a hydrogen atom, or $R^4$ and $R^5$ are both methyl groups, or $R^4$ and $R^5$ in combination form, together with the carbon atom which they are bonded to, a $C_{3-8}$ cycloalkane (e.g., cyclopropane, cyclobutane);

$R^6$ is $C_{2-6}$ alkyl (e.g., ethyl);

$R^7$ is $C_{1-6}$ alkyl (e.g., propyl);

$R^8$ and $R^9$ in combination form, together with the carbon atom which they are bonded to, a $C_{3-8}$ cycloalkane (e.g., cyclopentane);

$R^{10}$ is a $C_{1-12}$ alkyl group (e.g., methyl) optionally substituted by 1 to 3 $C_{3-8}$ cycloalkyl groups (e.g., cyclopropyl);

$R^{11}$ is a $C_{1-6}$ alkyl group (e.g., ethyl):

$R^{12}$ is a $C_{1-6}$ alkyl group (e.g., methyl);

$R^{13}$ is a $C_{1-6}$ alkyl group (e.g., methyl) optionally substituted by one $C_{3-8}$ cycloalkyl group (e.g., cyclopropyl);

$D^1$ is benzene, pyridine or pyrazine, each optionally substituted by halogen atom(s) (e.g., a fluorine atom);

$D^2$ is benzene;

Q is
(a) when Q is (Ia), A are the same or different and each is a methylene group optionally substituted by substituent(s) selected from hydroxy and a methyl group,
(b) when Q is (Ib), A are the same or different and each is a methylene group optionally substituted by substituent(s) selected from a $C_{1-3}$ alkyl group (e.g., methyl, isopropyl) and a $C_{6-14}$ aryl group (e.g., phenyl),
(c) when Q is (Ic), A are the same or different and each is a methylene group optionally substituted by substituent(s) selected from a $C_{1-3}$ alkyl group (e.g., methyl),
(d) when Q is (Id), A are the same or different and each is a methylene group optionally substituted by substituent(s) selected from a $C_{1-3}$ alkyl group (e.g., methyl),
(e) when Q is (Ie), A are each a methylene group, and
(f) when Q is (If), A are each a methylene group, and the two bond in Q may be bonded to any of Ar and B; and B is a $C_{6-14}$ aromatic hydrocarbon, a 5- to 10-membered aromatic heterocycle, a fused ring formed by a $C_{6-14}$ aromatic hydrocarbon and a $C_{3-8}$ cycloalkane, or a fused ring formed by a $C_{6-14}$ aromatic hydrocarbon and a heterocycle (preferably a $C_{6-10}$ aromatic hydrocarbon, a fused ring formed by a benzene ring and a $C_{3-8}$ cycloalkane, a 5- or 6-membered aromatic heterocycle, or a fused ring formed by a benzene ring and a heterocycle, more preferably benzene, indane, pyridine, pyrrole, thiadiazole, thiazole, thiophene, benzothiazole, 2,3-dihydrobenzothiazole, 2,3-dihydrobenzoxazole, particularly preferably benzene), each optionally substituted by 1 to 3 substituents selected from,
- (1) a halogen atom (e.g., a fluorine atom, a chlorine atom, a bromine atom),
- (2) cyano,
- (3) hydroxy,
- (4) $C_{1-6}$ alkyl (e.g., methyl) optionally substituted by 1 to 3 substituents selected from
  - (i) a halogen atom (e.g., a fluorine atom), and
  - (ii) cyano,
- (5) $C_{1-6}$ alkoxy (e.g., methoxy) optionally substituted by 1 to 3 cyano groups,
- (6) $C_{2-6}$ alkynyl (e.g., ethynyl),
- (7) $C_{1-6}$ alkylsulfanyl (e.g., methylsulfanyl),
- (8) optionally halogenated sulfanyl (preferably sulfanyl optionally substituted by 1 to 5 halogen atoms (e.g., a fluorine atom)) (e.g., pentafluorosulfanyl),
- (9) $C_{1-6}$ alkyl-carbonyl (e.g., acetyl),
- (10) a non-aromatic heterocyclic group (e.g., morpholino), and
- (11) oxo.

[Compound B-1]
The compound wherein
Ar is the partial structure (1);
$R^1$ is
(1) a methyl group substituted by 1 to 3 substituents selected from
- (a) a $C_{3-8}$ cycloalkyl group (e.g., cyclopropyl),
- (b) a $C_{1-6}$ alkoxy group (e.g., methoxy), and
- (c) a $C_{1-6}$ alkylsulfanyl group (e.g., methylsulfanyl), (2) a $C_{2-6}$ alkyl group (e.g., ethyl, propyl) optionally substituted by 1 to 3 substituents selected from
- (a) a hydroxy group, and
- (b) a $C_{1-6}$ alkoxy group (e.g., methoxy), or (3) a $C_{3-8}$ cycloalkyl group (e.g., cyclopropyl);
$R^2$ is
(1) a $C_{1-6}$ alkyl group (e.g., methyl, ethyl, propyl) optionally substituted by 1 to 3 substituents selected from
- (a) a cyano group,
- (b) a hydroxy group,
- (c) a $C_{3-8}$ cycloalkyl group (e.g., cyclopropyl),
- (d) a $C_{1-6}$ alkoxy group (e.g., methoxy),
- (e) a $C_{1-6}$ alkylsulfanyl group (e.g., methylsulfanyl),
- (f) a $C_{1-6}$ alkylsulfonyl group (e.g., methylsulfonyl),
- (g) a carbamoyl group optionally mono- or di-substituted by $C_{1-6}$ alkyl group(s) (e.g., methyl), and
- (h) a tri-$C_{1-6}$ alkylsilyl group (e.g., trimethylsilyl), (2) a $C_{2-6}$ alkynyl group (e.g., 2-propynyl), or
(3) a $C_{3-8}$ cycloalkyl group (e.g., cyclopropyl);
Z is a carbonyl group or a methylene group;
$D^1$ is benzene or pyridine;
Q is
(a) when Q is (Ia), A are the same or different and each is a methylene group optionally substituted by substituent(s) selected from hydroxy and a methyl group,
(b) when Q is (Ib), A are the same or different and each is a methylene group optionally substituted by substituent(s) selected from a $C_{1-3}$ alkyl group (e.g., methyl, isopropyl) and a $C_{6-14}$ aryl group (e.g., phenyl),
(c) when Q is (Ic), A are the same or different and each is a methylene group optionally substituted by substituent(s) selected from a $C_{1-3}$ alkyl group (e.g., methyl),
(d) when Q is (Id), A are the same or different and each is a methylene group optionally substituted by substituent(s) selected from a $C_{1-3}$ alkyl group (e.g., methyl), and
(e) when Q is (Ie), A are each a methylene group, and the two bond in Q may be bonded to any of Ar and B; and
B is a $C_{6-14}$ aromatic hydrocarbon, a 5- to 10-membered aromatic heterocycle, a fused ring formed by a $C_{6-14}$ aromatic hydrocarbon and a $C_{3-8}$ cycloalkane, or a fused ring formed by a $C_{6-14}$ aromatic hydrocarbon and a heterocycle (preferably a $C_{6-10}$ aromatic hydrocarbon, a fused ring formed by a benzene ring and a $C_{3-8}$ cycloalkane, a 5- or 6-membered aromatic heterocycle, or a fused ring formed by a benzene ring and a heterocycle, more preferably benzene, indane, pyridine, pyrrole, thiadiazole, thiazole, thiophene, benzothiazole, 2,3-dihydrobenzothiazole, 2,3-dihydrobenzoxazole, particularly preferably benzene), each optionally substituted by 1 to 3 substituents selected from
- (1) a halogen atom (e.g., a fluorine atom, a chlorine atom, a bromine atom),
- (2) cyano,
- (3) hydroxy,
- (4) $C_{1-6}$ alkyl (e.g., methyl) optionally substituted by 1 to 3 substituents selected from
  - (i) a halogen atom (e.g., a fluorine atom), and
  - (ii) cyano,
- (5) $C_{1-6}$ alkoxy (e.g., methoxy) optionally substituted by 1 to 3 cyano groups,
- (6) $C_{2-6}$ alkynyl (e.g., ethynyl),
- (7) $C_{1-6}$ alkylsulfanyl (e.g., methylsulfanyl),
- (8) optionally halogenated sulfanyl (preferably sulfanyl optionally substituted by 1 to 5 halogen atoms (e.g., a fluorine atom)) (e.g., pentafluorosulfanyl),
- (9) $C_{1-6}$ alkyl-carbonyl (e.g., acetyl),
- (10) a non-aromatic heterocyclic group (e.g., morpholino), and
- (11) oxo.

[Compound BB-1]
The compound wherein
Ar is the partial structure (1);
$R^1$ is
(1) a $C_{2-6}$ alkyl group (e.g., ethyl, isopropyl),
(2) a $C_{1-6}$ alkyl group (e.g., methyl, ethyl, propyl) substituted by 1 to 3 substituents selected from
- (a) a $C_{3-8}$ cycloalkyl group (e.g., cyclopropyl),
- (b) a $C_{1-6}$ alkoxy group (e.g., methoxy),
- (c) a $C_{1-6}$ alkylsulfanyl group (e.g., methylsulfanyl),
- (d) a hydroxy group,
- (e) a tri-$C_{1-6}$ alkylsilyl group (e.g., trimethylsilyl), and
- (f) a cyano group, (3) a $C_{3-8}$ cycloalkyl group (e.g., cyclopropyl), or
(4) a $C_{2-6}$ alkynyl group (e.g., 2-propynyl);
$R^2$ is
(1) a $C_{1-6}$ alkyl group (e.g., methyl, ethyl, propyl) optionally substituted by 1 to 3 substituents selected from
- (a) a cyano group,
- (b) a hydroxy group,
- (c) a $C_{3-8}$ cycloalkyl group (e.g., cyclopropyl),
- (d) a $C_{1-6}$ alkoxy group (e.g., methoxy),
- (e) a $C_{1-6}$ alkylsulfanyl group (e.g., methylsulfanyl),
- (f) a $C_{1-6}$ alkylsulfonyl group (e.g., methylsulfonyl),
- (g) a carbamoyl group optionally mono- or di-substituted by $C_{1-6}$ alkyl group(s) (e.g., methyl), (h) a tri-$C_{1-6}$ alkylsilyl group (e.g., trimethylsilyl), and
(i) a non-aromatic heterocyclic group (e.g., oxetanyl),
(2) a $C_{2-6}$ alkynyl group (e.g., 2-propynyl), or
(3) a $C_{3-8}$ cycloalkyl group (e.g., cyclopropyl);
Z is a carbonyl group or a methylene group;
$D^1$ is benzene, pyridine or pyrazine, each optionally substituted by halogen atom(s) (e.g., a fluorine atom);
Q is
(a) when Q is (Ia), A are the same or different and each is a methylene group optionally substituted by substituent(s) selected from hydroxy and a methyl group,
(b) when Q is (Ib), A are the same or different and each is a methylene group optionally substituted by substituent(s) selected from a $C_{1-3}$ alkyl group (e.g., methyl, isopropyl) and a $C_{6-14}$ aryl group (e.g., phenyl),
(c) when Q is (Ic), A are the same or different and each is a methylene group optionally substituted by substituent(s) selected from a $C_{1-3}$ alkyl group (e.g., methyl),
(d) when Q is (Id), A are the same or different and each is a methylene group optionally substituted by substituent(s) selected from a $C_{1-3}$ alkyl group (e.g., methyl),
(e) when Q is (Ie), A are each a methylene group, and
(f) when Q is (If), A are each a methylene group, and the two bond in Q may be bonded to any of Ar and B;
B is a $C_{6-14}$ aromatic hydrocarbon, a 5- to 10-membered aromatic heterocycle, a fused ring formed by a $C_{6-14}$ aromatic hydrocarbon and a $C_{3-8}$ cycloalkane, or a fused ring formed by a $C_{6-14}$ aromatic hydrocarbon and a heterocycle (preferably a $C_{6-10}$ aromatic hydrocarbon, a fused ring formed by a benzene ring and a $C_{3-8}$ cycloalkane, a 5- or 6-membered aromatic heterocycle, or a fused ring formed by a benzene ring and a heterocycle, more preferably benzene, indane, pyridine, pyrrole, thiadiazole, thiazole, thiophene, benzothiazole, 2,3-dihydrobenzothiazole, 2,3-dihydrobenzoxazole, particularly preferably benzene), each optionally substituted by 1 to 3 substituents selected from
   (1) a halogen atom (e.g., a fluorine atom, a chlorine atom, a bromine atom),
   (2) cyano,
   (3) hydroxy,
   (4) $C_{1-6}$ alkyl (e.g., methyl) optionally substituted by 1 to 3 substituents selected from
      (i) a halogen atom (e.g., a fluorine atom), and
      (ii) cyano,
   (5) $C_{1-6}$ alkoxy (e.g., methoxy) optionally substituted by 1 to 3 cyano groups,
   (6) $C_{2-6}$ alkynyl (e.g., ethynyl),
   (7) $C_{1-6}$ alkylsulfanyl (e.g., methylsulfanyl),
   (8) optionally halogenated sulfanyl (preferably sulfanyl optionally substituted by 1 to 5 halogen atoms (e.g., a fluorine atom)) (e.g., pentafluorosulfanyl),
   (9) $C_{1-6}$ alkyl-carbonyl (e.g., acetyl),
   (10) a non-aromatic heterocyclic group (e.g., morpholino), and
   (11) oxo.
Another preferable examples of compound (I) include the following compounds.
[Compound B-2]
The compound wherein
Ar is the partial structure (2);
$R^3$ is a $C_{2-6}$ alkyl group (e.g., ethyl);
Y is a methylene group optionally substituted by oxo (e.g., —C(=O)—);
$R^4$ is
(1) a $C_{2-6}$ alkyl group (e.g., ethyl, isopropyl),
(2) a $C_{1-6}$ alkyl group (e.g., methyl, ethyl) substituted by 1 to 3 substituents selected from
   (a) hydroxy,
   (b) $C_{1-6}$ alkoxy (e.g., methoxy),
   (c) $C_{1-6}$ alkoxy-carbonyl (e.g., ethoxycarbonyl), and
   (d) $C_{6-10}$ aryl (e.g., phenyl), or
(3) a $C_{6-10}$ aryl group (e.g., phenyl);
$R^5$ is a hydrogen atom, or
$R^4$ and $R^5$ are both methyl groups, or
$R^4$ and $R^5$ in combination form, together with the carbon atom which they are bonded to, a $C_{3-8}$ cycloalkane (e.g., cyclopropane, cyclobutane);
$D^2$ is benzene;
Q is (Ia) wherein A are each a methylene group optionally substituted by methyl, and the two bond in Q may be bonded to any of Ar and B; and
B is a $C_{6-10}$ aromatic hydrocarbon (more preferably benzene) optionally substituted by 1 to 3 substituents selected from
   (1) a halogen atom (e.g., a chlorine atom), and
   (2) cyano.
[Compound B-3]
The compound wherein
Ar is the partial structure (3);
$R^6$ is $C_{2-6}$ alkyl (e.g., ethyl);
$R^7$ is $C_{1-6}$ alkyl (e.g., propyl);
Q is
(a) when Q is (Ia), A are each a methylene group optionally substituted by methyl, and
(b) when Q is (Ib), A are each a methylene group optionally substituted by methyl, and
the two bond in Q may be bonded to any of Ar and B; and
B is a $C_{6-10}$ aromatic hydrocarbon (more preferably benzene) optionally substituted by 1 to 3 substituents selected from
   (1) a halogen atom (e.g., a chlorine atom), and
   (2) cyano.
[Compound BB-4]
The compound wherein
Ar is the partial structure (4);
$R^8$ and $R^9$ in combination form, together with the carbon atom which they are bonded to, a $C_{3-8}$ cycloalkane (e.g., cyclopentane);
$R^{10}$ is a $C_{1-12}$ alkyl group (e.g., methyl) optionally substituted by 1 to 3 $C_{3-8}$ cycloalkyl groups (e.g., cyclopropyl);
Q is (Ia) wherein A are each a methylene group optionally substituted by methyl, and the two bond in Q may be bonded to any of Ar and B; and
B is a $C_{6-10}$ aromatic hydrocarbon (more preferably benzene) optionally substituted by 1 to 3 substituents selected from
   (1) a halogen atom (e.g., a chlorine atom), and
   (2) cyano.
[Compound BB-5]
The compound wherein
Ar is the partial structure (5);
$R^{11}$ is a $C_{1-12}$ alkyl group (e.g., ethyl):
$R^{12}$ is a $C_{1-12}$ alkyl group (e.g., methyl);
$R^{13}$ is a $C_{1-12}$ alkyl group (e.g., methyl) optionally substituted by 1 to 3 $C_{3-8}$ cycloalkyl groups (e.g., cyclopropyl);
Q is (Ia) wherein A are each a methylene group optionally substituted by methyl, and the two bond in Q may be bonded to any of Ar and B; and
B is a $C_{6-10}$ aromatic hydrocarbon (more preferably benzene) optionally substituted by 1 to 3 substituents selected from
   (1) a halogen atom (e.g., a chlorine atom), and
   (2) cyano.
[Compound CC]
The compound wherein
Ar is the following partial structure (1), partial structure (2) or partial structure (4);

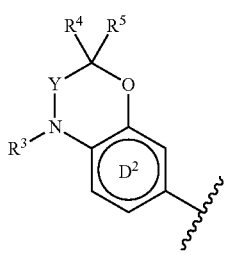

(1)

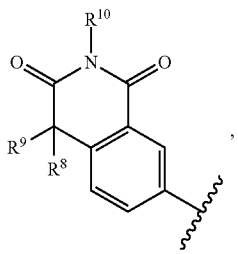

(2)

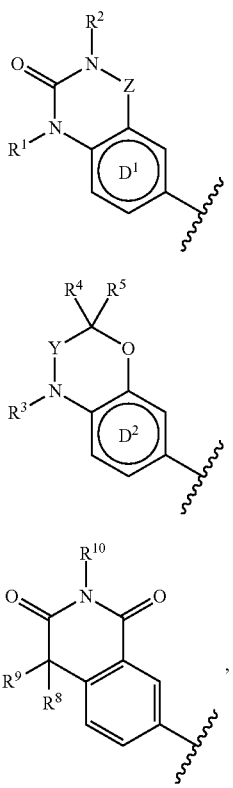

(4)

R¹ is
(1) a $C_{2-6}$ alkyl group (e.g., ethyl, isopropyl), or
(2) a $C_{1-6}$ alkyl group (e.g., methyl) substituted by 1 to 3 substituents selected from
  (a) a $C_{3-8}$ cycloalkyl group (e.g., cyclopropyl),
  (b) a $C_{1-6}$ alkylsulfanyl group (e.g., methylsulfanyl), and
  (c) a tri-$C_{1-6}$ alkylsilyl group (e.g., trimethylsilyl);
R² is
(1) a $C_{1-6}$ alkyl group (e.g., methyl, ethyl, propyl) optionally substituted by 1 to 3 substituents selected from
  (a) a $C_{3-8}$ cycloalkyl group (e.g., cyclopropyl),
  (b) a $C_{1-6}$ alkoxy group (e.g., methoxy),
  (c) a tri-$C_{1-6}$ alkylsilyl group (e.g., trimethylsilyl), and
  (d) a $C_{1-6}$ alkylsulfanyl group (e.g., methylsulfanyl),
(2) a $C_{3-8}$ cycloalkyl group (e.g., cyclopropyl), or
(3) a $C_{2-6}$ alkynyl group (e.g., 2-propynyl);
Z is a carbonyl group or a methylene group;
R³ is a $C_{2-6}$ alkyl group (e.g., ethyl);
Y is a methylene group substituted by oxo (e.g., —C(=O)—);
R⁴ is
(1) a $C_{2-6}$ alkyl group (e.g., ethyl), or
(2) a $C_{6-10}$ aryl group (e.g., phenyl);
R⁵ is a hydrogen atom;
R⁸ and R⁹ in combination form, together with the carbon atom which they are bonded to, a $C_{3-8}$ cycloalkane (e.g., cyclopentane);
R¹⁰ is a $C_{1-12}$ alkyl group (e.g., methyl) optionally substituted by $C_{3-8}$ cycloalkyl group(s) (e.g., cyclopropyl);
D¹ is benzene or pyridine, each optionally substituted by halogen atom(s) (e.g., a fluorine atom);
D² is benzene;

Q is
(a) when Q is (Ia), A are the same or different and each is a methylene group optionally substituted by substituent(s) selected from hydroxy and a methyl group, and
(b) when Q is (Ib), A are the same or different and each is a methylene group optionally substituted by $C_{1-3}$ alkyl group(s) (e.g., methyl, isopropyl), and
the two bond in Q may be bonded to any of Ar and B; and
B is a $C_{6-14}$ aromatic hydrocarbon (e.g., benzene) substituted by halogen atom(s) (e.g., a chlorine atom) and cyano group(s).

[Compound DD]
  The compound wherein
  Ar is the following partial structure (1) or partial structure (4);

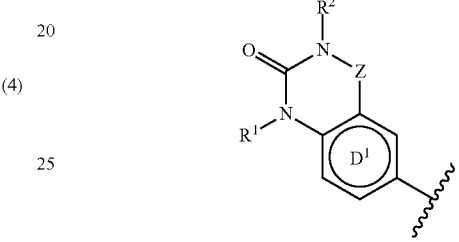

(1)

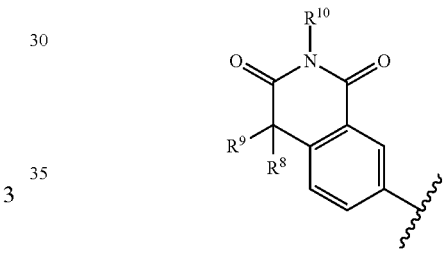

(4)

R¹ is
(1) a $C_{2-6}$ alkyl group (e.g., isopropyl), or
(2) a $C_{1-6}$ alkyl group (e.g., methyl) substituted by $C_{3-8}$ cycloalkyl group(s) (e.g., cyclopropyl);
R² is
(1) a $C_{1-6}$ alkyl group (e.g., methyl, propyl) optionally substituted by $C_{3-8}$ cycloalkyl group(s) (e.g., cyclopropyl);
R⁸ and R⁹ in combination form, together with the carbon atom which they are bonded to, a $C_{3-8}$ cycloalkane (e.g., cyclopentane);
R¹⁰ is a $C_{1-12}$ alkyl group (e.g., methyl) optionally substituted by $C_{3-8}$ cycloalkyl group(s) (e.g., cyclopropyl);
D¹ is benzene;
Q is (Ia) wherein A are the same or different and each is a methylene group optionally substituted by substituent(s) selected from hydroxy and a methyl group, and the two bond in Q may be bonded to any of Ar and B; and
B is a $C_{6-14}$ aromatic hydrocarbon (e.g., benzene) substituted by halogen atom(s) (e.g., a chlorine atom) and cyano group(s).

[Compound E-1]
  The compound wherein
  Ar is the partial structure (1);
  R¹ is
(1) a $C_{2-12}$ alkyl group,
(2) a substituted $C_{1-12}$ alkyl group,
(3) an optionally substituted $C_{3-12}$ cycloalkyl group, or
(4) an optionally substituted $C_{2-12}$ alkynyl group;

$R^2$ is (1) an optionally substituted $C_{1-12}$ alkyl group,
(2) an optionally substituted $C_{2-12}$ alkynyl group, or
(3) an optionally substituted $C_{3-12}$ cycloalkyl group;

Z is a carbonyl group or a methylene group;

$D^1$ is benzene, pyridine or pyrazine, each optionally substituted;

Q is (Ia) wherein A are the same or different and each is a methylene group optionally substituted by substituent(s) selected from hydroxy and a $C_{1-6}$ alkyl group (e.g., methyl), and the two bond in Q may be bonded to any of Ar and B; and B is a $C_{6-14}$ aromatic hydrocarbon, a 5- to 10-membered aromatic heterocycle, a fused ring formed by a $C_{6-14}$ aromatic hydrocarbon and a $C_{3-12}$ cycloalkane, or a fused ring formed by a $C_{6-14}$ aromatic hydrocarbon and a heterocycle, each optionally substituted.

[Compound E-2]

The compound wherein

Ar is the partial structure (1);

$R^1$ is (1) a $C_{2-12}$ alkyl group,
(2) a substituted $C_{1-12}$ alkyl group, or
(3) an optionally substituted $C_{3-12}$ cycloalkyl group;

$R^2$ is (1) an optionally substituted $C_{1-12}$ alkyl group, or
(2) an optionally substituted $C_{3-12}$ cycloalkyl group;

Z is a carbonyl group;

$D^1$ is benzene or pyridine, each optionally substituted;

Q is (Ib) wherein A are the same or different and each is a methylene group optionally substituted by substituent(s) selected from a $C_{1-6}$ alkyl group (e.g., methyl, isopropyl) and a $C_{6-14}$ aryl group (e.g., phenyl), and the two bond in Q may be bonded to any of Ar and B; and B is a $C_{6-14}$ aromatic hydrocarbon or a 5- to 10-membered aromatic heterocycle, each optionally substituted.

[Compound E-3]

The compound wherein

Ar is the partial structure (1);

$R^1$ is a $C_{2-12}$ alkyl group;

$R^2$ is an optionally substituted $C_{1-12}$ alkyl group;

Z is a carbonyl group;

$D^1$ is optionally substituted benzene;

Q is (Ic) wherein A are the same or different and each is a methylene group optionally substituted by $C_{1-6}$ alkyl group(s) (e.g., methyl), and the two bond in Q may be bonded to any of Ar and B; and B is a $C_{6-14}$ aromatic hydrocarbon, or a fused ring formed by a $C_{6-14}$ aromatic hydrocarbon and a $C_{3-12}$ cycloalkane, each optionally substituted.

[Compound E-4]

The compound wherein

Ar is the partial structure (1);

$R^1$ is a $C_{2-12}$ alkyl group;

$R^2$ is an optionally substituted $C_{1-12}$ alkyl group;

Z is a carbonyl group;

$D^1$ is optionally substituted benzene;

Q is (Id) wherein A are the same or different and each is a methylene group optionally substituted by $C_{1-6}$ alkyl group(s) (e.g., methyl), and the two bond in Q may be bonded to any of Ar and B; and B is an optionally substituted $C_{6-14}$ aromatic hydrocarbon.

[Compound E-5]

The compound wherein

Ar is the partial structure (1);

$R^1$ is a $C_{2-12}$ alkyl group;

$R^2$ is an optionally substituted $C_{1-12}$ alkyl group;

Z is a carbonyl group;

$D^1$ is optionally substituted benzene;

Q is (Ie) wherein A are each a methylene group, and the two bond in Q may be bonded to any of Ar and B; and B is an optionally substituted $C_{6-14}$ aromatic hydrocarbon.

[Compound E-6]

The compound wherein

Ar is the partial structure (1);

$R^1$ is a $C_{2-12}$ alkyl group;

$R^2$ is an optionally substituted $C_{1-12}$ alkyl group;

Z is a carbonyl group;

$D^1$ is optionally substituted benzene;

Q is (If) wherein A are each a methylene group, and the two bond in Q may be bonded to any of Ar and B; and B is an optionally substituted $C_{6-14}$ aromatic hydrocarbon.

[Compound E-7]

The compound wherein

Ar is the partial structure (2);

$R^3$ is a $C_{2-12}$ alkyl group (e.g., ethyl);

Y is a methylene group optionally substituted by oxo (e.g., —C(=O)—);

$R^4$ is a $C_{2-12}$ alkyl group, a substituted $C_{1-12}$ alkyl group or an optionally substituted $C_{6-14}$ aryl group;

$R^5$ is a hydrogen atom, or $R^4$ and $R^5$ are both methyl groups, or $R^4$ and $R^5$ in combination form, together with the carbon atom which they are bonded to, an optionally substituted $C_{3-12}$ cycloalkane (e.g., cyclopropane, cyclobutane);

$D^2$ is optionally substituted benzene;

Q is (Ia) wherein A are the same or different and each is a methylene group optionally substituted by $C_{1-6}$ alkyl group(s) (e.g., methyl), and the two bond in Q may be bonded to any of Ar and B; and B is an optionally substituted $C_{6-14}$ aromatic hydrocarbon.

[Compound E-8]

The compound wherein

Ar is the partial structure (3);

$R^6$ is $C_{2-12}$ alkyl (e.g., ethyl);

$R^7$ is optionally substituted $C_{1-12}$ alkyl (e.g., propyl);

Q is (Ia) wherein A are the same or different and each is a methylene group optionally substituted by $C_{1-6}$ alkyl group(s) (e.g., methyl), and the two bond in Q may be bonded to any of Ar and B; and B is an optionally substituted $C_{6-14}$ aromatic hydrocarbon.

[Compound E-9]

The compound wherein

Ar is the partial structure (3);

$R^6$ is $C_{2-12}$ alkyl (e.g., ethyl);

$R^7$ is optionally substituted $C_{1-12}$ alkyl (e.g., propyl);

Q is (Ib) wherein A are the same or different and each is a methylene group optionally substituted by $C_{1-6}$ alkyl group(s) (e.g., methyl, isopropyl), and the two bond in Q may be bonded to any of Ar and B; and B is an optionally substituted $C_{6-14}$ aromatic hydrocarbon.

[Compound E-10]

The compound wherein

Ar is the partial structure (4);

$R^8$ and $R^9$ in combination form, together with the carbon atom which they are bonded to, an optionally substituted $C_{3-12}$ cycloalkane (e.g., cyclopentane);

$R^{10}$ is an optionally substituted $C_{1-12}$ alkyl group;

Q is (Ia) wherein A are the same or different and each is a methylene group optionally substituted by $C_{1-6}$ alkyl group(s) (e.g., methyl), and the two bond in Q may be bonded to any of Ar and B; and B is an optionally substituted $C_{6-14}$ aromatic hydrocarbon.

[Compound E-11]
The compound wherein
Ar is the partial structure (5);
$R^{10}$ is an optionally substituted $C_{1-12}$ alkyl group;
$R^{11}$, $R^{12}$ and $R^{13}$ are each an optionally substituted $C_{1-12}$ alkyl group;
Q is
(a) when Q is (Ia), A are the same or different and each is a methylene group optionally substituted by $C_{1-6}$ alkyl group(s) (e.g., methyl), and the two bond in Q may be bonded to any of Ar and B; and
B is an optionally substituted $C_{6-14}$ aromatic hydrocarbon.

[Compound F-1]
The compound wherein
Ar is the partial structure (1);
$R^1$ is
(1) a $C_{2-6}$ alkyl group (e.g., ethyl, isopropyl),
(2) a $C_{1-6}$ alkyl group (e.g., methyl, ethyl, propyl) substituted by 1 to 3 substituents selected from
   (a) a $C_{3-8}$ cycloalkyl group (e.g., cyclopropyl),
   (b) a $C_{1-6}$ alkoxy group (e.g., methoxy),
   (c) a $C_{1-6}$ alkylsulfanyl group (e.g., methylsulfanyl),
   (d) a hydroxy group,
   (e) a tri-$C_{1-6}$ alkylsilyl group (e.g., trimethylsilyl), and
   (f) a cyano group,
(3) a $C_{3-6}$ cycloalkyl group (e.g., cyclopropyl), or
(4) a $C_{2-6}$ alkynyl group (e.g., 2-propynyl);
$R^2$ is
(1) a $C_{1-6}$ alkyl group (e.g., methyl, ethyl, propyl) optionally substituted by 1 to 3 substituents selected from
   (a) a cyano group,
   (b) a hydroxy group,
   (c) a $C_{3-6}$ cycloalkyl group (e.g., cyclopropyl),
   (d) a $C_{1-6}$ alkoxy group (e.g., methoxy),
   (e) a $C_{1-6}$ alkylsulfanyl group (e.g., methylsulfanyl),
   (f) a $C_{1-6}$ alkylsulfonyl group (e.g., methylsulfonyl),
   (g) a carbamoyl group optionally mono- or di-substituted by $C_{1-6}$ alkyl group(s) (e.g., methyl),
   (h) a tri-$C_{1-6}$ alkylsilyl group (e.g., trimethylsilyl), and
   (i) a non-aromatic heterocyclic group (e.g., oxetanyl),
(2) a $C_{2-6}$ alkynyl group (e.g., 2-propynyl), or
(3) a $C_{3-8}$ cycloalkyl group (e.g., cyclopropyl);
Z is a carbonyl group or a methylene group;
$D^1$ is benzene, pyridine or pyrazine, each optionally substituted by halogen atom(s) (e.g., a fluorine atom);
Q is (Ia) wherein A are the same or different and each is a methylene group optionally substituted by substituent(s) selected from hydroxy and a methyl group, and the two bond in Q may be bonded to any of Ar and B; and
B is a $C_{6-14}$ aromatic hydrocarbon, a 5- to 10-membered aromatic heterocycle, or a fused ring formed by a $C_{6-14}$ aromatic hydrocarbon and a heterocycle (preferably a $C_{6-10}$ aromatic hydrocarbon, a 5- or 6-membered aromatic heterocycle, or a fused ring formed by a benzene ring and a heterocycle, more preferably benzene, pyridine, pyrrole, thiazole, thiophene, benzothiazole, 2,3-dihydrobenzothiazole, 2,3-dihydrobenzoxazole, particularly preferably benzene), each optionally substituted by 1 to 3 substituents selected from
   (1) a halogen atom (e.g., a chlorine atom),
   (2) cyano,
   (3) $C_{1-6}$ alkyl (e.g., methyl),
   (4) $C_{1-6}$ alkoxy (e.g., methoxy) optionally substituted by 1 to 3 cyano groups, and
   (5) oxo.

[Compound F-2]
The compound wherein
Ar is the partial structure (1);
$R^1$ is
(1) a $C_{2-6}$ alkyl group (e.g., ethyl),
(2) a $C_{1-6}$ alkyl group (e.g., methyl) substituted by $C_{3-8}$ cycloalkyl group(s) (e.g., cyclopropyl), or
(3) a $C_{3-8}$ cycloalkyl group (e.g., cyclopropyl);
$R^2$ is
(1) a $C_{1-6}$ alkyl group (e.g., methyl, ethyl) optionally substituted by $C_{3-8}$ cycloalkyl group(s) (e.g., cyclopropyl), or
(2) a $C_{3-8}$ cycloalkyl group (e.g., cyclopropyl);
Z is a carbonyl group;
$D^1$ is benzene or pyridine;
Q is (Ib) wherein A are the same or different and each is a methylene group optionally substituted by substituent(s) selected from a $C_{1-3}$ alkyl group (e.g., methyl, isopropyl) and a $C_{6-14}$ aryl group (e.g., phenyl), and the two bond in Q may be bonded to any of Ar and B; and
B is a $C_{6-14}$ aromatic hydrocarbon or a 5- to 10-membered aromatic heterocycle (preferably a $C_{6-10}$ aromatic hydrocarbon, or 5- or 6-membered aromatic heterocycle, more preferably benzene, pyridine, pyrrole, thiadiazole, thiazole, particularly preferably benzene), each optionally substituted by 1 to 3 substituents selected from
   (1) a halogen atom (e.g., a fluorine atom, a chlorine atom, a bromine atom),
   (2) cyano,
   (3) hydroxy,
   (4) $C_{1-6}$ alkyl (e.g., methyl) optionally substituted by 1 to 3 halogen atoms (e.g., a fluorine atom),
   (5) $C_{1-6}$ alkoxy (e.g., methoxy),
   (6) optionally halogenated sulfanyl (preferably sulfanyl optionally substituted by 1 to 5 halogen atoms (e.g., a fluorine atom)) (e.g., pentafluorosulfanyl),
   (7) $C_{1-6}$ alkyl-carbonyl (e.g., acetyl), and
   (8) a non-aromatic heterocyclic group (e.g., morpholino).

[Compound F-3]
The compound wherein
Ar is the partial structure (1);
$R^1$ is a $C_{2-6}$ alkyl group (e.g., ethyl);
$R^2$ is a $C_{1-6}$ alkyl group (e.g., ethyl);
Z is a carbonyl group;
$D^1$ is benzene;
Q is (Ic) wherein A are the same or different and each is a methylene group optionally substituted by $C_{1-3}$ alkyl group(s) (e.g., methyl), and the two bond in Q may be bonded to any of Ar and B; and
B is a $C_{6-14}$ aromatic hydrocarbon, or a fused ring formed by a $C_{6-14}$ aromatic hydrocarbon and a $C_{3-8}$ cycloalkane (preferably a $C_{6-10}$ aromatic hydrocarbon, or a fused ring formed by a benzene ring and a $C_{3-8}$ cycloalkane, more preferably benzene, or indane, particularly preferably benzene), each optionally substituted by 1 to 3 substituents selected from
   (1) a halogen atom (e.g., a fluorine atom, a chlorine atom),
   (2) cyano,
   (3) $C_{1-6}$ alkyl (e.g., methyl) optionally substituted by cyano group(s),
   (4) $C_{1-6}$ alkoxy (e.g., methoxy),
   (5) $C_{2-6}$ alkynyl (e.g., ethynyl),
   (6) $C_{1-6}$ alkylsulfanyl (e.g., methylsulfanyl), and
   (7) oxo.

[Compound F-4]
The compound wherein
Ar is the partial structure (1);
$R^1$ is a $C_{2-6}$ alkyl group (e.g., ethyl);

$R^2$ is a $C_{1-6}$ alkyl group (e.g., ethyl);

Z is a carbonyl group;

$D^1$ is benzene;

Q is (Id) wherein A are the same or different and each is a methylene group optionally substituted by $C_{1-3}$ alkyl group(s) (e.g., methyl), and the two bond in Q may be bonded to any of Ar and B; and B is a $C_{6-14}$ aromatic hydrocarbon (preferably a $C_{6-10}$ aromatic hydrocarbon, more preferably benzene) optionally substituted by 1 to 3 substituents selected from (1) a halogen atom (e.g., a chlorine atom), and (2) cyano.

[Compound F-5]

The compound wherein

Ar is the partial structure (1);

$R^1$ is a $C_{2-6}$ alkyl group (e.g., ethyl);

$R^2$ is a $C_{1-6}$ alkyl group (e.g., ethyl);

Z is a carbonyl group;

$D^1$ is benzene;

Q is (Ie) wherein A are each a methylene group, and the two bond in Q may be bonded to any of Ar and B; and B is a $C_{6-14}$ aromatic hydrocarbon (preferably a $C_{6-10}$ aromatic hydrocarbon, more preferably benzene) optionally substituted by 1 to 3 substituents selected from (1) a halogen atom (e.g., a chlorine atom), and (2) cyano.

[Compound F-6]

The compound wherein

Ar is the partial structure (1);

$R^1$ is a $C_{2-6}$ alkyl group (e.g., ethyl);

$R^2$ is a $C_{1-6}$ alkyl group (e.g., ethyl);

Z is a carbonyl group;

$D^1$ is benzene;

Q is (If) wherein A are each a methylene group, and the two bond in Q may be bonded to any of Ar and B; and B is a $C_{6-14}$ aromatic hydrocarbon (preferably a $C_{6-10}$ aromatic hydrocarbon, more preferably benzene) optionally substituted by 1 to 3 substituents selected from (1) a halogen atom (e.g., a chlorine atom), and (2) cyano.

[Compound F-7]

The compound wherein

Ar is the partial structure (2);

$R^3$ is a $C_{2-6}$ alkyl group (e.g., ethyl);

Y is a methylene group optionally substituted by oxo (e.g., —C(=O)—);

$R^4$ is (1) a $C_{2-6}$ alkyl group (e.g., ethyl, isopropyl), (2) a $C_{1-6}$ alkyl group (e.g., methyl, ethyl) substituted by 1 to 3 substituents selected from (a) hydroxy, (b) $C_{1-6}$ alkoxy (e.g., methoxy), (c) $C_{1-6}$ alkoxy-carbonyl (e.g., ethoxycarbonyl), and (d) $C_{6-10}$ aryl (e.g., phenyl), or (3) a $C_{6-10}$ aryl group (e.g., phenyl);

$R^5$ is a hydrogen atom, or $R^4$ and $R^5$ are both methyl groups, or $R^4$ and $R^5$ in combination form, together with the carbon atom which they are bonded to, a $C_{3-8}$ cycloalkane (e.g., cyclopropane, cyclobutane);

$D^2$ is benzene;

Q is (Ia) wherein A are each a methylene group optionally substituted by methyl, and the two bond in Q may be bonded to any of Ar and B; and B is a $C_{6-10}$ aromatic hydrocarbon (more preferably benzene) optionally substituted by 1 to 3 substituents selected from (1) a halogen atom (e.g., a chlorine atom), and (2) cyano.

[Compound F-8]

The compound wherein

Ar is the partial structure (3);

$R^6$ is $C_{2-6}$ alkyl (e.g., ethyl);

$R^7$ is $C_{1-6}$ alkyl (e.g., propyl);

Q is (Ia) wherein A are each a methylene group optionally substituted by methyl, and the two bond in Q may be bonded to any of Ar and B; and B is a $C_{6-10}$ aromatic hydrocarbon (more preferably benzene) optionally substituted by 1 to 3 substituents selected from (1) a halogen atom (e.g., a chlorine atom), and (2) cyano.

[Compound F-9]

The compound wherein

Ar is the partial structure (3);

$R^6$ is $C_{2-6}$ alkyl (e.g., ethyl);

$R^7$ is $C_{1-6}$ alkyl (e.g., propyl);

Q is (Ib) wherein A are each a methylene group optionally substituted by methyl, and the two bond in Q may be bonded to any of Ar and B; and B is a $C_{6-10}$ aromatic hydrocarbon (more preferably benzene) optionally substituted by 1 to 3 substituents selected from (1) a halogen atom (e.g., a chlorine atom), and (2) cyano.

[Compound F-10]

The compound wherein

Ar is the partial structure (4);

$R^8$ and $R^9$ in combination form, together with the carbon atom which they are bonded to, a $C_{3-8}$ cycloalkane (e.g., cyclopentane);

$R^{10}$ is a $C_{1-6}$ alkyl group (e.g., methyl) substituted by $C_{3-8}$ cycloalkyl group(s) (e.g., cyclopropyl);

Q is (Ia) wherein A are each a methylene group optionally substituted by methyl, and the two bond in Q may be bonded to any of Ar and B; and B is a $C_{6-10}$ aromatic hydrocarbon (more preferably benzene) optionally substituted by 1 to 3 substituents selected from (1) a halogen atom (e.g., a chlorine atom), and (2) cyano.

[Compound F-11]

The compound wherein

Ar is the partial structure (5);

$R^{11}$ is a $C_{1-6}$ alkyl group (e.g., ethyl):

$R^{12}$ is a $C_{1-6}$ alkyl group (e.g., methyl);

$R^{13}$ is a $C_{1-6}$ alkyl group (e.g., methyl) substituted by $C_{3-8}$ cycloalkyl group(s) (e.g., cyclopropyl);

Q is (Ia) wherein A are each a methylene group optionally substituted by methyl, and the two bond in Q may be bonded to any of Ar and B; and B is a $C_{6-10}$ aromatic hydrocarbon (more preferably benzene) optionally substituted by 1 to 3 substituents selected from (1) a halogen atom (e.g., a chlorine atom), and (2) cyano.

[Compound G-1]

The compound wherein

Ar is the partial structure (1);

$R^1$ is
(1) a $C_{2-6}$ alkyl group (e.g., ethyl, isopropyl), or
(2) a $C_{1-6}$ alkyl group (e.g., methyl) substituted by 1 to 3 substituents selected from
    (a) a $C_{3-8}$ cycloalkyl group (e.g., cyclopropyl),
    (b) a $C_{1-6}$ alkylsulfanyl group (e.g., methylsulfanyl), and
    (c) a tri-$C_{1-6}$ alkylsilyl group (e.g., trimethylsilyl);

$R^2$ is
(1) a $C_{1-6}$ alkyl group (e.g., methyl, ethyl, propyl) optionally substituted by 1 to 3 substituents selected from
    (a) a $C_{3-8}$ cycloalkyl group (e.g., cyclopropyl),
    (b) a $C_{1-6}$ alkoxy group (e.g., methoxy),
    (c) a $C_{1-6}$ alkylsulfanyl group (e.g., methylsulfanyl), and
    (d) a tri-$C_{1-6}$ alkylsilyl group (e.g., trimethylsilyl),
(2) a $C_{2-6}$ alkynyl group (e.g., 2-propynyl), or
(3) a $C_{3-8}$ cycloalkyl group (e.g., cyclopropyl);

Z is a carbonyl group or a methylene group;

$D^1$ is benzene or pyridine, each optionally substituted by halogen atom(s) (e.g., a fluorine atom);

Q is (Ia) wherein A are the same or different and each is a methylene group optionally substituted by substituent(s) selected from hydroxy and a methyl group, and the two bond in Q may be bonded to any of Ar and B; and B is a $C_{6-14}$ aromatic hydrocarbon (preferably a $C_{6-10}$ aromatic hydrocarbon, more preferably benzene), each optionally substituted by 1 to 3 substituents selected from
    (1) a halogen atom (e.g., a chlorine atom), and
    (2) cyano.

[Compound G-2]
The compound wherein
Ar is the partial structure (1);
$R^1$ is
(1) a $C_{2-6}$ alkyl group (e.g., ethyl), or
(2) a $C_{1-6}$ alkyl group (e.g., methyl) substituted by $C_{3-8}$ cycloalkyl group(s) (e.g., cyclopropyl);

$R^2$ is a $C_{1-6}$ alkyl group (e.g., methyl, ethyl) optionally substituted by $C_{3-8}$ cycloalkyl group(s) (e.g., cyclopropyl);

Z is a carbonyl group;

$D^1$ is benzene or pyridine;

Q is (Ib) wherein A are the same or different and each is a methylene group optionally substituted by $C_{1-3}$ alkyl group(s) (e.g., methyl, isopropyl), and the two bond in Q may be bonded to any of Ar and B; and B is a $C_{6-14}$ aromatic hydrocarbon (preferably a $C_{6-10}$ aromatic hydrocarbon, more preferably benzene), each optionally substituted by 1 to 3 substituents selected from
    (1) a halogen atom (e.g., a chlorine atom), and
    (2) cyano.

[Compound G-3]
The compound wherein
Ar is the partial structure (2);
$R^3$ is a $C_{2-6}$ alkyl group (e.g., ethyl);
Y is a methylene group optionally substituted by oxo (e.g., —C(═O)—);
$R^4$ is
(1) a $C_{2-6}$ alkyl group (e.g., ethyl), or
(2) a $C_{6-10}$ aryl group (e.g., phenyl);
$R^5$ is a hydrogen atom;
$D^2$ is benzene;

Q is (Ia) wherein A are each a methylene group optionally substituted by methyl, and the two bond in Q may be bonded to any of Ar and B; and B is a $C_{6-14}$ aromatic hydrocarbon (preferably a $C_{6-10}$ aromatic hydrocarbon, more preferably benzene) optionally substituted by 1 to 3 substituents selected from
    (1) a halogen atom (e.g., a chlorine atom), and
    (2) cyano.

Specific examples of compound (I) include the compounds of Examples 1 to 145.

Examples of salt of compound (I) include metal salts, ammonium salts, salts with organic base, salts with inorganic acid, salts with organic acid, salts with basic or acidic amino acids, and the like. Preferable examples of the metal salt include alkaline metal salts such as sodium salt, potassium salt and the like; alkaline earth metal salts such as calcium salt, magnesium salt, barium salt and the like; aluminum salts, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salt with aspartic acid, glutamic acid and the like.

Among them, pharmaceutically acceptable salts are preferable. For example, if the compound has an acidic functional group therein, examples of the salt include inorganic salts such as alkaline metal salts (e.g., sodium salt, potassium salt and the like), alkaline earth metal salts (e.g., calcium salt, magnesium salt, barium salt and the like) and the like; ammonium salt, and the like. If the compound has a basic functional group therein, examples of the salt thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

The production method of compound (I) of the present invention is explained below.

The intermediates produced in the following production methods may be isolated and purified according to methods such as column chromatography, recrystallization, distillation and the like, or may be directly used without isolation for the next step.

Compounds (IIa), (IIb), (IIb-I), (IIb-II), (IIb-III), (IIc), (IIc-I), (IIc-II), (IId), (IIe), (IIIa), (IIIb), (IIIb-I), (IIIb-II), (IIIb-III), (IIIc), (IIId), (IIIe), (IVa), (IVb), (IVb-I), (IVb-II), (IVb-III), (IVc), (IVd) and (IVe) or a salt thereof of the present invention can be produced according to the following Method A to Method K.

[Method A]

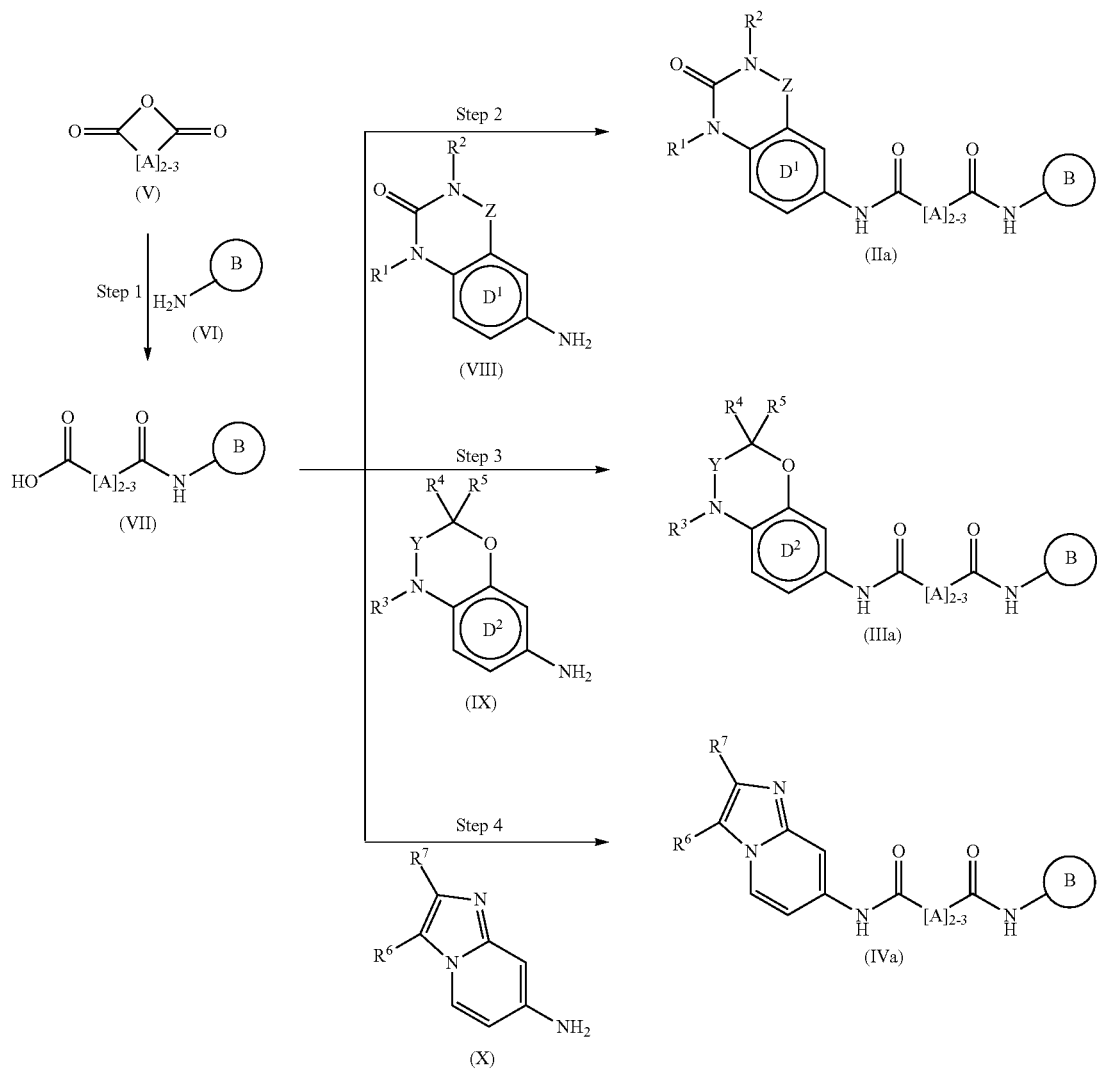

wherein each symbol is as defined above.

(Step 1)

This step is a step of producing compound (VII) or a salt thereof by reacting compound (V) or a salt thereof with compound (VI) or a salt thereof.

Compound (V) and compound (VI) may be a commercially available product, or can also be produced according to a method known per se or a method analogous thereto.

The step can be carried out in a solvent that does not adversely influence the reaction. Examples of the solvent include alcohols (methanol, ethanol, propanol, 2-propanol, butanol, isobutanol, t-butanol and the like), hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like) and the like, and they may be mixed as appropriate. Among them, tetrahydrofuran is preferably used.

The amount of compound (VI) to be used is generally about 0.5 to 10 mol equivalent, preferably about 0.9 to 1.1 mol equivalent, per 1 mol of compound (V).

While the reaction time varies depending on the kind of the solvent, it is generally about −80 to 200° C., preferably about 25 to 150° C., and the reaction time is generally about 0.5 to 72 hr, preferably 1 to 48 hr.

(Step 2)

This step is a step of producing compound (IIa) or a salt thereof by reacting compound (VII) or a salt thereof with compound (VIII) or a salt thereof in the presence of a condensing agent.

Compound (VIII) can be produced according to the method described in the below-mentioned Method L or M, or a method analogous thereto.

Examples of the condensing agent to be used in this step include dicyclohexylcarbodiimide (DCC), diisopropylcarbodiimide (DIC), $N^1$-((ethylimino)methylene)-$N^3,N^3$-dimethylpropane-1,3-diamine hydrochloride (WSC), benzotriazol-1-yl-tris(dimethylamino)phosphonium hexafluorophosphorate (BOP), diphenylphosphorylazide (DPPA), (1-cyano-2-ethoxy-2-oxoethylidenaminooxy)dimethylamino-morpholino-carbenium hexafluorophosphorate (COMU), ethyl (hydroxyimino)cyanoacetate (Oxyma), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 2-(1H-7-azabenzotriazol-1-yl)-1,1,3,3-tetramethyluronium hexafluorophosphate (HATU), O-[(ethoxycarbonyl)cyanomethylenamino]-N,N,N',N'-tetramethyluronium hexafluorophosphate (HOTU), 2,4,6-tripropyl-1,3,5,2,4,6-trioxatriphosphorinane-2,4,6-trioxide (T3P) and the like. They are used alone or in combination with an additive (e.g., N-hydroxysuccinimide (HOSu), 1-hydroxybenzotriazole (HOBt), 6-chloro-1-hydroxybenzotriazole (Cl-HOBt), 1-hydroxy-7-azabenzotriazole (HOAt), 3-hydroxy-4-oxo-3,4-dihydro-1,2,3-benzotriazine and the like). The amount of the condensing agent to be used is about 1 to 10 mol equivalent, preferably about 1 to 2 mol equivalent, per 1 mol of compound (VII). The amount of the additive to be used is generally about 1 to 10 mol equivalent, preferably about 1 to 2 mol equivalent, per 1 mol of compound (VII).

The amount of compound (VIII) to be used is generally about 1 to 10 mol equivalent, preferably about 1 to 2 mol equivalent, per 1 mol of compound (VII).

The above-mentioned reaction is generally carried out in a solvent that does not adversely influence the reaction, and a base may be added for the progress of the reaction. Examples of the solvent include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like) and the like, and they may be mixed as appropriate. Examples of the base include alkali metal hydroxides (sodium hydroxide, potassium hydroxide and the like), hydrogencarbonates (sodium hydrogencarbonate, potassium hydrogencarbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1 to 100 mol equivalent, preferably about 1 to 5 mol equivalent, per 1 mol of compound (VII). While the reaction time varies depending on the kind of the solvent, it is generally about −80 to 150° C., preferably about 0 to 50° C., and the reaction time is generally about 0.5 to 100 hr, preferably 0.5 to 60 hr.

(Step 3)

This step is a step of producing compound (IIIa) or a salt thereof by reacting compound (VII) or a salt thereof with compound (IX) or a salt thereof in the presence of a condensing agent. This step can be carried out in the same manner as in the method described in Step 2 of Method A.

Compound (IX) can be produced according to the method described in the below-mentioned Method P, Q, R or S, or a method analogous thereto.

(Step 4)

This step is a step of producing compound (IVa) or a salt thereof by reacting compound (VII) or a salt thereof with compound (X) or a salt thereof in the presence of a condensing agent. This step can be carried out in the same manner as in the method described in Step 2 of Method A.

Compound (X) can be produced according to the method described in the below-mentioned Method T, or a method analogous thereto.

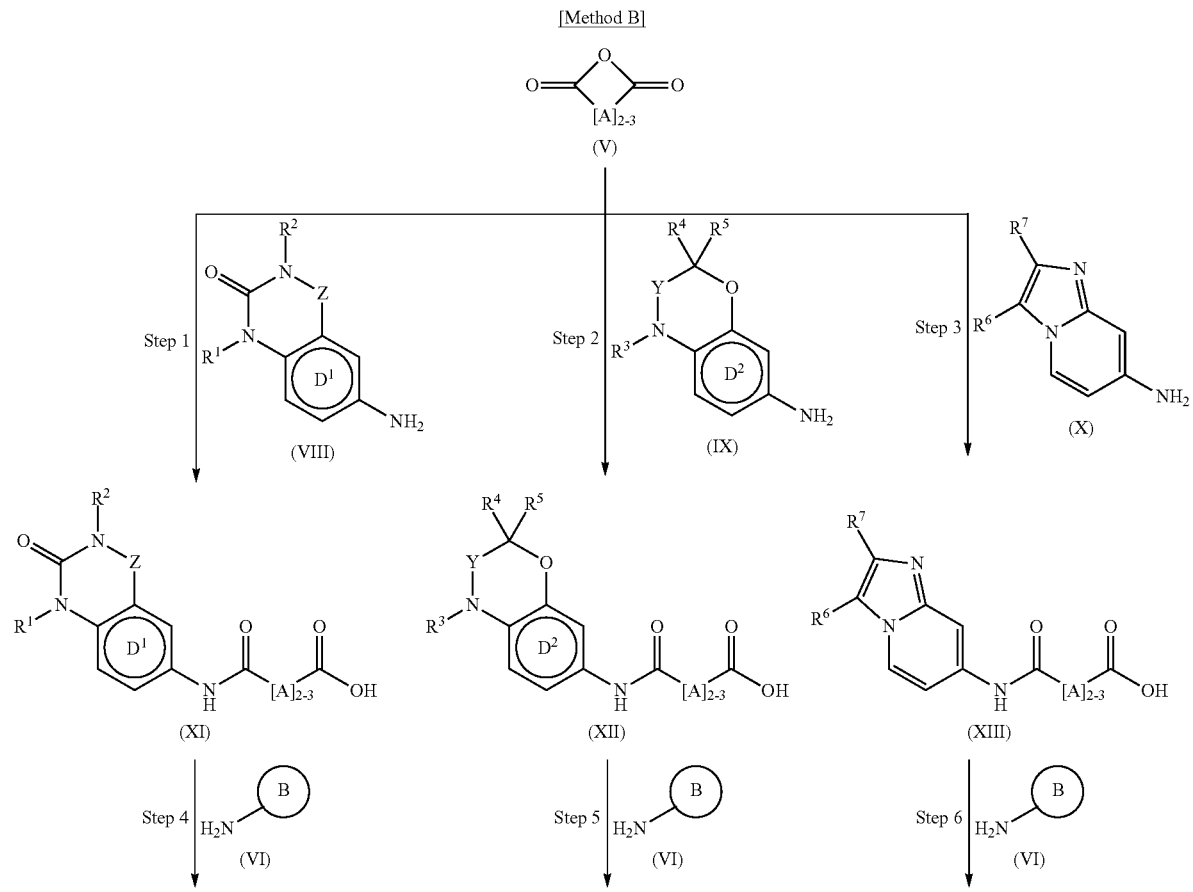

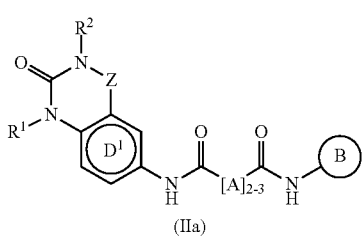
(IIa)

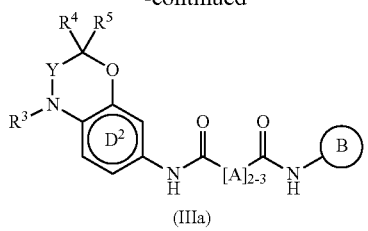
(IIIa)

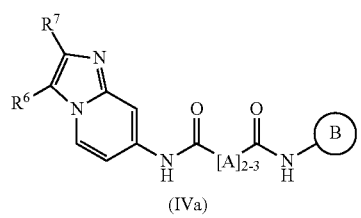
(IVa)

wherein each symbol is as defined above.

(Step 1)

This step is a step of producing compound (XI) or a salt thereof by reacting compound (V) or a salt thereof with compound (VIII) or a salt thereof. This step can be carried out in the same manner as in the method described in Step 1 of Method A.

Compound (V) may be a commercially available product, or can also be produced according to a method known per se or a method analogous thereto.

Compound (VIII) can be produced according to the method described in the below-mentioned Method L or M, or a method analogous thereto.

(Step 2)

This step is a step of producing compound (XII) or a salt thereof by reacting compound (V) or a salt thereof with compound (IX) or a salt thereof. This step can be carried out in the same manner as in the method described in Step 1 of Method A.

Compound (IX) can be produced according to the method described in the below-mentioned Method P, Q, R or S, or a method analogous thereto.

(Step 3)

This step is a step of producing compound (XIII) or a salt thereof by reacting compound (V) or a salt thereof with compound (X) or a salt thereof. This step can be carried out in the same manner as in the method described in Step 1 of Method A.

Compound (X) can be produced according to the method described in the below-mentioned Method T, or a method analogous thereto.

(Step 4)

This step is a step of producing compound (IIa) or a salt thereof by reacting compound (XI) or a salt thereof with compound (VI) or a salt thereof in the presence of a condensing agent. This step can be carried out in the same manner as in the method described in Step 2 of Method A.

(Step 5)

This step is a step of producing compound (IIIa) or a salt thereof by reacting compound (XII) or a salt thereof with compound (VI) or a salt thereof in the presence of a condensing agent. This step can be carried out in the same manner as in the method described in Step 2 of Method A.

(Step 6)

This step is a step of producing compound (IVa) or a salt thereof by reacting compound (XIII) or a salt thereof with compound (VI) or a salt thereof in the presence of a condensing agent. This step can be carried out in the same manner as in the method described in Step 2 of Method A.

[Method C]

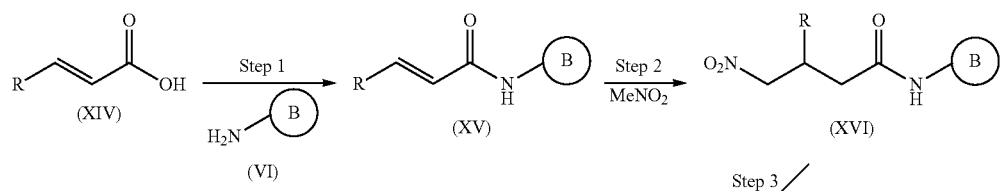

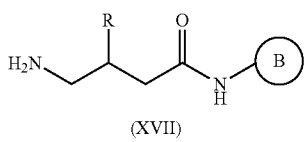

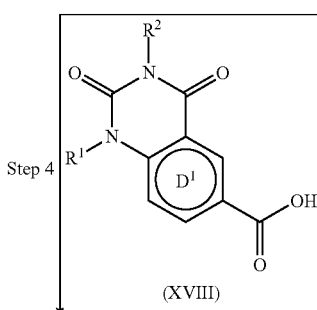
(XVIII)

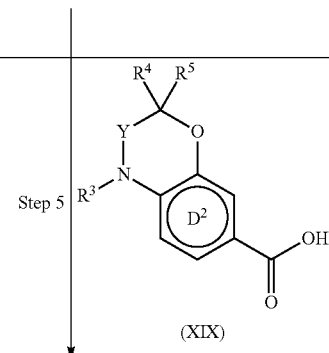
(XIX)

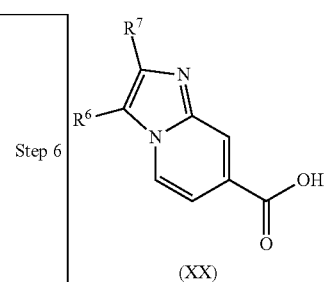
(XX)

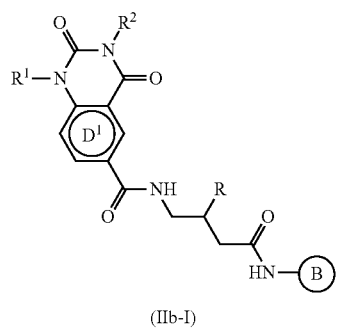

(IIb-I)

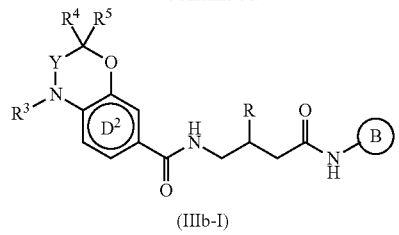

(IIIb-I)

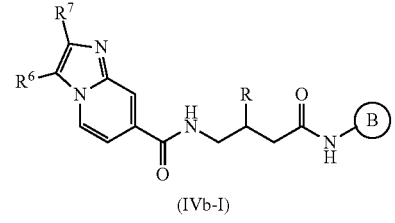

(IVb-I)

wherein R is a hydroxy group or an optionally substituted $C_{1-6}$ alkyl group, and the other symbols are as defined above.
(Step 1)

This step is a step of producing compound (XV) or a salt thereof by reacting compound (XIV) or a salt thereof with compound (VI) or a salt thereof in the presence of a condensing agent. This step can be carried out in the same manner as in the method described in Step 2 of Method A.

Compound (XIV) may be a commercially available product, or can also be produced according to a method known per se or a method analogous thereto.
(Step 2)

This step is a step of producing compound (XVI) or a salt thereof by reacting compound (XV) or a salt thereof with nitromethane. This reaction is carried out in the presence of a base, in a solvent that does not adversely influence the reaction, if necessary.

Examples of the base include organic bases (amines such as 1,8-diazabicyclo[5.4.0]undec-7-ene (DBU), trimethylamine, triethylamine (TEA), diisopropylethylamine (DIEA) and the like; aromatic amines such as pyridine, 4-dimethylaminopyridine and the like, and the like) and the like. Among them, DBU is preferable. While the amount of the base to be used varies depending on the kind of the solvent and other reaction condition, it is generally about 1 to 10 mol equivalent, preferably about 1 to 5 mol equivalent, per 1 mol of compound (XV).

While the amount of the nitromethane to be used varies depending on the kind of the solvent and other reaction condition, it is generally about 1 to 100 mol equivalent, per 1 mol of compound (XV). Nitromethane can also be used as a solvent.

Examples of the solvent that does not adversely influence the reaction include hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), amides (dimethylformamide, dimethylacetamide and the like) and the like. Among them, dimethylformamide is preferable. These solvents may be used in a mixture of two or more kinds thereof in an appropriate ratio.

While the reaction time varies depending on the kind of the solvent, it is, for example, within about 0 to 200° C., preferably about 20 to 80° C. While the reaction time varies depending on the kind of compound (XV) or a salt thereof, the reaction temperature and the like, it is, for example, about 0.5 to 100 hr, preferably about 0.5 to 24 hr.
(Step 3)

This step is a step of producing compound (XVII) or a salt thereof by subjecting compound (XVI) or a salt thereof to a reduction reaction.

The reduction reaction can be carried out by employing reduction using a metal or a metal salt or reduction by catalytic hydrogenation using a transition metal catalyst, in a solvent that does not adversely influence.

Preferable examples of the metal or metal salt used in the "reduction using a metal or a metal salt" include alkali metals (lithium, sodium, potassium and the like), alkaline-earth metals (magnesium, calcium and the like), other metals (zinc, chromium, titanium, iron, samarium, selenium and the like), metal salts (zinc-amalgam, zinc-copper alloy, aluminium-amalgam, sodium hydrosulfite and the like) and the like. The amount of the metal or metal salt to be used is, for example, 1 to 50 mol equivalent, preferably 1 to 5 mol equivalent, per 1 mol of compound (XVI).

Examples of the solvent used in the reaction include alcohols (methanol, ethanol, 2-propanol, t-butanol, benzyl alcohol and the like), amines (liquid ammonia, methylamine, ethylamine, ethylene diamine and the like), ethers (diethyl ether, tetrahydrofuran, dioxane, dimethoxyethane and the like), mineral acids (hydrochloric acid, hydrobromic acid, sulfuric acid and the like), carboxylic acids (acetic acid and the like), amides (hexamethylphosphoramide), water and the like. These solvents are used alone or in mixture thereof.

While the reaction time varies depending on the kind of the solvent, it is generally about −80 to 150° C., preferably about −80 to 100° C., and the reaction time is generally 5 min to 48 hr, preferably 1 to 24 hr.

Examples of the transition metal catalyst used in the "reduction by catalytic hydrogenation using a transition metal catalyst" include palladiums (palladium on carbon, palladium hydroxide, palladium oxide and the like), nickels (Raney nickel and the like), platinums (platinum oxide, platinum on carbon and the like), rhodiums (rhodium acetate, rhodium on carbon and the like) and the like. The amount thereof to be used is, for example, about 0.001 to 1 equivalent, preferably about 0.01 to 0.5 equivalent, per 1 mol of compound (XVI). The catalytic hydrogenation reaction is generally carried out in a solvent inert to the reaction. Examples of the solvent include alcohols (methanol, ethanol, propanol, butanol and the like), hydrocarbons (benzene, toluene, xylene and the like), halogenated hydrocarbons (dichloromethane, chloroform and the like), ethers (diethyl ether, dioxane, tetrahydrofuran and the like), esters (ethyl acetate and the like), amides (N,N-dimethylformamide and the like), carboxylic acids (acetic acid and the like), water and mixtures thereof. The hydrogen pressure of the reaction is generally about 1 to 500 atm, preferably about 1 to 100 atm. While the reaction time varies depending on the kind of the solvent, it is generally about 0 to 150° C., preferably about 20 to 100° C., and the reaction time is generally 5 min to 72 hr, preferably 0.5 to 40 hr.

(Step 4)

This step is a step of producing compound (IIb-I) or a salt thereof by reacting compound (XVII) or a salt thereof with compound (XVIII) or a salt thereof in the presence of a condensing agent. This step can be carried out in the same manner as in the method described in Step 2 of Method A.

Compound (XVIII) can be produced according to the method described in the below-mentioned Method L or O, or a method analogous thereto.

(Step 5)

This step is a step of producing compound (IIIb-I) or a salt thereof by reacting compound (XVII) or a salt thereof with compound (XIX) or a salt thereof in the presence of a condensing agent. This step can be carried out in the same manner as in the method described in Step 2 of Method A.

Compound (XIX) can be produced according to the method described in the below-mentioned Method U, or a method analogous thereto.

(Step 6)

This step is a step of producing compound (IVb-I) or a salt thereof by reacting compound (XVII) or a salt thereof with compound (XX) or a salt thereof in the presence of a condensing agent. This step can be carried out in the same manner as in the method described in Step 2 of Method A.

Compound (XX) can be produced according to the method described in the below-mentioned Method T, or a method analogous thereto.

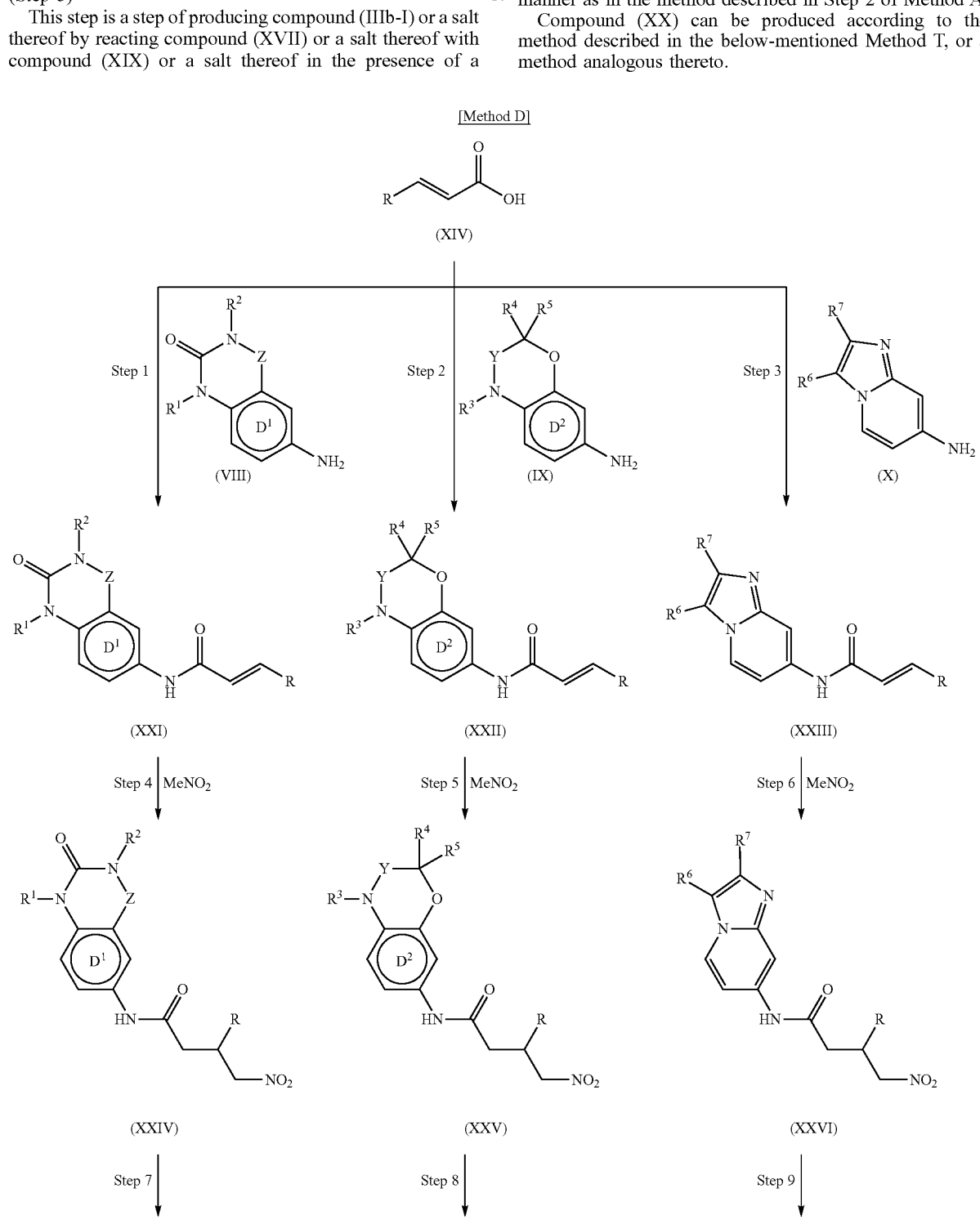

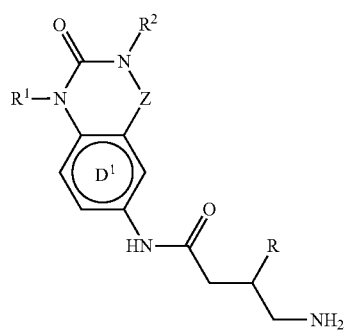 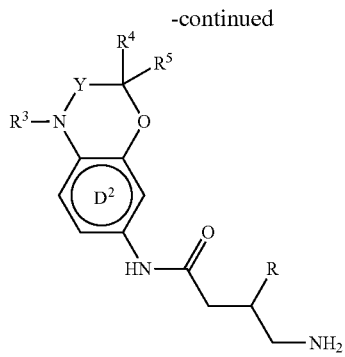 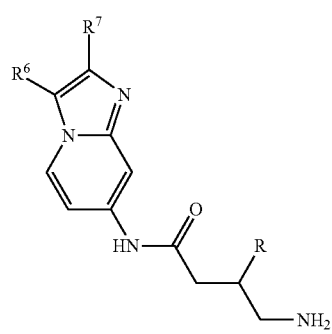

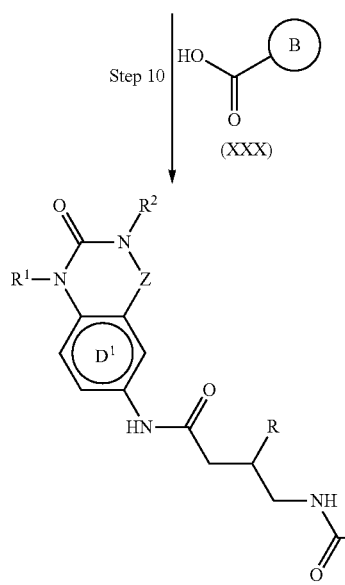 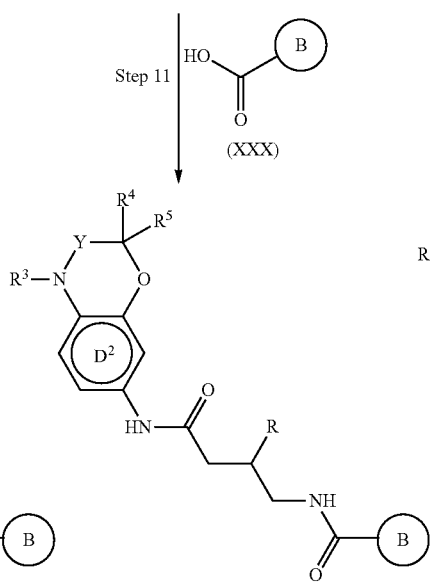 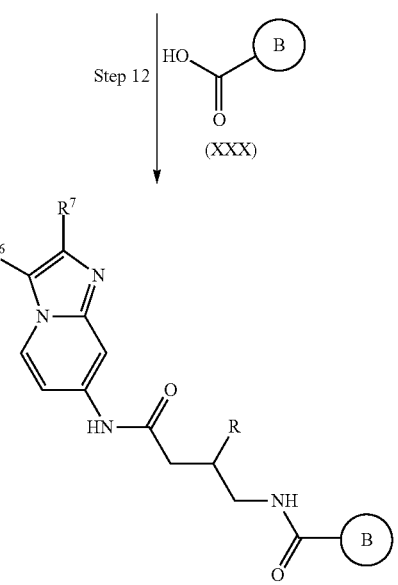

wherein R is a hydroxy group or an optionally substituted $C_{1-6}$ alkyl group, and the other symbols are as defined above.

(Step 1)

This step is a step of producing compound (XXI) or a salt thereof by reacting compound (XIV) or a salt thereof with compound (VIII) or a salt thereof in the presence of a condensing agent. This step can be carried out in the same manner as in the method described in Step 2 of Method A.

Compound (XIV) may be a commercially available product, or can also be produced according to a method known per se or a method analogous thereto.

Compound (VIII) can be produced according to the method described in the below-mentioned Method L or M, or a method analogous thereto.

(Step 2)

This step is a step of producing compound (XXII) or a salt thereof by reacting compound (XIV) or a salt thereof with compound (IX) or a salt thereof in the presence of a condensing agent. This step can be carried out in the same manner as in the method described in Step 2 of Method A.

Compound (IX) can be produced according to the method described in the below-mentioned Method P, Q, R or S, or a method analogous thereto.

(Step 3)

This step is a step of producing compound (XXIII) or a salt thereof by reacting compound (XIV) or a salt thereof with compound (X) or a salt thereof in the presence of a condensing agent. This step can be carried out in the same manner as in the method described in Step 2 of Method A.

Compound (X) can be produced according to the method described in the below-mentioned Method T, or a method analogous thereto.

(Step 4)

This step is a step of producing compound (XXIV) or a salt thereof by reacting, compound (XXI) or a salt thereof with nitromethane. This step can be carried out in the same manner as in the method described in Step 2 of Method C.

(Step 5)

This step is a step of producing compound (XXV) or a salt thereof by reacting compound (XXII) or a salt thereof with nitromethane. This step can be carried out in the same manner as in the method described in Step 2 of Method C.

(Step 6)

This step is a step of producing compound (XXVI) or a salt thereof by reacting compound (XXIII) or a salt thereof with nitromethane. This step can be carried out in the same manner as in the method described in Step 2 of Method C.

(Step 7)

This step is a step of producing compound (XXVII) or a salt thereof by subjecting compound (XXIV) or a salt thereof to a reduction reaction. This step can be carried out in the same manner as in the method described in Step 3 of Method C.

(Step 8)

This step is a step of producing compound (XXVIII) or a salt thereof by subjecting compound (XXV) or a salt thereof to a reduction reaction. This step can be carried out in the same manner as in the method described in Step 3 of Method C.

(Step 9)

This step is a step of producing compound (XXIX) or a salt thereof by subjecting compound (XXVI) or a salt thereof to a reduction reaction. This step can be carried out in the same manner as in the method described in Step 3 of Method C.

(Step 10)

This step is a step of producing compound (IIb-II) or a salt thereof by reacting compound (XXVII) or a salt thereof with compound (XXX) or a salt thereof in the presence of a condensing agent. This step can be carried out in the same manner as in the method described in Step 2 of Method A.

Compound (XXX) may be a commercially available product, or can also be produced according to a method known per se or a method analogous thereto.

(Step 11)

This step is a step of producing compound (IIIb-II) or a salt thereof by reacting compound (XXVIII) or a salt thereof with compound (XXX) or a salt thereof in the presence of a condensing agent. This step can be carried out in the same manner as in the method described in Step 2 of Method A.

Compound (XXX) may be a commercially available product, or can also be produced according to a method known per se or a method analogous thereto.

(Step 12)

This step is a step of producing compound (IVb-II) or a salt thereof by reacting compound (XXIX) or a salt thereof with compound (XXX) or a salt thereof in the presence of a condensing agent. This step can be carried out in the same manner as in the method described in Step 2 of Method A.

Compound (XXX) may be a commercially available product, or can also be produced according to a method known per se or a

[Method E]

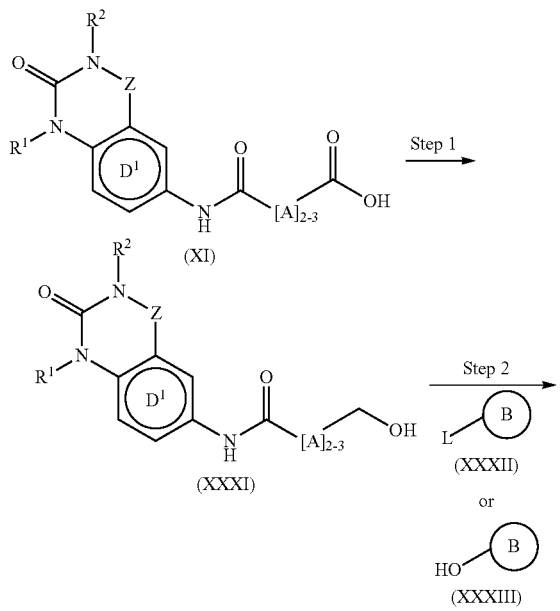

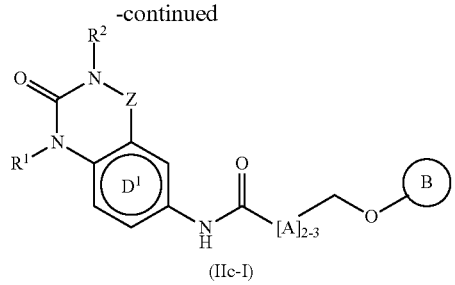

(IIc-I)

wherein L is a leaving group, and the other each symbol is as defined above.

Examples of the leaving group represented by L include halogen atoms (a chlorine atom, a bromine atom, an iodine atom and the like), substituted sulfonyloxy groups ($C_{1-6}$ alkylsulfonyloxy groups such as methanesulfonyloxy, ethanesulfonyloxy and the like; $C_{6-14}$ arylsulfonyloxy groups such as benzenesulfonyloxy, p-toluenesulfonyloxy and the like; $C_{7-16}$ aralkylsulfonyloxy groups such as benzylsulfonyloxy group and the like, and the like), acyloxy (acetoxy, benzoyloxy and the like), oxy groups substituted by a heterocycle or an aryl group (succinimide, benzotriazole, quinoline, 4-nitrophenyl and the like), heterocycle (imidazole and the like) and the like.

(Step 1)

This step is a step of producing compound (XXXI) or a salt thereof by subjecting compound (XI) or a salt thereof to a reduction reaction.

The reduction reaction can be carried out by employing reduction using a metal hydride, in a solvent that does not adversely influence.

Examples of the metal hydride include diisobutylaluminium hydride, aluminium hydride, lithium aluminium hydride, borane complexes (borane-THF complex, catecholborane, etc.) and the like, and borane-THF complexes and the like are preferable. The amount of the metal hydride to be used is, for example, about 1 to 50 mol, preferably about 1 to 10 mol, per 1 mol of compound (XI).

The reduction reaction using a metal hydride is generally carried out in a solvent inert to the reaction. Examples of the solvent include aromatic hydrocarbons (toluene, xylene, etc.), aliphatic hydrocarbons (heptane, hexane, etc.), halogenated hydrocarbons (chloroform, dichloromethane, etc.), ethers (diethyl ether, tetrahydrofuran, dioxane, etc.), alcohols (methanol, ethanol, 2-propanol, butanol, benzyl alcohol, etc.), nitriles (acetonitrile, etc.), N,N-dimethylformamide, dimethyl sulfoxide and the like. These solvents may be used in a mixture thereof in an appropriate ratio.

While the reaction time varies depending on the kind of the solvent, it is generally about −80 to 80° C., preferably about −40 to 40° C., and the reaction time is generally about 5 min to 48 hr, preferably about 1 to 24 hr.

(Step 2)

This step is a step of producing compound (IIc-I) or a salt thereof by reacting compound (XXXI) or a salt thereof with compound (XXXII) or a salt thereof in the presence of a base, or a step of producing compound (IIc-I) or a salt thereof by reacting compound (XXXI) or a salt thereof with compound (XXXIII) or a salt thereof in the presence of the Mitsunobu reagent and an organophosphorous reagent.

Compound (XXXII) and compound (XXXIII) may be a commercially available product, or can also be produced according to a method known per se or a method analogous thereto.

While the amount of compound (XXXII) to be used varies depending on the kind of the solvent and other reaction condition, it is about 1 to 10 mol equivalent, preferably about 1 to 5 mol equivalent, per 1 mol of compound (XXXI).

Examples of the base used in the reaction of compound (XXXI) or a salt thereof with compound (XXXII) or a salt thereof include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, and the like), organic bases (amines such as trimethylamine, triethylamine, diisopropylethylamine and the like, aromatic amines such as pyridine, 4-dimethylaminopyridine and the like, and the like) and the like. Among them, sodium hydride, potassium carbonate or cesium carbonate is preferable. While the amount of the base to be used varies depending on the kind of the solvent and other reaction condition, it is about 1 to 10 mol equivalent, preferably about 1 to 5 mol equivalent, per 1 mol of compound (XXXI).

The reaction of compound (XXXI) or a salt thereof with compound (XXXII) or a salt thereof is generally carried out in a solvent that does not adversely influence.

Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. Among them, tetrahydrofuran, acetonitrile or dimethylformamide is preferable. These solvents may be used in a mixture of two or more kinds thereof in an appropriate ratio.

While the reaction time varies depending on the kind of the solvent, it is, for example, within about 0 to 200° C., preferably about 50 to 100° C. While the reaction time varies depending on the kind of compound (XXXI) or a salt thereof and the reaction temperature and the like, it is, for example, about 0.5 to 100 hr, preferably about 0.5 to 24 hr.

While the amount of compound (XXXIII) to be used varies depending on the kind of the solvent and other reaction condition, it is about 1 to 10 mol equivalent, preferably about 1 to 5 mol equivalent, per 1 mol of compound (XXXI).

Examples of the Mitsunobu reagent used in the reaction of compound (XXXI) or a salt thereof with compound (XXXIII) or a salt thereof include azodicarboxylates such as diethyl azodicarboxylate, diisopropyl azodicarboxylate and the like, and the like. Among them, diisopropyl azodicarboxylate is preferable. While the amount of the Mitsunobu reagent to be used varies depending on the kind of the solvent and other reaction condition, it is about 1 to 10 mol equivalent, preferably about 1 to 5 mol equivalent, per 1 mol of compound (XXXI).

Examples of the organophosphorous reagent used in the reaction of compound (XXXI) or a salt thereof with compound (XXXIII) or a salt thereof include organophosphorous compounds such as tributylphosphine, triphenylphosphine and the like. Among them, triphenylphosphine is preferable. While the amount of the organophosphorous reagent to be used varies depending on the kind of the solvent and other reaction condition, it is generally about 1 to 10 mol equivalent, preferably about 1 to 5 mol equivalent, per 1 mol of compound (XXXI).

The reaction of compound (XXXI) or a salt thereof with the compound represented by the formula (XXXIII) or a salt thereof is generally carried out in a solvent that does not adversely influence.

Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. Among them, toluene or tetrahydrofuran is preferable. These solvents may be used in a mixture of two or more kinds thereof in an appropriate ratio.

While the reaction time varies depending on the kind of the solvent, it is, for example, within about 0 to 200° C., preferably about 50 to 100° C. While the reaction time varies depending on the kind of compound (XXXI) or a salt thereof and the reaction temperature and the like, it is, for example, about 0.5 to 100 hr, preferably about 0.5 to 24 hr.

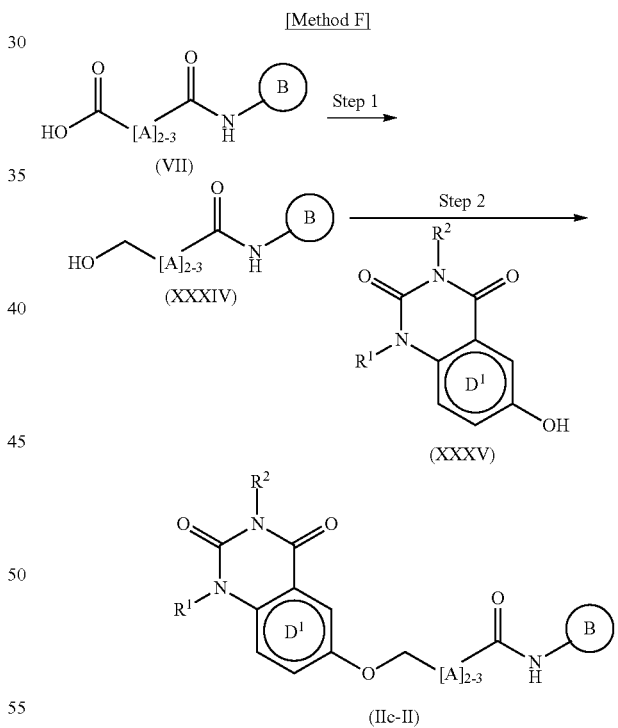

wherein each symbol is as defined above.

(Step 1)

This step is a step of producing compound (XXXIV) or a salt thereof by subjecting compound (VII) or a salt thereof to a reduction reaction. This step can be carried out in the same manner as in the method described in Step 1 of Method E.

Compound (VII) may be a commercially available product, or can also be produced according to a method known per se or a method analogous thereto.

(Step 2)

This step is a step of producing compound (IIc-II) or a salt thereof by reacting compound (XXXIV) or a salt thereof with compound (XXXV) or a salt thereof in the presence of the Mitsunobu reagent and an organophosphorous reagent. This step can be carried out in the same manner as in the method described in the reaction using the "Mitsunobu reagent and organophosphorous reagent" of Step 2 of Method E.

Compound (XXXV) can be produced according to the method described in the below-mentioned Method N, or a method analogous thereto.

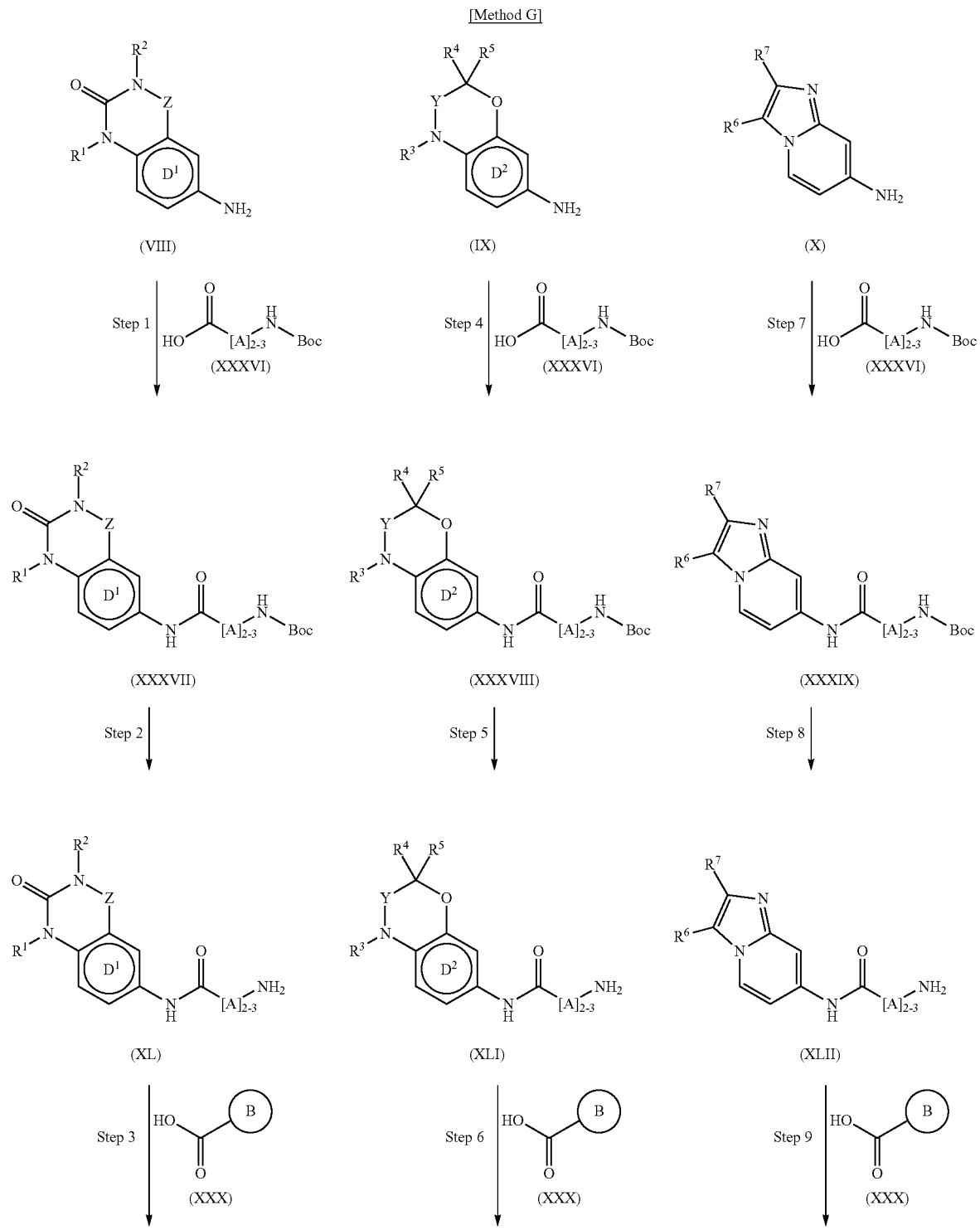

-continued

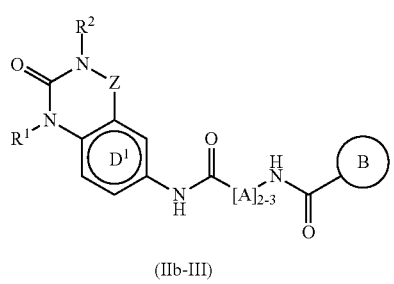

(IIb-III)

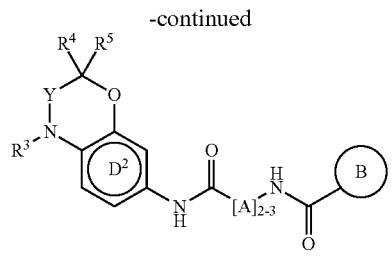

(IIIb-III)

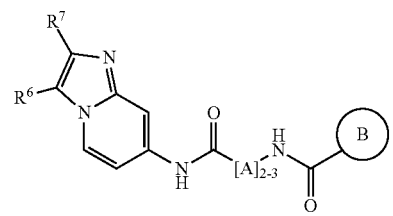

(IVb-III)

wherein each symbol is as defined above.

(Step 1)

This step is a step of producing compound (XXXVII) or a salt thereof by reacting compound (VIII) or a salt thereof with compound (XXXVI) or a salt thereof in the presence of a condensing agent. This step can be carried out in the same manner as in the method described in Step 2 of Method A.

Compound (XXXVI) may be a commercially available product, or can also be produced according to a method known per se or a method analogous thereto.

(Step 2)

This step is a step of producing compound (XL) or a salt thereof by subjecting compound (XXXVII) or a salt thereof to a deprotection reaction.

The deprotection reaction can be carried out according to a method known per se (e.g., the method described in "Protective Groups in Organic Synthesis, 3rd Ed", Wiley-Interscience, Inc. (1999) (Theodora W. Greene, Peter G. M. Wuts)). The deprotection reaction is generally carried out, for example, in the presence of an acid, in a solvent that does not adversely influence the reaction, if necessary, while depending on the kind of compound (XXXVII).

Examples of the acid include mineral acids (hydrochloric acid, hydrobromic acid, sulfuric acid, hydrogen chloride and the like), carboxylic acids (acetic acid, trifluoroacetic acid, trichloroacetic acid and the like), sulfonic acids (methanesulfonic acid, p-toluenesulfonic acid and the like), Lewis acids (aluminium chloride, tin chloride, zinc bromide and the like) and the like. They may be used in a mixture of two or more kinds thereof, if necessary. While the amount of the acid to be used varies depending on the kind of the solvent and other reaction condition, it is generally about 0.1 mol equivalent or more, per 1 mol of compound (XXXVII), and the acid may be used as a solvent.

Examples of the solvent that does not adversely influence the reaction include alcohols (methanol, ethanol, propanol, 2-propanol, butanol, isobutanol, t-butanol and the like), aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), carboxylic acids (acetic acid and the like), amides (N,N-dimethylformamide and the like), sulfoxides (dimethyl sulfoxide and the like), water and mixed solvents thereof.

While the reaction time varies depending on the kind of the solvent, it is, for example, within about −50 to 200° C., preferably about 0 to 100° C. While the reaction time varies depending on the kind of compound (XXXVII), the reaction temperature and the like, it is, for example, about 0.5 to 100 hr, preferably about 0.5 to 24 hr.

(Step 3)

This step is a step of producing compound (IIb-III) or a salt thereof by reacting compound (XL) or a salt thereof with compound (XXX) or a salt thereof in the presence of a condensing agent. This step can be carried out in the same manner as in the method described in Step 2 of Method A.

Compound (XXX) may be a commercially available product, or can also be produced according to a method known per se or a method analogous thereto.

(Step 4)

This step is a step of producing compound (XXXVIII) or a salt thereof by reacting compound (IX) or a salt thereof with compound (XXXVI) or a salt thereof in the presence of a condensing agent. This step can be carried out in the same manner as in the method described in Step 2 of Method A.

Compound (XXXVI) may be a commercially available product, or can also be produced according to a method known per se or a method analogous thereto.

(Step 5)

This step is a step of producing compound (XLI) or a salt thereof by subjecting compound (XXXVIII) or a salt thereof to a deprotection reaction. This step can be carried out in the same manner as in the method described in Step 2 of Method G.

(Step 6)

This step is a step of producing compound (IIIb-III) or a salt thereof by reacting compound (XLI) or a salt thereof with compound (XXX) or a salt thereof in the presence of a condensing agent. This step can be carried out in the same manner as in the method described in Step 2 of Method A.

Compound (XXX) may be a commercially available product, or can also be produced according to a method known per se or a method analogous thereto.

(Step 7)

This step is a step of producing compound (XXXIX) or a salt thereof by reacting compound (X) or a salt thereof with compound (XXXVI) or a salt thereof in the presence of a condensing agent. This step can be carried out in the same manner as in the method described in Step 2 of Method A.

Compound (XXXVI) may be a commercially available product, or can also be produced according to a method known per se or a method analogous thereto.

(Step 8)

This step is a step of producing compound (XLII) or a salt thereof by subjecting compound (XXXIX) or a salt thereof to a deprotection reaction. This step can be carried out in the same manner as in the method described in Step 2 of Method G.

(Step 9)

This step is a step of producing compound (IVb-III) or a salt thereof by reacting compound (XLII) or a salt thereof with compound (XXX) or a salt thereof in the presence of a condensing agent. This step can be carried out in the same manner as in the method described in Step 2 of Method A.

Compound (XXX) may be a commercially available product, or can also be produced according to a method known per se or a method analogous thereto.

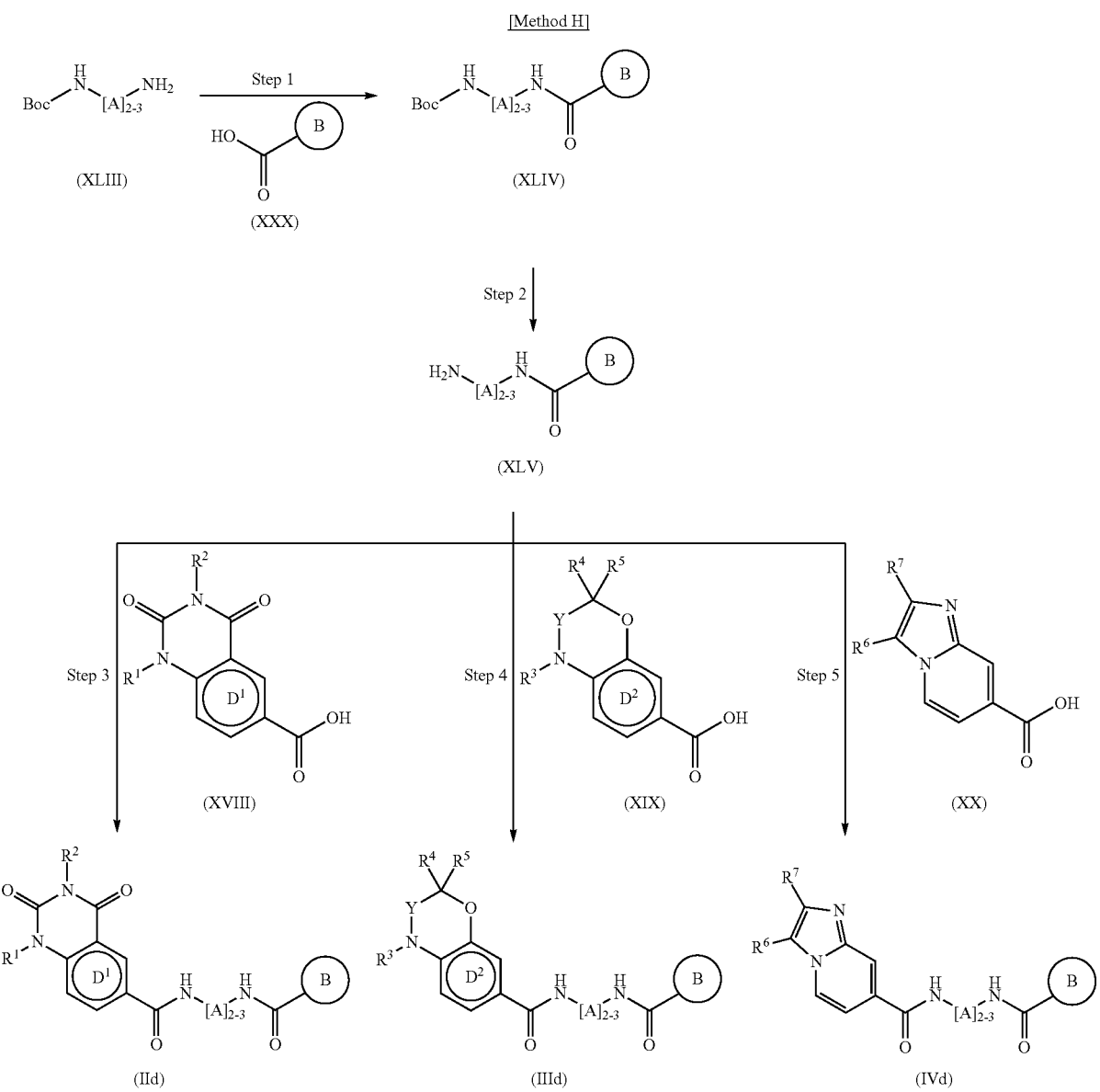

wherein each symbol is as defined above.

(Step 1)

This step is a step of producing compound (XLIV) or a salt thereof by reacting compound (XLIII) or a salt thereof with compound (XXX) or a salt thereof in the presence of a condensing agent. This step can be carried out in the same to manner as in the method described in Step 2 of Method A.

Compound (XLIII) may be a commercially available product, or can also be produced according to a method known per se or a method analogous thereto.

(Step 2)

This step is a step of producing compound (XLV) or a salt thereof by subjecting compound (XLIV) or a salt thereof to a deprotection reaction. This step can be carried out in the same manner as in the method described in Step 2 of Method G.

(Step 3)

This step is a step of producing compound (IId) or a salt thereof by reacting compound (XLV) or a salt thereof with compound (XVIII) or a salt thereof in the presence of a condensing agent. This step can be carried out in the same manner as in the method described in Step 2 of Method A.

Compound (XVIII) can be produced according to the method described in the below-mentioned Method L or O, or a method analogous thereto.

(Step 4)

This step is a step of producing compound (IIId) or a salt thereof by reacting compound (XLV) or a salt thereof with compound (XIX) or a salt thereof in the presence of a condensing agent. This step can be carried out in the same manner as in the method described in Step 2 of Method A.

Compound (XIX) can be produced according to the method described in the below-mentioned Method U, or a method analogous thereto.

(Step 5)

This step is a step of producing compound (IVd) or a salt thereof by reacting compound (XLV) or a salt thereof with compound (XX) or a salt thereof in the presence of a condensing agent. This step can be carried out in the same manner as in the method described in Step 2 of Method A.

Compound (XX) can be produced according to the method described in the below-mentioned Method T, or a method analogous thereto.

(Step 3)

This step is a step of producing compound (IIIe) or a salt thereof by reacting compound (XLVII) or a salt thereof with compound (IX) or a salt thereof in the presence of a

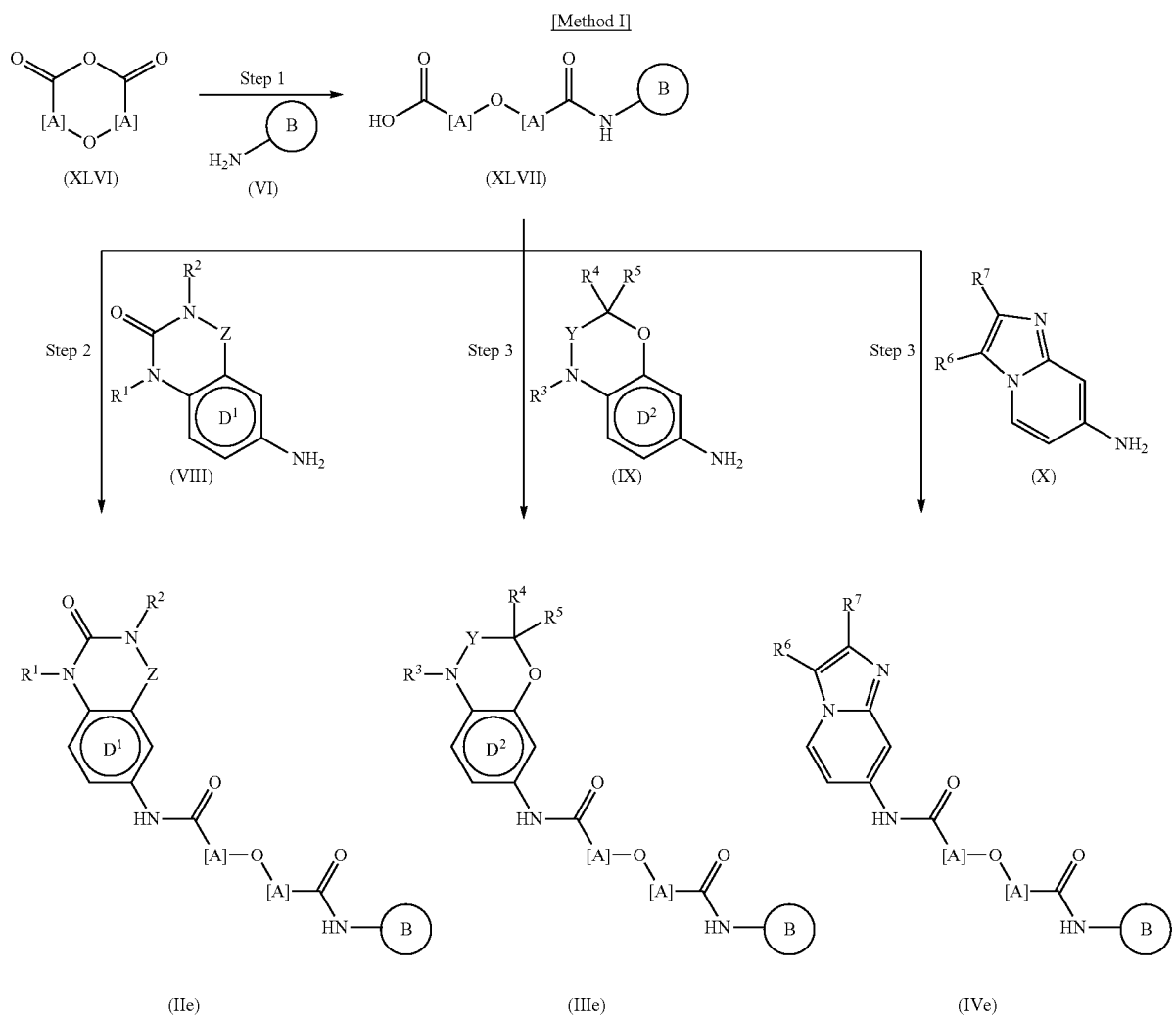

wherein each symbol is as defined above.

(Step 1)

This step is a step of producing compound (XLVII) or a salt thereof by reacting compound (XLVI) or a salt thereof with compound (VI) or a salt thereof.

Compound (XLVI) and compound (VI) may be a commercially available product, or can also be produced according to a method known per se or a method analogous thereto.

(Step 2)

This step is a step of producing compound (IIe) or a salt thereof by reacting compound (XLVII) or a salt thereof with compound (VIII) or a salt thereof in the presence of a condensing agent. This step can be carried out in the same manner as in the method described in Step 2 of Method A.

Compound (VIII) can be produced according to the method described in the below-mentioned Method L, or a method analogous thereto.

condensing agent. This step can be carried out in the same manner as in the method described in Step 2 of Method A.

Compound (IX) can be produced according to the method described in the below-mentioned Method P, Q, R or S, or a method analogous thereto.

(Step 4)

This step is a step of producing compound (IVe) or a salt thereof by reacting compound (XLVII) or a salt thereof with compound (X) or a salt thereof in the presence of a condensing agent. This step can be carried out in the same manner as in the method described in Step 2 of Method A.

Compound (X) can be produced according to the method described in the below-mentioned Method T, or a method analogous thereto.

[Method J]

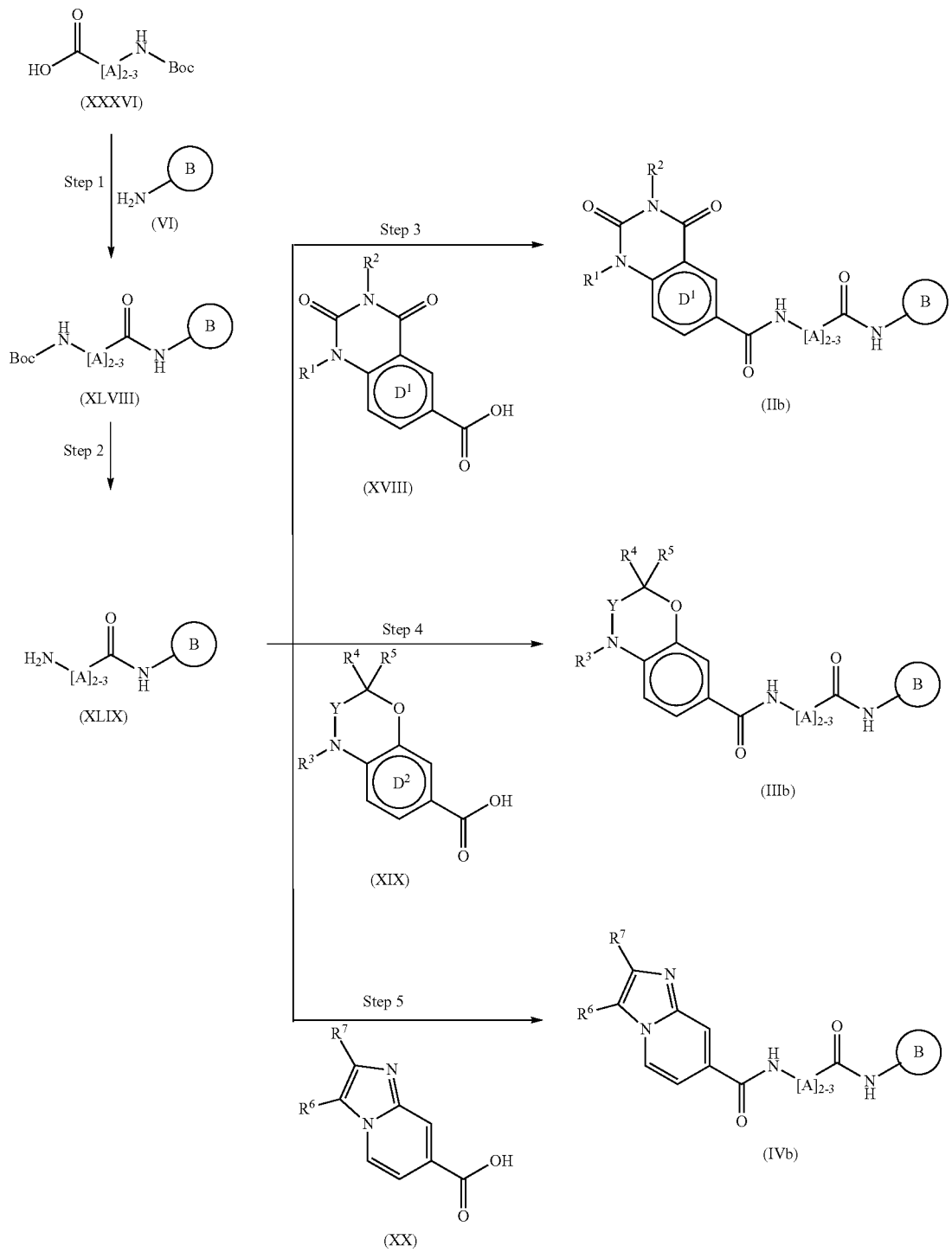

wherein each symbol is as defined above.

(Step 1)

This step is a step of producing compound (XLVIII) or a salt thereof by reacting compound (XXXVI) or a salt thereof with compound (VI) or a salt thereof in the presence of a condensing agent. This step can be carried out in the same manner as in the method described in Step 2 of Method A.

Compound (XXXVI) and compound (VI) may be a commercially available product, or can also be produced according to a method known per se or a method analogous thereto.

(Step 2)

This step is a step of producing compound (XLIX) or a salt thereof by subjecting compound (XLVIII) or a salt thereof to a deprotection reaction. This step can be carried out in the same manner as in the method described in Step 2 of Method G.
(Step 3)
This step is a step of producing compound (IIb) or a salt thereof by reacting compound (XLIX) or a salt thereof with compound (XVIII) or a salt thereof in the presence of a condensing agent. This step can be carried out in the same manner as in the method described in Step 2 of Method A.

Compound (XVIII) can be produced according to the method described in the below-mentioned Method O, or a method analogous thereto.
(Step 4)
This step is a step of producing compound (IIIb) or a salt thereof by reacting compound (XLIX) or a salt thereof with compound (XIX) or a salt thereof in the presence of a condensing agent. This step can be carried out in the same manner as in the method described in Step 2 of Method A.

Compound (XIX) can be produced according to the method described in the below-mentioned Method U, or a method analogous thereto.
(Step 5)
This step is a step of producing compound (IVb) or a salt thereof by reacting compound (XLIX) or a salt thereof with compound (XX) or a salt thereof in the presence of a condensing agent. This step can be carried out in the same manner as in the method described in Step 2 of Method A.

Compound (XX) can be produced according to the method described in the below-mentioned Method T, or a method analogous thereto.

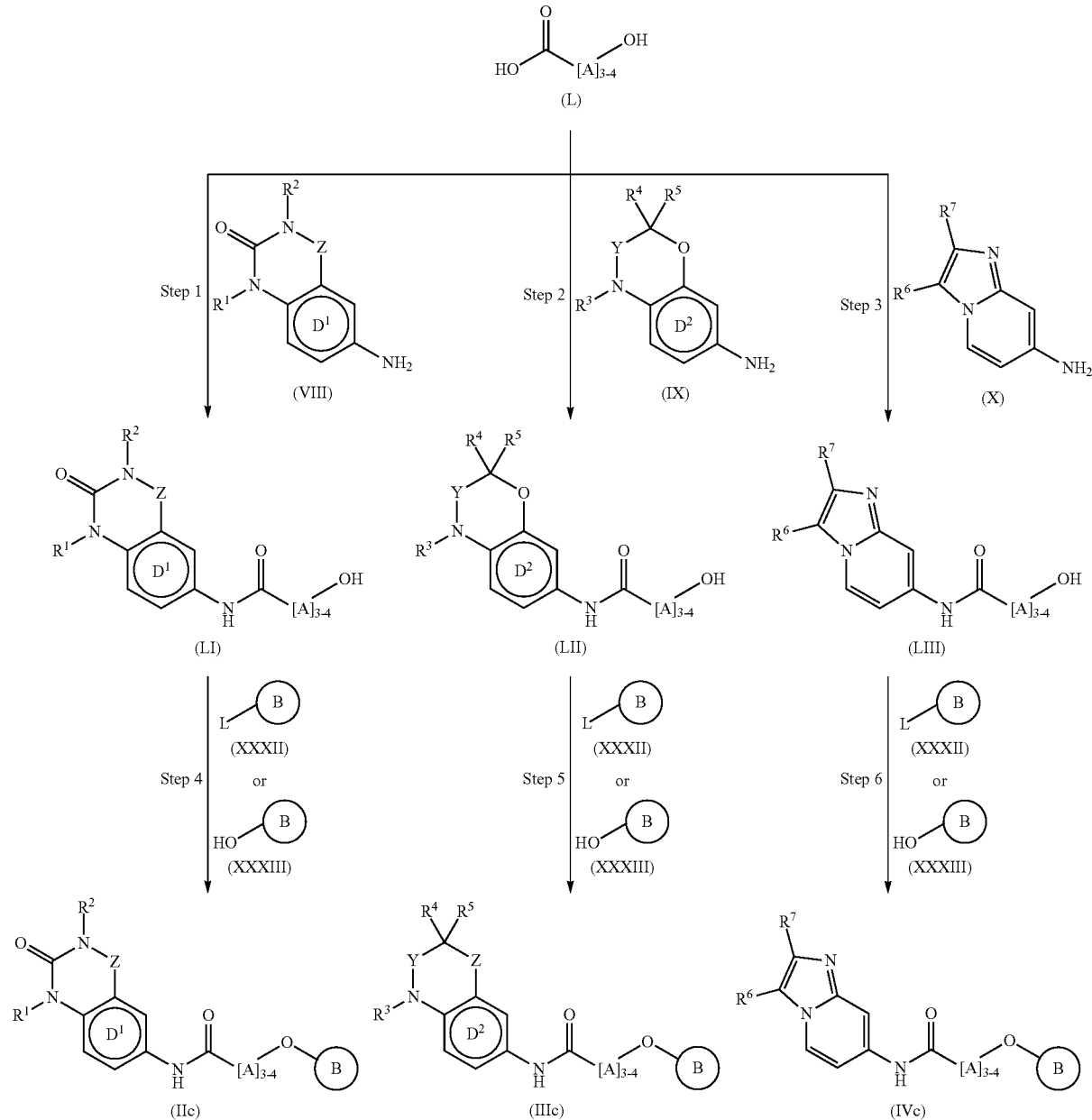

wherein each symbol is as defined above.

(Step 1)

This step is a step of producing compound (LI) or a salt thereof by reacting compound (L) or a salt thereof with compound (VIII) or a salt thereof in the presence of a condensing agent. This step can be carried out in the same manner as in the method described in Step 2 of Method A.

Compound (L) may be a commercially available product, or can also be produced according to a method known per se or a method analogous thereto.

Compound (VIII) can be produced according to the method described in the below-mentioned Method L or M, or a method analogous thereto.

(Step 2)

This step is a step of producing compound (LII) or a salt thereof by reacting compound (L) or a salt thereof with compound (IX) or a salt thereof in the presence of a condensing agent. This step can be carried out in the same manner as in the method described in Step 2 of Method A.

Compound (IX) can be produced according to the method described in the below-mentioned Method P, Q, R or S, or a method analogous thereto.

(Step 3)

This step is a step of producing compound (LIII) or a salt thereof by reacting compound (L) or a salt thereof with compound (X) or a salt thereof in the presence of a condensing agent. This step can be carried out in the same manner as in the method described in Step 2 of Method A.

Compound (X) can be produced according to the method described in the below-mentioned Method T, or a method analogous thereto.

(Step 4)

This step is a step of producing compound (IIc) or a salt thereof by reacting compound (LI) or a salt thereof with compound (XXXII) or a salt thereof in the presence of a base, or a step of producing compound (IIc) or a salt thereof by reacting compound (LI) or a salt thereof with compound (XXXIII) or a salt thereof in the presence of the Mitsunobu reagent and an organophosphorous reagent. This step can be carried out in the same manner as in the method described in Step 2 of Method E.

Compound (XXXII) or compound (XXXIII) may be a commercially available product, or can also be produced according to a method known per se or a method analogous thereto.

(Step 5)

This step is a step of producing compound (IIIc) or a salt thereof by reacting compound (LII) or a salt thereof with compound (XXXII) or a salt thereof in the presence of a base, or a step of producing compound (IIIc) or a salt thereof by reacting compound (LII) or a salt thereof with compound (XXXIII) or a salt thereof in the presence of the Mitsunobu reagent and an organophosphorous reagent. This step can be carried out in the same manner as in the method described in Step 2 of Method E.

(Step 6)

This step is a step of producing compound (IVc) or a salt thereof by reacting compound (LIII) or a salt thereof with compound (XXXII) or a salt thereof in the presence of a base, or is a step of producing compound (IVc) or a salt thereof by reacting compound (LIII) or a salt thereof with compound (XXXIII) or a salt thereof in the presence of the Mitsunobu reagent and an organophosphorous reagent. This step can be carried out in the same manner as in the method described in Step 2 of Method E.

Compounds (VIII), (VIII-I), (IX), (IX-I), (IX-II), (IX-III), (IX-IV), (IX-V), (IX-VI), (X), (XVIII), (XVIII-I), (XIX), (XIX-I), (XIX-II), (XX) and (XXXV) used in Method A to Method K can be produced according to the following Method L to Method U.

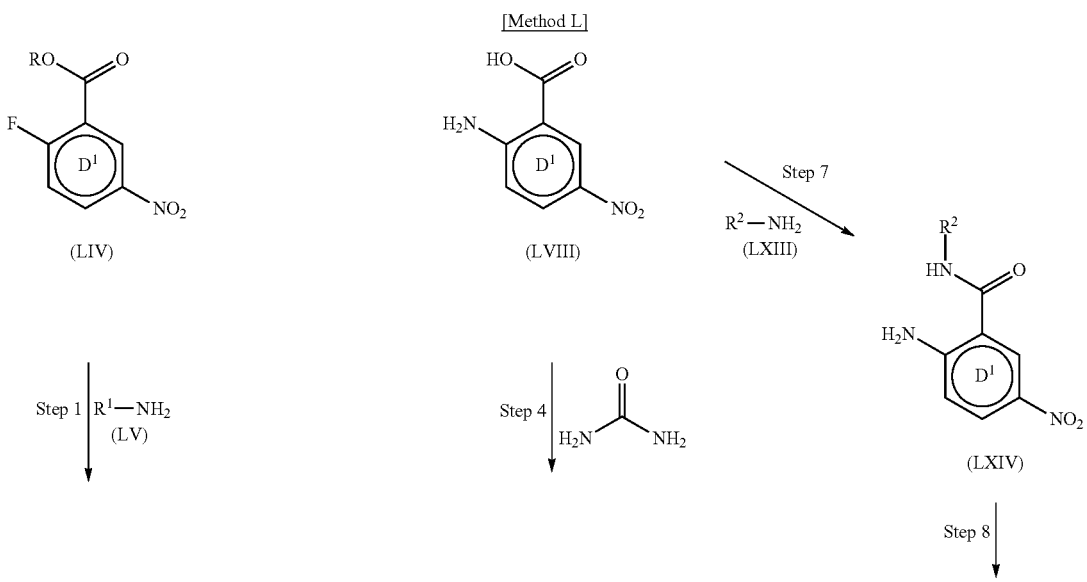

[Method L]

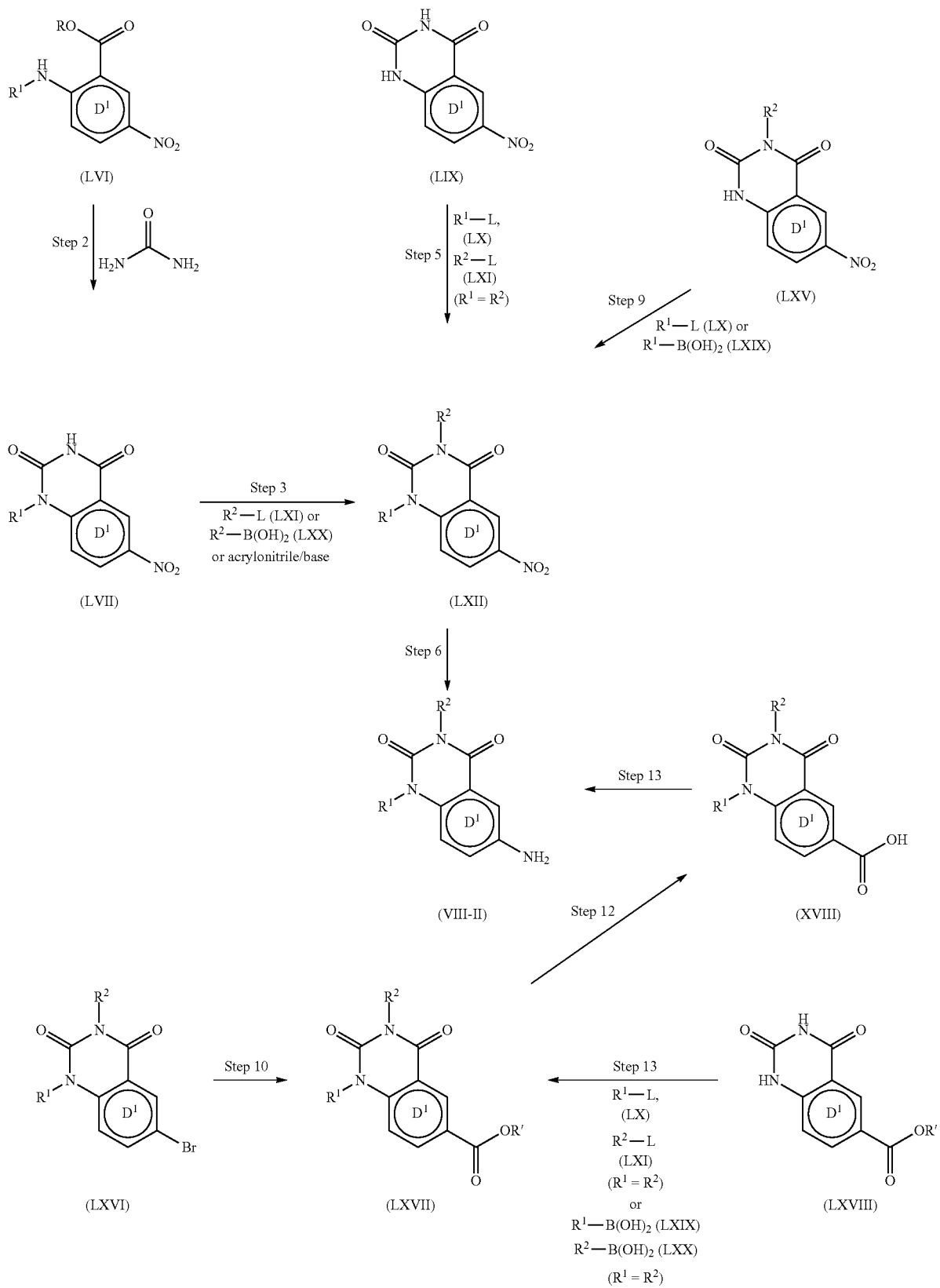

wherein R' is an optionally substituted hydrocarbon group, and the other each symbol is as defined above.
(Step 1)

This step is a step of producing compound (LVI) or a salt thereof by reacting compound (LIV) or a salt thereof with compound (LV) or a salt thereof in the presence of a base.

Compound (LIV) and compound (LV) may be a commercially available product, or can also be produced according to a method known per se or a method analogous thereto.

Examples of the base used in this step include alkali metal hydroxides (sodium hydroxide, potassium hydroxide and the like), hydrogencarbonates (sodium hydrogencarbonate, potassium hydrogencarbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1 to 100 mol equivalent, preferably about 1 to 5 mol equivalent, per 1 mol of compound (LIV).

The above-mentioned reaction is carried out in a solvent that does not adversely influence. Examples of the solvent to be used include hydrocarbons (benzene, toluene and the like), ethers (diethyl ether, dioxane, tetrahydrofuran and the like), esters (ethyl acetate and the like), halogenated hydrocarbons (chloroform, dichloromethane and the like), amides (N,N-dimethylformamide and the like) and the like, and they may be mixed as appropriate.

While the reaction time varies depending on the kind of the solvent, it is, for example, within about 0 to 200° C., preferably about 25 to 100° C., and the reaction time is, for example, about 0.5 to 100 hr, preferably about 0.5 to 24 hr.
(Step 2)

This step is a step of producing compound (LVII) or a salt thereof by reacting compound (LVI) or a salt thereof with urea.

This step is carried out in a solvent that does not adversely influence. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylacetamide and the like), sulfoxides (dimethyl sulfoxide and the like) and the like. Among them, dimethylacetamide is preferable. These solvents may be used in a mixture of two or more kinds thereof in an appropriate ratio. Alternatively, the reaction can be carried out without a solvent.

When a solvent is used, the amount of the urea to be used is about 1 to 10 mol equivalent, preferably about 1 to 5 mol equivalent, per 1 mol of compound (LVI). When a solvent is not used, the amount thereof is about 1 to 500 mol equivalent, preferably about 1 to 50 mol equivalent, per 1 mol of compound (LVI).

When a solvent is used, while the reaction time varies depending on the kind of the solvent, it is, for example, within about 0 to 200° C., preferably about 100 to 200° C. In this case, the reaction may be carried out under microwave irradiation for the progress of the reaction. The reaction time is, for example, about 0.1 to 100 hr, preferably about 0.1 to 24 hr.

When a solvent is not used, the reaction temperature is, for example, within about 0 to 300° C., preferably about 100 to 200° C. The reaction time is, for example, about 0.1 to 100 hr, preferably about 0.1 to 24 hr.
(Step 3)

This step is a step of producing compound (LXII) or a salt thereof from compound (LVII). For example, (1) a method of reacting compound (LVII) with compound (LXI) in the presence of a base, (2) a method of reacting compound (LVII) with compound (LXX) in the presence of copper(II) acetate and bipyridine, or (3) a method of reacting compound (LVII) with acrylonitrile in the presence of a base, can be employed.

Examples of the base used in the "method of reacting compound (LVII) with compound (LXI) in the presence of a base" include alkali metal hydroxides (sodium hydroxide, potassium hydroxide and the like), alkali metal hydrides (sodium hydride, lithium hydride and the like), hydrogencarbonates (sodium hydrogencarbonate, potassium hydrogencarbonate and the like), carbonates (sodium carbonate, potassium carbonate and the like), acetates (sodium acetate and the like), tertiary amines (trimethylamine, triethylamine, N-methylmorpholine and the like), aromatic amines (pyridine, picoline, N,N-dimethylaniline and the like) and the like. The amount of the base to be used is generally about 1 to 100 mol equivalent, preferably about 1 to 5 mol equivalent, per 1 mol of compound (LVII).

This reaction is carried out in a solvent that does not adversely influence. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. These solvents may be used in a mixture of two or more kinds thereof in an appropriate ratio.

While the reaction time varies depending on the kind of the solvent, it is, for example, within about −50 to 200° C., preferably about 0 to 100° C. While the reaction time varies depending on the kind of compound (LVII) or a salt thereof, the reaction temperature and the like, it is, for example, about 0.5 to 100 hr, preferably about 0.5 to 24 hr.

Compound (LXI) may be a commercially available product, or can also be produced according to a method known per se or a method analogous thereto. The amount of compound (LXI) to be used is about 1 to 10 mol equivalent, preferably about 1 to 5 mol equivalent, per 1 mol of compound (LVII).

The amount of the copper(II) acetate to be used in the "method of reacting compound (LVII) with compound (LXX) in the presence of copper(II) acetate and bipyridine" is about 1 to 10 mol equivalent, preferably about 1 to 2 mol equivalent, per 1 mol of compound (LVII).

The amount of the bipyridine to be used is about 1 to 10 mol equivalent, preferably about 1 to 2 mol equivalent, per 1 mol of compound (LVII).

This reaction is carried out in a solvent that does not adversely influence. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, dichloroethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. These solvents may be used in a mixture of two or more kinds thereof in an appropriate ratio.

While the reaction time varies depending on the kind of the solvent, it is, for example, within about −50 to 200° C., preferably about 0 to 100° C. While the reaction time varies depending on the kind of compound (LVII) or a salt thereof, the reaction temperature and the like, it is, for example, about 0.5 to 100 hr, preferably about 0.5 to 24 hr.

A base may be added for the progress of the reaction. Examples of the base used in this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, and the like), organic bases (amines such as trimethylamine, triethylamine, diisopropylethylamine and the like, aromatic amines such as pyridine, 4-dimethylaminopyridine and the like, and the like) and the like. While the amount of the base to be used varies depending on the kind of the solvent and other reaction condition, it is generally about 1 to 10 mol equivalent, preferably about 1 to 5 mol equivalent, per 1 mol of compound (LVII).

Compound (LXX) may be a commercially available product, or can also be produced according to a method known per se or a method analogous thereto. The amount of compound (LXX) to be used is about 1 to 10 mol equivalent, preferably about 1 to 5 mol equivalent, per 1 mol of compound (LVII).

Examples of the base used in the "method of reacting compound (LVII) with acrylonitrile in the presence of a base" include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, alkali metal alkoxides such as sodium methoxide, sodium ethoxide and the like, and the like), organic bases (amines such as trimethylamine, triethylamine, diisopropylethylamine and the like, aromatic amines such as pyridine, 4-dimethylaminopyridine and the like, and the like) and the like. While the amount of the base to be used varies depending on the kind of the solvent and other reaction condition, it is generally about 1 to 10 mol equivalent, preferably about 1 to 5 mol equivalent, per 1 mol of compound (LVII).

While the amount of the acrylonitrile to be used varies depending on the kind of the solvent and other reaction condition, it is generally about 1 to 10 mol equivalent, preferably about 1 to 5 mol equivalent, per 1 mol of compound (LVII).

This reaction is carried out in a solvent that does not adversely influence. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, dichloroethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), amides (dimethylformamide and the like), sulfoxides (dimethyl sulfoxide and the like) and the like. These solvents may be used in a mixture of two or more kinds thereof in an appropriate ratio.

While the reaction time varies depending on the kind of the solvent, it is, for example, within about −50 to 200° C., preferably about 0 to 100° C. While the reaction time varies depending on the kind of compound (LVII) or a salt thereof, the reaction temperature and the like, it is, for example, about 0.5 to 100 hr, preferably about 0.5 to 24 hr.

(Step 4)

This step is a step of producing compound (LIX) or a salt thereof by reacting compound (LVIII) or a salt thereof with urea.

Compound (LVIII) may be a commercially available product, or can also be produced according to a method known per se or a method analogous thereto.

This step can be carried out in the same manner as in the method described in Step 2 of Method L.

(Step 5)

This step is a step of producing compound (LXII) or a salt thereof from compound (LIX) in the presence of a base, when compound (LX) and compound (LXI) are same.

Compound (LX) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 6)

This step is a step of producing compound (VIII-II) or a salt thereof by subjecting compound (LXII) or a salt thereof to a reduction reaction. This step can be carried out in the same manner as in the method described in Step 3 of Method C.

(Step 7)

This step is a step of producing compound (LXIV) or a salt thereof by reacting compound (LVIII) or a salt thereof with compound (LXIII) or a salt thereof in the presence of a condensing agent.

Compound (LXIII) may be a commercially available product, or can also be produced according to a method known per se or a method analogous thereto.

This step can be carried out in the same manner as in the method described in Step 2 of Method A.

(Step 8)

This step is a step of producing compound (LXV) or a salt thereof from compound (LXIV) or a salt thereof using a carbonylating reagent.

Examples of the carbonylating reagent include phosgene, carbodiimide and the like. In addition, a base may be added for the favorable progress of the reaction.

While the amount of the carbonylating reagent to be used varies depending on the kind of the solvent and other reaction condition, it is generally about 1 to 10 mol equivalent, preferably about 1 to 5 mol equivalent, per 1 mol of compound (LXIV).

Examples of the base include organic bases (amines such as trimethylamine, triethylamine, diisopropylethylamine and the like, aromatic amines such as pyridine and the like, and the like) and the like.

While the amount of the base to be used varies depending on the kind of the solvent and other reaction condition, it is generally about 1 to 10 mol equivalent, preferably about 1 to 5 mol equivalent, per 1 mol of compound (LXIV).

This reaction is carried out in a solvent that does not adversely influence. Examples of the solvent that does not adversely influence the reaction include aromatic hydrocarbons (benzene, toluene, xylene and the like), aliphatic hydrocarbons (hexane, heptane and the like), halogenated hydrocarbons (dichloromethane, dichloroethane, chloroform and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like) and the like. These solvents may be used in a mixture of two or more kinds thereof in an appropriate ratio.

While the reaction time varies depending on the kind of the solvent, it is, for example, within about −50 to 200° C., preferably about 0 to 100° C. While the reaction time varies depending on the kind of compound (LXIV) or a salt thereof, the reaction temperature and the like, it is, for example, about 0.5 to 100 hr, preferably about 0.5 to 24 hr.
(Step 9)

This step is a step of producing compound (LXII) or a salt thereof from compound (LXV) or a salt thereof. For example, (1) a method of reacting compound (LXV) or a salt thereof with compound (LX) in the presence of a base, or (2) a method of reacting compound (LXV) or a salt thereof with compound (LXIX) in the presence of copper(II) acetate and bipyridine can be employed.

Compound (LX) and compound (LXIX) may be a commercially available product, or can also be produced according to a method known per se or a method analogous thereto.

This step can be carried out in the same manner as in the method described in the "method of reacting compound (LVII) with compound (LXI) in the presence of a base" or the "method of reacting compound (LVII) with compound (LXX) in the presence of copper(II) acetate and bipyridine" of Step 3 of Method L.
(Step 10)

This step is a step of producing compound (LXVII) or a salt thereof by reacting compound (LXVI) or a salt thereof with an alkyl alcohol optionally having substituent(s) using a transition metal catalyst under carbon monoxide atmosphere.

Examples of the transition metal catalyst include palladium catalysts (palladium acetate, palladium chloride, tetrakis(triphenylphosphine)palladium and the like), nickel catalysts (nickel chloride and the like) and the like. An organophosphorous reagent such as triphenylphosphine, 1,1'-bis(diphenylphosphino)ferrocene (dppf) and the like can be used, if necessary. While the amount of the catalyst to be used varies depending on the kind thereof, it is generally about 0.0001 to 1 mol, preferably about 0.01 to 0.5 mol, per 1 mol of compound (LXVI). The amount of the organophosphorous reagent to be used is preferably about 0.01 to 2 mol, per 1 mol of compound (LXVI).

As an alkyl alcohol optionally having substituent(s), an excess amount of methanol or ethanol is generally used.

This reaction is carried out in a solvent that does not adversely influence. Examples of the solvent that does not adversely influence the reaction include aromatic hydrocarbons (benzene, toluene, xylene and the like), alcohols (methanol, ethanol and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), aprotic polar solvents (dimethylformamide, dimethyl sulfoxide, hexamethylphosphoroamide and the like), water and the like. These solvents may be used in a mixture of two or more kinds thereof in an appropriate ratio.

In addition, the reaction can advantageously proceed by addition of a base or a salt. Examples of the base or salt include inorganic bases (alkali metal hydroxides such as sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, and the like), organic bases (amines such as trimethylamine, triethylamine, diisopropylethylamine and the like, aromatic amines such as pyridine and the like, and the like) and the like. The amount of the base or salt to be used is about 1 to 100 mol equivalent, preferably about 1 to 10 mol equivalent, per 1 mol of compound (LXVI).

The reaction is generally carried out under carbon monoxide atmosphere at normal pressure, and it can be carried out under pressured (for example about 3 to 10 atm), if necessary.

While the reaction time varies depending on the kind of the solvent, it is, for example, within about −50 to 200° C., preferably about 20 to 150° C. While the reaction time varies depending on the kind of compound (LXVI) or a salt thereof, the reaction temperature and the like, it is, for example, about 0.5 to 100 hr, preferably about 0.5 to 24 hr.
(Step 11)

This step is a step of producing compound (LXVII) or a salt thereof from compound (LXVIII) in the presence of a base, when compound (LX) and compound (LXI) are same, or compound (LXIX) and compound (LXX) are same.

Compound (LX) or compound (LXIX) may be a commercially available product, or can also be produced according to a method known per se or a method analogous thereto.

This step can be carried out in the same manner as in the method described in the "method of reacting compound (LVII) with compound (LXI) in the presence of a base" or the "method of reacting compound (LVII) with compound (LXX) in the presence of copper(II) acetate and bipyridine" of Step 3 of Method L.
(Step 12)

This step is a step of converting compound (LXVII) or a salt thereof to compound (XVIII) or a salt thereof by hydrolysis. This reaction can be carried out according to a method known per se, generally carried out in the presence of an acid or a base, in a solvent that does not adversely influence the reaction, if necessary.

Examples of the acid include mineral acids (hydrochloric acid, hydrobromic acid, sulfuric acid and the like), carboxylic acids (acetic acid, trifluoroacetic acid, trichloroacetic acid and the like), sulfonic acids (methanesulfonic acid, toluenesulfonic acid and the like), Lewis acids (aluminium chloride, tin chloride, zinc bromide and the like) and the like. They may be used in a mixture of two or more kinds thereof, if necessary. While the amount of the acid to be used varies depending on the kind of the solvent and other reaction condition, it is generally about 0.1 mol equivalent or more, per 1 mol of compound (LXVII), and the acid may be used as a solvent.

Examples of the base include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, alkoxides such as sodium methoxide, sodium ethoxide and the like, and the like), organic bases (amines such as trimethylamine, triethylamine, diisopropylethylamine and the like, aromatic amines such as pyridine, 4-dimethylaminopyridine and the like, and the like) and the like. Among them, sodium hydroxide is preferable. While the amount of the base to be used varies depending on the kind of the solvent and other reaction condition, it is generally about 0.1 to 10 mol equivalent, preferably about 1 to 5 mol equivalent, per 1 mol of compound (LXVII).

Examples of the solvent that does not adversely influence the reaction include alcohols (methanol, ethanol, propanol, 2-propanol, butanol, isobutanol, t-butanol and the like), hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), carboxylic acids (acetic acid and the like), amides (dimethylformamide, dimethylacetamide and the like), sulfoxides (dimethyl sulfoxide and the like), water and the like. Among them, ethanol, tetrahydrofuran or water is preferable. These solvents may be used in a mixture of two or more kinds thereof in an appropriate ratio.

While the reaction time varies depending on the kind of the solvent, it is, for example, within about −50 to 200° C., preferably about 0 to 100° C. While the reaction time varies depending on the kind of compound (LXVII) or a salt thereof, the reaction temperature and the like, it is, for example, about 0.5 to 100 hr, preferably about 0.5 to 24 hr.

(Step 13)

This step is a step of converting compound (XVIII) or a salt thereof to compound (VIII-II) or a salt thereof by a rearrangement reaction step (Step 13-1), followed by a hydrolysis reaction step (Step 13-2).

(Step 13-1)

This step can be carried out according to a method known per se (for example, method described in "Jikken Kagaku Kouza, 4th Edition, vol. 20, organic synthesis II" 1991, (the Chemical Society of Japan ed.) and the like), or a method analogous thereto.

Examples of the rearrangement reaction include Hofmann rearrangement reaction, Schmidt rearrangement reaction, Curtius rearrangement reaction and the like. Curtius rearrangement reaction is generally preferably used, while depending on compound (XVIII).

Curtius rearrangement reaction is generally carried out by reacting compound (XVIII) or a salt thereof with an azidating agent in the presence of a base, in a solvent that does not adversely influence, and then heating the resulting compound.

Examples of the base include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, alkoxides such as sodium methoxide, sodium ethoxide and the like, and the like), organic bases (amines such as trimethylamine, triethylamine, diisopropylethylamine and the like, aromatic amines such as pyridine, 4-dimethylaminopyridine and the like, and the like) and the like. Among them, organic bases (triethylamine, diisopropylethylamine and the like) and the like are preferable. While the amount of the base to be used varies depending on the kind of the solvent and other reaction condition, it is generally about 1 to 10 mol equivalent, preferably about 1 to 5 mol equivalent, per 1 mol of compound (XVIII).

Preferable examples of the azidating agent include diphenylphosphoryl azide (DPPA).

Examples of the solvent that does not adversely influence the reaction include hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), amides (N,N-dimethylformamide, N,N-dimethylacetamide and the like), sulfoxides (dimethyl sulfoxide and the like) and the like. These solvents may be used in a mixture of two or more kinds thereof in an appropriate ratio.

While the reaction time varies depending on the kind of the solvent, it is, for example, within about −50 to 200° C., preferably about 0 to 100° C. While the reaction time varies depending on the kind of compound (XVIII), the reaction temperature and the like, it is, for example, about 0.5 to 24 hr, preferably about 0.5 to 2 hr.

(Step 13-2)

The hydrolysis reaction can be carried out according to a method known per se, for example, in the presence of a base, in a solvent that does not adversely influence the reaction, if necessary.

Examples of the base include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, alkoxides such as sodium methoxide, sodium ethoxide and the like, and the like), organic bases (amines such as trimethylamine, triethylamine, diisopropylethylamine and the like, aromatic amines such as pyridine, 4-dimethylaminopyridine and the like, and the like) and the like. Among them, lithium hydroxide, sodium hydroxide, potassium hydroxide and the like are preferable. While the amount of the base to be used varies depending on the kind of the solvent and other reaction condition, it is generally about 1 to 100 mol equivalent, preferably about 1 to 20 mol equivalent, per 1 mol of compound (XVIII).

Examples of the solvent that does not adversely influence the reaction include hydrocarbons (benzene, toluene, xylene, hexane, heptane and the like), halogenated hydrocarbons (dichloromethane, chloroform and the like), ethers (diethyl ether, diisopropyl ether, t-butyl methyl ether, tetrahydrofuran, dioxane, dimethoxyethane and the like), nitriles (acetonitrile and the like), amides (N,N-dimethylformamide, N,N-dimethylacetamide and the like), sulfoxides (dimethyl sulfoxide and the like), water and the like. These solvents may be used in a mixture of two or more kinds thereof in an appropriate ratio.

While the reaction time varies depending on the kind of the solvent, it is, for example, within about −50 to 200° C., preferably about 0 to 100° C. While the reaction time varies depending on the kind of compound (XVIII), the reaction temperature and the like, it is, for example, about 0.5 to 24 hr, preferably about 0.5 to 2 hr.

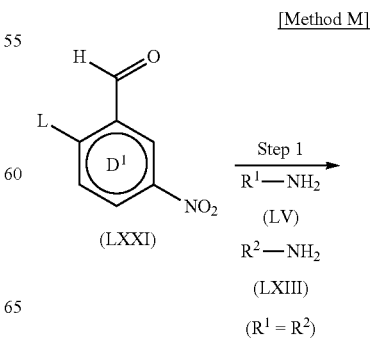

[Method M]

($R^1 = R^2$)

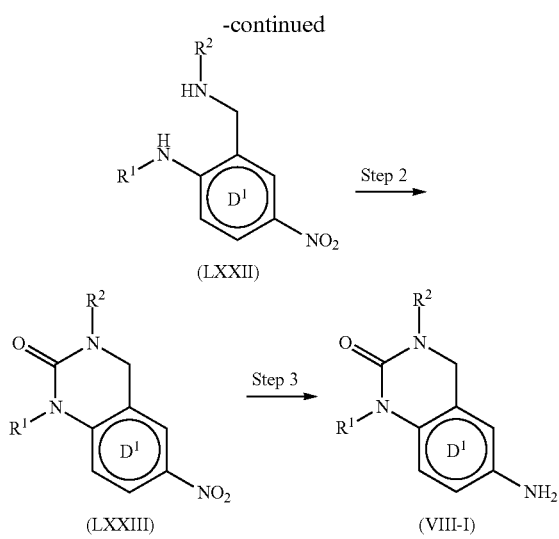

wherein each symbol is as defined above.
(Step 1)

This step is a step of producing compound (LXXII) or a salt thereof from compound (LXXI) or a salt thereof in the presence of a reducing agent, when compound (LV) and compound (LXIII) are same.

Compound (LXXI) and compound (LV) may be a commercially available product, or can also be produced according to a method known per se or a method analogous thereto.

Examples of the reducing agent include metal hydrides (sodium borohydride, lithium borohydride, zinc borohydride, sodium cyanoborohydride, sodium triacetoxyborohydride, lithium cyanoborohydride, dibutylaluminium hydride, aluminium hydride, lithium aluminium hydride and the like), borane complexes (borane-THF complex, catecholborane, etc.) and the like. The amount of the reducing agent to be used is about 1 to 50 mol, preferably about 1 to 5 mol, per 1 mol of compound (LXXI).

This reaction is carried out in a solvent inert to the reaction. Examples of the solvent include aromatic hydrocarbons (toluene, xylene and the like), aliphatic hydrocarbons (heptane, hexane and the like), halogenated hydrocarbons (chloroform, dichloromethane and the like), ethers (diethyl ether, tetrahydrofuran, dioxane and the like), alcohols (methanol, ethanol, 2-propanol, butanol, benzyl alcohol and the like), nitriles (acetonitrile and the like), N,N-dimethylformamide, dimethyl sulfoxide and the like. These solvents may be used in a mixture thereof in an appropriate ratio. In addition, an acid (acetic acid, hydrochloric acid and the like) may be added for the favorable progress of the reaction.

While the reaction time varies depending on the kind of the solvent, it is generally about −80 to 80° C., preferably about −40 to 40° C., and the reaction time is generally about 5 min to 48 hr, preferably about 1 to 24 hr.

The amount of compound (LV) and compound (LXIII) to be used is about 2 to 50 mol, preferably about 2 to 5 mol, per 1 mol of compound (LXXI), respectively.

(Step 2)

This step is a step of producing compound (LXXIII) or a salt thereof from compound (LXXII) or a salt thereof using a carbonylating reagent.

This step can be carried out in the same manner as in the method described in Step 8 of Method L.

(Step 3)

This step is a step of producing compound (VIII-I) or a salt thereof by subjecting compound (LXXIII) or a salt thereof to a reduction reaction. This step can be carried out in the same manner as in the method described in Step 3 of Method C.

[Method N]

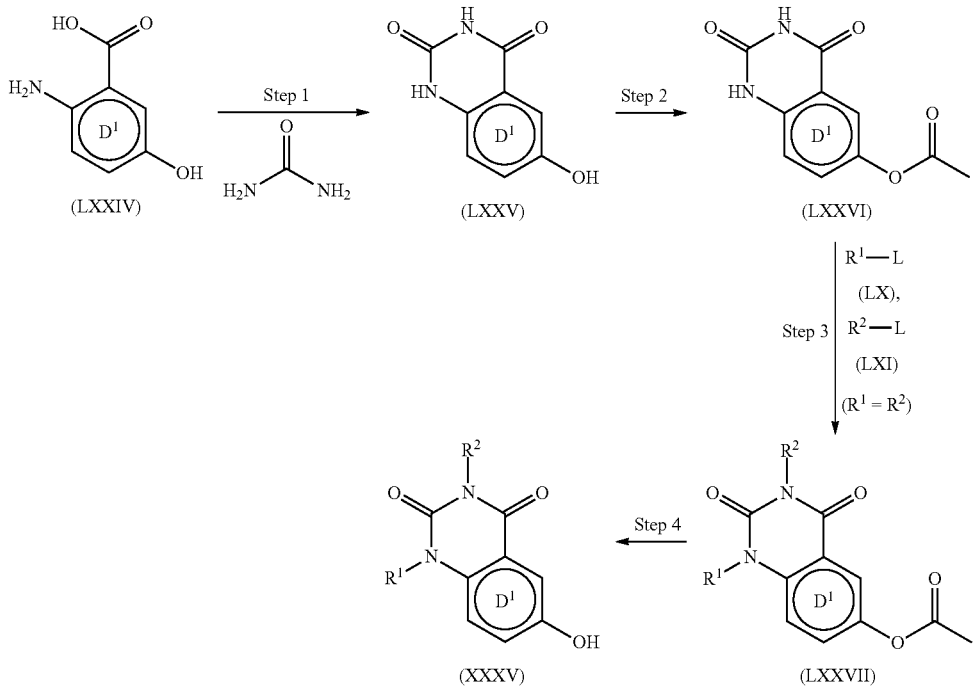

wherein each symbol is as defined above.]

(Step 1)

This step is a step of producing compound (LXXV) or a salt thereof by reacting compound (LXXIV) or a salt thereof with urea. This step can be carried out in the same manner as in the method described in Step 2 of Method L.

Compound (LXXIV) may be a commercially available product, or can also be produced according to a method known per se or a method analogous thereto.

(Step 2)

This step is a step of producing compound (LXXVI) or a salt thereof by reacting compound (LXXV) or a salt thereof with an acetoxylating agent.

Examples of the acetoxylating agent include acetyl chloride and acetic anhydride.

The amount of the acetoxylating agent to be used is about 1 to 10 mol, preferably about 1 to 5 mol, per 1 mol of compound (LXXV).

The reaction is carried out in a solvent inert to the reaction. Examples of the solvent include aromatic hydrocarbons (toluene, xylene and the like), aliphatic hydrocarbons (heptane, hexane and the like), halogenated hydrocarbons (chloroform, dichloromethane and the like), ethers (diethyl ether, tetrahydrofuran, dioxane and the like), nitriles (acetonitrile and the like), N,N-dimethylformamide, dimethyl sulfoxide and the like. These solvents may be used in a mixture thereof in an appropriate ratio. In addition, a base may be added for the favorable progress of the reaction.

Examples of the base include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, alkoxides such as sodium methoxide, sodium ethoxide and the like, and the like), organic bases (amines such as trimethylamine, triethylamine, diisopropylethylamine and the like, aromatic amines such as pyridine, 4-dimethylaminopyridine and the like, and the like) and the like. While the amount of the base to be used varies depending on the kind of the solvent and other reaction condition, it is generally about 1 to 100 mol equivalent, preferably about 1 to 20 mol equivalent, per 1 mol of compound (LXXV). In addition, pyridine may be used as a solvent.

While the reaction time varies depending on the kind of the solvent, it is generally about −80 to 100° C., preferably about −40 to 40° C., and the reaction time is generally about 5 min to 48 hr, preferably about 1 to 24 hr.

(Step 3)

This step is a step of producing compound (LXXVII) or a salt thereof from compound (LXXVI) or a salt thereof in the presence of a base, when compound (LX) and compound (LXI) are same.

Compound (LX) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 4)

This step is a step of producing compound (XXXV) or a salt thereof by subjecting compound (LXXVII) or a salt thereof to a deprotection reaction. This step can be carried out in the same manner as in the method described in Step 12 of Method L.

[Method O]

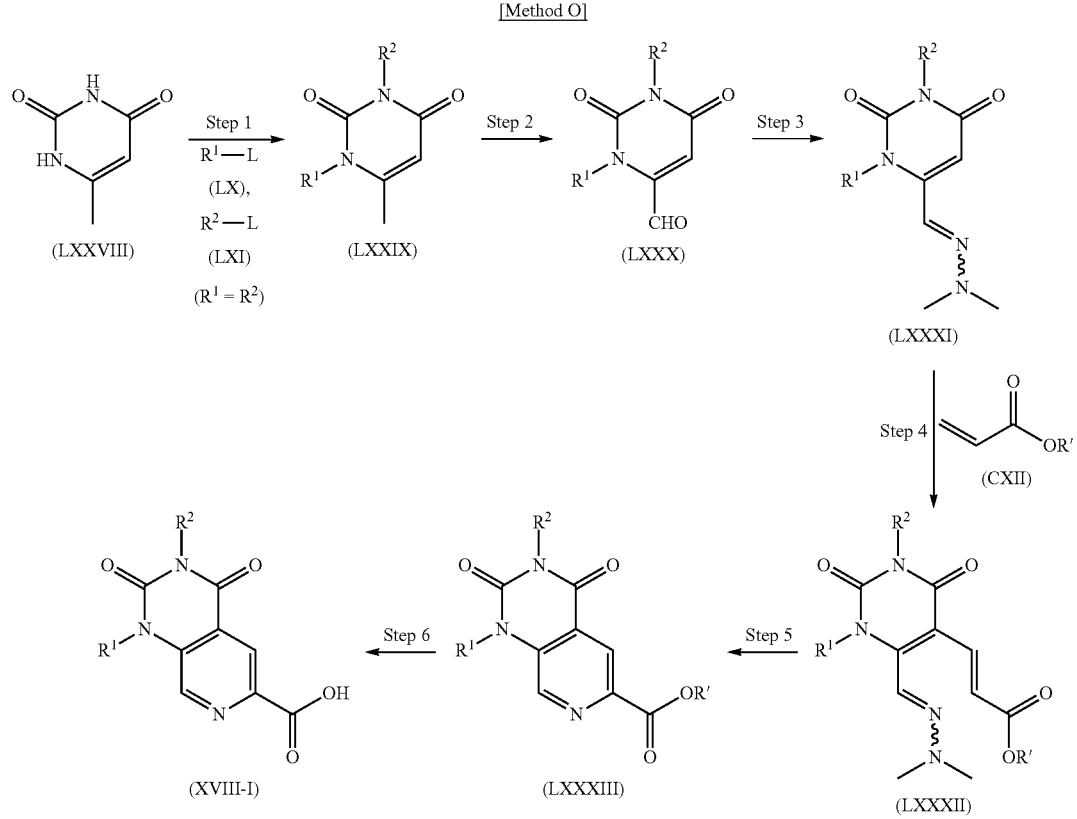

wherein each symbol is as defined above.

(Step 1)

This step is a step of producing compound (LXXIX) or a salt thereof from compound (LXXVIII) in the presence of a base, when compound (LX) and compound (LXI) are same.

Compound (LXXVIII) and compound (LX) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 2)

This step is a step of producing compound (LXXX) or a salt thereof by subjecting compound (LXXIX) or a salt thereof to an oxidation reaction.

As the reagent used in the oxidation reaction, selenium dioxide is preferably used.

The amount of the selenium dioxide to be used is about 1 to 10 mol, preferably about 1 to 5 mol, per 1 mol of compound (LXXIX).

The reaction is carried out in a solvent inert to the reaction. Examples of the solvent include aromatic hydrocarbons (toluene, xylene and the like), aliphatic hydrocarbons (heptane, hexane and the like), ethers (diethyl ether, tetrahydrofuran, dioxane and the like), acids (hydrochloric acid, acetic acid and the like) and the like. These solvents may be used in a mixture thereof in an appropriate ratio.

While the reaction time varies depending on the kind of the solvent, it is generally about −40 to 200° C., preferably about 0 to 100° C., and the reaction time is generally about 5 min to 48 hr, preferably about 1 to 24 hr.

(Step 3)

This step is a step of producing compound (LXXXI) or a salt thereof by reacting compound (LXXX) or a salt thereof with N,N-dimethylhydrazine.

The amount of the N,N-dimethylhydrazine to be used is about 1 to 100 mol, preferably about 1 to 50 mol, per 1 mol of compound (LXXX).

The reaction is carried out in a solvent inert to the reaction. Examples of the solvent include aromatic hydrocarbons (toluene, xylene and the like), aliphatic hydrocarbons (heptane, hexane and the like), ethers (diethyl ether, tetrahydrofuran, dioxane and the like), nitriles (acetonitrile and the like), N,N-dimethylformamide, dimethyl sulfoxide and the like. These solvents may be used in a mixture thereof in an appropriate ratio.

While the reaction time varies depending on the kind of the solvent, it is generally about 0 to 200° C., preferably about 0 to 100° C., and the reaction time is generally about 5 min to 48 hr, preferably about 1 to 24 hr. The reaction is carried out in a seal tube, if necessary.

(Step 4)

This step is a step of producing compound (LXXXII) or a salt thereof by reacting compound (LXXXI) or a salt thereof with compound (CXII) in the presence of a transition metal catalyst.

Examples of the transition metal catalyst include palladium catalysts (palladium acetate, palladium chloride, tetrakis(triphenylphosphine)palladium and the like) and the like. While the amount of the catalyst to be used varies depending on the kind thereof, it is generally about 1 to 10 mol, preferably about 1 to 1.5 mol, per 1 mol of compound (LXXXI).

Compound (CXII) may be a commercially available product, or can also be produced according to a method known per se or a method analogous thereto.

This reaction is carried out in a solvent that does not adversely influence. Examples of the solvent that does not adversely influence the reaction include aromatic hydrocarbons (benzene, toluene, xylene and the like), ethers (diethyl ether, diisopropyl ether, t-butyl methyl ether, tetrahydrofuran, dioxane, dimethoxyethane and the like), nitriles (acetonitrile and the like) and the like. These solvents may be used in a mixture of two or more kinds thereof in an appropriate ratio.

While the reaction time varies depending on the kind of the solvent, it is, for example, within about 0 to 200° C., preferably about 20 to 100° C. While the reaction time varies depending on the kind of compound (LXXXI) or a salt thereof, the reaction temperature and the like, it is, for example, about 0.1 to 48 hr.

(Step 5)

This step is a step of producing compound (LXXXIII) or a salt thereof by subjecting compound (LXXXII) or a salt thereof to a ring closure reaction.

This reaction is carried out in a solvent that does not adversely influence. Examples of the solvent that does not adversely influence the reaction include aromatic hydrocarbons (benzene, chlorobenzene, toluene, xylene and the like) and the like. In addition, the reaction can advantageously proceed by addition of an acid. Examples of the acid include mineral acids (hydrochloric acid, hydrobromic acid, sulfuric acid and the like), carboxylic acids (acetic acid and the like) and the like.

While the reaction time varies depending on the kind of the solvent, it is, for example, within about 0 to 300° C., preferably about 60 to 150° C. While the reaction time varies depending on the kind of compound (LXXXII) or a salt thereof, the reaction temperature and the like, it is, for example, about 0.1 to 48 hr.

(Step 6)

This step is a step of converting compound (LXXXIII) or a salt thereof to compound (XVIII-I) or a salt thereof by hydrolysis.

This step can be carried out in the same manner as in the method described in Step 12 of Method L.

[Method P]

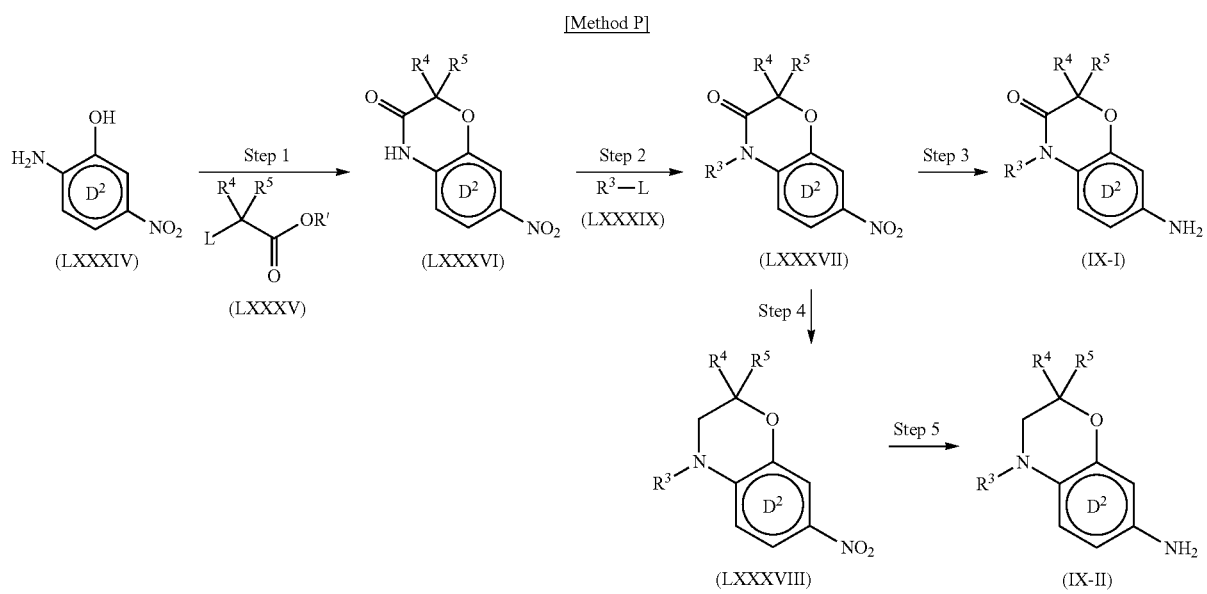

wherein each symbol is as defined above.

(Step 1)

This step is a step of producing compound (LXXXVI) or a salt thereof by reacting compound (LXXXIV) or a salt thereof with compound (LXXXV) or a salt thereof in the presence of a base or a salt.

Compound (LXXXIV) and compound (LXXXV) may be a commercially available product, or can also be produced according to a method known per se or a method analogous thereto.

Examples of the base or salt include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, and the like), inorganic salt (alkali metal salts such as sodium fluoride, potassium fluoride and the like, and the like) and the like. While the amount of the base or salt to be used varies depending on the kind of the solvent and other reaction condition, it is generally about 1 to 10 mol equivalent, preferably about 1 to 5 mol equivalent, per 1 mol of compound (LXXXIV).

This reaction is carried out in a solvent that does not adversely influence. Examples of the solvent that does not adversely influence the reaction include aromatic hydrocarbons (benzene, toluene, xylene and the like), alcohols (methanol, ethanol, propanol and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), aprotic polar solvents (dimethylformamide, dimethyl sulfoxide, hexamethylphosphoroamide and the like) and the like. These solvents may be used in a mixture of two or more kinds thereof in an appropriate ratio.

While the reaction time varies depending on the kind of the solvent, it is, for example, within about 0 to 200° C., preferably about 10 to 100° C. While the reaction time varies depending on the kind of compound (LXXXIV) or a salt thereof, the reaction temperature and the like, it is, for example, about 0.1 to 48 hr.

(Step 2)

This step is a step of producing compound (LXXXVII) or a salt thereof by reacting compound (LXXXVI) or a salt thereof with compound (LXXXIX) in the presence of a base.

Compound (LXXXIX) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 3)

This step is a step of producing compound (IX-I) or a salt thereof by subjecting compound (LXXXVII) or a salt thereof to a reduction reaction. This step can be carried out in the same manner as in the method described in Step 3 of Method C.

(Step 4)

This step is a step of producing compound (LXXXVIII) or a salt thereof by subjecting compound (LXXXVII) or a salt thereof to a reduction reaction. This step can be carried out in the same manner as in the method described in Step 1 of Method E.

(Step 5)

This step is a step of producing compound (IX-II) or a salt thereof by subjecting compound (LXXXVIII) or a salt thereof to a reduction reaction. This step can be carried out in the same manner as in the method described in Step 3 of Method C.

[Method Q]

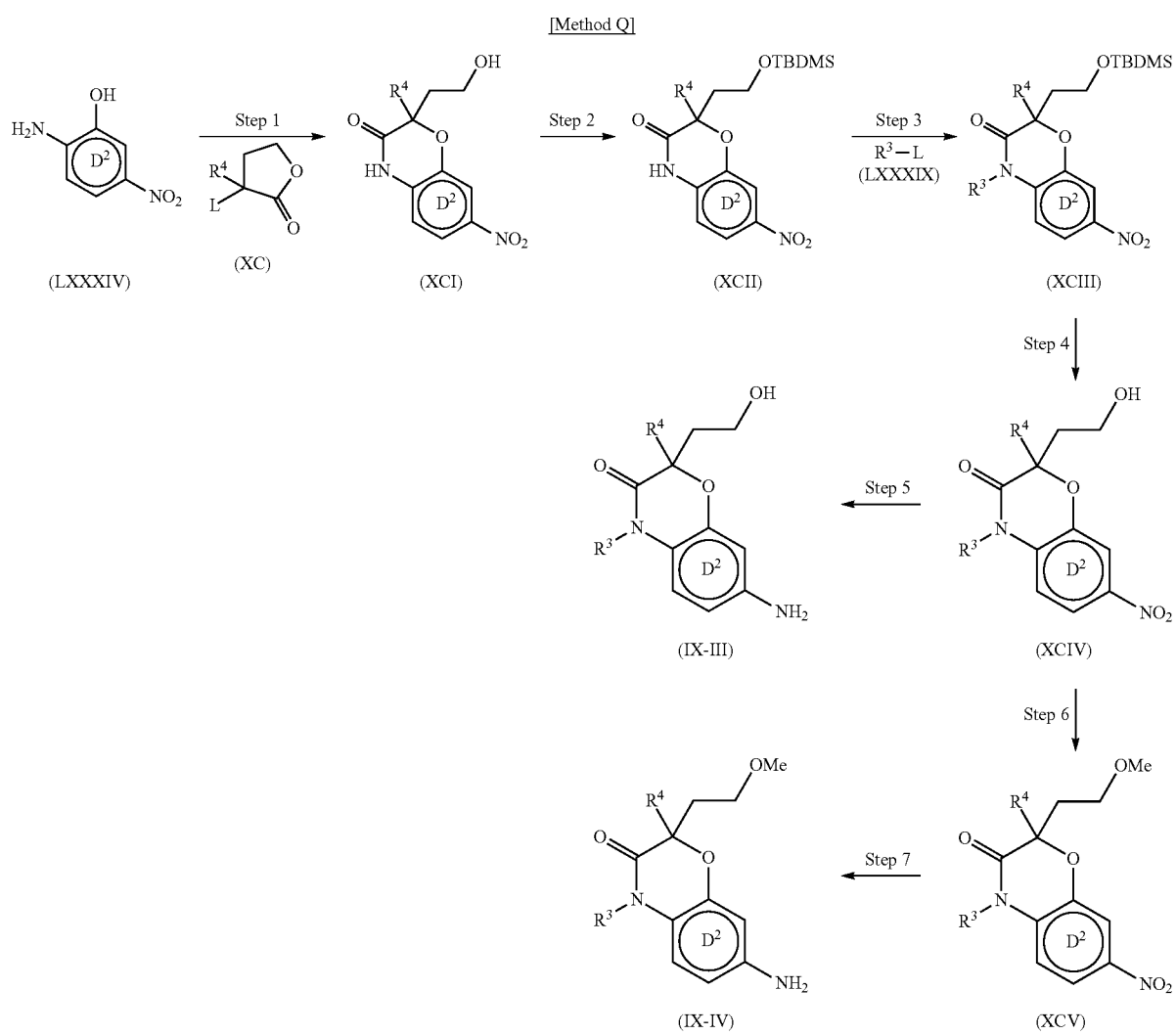

wherein TBDMS is a tert-butyldimethylsilyl group, and the other each symbol is as defined above.

(Step 1)

This step is a step of producing compound (XCI) or a salt thereof by reacting compound (LXXXIV) or a salt thereof with compound (XC) or a salt thereof in the presence of a base or a salt. This step can be carried out in the same manner as in the method described in Step 1 of Method P.

Compound (LXXXIV) and compound (XC) may be a commercially available product, or can also be produced according to a method known per se or a method analogous thereto.

(Step 2)

This step is a step of producing compound (XCII) or a salt thereof by protecting compound (XCI) or a salt thereof with a TBDMS group.

The protection with a TBDMS group can be carried out according to a method known per se or the method described in "Protective Groups in Organic Synthesis, 3rd Ed", Wiley-Interscience, Inc. (1999) (Theodora W. Greene, Peter G. M. Wuts) and the like, or a method analogous thereto. For example, a method using chlorotert-butyldimethylsilane and imidazole in dimethylformamide solvent is employed.

The amount of the chlorotert-butyldimethylsilane and imidazole to be used is about 1 to 10 mol equivalent, preferably about 1 to 2 mol equivalent, per 1 mol of compound (XCI), respectively.

While the reaction time varies depending on the kind of the solvent, it is, for example, within about −40 to 100° C., preferably about 0 to 40° C. While the reaction time varies depending on the kind of compound (XCI) or a salt thereof, the reaction temperature and the like, it is, for example, about 0.1 to 24 hr.

(Step 3)

This step is a step of producing compound (XCIII) or a salt thereof by reacting compound (XCII) or a salt thereof with compound (LXXXIX) in the presence of a base.

Compound (LXXXIX) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 4)

This step is a step of producing compound (XCIV) or a salt thereof by removing of the TBDMS group of compound (XCIII) or a salt thereof.

The removal of the TBDMS group can be carried out according to a method known per se or the method described in "Protective Groups in Organic Synthesis, 3rd Ed", Wiley-Interscience, Inc. (1999) (Theodora W. Greene, Peter G. M. Wuts) and the like, or a method analogous thereto. For example, a method using an acid (for example, hydrochloric acid, sulfuric acid, acetic acid, hydrogen fluoride, trifluoroacetic acid, p-toluenesulfonic acid and the like), a salt (for example, tetrabutylammonium fluoride, pyridine-hydrogen fluoride complex, lithium tetrafluoroborate and the like) and the like is employed.

The amount of the acid or salt to be used is about 1 to 10 mol equivalent, preferably about 1 to 2 mol equivalent, per 1 mol of compound (XCIII), respectively. The acid or base may be used as a solvent.

While the reaction time varies depending on the kind of the solvent, it is, for example, within about −40 to 100° C., preferably about 0 to 40° C. While the reaction time varies depending on the kind of compound (XCIII) or a salt thereof, the reaction temperature and the like, it is, for example, about 0.1 to 24 hr.

(Step 5)

This step is a step of producing compound (IX-III) or a salt thereof by subjecting compound (XCIV) or a salt thereof to a reduction reaction. This step can be carried out in the same manner as in the method described in Step 1 of Method E.

The amount of the base and methyl iodide to be used is about 1 to 10 mol equivalent, preferably about 1 to 5 mol equivalent, per 1 mol of compound (XCIV), respectively.

This reaction is carried out in a solvent that does not adversely influence. Examples of the solvent that does not adversely influence the reaction include aromatic hydrocarbons (benzene, toluene, xylene and the like), ethers (diethyl ether, diisopropyl ether, t-butyl methyl ether, tetrahydrofuran, dioxane, dimethoxyethane and the like), nitriles (acetonitrile and the like), aprotic polar solvents (dimethylformamide, dimethyl sulfoxide, hexamethylphosphoroamide and the like) and the like. These solvents may be used in a mixture of two or more kinds thereof in an appropriate ratio.

While the reaction time varies depending on the kind of the solvent, it is, for example, within about 0 to 200° C., preferably about 10 to 100° C. While the reaction time varies depending on the kind of compound (XCIV) or a salt thereof, the reaction temperature and the like, it is, for example, about 0.1 to 48 hr.

(Step 7)

This step is a step of producing compound (IX-IV) or a salt thereof by subjecting compound (XCV) or a salt thereof to a reduction reaction. This step can be carried out in the same manner as in the method described in Step 1 of Method E.

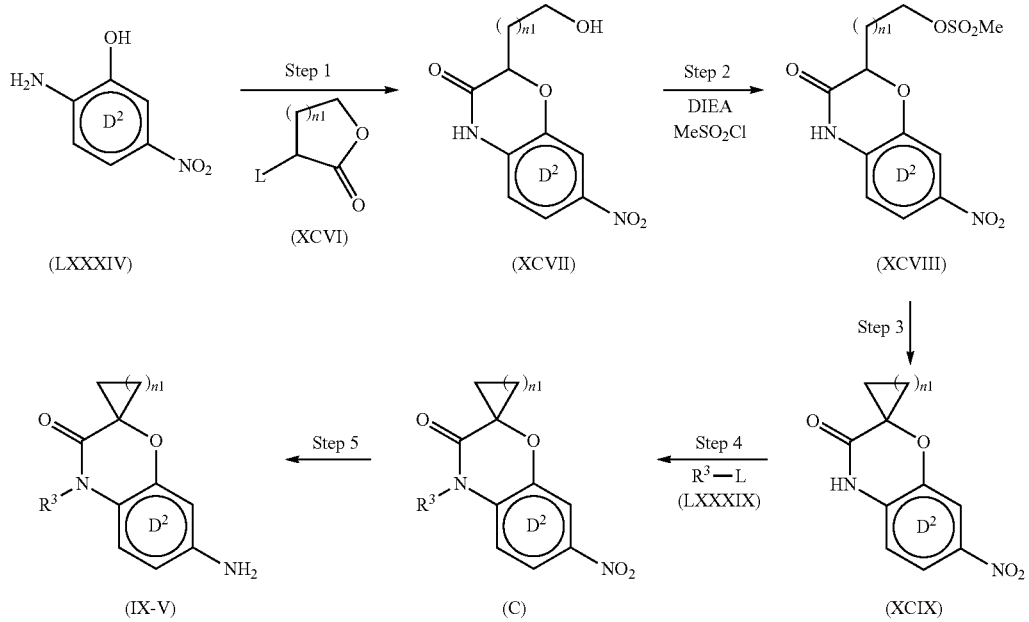

(Step 6)

This step is a step of producing compound (XCV) or a salt thereof by reacting compound (XCIV) or a salt thereof with methyl iodide in the presence of a base.

Examples of the base include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, and the like) and the like.

wherein each symbol is as defined above.

(Step 1)

This step is a step of producing compound (XCVII) or a salt thereof by reacting compound (LXXXIV) or a salt thereof with compound (XCVI) or a salt thereof in the presence of a base or a salt. This step can be carried out in the same manner as in the method described in Step 1 of Method P.

Compound (LXXXIV) and compound (XCVI) may be a commercially available product, or can also be produced according to a method known per se or a method analogous thereto.

(Step 2)

This step is a step of producing compound (XCVIII) or a salt thereof by reacting compound (XCVII) or a salt thereof with methanesulfonyl chloride, in the presence of DIEA.

The amount of the DIEA and methanesulfonyl chloride to be used is about 1 to 10 mol equivalent, preferably about 1 to 2 mol equivalent, per 1 mol of compound (XCVII), respectively.

This reaction is carried out in a solvent that does not adversely influence. Examples of the solvent that does not adversely influence the reaction include aromatic hydrocarbons (benzene, toluene, xylene and the like), ethers (diethyl ether, diisopropyl ether, t-butyl methyl ether, tetrahydrofuran, dioxane, dimethoxyethane and the like), nitriles (acetonitrile and the like) and the like. These solvents may be used in a mixture of two or more kinds thereof in an appropriate ratio.

While the reaction time varies depending on the kind of the solvent, it is, for example, within about −20 to 100° C., preferably about 0 to 30° C. While the reaction time varies depending on the kind of compound (XCVII) or a salt thereof, the reaction temperature and the like, it is, for example, about 0.1 to 48 hr.

(Step 3)

This step is a step of producing compound (XCIX) or a salt thereof by subjecting compound (XCVIII) or a salt thereof to a ring closure reaction in the presence of a base.

Examples of the base include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like, and the like) and the like.

The amount of the base to be used is about 1 to 5 mol equivalent, preferably about 1 to 3 mol equivalent, per 1 mol of compound (XCVIII).

This reaction is carried out in a solvent that does not adversely influence. Examples of the solvent that does not adversely influence the reaction include aromatic hydrocarbons (benzene, toluene, xylene and the like), ethers (diethyl ether, diisopropyl ether, t-butyl methyl ether, tetrahydrofuran, dioxane, dimethoxyethane and the like), nitriles (acetonitrile and the like), aprotic polar solvents (dimethylformamide, dimethyl sulfoxide, hexamethylphosphoroamide and the like) and the like.

When solvent is used, the reaction temperature is, for example, within about 0 to 300° C., preferably about 100 to 200° C. In this case, the reaction may be carried out under microwave irradiation for the progress of the reaction. The reaction time is, for example, about 0.1 to 100 hr, preferably about 0.1 to 24 hr.

(Step 4)

This step is a step of producing compound (C) or a salt thereof by reacting compound (XCIX) or a salt thereof with compound (LXXXIX) in the presence of a base.

Compound (LXXXIX) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 5)

This step is a step of producing compound (IX-V) or a salt thereof by subjecting compound (C) or a salt thereof to a reduction reaction. This step can be carried out in the same manner as in the method described in Step 1 of Method E.

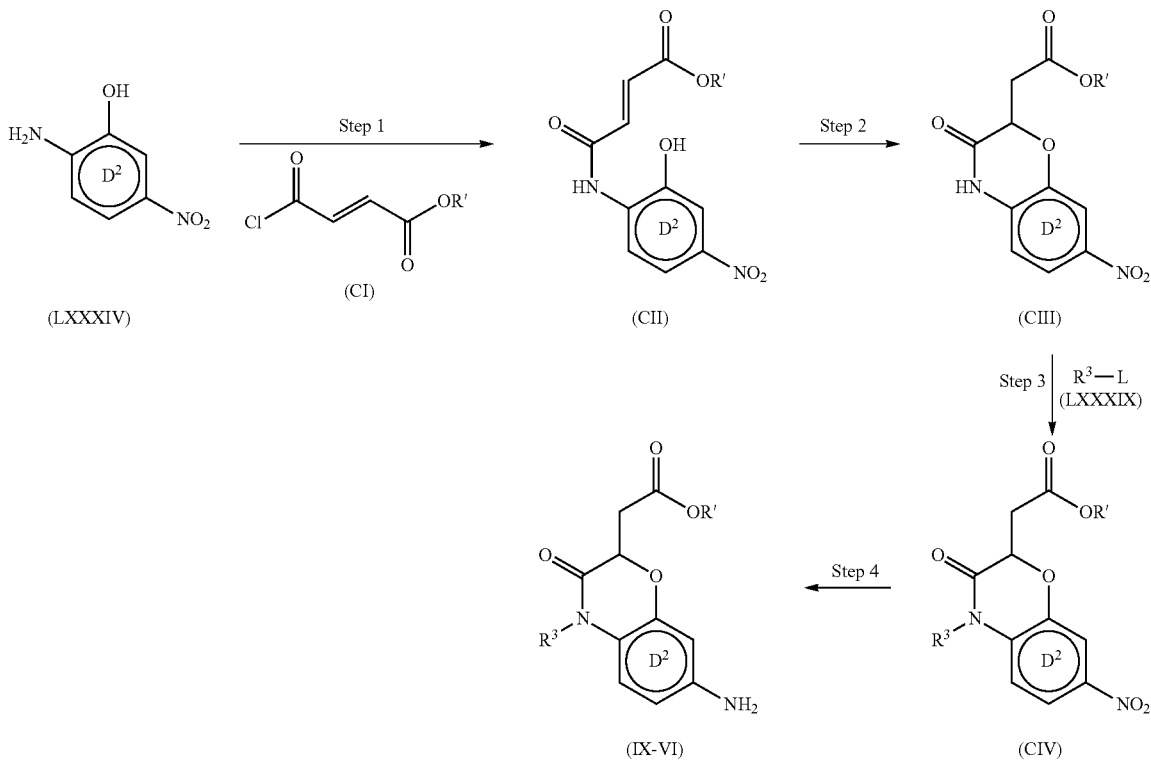

wherein each symbol is as defined above.

(Step 1)

This step is a step of producing compound (CII) or a salt thereof by reacting compound (LXXXIV) or a salt thereof with compound (CI) or a salt thereof in the presence of a base or a salt. This step can be carried out in the same manner as in the method described in Step 1 of Method P.

Compound (LXXXIV) and compound (CI) may be a commercially available product, or can also be produced according to a method known per se or a method analogous thereto.

(Step 2)

This step is a step of producing compound (CIII) or a salt thereof by subjecting compound (CII) or a salt thereof to a ring closure reaction in the presence of a base. This step can be carried out in the same manner as in the method described in Step 3 of Method R.

(Step 3)

This step is a step of producing compound (CIV) or a salt thereof by reacting compound (CIII) or a salt thereof with compound (LXXXIX) in the presence of a base.

Compound (LXXXIX) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 4)

This step is a step of producing compound (IX-VI) or a salt thereof by subjecting compound (CIV) or a salt thereof to a reduction reaction. This step can be carried out in the same manner as in the method described in Step 1 of Method E.

(Step 1)

This step is a step of producing compound (CVII) or a salt thereof by reacting compound (CV) or a salt thereof with compound (CVI) or a salt thereof in the presence of a base or a salt. This step can be carried out in the same manner as in the method described in Step 1 of Method P.

Compound (CV) and compound (CVI) may be a commercially available product, or can also be produced according to a method known per se or a method analogous thereto.

(Step 2)

This step is a step of converting compound (CVII) or a salt thereof to compound (XX) or a salt thereof by hydrolysis.

This step can be carried out in the same manner as in the method described in Step 12 of Method L.

(Step 3)

This step is a step of converting compound (XX) or a salt thereof to compound (X) or a salt thereof by a rearrangement reaction, followed by a hydrolysis reaction.

This step can be carried out in the same manner as in the method described in Step 13 of Method L.

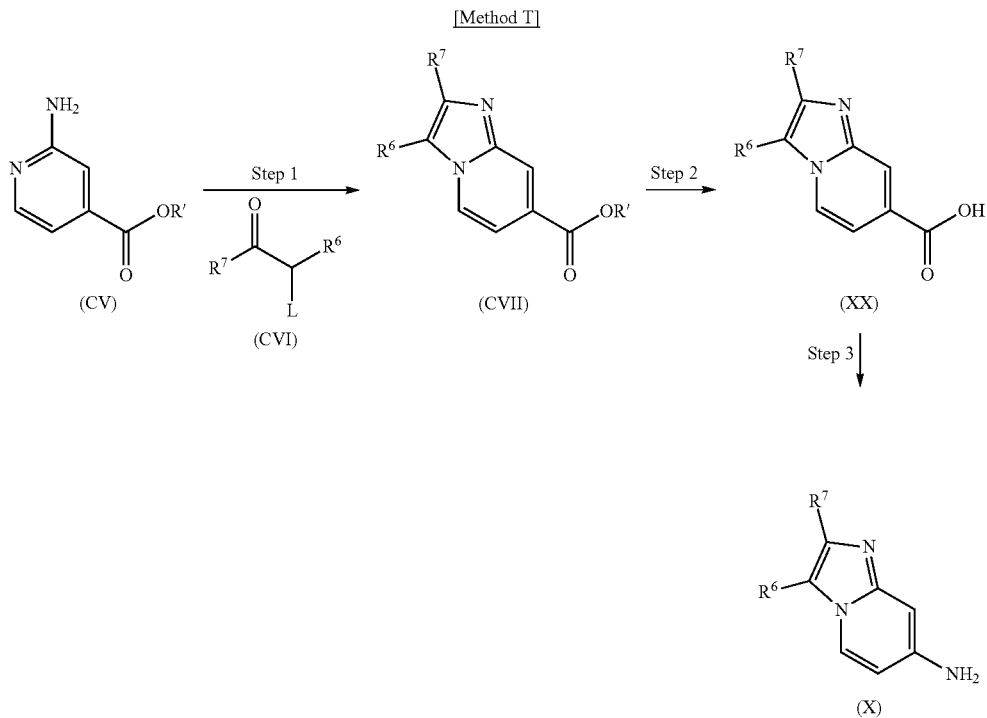

wherein each symbol is as defined above.

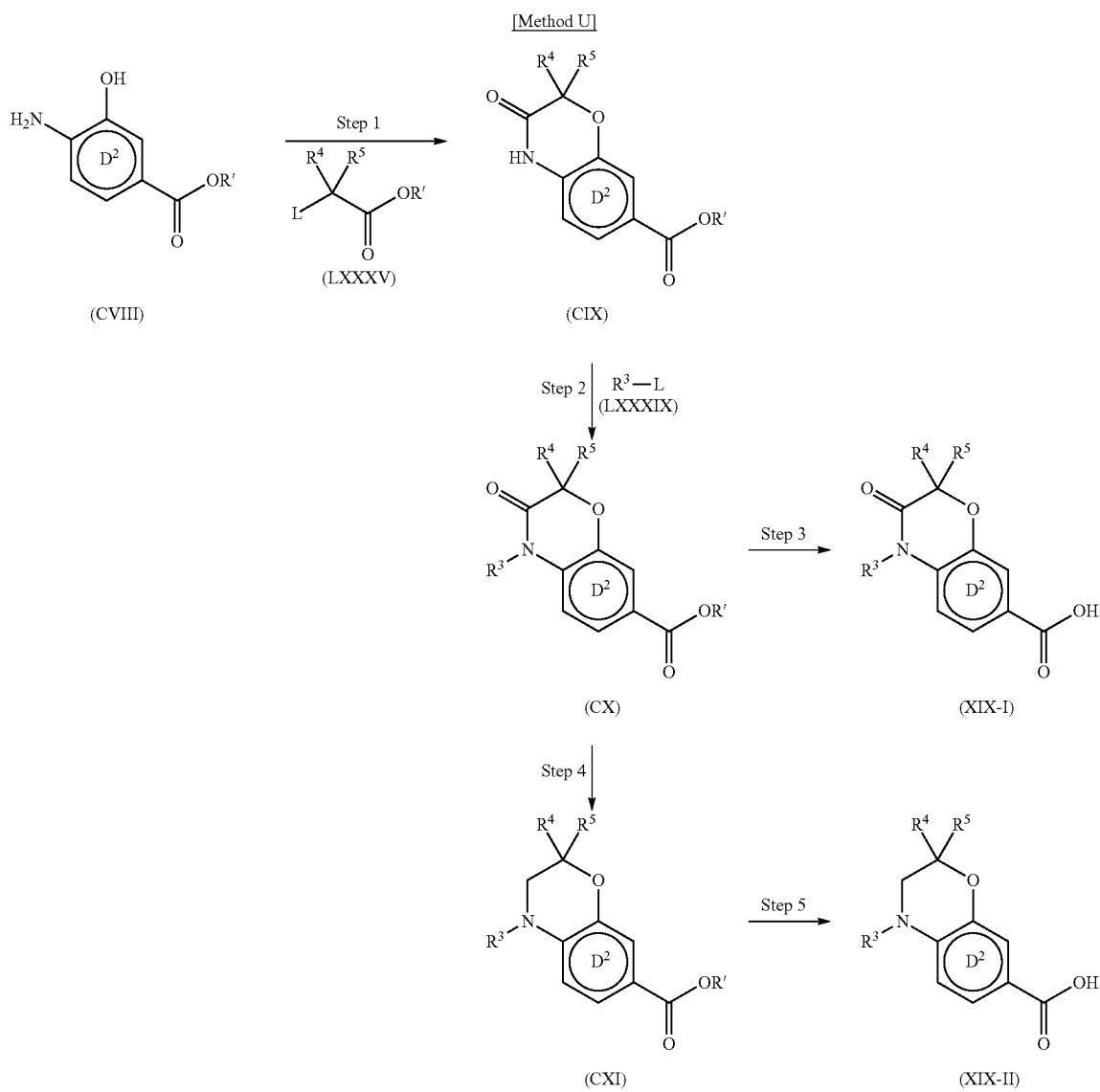

wherein each symbol is as defined above.

(Step 1)

This step is a step of producing compound (CIX) or a salt thereof by reacting compound (CVIII) or a salt thereof with compound (LXXXV) or a salt thereof in the presence of a base or a salt.

Compound (CVIII) and compound (LXXXV) may be a commercially available product, or can also be produced according to a method known per se or a method analogous thereto.

This step can be carried out in the same manner as in the method described in Step 1 of Method P.

(Step 2)

This step is a step of producing compound (CX) or a salt thereof by reacting compound (CIX) or a salt thereof with compound (LXXXIX) in the presence of a base.

Compound (LXXXIX) may be a commercially available product, or can also be produced according to a method known per se or a method analogous thereto.

This step can be carried out in the same manner as in the method described in the "method of reacting compound (LVII) with compound (LXI) in the presence of abase" of Step 3 of Method L.

(Step 3)

This step is a step of converting compound (CX) or a salt thereof to compound (XIX-I) or a salt thereof by hydrolysis.

This step can be carried out in the same manner as in the method described in Step 12 of Method L.

(Step 4)

This step is a step of producing compound (CXI) or a salt thereof by subjecting compound (CX) or a salt thereof to a reduction reaction.

This step can be carried out in the same manner as in the method described in Step 1 of Method E.

(Step 5)

This step is a step of converting compound (CXI) or a salt thereof to compound (XIX-II) or a salt thereof by hydrolysis.

This step can be carried out in the same manner as in the method described in Step 12 of Method L.

Compounds (IIf), (IIIf), (IVf), (CXXIIIf) and (CXXVIIf) or a salt thereof of the present invention can be produced according to the following Method V.
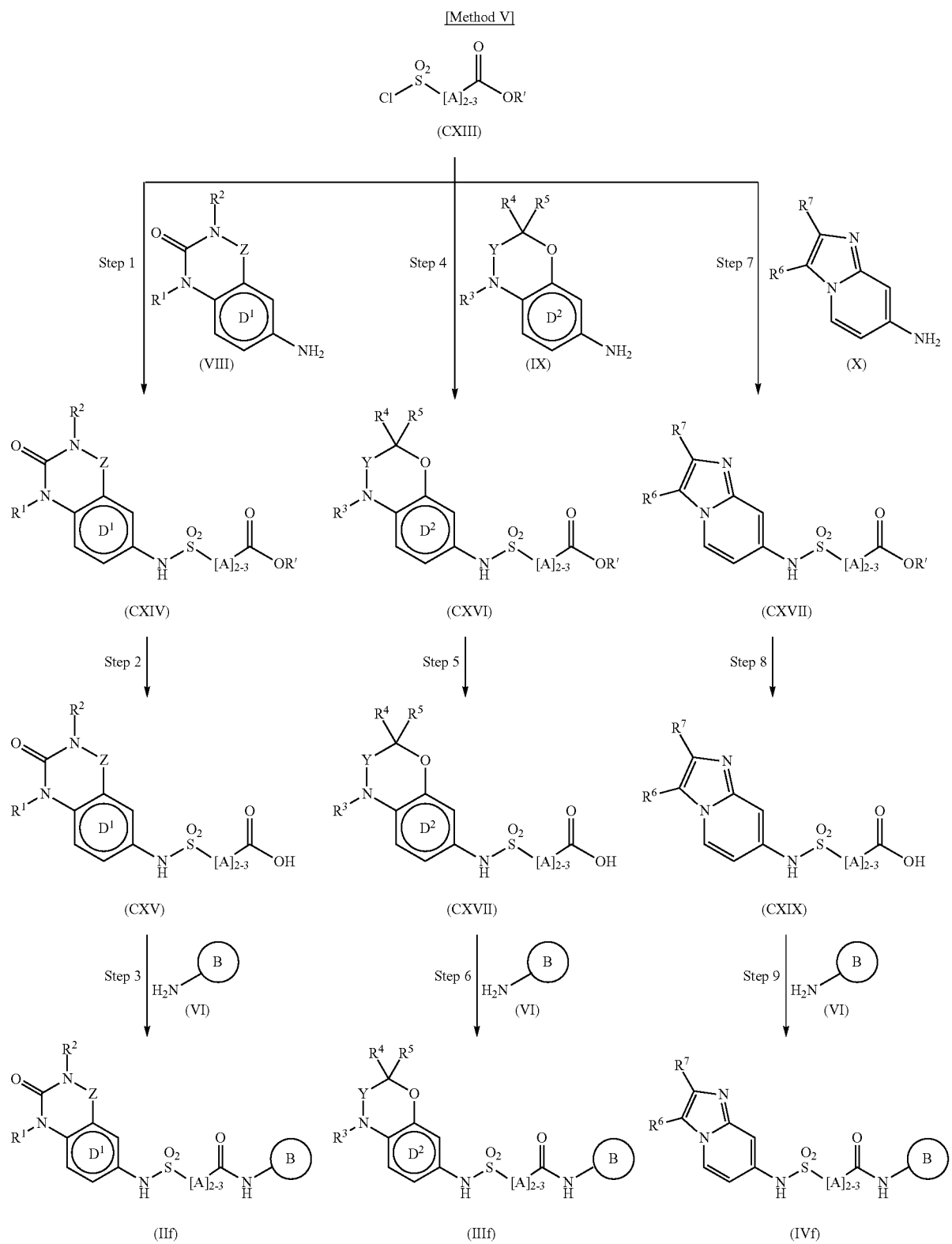
wherein each symbol is as defined above.

(Step 1)

This step is a step of producing compound (CXIV) or a salt thereof by reacting compound (CXIII) or a salt thereof with compound (VIII) or a salt thereof in the presence of a base or a salt.

Compound (CXIII) may be a commercially available product, or can also be produced according to a method known per se or a method analogous thereto.

Examples of the base or salt include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, and the like), tertiary amines (trimethylamine, triethylamine, diisopropylethylamine, N-methylmorpholine and the like), aromatic amines (pyridine, picoline, N,N-dimethylaniline and the like) and the like. While the amount of the base or salt to be used varies depending on the kind of the solvent and other reaction condition, it is generally about 1 to 10 mol equivalent, preferably about 1 to 5 mol equivalent, per 1 mol of compound (CXIII).

This reaction is carried out in a solvent that does not adversely influence. Examples of the solvent that does not adversely influence the reaction include aromatic hydrocarbons (benzene, toluene, xylene and the like), ethers (diethyl ether, diisopropyl ether, t-butyl methyl ether, tetrahydrofuran, dioxane, dimethoxyethane and the like), nitriles (acetonitrile and the like), esters (ethyl acetate and the like), aprotic polar solvents (dimethylformamide, dimethyl sulfoxide, hexamethylphosphoroamide and the like), pyridine and the like. These solvents may be used in a mixture of two or more kinds thereof in an appropriate ratio.

While the reaction time varies depending on the kind of the solvent, it is, for example, within about 0 to 200° C., preferably about 10 to 100° C. While the reaction time varies depending on the kind of compound (CXIII) or a salt thereof, the reaction temperature and the like, it is, for example, about 0.1 to 48 hr.

(Step 2)

This step is a step of converting compound (CXIV) or a salt thereof to compound (CXV) or a salt thereof by hydrolysis.

This step can be carried out in the same manner as in the method described in Step 12 of Method L.

(Step 3)

This step is a step of producing compound (IIf) or a salt thereof by reacting compound (CXV) or a salt thereof with compound (VI) or a salt thereof in the presence of a condensing agent. This step can be carried out in the same manner as in the method described in Step 2 of Method A.

(Step 4)

This step is a step of producing compound (CXVI) or a salt thereof by reacting compound (CXIII) or a salt thereof with compound (IX) or a salt thereof in the presence of a base or a salt.

This step can be carried out in the same manner as in the method described in Step 1 of Method V.

(Step 5)

This step is a step of converting compound (CXVI) or a salt thereof to compound (CXVII) or a salt thereof by hydrolysis.

This step can be carried out in the same manner as in the method described in Step 12 of Method L.

(Step 6)

This step is a step of producing compound (IIIf) or a salt thereof by reacting compound (CXVII) or a salt thereof with compound (VI) or a salt thereof in the presence of a condensing agent. This step can be carried out in the same manner as in the method described in Step 2 of Method A.

(Step 7)

This step is a step of producing compound (CXVIII) or a salt thereof by reacting compound (CXIII) or a salt thereof with compound (X) or a salt thereof in the presence of a base or a salt.

This step can be carried out in the same manner as in the method described in Step 1 of Method V.

(Step 8)

This step is a step of converting compound (CXVIII) or a salt thereof to compound (CXIX) or a salt thereof by hydrolysis.

This step can be carried out in the same manner as in the method described in Step 12 of Method L.

(Step 9)

This step is a step of producing compound (IVf) or a salt thereof by reacting compound (CXIX) or a salt thereof with compound (VI) or a salt thereof in the presence of a condensing agent. This step can be carried out in the same manner as in the method described in Step 2 of Method A.

Compounds (VIII-II) and (LXII) can also be produced according to the following Method LA or Method LB.

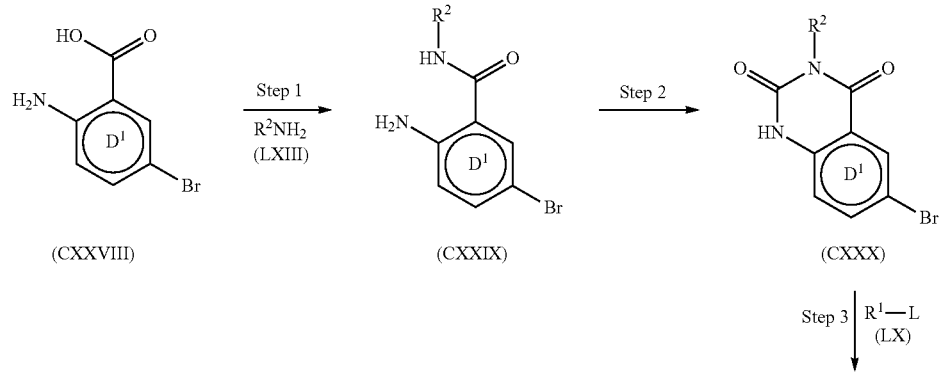

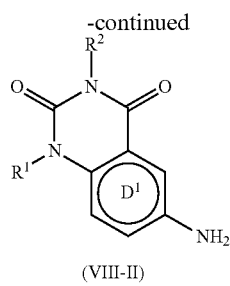

(VIII-II)

Step 4 ←

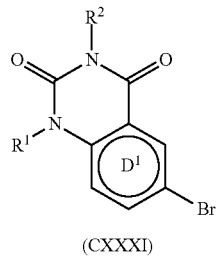

(CXXXI)

wherein each symbol is as defined above.

(Step 1)

This step is a step of producing compound (CXXIX) or a salt thereof by reacting compound (CXXVIII) or a salt thereof with compound (LXIII) or a salt thereof in the presence of a condensing agent. This step can be carried out in the same manner as in the method described in Step 2 of Method A.

Compound (CXXVIII) and compound (LXIII) may be a commercially available product, or can also be produced according to a method known per se or a method analogous thereto.

(Step 2)

This step is a step of producing compound (CXXX) or a salt thereof from compound (CXXIX) or a salt thereof using a carbonylating reagent.

This step can be carried out in the same manner as in the method described in Step 8 of Method L.

(Step 3)

This step is a step of producing compound (CXXXI) or a salt thereof by reacting compound (CXXX) or a salt thereof with compound (LX) or a salt thereof in the presence of a base.

This step can be carried out in the same manner as in the method described in Step 5 of Method L.

(Step 4)

This step is a step of producing compound (VIII-II) or a salt thereof by reacting compound (CXXXI) or a salt thereof with an aminating agent in the presence of a transition metal catalyst and a base, and then treating the resulting compound with hydrochloric acid, or hydroxyamine hydrochloride and sodium acetate.

Examples of the transition metal catalyst used in this reaction include palladium catalysts (palladium acetate, palladium chloride, tetrakistriphenylphosphine palladium, tris(dibenzylideneacetone)dipalladium(0) and the like), nickel catalysts (nickel chloride and the like) and the like. Where necessary, a ligand (triphenylphosphine, tri-t-butylphosphine, S-Phos, XPhos, BINAP, 2'-(di-tert-butylphosphino)-N,N-dimethyl-[1,1'-biphenyl]-2-amine and the like) or a base (for example, organic amines (trimethylamine, triethylamine, diisopropylamine, N-methylmorpholine, 1,8-diazabicyclo[5,4,0]undec-7-ene, pyridine, N,N-dimethylaniline and the like), alkali metal salts (sodium hydrogencarbonate, potassium hydrogencarbonate, sodium carbonate, potassium carbonate, cesium carbonate, sodium phosphate, potassium phosphate, sodium hydroxide, potassium hydroxide, lithium acetate and the like), metal hydrides (potassium hydride, sodium hydride and the like), alkali metal alkoxides (sodium methoxide, sodium ethoxide, sodium t-butoxide, potassium t-butoxide and the like), alkali disilazides (lithium disilazide, sodium disilazide, potassium disilazide and the like)) may be added, or a metal oxide (copper oxide, silver oxide and the like) and the like may be used as a co-catalyst. The amount of the catalyst to be used is about 0.0001 to 1 mol equivalent, preferably about 0.01 to 0.5 mol equivalent, per 1 mol of compound (CXXXI). The amount of the ligand to be used is about 0.0001 to 4 mol equivalent, preferably about 0.01 to 2 mol equivalent, per 1 mol of compound (CXXXI). The amount of the base to be used is about 1 to 10 mol equivalent, preferably about 1 to 2 mol equivalent, per 1 mol of compound (CXXXI). The amount of the co-catalyst to be used is about 0.0001 to 4 mol equivalent, preferably about 0.01 to 2 mol equivalent, per 1 mol of compound (CXXXI).

The solvent to be used is not particularly limited as long as it does not adversely influence the reaction, and examples thereof include hydrocarbons (benzene, toluene, xylene and the like), halogenated hydrocarbons (chloroform, 1,2-dichloroethane and the like), nitriles (acetonitrile and the like), ethers (dimethoxyethane, tetrahydrofuran), alcohols (methanol, ethanol and the like), aprotic polar solvents (dimethylformamide, dimethyl sulfoxide, hexamethylphosphoroamide and the like), water and mixtures thereof. The reaction temperature is generally about −100 to 200° C., preferably about −80 to 150° C., and the reaction time is generally about 0.5 to 48 hr, preferably about 0.5 to 24 hr. The reaction may be carried out under microwave irradiation, if necessary.

The aminating agent to be used is preferably diphenylmethanimine. The amount of the aminating agent to be used is about 1 to 5 mol equivalent, preferably about 1 to 2 mol equivalent, per 1 mol of compound (CXXXI).

In the treatment with hydrochloric acid, hydrochloric acid may be used as a solvent mixed with an organic solvent such as THF and the like. The reaction temperature is about −20 to 100° C., preferably about 0 to 30° C., and the reaction time is generally about 1 to 10 hr, preferably about 1 to 2 hr.

In the treatment with hydroxyamine hydrochloride and sodium acetate, the amount thereof to be used is about 1 to 5 mol equivalent, preferably about 1 to 2 mol equivalent, per 1 mol of compound (CXXXI), respectively. The solvent to be used is preferably methanol. The reaction temperature is about −20 to 100° C., preferably about 0 to 30° C., and the reaction time is generally about 1 to 100 hr, preferably about 1 to 72 hr.

Compound (VIII-II) or a salt thereof can also be produced by treating compound (CXXXI) or a salt thereof with aqueous ammonia in the presence of copper(II) oxide.

The amount of the copper(II) oxide to be used is about 0.1 to 5 mol equivalent, preferably about 0.1 to 1 mol equivalent, per 1 mol of compound (CXXXI).

Aqueous ammonia may be used as a solvent mixed with an organic solvent such as NMP and the like. The reaction temperature is about 10 to 200° C., preferably about 50 to 100° C., and the reaction time is generally about 1 to 48 hr, preferably about 1 to 16 hr.

[Method LB]

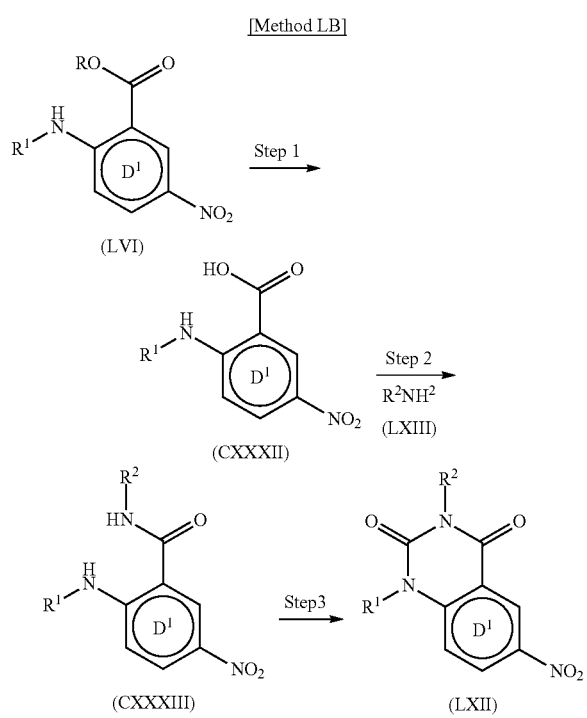

wherein each symbol is as defined above.

(Step 1)

This step is a step of converting compound (LVI) or a salt thereof to compound (CXXXII) or a salt thereof by hydrolysis.

This step can be carried out in the same manner as in the method described in Step 12 of Method L.

Compound (CXXVIII) and compound (LXIII) may be a commercially available product, or can also be produced according to a method known per se or a method analogous thereto.

(Step 2)

This step is a step of producing compound (CXXXIII) or a salt thereof by reacting compound (CXXXII) or a salt thereof with compound (LXIII) or a salt thereof in the presence of a condensing agent. This step can be carried out in the same manner as in the method described in Step 2 of Method A.

(Step 3)

This step is a step of producing compound (LXII) or a salt thereof from compound (CXXXIII) or a salt thereof using a carbonylating reagent.

This step can be carried out in the same manner as in the method described in Step 8 of Method L.

Compounds (CXXXVI) and (CXXXVIII) or a salt thereof of the present invention can be produced according to the following Method W.

[Method W]

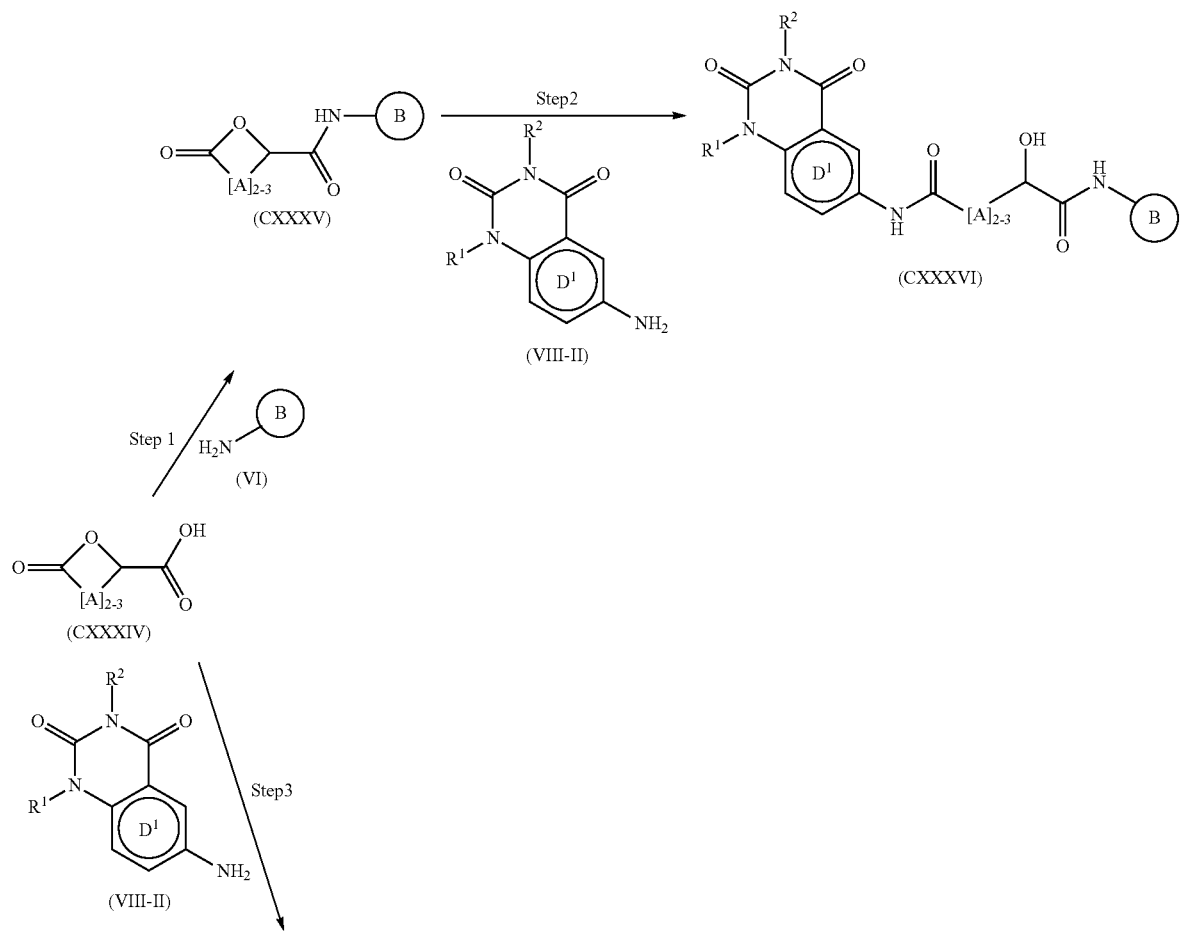

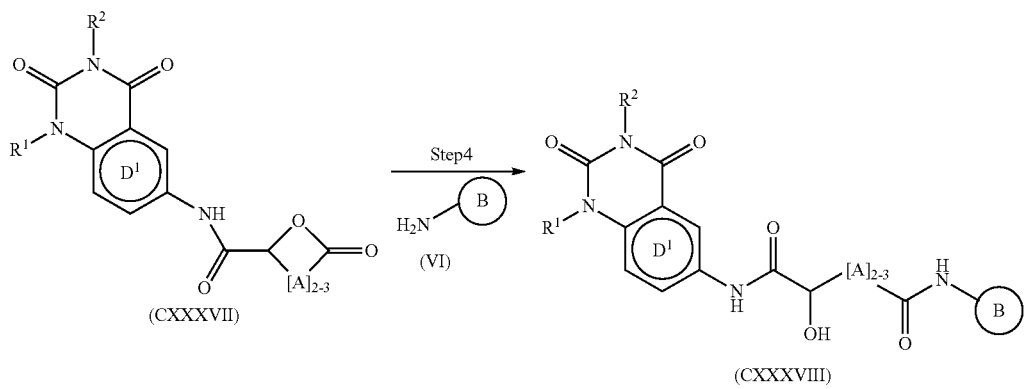

wherein each symbol is as defined above.

(Step 1)

This step is a step of producing compound (CXXXV) or a salt thereof by reacting compound (CXXXIV) or a salt thereof with compound (VI) or a salt thereof in the presence of a condensing agent. This step can be carried out in the same manner as in the method described in Step 2 of Method A.

Compound (CXXXIV) and compound (VI) may be a commercially available product, or can also be produced according to a method known per se or a method analogous thereto.

(Step 2)

This step is a step of producing compound (CXXXVI) or a salt thereof by reacting compound (CXXXV) or a salt thereof with compound (VIII-II) or a salt thereof in the presence of a base or a salt. This step can be carried out in the same manner as in the method described in Step 1 of Method P.

(Step 3)

This step is a step of producing compound (CXXXVII) or a salt thereof by reacting compound (CXXXIV) or a salt thereof with compound (VIII-II) or a salt thereof in the presence of a condensing agent. This step can be carried out in the same manner as in the method described in Step 2 of Method A.

(Step 4)

This step is a step of producing compound (CXXXVIII) or a salt thereof by reacting compound (CXXXVII) or a salt thereof with compound (VI) or a salt thereof in the presence of a base or a salt. This step can be carried out in the same manner as in the method described in Step 1 of Method P.

Compounds (CXLVIII) and (CLVII) or a salt thereof, and the above-mentioned compounds (CXLVII) and (CLVI) of the present invention can be produced according to the following XA and Method XB.

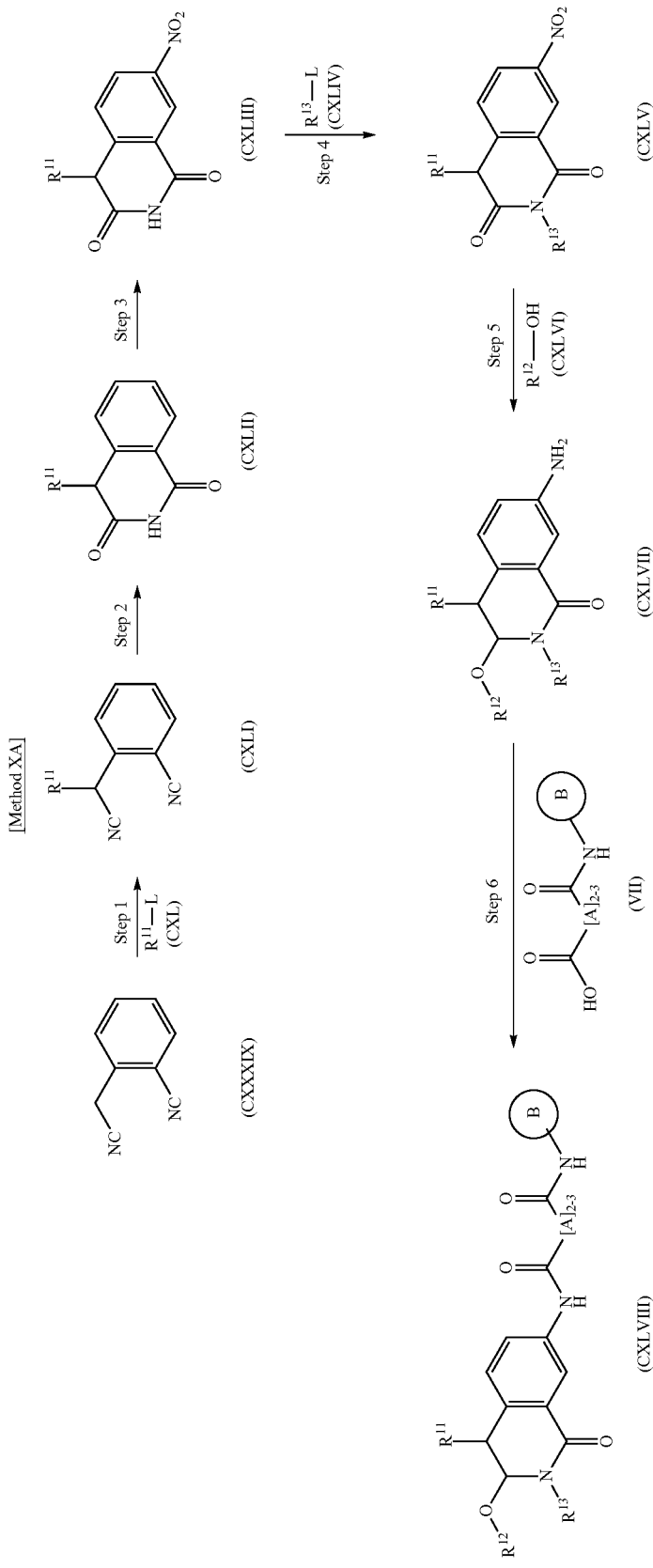

wherein each symbol is as defined above.
(Step 1)
This step is a step of producing compound (CXLI) or a salt thereof by reacting compound (CXXXIX) or a salt thereof with compound (CXL) or a salt thereof in the presence of a base.

Compound (CXXXIX) and compound (CXL) may be a commercially available product, or can also be produced according to a method known per se or a method analogous thereto.

This step can be carried out in the same manner as in the method described in Step 3 of Method S.
(Step 2)
This step is a step of producing compound (CXLII) or a salt thereof by treating compound (CXLI) or a salt thereof with an acid in the presence of a base.

The acid to be used is preferably conc. sulfuric acid, and it is generally used as a solvent. The reaction temperature is about 0 to 100° C., preferably about 0 to 80° C., and the reaction time is generally about 1 to 24 hr, preferably about 1 to 14 hr.
(Step 3)
This step is a step of producing compound (CXLIII) or a salt thereof by subjecting compound (CXLII) or a salt thereof to a nitration reaction in the presence of a base.

In this reaction, nitric acid and conc. sulfuric acid are preferably used. The amount of the nitric acid to be used is about 1 to 5 mol equivalent, preferably about 1 to 2 mol equivalent, per 1 mol of compound (CXLII).

This step can be carried out in the same manner as in the method described in the "method of reacting compound (LVII) with compound (LXI) in the presence of a base" of Step 3 of Method L.
(Step 5)
This step is a step of producing compound (CXLVII) or a salt thereof by subjecting compound (CXLV) or a salt thereof to a reduction reaction by catalytic hydrogenation using a transition metal catalyst in the presence of compound (CXLVI).

Compound (CXLVI) may be a commercially available product, or can also be produced according to a method known per se or a method analogous thereto. Compound (CXLVI) is preferably methanol, ethanol, propanol and the like, and it is used as a solvent in the reduction reaction by catalytic hydrogenation using a transition metal catalyst.

This step can be carried out in the same manner as in the method described in the "reduction by catalytic hydrogenation using a transition metal catalyst" of Step 3 of Method C.
(Step 6)
This step is a step of producing compound (CXLVIII) or a salt thereof by reacting compound (CXLVII) or a salt thereof with compound (VII) or a salt thereof in the presence of a condensing agent. This step can be carried out in the same manner as in the method described in Step 2 of Method A.

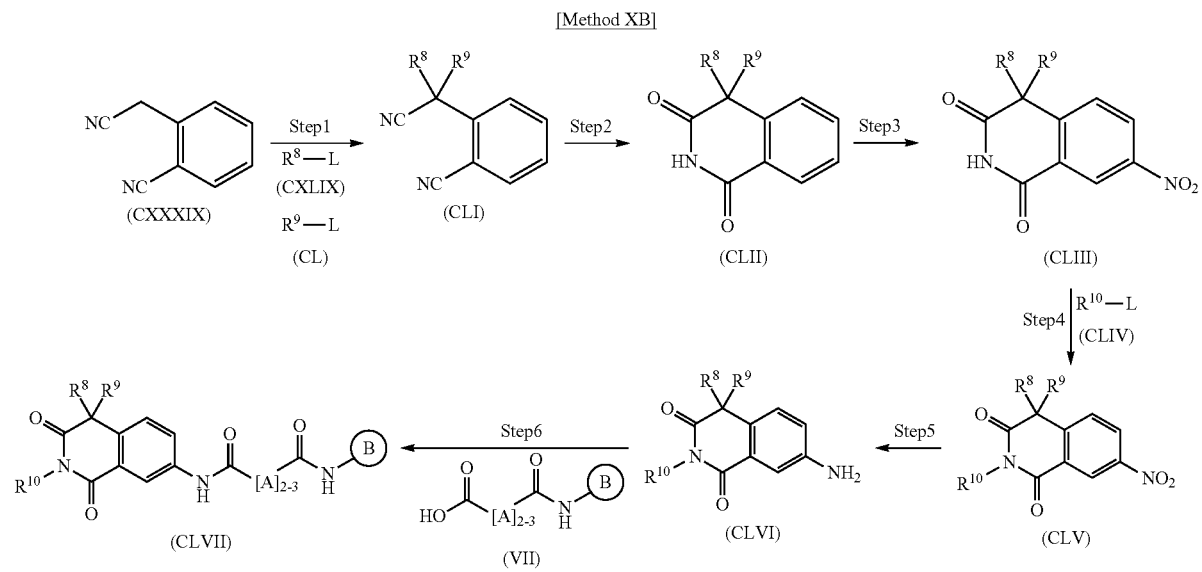

[Method XB]

Conc. sulfuric acid is generally used as a solvent. The reaction temperature is about −80 to 50° C., preferably about 0 to 30° C., and the reaction time is generally about 1 to 24 hr, preferably about 1 to 14 hr.
(Step 4)
This step is a step of producing compound (CXLV) or a salt thereof by reacting compound (CXLIII) or a salt thereof with compound (CXLIV) or a salt thereof in the presence of a base.

Compound (CXLIV) may be a commercially available product, or can also be produced according to a method known per se or a method analogous thereto.

wherein each symbol is as defined above.
(Step 1)
This step is a step of producing compound (CLI) or a salt thereof by reacting compound (CXXXIX) or a salt thereof with compound (CXLIX) or a salt thereof and compound (CL) or a salt thereof ($R^8$ and $R^9$ are bonded to each other) in the presence of a base.

Compound (CXLIX) and compound (CL) ($R^8$ and $R^9$ are bonded to each other) may be a commercially available product, or can also be produced according to a method known per se or a method analogous thereto.

This step can be carried out in the same manner as in the method described in Step 3 of Method S.

(Step 2)

This step is a step of producing compound (CLII) or a salt thereof by treating compound (CLI) or a salt thereof with an acid in the presence of a base.

This step can be carried out in the same manner as in the method described in Step 2 of Method XA.

(Step 3)

This step is a step of producing compound (CLIII) or a salt thereof by subjecting compound (CLII) or a salt thereof to a nitration reaction in the presence of a base.

This step can be carried out in the same manner as in the method described in Step 3 of Method XA.

(Step 4)

This step is a step of producing compound (CLV) or a salt thereof by reacting compound (CLIII) or a salt thereof compound (CLIV) or a salt thereof in the presence of a base.

Compound (CLIV) may be a commercially available product, or can also be produced according to a method known per se or a method analogous thereto.

This step can be carried out in the same manner as in the method described in the "method of reacting compound (LVII) with compound (LXI) in the presence of a base" of Step 3 of Method L.

(Step 5)

This step is a step of producing compound (CLVI) or a salt thereof by subjecting compound (CLV) or a salt thereof to a reduction reaction.

This step can be carried out in the same manner as in the method described in Step 3 of Method M.

(Step 6)

This step is a step of producing compound (CLVII) or a salt thereof by reacting compound (CLVI) or a salt thereof with compound (VII) or a salt thereof in the presence of a condensing agent. This step can be carried out in the same manner as in the method described in Step 2 of Method A.

When the object product is obtained in a free form by the above-mentioned reaction, it may be converted to a salt by a conventional method. When it is obtained as a salt, it can also be converted to a free form or other salt by a conventional method. The thus-obtained compound (I) can be isolated and purified from the reaction solution by a known means, for example, phase transfer, concentration, solvent extraction, fractionation, crystallization, recrystallization, chromatography and the like.

When compound (I) contains an isomer such as a tautomer, an optical isomer, a stereoisomer, a regioisomer, a rotamer and the like, any isomer and a mixture thereof are also encompassed in the compound of the present invention. Furthermore, when compound (I) has an optical isomer, an optical isomer resolved from racemic compound is also encompassed in compound (I).

Compound (I) may be a crystal, and both a single crystal and crystal mixtures are encompassed in compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) may be a solvate (e.g., a hydrate) or a non-solvate. Any of them is encompassed in compound (I).

A compound labeled or substituted with an isotope (e.g., $^3$H, $^{11}$C, $^{14}$C, 18F, $^{35}$S, $^{125}$I) is also encompassed in compound (I). Deuterium wherein 1H is converted to $^2$H(D) is also encompassed in compound (I).

Compound (I) labeled with or substituted by an isotope can be used, for example, as a tracer used for Positron Emission Tomography (PET) (PET tracer), and is useful in the field of medical diagnosis and the like.

The prodrug of compound (I) means a compound which can be converted into compound (I) by reaction with an enzyme, gastric acid, or the like under physiological conditions in the living body. In other words, it means a compound which can be converted into compound (I) by enzymatic oxidation, reduction, hydrolysis or the like, or a compound which can be converted into compound (I) by hydrolysis with gastric acid or the like. Examples of the prodrug of compound (I) include a compound in which amino of compound (I) is acylated, alkylated or phosphorylated (e.g., the amino of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated etc.); a compound in which hydroxyl of compound (I) is acylated, alkylated, phosphorylated or borated (e.g., hydroxyl of compound (I) is acetylated, palmitoylated, propanoylated, pivaloylated, succinylated, fumarylated, alanylated, dimethylaminomethylcarbonylated etc.); a compound in which carboxy of compound (I) is esterified or amidated (e.g., a compound in which carboxy of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, methylamidated etc.). These compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

Since compound (I) and a prodrug thereof [hereinafter sometimes to be abbreviated as the compound of the present invention] show superior RORγt inhibitory activity, they are also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for RORγt associated diseases, Th17 cell associated diseases and IL-17A or IL-17F associated diseases, more specifically, the diseases described in (1)-(4) below. (1) inflammatory diseases (e.g., rheumatoid arthritis, acute pancreatitis, chronic pancreatitis, asthma, bronchial asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis etc.), (2) autoimmune diseases (e.g., rheumatoid arthritis, ankylosing spondylitis, psoriasis, multiple sclerosis (MS), polymyositis, dermatomyositis (DM), polyarteritis nodosa (PN), mixed connective tissue disease (MCTD), Sjogren's syndrome nephritis, systemic lupus erythematosus, scleroderma, profundus lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, inflammatory bowel disease (IBD), ulcerative colitis (UC), Crohn's disease, graft versus host disease, Addison's disease, abnormal immunoresponse, arthritis, dermatitis, radiodermatitis etc.), (3) bone or joint degenerative diseases (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sacroma, vascular proliferation, cachexia, metastasis of the breast cancer, cancer (e.g., colorectal cancer (e.g., familial colorectal cancer, hereditary nonpolyposis colorectal cancer, gastrointestinal stromal tumor and the like), lung cancer (e.g., non-small cell lung cancer, small cell lung cancer, malignant mesothelioma and the like), mesothelioma, pancreatic cancer (e.g., pancreatic duct cancer and the like), gastric cancer (e.g., papillary adenocarcinoma, mucinous adenocarcinoma, adenosquamous carcinoma and the like), breast cancer (e.g., invasive ductal carcinoma, ductal carcinoma in situ, inflammatory breast cancer and the like), ovarian cancer (e.g., ovarian epithelial carcinoma, extragonadal germ cell tumor, ovarian germ cell tumor, ovarian low malignant potential tumor and the like), prostate cancer (e.g., hormone-dependent prostate cancer, non-hormone dependent prostate cancer and the like), liver cancer (e.g., primary liver cancer, extrahepatic bile duct cancer and the like), thyroid cancer (e.g., medullary thyroid carcinoma and the like), kidney cancer (e.g., renal cell carcinoma, transitional cell carcinoma in kidney and urinary duct and the like), uterine cancer, endometrial cancer, brain tumor (e.g., pineal astrocytoma, pilocytic astrocytoma, diffuse astrocytoma, anaplastic astrocytoma and the like), melanoma, sarcoma, urinary bladder cancer, hematologic cancer and the like including multiple myeloma, hypophyseal adenoma, glioma, acoustic neurinoma, retinoblastoma, head and neck carcinoma, pharyngeal cancer, laryngeal cancer, cancer of the tongue, thymoma, esophagus cancer, duodenal cancer, colorectal cancer, rectal cancer, hepatoma, pancreatic endocrine tumor, bile duct cancer, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary].

The medicament of the present invention can be used as a prophylactic or therapeutic agent for preferably autoimmune disease, inflammatory disease, bone or articular disease or neoplastic disease, particularly preferably, rheumatoid arthritis, inflammatory bowel disease, psoriasis, ankylosing spondylitis, bronchial asthma, chronic obstructive pulmonary diseases, ovarian cancer, non-small cell lung cancer, breast cancer, gastric cancer, cervical cancer, prostate cancer or uterine body cancer.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. While the dose varies depending on the subject of administration, administration route, disease and the like, for example, for oral administration to an adult inflammatory bowel disease (IBD) patient (body weight about 60 kg), it is about 0.1 mg/kg body weight to 30 mg/kg body weight, preferably about 1 mg/kg body weight to 20 mg/kg body weight as an active ingredient (compound (I)) for one day, which is administered once to several times, preferably, once, or twice to 3 times a day.

The pharmaceutically acceptable carrier, which may be used for the production of the medicament of the present invention, may be exemplified by various organic or inorganic carrier materials that are conventionally used as preparation materials, for example, excipient, lubricant, bin ding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as an RORγt inhibitor, Th17 cell inhibitor, IL-17A or IL-17F inhibitor, it can be used in combination with the following drugs.

(1) non-steroidal anti-inflammatory drug (NSAIDs)
(i) Classical NSAIDs
    alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.

(ii) cyclooxygenase inhibitor (COX-1 selective inhibitor, COX-2 selective inhibitor and the like)
    salicylic acid derivatives (e.g., celecoxib, aspirin), etoricoxib, valdecoxib, diclofenac, indomethacin, loxoprofen and the like.
(iii) nitric oxide-releasing NSAIDs
(2) disease-modifying anti-rheumatic drugs (DMARDs)
(i) Gold preparation
    auranofin and the like.
(ii) penicillamine
    D-penicillamine.
(iii) aminosalicylic acid preparation
    sulfasalazine, mesalamine, olsalazine, balsalazide.
(iv) antimalarial drug
    chloroquine and the like.
(v) pyrimidine synthesis inhibitor
    leflunomide and the like.
(vi) tacrolimus
(3) anti-cytokine drug
(I) protein drug
(i) TNF inhibitor
    etanercept, infliximab, adalimumab, certolizumab pegol, golimumab, PASSTNF-α, soluble TNF-α receptor, TNF-α binding protein, anti-TNF-α antibody and the like.
(ii) interleukin-1 inhibitor
    anakinra (interleukin-1 receptor antagonist), soluble interleukin-1 receptor and the like.
(iii) interleukin-6 inhibitor
    tocilizumab (anti-interleukin-6 receptor antibody), anti-interleukin-6 antibody and the like.
(iv) interleukin-10 drug
    interleukin-10 and the like.
(v) interleukin-12/23 inhibitor
    ustekinumab, briakinumab (anti-interleukin-12/23 antibody) and the like.
(vi) B cell activation inhibitor
    rituxan, benrista and the like.
(vii) co-stimulatory molecules related protein drug
    abatacept and the like.
(II) non-protein drug
(i) MAPK inhibitor
    BMS-582949 and the like.
(ii) gene modulator
    inhibitor of molecule involved in signal transduction, such as NF-κ, NF-κB, IKK-1, IKK-2, AP-1 and the like, and the like.
(iii) cytokine production inhibitor
    iguratimod, tetomilast and the like.
(iv) TNF-α converting enzyme inhibitor
(v) interleukin-1β converting enzyme inhibitor
    belnacasan and the like.
(vi) interleukin-6 antagonist
    HMPL-004 and the like.
(vii) interleukin-8 inhibitor
    IL-8 antagonist, CXCR1 & CXCR2 antagonist, reparixin and the like.
(viii) chemokine antagonist
    CCR9 antagonist (vercirnon sodium, CCX0025, N-{4-chloro-2-[(1-oxidepyridin-4-yl)carbonyl]phenyl}-4-(propan-2-yloxy)benzenesulfonamide), MCP-1 antagonist and the like.
(ix) interleukin-2 receptor antagonist
    denileukin, diftitox and the like.
(x) therapeutic vaccines
    TNF-α vaccine and the like.

(xi) gene therapy drug
gene therapy drugs aiming at promoting the expression of gene having an anti-inflammatory action such as interleukin-4, interleukin-10, soluble interleukin-1 receptor, soluble TNF-α receptor and the like.
(xii) antisense compound
ISIS 104838 and the like.
(4) integrin inhibitor
natalizumab, vedolizumab, AJM300, TRK-170, E-6007 and the like.
(5) immunomodulator (immunosuppressant)
methotrexate, cyclophosphamide, MX-68, atiprimod dihydrochloride, abatacept, CKD-461, rimexolone, cyclosporine, tacrolimus, gusperimus, azathiopurine, anti-lymphocyte serum, freeze-dried sulfonated normal immunoglobulin, erythropoietin, colony stimulating factor, interleukin, interferon and the like.
(6) proteasome inhibitor
velcade and the like.
(7) JAK inhibitor
tofacitinib and the like.
(8) steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.
(9) angiotensin converting enzyme inhibitor
enalapril, captopril, ramipril, lisinopril, cilazapril, perindopril and the like.
(10) angiotensin II receptor antagonist
candesartan, cilexetil (TCV-116), valsartan, irbesartan, olmesartan, eprosartan and the like.
(11) diuretic drug
hydrochlorothiazide, spironolactone, furosemide, indapamide, bendrofluazide, cyclopenthiazide and the like.
(12) cardiotonic drug
digoxin, dobutamine and the like.
(13) β receptor antagonist
carvedilol, metoprolol, atenolol and the like.
(14) Ca sensitizer
caldaret hydrate and the like.
(15) Ca channel antagonist
nifedipine, diltiazem, verapamil and the like.
(16) anti-platelet drug, anticoagulator
heparin, aspirin, warfarin and the like.
(17) HMG-CoA reductase inhibitor
atorvastatin, simvastatin and the like.
(18) contraceptive
(i) sex hormone or derivatives thereof
gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, tosagestin, TX-525, ethinylestradiol/TX525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) antiestrogen
ormeloxifene, mifepristone, Org-33628 and the like.

(iii) spermatocide
ushercell and the like.
(19) others
(i) T cell inhibitors
(ii) inosine monophosphate dehydrogenase (IMPDH) inhibitor
mycophenolate mofetil and the like.
(iii) adhesion molecule inhibitor
alicaforsen sodium, selectin inhibitor, ELAM-1 inhibitor, VCAM-1 inhibitor, ICAM-1 inhibitor and the like.
(iv) thalidomide
(v) cathepsin inhibitor
(vi) matrix metalloprotease (MMPs) inhibitor
V-85546 and the like.
(vii) glucose-6-phosphate dehydrogenase inhibitor
(viii) Dihydroorotate dehydrogenase (DHODH) inhibitor
(ix) phosphodiesterase IV (PDE IV) inhibitor
roflumilast, CG-1088 and the like.
(x) phospholipase $A_2$ inhibitor
(xi) iNOS inhibitor
VAS-203 and the like.
(xii) microtubule stimulating drug
paclitaxel and the like.
(xiii) microtuble inhibitor
reumacon and the like.
(xiv) MHC class II antagonist
(xv) prostacyclin agonist
iloprost and the like.
(xvi) CD4 antagonist
zanolimumab and the like.
(xvii) CD23 antagonist
(xviii) LTB4 receptor antagonist
DW-1350 and the like.
(xix) 5-lipoxygenase inhibitor
zileuton and the like.
(xx) cholinesterase inhibitor
galanthamine and the like.
(xxi) tyrosine kinase inhibitor
Tyk2 inhibitor (WO2010142752) and the like.
(xxii) carepsin B inhibitor
(xxiii) adenosine deaminase inhibitor
pentostatin and the like.
(xxiv) osteogenesis stimulator
(xxv) dipeptidylpeptidase inhibitor
(xxvi) collagen agonist
(xxvii) capsaicin cream
(xxviii) hyaluronic acid derivative
synvisc (hylan G-F 20), orthovisc and the like.
(xxix) glucosamine sulfate
(xxx) amiprilose
(xxxi) CD-20 inhibitor
rituximab, ibritumomab, tositumomab, ofatumumab and the like.
(xxxii) BAFF inhibitor
belimumab, tabalumab, atacicept, blisibimod and the like.
(xxxiii) CD52 inhibitor
alemtuzumab and the like.
Other concomitant drugs besides the above-mentioned include, for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, therapeutic drug for diabetes, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.

(1) Antibacterial Agent (i) sulfa drug sulfamethizole, sulfisoxazole, sulfamonomethoxine, sulfamethizole, salazosulfapyridine, silver sulfadiazine and the like.

(ii) quinolone antibacterial agent nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.

(iii) antiphthisic isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.

(iv) antiacidfast bacterium drug diaphenylsulfone, rifampicin and the like.

(v) antiviral drug idoxuridine, acyclovir, vidarabine, gancyclovir and the like.

(vi) anti-HIV agent zidovudine, didanosine, zalcitabine, indinavir sulfate ethanolate, ritonavir and the like.

(vii) antispirochetele (viii) antibiotic tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885(1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3-(2H, 4H)-1,2,4-triazolone, fluconazole, itraconazole and the like] and the like.

(2) Antifungal Agent (i) polyethylene antibiotic (e.g., amphotericin B, nystatin, trichomycin)

(ii) griseofulvin, pyrrolnitrin and the like (iii) cytosine metabolism antagonist (e.g., flucytosine)

(iv) imidazole derivative (e.g., econazole, clotrimazole, miconazole nitrate, bifonazole, croconazole)

(v) triazole derivative (e.g., fluconazole, itraconazole)

(vi) thiocarbamic acid derivative (e.g., trinaphthol) and the like.

(3) Antiprotozoal Agent metronidazole, tinidazole, diethylcarbamazine citrate, quinine hydrochloride, quinine sulfate and the like.

(4) Antitussive and Expectorant Drug ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terputaline, oxypetebanol, morphine hydrochloride, dextropethorfan hydrobromide, oxycodone hydrochloride, dimorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) Sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic (6-1) Local Anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(6-2) General Anesthetic (i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) Antiulcer Drug histidine hydrochloride, lansoprazole, metoclopramide, pirenzepine, cimetidine, ranitidine, famotidine, urogastrine, oxethazaine, proglumide, omeprazole, sucralfate, sulpiride, cetraxate, gefarnate, aldioxa, teprenone, prostaglandin and the like.

(8) Antiarrhythmic Agent (i) sodium channel blocker (e.g., quinidine, procainamide, disopyramide, ajmaline, lidocaine, mexiletine, phenytoin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone), (iv) calcium channel blocker (e.g., verapamil, diltiazem) and the like.

(9) Hypotensive Diuretic Drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) Anticoagulant heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, zusulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Hypolipidemic Drug clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) Antiepileptic Drug phenytoin, ethosuximide, acetazolamide, chlordiazepoxide, tripethadione, carbamazepine, phenobarbital, primidone, sulthiame, sodium valproate, clonazepam, diazepam, nitrazepam and the like.

(17) Antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiac Stimulants trans-π-oxocamphor, terephyllol, aminophylline, etilefrine, dopamine, dobutamine, denopamine, aminophylline, vesinarine, amrinone, pimobendan, ubidecarenone, digitoxin, digoxin, methyldigoxin, lanatoside C, G-strophanthin and the like.

(20) Vasodilator oxyfedrine, diltiazem, tolazoline, hexobendine, bamethan, clonidine, methyldopa, guanabenz and the like.

(21) Vasoconstrictor dopamine, dobutamine denopamine and the like.

(22) Hypotensive Diuretic hexamethonium bromide, pentolinium, mecamylamine, ecarazine, clonidine, diltiazem, nifedipine and the like.

(23) Therapeutic Drug for Diabetes tolbutamide, chlorpropamide, acetohexamide, glibenclamide, tolazamide, acarbose, epalrestat, troglitazone, glucagon, glymidine, glipuzide, phenformin, puformin, metformin and the like.

(24) Antinarcotic levallorphan, nalorphine, naloxone or a salt thereof and the like.

(25) Liposoluble Vitamins (i) vitamin A: vitamin $A_1$, vitamin $A_2$ and retinol palmitate
(ii) vitamin D: vitamin $D_1$, $D_2$, $D_3$, $D_4$ and $D_5$
(iii) vitamin E: α-tocopherol, β-tocopherol, γ-tocopherol, 5-tocopherol, dl-α-tocopherol nicotinate
(iv) vitamin K: vitamin $K_1$, $K_2$, $K_3$ and $K_4$
(v) folic acid (vitamin M) and the like.

(26) Vitamin Derivative various derivatives of vitamins, for example, vitamin $D_3$ derivatives such as 5,6-trans-cholecalciferol, 2,5-hydroxycholecalciferol, 1-α-hydroxycholecalciferol, calcipotriol and the like, vitamin $D_2$ derivatives such as 5,6-trans-ergocalciferol and the like, and the like.

(27) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate, ciclesonide and the like.

(28) Therapeutic Agent for Pollakisuria/Anischuria flavoxate hydrochloride and the like.

(29) Therapeutic Agent for Atopic Dermatitis sodium cromoglicate and the like.

(30) therapeutic agent for allergic rhinitis sodium cromoglicate, chlorpheniramine maleate, alimemazine tartrate, clemastine fumarate, homochlorcyclizine hydrochloride, fexofenadine, mequitazine, ketotifen fumarate, cetirizine hydrochloride, oxatomide, azelastine, ebastine, epinastine hydrochloride, loratadine and the like.

(31) Hypertensor dopamine, dobutamine, denopamine, digitoxin, digoxin, methyldigoxin, lanatoside C, G-strophanthin and the like.

(32) Others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose of the combination agent varies depending on the kind of the compound of the present invention, administration route, symptom, age of patients and the like. For example, for oral administration to patients (body weight about 60 kg) with inflammatory bowel disease (IBD), about 0.1 mg/kg body weight-about 30 mg/kg body weight, preferably about 1 mg/kg body weight-20 mg/kg body weight, of compound (I) can be administered once to several portions per day.

The dose of the medicament of the present invention as a sustained-release preparation varies depending on the kind and content of compound (I), dosage form, period of sustained drug release, subject animal of administration (e.g., mammals such as mouse, rat, hamster, guinea pig, rabbit, cat, dog, bovine, horse, swine, sheep, monkey, human and the like), and administration object. For example, for application by parenteral administration, about 0.1 to about 100 mg of compound (I) needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLE

The present invention is explained in more detail in the following by referring to Examples, Preparation Examples and Experimental Examples, which are not to be construed as limitative and may be modified without departing from the scope of the invention.

Unless particularly indicated, the elution in column chromatography in the Examples was performed under observation by TLC (Thin Layer Chromatography). For TLC observation, 60F254 manufactured by Merck was used as a TLC plate, and the solvent used as an elution solvent for column chromatography was used. For detection, moreover, a UV detector was adopted. As silica gel for column chromatography, silica gel 60 (70-230 mesh) manufactured by Merck was used. The room temperature generally means a temperature about 10° C. to 35° C. For drying extracts, sodium sulfate or magnesium sulfate was used.

The abbreviations in the Examples mean as follows.
LC: liquid chromatography
MS: mass analysis spectrum
API: atmospheric pressure ionization method
M: molecular weight of the compound
NMR: nuclear magnetic resonance spectrum
Hz: hertz
J: coupling constant
m: multiplet
q: quartet
t: triplet
d: doublet
s: singlet
dt: double triplet
sxt: sextet
septet: septet
brs: broad singlet
Boc: tert-butyloxycarbonyl group
N: normal concentration
THF: tetrahydrofuran
HOBt: 1H-benzo[d][1,2,3]triazol-1-ol hydrate
WSC: $N^1$-((ethylimino)methylene)-$N^3$,$N^3$-dimethylpropane-1,3-diamine hydrochloride
DMF: N,N-dimethylformamide
DMA: dimethylacetamide
DMAP: N,N-dimethylpyridin-4-amine DMSO: dimethyl sulfoxide
DIEA: diisopropylethylamine
HATU: 2-(1H-7-azabenzotriazol-1-yl)-1,1,3,3-tetramethyluronium hexafluorophosphorate
IPE: diisopropyl ether
TEA: triethylamine
DBU: 1,8-diazabicyclo[5.4.0]undec-7-ene
DPPA: diphenylphosphoryl azide
T3P: 2,4,6-tripropyl-1,3,5,2,4,6-trioxatriphosphorinane-2,4,6-trioxide
CDI: carbonyldiimidazole
ADDP: 1,1'-(azodicarbonyl)dipiperidine
$Pd_2(dba)_3$: tris(dibenzylideneacetone)dipalladium(0)
XPhos: 2-dicyclohexylphosphino-2',4',6'-triisopropylbiphenyl NMP: N-methylpyrrolidone Reference Example 1

N-(3-chloro-4-cyanophenyl)-N'-(4-ethyl-3-oxo-3,4-dihydro-2H-1,4-benzoxazin-7-yl)-3-methylpentanediamide (Step 1)
To a solution of 7-nitro-2H-benzo[b][1,4]oxazin-3-(4H)-one (500 mg, 2.58 mmol) and potassium carbonate (1.780 g, 12.88 mmol) in DMF (12 mL) was added iodoethane (0.515 mL, 6.44 mmol), and the mixture was stirred at 70° C. for 12 hr. The reaction mixture was allowed to be cooled to room temperature, water was added thereto, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→65% ethyl acetate/hexane) to give 4-ethyl-7-nitro-2H-benzo[b][1,4]oxazin-3(4H)-one (560 mg, 2.52 mmol, 98%) as a pale yellow solid.
$^1$H-NMR (300 MHz, $CDCl_3$): δ1.31 (3H, t, J=7.2 Hz), 4.05 (2H, q, J=7.2 Hz), 4.69 (2H, s), 7.08 (1H, d, J=9.1 Hz), 7.86 (1H, d, J=2.6 Hz), 7.97 (1H, dd, J=8.9, 2.5 Hz).
(Step 2)
A solution of the compound obtained in Step 1 (550 mg, 2.48 mmol) and 10% palladium on carbon (50% hydrous, 50 mg, 0.47 mmol) in methanol (15 mL) was stirred at room temperature under 1 atm of under hydrogen atmosphere for 2 days. The catalyst was removed by filtration, and the filtrate was concentrated under reduced pressure to give 7-amino-4-ethyl-2H-benzo[b][1,4]oxazin-3 (4H)-one (472 mg, 2.456 mmol, 99%) as a pale gray solid.
$^1$H-NMR (300 MHz, $CDCl_3$): δ1.25 (3H, t, J=7.2 Hz), 3.59 (2H, brs), 3.93 (2H, q, J=6.9 Hz), 4.53 (2H, s), 6.25-6.46 (1H, m), 6.78 (1H, d, J=9.1 Hz), 7.26 (1H, s).
(Step 3)
A solution of 3-methylglutaric anhydride (420 mg, 3.28 mmol) and 4-amino-2-chlorobenzonitrile (500 mg, 3.28 mmol) in THF (15 mL) was refluxed overnight. The reaction mixture was concentrated under reduced pressure to give 5-(3-chloro-4-cyanophenylamino)-3-methyl-5-oxopentanoic acid (1.143 g, 4.07 mmol, 100%) as a pale brown oil.
$^1$H-NMR (300 MHz, DMSO-$d_6$): δ0.82-1.07 (3H, m), 2.05-2.42 (5H, m), 7.60 (1H, dd, J=8.7, 1.9 Hz), 7.88 (1H, d, J=8.7 Hz), 8.06 (1H, d, J=1.5 Hz), 10.50 (1H, s), 12.08 (1H, s).
(Step 4)
To a solution of the compound obtained in Step 2 (460 mg, 2.39 mmol), the compound obtained in Step 3 (250 mg, 0.89 mmol) and DIEA (0.778 mL, 4.45 mmol) in DMF (10 mL) was added HATU (847 mg, 2.23 mmol) at room temperature. The reaction mixture was stirred overnight at room temperature, water was added thereto, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane), and then purified by NH-silica gel column chromatography (solvent gradient; 20→100% ethyl acetate/hexane, 0→20% methanol/ethyl acetate) to give the title compound (38.7 mg, 0.085 mmol, 9.55%) as a white solid.
MS(API): 453 (M−H)

Reference Example 2

N-(3-chloro-4-cyanophenyl)-N'-(4-ethyl-3,4-dihydro-2H-1,4-benzoxazin-7-yl)-3-methylpentanediamide (Step 1)
To a solution of the compound obtained in Step 1 of Reference Example 1 (590 mg, 2.66 mmol) in THF (12 mL) was added borane-dimethyl sulfide complex (1.9 mol/L, THF solution, 5.59 mL, 10.62 mmol), and the mixture was stirred at 50° C. for 12 hr. The reaction mixture was allowed to be cooled to room temperature, methanol (5 mL) was added thereto, and the mixture was concentrated under reduced pressure. The obtained residue was purified by silica gel column chromatography (solvent gradient; 5-65% ethyl acetate/hexane) to give 4-ethyl-7-nitro-3,4-dihydro-2H-benzo[b][1,4]oxazine (535 mg, 2.57 mmol, 97%) as a yellow solid.
$^1$H-NMR (300 MHz, $CDCl_3$): δ1.22 (3H, t, J=7.2 Hz), 3.37-3.57 (4H, m), 4.15-4.31 (2H, m), 6.59 (1H, d, J=9.1 Hz), 7.65 (1H, d, J=2.6 Hz), 7.80 (H, dd, J=9.1, 2.6 Hz)
(Step 2)
4-Ethyl-3,4-dihydro-2H-benzo[b][1,4]oxazin-7-amine (447 mg, 2.506 mmol, 98%) was obtained as a purple oil using the compound obtained in Step 1 (530 mg, 2.55 mmol) by the reaction in the same manner as in Step 2 of Reference Example 1.
MS(API): 179 (M+H)
(Step 3)
The title compound (355 mg, 0.805 mmol, 32.6%) was obtained as a pale yellow solid using the compound obtained in Step 2 (440 mg, 2.47 mmol) by the reaction and purification in the same manner as in Step 4 of Reference Example 1.
MS(API): 441 (M+H)

Reference Example 3

N-(3-chloro-4-cyanophenyl)-N'-(4-ethyl-2-methyl-3-oxo-3,4-dihydro-2H-1, 4-benzoxazin-7-yl)-3-methylpentanediamide (Step 1)
To a suspension of potassium fluoride (2.36 g, 40.55 mmol) in DMF (15 mL) was added methyl 2-bromopropionate (1.99 mL, 17.84 mmol), and the mixture was stirred at room temperature for 15 min. To the reaction mixture was added 2-amino-5-nitrophenol (2.5 g, 16.22 mmol), and the mixture was stirred at 50 to 60° C. for 6 hr, and then at room temperature for 14 hr. The same reaction was repeated, and both of the reaction mixtures were combined. Ice (175 g)

was added thereto, the precipitated white solid was collected by filtration, and the obtained white solid was washed with water and hexane, and dried under reduced pressure to give 2-methyl-7-nitro-4H-benzo[1,4]oxazin-3-one (5.1 g, 75%) as a grayish white solid.

MS(API): 207 (M−H)

(Step 2)

The compound obtained in Step 1 (3.0 g, 14.42 mmol) was dissolved in DMF (45 mL), and potassium carbonate (4.98 g, 36.06 mmol) was added thereto at 0° C. under nitrogen atmosphere. The mixture was stirred at room temperature for 15 min, iodoethane (1.85 mL, 21.63 mmol) was added thereto, and the mixture was stirred for additional 14 hr. To the reaction mixture was added water, and the mixture was extracted with ethyl acetate. The organic layer was washed with water and saturated brine, and dried over sodium sulfate, and the solvent was evaporated under reduced pressure to give 4-ethyl-2-methyl-7-nitro-4H-benzo [1,4]oxazin-3-one (2.3 g, 77.3%) as a brown oil.

MS(API): 237 (M+H)

(Step 3)

7-Amino-4-ethyl-2-methyl-4H-benzo[1,4]oxazin-3-one (0.37 g, 84.7%) was obtained as a brown solid using the compound obtained in Step 2 (0.50 g, 2.12 mmol) by the reaction in the same manner as in Step 2 of Reference Example 1.

MS(API): 207 (M+H)

(Step 4)

To a solution of the compound obtained in Step 3 (0.36 g, 1.74 mmol) and 4-(3-chloro-4-cyanophenylcarbamoyl)-3-methylbutyric acid (0.59 g, 2.09 mmol) in DMF (10 mL) were added HATU (0.79 g, 2.09 mmol) and DIEA (0.96 mL, 4.36 mmol), and the mixture was stirred at room temperature for 16 hr under argon atmosphere. The solvent was evaporated, to the residue was added ice water (20 mL), and the mixture was extracted with ethyl acetate. The organic layer was washed with water and saturated brine, and dried over sodium sulfate, and the solvent was evaporated under reduced pressure. The obtained residue was purified by preparative HPLC to give the title compound (0.078 g, 9.5%) as a white solid.

MS(API): 467 (M−H)

$^1$H-NMR (400 MHz, DMSO-d$_6$): δ0.98 (d, 3H, J=6.04 Hz), 1.11 (t, 3H, J=6.96 Hz), 1.39 (d, 3H, J=6.68 Hz), 2.21-2.44 (m, 5H), 3.88 (q, 2H, J=8.04 Hz), 4.64 (q, 1H, J=6.48 Hz), 7.10 (d, 1H, J=8.84 Hz), 7.19 (d, 1H, J=8.76 Hz), 7.37 (brs, 1H), 7.59 (d, 1H, J=8.76 Hz), 7.86 (d, H, J=8.56 Hz), 8.05 (brs, H), 9.89 (brs, 1H), 10.50 (brs, 1H).

purification condition by preparative HPLC
  instrument: Waters Semi-Preparative HPLC instrument
  column: Prep Scalar 10 μm C18 (250×30 mm)
  solvent: A=5 mM aqueous ammonium acetate solution, B=acetonitrile
  solvent gradient: 70% A/B(0 min)→50% A/B(60 min)→5% A/B(61 min)→5% A/B(70 min)→70% A/B(71 min)
  flow rate: 30 mL/min
  temperature: room temperature Example 1

N-(3-chloro-4-cyanophenyl)-N'-(1,3-diethyl-2,4-dioxo-1,2,3,4-tetrahydroquinazolin-6-yl)-3-methyl-pentanediamide (Step 1)

A mixture of 2-amino-5-nitro-benzoic acid (30 g, 164.71 mmol) and urea (99 g, 1647.14 mmol) was stirred overnight at 160° C. The reaction mixture was cooled to 100° C., and water (300 mL) was added thereto. The resulting precipitate was washed successively with water, acetic acid (50 mL) and methanol (100 mL), and dried to give 6-nitroquinazo-line-2,4(1H,3H)-dione (33.8 g, 163 mmol, 99%) as a yellow solid.

$^1$H-NMR (300 MHz, DMSO-d$_6$): δ7.32 (1H, d, J=9.1 Hz), 8.45 (1H, dd, J=9.1, 2.6 Hz), 8.58 (1H, d, J=2.6 Hz), 11.65 (2H, brs)

(Step 2)

To a solution of the compound obtained in Step 1 (750 mg, 3.62 mmol) and iodoethane (1.448 mL, 18.10 mmol) in DMF (15 mL) was added potassium carbonate (2.502 g, 18.10 mmol), and the mixture was stirred overnight at 70° C. The reaction mixture was allowed to be cooled to room temperature, water was added thereto, and the mixture was extracted with ethyl acetate. The organic layer was washed with water and saturated brine, and dried over magnesium sulfate, and the solvent was evaporated under reduced pressure. The obtained powder was washed with a mixed solvent of DMF-ethyl acetate-hexane to give 1,3-diethyl-6-nitroquinazoline-2,4(1H,3H)-dione (664 mg, 2.52 mmol, 69.7%) as a pale yellow solid.

$^1$H-NMR (300 MHz, DMSO-d$_6$): δ1.24 (3H, t, J=7.2 Hz), 1.18 (3H, t, J=7.2 Hz), 3.99 (2H, q, J=6.9 Hz), 4.20 (2H, q, J=6.9 Hz), 7.72 (1H, d, J=9.4 Hz), 8.51 (1H, dd, J=9.3, 2.8 Hz), 8.72 (1H, d, J=3.0 Hz).

(Step 3)

A solution of the compound obtained in Step 2 (655 mg, 2.49 mmol) and 10% palladium on carbon (50% hydrous, 50 mg, 0.47 mmol) in methanol (15 mL)/ethyl acetate (15 mL) was stirred overnight at room temperature under 1 atm of under hydrogen atmosphere. The catalyst was removed by filtration, and the filtrate was concentrated under reduced pressure to give 6-amino-1,3-diethylquinazoline-2,4(1H, 3H)-dione (572 mg, 2.452 mmol, 99%) as a grayish solid.

$^1$H-NMR (300 MHz, DMSO-d$_6$): δ1.01-1.32 (6H, m), 3.84-4.16 (4H, m), 5.28 (2H, s), 7.04 (1H, dd, J=8.7, 2.6 Hz), 7.15-7.32 (2H, m).

(Step 4)

To a solution of the compound obtained in Step 3 (550 mg, 2.36 mmol), the compound obtained in Step 3 of Reference Example 1 (662 mg, 2.36 mmol) and DIEA (2.059 mL, 11.79 mmol) in DMF (10 mL) was added HATU (2.241 g, 5.89 mmol) at room temperature. The reaction mixture was stirred overnight at room temperature, water was added thereto, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane), and then purified by NH-silica gel column chromatography (solvent gradient; 20→100% ethyl acetate/hexane, 0→20% methanol/ethyl acetate) to give the title compound (21.10 mg, 0.043 mmol, 1.8%) as a white solid.

MS(API): 496 (M+H)

$^1$H-NMR (300 MHz, DMSO-d$_6$): δ1.00 (3H, d, J=6.4 Hz), 1.07-1.31 (6H, m), 2.21-2.48 (5H, m), 3.85-4.24 (4H, m), 7.44 (1H, d, J=9.4 Hz), 7.57 (1H, dd, J=8.7, 1.9 Hz), 7.76-7.97 (2H, m), 8.02 (1H, d, J=1.5 Hz), 8.34 (1H, d, J=2.3 Hz), 10.14 (1H, s), 10.53 (1H, s).

Example 2

N-(1,3-bis(cyclopropylmethyl)-2,4-dioxo-1,2,3,4-tetrahydroquinazolin-6-yl)-N'-(3-chloro-4-cyanophenyl)-3-methylpentanediamide (Step 1)

To a solution of the compound obtained in Step 1 of Example 1 (2.00 g, 9.66 mmol) and (bromomethyl)cyclopropane (2.341 mL, 24.14 mmol) in DMF (20 mL) was added potassium carbonate (2.50 g, 18.10 mmol), and the mixture was stirred overnight at 70° C. The reaction mixture was allowed to be cooled to room temperature, and filtered through silica gel. The filtrate was concentrated under reduced pressure to give 1,3-bis(cyclopropylmethyl)-6-nitroquinazoline-2,4(1H,3H)-dione as a pale brown oil (quantitative).

$^1$H-NMR (300 MHz, DMSO-$d_6$): δ0.21-0.57 (6H, m), 0.96-1.36 (2H, m), 2.69-2.78 (1H, m), 2.80-3.19 (1H, m), 3.75-3.99 (2H, m), 4.13 (2H, d, J=7.2 Hz), 7.84 (1H, d, J=9.4 Hz), 8.52 (H, dd, J=9.3, 2.8 Hz), 8.74 (1H, d, J=2.6 Hz).

(Step 2)

A solution of the compound obtained in Step 1 (3.00 g, 9.51 mmol) and 10% palladium on carbon (50% hydrous, 300 mg, 2.82 mmol) in methanol (30 mL)/ethyl acetate (30 mL) was stirred overnight at room temperature under 1 atm of under hydrogen atmosphere. The catalyst was removed by filtration, and the filtrate was concentrated under reduced pressure. The obtained residue was purified by silica gel column chromatography (solvent gradient; 5→75% ethyl acetate/hexane) to give 6-amino-1,3-bis(cyclopropylmethyl)quinazoline-2,4(1H,3H)-dione (1.93 g, 6.76 mmol, 71.1%) as a white solid.

MS(API): 286 (M+H)

(Step 3)

To a solution of the compound obtained in Step 2 (1.93 g, 6.76 mmol), the compound obtained in Step 3 of Reference Example 1 (1.899 g, 6.76 mmol) and DIEA (5.91 mL, 33.82 mmol) in ethyl acetate (20 mL) was added T3P (50% ethyl acetate solution, 6.03 mL, 10.15 mmol) at room temperature, and the mixture was refluxed overnight. The reaction mixture was allowed to be cooled to room temperature, water was added thereto, and the mixture was extracted with ethyl acetate. The organic layer was washed with water and saturated brine, and dried over magnesium sulfate, and the solvent was evaporated under reduced pressure. The obtained residue was purified successively by silica gel column chromatography (solvent gradient; 10→100% ethyl acetate/hexane) and NH-silica gel column chromatography (solvent gradient; 20→100% ethyl acetate/hexane, 0→20% methanol/ethyl acetate), and crystallized from ethyl acetate-hexane (1:5) to give the title compound (2.440 g, 4.45 mmol, 65.8%) as colorless crystals.

MS(API): 548 (M+H)

$^1$H-NMR (300 MHz, DMSO-$d_6$): δ0.26-0.62 (8H, m), 1.01 (3H, d, J=6.0 Hz), 1.11-1.35 (2H, m), 2.22-2.41 (3H, m), 2.41-2.49 (2H, m), 3.85 (2H, d, J=7.2 Hz), 4.03 (2H, d, J=6.8 Hz), 7.45-7.64 (2H, m), 7.78-7.97 (2H, m), 8.03 (1H, d, J=1.9 Hz), 8.37 (1H, d, J=2.6 Hz), 10.16 (1H, s), 10.53 (1H, s).

Example 3

N-(4-((3-chloro-4-cyanophenyl)amino)-2-methyl-4-oxobutyl)-3-ethyl-2-propylimidazo[1,2-a]pyridine-7-carboxamide (Step 1)

A solution of crotonic acid (2.75 mL, 32.77 mmol) and thionyl chloride (2.392 mL, 32.77 mmol) in DMA (40 mL) was stirred at 0° C. for 1 hr, 4-amino-2-chlorobenzonitrile (5 g, 32.77 mmol) was added thereto, and the mixture was stirred overnight at room temperature. To the reaction mixture was added saturated brine, and the mixture was extracted with ethyl acetate. The organic layer was washed successively with 1N aqueous sodium hydroxide solution, 1N hydrochloric acid and saturated brine, and dried over magnesium sulfate, and the solvent was evaporated under reduced pressure to give (E)-N-(3-chloro-4-cyanophenyl)but-2-enamide (6.04 g, 27.4 mmol, 84%) as a brown solid.

MS(API): 219 (M−H)

(Step 2)

A solution of the compound obtained in Step 1 (2.33 g, 10.56 mol) and DBU (1.91 mL, 12.67 mmol) in nitromethane (30 mL) was stirred at 60° C. for 2 hr. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10-30% ethyl acetate/hexane) to give N-(3-chloro-4-cyanophenyl)-3-methyl-4-nitrobutanamide (2.67 g, 9.48 mmol, 90%) as a pale yellow oil.

MS(API): 280 (M−H)

(Step 3)

A solution of the compound obtained in Step 2 (21.2 g, 75.26 mmol), iron (21.01 g, 376.29 mmol) and calcium chloride (25.06 g, 225.78 mmol) in methanol (100 mL)/water (20 mL) was stirred at 60° C. for 3 hr. The reaction mixture was allowed to be cooled to room temperature, saturated brine was added thereto, the mixture was filtered through Celite, and the filtrate was extracted with ethyl acetate. The organic layer was washed with saturated brine, and dried over magnesium sulfate, and the solvent was evaporated under reduced pressure. The obtained residue was purified by NH-silica gel column chromatography (solvent gradient; 10→50% ethyl acetate/hexane) to give 4-amino-N-(3-chloro-4-cyanophenyl)-3-methylbutanamide (6.02 g, 23.92 mmol, 31.8%) as a brown solid.

MS(API): 252 (M−H)

(Step 4)

A solution of the compound obtained in Step 3 (160 mg, 0.64 mmol), 3-ethyl-2-propylimidazo[1,2-a]pyridine-7-carboxylic acid (148 mg, 0.64 mmol), HATU (266 mg, 0.70 mmol) and TEA (0.098 mL, 0.70 mmol) in DMF (5 mL) was stirred at 50° C. for 3 hr. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) and NH-silica gel column chromatography (solvent gradient; 10→100% ethyl acetate/hexane). The obtained product was crystallized from ethanol-IPE to give the title compound (112 mg, 0.24 mmol, 37.7%) as colorless crystals.

MS(API): 466 (M+H)

Example 4

N-(4-((3-chloro-4-cyanophenyl)amino)-2-methyl-4-oxobutyl)-1,3-diethyl-2,4-dioxo-1,2,3,4-tetrahydroquinazoline-6-carboxamide (Step 1)

A solution of 6-bromo-1,3-diethylquinazoline-2,4(1H,3H)-dione (1.2 g, 4.04 mmol), palladium acetate (0.045 g, 0.20 mmol), 1,3-bis(diphenylphosphino)propane (0.083 g, 0.20 mmol) and TEA (1.407 mL, 10.10 mmol) in DMSO (5 mL)/methanol (5 mL) was stirred overnight at 70° C. under carbon monoxide atmosphere. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was triturated with IPE to give methyl 1,3-diethyl-2,4-dioxo-1,2,3,4-tetrahydroquinazoline-6-carboxylate (0.914 g, 3.31 mmol, 82%) as a white solid.

$^1$H-NMR (300 MHz, CDCl$_3$): δ1.19-1.46 (6H, m), 3.95 (3H, s), 4.06-4.34 (4H, m), 7.24 (1H, s), 8.30 (1H, dd, J=8.9, 2.1 Hz), 8.89 (1H, d, J=2.3 Hz).

(Step 2)

The compound obtained in Step 1 (280 mg, 1.01 mmol) was dissolved in THF (5 mL)/ethanol (5 mL)/water (5 mL), aqueous lithium hydroxide solution (4 mol/L, 2 mL, 8.00 mmol) was added thereto, and the mixture was stirred at room temperature for 3 hr. To the reaction mixture was added 6N hydrochloric acid (1.33 mL, 8.0 mmol), and the mixture was concentrated under reduced pressure. The obtained residue was dissolved in DMF (5 mL), the compound obtained in Step 3 of Example 3 (281 mg, 1.11 mmol), HATU (462 mg, 1.22 mmol) and TEA (0.706 mL, 5.07 mmol) were added thereto, and the mixture was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) and NH-silica gel column chromatography (solvent gradient; 10→100% ethyl acetate/hexane). The obtained product was triturated with IPE to give the title compound (120 mg, 0.242 mmol, 23.87%) as a white solid.

MS(API): 496 (M+H)

$^1$H-NMR (300 MHz, DMSO-d$_6$): δ0.96 (3H, d, J=6.0 Hz), 1.10-1.32 (6H, m), 2.16-2.30 (1H, m), 2.40 (3H, d, J=10.6 Hz), 3.11-3.26 (1H, m), 4.00 (2H, q, J=6.8 Hz), 4.08-4.24 (2H, m), 7.39-7.53 (2H, m), 7.74 (1H, d, J=8.3 Hz), 7.88 (1H, d, J=1.9 Hz), 8.15 (H, dd, J=8.7, 2.3 Hz), 8.51 (1H, d, J=1.9 Hz), 8.70 (1H, t, J=5.7 Hz), 10.45 (1H, s).

Example 5

5-(3-chloro-4-cyanophenoxy)-N-(1,3-diethyl-2,4-dioxo-1,2,3,4-tetrahydroquinazolin-6-yl)-3-methylpentanamide (Step 1)

A solution of the compound obtained in Step 3 of Example 1 (500 mg, 2.14 mmol) and 3-methylglutaric anhydride (412 mg, 3.22 mmol) in THF (15 mL) was refluxed overnight. The reaction mixture was concentrated under reduced pressure, and the obtained residue was purified by silica gel column chromatography (solvent gradient; 10→100% ethyl acetate/hexane) to give 5-((1,3-diethyl-2,4-dioxo-1,2,3,4-tetrahydroquinazolin-6-yl)amino)-3-methyl-5-oxopentanoic acid as a colorless foam (quantitative).

MS(API): 360 (M+H)

(Step 2)

To a solution of the compound obtained in Step 1 (150 mg, 0.42 mmol) in THF (5 mL) was added borane-dimethyl sulfide complex (1.9 mol/L, THF solution, 0.655 mL, 1.25 mmol) at room temperature. The reaction mixture was stirred overnight at room temperature, water was added thereto, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane) to give N-(1,3-diethyl-2,4-dioxo-1,2,3,4-tetrahydroquinazolin-6-yl)-5-hydroxy-3-methylpentanamide (117 mg, 0.338 mmol, 81%) as a white solid.

MS(API): 348 (M+H)

(Step 3)

To a solution of the compound obtained in Step 2 (115 mg, 0.33 mmol) and 2-chloro-4-fluorobenzonitrile (51.5 mg, 0.33 mmol) in THF (5 mL) was added potassium tert-butoxide (93 mg, 0.83 mmol) at room temperature. The reaction mixture was stirred overnight at room temperature, water was added thereto, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane) to give the title compound (94 mg, 0.194 mmol, 58.5%) as a white solid.

MS(API): 483 (M+H)

$^1$H-NMR (300 MHz, DMSO-d$_6$): δ1.00 (3H, d, J=6.0 Hz), 1.08-1.33 (6H, m), 1.68 (1H, dd, J=13.4, 6.6 Hz), 1.83 (1H, dd, J=13.2, 6.4 Hz), 2.12-2.31 (2H, m), 2.31-2.47 (1H, m), 3.88-4.27 (6H, m), 7.07 (1H, dd, J=8.7, 2.3 Hz), 7.29 (1H, d, J=2.3 Hz), 7.44 (1H, d, J=9.1 Hz), 7.81 (1H, d, J=8.7 Hz), 7.92 (1H, dd, J=8.9, 2.5 Hz), 8.32 (1H, d, J=2.3 Hz), 10.12 (1H, s).

Example 6

N-(3-chloro-4-cyanophenyl)-N'-(3-ethyl-2-propylimidazo[1,2-a]pyridin-7-yl)-3-methylpentanediamide (Step 1)

To a solution of methyl 2-aminopyridine-4-carboxylate (1.50 g, 9.86 mmol) and sodium hydrogencarbonate (1.656 g, 19.72 mmol) in ethanol (25 mL) was added 3-bromo-4-heptanone (3.81 mL, 24.65 mmol), and the mixture was refluxed overnight. The reaction mixture was allowed to be cooled to room temperature, and concentrated under reduced pressure. The obtained residue was diluted with saturated aqueous sodium hydrogencarbonate solution, and the mixture was extracted with ethyl acetate. The organic layer was washed successively with saturated aqueous sodium hydrogencarbonate solution and saturated brine, and dried over magnesium sulfate, and the solvent was evaporated under reduced pressure. The obtained residue was purified by silica gel column chromatography (solvent gradient; 5→75% ethyl acetate/hexane) to give methyl 3-ethyl-2-propylimidazo[1,2-a]pyridine-7-carboxylate (1.24 g, 5.03 mmol, 51.1%) as a pale yellow solid.

$^1$H-NMR (300 MHz, CDCl$_3$): δ0.99 (3H, t, J=7.4 Hz), 1.15-1.32 (3H, m), 1.64-1.91 (2H, m), 2.66-2.82 (2H, m), 2.93 (2H, q, J=7.6 Hz), 3.95 (3H, s), 7.38 (1H, dd, J=7.2, 1.9 Hz), 7.81-7.97 (1H, m), 8.19-8.33 (1H, m).

(Step 2)

The compound obtained in Step 1 (1.20 g, 4.87 mmol) was dissolved in methanol (10 mL)/THF (10 mL)/water (15 mL), aqueous sodium hydroxide solution (8 mol/L, 2 mL, 16.00 mmol) was added thereto, and the mixture was stirred overnight at room temperature. The reaction mixture was concentrated under reduced pressure, the residue was dissolved in water, and the solution was neutralized with 1N hydrochloric acid. The obtained aqueous solution was subjected to dianion HP-20 column, the column was washed with water, and the product was eluted with acetone. The eluate was concentrated under reduced pressure to give 3-ethyl-2-propylimidazo[1,2-a]pyridine-7-carboxylic acid (1.07 g, 4.61 mmol, 95%) as a pale yellow solid.

MS(API): 231 (M+H)

(Step 3)

To a solution of the compound obtained in Step 2 (750 mg, 3.23 mmol) and TEA (0.54 mL, 3.87 mmol) in tert-butyl alcohol (25 mL) was added DPPA (0.835 mL, 3.87 mmol), and the mixture was stirred at room temperature for 1 hr, and then under reflux for 2 hr. The reaction mixture was allowed to be cooled to room temperature, water was added thereto, and the mixture was stirred at room temperature for 1 hr, and extracted with ethyl acetate. The organic layer was washed with saturated brine, and dried over magnesium sulfate, and the solvent was evaporated under reduced pressure. The obtained residue was purified by NH-silica gel column chromatography (solvent gradient; 10→100% ethyl acetate/hexane) to give tert-butyl (3-ethyl-2-propylimidazo[1,2-a]pyridin-7-yl)carbamate (599 mg, 1.974 mmol, 61.1%) as a grayish white solid.

MS(API): 304 (M+H)

(Step 4)

The compound obtained in Step 3 (590 mg, 1.94 mmol) was dissolved in ethyl acetate (4 mL), 4N hydrogen chloride-ethyl acetate solution (1.458 mL, 5.83 mmol) was added thereto, and the mixture was stirred overnight at room temperature. The reaction mixture was concentrated under reduced pressure, and to the residue were added ethyl acetate and 5 mol/L aqueous sodium hydroxide solution. The organic layer was washed with saturated brine, and dried over magnesium sulfate, and the solvent was evaporated under reduced pressure to give 3-ethyl-2-propylimidazo[1,2-a]pyridin-7-amine as a pale yellow oil (quantitative).

MS(API): 204 (M+H)

(Step 5)

To a solution of the compound obtained in Step 4 (410 mg, 2.02 mmol), the compound obtained in Step 3 of Reference Example 1 (510 mg, 1.82 mmol) and DIEA (1.303 g, 10.08 mmol) in ethyl acetate (8 mL) was added T3P (50% ethyl acetate solution, 1.925 g, 3.03 mmol), and the mixture was refluxed overnight. The reaction mixture was allowed to be cooled to room temperature, water was added thereto, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane, 0→20% methanol/ethyl acetate), and purified by NH-silica gel column chromatography (solvent gradient; 10→100% ethyl acetate/hexane, 0→20% methanol/ethyl acetate) to give the title compound (62.5 mg, 0.134 mmol, 6.65%) as a grayish white solid.

MS(API): 466 (M+H)

$^1$H-NMR (300 MHz, DMSO-d): δ0.90 (3H, t, J=7.4 Hz), 1.00 (3H, d, J=6.0 Hz), 1.05-1.25 (3H, m), 1.64 (2H, sxt, J=7.3 Hz), 2.24-2.64 (7H, m), 2.85 (2H, q, J=7.2 Hz), 6.96 (1H, dd, J=7.2, 1.9 Hz), 7.59 (1H, dd, J=8.7, 1.9 Hz), 7.76-7.93 (2H, m), 8.05 (1H, d, J=1.9 Hz), 8.16 (1H, d, J=7.6 Hz), 10.08 (1H, s), 10.54 (1H, s).

Example 7

N-(3-chloro-4-cyanophenyl)-N'-(2,4-diethyl-3-oxo-3,4-dihydro-2H-1,4-benzoxazin-7-yl)-3-methylpentanediamide (Step 1)

To a suspension of potassium fluoride (2.36 g, 40.55 mmol) in DMF (15.0 mL) was added methyl 2-bromobutyrate (2.06 mL, 17.84 mmol), and the mixture was stirred at room temperature for 15 min. To the reaction mixture was added 2-amino-5-nitrophenol (2.5 g, 16.22 mmol), and the mixture was stirred at 50-60° C. for 6 hr, and then at room temperature for 14 hr. The same reaction was repeated, both of the reaction mixtures were combined, and ice (175 g) was added. The precipitate white solid was collected by filtration, and the obtained solid was washed successively with water and hexane, and dried under reduced pressure to give 2-ethyl-7-nitro-4H-benzo[1,4]oxazin-3-one (6.0 g, 83%) as a white solid.

MS(API): 221 (M+H)

(Step 2)

To a solution of the compound obtained in Step 1 (3.0 g, 13.62 mmol) in DMF (45 mL) was added potassium carbonate (4.14 g, 29.97 mmol) at 0° C., and the mixture was stirred at room temperature for 15 min under nitrogen atmosphere. To the reaction mixture was added iodoethane (1.63 mL, 20.44 mmol), the mixture was stirred at room temperature for 14 hr, water was added thereto, and the mixture was extracted with ethyl acetate. The organic layer was washed with water and saturated brine, and dried over sodium sulfate, and the solvent was evaporated under reduced pressure to give 2,4-diethyl-7-nitro-4H-benzo[1,4]oxazin-3-one (3.0 g, 88%) as a white solid.

MS(API): 251 (M+H)

(Step 3)

To a solution of the compound obtained in Step 2 (1.50 g, 6.00 mmol) in methanol (30 mL) was added 10% palladium on carbon (50% hydrous, 0.225 g), and the mixture was stirred for 14 hr at room temperature under 1 atm of under hydrogen atmosphere. The catalyst was removed by filtration, and the filtrate was concentrated under reduced pressure. The obtained residue was triturated with pentane to give 7-amino-2,4-diethyl-4H-benzo[1,4]oxazin-3-one (1.0 g, 75.7%) as a brown solid.

MS(API): 221 (M+H)

(Step 4)

To a solution of the compound obtained in Step 3 (0.35 g, 1.59 mmol) and the compound obtained in Step 3 of Reference Example 1 (0.53 g, 1.91 mmol) in ethyl acetate (10 mL) were added DIEA (0.70 mL, 3.98 mmol) and T3P (50% ethyl acetate solution, 2.4 mL, 3.97 mmol), and the mixture was refluxed for 5 hr under argon atmosphere. The reaction mixture was allowed to be cooled to room temperature, diluted with ethyl acetate, and washed successively with cooled saturated aqueous sodium hydrogencarbonate solution, water and saturated brine. The organic layer was dried over sodium sulfate, and the solvent was evaporated under reduced pressure. The obtained residue was purified by silica gel column chromatography (solvent gradient; 60→70% ethyl acetate/hexane) to give the title compound (0.350 g, 45.5%) as a white solid.

MS(API): 483 (M+H)

$^1$H-NMR (400 MHz, DMSO-d$_6$): δ0.97 (t, 6H, J=7.16 Hz), 1.12 (t, 3H, J=6.88 Hz), 1.67-1.78 (m, 2H), 2.23-2.44 (m, 5H), 3.87 (q, 2H, J=6.96 Hz), 4.49 (dd, 1H, J=4.52 Hz, J=8.12 Hz), 7.09 (d, 1H, J=8.68 Hz), 7.17 (d, H, J=8.80 Hz), 7.39 (brs, 1H), 7.59 (d, 1H, J=8.72 Hz), 7.87 (d, H, J=8.6 Hz), 8.05 (brs, H), 9.91 (brs, H), 0.52 (brs, 1H).

Example 8

N-(3-chloro-4-cyanophenyl)-N'-(4-ethyl-2-(2-hydroxyethyl)-3-oxo-3, 4-dihydro-2H-1,4-benzoxazin-7-yl)-3-methylpentanediamide (Step 1)
To a solution of 2-amino-5-nitrophenol (2.00 g, 13 mmol) in DMF (20 mL) were added 3-bromo-dihydrofuran-2-one and potassium carbonate (2.1 g, 15.57 mmol), and the mixture was stirred at 80° C. for 4 hr under nitrogen atmosphere. The reaction mixture was allowed to be cooled to room temperature, and filtered through Celite, and the filtrate was concentrated under reduced pressure. The obtained residue was dissolved in ethyl acetate, and the solution was washed with water and saturated brine, and dried over sodium sulfate, and the solvent was evaporated under reduced pressure. The obtained yellow solid was washed with pentane to give 2-(2-hydroxyethyl)-7-nitro-4H-benzo[1,4]oxazin-3-one (2.5 g, 80.9%) as a yellow solid.
MS(API): 239 (M+H)
(Step 2)
To a solution of the compound obtained in Step 1 (1.5 g, 6.3 mmol) in DMF (20 mL) were successively added imidazole (0.858 g, 13 mmol) and chlorotert-butyldimethylsilane (1.42 g, 9.33 mmol), and the mixture was stirred at room temperature for 16 hr under nitrogen atmosphere. To the reaction mixture was added water, and the mixture was extracted with ethyl acetate. The organic layer was washed with saturated brine, and dried over sodium sulfate, and the solvent was evaporated under reduced pressure to give 2-[2-(tert-butyl-dimethylsilanyloxy)-ethyl]-7-nitro-4H-benzo[1,4]oxazin-3-one (2.2 g, 100%) as a white solid.
MS(API): 353 (M+H)
(Step 3)
2-[2-(tert-Butyl-dimethylsilanyloxy)-ethyl]-4-ethyl-7-nitro-4H-benzo[1,4]oxazin-3-one (2.0 g, 97.38%) was obtained as a yellow solid using the compound obtained in Step 2 (1.9 g, 5.4 mmol) by the reaction and purification in the same manner as in Step 2 of Example 7.
MS(API): 382 (M+H)
(Step 4)
To a solution of the compound obtained in Step 3 (1.7 g, 4.47 mmol) in 1,4-dioxane (30 mL) was slowly added 4N hydrogen chloride-1,4-dioxane solution (2.5 mL) at 0° C., and the mixture was stirred at room temperature for 4 hr. The reaction mixture was concentrated under reduced pressure, and the obtained residue was washed with hexane to give 4-ethyl-2-(2-hydroxyethyl)-7-nitro-4H-benzo[1,4]oxazin-3-one (0.980 g, 82.3%) as a yellow solid.
MS(API): 267 (M+H)
(Step 5)
7-Amino-4-ethyl-2-(2-hydroxyethyl)-4H-benzo[1,4]oxazin-3-one (0.120 g, 90%) was obtained as a brown oil using the compound obtained in Step 4 (0.150 g, 0.564 mmol) by the reaction and purification in the same manner as in Step 3 of Example 7.
MS(API): 237 (M+H)
(Step 6)
The title compound (0.055 g, 6.5%) was obtained as a grayish white solid using the compound obtained in Step 5 (0.40 g, 1.7 mmol) by the reaction and purification by preparative HPLC in the same manner as in Step 4 of Example 7.
MS(API): 499 (M+H)
purification condition by preparative HPLC
  instrument: Waters auto purification instrument
  column: XBridge Prep RP 18 (19×250 mm)
  solvent: A=10 mM aqueous ammonium acetate solution, B=acetonitrile
  solvent gradient: 90% A/B(0 min)→55% A/B(1 min)→55% A/B(25 min)→5% A/B(32 min)→5% A/B(36 min)→90% A/B(37 min)
  flow rate: 14 mL/min
  temperature: room temperature Example 9

N-(3-chloro-4-cyanophenyl)-N'-(4-ethyl-2,2-dimethyl-3-oxo-3,4-dihydro-2H-1,4-benzoxazin-7-yl)-3-methylpentanediamide (Step 1)
2,2-Dimethyl-7-nitro-4H-benzo[1,4]oxazin-3-one (5.0 g, 69%) was obtained as a grayish white solid using methyl 2-bromo-2-methylpropionate (2.32 mL, 17.84 mmol) by the reaction and purification in the same manner as in Step 1 of Example 7.
MS(API): 221 (M+H)
(Step 2)
4-Ethyl-2,2-dimethyl-7-nitro-4H-benzo[1,4]oxazin-3-one (2.37 g, 70%) was obtained as a brown solid using the compound obtained in Step 1 (3.0 g, 13.50 mmol) by the reaction and purification in the same manner as in Step 2 of Example 7.
MS(API): 251 (M+H)
(Step 3)
7-Amino-4-ethyl-2,2-dimethyl-4H-benzo[1,4]oxazin-3-one (1.25 g, 91.5%) was obtained as a grayish solid using the compound obtained in Step 2 (1.55 g, 6.20 mmol) by the reaction and purification in the same manner as in Step 3 of Example 7.
MS(API): 221 (M+H)
(Step 4)
The title compound (0.300 g, 39%) was obtained as a grayish white solid using the compound obtained in Step 3 (0.35 g, 1.59 mmol) by the reaction and purification by preparative HPLC (instrument: Waters auto purification instrument, column: XBridge C18 (250×19 mm) 5 µm, eluent: 5 mM aqueous ammonium acetate solution/acetonitrile) in the same manner as in Step 4 of Example 7.
MS(API): 483 (M+H)

Example 10

N-(2-benzyl-4-ethyl-3-oxo-3,4-dihydro-2H-1,4-benzoxazin-7-yl)-N'-(3-chloro-4-cyanophenyl)-3-methylpentanediamide (Step 1)
To a suspension of potassium fluoride (1.88 g, 32.44 mmol) in DMF (10.0 mL) was added methyl 2-bromo-3-phenylpropionate (3.67 mL, 14.27 mmol), and the mixture was stirred at room temperature for 15 min. To the reaction mixture was added 2-amino-5-nitrophenol (2.0 g, 14.49 mmol), and the mixture was stirred at 50-60° C. for 6 hr, and then at room temperature for 14 hr. To the reaction mixture was added ice (100 g), and the precipitated white solid was collected by filtration. The obtained solid was washed successively with water and hexane, and dried under reduced pressure to give 2-benzyl-7-nitro-4H-benzo[1,4]oxazin-3-one (0.90 g, 24.4%) as a white solid.

MS(API): 283 (M+H)

(Step 2)

To a solution of the compound obtained in Step 1 (0.90 g, 3.17 mmol) in DMF (9 mL) was added potassium carbonate (0.96 g, 6.96 mmol) at 0° C., and the mixture was stirred at room temperature for 15 min under nitrogen atmosphere. To the reaction mixture was added iodoethane (0.38 mL, 4.75 mmol), the mixture was stirred at room temperature for 14 hr, water was added thereto, and the mixture was extracted with ethyl acetate. The organic layer was washed with water and saturated brine, and dried over sodium sulfate, and the solvent was evaporated under reduced pressure to give 2-benzyl-4-ethyl-7-nitro-4H-benzo[1,4]oxazin-3-one (0.79 g, 80%) as a brown solid.

MS(API): 313 (M+H)

(Step 3)

To a solution of the compound obtained in Step 2 (0.79 g, 3.16 mmol) in methanol (30 mL) was added 10% palladium on carbon (50% hydrous, 0.079 g), and the mixture was stirred for 14 hr at room temperature under 1 atm of under hydrogen atmosphere. The catalyst was removed by filtration, and the filtrate was concentrated under reduced pressure. The obtained residue was triturated with pentane to give 7-amino-2-benzyl-4-ethyl-4H-benzo[1,4]oxazin-3-one (0.615 g, 69%) as a brown solid.

MS(API): 283 (M+H)

(Step 4)

To a solution of the compound obtained in Step 3 (0.30 g, 1.06 mmol) and the compound obtained in Step 3 of Reference Example 1 (0.36 g, 1.28 mmol) in ethyl acetate (10 mL) were added DIEA (0.46 mL, 2.66 mmol) and T3P (50% ethyl acetate solution, 1.6 mL, 2.66 mmol), and the mixture was refluxed for 5 hr under argon atmosphere. The reaction mixture was allowed to be cooled to room temperature, diluted with ethyl acetate, and washed successively with cooled saturated aqueous sodium hydrogencarbonate solution, water and saturated brine. The organic layer was dried over sodium sulfate, and the solvent was evaporated under reduced pressure. The obtained residue was purified by preparative HPLC (instrument: Waters auto purification instrument, column: XBridge C18 (250×19 mm) 5 μm, eluent: 5 mM aqueous ammonium acetate solution/acetonitrile) to give the title compound (0.29 g, 50%) as a grayish white solid.

MS(API): 545 (M+H)

$^1$H-NMR (400 MHz, DMSO-$d_6$): δ0.96 (d, 3H, J=6.16 Hz), 1.12 (t, 3H, J=6.92 Hz), 2.23-2.46 (m, 5H), 2.96 (q, 1H, J=9.24 Hz), 3.15 (dd, 1H, J=3.64 Hz, 14.40 Hz), 3.88 (q, 2H, J=7.12 Hz), 4.81 (q, 1H, J=3.56 Hz), 7.10 (d, H, J=8.84 Hz), 71.8-7.30 (m, 7H), 7.58 (d, 1H, J=8.60 Hz), 7.86 (d, 1H, J=8.60 Hz), 8.05 (brs, 1H), 9.92 (brs, 1H), 10.55 (brs, H).

Example 11

4-bromo-3-chloro-N-(4-((1,3-diethyl-2,4-dioxo-1,2,3,4-tetrahydroquinazolin-6-yl)amino)-2-methyl-4-oxobutyl)benzamide (Step 1)

A solution of the compound obtained in Step 3 of Example 1 (460 mg, 1.97 mmol), crotonic acid (0.182 mL, 2.17 mmol), HATU (825 mg, 2.17 mmol) and TEA (0.302 mL, 2.17 mmol) in DMF (5 mL) was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure to give (E)-N-(1,3-diethyl-2,4-dioxo-1,2,3,4-tetrahydroquinazolin-6-yl)but-2-enamide (quantitative).

MS(API): 302 (M+H)

(Step 2)

A solution of the compound obtained in Step 1 (594 mg, 1.97 mmol), nitromethane (0.117 mL, 2.17 mmol) and DBU (0.327 mL, 2.17 mmol) in DMA (10 mL) was stirred at room temperature for 3 hr. To the reaction mixture was added saturated brine, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5-60% ethyl acetate/hexane) to give N-(1,3-diethyl-2,4-dioxo-1,2,3,4-tetrahydroquinazolin-6-yl)-3-methyl-4-nitrobutanamide (629 mg, 1.736 mmol, 88%) as a pale yellow oil.

MS(API): 363 (M+H)

(Step 3)

A solution of the compound obtained in Step 2 (629 mg, 1.74 mmol) and zinc (800 mg, 12.24) in acetic acid (10 mL) was stirred at 50° C. for 5 hr. The reaction mixture was filtered through Celite, to the obtained filtrate was added 10% palladium on carbon (50% hydrous, 185 mg, 1.74 mmol), and the mixture was stirred overnight at room temperature under 1 atm of under hydrogen atmosphere. The reaction mixture was filtered through Celite, and the filtrate was concentrated under reduced pressure. To the residue was added 1N aqueous sodium hydroxide solution, and the mixture was extracted with ethyl acetate. The organic layer was washed with saturated brine, and dried over magnesium sulfate, and the solvent was evaporated under reduced pressure to give 4-amino-N-(1,3-diethyl-2,4-dioxo-1,2,3,4-tetrahydroquinazolin-6-yl)-3-methylbutanamide (414 mg, 71.8%).

MS(API): 333 (M+H)

(Step 4)

A solution of the compound obtained in Step 3 (414 mg, 1.25 mmol), 4-bromo-3-chlorobenzoic acid (323 mg, 1.37 mmol), HATU (521 mg, 1.37 mmol) and TEA (0.191 mL, 1.37 mmol) in DMF (5 mL) was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5→100% ethyl acetate/hexane), and the obtained white solid was crystallized from DMF-water to give the title compound (180 mg, 0.327 mmol, 26.3%).

MS(API): 551 (M+H)

$^1$H-NMR (300 MHz, DMSO-$d_6$): δ0.95 (4H, d, J=6.0 Hz), 1.00-1.52 (7H, m), 2.13-2.46 (2H, m), 3.10-3.28 (1H, m), 3.70-4.39 (4H, m) 7.40 (1H, d, J=9.4 Hz) 7.60-7.80 (2H, m), 7.86 (1H, dd, J=9.1, 2.6 Hz), 7.95 (1H, d, J=1.9 Hz), 8.27 (1H, d, J=2.3 Hz), 8.57-8.72 (1H, m) 10.09 (1H, s).

Example 12

N-(3-chloro-4-cyanophenyl)-N'-(4-ethyl-3-oxo-2-phenyl-3,4-dihydro-2H-1,4-benzoxazin-7-yl)-3-methylpentanediamide (Step 1)

To a solution of 2-amino-5-nitrophenol (1.50 g, 9.73 mmol) in DMF (20 mL) were added methyl α-bromophenylacetate (2.45 g, 10.70 mmol) and potassium carbonate (1.34 g, 9.73 mmol), and the mixture was stirred at 80° C. for 4 hr under nitrogen atmosphere. The reaction mixture was allowed to be cooled to room temperature, ice (60 g) was added thereto, and the precipitated solid was collected by filtration. The obtained solid was washed successively with water and hexane, and dried under reduced pressure to give 7-nitro-2-phenyl-4H-benzo[1,4]oxazin-3-one (2.0 g, 76%) as a yellow solid.

MS(API): 269 (M−H)

(Step 2)

To a solution of the compound obtained in Step 1 (2.17 g, 7.63 mmol) in DMF (21 mL) was added potassium carbonate (2.32 g, 16.79 mmol) at 0° C., and the mixture was stirred at room temperature for 15 min under nitrogen atmosphere. To the reaction mixture was added iodoethane (0.92 mL, 11.45 mmol), the mixture was stirred at room temperature for 14 hr, water was added thereto, and the mixture was extracted with ethyl acetate. The organic layer was washed with water and saturated brine, and dried over sodium sulfate, and the solvent was evaporated under reduced pressure. The obtained residue was purified by silica gel column chromatography (solvent gradient; 8→10% ethyl acetate/hexane) to give 4-ethyl-7-nitro-2-phenyl-4H-benzo[1,4]oxazin-3-one (0.77 g, 33%) as a grayish solid.

MS(API): 299 (M+H)

(Step 3)

To a solution of the compound obtained in Step 2 (0.76 g, 2.55 mmol) in methanol (60 mL) was added 10% palladium on carbon (50% hydrous, 0.076 g), and the mixture was stirred for 14 hr at room temperature under 1 atm of under hydrogen atmosphere. The catalyst was removed by filtration, and the filtrate was concentrated under reduced pressure. The obtained residue was triturated with pentane to give 7-amino-4-ethyl-2-phenyl-4H-benzo[1,4]oxazin-3-one (0.527 g, 77%) as a brown oil.

MS(API): 269 (M+H)

(Step 4)

To a solution of the compound obtained in Step 3 (0.28 g, 1.04 mmol) and the compound obtained in Step 3 of Reference Example 1 (0.35 g, 1.25 mmol) in ethyl acetate (15 mL) were added DIEA (0.45 mL, 2.61 mmol) and T3P (50% ethyl acetate solution, 1.6 mL, 2.61 mmol), and the mixture was refluxed for 5 hr under argon atmosphere. The reaction mixture was allowed to be cooled to room temperature, diluted with ethyl acetate, and washed successively with cooled saturated aqueous sodium hydrogencarbonate solution, water and saturated brine. The organic layer was dried over sodium sulfate, and the solvent was evaporated under reduced pressure. The obtained residue was purified by preparative HPLC to give the title compound (0.28 g, 43%) as a white solid.

MS(API): 531 (M−H)

$^1$H-NMR (400 MHz, DMSO-d$_6$): δ0.96 (d, 3H, J=6.24 Hz), 1.17 (t, 3H, J=6.96 Hz), 2.30-2.46 (m, 5H), 3.96 (q, 2H, J=7.56 Hz), 5.80 (brs, 1H), 7.18 (m, 2H), 7.30-7.37 (m, 6H), 7.58 (d, 1H, J=8.76 Hz), 7.86 (d, 1H, J=8.60 Hz), 8.05 (d, 1H, J=1.88 Hz), 9.90 (brs, 1H), 10.51 (brs, 1H).

purification condition by preparative HPLC
  instrument: Waters semi-preparative HPLC instrument
  column: Prep Scalar 10 μm C18 (250×30 mm)
  solvent: A=5 mM aqueous ammonium acetate solution, B=acetonitrile
  solvent gradient: 60% A/B(0 min)→40% A/B(60 min)→5% A/B(61 min)→5% A/B(70 min)→60% A/B(71 min)
  flow rate: 30 mL/min
  temperature: room temperature

Example 13

N-(3-chloro-4-cyanophenyl)-N'-(4-ethyl-3-oxo-3,4-dihydrospiro[1,4-benzoxazine-2,1'-cyclobutane]-7-yl)-3-methylpentanediamide (Step 1)

To a suspension of potassium fluoride (1.41 g, 24.33 mmol) in DMF (13.0 mL) was added 2-amino-5-nitrophenol (1.5 g, 9.73 mmol), and the mixture was stirred at room temperature for 15 min. To the reaction mixture was added ethyl 1-bromocyclobutanecarboxylate (2.22 g, 10.70 mmol), and the mixture was stirred at 50—at 60° C. for 36 hr. The reaction mixture was allowed to be cooled to room temperature, ice (100 g) was added thereto, and the mixture was extracted with ethyl acetate. The organic layer was dried over sodium sulfate, and the solvent was evaporated under reduced pressure. The obtained residue was purified by silica gel column chromatography (solvent gradient; 18→20% ethyl acetate/hexane) to give 7-nitro-3,4-dihydrospiro[1,4-benzoxazine-2,1'-cyclobutane]-3-one (0.38 g, 17%) as a yellow solid.

MS(API): 233 (M−H)

(Step 2)

To a solution of the compound obtained in Step 1 (0.37 g, 1.58 mmol) in DMF (9 mL) was added potassium carbonate (0.48 g, 3.48 mmol) at 0° C., and the mixture was stirred at room temperature for 15 min under nitrogen atmosphere. To the reaction mixture was added iodoethane (0.19 mL, 2.37 mmol), the mixture was stirred at room temperature for 14 hr, water was added thereto, and the mixture was extracted with ethyl acetate. The organic layer was washed with water and saturated brine, and dried over sodium sulfate, and the solvent was evaporated under reduced pressure to give 4-ethyl-7-nitro-3,4-dihydrospiro[1,4-benzoxazine-2,1'-cyclobutane]-3-one (0.25 g, 61.5%) as a pale yellow solid.

MS(API): 263 (M+H)

(Step 3)

To a solution of the compound obtained in Step 2 (0.245 g, 0.94 mmol) in methanol (50 mL) was added 10% palladium on carbon (50% hydrous, 0.025 g), and the mixture was stirred for 14 hr at room temperature under 1 atm of under hydrogen atmosphere. The catalyst was removed by filtration, and the filtrate was concentrated under reduced pressure. The obtained residue was triturated with pentane to give 7-amino-4-ethyl-3,4-dihydrospiro[1,4-benzoxazine-2,1'-cyclobutane]-3-one (0.205 g, 94.4%) as a brown solid.

MS(API): 233 (M+H)

(Step 4)

To a solution of the compound obtained in Step 3 (0.18 g, 0.77 mmol) and the compound obtained in Step 3 of Reference Example 1 (0.26 g, 0.93 mmol) in ethyl acetate (10 mL) were added DIEA (0.34 mL, 1.94 mmol) and T3P (50% ethyl acetate solution, 1.15 mL, 1.94 mmol), and the mixture was refluxed for 5 hr under argon atmosphere. The reaction mixture was allowed to be cooled to room temperature, diluted with ethyl acetate, and washed successively with cooled saturated aqueous sodium hydrogencarbonate solution, water and saturated brine. The organic layer was dried over sodium sulfate, and the solvent was evaporated under reduced pressure. The obtained residue was purified by preparative HPLC to give the title compound (0.27 g, 70%) as a white solid.

MS(API): 495 (M+H)

$^1$H-NMR (400 MHz, DMSO-$d_6$): δ0.98 (d, 3H, J=6.28 Hz), 1.11 (t, 3H, J=7.00 Hz), 1.16-1.95 (m, 2H), 2.17-2.50 (m, 9H), 3.88 (q, 2H, J=7.08 Hz), 7.09 (d, 1H, J=8.76 Hz), 7.18 (dd, 1H, J=2.12 Hz, 8.76 Hz), 7.43 (d, 1H, J=2.00 Hz), 7.60 (dd, 1H, J=1.76 Hz, 8.60 Hz), 7.87 (d, 1H, J=8.64 Hz), 8.05 (d, 1H, J=1.80 Hz), 9.93 (brs, 1H), 10.54 (brs, 1H).

purification condition by preparative HPLC
   instrument: Waters Semi-Preparative HPLC instrument
   column: Prep Scalar 10 μm C18 (250×30 mm)
   solvent: A=5 mM aqueous ammonium acetate solution, B=acetonitrile
   solvent gradient: 60% A/B(0 min)→40% A/B(60 min)→5% A/B(61 min)→5% A/B(70 min)→60% A/B(71 min)
   flow rate: 30 mL/min
   temperature: room temperature Example 14

N-(3-chloro-4-cyanophenyl)-N'-(4-ethyl-2-isopropyl-3-oxo-3,4-dihydro-2H-1,4-benzoxazin-7-yl)-3-methylpentanediamide (Step 1)

To a suspension of potassium fluoride (2.83 g, 48.66 mmol) in DMF (15.0 mL) was added methyl 2-bromo-3-methylbutyrate (3.09 mL, 21.41 mmol), and the mixture was stirred at room temperature for 15 min. To the reaction mixture was added 2-amino-5-nitrophenol (3.0 g, 19.46 mmol), and the mixture was stirred at 50-60° C. for 6 hr, and then at room temperature for 14 hr. To the reaction mixture was added ice (100 g), and the precipitated white solid was collected by filtration. The obtained solid was washed successively with water and hexane, and dried under reduced pressure to give 2-isopropyl-7-nitro-4H-benzo[1,4]oxazin-3-one (2.0 g, 43.5%) as a brown solid.

MS(API): 235 (M+H)

(Step 2)

To a solution of the compound obtained in Step 1 (0.59 g, 2.50 mmol) in DMF (10 mL) was added potassium carbonate (0.76 g, 5.50 mmol) at 0° C., and the mixture was stirred at room temperature for 15 min under nitrogen atmosphere. To the reaction mixture was added iodoethane (0.30 mL, 3.75 mmol), the mixture was stirred at room temperature for 14 hr, water was added thereto, and the mixture was extracted with ethyl acetate. The organic layer was washed with water and saturated brine, and dried over sodium sulfate, and the solvent was evaporated under reduced pressure. The obtained residue was purified by silica gel column chromatography (solvent gradient; 8→10% ethyl acetate/hexane) to give 4-ethyl-2-isopropyl-7-nitro-4H-benzo[1,4]oxazin-3-one (0.55 g, 33.2%) as a pale yellow solid.

MS(API): 265 (M+H)

(Step 3)

To a solution of the compound obtained in Step 2 (0.54 g, 2.04 mmol) in methanol (60 mL) was added 10% palladium on carbon (50% hydrous, 0.054 g), and the mixture was stirred for 14 hr at room temperature under 1 atm of under hydrogen atmosphere. The catalyst was removed by filtration, and the filtrate was concentrated under reduced pressure. The obtained residue was washed with pentane to give 7-amino-4-ethyl-2-isopropyl-4H-benzo[1,4]oxazin-3-one (0.46 g, 96%) as a brown oil.

MS(API): 235 (M+H)

(Step 4)

To a solution of the compound obtained in Step 3 (0.40 g, 1.71 mmol) and the compound obtained in Step 3 of Reference Example 1 (0.57 g, 2.05 mmol) in ethyl acetate (16 mL) were added DIEA (0.74 mL, 4.27 mmol) and T3P (50% ethyl acetate solution, 2.4 mL, 4.27 mmol), and the mixture was refluxed for 5 hr under argon atmosphere. The reaction mixture was allowed to be cooled to room temperature, diluted with ethyl acetate, and washed successively with cooled saturated aqueous sodium hydrogencarbonate solution, water and saturated brine. The organic layer was dried over sodium sulfate, and the solvent was evaporated under reduced pressure. The obtained residue was purified by preparative HPLC to give the title compound (0.518 g, 54%) as a white solid.

MS(API): 497 (M+H)

$^1$H-NMR (400 MHz, DMSO-$d_6$): δ0.91 (d, 3H, J=6.64 Hz), 0.95-0.98 (m, 6H), 1.11 (t, 3H, J=6.96 Hz), 2.04-2.09 (m, 1H), 2.23-2.50 (m, 5H), 3.84-3.92 (m, 2H), 4.30 (d, 1H, J=6.36 Hz), 7.07 (d, 1H, J=8.76 Hz), 7.15 (d, 1H, J=8.64 Hz), 7.39 (d, 1H, J=1.28 Hz), 7.59 (d, 1H, J=8.64 Hz), 7.86 (d, 1H, J=8.60 Hz), 8.04 (d, 1H, J=1.72 Hz), 9.92 (brs, 1H), 10.55 (brs, H).

purification condition by preparative HPLC
   instrument: Waters Semi-Preparative HPLC instrument
   column: Prep Scalar 10 μm C18 (250×30 mm)
   solvent: A=5 mM aqueous ammonium acetate solution, B=acetonitrile
   solvent gradient: 60% A/B(0 min)→40% A/B(60 min)→5% A/B(61 min)→5% A/B(70 min)→60% A/B(71 min)
   flow rate: 30 mL/min
   temperature: room temperature Example 15

N-(3-chloro-4-cyanophenyl)-N'-(4-ethyl-2-(2-methoxyethyl)-3-oxo-3,4-dihydro-2H-1,4-benzoxazin-7-yl)-3-methylpentanediamide (Step 1)

To a solution of the compound obtained in Step 4 of Example 8 (2 g, 7.51 mmol) in DMF (2.5 mL) was added sodium hydride (60% oil, 0.360 g, 9.02 mmol), and the mixture was stirred at 0° C. for 5 min. To the reaction mixture was added iodomethane (1.4 mL, 22.56 mmol), the mixture was stirred at room temperature for 16 hr, water was added thereto, and the mixture was extracted with ethyl acetate. The organic layer was washed with water and saturated brine, and dried over sodium sulfate, and the solvent was evaporated under reduced pressure. The obtained residue was purified by silica gel column chromatography (solvent; 20% ethyl acetate/hexane) to give 4-ethyl-2-(2-methoxy-ethyl)-7-nitro-4H-benzo[1,4]oxazin-3-one (2.0 g, 94.9%) as a pale yellow solid.

MS(API): 281 (M+H)

(Step 2)

To a solution of the compound obtained in Step 1 (1.0 g, 3.57 mmol) in methanol (30 mL) was added 10% palladium on carbon (50% hydrous, 0.38 g), and the mixture was stirred at room temperature for 5 hr under 1 atm of under hydrogen atmosphere. The catalyst was removed by filtration, and the filtrate was concentrated under reduced pressure to give 7-amino-4-ethyl-2-(2-methoxy-ethyl)-4H-benzo[1,4]oxazin-3-one (0.85 g, 95%) as a brown oil.
MS(API): 251 (M+H)
(Step 3)
To a solution of the compound obtained in Step 2 (0.50 g, 2.0 mmol) and the compound obtained in Step 3 of Reference Example 1 (0.784 g, 2.8 mmol) in ethyl acetate (16 mL) were added DIEA (0.521 mL, 3 mmol) and T3P (50% ethyl acetate solution, 3 mL, 5 mmol), and the mixture was refluxed for 6 hr under argon atmosphere. The reaction mixture was allowed to be cooled to room temperature, diluted with ethyl acetate, and washed successively with cooled saturated aqueous sodium hydrogencarbonate solution, water and saturated brine. The organic layer was dried over sodium sulfate, and the solvent was evaporated under reduced pressure. The obtained residue was purified by preparative HPLC to give the title compound (0.165 g, 16%) as a white solid.
MS(API): 513 (M+H)
$^1$H-NMR (400 MHz, DMSO-$d_6$): δ0.97 (d, 3H, J=6.28 Hz), 1.11 (t, 3H, J=7.04 Hz), 1.86-1.87 (m, 1H), 2.04-2.09 (m, 1H), 2.23-2.50 (m, 5H), 3.23 (s, 3H), 3.43-3.51 (m, 2H), 3.87 (q, 2H, J=6.96 Hz), 4.61 (dd, 1H, J=4.06 Hz, 8.96 Hz), 7.10 (d, 1H, J=8.80 Hz, 7.17 (d, 1H, J=8.84 Hz), 7.40 (d, H, J=1.96 Hz), 7.59 (dd, 1H, J=1.92 Hz, 8.68 Hz), 7.86 (d, 1H, J=8.64 Hz), 8.05 (d, 1H, J=1.84 Hz), 9.94 (s, 1H), 10.55 (s, 1H).
purification condition by preparative HPLC
   instrument: Waters auto purification instrument
   column: XBridge Prep RP 18 (19×250 mm)
   solvent: A=10 mM aqueous ammonium acetate solution, B=acetonitrile
   solvent gradient: 90% A/B(0 min)→55% A/B(1 min)→55% A/B(25 min)→5% A/B(32 min). 5% A/B(36 min)→90% A/B(37 min)
   flow rate: 14 mL/min
   temperature: room temperature Example 16

N-(3-chloro-4-cyanophenyl)-N'-(1,3-diethyl-2-oxo-1,2,3,4-tetrahydroquinazolin-6-yl)-3-methylpentanediamide (Step 1)
To a solution of 2-fluoro-5-nitrobenzaldehyde (3.0 g, 17.74 mmol) in THF (15 mL) was added ethylamine (2 mol/L, THF solution, 22.17 mL, 44.35 mmol), and the mixture was stirred at room temperature for 3 hr. The reaction mixture was cooled to 0° C., and acetic acid (10 mL) and sodium triacetoxyborohydride (5.64 g, 26.61 mmol) were added thereto. The reaction mixture was stirred overnight at room temperature, and concentrated under reduced pressure. The residue was diluted with 3 mol/L aqueous sodium hydroxide solution, and the mixture was extracted with ethyl acetate. The organic layer was washed with water and saturated brine, and dried over magnesium sulfate, and the solvent was evaporated under reduced pressure. The obtained residue was purified by NH-silica gel column chromatography (solvent gradient; 5→75% ethyl acetate/hexane) to give N-ethyl-2-((ethylamino)methyl)-4-nitroaniline (2.031 g, 9, 10 mmol, 51.3%) as a yellow oil.
$^1$H-NMR (300 MHz, CDCl$_3$): δ1.05-1.16 (3H, m), 1.26-1.40 (3H, m), 2.53-2.70 (2H, m), 3.25 (2H, qd, J=7.2, 5.3 Hz), 3.79-3.93 (2H, m), 6.50 (1H, d, J=9.1 Hz), 7.58 (1H, brs), 7.93 (1H, d, J=2.6 Hz), 8.08 (1H, dd, J=9.1, 2.6 Hz).

(Step 2)
To a solution of the compound obtained in Step 1 (2.00 g, 8.96 mmol) in THF (20 mL) was added CDI (2.179 g, 13.44 mmol) at room temperature in several parts. The reaction mixture was stirred overnight at 60° C., allowed to be cooled to room temperature, and concentrated under reduced pressure. The obtained residue was triturated with ethyl acetate-water, and collected by filtration to give 1,3-diethyl-6-nitro-3,4-dihydroquinazolin-2 (1H)-one (2.010 g, 8.06 mmol, 90%) as a yellow solid.
$^1$H-NMR (300 MHz, CDCl$_3$): δ1.11-1.47 (6H, m), 3.17-3.42 (4H, m), 4.68 (2H, s), 6.45-6.70 (1H, m), 8.04 (1H, d, J=2.6 Hz), 8.10-8.23 (1H, m).
(Step 3)
To a solution of the compound obtained in Step 2 (2.00 g, 8.02 mmol) in methanol (30 mL) was added 10% palladium on carbon (50% hydrous, 100 mg, 0.94 mmol), and the mixture was stirred overnight at room temperature under 1 atm of under hydrogen atmosphere. The catalyst was removed by filtration, and the filtrate was concentrated under reduced pressure. The obtained residue was purified by silica gel column chromatography (solvent gradient; 5→100% ethyl acetate/hexane) to give 6-amino-1,3-diethyl-3,4-dihydroquinazolin-2(1H)-one (0.727 g, 3.32 mmol, 41.3%) as a colorless solid.
MS(API): 220 (M+H)
(Step 4)
To a solution of the compound obtained in Step 3 (145 mg, 0.52 mmol), the compound obtained in Step 3 of Reference Example 1 (113 mg, 0.52 mmol) and DIEA (0.45 mL, 2.58 mmol) in ethyl acetate (4 mL) was added T3P (50% ethyl acetate solution, 0.46 mL, 0.77 mmol), and the mixture was refluxed overnight. The reaction mixture was allowed to be cooled to room temperature, water was added thereto, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane) and NH-silica gel column chromatography (solvent gradient; 20→100% ethyl acetate/hexane, 0→15% methanol/ethyl acetate) to give the title compound (157 mg, 0.325 mmol, 63%) as a colorless solid.
MS(API): 482 (M+H)
$^1$H-NMR (300 MHz, DMSO-$d_6$): δ0.99 (3H, d, J=5.3 Hz), 1.03-1.38 (6H, m), 2.14-2.42 (3H, m), 2.42-2.65 (2H, m), 3.15-3.52 (2H, m), 3.62-3.94 (2H, m), 4.31 (2H, brs), 6.88 (1H, d, J=8.7 Hz), 7.25-7.53 (2H, m), 7.60 (1H, d, J=8.3 Hz), 7.87 (1H, d, J=8.3 Hz), 8.06 (1H, brs), 9.84 (1H, brs), 10.53 (1H, brs).

Example 17

N-(4-((3-chloro-4-cyanophenyl)amino)-2-isopropyl-4-oxobutyl)-1,3-diethyl-2, 4-dioxo-1,2,3,4-tetrahydroquinazoline-6-carboxamide (Step 1)
A mixture of the compound obtained in Step 1 of Example 4 (630 mg, 2.28 mmol), 4 mol/L aqueous lithium hydroxide solution (5 mL, 20.00 mmol), THF (5 mL), ethanol (5 mL) and water (5 mL) was stirred at room temperature for 3 hr. To the reaction mixture was added 1N hydrochloric acid, and the mixture was extracted with ethyl acetate. The organic layer was dried over magnesium sulfate, and the solvent was evaporated under reduced pressure to give 1,3-diethyl-2,4-dioxo-1,2,3,4-tetrahydroquinazoline-6-carboxylic acid (quantitative).

MS(API): 261 (M−H)

(Step 2)

A solution of 4-methyl-2-pentenoic acid (1.567 mL, 13.11 mmol) and thionyl chloride (0.957 mL, 13.11 mmol) in DMA (10 mL) was stirred at 0° C. for 30 min, 4-amino-2-chlorobenzonitrile (2 g, 13.11 mmol) was added thereto, and the mixture was stirred at room temperature for 3 hr. To the reaction mixture was added saturated brine, and the mixture was extracted with ethyl acetate. The organic layer was washed with 1N hydrochloric acid and saturated brine, and dried over magnesium sulfate, and the solvent was evaporated under reduced pressure to give (E)-N-(3-chloro-4-cyanophenyl)-4-methylpent-2-enamide as a brown oil (quantitative).

MS(API): 247 (M−H)

(Step 3)

A solution of the compound obtained in Step 2 (1.7 g, 6.84 mmol) and DBU (1.03 mL, 6.84 mmol) in nitromethane (10 mL) was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5→50% ethyl acetate/hexane) to give N-(3-chloro-4-cyanophenyl)-4-methyl-3-(nitromethyl)pentanamide (1.170 g, 3.78 mmol, 55.3%) as a pale yellow oil.

MS(API): 308 (M−H)

(Step 4)

A mixture of the compound obtained in Step 3 (1.17 g, 3.78 mmol), iron (2.109 g, 37.77 mmol), calcium chloride (1.258 g, 11.33 mmol), methanol (10 mL) and water (5 mL) was stirred overnight at 60° C. The reaction mixture was allowed to be cooled to room temperature, saturated brine was added thereto, the mixture was filtered through Celite, and the filtrate was extracted with ethyl acetate. The organic layer was washed with saturated brine, and dried over magnesium sulfate, and the solvent was evaporated under reduced pressure. The obtained residue was purified by NH-silica gel column chromatography (solvent gradient; 10→50% ethyl acetate/hexane) to give 3-(aminomethyl)-N-(3-chloro-4-cyanophenyl)-4-methylpentanamide (0.056 g, 0.20 mmol, 5.3%) as a brown oil.

MS(API): 280 (M+H)

(Step 5)

A solution of the compound obtained in Step 1 (52.5 mg, 0.20 mmol), the compound obtained in Step 4 (56 mg, 0.20 mmol), HATU (76 mg, 0.20 mmol) and TEA (0.028 mL, 0.20 mmol) in DMF (5 mL) was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) to give a colorless solid. The obtained solid was crystallized from ethanol-water to give the title compound (30.0 mg, 0.057 mmol, 28.6%) as colorless crystals.

MS(API): 524 (M+H)

$^1$H-NMR (300 MHz, DMSO-d$_6$): δ0.93 (6H, t, J=6.4 Hz), 1.20 (6H, q, J=7.2 Hz), 1.64-1.92 (1H, m), 2.12-2.40 (3H, m), 3.13-3.28 (1H, m), 3.36-3.66 (1H, m), 3.99 (2H, q, J=7.2 Hz), 4.13 (2H, q, J=7.1 Hz), 7.27-7.44 (2H, m), 7.61 (1H, d, J=8.3 Hz), 7.71 (1H, d, J=1.9 Hz), 8.07 (1H, dd, J=8.7, 2.3 Hz), 8.42 (1H, d, J=2.3 Hz), 8.50-8.64 (1H, m), 10.39 (1H, s).

Example 18 ethyl (7-((5-((3-chloro-4-cyanophenyl)amino)-3-methyl-5-oxopentanoyl)amino)-4-ethyl-3-oxo-3,4-dihydro-2H-1,4-benzoxazin-2-yl)acetate (Step 1)

To a solution of 2-amino-5-nitrophenol (0.200 g, 1.3 mmol) in 1,4-dioxane (60 mL) were added sodium hydrogencarbonate (0.131 g, 1.56 mmol) and ethyl (E)-3-chlorocarbonylacrylate (0.232 g, 1.42 mmol), and the mixture was stirred at room temperature for 16 hr. The reaction mixture was concentrated, and the residue was washed with hexane to give ethyl (Z)-3-(2-hydroxy-4-nitrophenylcarbamoyl)-acrylate (0.300 g, 82.6%).

MS(API): 281 (M+H)

(Step 2)

To a solution of the compound obtained in Step 1 (1 g, 3.6 mmol) in ethanol (20 mL) was added potassium carbonate (247 mg, 1.78 mmol), and the mixture was stirred at 80° C. for 1 hr under microwave irradiation. To the reaction mixture was added water, and the mixture was extracted with ethyl acetate. The organic layer was washed with saturated brine, and dried over sodium sulfate, and the solvent was evaporated under reduced pressure to give ethyl (7-nitro-3-oxo-3,4-dihydro-2H-benzo[1,4]oxazin-2-yl)-acetate (0.500 g, 50%).

$^1$H-NMR (400 MHz, DMSO-d$_6$): δ1.66 (t, 3H, J=7.08 Hz), 3.05 (d, 2H, J=5.12 Hz), 4.08 (q, 2H, J=7.08 Hz), 5.12 (t, 1H, J=5.00 Hz), 7.05 (d, 1H, J=8.36 Hz), 7.68 (d, 1H, J=2.36 Hz), 7.90 (dd, 1H, J=2.36 Hz, 8.72 Hz), 11.36 (brs, 1H).

(Step 3)

To a solution of the compound obtained in Step 2 (1 g, 3.6 mmol) in DMF (45 mL) was added potassium carbonate (0.444 g, 3.24 mmol), and the mixture was stirred at room temperature for 1 hr. To the reaction mixture was added water, and the mixture was extracted with ethyl acetate. The organic layer was washed with saturated brine, and dried over sodium sulfate, and the solvent was evaporated under reduced pressure. The obtained residue was purified by silica gel column chromatography (solvent; 10% ethyl acetate/hexane) to give ethyl (4-ethyl-7-nitro-3-oxo-3,4-dihydro-2H-benzo[1,4]oxazin-2-yl)-acetate (0.360 g, 32.7%) as a yellow solid.

MS(API): 309 (M+H)

(Step 4)

To a solution of the compound obtained in Step 3 (0.70 g, 2.27 mmol) in methanol (20 mL) was added 10% palladium on carbon (50% hydrous, 0.27 g), and the mixture was stirred at room temperature for 5 hr under 1 atm of under hydrogen atmosphere. The catalyst was removed by filtration, and the filtrate was concentrated under reduced pressure. The obtained residue was washed with pentane to give ethyl (7-amino-4-ethyl-3-oxo-3,4-dihydro-2H-benzo[1,4]oxazin-2-yl)-acetate (0.60 g, 95%) as a brown oil.

MS(API): 279 (M+H)

(Step 5)

To a solution of the compound obtained in Step 4 (0.50 g, 1.8 mmol) and the compound obtained in Step 3 of Reference Example 1 (0.784 g, 2.8 mmol) in ethyl acetate (20 mL) were added DIEA (0.521 mL, 3.0 mmol) and T3P (50% ethyl acetate solution, 3 mL, 5 mmol), and the mixture was refluxed for 6 hr under argon atmosphere. The reaction mixture was allowed to be cooled to room temperature, diluted with ethyl acetate, and washed successively with cooled saturated aqueous sodium hydrogencarbonate solution, water and saturated brine. The organic layer was dried over sodium sulfate, and the solvent was evaporated under reduced pressure. The obtained residue was purified by preparative HPLC to give the title compound (0.50 g, 52.7%) as a grayish white solid.

MS(API): 541 (M+H)

$^1$H-NMR (400 MHz, DMSO-$d_6$): δ0.978 (d, 3H, J=6.28 Hz), 1.10 (t, 3H, J=7.04 Hz), 1.18 (t, 3H, J=7.20 Hz), 2.16-2.49 (m, 5H), 2.84 (dd, 1H, J=7.24 Hz, 16.36 Hz), 2.98 (dd, 1H, J=4.56 Hz, 16.36 Hz), 3.88 (q, 2H, J=6.88 Hz), 4.08 (q, 2H, J=4.36 Hz), 4.88 (dd, 1H, J=4.64 Hz, 11.36 Hz), 7.11 (d, 1H, J=8.80 Hz), 7.18 (d, 1H, J=8.92 Hz), 7.36 (d, 1H, J=1.84 Hz), 7.59 (dd, 1H, J=1.84 Hz, 8.68 Hz), 7.86 (d, 1H, J=8.60 Hz), 8.05 (d, 1H, J=1.76 Hz), 9.93 (s, 1H), 10.54 (s, 1H).

purification condition by preparative HPLC
  instrument: Waters Semi-Preparative HPLC instrument
  column: Prep Scalar 10 τm C18 (250×30 mm)
  solvent: A=5 mM aqueous ammonium acetate solution, B=acetonitrile
  solvent gradient: 60% A/B(0 min)→40% A/B(50 min)→5% A/B(60 min)→5% A/B(65 min)→60% A/B(70 min)
  flow rate: 30 mL/min
  temperature: room temperature Example 19

N-(3-chloro-4-cyanophenyl)-N'-(1-ethyl-3-(methoxymethyl)-2,4-dioxo-1,2,3,4-tetrahydroquinazolin-6-yl)-3-methylpentanediamide (Step 1)

A solution of methyl 2-fluoro-5-nitrobenzoate (5.0 g, 25.11 mmol), ethylamine (2 mol/L, THF solution, 31.5 mL, 62.77 mmol) and potassium carbonate (3.47 g, 25.11 mmol) in THF (50 mL) was sealed, and stirred at 60° C. for 16 hr. The reaction mixture was concentrated under reduced pressure, and the obtained residue was washed with ethyl acetate/hexane (2:98) to give methyl 2-ethylamino-5-nitrobenzoate (5.0 g, 88.82%) as a yellow solid.

$^1$H-NMR (400 MHz, DMSO-$d_6$): δ1.23 (t, 3H, J=7.08 Hz), 3.29-3.41 (q, 2H), 3.86 (s, 3H), 6.92 (d, 1H, J=9.48 Hz), 8.18 (dd, 1H, J=9.52 Hz, 2.68 Hz), 8.48 (brs, 1H), 8.62 (d, 1H, J=2.76 Hz).

(Step 2)

A mixture of the compound obtained in Step 1 (5.0 g, 22.32 mmol) and urea (40.58 g, 669.64 mmol) was stirred at 160° C. for 48 hr. The reaction mixture was allowed to be cooled to room temperature, and water was added thereto. The precipitate was collected by filtration, and the obtained solid was washed with dichloromethane to give 1-ethyl-6-nitro-1H-quinazoline-2,4-dione (3.0 g, 57.14%) as a yellow solid.

MS(API): 234 (M−H)

(Step 3)

To a solution of the compound obtained in Step 2 (400 mg, 1.70 mmol) in DMF (10 mL) were added sodium hydride (60% oil, 102 mg, 2.55 mmol) and bromomethoxymethane (425 mg, 3.40 mmol), and the mixture was stirred at room temperature for 16 hr. The reaction mixture was poured into water, and the precipitated solid was collected by filtration, and dried under reduced pressure. The obtained solid was washed with ethyl acetate/hexane (10:90) to give 1-ethyl-3-methoxymethyl-6-nitro-1H-quinazoline-2,4-dione (240 mg, 51.75%) as a brown solid.

$^1$H-NMR (400 MHz, DMSO-$d_6$): δ1.24 (t, 3H, J=7.00 Hz), 3.32 (s, 3H), 4.20 (q, 2H, J=7.08 Hz), 5.35 (s, 2H), 7.74 (d, 1H, J=9.32 Hz), 8.54 (dd, 1H, J=9.26 Hz, 2.84 Hz), 8.74 (d, 1H, J=2.68 Hz).

(Step 4)

To a solution of the compound obtained in Step 3 (246 mg, 0.88 mmol) in ethyl acetate (30 mL) was added 10% palladium on carbon (50% hydrous, 50 mg), and the mixture was stirred at room temperature for 3 hr under 2 atm of hydrogen atmosphere. The catalyst was removed by filtration, and the filtrate was concentrated under reduced pressure to give 6-amino-1-ethyl-3-methoxymethyl-1H-quinazoline-2,4-dione (207 mg, 94.19%) as a yellow solid.

MS(API): 250 (M+H)

(Step 5)

To a solution of the compound obtained in Step 3 of Reference Example 1 (233 mg, 0.83 mmol) in ethyl acetate (100 mL) were added DIEA (0.27 mL, 2.08 mmol), T3P (50% ethyl acetate solution, 0.66 mL, 2.08 mmol) and the compound obtained in Step 4 (207 mg, 0.83 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (225 mg, 52.91%) as a grayish white solid.

MS(API): 510 (M−H)

$^1$H-NMR (400 MHz, DMSO-$d_6$): δ0.99 (s, 3H, J=6.36 Hz), 1.20 (t, 3H, J=6.92 Hz), 2.26-2.50 (m, 5H), 3.25 (s, 3H), 4.08-4.13 (m, 2H), 5.33 (s, 2H), 7.46 (d, H, J=9.16 Hz), 7.578 (dd, H, J=8.60 Hz, 1.64 Hz), 7.84 (d, 1H, J=8.64 Hz), 7.92 (dd, 1H, J=9.00 Hz, 2.40 Hz), 8.02 (d, 1H, J=1.72 Hz), 8.36 (d, 1H, J=2.44 Hz), 10.20 (s, 1H), 10.58 (s, 1H)

purification condition by preparative HPLC
  instrument: Waters Semi-Preparative HPLC instrument
  column: Prep Scalar 10 μm C18 (250×30 mm)
  solvent: A=5 mM aqueous ammonium acetate solution, B=acetonitrile
  solvent gradient: 70% A/B(0 min)→60% A/B(60 min)→5% A/B(61 min)→5% A/B(70 min)→60% A/B(71 min)
  flow rate: 30 mL/min
  temperature: room temperature Example 20

N-(3-chloro-4-cyanophenyl)-N'-(1-ethyl-3-(2-methoxyethyl)-2,4-dioxo-1,2,3,4-tetrahydroquinazolin-6-yl)-3-methylpentanediamide (Step 1)

To a solution of the compound obtained in Step 2 of Example 19 (400 mg, 1.70 mmol) in DMF (10 mL) were added sodium hydride (60% oil, 102 mg, 2.55 mmol) and 1-bromo-2-methoxyethane (0.473 mL, 3.40 mmol), and the mixture was stirred at room temperature for 16 hr. The reaction mixture was poured into water, and the mixture was extracted with ethyl acetate. The organic layer was washed with saturated brine, and dried over sodium sulfate, and the solvent was evaporated under reduced pressure. The obtained residue was purified by silica gel column chromatography (solvent; 25% ethyl acetate/hexane) to give 1-ethyl-3-(2-methoxyethyl)-6-nitro-1H-quinazoline-2,4-dione (196 mg, 39.26%) as a brown solid.

MS(API): 294 (M+H)

(Step 2)

To a solution of the compound obtained in Step 1 (200 mg, 0.68 mmol) in ethyl acetate (30 mL) was added 10% palladium on carbon (50% hydrous, 50 mg), and the mixture was stirred at room temperature for 3 hr under 2 atm of hydrogen atmosphere. The catalyst was removed by filtration, and the filtrate was concentrated under reduced pressure to give 6-amino-1-ethyl-3-(2-methoxyethyl)-1H-quinazoline-2,4-dione (180 mg, 94.96%) as a yellow solid.

MS(API): 264 (M+H)

(Step 3)

To a solution of the compound obtained in Step 3 of Reference Example 1 (206 mg, 0.73 mmol) in ethyl acetate (100 mL) were added DIEA (0.24 mL, 1.83 mmol), T3P (50% ethyl acetate solution, 0.58 mL, 1.83 mmol) and the compound obtained in Step 2 (207 mg, 0.83 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (170 mg, 44.08%) as a grayish white solid.

MS(API): 524 (M−H)

$^1$H-NMR (400 MHz, DMSO-$d_6$): δ0.99 (d, 3H, J=6.36 Hz), 1.19 (t, 3H, J=6.92 Hz), 2.25-2.50 (m, 5H), 3.24 (s, 3H), 3.53 (t, 2H, J=6.08 Hz), 4.08-4.15 (m, 4H), 7.43 (d, 1H, J=9.12 Hz), 7.56 (dd, 1H, J=8.64 Hz, 1.72 Hz), 7.83 (d, 1H, J=8.56 Hz), 7.89 (dd, 1H, J=9.00 Hz, 2.40 Hz), 8.00 (d, 1H, J=1.68 Hz), 8.34 (d, 1H, J=2.40 Hz), 10.25 (s, 1H), 10.66 (s, 1H).

purification condition by preparative HPLC
  instrument: Waters Semi-Preparative HPLC instrument
  column: Prep Scalar 10 μm C18 (250×30 mm)
  solvent: A=5 mM aqueous ammonium acetate solution, B=acetonitrile
  solvent gradient: 65% A/B(0 min)→55% A/B(60 min)→5% A/B(61 min)→5% A/B(70 min)→65% A/B(71 min)
  flow rate: 30 mL/min
  temperature: room temperature Example 21

N-(3-chloro-4-cyanophenyl)-N'-(1-ethyl-3-(3-methoxypropyl)-2,4-dioxo-1,2,3,4-tetrahydroquinazolin-6-yl)-3-methylpentanediamide (Step 1)

To a solution of the compound obtained in Step 2 of Example 19 (400 mg, 1.70 mmol) in DMF (10 mL) were added sodium hydride (60% oil, 102 mg, 2.55 mmol) and 1-bromo-2-methoxypropane (0.521 mL, 3.40 mmol), and the mixture was stirred at room temperature for 16 hr. The reaction mixture was poured into water, and the precipitated solid was collected by filtration, and dried under reduced pressure. The obtained solid was washed with ethyl acetate/hexane (10:90) to give 1-ethyl-3-(3-methoxypropyl)-6-nitro-1H-quinazoline-2,4-dione (290 mg, 55.44%) as a brown solid.

MS(API): 308 (M+H)

(Step 2)

To a solution of the compound obtained in Step 1 (186 mg, 0.61 mmol) in ethyl acetate (25 mL) was added 10% palladium on carbon (50% hydrous, 40 mg), and the mixture was stirred at room temperature for 3 hr under 2 atm of hydrogen atmosphere. The catalyst was removed by filtration, and the filtrate was concentrated under reduced pressure to give 6-amino-1-ethyl-3-(3-methoxypropyl)-1H-quinazoline-2,4-dione (140 mg, 83.32%) as a yellow solid.

MS(API): 278 (M+H)

(Step 3)

To a solution of the compound obtained in Step 3 of Reference Example 1 (134 mg, 0.47 mmol) in ethyl acetate (100 mL) was added DIEA (0.15 mL, 1.19 mmol), T3P (50% ethyl acetate solution, 0.38 mL, 1.19 mmol) and the compound obtained in Step 2 (132 mg, 0.47 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (180 mg, 71.86%) as a grayish white solid.

MS(API): 538 (M−H)

$^1$H-NMR (400 MHz, DMSO-$d_6$): δ0.99 (d, 3H, J=6.44 Hz), 1.20 (t, 3H, J=7.00 Hz), 1.79-1.84 (m, 2H), 2.26-2.50 (m, 5H), 3.20 (s, 3H), 3.37 (t, 2H, J=6.12 Hz), 4.00 (t, 2H, J=7.00 Hz), 4.08-4.13 (m, 2H), 7.43 (d, 1H, J=9.20 Hz), 7.57 (dd, 1H, J=8.68 Hz, 1.84 Hz), 7.84 (d, 1H, J=8.68 Hz), 7.91 (dd, 1H, J=9.00 Hz, 2.48 Hz), 8.02 (d, 1H, J=1.84 Hz), 8.33 (d, 1H, J=1.84 Hz), 10.14 (s, 1H), 10.53 (s, 1H)

purification condition by preparative HPLC
  instrument: Waters Semi-Preparative HPLC instrument
  column: Prep Scalar 10 μm C18 (250×30 mm)
  solvent: A=5 mM aqueous ammonium acetate solution, B=acetonitrile
  solvent gradient: 90% A/B(0 min)→65% A/B(10 min)→45% A/B(50 min)→5% A/B(51 min)→5% A/B(60 min)→90% A/B(61 min)
  flow rate: 30 mL/min
  temperature: room temperature Example 22

N-(3-chloro-4-cyanophenyl)-N'-(3-(2-(dimethylamino)-2-oxoethyl)-1-ethyl-2,4-dioxo-1,2,3,4-tetrahydroquinazolin-6-yl)-3-methylpentanediamide (Step 1)

To a solution of the compound obtained in Step 2 of Example 19 (350 mg, 1.49 mmol) in DMF (10 mL) were added sodium hydride (60% oil, 71 mg, 1.78 mmol), 2-chloro-N,N-dimethylacetamide (362 mg, 2.98 mmol) and sodium iodide (11 mg, 0.074 mmol), and the mixture was stirred. After confirming disappearance of the raw material, the reaction mixture was poured into water, and the mixture was extracted with ethyl acetate. The organic layer was washed with saturated brine, and dried over sodium sulfate, and the solvent was evaporated under reduced pressure. The obtained residue was purified by silica gel column chromatography (solvent; 50% ethyl acetate/hexane) to give 2-(1-ethyl-6-nitro-2,4-dioxo-1,4-dihydro-2H-quinazolin-3-yl)-N,N-dimethylacetamide (210 mg, 44.02%) as a grayish white solid.

$^1$H-NMR (400 MHz, DMSO-$d_6$): δ1.23 (t, 3H, J=7.00 Hz), 2.85 (s, 3H), 3.09 (s, 3H), 4.21 (q, 2H, J=7.00 Hz), 4.82 (s, 2H), 7.79 (d, 1H, J=9.32 Hz), 8.56 (dd, 1H, J=9.28 Hz, 2.76 Hz), 8.73 (d, 1H, J=2.72 Hz)

(Step 2)

To a solution of the compound obtained in Step 1 (250 mg, 0.78 mmol) in ethyl acetate (25 mL) was added 10% palladium on carbon (50% hydrous, 100 mg), and the mixture was stirred at room temperature for 3 hr under 2 atm of hydrogen atmosphere. The catalyst was removed by filtration, and the filtrate was concentrated under reduced pressure to give 2-(6-amino-1-ethyl-2,4-dioxo-1,4-dihydro-2H-quinazolin-3-yl)-N,N-dimethylacetamide (200 mg, 88.27%) as a yellow solid.

$^1$H-NMR (400 MHz, DMSO-d$_6$): δ1.17 (t, 3H, J=6.96 Hz), 2.83 (s, 3H), 3.07 (s, 3H), 4.03-4.08 (m, 2H), 4.74 (s, 2H), 5.30 (s, 2H), 7.04-7.07 (m, 1H), 7.23-7.26 (m, 2H).

(Step 3)

To a solution of the compound obtained in Step 3 of Reference Example 1 (279 mg, 0.99 mmol) in ethyl acetate (25 mL) were added DIEA (0.27 mL, 2.08 mmol), T3P (50% ethyl acetate solution, 0.66 mL, 2.08 mmol) and the compound obtained in Step 2 (241 mg, 0.83 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (100 mg, 21.76%) as a grayish white solid.

MS(API): 551 (M−H)

$^1$H-NMR (400 MHz, DMSO-d$_6$): δ1.00 (d, 3H, J=6.28 Hz), 1.20 (t, 3H, J=7.08 Hz), 2.32-2.50 (m, 5H), 2.84 (s, 3H), 3.08 (s, 3H), 4.10-4.12 (m, 2H), 4.78 (s, 2H), 7.49 (d, 1H, J=9.16 Hz), 7.58 (dd, 1H, J=8.60 Hz, 1.68 Hz), 7.86 (d, Hz), 7.96 (dd, H, J=9.08 Hz, 2.36 Hz), 8.03 (d, 1H, J=1.68 Hz), 8.33 (d, 1H, J=2.36 Hz), 10.17 (s, 1H), 10.52 (s, 1H).

purification condition by preparative HPLC
instrument: Waters Semi-Preparative HPLC instrument
column: Prep Scalar 10 μm C18 (250×30 mm)
solvent: A=5 mM aqueous ammonium acetate solution, B=acetonitrile
solvent gradient: 80% A/B(0 min)→50% A/B(60 min)→5% A/B(61 min)→5% A/B(70 min)→80% A/B(71 min)
flow rate: 30 mL/min
temperature: room temperature Example 23

3-chloro-4-cyano-N-(4-((1,3-diethyl-2,4-dioxo-1,2,3,4-tetrahydroquinazolin-6-yl)amino)-2-methyl-4-oxobutyl)benzamide A solution of the compound of Example 11 (95 mg, 0.17 mmol), zinc cyanide (22.32 mg, 0.19 mmol) and tetrakis(triphenylphosphine)palladium (19.97 mg, 0.02 mmol) in N-methylmorpholine (2 mL) was stirred overnight at 80° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5→50% ethyl acetate/hexane), and then preparative HPLC (column: L-Column 2 ODS (20×150 mm, 5 μm), eluent: acetonitrile containing 0.1% trifluoroacetic acid/water), and then preparative HPLC (column: Sunrise C18-SAC(20×50 mm, 5 μm), eluent: acetonitrile containing 0.1% trifluoroacetic acid/water) to give the title compound (16.00 mg, 0.032 mmol, 18.67%) as a colorless solid.

MS(API): 496 (M+H)

$^1$H-NMR (300 MHz, CDCl$_3$): δ1.11 (3H, d, J=6.0 Hz), 1.29-1.41 (6H, m), 2.29-2.58 (3H, m), 3.34-3.62 (2H, m), 4.14-4.25 (4H, m), 7.15 (1H, d, J=9.1 Hz), 7.47 (1H, brs), 7.62-7.72 (1H, m), 1H, dd, J=8.3, 1.5 Hz), 7.92 (1H, d, J=1.1 Hz), 8.01-8.19 (2H, m) 8.54 (1H, brs).

Example 24

3-chloro-N-(4-((1,3-diethyl-2,4-dioxo-1,2,3,4-tetrahydroquinazolin-6-yl)amino)-2-methyl-4-oxobutyl)-4-(morpholin-4-yl)benzamide A solution of the compound of Example 11 (68 mg, 0.12 mmol), morpholine (0.012 mL, 0.14 mmol), 2-dicyclohexylphosphino-2',6'-diisopropoxy-1,1'-biphenyl (5.77 mg, 0.01 mmol), Pd$_2$(dba)$_3$ (5.66 mg, 6.18 mmol) and potassium tert-butoxide (13.07 mg, 0.14 mmol) in toluene (1 mL) was stirred overnight at 90° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane), and then preparative HPLC (column: L-Column 2 ODS (20×150 mm, 5 μm), eluent: acetonitrile containing 0.1% trifluoroacetic acid/water) to give the title compound (16.00 mg, 0.032 mmol, 18.67%) as a colorless solid.

MS(API): 556 (M+H)

Example 25

N-(3-chloro-4-cyanophenyl)-N'-(1,3-diethyl-2,4-dioxo-1,2,3,4-tetrahydroquinazolin-6-yl)succinamide (Step 1)

A solution of 4-amino-2-chlorobenzonitrile (1.0 g, 6.55 mmol), TEA (0.913 mL, 6.55 mmol) and succinic anhydride (0.656 g, 6.55 mmol) in toluene (10 mL) was stirred overnight at 80° C. The reaction mixture was allowed to be cooled to room temperature, 1N hydrochloric acid was added thereto, and the mixture was extracted with ethyl acetate. The organic layer was washed with saturated brine, and dried over magnesium sulfate, and the solvent was evaporated under reduced pressure to give 4-((3-chloro-4-cyanophenyl)amino)-4-oxobutanoic acid (quantitative).

MS(API): 251 (M−H)

(Step 2)

A solution of the compound obtained in Step 1 (162 mg, 0.64 mmol), the compound obtained in Step 3 of Example 1 (150 mg, 0.64 mmol), DIEA (0.562 mL, 3.22 mmol) and T3P (50% ethyl acetate solution, 0.284 mL, 0.96 mmol) in DMF (5 mL) was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by preparative HPLC (column: L-Column 2 ODS (20×150 mm, 5 μm), eluent: acetonitrile containing 0.1% trifluoroacetic acid/water) to give the title compound (10.0 mg, 0.021 mmol, 3.32%) as a colorless oil.

MS(API): 468 (M+H)

$^1$H-NMR (300 MHz, CD$_3$OD): δ1.18 (9H, dt, J=18.6, 6.9 Hz), 3.86-4.27 (5H, m), 4.49 (2H, brs), 7.31 (1H, d, J=9.1 Hz), 7.39-7.69 (3H, m), 7.76-8.02 (2H, m), 8.23 (1H, s).

Example 26

N-(3-chloro-4-cyanophenyl)-5-((1,3-diethyl-2,4-dioxo-1,2,3,4-tetrahydroquinazolin-6-yl)oxy)-3-methylpentanamide (Step 1)

A solution of 2-amino-5-hydroxybenzoic acid (5 g, 32.65 mmol) and urea (1.961 g, 32.65 mmol) in DMA (15 mL) was stirred at 180° C. for 10 min under microwave irradiation. The reaction mixture was allowed to be cooled to room temperature, and water was added thereto. The precipitated solid was collected by filtration to give 6-hydroxyquinazoline-2,4(1H,3H)-dione (1.26 g, 7.07 mmol, 21.66%) as a brown solid. A solution of the obtained solid (1.26 g, 7.07 mmol) and acetic anhydride (0.734 mL, 7.78 mmol) in pyridine (10 mL) was stirred overnight at 50° C. The reaction mixture was allowed to be cooled to room temperature, water was added thereto, and the precipitated solid was collected by filtration to give 2,4-dioxo-1,2,3,4-tetrahydroquinazolin-6-yl acetate (1.36 g, 6.18 mmol, 87%) as a brown solid.

MS(API): 221 (M+H)

(Step 2)

A solution of the compound obtained in Step 1 (1.06 g, 4.81 mmol), iodoethane (1.155 mL, 14.44 mmol) and potassium carbonate (1.966 g, 14.44 mmol) in DMF (10 mL) was stirred at room temperature for 2 days. To the reaction mixture was added saturated brine, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5→30% ethyl acetate/hexane) to give 1,3-diethyl-2,4-dioxo-1,2,3,4-tetrahydroquinazolin-6-yl acetate (1.04 g, 3.76 mmol, 78%) as a pale orange solid.

$^1$H-NMR (300 MHz, CDCl$_3$): δ1.19-1.45 (6H, m), 2.33 (3H, s), 3.95-4.32 (4H, m), 7.21 (1H, d, J=9.1 Hz), 7.37-7.46 (11H, m), 7.94 (1H, d, J=2.6 Hz).

(Step 3)

A solution of the compound obtained in Step 2 (1.06 g, 3.84 mmol) and potassium carbonate (0.53 g, 3.84 mmol) in methanol (10 mL) was stirred at room temperature for 3 hr. To the reaction mixture was added 1N hydrochloric acid, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→50% ethyl acetate/hexane) to give 1,3-diethyl-6-hydroxyquinazoline-2,4(1H,3H)-dione (0.581 g, 2.48 mmol, 64.6%) as a colorless solid.

MS(API): 235 (M+H)

(Step 4)

A solution of the compound obtained in Step 3 of Reference Example 1 (3 g, 10.69 mmol), isobutyl chloroformate (1.532 mL, 11.76 mmol) and TEA (1.49 mL, 10.69 mmol) in THF (30 mL) was stirred at room temperature for 2 hr. The reaction mixture was added dropwise to a solution of sodium borohydride (2.02 g, 53.44 mmol) in THF (10 mL)/water (10 mL) at 0° C., and the mixture was stirred at 0° C. for 1 hr. To the reaction mixture was added saturated brine, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) to give N-(3-chloro-4-cyanophenyl)-5-hydroxy-3-methylpentanamide (1.72 g, 6.45 mmol, 60.3%) as a white solid.

MS(API): 265 (M–H)

(Step 5)

A solution of the compound obtained in Step 3 (261 mg, 1.11 mmol), the compound obtained in Step 4 (297 mg, 1.11 mmol) and ADDP (562 mg, 2.23 mmol) in THF (10 mL) was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10>100% ethyl acetate/hexane), and then preparative HPLC (column: L-Column 2 ODS (20×150 mm, 5 μm), eluent: 10 mM acetonitrile containing ammonium hydrogencarbonate/water) to give the title compound (40 mg, 0.083 mmol, 7.43%) as a white solid.

MS(API): 483 (M+H)

Example 27

N-(3-chloro-4-cyanophenyl)-N'-(3-(cyclopropylmethyl)-1-ethyl-2,4-dioxo-1,2,3,4-tetrahydroquinazolin-6-yl)-3-methylpentanediamide (Step 1)

To a solution of the compound obtained in Step 2 of Example 19 (350 mg, 1.49 mmol) in DMF (10 mL) was added sodium hydride (60% oil, 119.15 mg, 2.98 mmol) at room temperature under nitrogen atmosphere. The mixture was stirred at room temperature for 5 min, bromomethylcyclopropane (0.239 mL, 2.98 mmol) was added thereto, and the mixture was stirred at room temperature for 5 hr. To the reaction mixture was added ice water, and the mixture was extracted with ethyl acetate. The organic layer was washed with water, and dried over sodium sulfate, and the solvent was evaporated under reduced pressure. The residue was washed with ethyl acetate-hexane (2:98) to give 3-(cyclopropylmethyl)-1-ethyl-6-nitro-1H-quinazoline-2,4-dione (350 mg, 81.23%) as a pale green viscous solid.

$^1$H-NMR (400 MHz, DMSO-d$_6$): δ0.37-0.46 (m, 4H), 1.17-1.20 (m, 1H), 1.24 (t, 3H, J=7.04 Hz), 3.86 (d, 2H, J=7.16 Hz), 4.19-4.24 (m, 2H), 7.74 (d, 1H, J=9.32 Hz), 8.53 (dd, 1H, J=9.24 Hz, 2.68 Hz), 8.75 (d, 1H, J=2.64 Hz)

(Step 2)

To a solution of the compound obtained in Step 1 (420 mg, 1.45 mmol) in ethyl acetate (20 mL) was added 10% palladium on carbon (50% hydrous, 50 mg), and the mixture was stirred at room temperature for 3 hr under 2 atm of hydrogen atmosphere. The catalyst was removed by filtration, and the filtrate was concentrated under reduced pressure to give 6-amino-3-(cyclopropylmethyl)-1-ethyl-1H-quinazoline-2,4-dione (292 mg, 77.54%) as a yellow solid.

MS(API): 260 (M+H)

(Step 3)

To a solution of the compound obtained in Step 3 of Reference Example 1 (378.81 mg, 1.14 mmol) in ethyl acetate (30 mL) were added DIEA (0.362 mL, 2.82 mmol), T3P (0.89 mL, 2.82 mmol) and the compound obtained in Step 2 (292 mg, 1.13 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (325 mg, 76.65%) as a grayish white solid.

MS(API): 520 (M−H)

$^1$H-NMR (300 MHz, DMSO-$d_6$): δ0.35-0.36 (m, 2H), 0.39-0.43 (m, 2H), 0.99 (d, 3H, J=6.16 Hz), 1.20 (t 3H, J=6.76 Hz), 22 (m, 1H), 2.26-2.50 (m, 5H), 3.83 (d, 2H, J=6.96 Hz), 4.09-4.14 (m, 2H), 7.44 (d, 1H, J=9.12 Hz), 7.56 (d, 1H, J=9.32 Hz), 7.84 (d, 1H, J=8.64 Hz), 7.90 (dd, 1H, J=9.00 Hz, 1.80 Hz), 8.01 (s, 1H), 8.36 (s, 1H), 10.16 (s, 1H), 10.54 (s, 1H).

purification condition by preparative HPLC
instrument: Waters Semi-Preparative HPLC instrument
column: Prep Scalar 10 μm C18 (250×30 mm)
solvent: A=5 mM aqueous ammonium acetate solution, B=acetonitrile
solvent gradient: 60% A/B(0 min)→60% A/B(60 min)→5% A/B(61 min)→5% A/B(70 min)→60% A/B(71 min)
flow rate: 30 mL/min
temperature: room temperature Example 28

N-(3-chloro-4-cyanophenyl)-N'-(1-ethyl-2,4-dioxo-3-(prop-2-yn-1-yl)-1,2,3, 4-tetrahydroquinazolin-6-yl)-3-methylpentanediamide (Step 1)

To a solution of the compound obtained in Step 2 of Example 19 (350 mg, 1.49 mmol) in DMF (15 mL) were added sodium hydride (60% oil, 71.0 mg, 2.98 mmol) and bromoethyne (0.35 mL, 2.98 mmol), and the mixture was stirred at room temperature for 16 hr. To the reaction mixture was added water, and the precipitate was collected by filtration, and dried under reduced pressure. The obtained solid was washed with ethyl acetate-hexane (10:90) to give 1-ethyl-6-nitro-3-(propa-2-ynyl)-1H-quinazoline-2,4-dione (230 mg, 56.52%) as a brown solid.

$^1$H-NMR (400 MHz, DMSO-$d_6$): δ1.25 (t, 3H, J=7.04 Hz), 3.19 (s, 1H), 4.21 (q, 2H, J=7.04 Hz), 4.69 (s, 2H), 7.76 (d, H, J=9.32 Hz), 8.54 (dd, 1H, J=9.26 Hz, 2.76 Hz), 8.74 (d, H, J=2.64 Hz).

(Step 2)

To a solution of the compound obtained in Step 1 (172 mg, 0.62 mmol) in ethanol (30 mL) was added tin(II) chloride (594 mg, 3.14 mmol), and the mixture was stirred at 80° C. for 2 hr. The reaction mixture was concentrated under reduced pressure, and to the residue was added water. The pH of the mixture was adjusted to 8 with saturated aqueous sodium carbonate solution, and the mixture was extracted with ethyl acetate. The organic layer was washed with water, and dried over sodium sulfate, and the solvent was evaporated under reduced pressure to give 6-amino-1-ethyl-3-(propa-2-ynyl)-1H-quinazoline-2,4-dione (170 mg, 95.48%) as a yellow solid.

$^1$H-NMR (400 MHz, DMSO-$d_6$): δ0.97 (d, 3H, J=5.64 Hz), 3.11 (s, 1H), 4.27 (d, 2H, J=5.2 Hz), 4.65 (s, 2H), 5.35 (s, 2H), 7.05 (d, 1H, J=8.88 Hz), 7.24-7.26 (m, 2H).

(Step 3)

To a solution of the compound obtained in Step 3 of Reference Example 1 (235 mg, 0.84 mmol) in ethyl acetate (25 mL) were added DIEA (0.303 mL, 1.75 mmol), T3P (50% ethyl acetate solution, 0.556 mL, 1.75 mmol) and the compound obtained in Step 2 (170 mg, 0.70 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (150 mg, 42.38%) as a grayish white solid.

MS(API): 504 (M−H)

$^1$H-NMR (400 MHz, DMSO-$d_6$): δ1.00 (d, 3H, J=6.40 Hz), 1.21 (t, 3H, J=7.68 Hz), 2.33-2.50 (m, 5H), 3.13 (s, 1H), 4.10-4.15 (m, 2H), 4.68 (s, 2H), 7.47 (d, 1H, J=9.16 Hz), 7.57 (dd, 1H, J=8.62 Hz, 1.80 Hz), 7.84 (d, 1H, J=8.68 Hz), 7.94 (dd, 1H, J=9.04 Hz, 2.6 Hz), 8.02 (d, 1H, J=1.80 Hz), 8.36 (d, 1H, J=2.48 Hz), 10.21 (s, 1H), 10.57 (s, 1H).

purification condition by preparative HPLC
instrument: Waters Semi-Preparative HPLC instrument
column: Prep Scalar 10 μm C18 (250×30 mm)
solvent: A=5 mM aqueous ammonium acetate solution, B=acetonitrile
solvent gradient: 70% A/B(0 min)→50% A/B(60 min)→5% A/B(61 min)→5% A/B(70 min)→70% A/B(71 min)
flow rate: 30 mL/min
temperature: room temperature Example 29

N-(3-(2-amino-2-oxoethyl)-1-ethyl-2,4-dioxo-1,2,3, 4-tetrahydroquinazolin-6-yl)-N'-(3-chloro-4-cyanophenyl)-3-methylpentanediamide (Step 1)

2-(1-Ethyl-6-nitro-2, 4-dioxo-1,4-dihydro-2H-quinazolin-3-yl)-acetamide (152 mg, 76.39%) was obtained as a grayish white solid using 2-bromoacetamide (188 mg, 1.36 mmol) by the reaction and purification in the same manner as in Step 1 of Example 27.

$^1$H-NMR (400 MHz, DMSO-$d_6$): δ1.24 (t, 3H, J=7.02 Hz), 4.19-4.24 (m, 2H), 4.50 (s, 2H), 7.19 (s, 1H), 7.64 (s, 1H), 7.77 (d, 1H, J=9.32 Hz), 8.55 (dd, 1H, J=9.24 Hz, 2.60 Hz), 8.73 (d, 1H, J=2.68 Hz).

(Step 2)

2-(6-Amino-1-ethyl-2,4-dioxo-1,4-dihydro-2H-quinazolin-3-yl)-acetamide (113 mg, 81.08%) was obtained as a yellow solid using the compound obtained in Step 1 (148 mg, 0.50 mmol) by the reaction and purification in the same manner as in Step 2 of Example 27.

MS(API): 504 (M+H)

(Step 3)

The title compound (30 mg, 13.29%) was obtained as a grayish white solid using the compound obtained in Step 2 (113 mg, 0.43 mmol) by the reaction and purification in the same manner as in Step 3 of Example 27.

MS(API): 523 (M−H)

purification condition by preparative HPLC
instrument: Waters auto purification instrument
column: XBridge C18 (250×19 mm, 5 μm)
solvent: A=5 mM aqueous ammonium acetate solution, B=acetonitrile
solvent gradient: 90% A/B(0 min)→65% A/B(1 min)→60% A/B(10 min)→50% A/B(26 min)→0% A/B(27 min)→0% A/B(29 min)→90% A/B(30 min)
flow rate: 14 mL/min
temperature: room temperature

Example 30

N-(3-chloro-4-cyanophenyl)-N'-(4-ethyl-3-oxo-3,4-dihydrospiro[1,4-benzoxazine-2,1'-cyclopropane]-7-yl)-3-methylpentanediamide (Step 1)
To a solution of the compound obtained in Step 4 of Example 8 (2.85 g, 10.71 mmol) in THF (145 mL) were added DIEA (5.31 mL, 32.14 mmol) and methanesulfonyl chloride (2.07 mL, 26.78 mmol) at 0° C., and the mixture was stirred for 15 min, and then at room temperature for 4 hr. The reaction mixture was diluted with ethyl acetate (100 mL), and the mixture was washed with cooled saturated aqueous sodium hydrogencarbonate solution, water and saturated brine. The organic layer was dried over sodium sulfate, and the solvent was evaporated under reduced pressure. The obtained residue was purified by silica gel column chromatography (solvent gradient; 30→50% ethyl acetate/hexane) to give 2-(4-ethyl-7-nitro-3-oxo-3,4-dihydro-2H-benzo[1,4]oxazin-2-yl)-ethyl methanesulfonate (3.43 g, 93%) as a yellow solid.

MS(API): 345 (M+H)

(Step 2)
To a solution of the compound obtained in Step 1 (1.50 g, 4.36 mmol) in DMSO (15 mL) was added sodium hydride (60% oil, 0.261 g, 6.54 mmol) in several parts, and the mixture was stirred at room temperature for 16 hr. To the reaction mixture was added cold water (45 mL), and the mixture was extracted with ethyl acetate. The organic layer was washed with water and saturated brine, and dried over sodium sulfate, and the solvent was evaporated under reduced pressure. The obtained residue was purified by silica gel column chromatography (solvent gradient; 12→15% ethyl acetate/hexane) to give 4-ethyl-7-nitro-3,4-dihydrospiro[1,4-benzoxazine-2,1'-cyclopropane]-3-one (0.46 g, 42%) as a yellow solid.

MS(API): 249 (M+H)

(Step 3)
To a solution of the compound obtained in Step 2 (0.300 g, 1.21 mmol) in ethanol (10 mL) was added tin(II) chloride (1.15 g, 6.05 mmol), and the mixture was refluxed for 6 hr. The reaction mixture was allowed to be cooled to room temperature, and concentrated under reduced pressure. The residue was dissolved in ethyl acetate, and the solution was washed with cooled saturated aqueous sodium hydrogencarbonate solution, water and saturated brine. The organic layer was dried over sodium sulfate, and the solvent was evaporated under reduced pressure. The obtained residue was purified by aminopropyl silica gel column chromatography (solvent gradient; 10→12% ethyl acetate/hexane) to give 7-amino-4-ethyl-3,4-dihydrospiro[1,4-benzoxazine-2,1'-cyclopropane]-3-one (0.165 g, 62.5%) as a pale yellow solid.

MS(API): 219 (M+H)

(Step 4)
To a solution of the compound obtained in Step 3 (0.12 g, 0.55 mmol) and the compound obtained in Step 3 of Reference Example 1 (0.185 g, 0.66 mmol) in ethyl acetate (10 mL) were added DIEA (0.24 mL, 1.38 mmol) and T3P (50% ethyl acetate solution, 0.85 mL, 1.38 mmol), and the mixture was refluxed for 14 hr under argon atmosphere. The reaction mixture was allowed to be cooled to room temperature, diluted with ethyl acetate (50 mL), and washed with cooled saturated aqueous sodium hydrogencarbonate solution, water and saturated brine. The organic layer was dried over sodium sulfate, and the solvent was evaporated under reduced pressure. The obtained residue was purified by preparative HPLC to give the title compound (0.135 g, 51%) as a grayish white solid.

MS(API): 481 (M+H)

$^1$H-NMR (400 MHz, DMSO-$d_6$): δ0.97 (d, 3H, J=6.08 Hz), 1.12-1.24 (m, 7H), 2.23-2.46 (m, 5H), 3.90 (q, 2H, J=6.84 Hz), 7.12 (d, 1H, J=8.80 Hz), 7.19 (d, 1H, J=8.60 Hz), 7.34 (s, 1H), 7.58 (d, 1H, J=8.76 Hz), 7.87 (d, 1H, J=8.64 Hz), 8.05 (s, 1H), 9.95 (brs, 1H), 10.54 (brs, 1H)

purification condition by preparative HPLC
  instrument: Waters Semi-Preparative HPLC instrument
  column: Prep Scalar 10 μm C18 (250×30 mm)
  solvent: A=5 mM aqueous ammonium acetate solution, B=acetonitrile
  solvent gradient: 60% A/B(0 min)→40% A/B(50 min)→5% A/B(60 min)→5% A/B(65 min)→60% A/B(70 min)
  flow rate: 30 mL/min
  temperature: room temperature

Example 31

N-(3-chloro-4-cyanophenyl)-N'-(3-(cyanomethyl)-1-ethyl-2,4-dioxo-1,2,3,4-tetrahydroquinazolin-6-yl)-3-methylpentanediamide (Step 1)
To a solution of the compound obtained in Step 3 of Reference Example 1 (145 mg, 0.52 mmol) in ethyl acetate (30 mL) were added DIEA (0.18 mL, 1.07 mmol), T3P (50% ethyl acetate solution, 0.31 mL, 1.07 mmol) and the compound obtained in Step 2 of Example 29 (113 mg, 0.43 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (30 mg) as a grayish white solid.

MS(API): 505 (M−H)

$^1$H-NMR (400 MHz, DMSO-$d_6$): δ1.00 (d, 3H, J=6.36 Hz), 1.22 (t, 3H, J=6.88 Hz), 2.30-2.50 (m, 5H), 4.13-4.14 (m, 2H), 4.95 (s, 2H), 7.50 (d, 1H, J=9.20 Hz), 7.58 (dd, 1H, J=8.58 Hz, 1.80 Hz), 7.85 (d, 1H, J=8.56 Hz), 7.95 (dd, 1H, J=9.04 Hz, 2.28 Hz), 8.03 (d, 1H, J=1.80 Hz), 8.38 (d, 1H, J=2.40 Hz), 10.21 (s, 1H), 10.55 (s, 1H).

purification condition by preparative HPLC
  instrument: Waters auto purification instrument
  column: XBridge C18 (250×19 mm, 5 μm)
  solvent: A=5 mM aqueous ammonium acetate solution, B=acetonitrile
  solvent gradient: 90% A/B(0 min)→65% A/B(1 min)→60% A/B(10 min)→50% A/B(26 min)→0% A/B(27 min)→0% A/B(29 min)→90% A/B(30 min)
  flow rate: 14 mL/min
  temperature: room temperature

Example 32

N-(3-chloro-4-cyanophenyl)-N'-(1-ethyl-2,4-dioxo-3-((trimethylsilyl)methyl)-1,2,3,4-tetrahydroquinazolin-6-yl)-3-methylpentanediamide (Step 1)
To a solution of the compound obtained in Step 2 of Example 19 (300 mg, 1.27 mmol) in DMF (10 mL) was added potassium carbonate (353 mg, 2.55 mmol) at room temperature, and the mixture was stirred for 5 min. The reaction mixture was cooled to 0° C., chloromethyltrimethylsilane (0.36 mL, 2.55 mmol) was added thereto, and the mixture was stirred at 0° C. for 30 min. The reaction mixture was allowed to be warmed to room temperature, and stirred for 16 hr. To the reaction mixture was added ice water, and the mixture was extracted with ethyl acetate. The organic layer was washed with water, and dried over sodium sulfate, and the solvent was evaporated under reduced pressure to give 1-ethyl-6-nitro-3-trimethylsilanylmethyl-1H-quinazoline-2,4-dione (200 mg, 48.74%) as a pale yellow viscous solid.

MS(API): 339 (M+NH$_4$)

(Step 2)

To a solution of the compound obtained in Step 1 (45 mg, 0.14 mmol) in ethyl acetate (20 mL) was added 10% palladium on carbon (50% hydrous, 10 mg), and the mixture was stirred at room temperature for 3 hr under 2 atm of hydrogen atmosphere. The catalyst was removed by filtration, and the filtrate was concentrated under reduced pressure to give 6-amino-1-ethyl-3-trimethylsilanylmethyl-1H-quinazoline-2,4-dione (35 mg, 85.78%) as a yellow solid.

MS(API): 292 (M+H)

(Step 3)

To a solution of the compound obtained in Step 3 of Reference Example 1 (173 mg, 0.62 mmol) in ethyl acetate (25 mL) were added DIEA (0.167 mL, 1.28 mmol), T3P (50% ethyl acetate solution, 0.41 mL, 1.28 mmol) and the compound obtained in Step 2 (150 mg, 0.52 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (260 mg, 91.12%) as a grayish white solid.

MS(API): 552 (M–H)

$^1$H-NMR (400 MHz, DMSO-d$_6$): δ0.014 (s, 9H), 0.99 (d, 3H, J=6.16 Hz), 1.18 (t, 3H, J=6.80 Hz), 2.27-2.50 (m, 5H), 3.53 (s, 2H), 4.10-4.14 (m, 2H), 7.46 (d, 1H, J=9.08 Hz), 7.57 (d, 1H, J=8.52 Hz), 7.84-7.89 (m, 2H), 8.02 (s, 1H), 8.35 (s, 1H), 10.17 (s, 1H), 10.58 (s, 1H).

purification condition by preparative HPLC instrument: Shimadzu LC-2010C HT instrument column: XBridge C18 (50×4.6 mm, 5 μm)

solvent: A=10 mM aqueous ammonium acetate solution, B=acetonitrile solvent gradient: 80% A/B(0 min)→70% A/B(3 min)→50% A/B(5 min)→10% A/B(8 min)→10% A/B(13.5 min)→80% A/B(14 min)

flow rate: 1.0 mL/min temperature: room temperature

Example 33

N-(3-chloro-4-cyanophenyl)-N'-(1-ethyl-3-(2-hydroxyethyl)-2,4-dioxo-1,2,3,4-tetrahydroquinazolin-6-yl)-3-methylpentanediamide To a solution of the compound of Example 20 (113 mg, 0.21 mmol) in dichloromethane (20 mL) was added boron tribromide (1 mol/L, dichloromethane solution, 0.21 mL, 0.86 mmol) at −10° C., and the mixture was stirred for 6 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative TLC (developing solvent; 5% methanol/dichloromethane) to give [1-ethyl-3-(2-hydroxyethyl)-2,4-dioxo-1,2,3,4-tetrahydroquinazolin-6-yl]-amide (40 mg, 35.40%) as a grayish white solid.

MS(API): 512 (M+H)

Example 34

N-(4-((3-chloro-4-cyanophenyl)amino)-2-isopropyl-4-oxobutyl)-1,3-diethyl-2,4-dioxo-1,2,3,4-tetrahydroquinazoline-6-carboxamide (Optical Active Form, Shorter Retention Time)

Example 35

N-(4-((3-chloro-4-cyanophenyl)amino)-2-isopropyl-4-oxobutyl)-1,3-diethyl-2,4-dioxo-1,2,3,4-tetrahydroquinazoline-6-carboxamide (Optical Active Form, Longer Retention Time)

The compound of Example 17 (20 mg) was subjected to optical resolution using a chiral column chromatography. The preparative fraction having a shorter retention time was concentrated to give the title compound of Example 34 (7.8 mg, >99.9% ee), and the preparative fraction having a longer retention time was concentrated to give the title compound of Example 35 (7.9 mg, >99.9% ee).

the compound of Example 34

MS(API): 524 (M+H)

the compound of Example 35

MS(API): 524 (M+H)

purification condition by chiral column chromatography column: CHIRALCELL OD(NL001) 50 mmID×500 mmL solvent: ethanol=100% flow rate: 60 mL/min temperature: 30° C.

detection method: UV 220 nm

Example 36

N-(1,3-diethyl-2,4-dioxo-1,2,3,4-tetrahydroquinazolin-6-yl)-5-(3-fluorophenoxy)-3-methylpentanamide To a solution of the compound obtained in Step 2 of Example 5 (27.8 mg, 80 μmol), ADDP (24.22 mg, 96 μmol) and tributylphosphine (19.42 mg, 96 μmol) in toluene (0.5 mL) was added 3-fluorophenol (17.9 mg, 160 μmol), and the mixture was stirred overnight at room temperature. The reaction mixture was poured into ethyl acetate (3 mL)/water (1 mL), and the mixture was stirred for 5 min. The organic layer was filtered using Top-Phase Separation Filter Tube, and the filtrate was concentrated by blow of air at 60° C. The obtained residue was purified by preparative HPLC to give the title compound (3.0 mg).

MS(ES): 442 (M+H)

Example 37

N-(1,3-diethyl-2,4-dioxo-1,2,3,4-tetrahydroquinazolin-6-yl)-5-(3-ethynylphenoxy)-3-methylpentanamide The title compound (13.1 mg) was obtained using 3-hydroxyphenylacetylene by the reaction and purification in the same manner as in Example 36.

MS(ES): 448 (M+H)

Example 38

5-(3-cyanophenoxy)-N-(1,3-diethyl-2,4-dioxo-1,2,3,4-tetrahydroquinazolin-6-yl)-3-methylpentanamide The title compound (8.2 mg) was obtained using 3-cyanophenol by the reaction and purification in the same manner as in Example 36.
MS(ES): 449 (M+H)

Example 39

N-(1,3-diethyl-2,4-dioxo-1,2,3,4-tetrahydroquinazolin-6-yl)-5-(2,4-dimethylphenoxy)-3-methylpentanamide The title compound (3.3 mg) was obtained using 2,4-dimethylphenol by the reaction and purification in the same manner as in Example 36.
MS(ES): 452 (M+H)

Example 40

N-(1,3-diethyl-2,4-dioxo-1,2,3,4-tetrahydroquinazolin-6-yl)-5-(3,4-dimethylphenoxy)-3-methylpentanamide The title compound (8.3 mg) was obtained using 3,4-dimethylphenol by the reaction and purification in the same manner as in Example 36.
MS(ES): 452 (M+H)

Example 41

N-(1,3-diethyl-2,4-dioxo-1,2,3,4-tetrahydroquinazolin-6-yl)-5-(4-methoxyphenoxy)-3-methylpentanamide The title compound (9.6 mg) was obtained using 4-methoxyphenol by the reaction and purification in the same manner as in Example 36.
MS(ES): 454 (M+H)

Example 42

N-(1,3-diethyl-2,4-dioxo-1,2,3,4-tetrahydroquinazolin-6-yl)-5-(4-fluoro-2-methylphenoxy)-3-methylpentanamide The title compound (5.0 mg) was obtained using 4-fluoro-2-methylphenol by the reaction and purification in the same manner as in Example 36.
MS(ES): 456 (M+H)

Example 43

N-(1,3-diethyl-2,4-dioxo-1,2,3,4-tetrahydroquinazolin-6-yl)-5-(5-fluoro-2-methylphenoxy)-3-methylpentanamide The title compound (10.5 mg) was obtained using 5-fluoro-2-methylphenol by the reaction and purification in the same manner as in Example 36.
MS(ES): 456 (M+H)

Example 44

N-(1,3-diethyl-2,4-dioxo-1,2,3,4-tetrahydroquinazolin-6-yl)-5-(4-fluoro-3-methylphenoxy)-3-methylpentanamide The title compound (8.0 mg) was obtained using 4-fluoro-3-methylphenol by the reaction and purification in the same manner as in Example 36.
MS(ES): 456 (M+H)

Example 45

5-(3-chlorophenoxy)-N-(1,3-diethyl-2,4-dioxo-1,2,3,4-tetrahydroquinazolin-6-yl)-3-methylpentanamide The title compound (12.5 mg) was obtained using 3-chlorophenol by the reaction and purification in the same manner as in Example 36.
MS(ES): 458 (M+H)

Example 46

5-(4-chlorophenoxy)-N-(1,3-diethyl-2,4-dioxo-1,2,3,4-tetrahydroquinazolin-6-yl)-3-methylpentanamide The title compound (11.5 mg) was obtained using 4-chlorophenol by the reaction and purification in the same manner as in Example 36.
MS(ES): 458 (M+H)

Example 47

N-(1,3-diethyl-2,4-dioxo-1,2,3,4-tetrahydroquinazolin-6-yl)-5-(3,4-difluorophenoxy)-3-methylpentanamide The title compound (11.8 mg) was obtained using 3,4-difluorophenol by the reaction and purification in the same manner as in Example 36.
MS(ES): 460 (M+H)

Example 48

N-(1,3-diethyl-2,4-dioxo-1,2,3,4-tetrahydroquinazolin-6-yl)-5-(2,3-difluorophenoxy)-3-methylpentanamide The title compound (2.0 mg) was obtained using 2,3-difluorophenol by the reaction and purification in the same manner as in Example 36.
MS(ES): 460 (M+H)

Example 49

N-(1,3-diethyl-2,4-dioxo-1,2,3,4-tetrahydroquinazolin-6-yl)-5-(2,4-difluorophenoxy)-3-methylpentanamide The title compound (7.2 mg) was obtained using 2,4-difluorophenol by the reaction and purification in the same manner as in Example 36.
MS(ES): 460 (M+H)

Example 50

N-(1,3-diethyl-2,4-dioxo-1,2,3,4-tetrahydroquinazolin-6-yl)-5-(3,5-difluorophenoxy)-3-methylpentanamide The title compound (9.7 mg) was obtained using 3,5-difluorophenol by the reaction and purification in the same manner as in Example 36.
MS(ES): 460 (M+H)

Example 51

5-(4-(cyanomethyl)phenoxy)-N-(1,3-diethyl-2,4-dioxo-1,2,3,4-tetrahydroquinazolin-6-yl)-3-methylpentanamide The title compound (6.8 mg) was obtained using 4-hydroxyphenylacetonitrile by the reaction and purification in the same manner as in Example 36.
MS(ES): 463 (M+H)

Example 52

N-(1,3-diethyl-2,4-dioxo-1,2,3,4-tetrahydroquinazolin-6-yl)-3-methyl-5-(4-(methylsulfanyl)phenoxy)pentanamide The title compound (11.7 mg) was obtained using 4-(methylsulfanyl)phenol by the reaction and purification in the same manner as in Example 36.
MS(ES): 470 (M+H)

Example 53

5-(4-chloro-3-methylphenoxy)-N-(1,3-diethyl-2,4-dioxo-1,2,3,4-tetrahydroquinazolin-6-yl)-3-methylpentanamide The title compound (6.8 mg) was obtained using 4-chloro-3-methylphenol by the reaction and purification in the same manner as in Example 36.
MS(ES): 472 (M+H)

Example 54

5-(4-chloro-2-fluorophenoxy)-N-(1,3-diethyl-2,4-dioxo-1,2,3,4-tetrahydroquinazolin-6-yl)-3-methylpentanamide The title compound (11.1 mg) was obtained using 4-chloro-2-fluorophenol by the reaction and purification in the same manner as in Example 36.
MS(ES): 476 (M+H)

Example 55

5-(4-chloro-3-fluorophenoxy)-N-(1,3-diethyl-2,4-dioxo-1,2,3,4-tetrahydroquinazolin-6-yl)-3-methylpentanamide The title compound (12.9 mg) was obtained using 4-chloro-3-fluorophenol by the reaction and purification in the same manner as in Example 36.
MS(ES): 476 (M+H)

Example 56

5-(3-chloro-4-fluorophenoxy)-N-(1,3-diethyl-2,4-dioxo-1,2,3,4-tetrahydroquinazolin-6-yl)-3-methylpentanamide The title compound (12.7 mg) was obtained using 3-chloro-4-fluorophenol by the reaction and purification in the same manner as in Example 36.
MS(ES): 476 (M+H)

Example 57

N-(1,3-diethyl-2,4-dioxo-1,2,3,4-tetrahydroquinazolin-6-yl)-3-methyl-5-(2,3,5-trifluorophenoxy)pentanamide The title compound (3.0 mg) was obtained using 2,3,5-trifluorophenol by the reaction and purification in the same manner as in Example 36.
MS(ES): 478 (M+H)

Example 58

N-(1,3-diethyl-2,4-dioxo-1,2,3,4-tetrahydroquinazolin-6-yl)-3-methyl-5-((1-oxo-2,3-dihydro-1H-inden-5-yl)oxy)pentanamide The title compound (6.3 mg) was obtained using 5-hydroxy-1-indanone by the reaction and purification in the same manner as in Example 36.
MS(ES): 478 (M+H)

Example 59

5-(4-cyano-2-methoxyphenoxy)-N-(1,3-diethyl-2,4-dioxo-1,2,3,4-tetrahydroquinazolin-6-yl)-3-methylpentanamide The title compound (5.8 mg) was obtained using 4-hydroxy-3-methoxybenzonitrile by the reaction and purification in the same manner as in Example 36.
MS(ES): 479 (M+H)

Example 60

N-(3-chloro-4-cyanophenyl)-N'-(3-cyclopropyl-1-ethyl-2,4-dioxo-1,2,3,4-tetrahydroquinazolin-6-yl)-3-methylpentanediamide (Step 1)
To a solution of bipyridine (59.82 mg, 0.38 mmol) in dichloromethane (5 mL) was added copper(II) acetate (69.32 mg, 0.38 mmol), and the mixture was stirred at 60° C. for 10 min. To the reaction mixture were added cyclopropylboronic acid (65 mg, 0.76 mmol), the compound obtained in Step 2 of Example 19 (90 mg, 0.38 mmol) and sodium carbonate (81 mg, 0.76 mmol), and the mixture was stirred at 80° C. for 16 hr. To the reaction mixture was added water, and the mixture was extracted with ethyl acetate. The organic layer was washed with saturated brine, and dried over sodium sulfate, and the solvent was evaporated under reduced pressure. The obtained residue was purified by silica gel column chromatography (solvent gradient; 20→80% ethyl acetate/hexane) to give 3-cyclopropyl-1-ethyl-6-nitro-1H-quinazoline-2,4-dione (30 mg, 28.46%) as a viscous solid.
MS(API): 276 (M+H)

(Step 2)

To a solution of the compound obtained in Step 1 (148.0 mg, 0.53 mmol) in ethyl acetate (20 mL) was added 10% palladium on carbon (50% hydrous, 50 mg), and the mixture was stirred at room temperature for 5 hr under 2 atm of hydrogen atmosphere. The catalyst was removed by filtration, and the filtrate was concentrated under reduced pressure to give 6-amino-3-cyclopropyl-1-ethyl-1H-quinazoline-2,4-dione (100 mg, 76.99%) as a yellow solid.

$^1$H-NMR (400 MHz, DMSO-$d_6$): δ0.77 (s, 2H), 0.99 (q, 2H, J=7.04 Hz), 1.15 (t, 3H, J=6.98 Hz), 2.65 (m, 1H), 4.01 (m, 2H), 5.24 (s, 2H), 6.99 (dd, 1H, J=9.08 Hz, 2.6 Hz), 7.16 (d, 1H, J=8.88 Hz), 7.20 (d, 1H, J=2.64 Hz).

(Step 3)

To a solution of the compound obtained in Step 3 of Reference Example 1 (164 mg, 0.58 mmol) in ethyl acetate (25 mL) were added DIEA (0.16 mL, 1.22 mmol), T3P (50% ethyl acetate solution, 0.39 mL, 1.22 mmol) and the compound obtained in Step 2 (120 mg, 0.49 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (110 mg, 44.26%) as a grayish white solid.

MS(API): 508 (M+H)

$^1$H-NMR (400 MHz, DMSO-$d_6$): δ0.71 (m, 2H), 0.99-1.03 (m, 5H), 1.18 (t, 3H, J=7.04 Hz), 2.27-2.50 (m, 1H), 2.67-2.69 (m, 1H), 4.04-4.08 (m, 2H), 7.38 (d, 1H, J=9.20 Hz), 7.57 (dd, 1H, J=8.68 Hz, 1.84 Hz), 7.83 (d, 1H, J=8.64 Hz), 7.87 (dd, 1H, J=9.04 Hz, 2.56 Hz), 8.01 (d, 1H, J=1.84 Hz), 8.29 (d, 1H, J=2.44 Hz), 10.17 (s, 1H), 10.61 (s, 1H).

purification condition by preparative HPLC
  instrument: Waters Semi-Preparative HPLC instrument
  column: Prep Scalar 10 μm C18 (250×30 mm)
  solvent: A=5 mM aqueous ammonium acetate solution, B=acetonitrile
  solvent gradient: 50% A/B(O min)→45% A/B(15 min)→40% A/B(60 min)→5% A/B(61 min)→5% A/B(70 min)→50% A/B(71 min)
  flow rate: 30 mL/min
  temperature: room temperature Example 61

3-chloro-4-cyano-N-(4-((1,3-diethyl-2,4-dioxo-1,2,3,4-tetrahydroquinazolin-6-yl)amino)-4-oxobutan-2-yl)benzamide (Step 1)

tert-Butyl (4-((1,3-diethyl-2,4-dioxo-1,2,3,4-tetrahydroquinazolin-6-yl)amino)-4-oxobutan-2-yl)carbamate (520 mg, 1.243 mmol, 97%) was obtained as a colorless solid using 3-((tert-butoxycarbonyl)amino)butanoic acid (261 mg, 1.29 mmol) by the reaction and purification in the same manner as in Step 1 of Example 11.

MS(API): 319 (M+H-Boc)

(Step 2)

A mixture of the compound obtained in Step 1 (520 mg, 1.24 mmol) and trifluoroacetic acid (0.096 mL, 1.24 mmol) was stirred overnight at room temperature. To the reaction mixture was added saturated aqueous sodium hydrogencarbonate solution, and the mixture was extracted with ethyl acetate. The organic layer was washed with saturated brine, and dried over magnesium sulfate, and the solvent was evaporated under reduced pressure to give 3-amino-N-(1,3-diethyl-2,4-dioxo-1,2,3,4-tetrahydroquinazolin-6-yl)butanamide (167 mg, 42.2%).

MS(API): 319 (M+H)

(Step 3)

A mixture of methyl 4-bromo-3-chlorobenzoate (5.84 g, 23.41 mmol), tetrakis(triphenylphosphine)palladium (1.352 g, 1.17 mmol), copper(I) cyanide (1.484 mL, 23.41 mmol) and DMF (50 mL) was stirred at 100° C. overnight. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5→50% ethyl acetate/hexane) to give methyl 3-chloro-4-cyanobenzoate (2.0 g, 10.22 mmol, 43.7%) as a colorless solid.

$^1$H-NMR (300 MHz, CDCl$_3$): δ4.01 (3H, s), 7.92 (1H, d, J=8.7 Hz), 8.38 (H, dd, J=8.1, 1.7 Hz), 8.46 (1H, d, J=1.5 Hz).

(Step 4)

A mixture of the compound obtained in Step 3 (500 mg, 2.56 mmol), 4 mol/L aqueous lithium hydroxide solution (10 mL, 40.00 mmol) and THF (10 mL) was stirred at room temperature for 3 hr. The reaction mixture was washed with toluene, acidified with 1N hydrochloric acid, and extracted with ethyl acetate. The organic layer was washed with saturated brine, and dried over magnesium sulfate, and the solvent was evaporated under reduced pressure to give 3-chloro-4-cyanobenzoic acid as a colorless solid (quantitative).

MS(API): 180 (M−H)

(Step 5)

The title compound (13.00 mg, 0.027 mmol, 5.08%) was obtained as a colorless solid using the compound obtained in Step 2 (169 mg, 0.53 mmol) and the compound obtained in Step 4 (96 mg, 0.53 mmol) by the reaction and purification in the same manner as in Step 4 of Example 1.

MS(API): 482 (M+H)

Example 62

N-(3-chloro-4-cyanophenyl)-N'-(1,3-diethyl-2,4-dioxo-1,2,3,4-tetrahydroquinazolin-6-yl)-3-hydroxy-3-methylpentanediamide (Step 1)

A solution of 4-amino-2-chlorobenzonitrile (1.059 g, 6.94 mmol) and 4-hydroxy-4-methyldihydro-2H-pyran-2,6(3H)-dione in THF (30 mL) was stirred overnight at 80° C. The reaction mixture was allowed to be cooled to room temperature, 1N hydrochloric acid was added thereto, and the mixture was extracted with ethyl acetate. The organic layer was washed with saturated brine, and dried over magnesium sulfate, and the solvent was evaporated under reduced pressure to give 5-((3-chloro-4-cyanophenyl)amino)-3-hydroxy-3-methyl-5-oxopentanoic acid (1.52 g, 73.8%) as a brown oil.

MS(API): 297 (M+H)

(Step 2)

A mixture of the compound obtained in Step 1 (200 mg, 0.67 mmol), the compound obtained in Step 3 of Example 1 (157 mg, 0.67 mmol), T3P (50% ethyl acetate solution, 0.436 mL, 0.74 mmol), DIEA (0.13 mL, 0.74 mmol) and ethyl acetate (10 mL) was stirred overnight at 60° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) to give the title compound (70.00 mg, 0.137 mmol, 20.28%) as a colorless solid.

MS(API): 512 (M+H)

$^1$H-NMR (300 MHz, CDCl$_3$): δ1.32 (6H, dt, J=19.5, 7.3 Hz), 1.46 (3H, s), 2.55-2.83 (3H, m), 4.17 (4H, dd, J=13.4, 7.0 Hz), 5.18 (1H, s), 7.21 (1H, d, J=9.1 Hz), 7.44-7.54 (1H, m), 7.56-7.64 (1H, m), 7.90 (1H, d, J=0.9 Hz), 8.03 (1H, dd, J=9.1, 2.6 Hz), 8.16 (H, d, J=2.3 Hz), 8.23 (1H, brs), 9.28 (1H, s).

Example 63

3-chloro-4-cyano-N-(3-((1,3-diethyl-2,4-dioxo-1,2,3,4-tetrahydroquinazolin-6-yl)amino)-2-methyl-3-oxopropyl)benzamide (Step 1)

tert-Butyl (3-((1,3-diethyl-2,4-dioxo-1,2,3,4-tetrahydroquinazolin-6-yl)amino)-2-methyl-3-oxopropyl)carbamate (250 mg, 0.597 mmol, 60.6%) was obtained as a colorless solid using 3-((tert-butoxycarbonyl)amino)-2-methylpropanoic acid (200 mg, 0.99 mmol) by the reaction and purification in the same manner as in Step 2 of Example 62.

MS(API): 417 (M−H)

(Step 2)

3-Amino-N-(1,3-diethyl-2,4-dioxo-1,2,3,4-tetrahydroquinazolin-6-yl)-2-methylpropanamide (66 mg, 34.7%) was obtained using the compound obtained in Step 1 (250 mg, 0.60 mmol) by the reaction and purification in the same manner as in Step 2 of Example 61.

MS(API): 319 (M+H)

(Step 3)

The title compound (20 mg, 17.16%) was obtained as a colorless solid using the compound obtained in Step 2 (77 mg, 0.24 mmol) by the reaction and purification in the same manner as in Step 5 of Example 61.

MS(API): 482 (M+H)

Example 64

4-(3-chloro-4-cyanophenoxy)-N-(1,3-diethyl-2,4-dioxo-1,2,3,4-tetrahydroquinazolin-6-yl)-3-methylbutanamide (Step 1)

N-(1,3-Diethyl-2,4-dioxo-1,2,3,4-tetrahydroquinazolin-6-yl)-4-hydroxy-3-methylbutanamide (333 mg, 0.999 mmol, 61.3%) was obtained as a colorless oil using the compound obtained in Step 3 of Example 1 (380 mg, 1.63 mmol) and 3-methyldihydrofuran-2,5-dione (186 mg, 1.63 mmol) by the reaction and purification in the same manner as in Step 4 of Example 26.

MS(API): 334 (M+H)

(Step 2)

The title compound (27.0 mg, 0.058 mmol, 9.36%) was obtained as a colorless solid using the compound obtained in Step 2 (205 mg, 0.61 mmol) and sodium tert-butoxide (148 mg, 1.54 mmol) by the reaction and purification in the same manner as in Step 3 of Example 5.

MS(API): 469 (M+H)

Example 65

N-(3-chloro-4-cyanophenyl)-N'-(1-ethyl-3-((methylsulfanyl)methyl)-2,4-dioxo-1,2,3,4-tetrahydroquinazolin-6-yl)-3-methylpentanediamide (Step 1)

To a solution of the compound obtained in Step 2 of Example 19 (400 mg, 1.70 mmol) in DMF (10 mL) was added sodium hydride (60% oil, 136 mg, 3.40 mmol), and the mixture was stirred at room temperature for 5 min. The reaction mixture was cooled to 000° C., and chloromethylsulfanylmethane (0.285 mL, 3.40 mmol) was added thereto. The reaction mixture was stirred at room temperature for 16 hr, ice water was added thereto, and the mixture was extracted with ethyl acetate. The organic layer was washed with water, and dried over sodium sulfate, and the solvent was evaporated under reduced pressure. The obtained residue was washed with ethyl acetate-hexane (2:98), and then dichloromethane-diethyl ether (10:90) to give 1-ethyl-3-methylsulfanylmethyl-6-nitro-1H-quinazoline-2,4-dione (400 mg, 79.58%) as a pale yellow viscous solid.

MS(API): 313 (M+NH$_4$)

(Step 2)

To a solution of the compound obtained in Step 1 (600 mg, 2.03 mmol) in ethanol (40 mL) was added tin(II) chloride (1928 mg, 10.17 mmol), and the mixture was refluxed for 5 hr. The reaction mixture was concentrated under reduced pressure, and to the residue was added water. The pH of the mixture was adjusted to 8 with saturated aqueous sodium carbonate solution, and the mixture was extracted with ethyl acetate. The organic layer was washed with water, and dried over sodium sulfate, and the solvent was evaporated under reduced pressure to give 6-amino-1-ethyl-3-methylsulfanylmethyl-1H-quinazoline-2,4-dione (165 mg, 30.57%) as a yellow solid.

$^1$H-NMR (400 MHz, DMSO-d$_6$): δ1.18 (t, 3H, J=7.00 Hz), 2.22 (s, 3H), 4.04-4.10 (m, 2H), 5.02 (s, 2H), 5.32 (s, 2H), 7.04-7.07 (m, 1H), 7.24-7.26 (m, 2H)

(Step 3)

To a solution of the compound obtained in Step 3 of Reference Example 1 (209 mg, 0.75 mmol) in ethyl acetate (30 mL) were added DIEA (0.20 mL, 1.55 mmol), T3P (50% ethyl acetate solution, 0.86 mL, 1.55 mmol) and the compound obtained in Step 2 (165 mg, 0.62 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (160 mg, 48.73%) as a grayish white solid.

MS(API): 526 (M−H)

$^1$H-NMR (400 MHz, DMSO-d$_6$): δ1.00 (d, 3H, J=6.32 Hz), 1.21 (t, 3H, J=6.96 Hz), 2.23 (s, 3H) 2.26-2.50 (m, 5H), 4.10-4.15 (m, 2H), 5.05 (s, 2H), 7.47 (d, 1H, J=9.12 Hz), 7.57 (d, 1H, J=9.80 Hz), 7.85 (d, 1H, J=8.56 Hz), 7.92 (dd, 1H, J=9.12 Hz, 2.08 Hz), 8.02 (s, 1H), 8.36 d, 1H, J=2.20 Hz), 10.18 (s, 1H), 10.54 (s, 1H).

purification condition by preparative HPLC
  instrument: Waters auto purification instrument
  column: Gemini-NX 5 μm C18 110 A (100×30 mm)
  solvent: A=5 mM aqueous ammonium acetate solution, B=acetonitrile
  solvent gradient: 90% A/B(O min)→60% A/B(1 min)→30% A/B(15 min)→5% A/B(16 min)→5% A/B(18 min)→90% A/B(19 min)
  flow rate: 30 mL/min
  temperature: room temperature

Example 66

4-cyano-N-(4-((1,3-diethyl-2,4-dioxo-1,2,3,4-tetrahydroquinazolin-6-yl)amino)-2-methyl-4-oxobutyl)benzamide To a solution of the compound obtained in Step 3 of Example 11 (13.30 mg, 40 μmol) in DMF (0.2 mL) were added WSC (19.17 mg, 100 μmol), HOBt (13.51 mg, 100 μmol) and 4-cyanobenzoic acid, and the mixture was stirred overnight at room temperature. The reaction mixture was concentrated by blow of air at 60° C. The obtained residue was purified by preparative HPLC to give the title compound (17.6 mg).

MS(ES): 462 (M+H)

purification condition by preparative HPLC
  instrument: Gilson high-throughput purification system
  column: CombiPrep ODS-A S-5 μm, 50×20 mm (YMC)
  solvent: solution A; water containing 0.1% trifluoroacetic acid, solution B; acetonitrile containing 0.1% trifluoroacetic acid
  gradient cycle: 0.00 min (solution A/solution B=95/5), 1.00 min (solution A/solution B=95/5), 5.20 min (solution A/solution B=5/95), 6.40 min (solution A/solution B=5/95), 6.50 min (solution A/solution B=95/5), 6.60 min (solution A/solution B=95/5)
  flow rate: 25 mL/min

Example 67

3-cyano-N-(4-((1,3-diethyl-2,4-dioxo-1,2,3,4-tetrahydroquinazolin-6-yl)amino)-2-methyl-4-oxobutyl)benzamide The title compound (10.3 mg) was obtained using 3-cyanobenzoic acid by the reaction and purification in the same manner as in Example 66.

MS(ES): 462 (M+H)

Example 68

6-cyano-N-(4-((1,3-diethyl-2,4-dioxo-1,2,3,4-tetrahydroquinazolin-6-yl)amino)-2-methyl-4-oxobutyl)nicotinamide The title compound (15.9 mg) was obtained using 6-cyanopyridine-3-carboxylic acid by the reaction and purification in the same manner as in Example 66.

MS(ES): 463 (M+H)

Example 69

5-cyano-N-(4-((1,3-diethyl-2,4-dioxo-1,2,3,4-tetrahydroquinazolin-6-yl)amino)-2-methyl-4-oxobutyl)pyridine-2-carboxamide The title compound (3.6 mg) was obtained using 5-cyanopyridine-2-carboxylic acid by the reaction and purification in the same manner as in Example 66.

MS(ES): 463 (M+H)

Example 70

4-cyano-N-(4-((1,3-diethyl-2,4-dioxo-1,2,3,4-tetrahydroquinazolin-6-yl)amino)-2-methyl-4-oxobutyl)-2-fluorobenzamide The title compound (19.7 mg) was obtained using 4-cyano-2-fluorobenzoic acid by the reaction and purification in the same manner as in Example 66.

MS(ES): 480 (M+H)

Example 71

N-(4-((1,3-diethyl-2,4-dioxo-1,2,3,4-tetrahydroquinazolin-6-yl)amino)-2-methyl-4-oxobutyl)isonicotinamide The title compound (16.3 mg) was obtained using 4-pyridinecarboxylic acid by the reaction and purification in the same manner as in Example 66.

MS(ES): 438 (M+H)

Example 72

N-(4-((1,3-diethyl-2,4-dioxo-1,2,3,4-tetrahydroquinazolin-6-yl)amino)-2-methyl-4-oxobutyl)-3,4-difluorobenzamide The title compound (14.8 mg) was obtained using 3,4-difluorobenzoic acid by the reaction and purification in the same manner as in Example 66.

MS(ES): 473 (M+H)

Example 73

N-(4-((1,3-diethyl-2,4-dioxo-1,2,3,4-tetrahydroquinazolin-6-yl)amino)-2-methyl-4-oxobutyl)-2,4-difluorobenzamide The title compound (15.1 mg) was obtained using 2,4-difluorobenzoic acid by the reaction and purification in the same manner as in Example 66.

MS(ES): 473 (M+H)

Example 74

4-chloro-N-(4-((1,3-diethyl-2,4-dioxo-1,2,3,4-tetrahydroquinazolin-6-yl)amino)-2-methyl-4-oxobutyl)-2-fluorobenzamide The title compound (17.9 mg) was obtained using 4-chloro-2-fluorobenzoic acid by the reaction and purification in the same manner as in Example 66.

MS(ES): 489 (M+H)

Example 75

N-(4-((1,3-diethyl-2,4-dioxo-1,2,3,4-tetrahydroquinazolin-6-yl)amino)-2-methyl-4-oxobutyl)-4-hydroxybenzamide The title compound (13.1 mg) was obtained using 4-hydroxybenzoic acid by the reaction and purification in the same manner as in Example 66.

MS(ES): 453 (M+H)

Example 76

N-(4-((1,3-diethyl-2,4-dioxo-1,2,3,4-tetrahydroquinazolin-6-yl)amino)-2-methyl-4-oxobutyl)-6-fluoronicotinamide The title compound (16.7 mg) was obtained using 6-fluoropyridine-3-carboxylic acid by the reaction and purification in the same manner as in Example 66.

MS(ES): 456 (M+H)

Example 77

2-chloro-N-(4-((1,3-diethyl-2,4-dioxo-1,2,3,4-tetrahydroquinazolin-6-yl)amino)-2-methyl-4-oxobutyl) isonicotinamide The title compound (12.2 mg) was obtained using 2-chloroisonicotinic acid by the reaction and purification in the same manner as in Example 66.
MS(ES): 472 (M+H)

Example 78

6-chloro-N-(4-((1,3-diethyl-2,4-dioxo-1,2,3,4-tetrahydroquinazolin-6-yl)amino)-2-methyl-4-oxobutyl) nicotinamide The title compound (10.9 mg) was obtained using 6-chloronicotinic acid by the reaction and purification in the same manner as in Example 66.
MS(ES): 472 (M+H)

Example 79

N-(4-((1,3-diethyl-2,4-dioxo-1,2,3,4-tetrahydroquinazolin-6-yl)amino)-2-methyl-4-oxobutyl)-6-methoxynicotinamide The title compound (17.9 mg) was obtained using 2-methoxy-5-pyridinecarboxylic acid by the reaction and purification in the same manner as in Example 66.
MS(ES): 467 (M+H)

Example 80

N-(4-((1,3-diethyl-2,4-dioxo-1,2,3,4-tetrahydroquinazolin-6-yl)amino)-2-methyl-4-oxobutyl)-4-(pentafluorosulfanyl)benzamide The title compound (17.2 mg) was obtained using 4-(pentafluorosulfanyl)benzoic acid by the reaction and purification in the same manner as in Example 66.
MS(ES): 563 (M+H)

Example 81

N-(4-((1,3-diethyl-2,4-dioxo-1,2,3,4-tetrahydroquinazolin-6-yl)amino)-2-methyl-4-oxobutyl)-4-(trifluoromethyl)benzamide The title compound (12.9 mg) was obtained using 4-(trifluoromethyl)benzoic acid by the reaction and purification in the same manner as in Example 66.
MS(ES): 505 (M+H)

Example 82

N-(4-((1,3-diethyl-2,4-dioxo-1,2,3,4-tetrahydroquinazolin-6-yl)amino)-2-methyl-4-oxobutyl)-3-fluoro-4-(trifluoromethyl)benzamide The title compound (14.4 mg) was obtained using 3-fluoro-4-trifluoromethylbenzoic acid by the reaction and purification in the same manner as in Example 66.
MS(ES): 523 (M+H)

Example 83

N-(4-((1,3-diethyl-2,4-dioxo-1,2,3,4-tetrahydroquinazolin-6-yl)amino)-2-methyl-4-oxobutyl)-2-fluoro-4-(trifluoromethyl)benzamide The title compound (15.3 mg) was obtained using 2-fluoro-4-(trifluoromethyl)benzoic acid by the reaction and purification in the same manner as in Example 66.
MS(ES): 523 (M+H)

Example 84

N-(4-((1,3-diethyl-2,4-dioxo-1,2,3,4-tetrahydroquinazolin-6-yl)amino)-2-methyl-4-oxobutyl)-6-(trifluoromethyl)nicotinamide The title compound (17.3 mg) was obtained using 6-(trifluoromethyl)nicotinic acid by the reaction and purification in the same manner as in Example 66.
MS(ES): 506 (M+H)

Example 85

N-(4-((1,3-diethyl-2,4-dioxo-1,2,3,4-tetrahydroquinazolin-6-yl)amino)-2-methyl-4-oxobutyl)-4-(difluoromethyl)benzamide The title compound (8.0 mg) was obtained using 4-(difluoromethyl)benzoic acid by the reaction and purification in the same manner as in Example 66.
MS(ES): 487 (M+H)

Example 86

4-acetyl-N-(4-((1,3-diethyl-2,4-dioxo-1,2,3,4-tetrahydroquinazolin-6-yl)amino)-2-methyl-4-oxobutyl) benzamide The title compound (12.4 mg) was obtained using 4-acetylbenzoic acid by the reaction and purification in the same manner as in Example 66.
MS(ES): 479 (M+H)

Example 87

4-cyano-N-(4-((1,3-diethyl-2,4-dioxo-1,2,3,4-tetrahydroquinazolin-6-yl)amino)-2-methyl-4-oxobutyl)-1H-pyrrole-2-carboxamide The title compound (18.0 mg) was obtained using 4-cyano-1H-pyrrole-2-carboxylic acid by the reaction and purification in the same manner as in Example 66.
MS(ES): 451 (M+H)

Example 88

N-(4-((1,3-diethyl-2,4-dioxo-1,2,3,4-tetrahydroquinazolin-6-yl)amino)-2-methyl-4-oxobutyl)-4-methyl-1,2,3-thiadiazole-5-carboxamide The title compound (14.9 mg) was obtained using 4-methyl-1,2,3-thiadiazole-5-carboxylic acid by the reaction and purification in the same manner as in Example 66.
MS(ES): 459 (M+H)

Example 89

2-bromo-N-(4-((1,3-diethyl-2,4-dioxo-1,2,3,4-tetrahydroquinazolin-6-yl)amino)-2-methyl-4-oxobutyl)-1,3-thiazole-5-carboxamide The title compound (15.7 mg) was obtained using 2-bromo-5-thiazolecarboxylic acid by the reaction and purification in the same manner as in Example 66.
MS(ES): 822 (M+H)

Example 90

N-(3-((3-chloro-4-cyanobenzoyl)amino)-2-methylpropyl)-1,3-diethyl-2,4-dioxo-1,2,3,4-tetrahydroquinazoline-6-carboxamide (Step 1)
tert-Butyl (3-(3-chloro-4-cyanobenzamido)-2-methylpropyl)carbamate (260 mg, 0.739 mmol, 59.4%) was obtained as a colorless oil using N-(tert-butoxycarbonyl)-2-methyl-1,3-diaminopropane (258 mg, 1.37 mmol) and the compound obtained in Step 4 of Example 61 (225.9 mg, 1.24 mmol) by the reaction and purification in the same manner as in Step 1 of Example 63.
MS(API): 350 (M−H)

(Step 2)
N-(3-amino-2-methylpropyl)-3-chloro-4-cyanobenzamide (155 mg, 0.616 mmol, 83%) was obtained as a colorless oil using the compound obtained in Step 1 (260 mg, 0.739 mmol) by the reaction and purification in the same manner as in Step 2 of Example 63.
MS(API): 252 (M+H)

(Step 3)
The title compound (110 mg, 0.222 mmol, 36%) was obtained as a colorless solid using the compound obtained in Step 2 (155 mg, 0.616 mmol) and the compound obtained in Step 1 of Example 17 (178 mg, 0.68 mmol) by the reaction and purification in the same manner as in Step 3 of Example 63.
$^1$H-NMR (300 MHz, DMSO-$d_6$): δ0.92 (3H, d, J=6.8 Hz), 1.10-1.30 (6H, m), 1.95-2.18 (1H, m), 3.08-3.29 (4H, m), 4.00 (2H, q, J=7.1 Hz), 4.17 (2H, q, J=7.2 Hz), 7.57 (1H, d, J=9.1 Hz), 7.93 (1H, dd, J=8.3, 1.5 Hz), 8.02-8.14 (2H, m), 8.20 (1H, dd, J=8.9, 2.1 Hz), 8.57 (H, d, J=0.9 Hz), 8.74 (1H, t, J=5.7 Hz), 8.78-8.87 (1H, m).

Example 91

N-(3-chloro-4-cyanophenyl)-N'-(3-(2-cyanoethyl)-1-ethyl-2,4-dioxo-1,2,3,4-tetrahydroquinazolin-6-yl)-3-methylpentanediamide (Step 1)
To a solution of the compound obtained in Step 2 of Example 19 (1000 mg, 4.25 mmol) in DMF (30 mL) were added sodium hydride (60% oil, 153 mg, 6.38 mmol) and acrylonitrile (0.452 mL, 8.51 mmol), and the mixture was stirred at 80° C. for 16 hr. To the reaction mixture was added water (1 mL), and the precipitate was collected by filtration. The obtained solid was washed with ethyl acetate-hexane (10:90) to give 3-(1-ethyl-6-nitro-2,4-dioxo-1,4-dihydro-2H-quinazolin-3-yl)-propionitrile (300 mg, 24.46%) as a brown solid.
$^1$H-NMR (400 MHz, DMSO-$d_6$): δ1.24 (t, 3H, J=7.02 Hz), 2.90-2.92 (m, 2H), 4.13 (q, 2H J=6.94 Hz), 4.19-4.22 (m, 2H), 7.76 (d, 1H, J=9.32 Hz), 8.48-8.55 (m, 1H), 7.03 (m, 1H), 8.74 (s, 1H).

(Step 2)
To a solution of the compound obtained in Step 1 (590 mg, 2.05 mmol) in ethanol (25 mL) was added tin(II) chloride (1165 mg, 6.15 mmol), and the mixture was refluxed for 5 hr. The reaction mixture was concentrated under reduced pressure, and to the residue was added water. The pH of the mixture was adjusted to 8 with saturated aqueous sodium carbonate solution, and the mixture was extracted with ethyl acetate. The organic layer was washed with water, and dried over sodium sulfate, and the solvent was evaporated under reduced pressure to give 3-(6-amino-1-ethyl-2,4-dioxo-1,4-dihydro-2H-quinazolin-3-yl)-propionitrile (145 mg, 27.40%) as a yellow solid.
$^1$H-NMR (400 MHz, DMSO-$d_6$): δ1.18 (t, 3H, J=6.96 Hz), 2.87 (t, 2H, J=6.6 Hz), 4.05-4.10 (m, 2H), 4.19 (t, 2H, J=6.66 Hz), 5.32 (s, 2H), 7.06 (dd, 1H, J=9.2 Hz, 2.4 Hz), 7.23-7.26 (m, 2H).

(Step 3)
To a solution of the compound obtained in Step 3 of Reference Example 1 (188 mg, 0.56 mmol) in ethyl acetate (100 mL) were added DIEA (0.181 mL, 1.41 mmol), T3P (50% ethyl acetate solution, 0.9 mL, 1.41 mmol) and the compound obtained in Step 2 (145 mg, 0.56 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (50 mg, 17.56%) as a grayish white solid.
MS(API): 519 (M−H)
$^1$H-NMR (400 MHz, DMSO-$d_6$): δ1.00 (d, 3H, J=6.40 Hz), 1.20 (t, 3H, J=6.96 Hz), 2.26-2.50 (m, 5H), 2.89 (t, 2H, J=6.56 Hz), 4.10-4.15 (m, 2H), 4.20 (t, 2H, J=6.52 Hz), 7.48 (d, 1H, J=9.16 Hz), 7.57 (dd, 1H, J=8.64 Hz, 1.84 Hz), 7.85 (d, 1H, J=8.56 Hz), 7.93 (dd, 1H, J=9.08 Hz, 2.56 Hz), 8.03 (d, 1H, J=1.76 Hz), 8.37 (d, H, J=2.48 Hz), 10.16 (s, 1H), 10.52 (s, 1H).

purification condition by preparative HPLC
  instrument: Waters semi-preparative HPLC instrument
  column: Prep Scalar 10 μm C18 (250×30 mm)
  solvent: A=5 mM aqueous ammonium acetate solution, B=acetonitrile
  solvent gradient: 70% A/B(0 min)→30% A/B(60 min)→5% A/B(61 min)→5% A/B(70 min)→70% A/B(71 min)
  flow rate: 30 mL/min
  temperature: room temperature

Example 92

N-(3-chloro-4-cyanophenyl)-N'-(1-ethyl-3-((methylsulfonyl)methyl)-2,4-dioxo-1,2,3,4-tetrahydroquinazolin-6-yl)-3-methylpentanediamide To a solution of the compound of Example 99 (120 mg, 0.23 mmol) in chloroform was added metachloroperbenzoic acid (118 mg, 0.68 mmol) at 5-10° C., and the mixture was stirred at room temperature for 4 hr. To the reaction mixture was added saturated aqueous sodium carbonate solution, and the mixture was extracted with ethyl acetate. The organic layer was washed with brine, and dried over sodium sulfate, and the solvent was evaporated under reduced pressure. The obtained residue was purified by preparative HPLC to give the title compound (30 mg, 23.5%) as a grayish white solid.
MS(API): 558 (M−H)
purification condition by preparative HPLC
  instrument: Waters auto purification instrument
  column: Gemini-NX 5 μm C18 110 A (100×30 mm)

solvent: A=5 mM aqueous ammonium acetate solution, B=acetonitrile
solvent gradient: 90% A/B(0 min)→70% A/B(1 min)→40% A/B(10 min)→5% A/B(11 min)→5% A/B(12 min)→90% A/B(13 min)
flow rate: 30 mL/min
temperature: room temperature Example 93

N-(5-cyano-2-thienyl)-N'-(1,3-diethyl-2,4-dioxo-1,2,3,4-tetrahydroquinazolin-6-yl)-3-methylpentanediamide To a solution of the compound obtained in Step 1 of Example 94 (0.25 g, 0.69 mmol) and 5-aminothiophene-2-carbonitrile (0.086 g, 0.69 mmol) in ethyl acetate (5 mL) were added DIEA (0.36 mL, 2.08 mmol) and T3P (50% ethyl acetate solution, 1.03 mL, 1.73 mmol), and the mixture was refluxed for 16 hr. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (0.085 g, 25.33%) as a grayish white solid.
MS(API): 468 (M+H)
$^1$H-NMR (400 MHz, DMSO-d$_6$): δ0.97 (d, 3H, J=6.16 Hz), 1.15 (t, 3H, J=7.00 Hz), 1.20 (t, 3H, J=7.00 Hz), 2.29-2.40 (m, 4H), 2.50-2.53 (m, 1H), 3.98 (q, 2H, J=6.96 Hz), 4.11 (q, 2H, J=6.88 Hz), 6.70 (d, 1H, J=4.16 Hz), 7.46 (d, 1H, J=9.16 Hz), 7.70 (d, 1H, J=4.24 Hz), 7.92 (dd, 1H, J=2.24 Hz, 8.92 Hz), 8.35 (d, 1H, J=2.28 Hz), 10.17 (s, 1H), 11.99 (s, 1H).
purification condition by preparative HPLC
instrument: Waters auto purification instrument
column: Gemini-NX 5 μm C18 110 A (100×30 mm)
solvent: A=5 mM aqueous ammonium acetate solution, B=acetonitrile
solvent gradient: 90% A/B(0 min)→70% A/B(1 min)→40% A/B(15 min)→5% A/B(16 min)→5% A/B(18 min)→90% A/B(19 min) flow rate: 30 mL/min
temperature: room temperature Example 94

N-(5-cyano-1,3-thiazol-2-yl)-N'-(1,3-diethyl-2,4-dioxo-1,2,3,4-tetrahydroquinazolin-6-yl)-3-methylpentanediamide (Step 1)
To a solution of the compound obtained in Step 3 of Example 1 (2.4 g, 10.3 mmol) in dichloromethane (40 mL) was added 3-methylglutaric anhydride (1.32 g, 10.3 mmol), and the mixture was stirred at room temperature for 2 hr. To the reaction mixture was added water, and the mixture was extracted with dichloromethane. The organic layer was washed with saturated brine, and dried over sodium sulfate, and the solvent was evaporated under reduced pressure to give 4-(1,3-diethyl-2,4-dioxo-1,2,3,4-tetrahydroquinazolin-6-ylcarbamoyl)-3-methylbutyric acid (3.1 g, 83.37%) as a grayish white solid.
MS(API): 362 (M+H)
(Step 2)
To a solution of the compound obtained in Step 1 (0.2 g, 0.55 mmol) and 2-aminothiazole-5-carbonitrile (0.069 g, 0.55 mmol) in ethyl acetate (5 mL) were added DIEA (0.29 mL, 1.66 mmol) and T3P (50% ethyl acetate solution, 0.82 mL, 1.36 mmol), and the mixture was refluxed overnight. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (0.016 g, 6.16%) as a grayish white solid.
MS(API): 469 (M+H)
purification condition by preparative HPLC
instrument: Waters auto purification instrument
column: XBridge C18 (250×19 mm) 5 μm
solvent: A=5 mM aqueous ammonium acetate solution, B=acetonitrile
solvent gradient: 90% A/B(0 min)→65% A/B(3 min)→60% A/B(14 min)→55% A/B(26 min)→0% A/B(27 min)→0% A/B(29 min)→90% A/B(30 min)
flow rate: 14 mL/min
temperature: room temperature Example 95

N-(2-cyano-1,3-benzothiazol-6-yl)-N'-(1,3-diethyl-2,4-dioxo-1,2,3,4-tetrahydroquinazolin-6-yl)-3-methylpentanediamide To a solution of the compound obtained in Step 1 of Example 94 (0.2 g, 0.55 mmol) and 6-aminobenzothiazole-2-carbonitrile (0.097 g, 0.55 mmol) in ethyl acetate (5 mL) were added DIEA (0.29 mL, 1.66 mmol) and T3P (50% ethyl acetate solution, 0.82 mL, 1.36 mmol), and the mixture was refluxed overnight. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (0.08 g, 28.33%) as a grayish white solid.
MS(API): 519 (M+H)
$^1$H-NMR (400 MHz, DMSO-d$_6$): δ1.01 (d, 3H, J=6.44 Hz), 1.15 (t, 3H, J=7.00 Hz), 1.19 (t, 3H, J=7.16 Hz), 2.30-2.47 (m, 4H), 2.50-2.53 (m, 1H), 3.97 (q, 2H, J=6.96 Hz), 4.10 (q, 2H, J=7.04 Hz), 7.43 (d, 1H, J=9.08 Hz), 7.70 (dd, 1H, J=1.84 Hz, 9.12 Hz), 7.92 (dd, 1H, J=2.28 Hz, 9.08 Hz), 8.15 (d, 1H, J=9.04 Hz), 8.33 (d, 1H, J=2.32 Hz), 8.73 (d, 1H, J=1.52 Hz), 10.14 (s, 1H), 10.42 (s, 1H).
purification condition by preparative HPLC
instrument: Waters auto purification instrument
column: XBridge C18 (250×19 mm) 5 μm
solvent: A=5 mM aqueous ammonium acetate solution, B=acetonitrile
solvent gradient: 90% A/B(0 min)→60% A/B(2 min). 60% A/B(10 min)→55% A/B(14 min)→55% A/B(24 min)→0% A/B(25 min)→0% A/B(27 min)→90% A/B(28 min)
flow rate: 14 mL/min
temperature: room temperature Example 96

N-(6-cyanopyridin-3-yl)-N'-(1,3-diethyl-2,4-dioxo-1,2,3,4-tetrahydroquinazolin-6-yl)-3-methylpentanediamide The title compound (0.1 g, 31.22%) was obtained as a grayish white solid using 5-aminopyridine-2-carbonitrile (0.083 g, 0.69 mmol) by the reaction and purification in the same manner as in Example 95.

MS(API): 463 (M+H)

purification condition by preparative HPLC
   instrument: Waters auto purification instrument
   column: Gemini-NX 5 μm C18 110 A (100×30 mm)
   solvent: A=5 mM aqueous ammonium acetate solution, B=acetonitrile
   solvent gradient: 90% A/B(0 min)→75% A/B(1 min)→30% A/B(15 min)→5% A/B(16 min)→5% A/B(18 min)→90% A/B(19 min)
   flow rate: 14 mL/min
   temperature: room temperature

Example 97

N-(2-chloropyridin-4-yl)-N'-(1,3-diethyl-2,4-dioxo-1,2,3,4-tetrahydroquinazolin-6-yl)-3-methylpentanediamide The title compound (0.045 g, 13.77%) was obtained as a grayish white solid using 2-chloro-4-aminopyridine (0.089 g, 0.69 mmol) by the reaction and purification (the same condition by preparative HPLC) in the same manner as in Example 95.

MS(API): 472 (M+H)

Example 98

N-(3-chloro-4-cyanophenyl)-N'-(1-(cyclopropylmethyl)-3-ethyl-2,4-dioxo-1,2,3,4-tetrahydroquinazolin-6-yl)-3-methylpentanediamide (Step 1)

To a solution of the compound obtained in Step 2 of Example 19 (250 mg, 1.06 mmol) in DMF (10 mL) was added potassium carbonate (294 mg, 2.13 mmol) under nitrogen atmosphere, and the mixture was stirred at room temperature for 5 min. To the reaction mixture was added bromomethylcyclopropane (0.43 mL, 3.19 mmol), and the mixture was stirred at 80° C. for 8 hr. To the reaction mixture was added ice water, and the mixture was extracted with ethyl acetate. The organic layer was washed with water, and dried over sodium sulfate, and the solvent was evaporated under reduced pressure. The obtained residue was washed with ethyl acetate-hexane (2:98) to give 1-(cyclopropylmethyl)-3-ethyl-6-nitro-1H-quinazoline-2,4-dione (150 mg, 48.74%) as a yellow viscous solid.

MS(API): 290 (M+H)

(Step 2)

To a solution of the compound obtained in Step 1 (150 mg, 0.52 mmol) in ethyl acetate (15 mL) was added 10% palladium on carbon (50% hydrous, 80 mg), and the mixture was stirred at room temperature for 3 hr under 2 atm of hydrogen atmosphere. The catalyst was removed by filtration, and the filtrate was concentrated under reduced pressure to give 6-amino-1-(cyclopropylmethyl)-3-ethyl-1H-quinazoline-2,4-dione (130 mg, 97.03%) as a yellow solid.

MS(API): 260 (M+H)

(Step 3)

To a solution of the compound obtained in Step 3 of Reference Example 1 (129.6 mg, 0.462 mmol) in ethyl acetate (130 mL) were added DIEA (124 mg, 0.962 mmol), T3P (50% ethyl acetate solution, 306 mg, 0.962 mmol), the compound obtained in Step 2 (100 mg, 0.385 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (90 mg, 44.77%) as a grayish white solid.

MS(API): 522 (M+H)

$^1$H-NMR (400 MHz, DMSO-d$_6$): δ0.45-0.48 (m, 4H), 1.00 (d, 3H, J=6.44 Hz), 1.15 (t, 3H, J=6.96 Hz), 1.17-1.19 (m, 1H), 2.30-2.54 (m, 5H), 3.96-4.03 (m, 4H), 7.52 (d, 1H, J=9.24 Hz), 7.57 (dd, 1H, J=8.66 Hz, 1.88 Hz), 7.84 (d, H, J=8.60 Hz), 7.91 (d, H, J=7.72 Hz), 8.02 (d, H, J=1.84 Hz), 8.34 (d, 1H, J=2.48 Hz), 10.15 (s, 1H), 10.53 (s, 1H).

purification condition by preparative HPLC
   instrument: Waters auto purification instrument
   column: X Terra RP18(250×19 mm) 10 μm
   solvent: A=5 mM aqueous ammonium acetate solution, B=acetonitrile
   solvent gradient: 90% A/B(0 min)→50% A/B(1 min)→50% A/B(14 min)→45% A/B(26 min)→0% A/B(28 min)→0% A/B(30 min)→90% A/B(31 min)
   flow rate: 14 mL/min
   temperature: room temperature

Example 99

N-(3-chloro-4-cyanophenyl)-N'-(3-ethyl-1-((methylsulfanyl)methyl)-2,4-dioxo-1,2,3,4-tetrahydroquinazolin-6-yl)-3-methylpentanediamide (Step 1)

To a solution of the compound obtained in Step 2 of Example 19 (400 mg, 1.70 mmol) in DMF (10 mL) was added sodium hydride (60% oil, 136 mg, 3.40 mmol), and the mixture was stirred at 0° C. for 5 min. To the reaction mixture was added chloromethylsulfanylmethane (0.285 mL, 3.40 mmol), and the mixture was stirred at room temperature for 16 hr. To the reaction mixture was added ice water, and the mixture was extracted with ethyl acetate. The organic layer was washed with water, and dried over sodium sulfate, and the solvent was evaporated under reduced pressure. The obtained residue was washed with ethyl acetate-hexane (2:98), and then dichloromethane-diethyl ether (10:90) to give 3-ethyl-1-methylsulfanylmethyl-6-nitro-1H-quinazoline-2,4-dione (400 mg, 79.58%) as a pale yellow viscous solid.

MS(API): 313 (M+NH$_4$)

(Step 2)

To a solution of the compound obtained in Step 1 (600 mg, 2.03 mmol) in ethanol (40 mL) was added tin(II) chloride (1928 mg, 10.17 mmol), and the mixture was refluxed for 5 hr. The reaction mixture was concentrated under reduced pressure, and to the residue was added water. The pH of the mixture was adjusted to 8 with saturated aqueous sodium carbonate solution, and the mixture was extracted with ethyl acetate. The organic layer was washed with water, and dried over sodium sulfate, and the solvent was evaporated under reduced pressure to give 6-amino-3-ethyl-1-methylsulfanylmethyl-1H-quinazoline-2,4-dione (165 mg, 30.57%) as a pale yellow solid.

$^1$H-NMR (400 MHz, DMSO-d$_6$): δ1.18 (t, 3H, J=7.00 Hz), 2.22 (s, 3H), 4.04-4.10 (m, 2H), 5.02 (s, 2H), 5.32 (s, 2H), 7.04-7.07 (m, 1H), 7.24-7.26 (m, 2H).

(Step 3)

To a solution of the compound obtained in Step 3 of Reference Example 1 (209 mg, 0.75 mmol) in ethyl acetate (30 mL) were added DIEA (0.20 mL, 1.55 mmol), T3P (50% ethyl acetate solution, 0.86 mL, 1.55 mmol) and the compound obtained in Step 2 (165 mg, 0.62 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (160 mg, 48.73%) as a grayish white solid.

MS(API): 526 (M−H)

$^1$H-NMR (400 MHz, DMSO-$d_6$): δ1.00 (d, 3H, J=6.32 Hz), 1.21 (t, 3H, J=6.96 Hz), 2.23 (s, 3H) 2.26-2.50 (m, 5H), 4.10-4.15 (m, 2H), 5.05 (s, 2H), 7.47 (d, 1H, J=9.12 Hz), 7.57 (d, 1H, J=9.80 Hz), 7.85 (d, 1H, J=8.56 Hz), 7.92 (dd, 1H, J=9.12 Hz, 2.08 Hz), 8.02 (s, 1H), 8.36 (d, 1H, J=2.20 Hz), 10.18 (s, 1H), 10.54 (s, 1H).

purification condition by preparative HPLC
  instrument: Waters auto purification instrument
  column: Gemini-NX 5 μm C18 110 A (100×30 mm)
  solvent: A=5 mM aqueous ammonium acetate solution, B=acetonitrile
  solvent gradient: 90% A/B(0 min)→60% A/B(1 min)→30% A/B(15 min)→5% A/B(16 min)→5% A/B(18 min)→90% A/B(19 min)
  flow rate: 30 mL/min
  temperature: room temperature Example 100

N-(1,3-diethyl-2,4-dioxo-1,2,3,4-tetrahydroquinazolin-6-yl)-3-methyl-N'-(3-methyl-2-oxo-2,3-dihydro-1,3-benzothiazol-6-yl)pentanediamide The title compound (0.035 g, 3.05%) was obtained as a grayish white solid using 6-amino-3-methyl-3H-benzothiazol-2-one (0.15 g, 0.83 mmol) by the reaction and purification in the same manner as in Example 95.

MS(API): 524 (M+H)

purification condition by preparative HPLC
  instrument: Waters Semi-Preparative HPLC instrument
  column: Prep Scalar 10 μm C18 (250×30 mm)
  solvent: A=5 mM aqueous ammonium acetate solution, B=acetonitrile
  solvent gradient: 80% A/B(0 min)→50% A/B(60 min)→5% A/B(61 min)→5% A/B(70 min)→80% A/B(71 min)
  flow rate: 30 mL/min
  temperature: room temperature Example 101

3-chloro-4-cyano-N-(4-((1,3-diethyl-2,4-dioxo-1,2,3,4-tetrahydroquinazolin-6-yl)amino)-4-oxo-2-phenylbutyl)benzamide (Step 1)

A solution of the compound obtained in Step 3 of Example 1 (600 mg, 2.57 mmol), cinnamic acid (381 mg, 2.57 mmol), T3P (50% ethyl acetate solution, 1.664 mL, 2.83 mmol) and DIEA (0.494 mL, 2.83 mmol) in ethyl acetate (10 mL) was stirred at 60° C. for 3 hr. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure to give N-(1,3-diethyl-2,4-dioxo-1,2,3,4-tetrahydroquinazolin-6-yl) cinnamamide (863 mg, 92%) as a pale brown solid.

MS(API): 364 (M+H)

(Step 2)

N-(1,3-Diethyl-2,4-dioxo-1,2,3,4-tetrahydroquinazolin-6-yl)-4-nitro-3-phenylbutanamide (552 mg, 1.301 mmol, 54.9%) was obtained as a brown oil using the compound obtained in Step 1 (861 mg, 2.37 mmol) by the reaction and purification in the same manner as in Step 2 of Example 3.

MS(API): 425 (M+H)

(Step 3)

To a solution of the compound obtained in Step 2 (552 mg, 1.30 mmol) in ethanol (10 mL) was added 10% palladium on carbon (50% hydrous, 138 mg, 0.13 mmol), and the mixture was stirred at room temperature for 5 hr under hydrogen atmosphere. The catalyst was removed by filtration, and the filtrate was concentrated under reduced pressure. The obtained residue was purified by NH-silica gel column chromatography (solvent gradient; 10→100% ethyl acetate/hexane) to give 4-amino-N-(1,3-diethyl-2,4-dioxo-1,2,3,4-tetrahydroquinazolin-6-yl)-3-phenylbutanamide (162 mg, 0.41 mmol, 31.6%) as a colorless oil.

MS(API): 395 (M+H)

(Step 4)

The title compound (100 mg, 0.179 mmol, 43.6%) was obtained as a colorless solid using the compound obtained in Step 3 (162 mg, 0.41 mmol) and the compound obtained in Step 4 of Example 61 (82 mg, 0.45 mmol) by the reaction and purification in the same manner as in Step 4 of Example 7.

MS(API): 558 (M+H)

Example 102

N-(1,3-bis(cyclopropylmethyl)-2,4-dioxo-1,2,3,4-tetrahydroquinazolin-6-yl)-N'-(3-chloro-4-cyanophenyl)-3-hydroxy-3-methylpentanediamide A mixture of the compound obtained in Step 1 of Example 62 (20 mg, 0.67 mmol), the compound obtained in Step 2 of Example 2 (212 mg, 0.74 mmol), DIEA (0.13 mL, 0.74 mmol), T3P (50% ethyl acetate solution, 0.436 mL, 0.74 mmol) and ethyl acetate (5 mL) was stirred at 60° C. for 3 hr. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) to give the title compound (109 mg, 0.193 mmol, 28.7%) as a colorless solid.

MS(API): 564 (M+H)

$^1$H-NMR (300 MHz, DMSO-$d_6$): δ0.20-0.62 (8H, m), 0.98-1.10 (3H, m), 1.14-1.28 (2H, m), 2.67 (4H, d, J=14.0 Hz), 3.85 (2H, d, J=7.2 Hz), 4.04 (2H, d, J=6.8 Hz), 5.15 (1H, s), 7.51-7.66 (2H, m), 7.80-7.96 (2H, m), 8.08 (1H, d, J=1.9 Hz), 8.41 (1H, d, J=2.3 Hz), 10.20 (1H, s), 10.55 (1H, s).

Example 103

N-(3-chloro-4-cyanophenyl)-N'-(1-cyclopropyl-3-ethyl-2,4-dioxo-1,2,3,4-tetrahydroquinazolin-6-yl)-3-methylpentanediamide (Step 1)

To a solution of 2-amino-5-nitrobenzoic acid (5.0 g, 27.45 mmol) in DMF (100 mL) were added ethylamine (2 mol/L, THF solution, 41.18 mL, 82.35 mmol), DIEA (47.81 mL, 274.51 mmol) and HATU (13.57 g, 35.69 mmol), and the mixture was stirred at room temperature for 24 hr. To the reaction mixture was added ice water, and the mixture was extracted with ethyl acetate. The organic layer was washed with water, and dried over sodium sulfate, and the solvent was evaporated under reduced pressure. The obtained residue was purified by silica gel column chromatography (solvent gradient; 10→20% ethyl acetate/hexane) to give 2-amino-N-ethyl-5-nitrobenzamide (5.0 g, 93.32%) as a yellow solid.

MS(API): 208 (M−H)

(Step 2)

To a solution of the compound obtained in Step 1 (6 g, 28.7 mmol) in THF (60 mL) was added TEA (8.7 mL) at room temperature. Phosgene (20% w/w-toluene solution, 18.6 mL, 37.3 mmol) was added thereto at room temperature, and the mixture was heated under reflux for 16 hr. Then, phosgene (20% w/w-toluene solution, 7.1 mL, 14.35 mmol) was added thereto, and the mixture was heated under reflux for 2 hr. The reaction mixture was concentrated under reduced pressure, and the residue was extracted with ethyl acetate. The organic layer was washed with water, and dried over sodium sulfate, and the solvent was evaporated under reduced pressure. The obtained residue was purified by silica gel column chromatography (solvent; 15% ethyl acetate/hexane) to give 3-ethyl-6-nitro-1H-quinazoline-2,4-dione (5 g, 74.13%) as a yellow solid.

MS(API): 234 (M−H)

(Step 3)

To a solution of bipyridine (199 mg, 1.28 mmol) in dichloroethane (50 mL) was added copper(II) acetate (231 mg, 1.28 mmol), and the mixture was stirred at 60° C. for 10 min. To 25 the reaction mixture were added cyclopropaneboronic acid (219 mg, 2.55 mmol), 3-ethyl-6-nitro-1H-quinazoline-2,4-dione (300 mg, 1.277 mmol) and sodium carbonate (271 mg, 2.55 mmol), and the mixture was stirred at 80° C. for 16 hr. To the reaction mixture was added water, and the mixture was extracted with ethyl acetate. The organic layer was washed with saturated brine, and dried over sodium sulfate, and the solvent was evaporated under reduced pressure. The obtained residue was purified by silica gel column chromatography (solvent gradient; 20→80% ethyl acetate/hexane) to give 1-cyclopropyl-3-ethyl-6-nitro-1H-quinazoline-2,4-dione (120 mg, 34.15%) as a viscous solid.

MS(API): 276 (M+H)

(Step 4)

To a solution of the compound obtained in Step 3 (150 mg, 0.54 mmol) in ethyl acetate (20 mL) was added 10% palladium on carbon (50% hydrous, 50 mg), and the mixture was stirred at room temperature for 3 hr under 2 atm of hydrogen atmosphere. The catalyst was removed by filtration, and the filtrate was concentrated to give 6-amino-3-cyclopropyl-1-ethyl-1H-quinazoline-2,4-dione (100 mg, 63.3%) as a yellow solid.

MS(API): 246 (M+H)

(Step 5)

To a solution of the compound obtained in Step 1 of Reference Example 1 (137 mg, 0.49 mmol) in ethyl acetate (125 mL) were added DIEA (132 mg, 1.02 mmol), T3P (50% ethyl acetate solution, 324 mg, 1.02 mmol) and the compound obtained in Step 4 (100 mg, 0.408 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (90 mg, 42.29%) as a grayish white solid.

MS(API): 506 (M−H)

$^1$H-NMR (400 MHz, DMSO-d$_6$): δ0.78 (m, 2H) 1.00 (d, 3H, J=6.32 Hz), 1.13 (t, 3H, J=7.04 Hz), 1.19-1.23 (m, 2H), 2.27-2.50 (m, 5H), 2.88 (m, 1H), 3.93-3.96 (m, 2H), 7.57 (d, 1H, J=9.28 Hz), 7.64 (d, 1H, J=9.12 Hz), 7.83-7.89 (m, 2H), 8.02 (s, 1H), 8.30 (s, 1H), 10.16 (s, 1H), 10.57 (s, 1H).

purification condition by preparative HPLC instrument: Waters auto purification instrument column: Gemini-NX 5 μm C18 110 A (100×30 mm)

solvent: A=5 mM aqueous ammonium acetate solution, B=acetonitrile solvent gradient: 90% A/B(0 min)→65% A/B(1 min)→20% A/B(15 min)→5% A/B(16 min)→5% A/B(18 min)→90% A/B(19 min)

flow rate: 30 mL/min temperature: room temperature

Example 104

N-(3-chloro-4-cyanophenyl)-N'-(3-ethyl-1-(methoxymethyl)-2,4-dioxo-1,2,3,4-tetrahydroquinazolin-6-yl)-3-methylpentanediamide (Step 1)

To a solution of the compound obtained in Step 2 of Example 103 (400 mg, 1.70 mmol) in DMF (40 mL) were added sodium hydride (60% oil, 170.21 mg, 4.25 mmol) and bromomethoxymethane (0.35 mL, 4.25 mmol) at 0° C., and the mixture was stirred at room temperature for 20 hr. To the reaction mixture was added ice water, and the mixture was extracted with ethyl acetate. The organic layer was washed with saturated brine, and dried over sodium sulfate, and the solvent was evaporated under reduced pressure. The obtained residue was washed with ethyl acetate-hexane (2:98) to give 3-ethyl-1-methoxymethyl-6-nitro-H-quinazoline-2,4-dione (250 mg, 52.60%) as a grayish white solid.

$^1$H-NMR (400 MHz, DMSO-d$_6$): δ1.19 (t, 3H, J=7.00 Hz), 3.35 (s, 3H), 4.01 (q, 2H), 5.57 (s, 2H) 7.67 (d, 1H, J=9.28 Hz), 8.54 (dd, 1H, J=9.26 Hz, 2.76 Hz), 8.73 (d, 1H, J=2.72).

(Step 2)

To a solution of the compound obtained in Step 1 (200 mg, 0.72 mmol) in ethyl acetate (20 mL) was added 10% palladium on carbon (50% hydrous, 80 mg), and the mixture was stirred at room temperature for 3 hr under 2 atm of hydrogen atmosphere. The catalyst was removed by filtration, and the filtrate was concentrated to give 6-amino-3-ethyl-1-methoxymethyl-1H-quinazoline-2,4-dione (150 mg, 83.94%) as a yellow solid.

MS(API): 250 (M+H)

(Step 3)

To a solution of the compound obtained in Step 1 of Reference Example 1 (238 mg, 0.851 mmol) in ethyl acetate (100 mL) were added DIEA (275 mg, 2.127 mmol), T3P (50% ethyl acetate solution, 676 mg, 2.127 mmol) and the compound obtained in Step 2 (212 mg, 0.851 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (160 mg, 36.74%) as a grayish white solid.

MS(API): 512 (M+H)

¹H-NMR (400 MHz, DMSO-d₆): δ1.00 (s, 3H, J=6.28 Hz), 1.16 (t, 3H, J=6.96 Hz), 2.26-2.50 (m, 5H), 3.24 (s, 3H), 3.96-4.01 (m, 2H), 5.49 (s, 2H), 7.39 (d, 1H, J=9.04 Hz), 7.57 (d, 1H, J=7.60 Hz), 7.83-7.88 (m, 2H), 8.03 (s, 1H), 8.35 (s, 1H), 10.17 (s, 1H), 10.55 (s, 1H).
purification condition by preparative HPLC
    instrument: Waters Semi-Preparative HPLC instrument
    column: Prep Scalar 10 μm C18 (250×30 mm)
    solvent: A=5 mM aqueous ammonium acetate solution, B=acetonitrile
    solvent gradient: 70% A/B(0 min)→50% A/B(60 min)→5% A/B(61 min)→5% A/B(70 min)→70% A/B(71 min)
    flow rate: 30 mL/min
    temperature: room temperature

Example 105

N-(3-chloro-4-cyanophenyl)-N'-(3-ethyl-1-(2-methoxyethyl)-2,4-dioxo-1,2,3,4-tetrahydroquinazolin-6-yl)-3-methylpentanediamide (Step 1)

To a solution of the compound obtained in Step 2 of Example 103 (400 mg, 1.70 mmol) in DMF (40 mL) were added sodium hydride (60% oil, 170.21 mg, 4.25 mmol) and 1-bromo-2-methoxyethane (0.4 mL, 4.25 mmol) at 0° C., and the mixture was stirred at room temperature for 20 hr. To the reaction mixture was added ice water, and the mixture was extracted with ethyl acetate. The organic layer was washed with saturated brine, and dried over sodium sulfate, and the solvent was evaporated under reduced pressure. The obtained residue was washed with ethyl acetate-hexane (2:98) to give 3-ethyl-1-(2-methoxyethyl)-6-nitro-1H-quinazoline-2,4-dione (350 mg, 70.11%) as a brown solid.

¹H-NMR (400 MHz, DMSO-d₆): δ1.18 (t, 3H, J=7.04 Hz), 3.25 (s, 3H), 3.64 (t, 2H, J=5.52 Hz), 3.97-4.02 (m, 2H), 4.36 (t, 2H, J=5.52 Hz), 7.78 (d, 1H, J=9.36 Hz), 8.50 (dd, 1H, J=9.32 Hz, 2.72 Hz), 8.73 (d, 1H, J=2.76 Hz).

(Step 2)

To a solution of the compound obtained in Step 1 (350 mg, 1.19 mmol) in ethyl acetate (50 mL) was added 10% palladium on carbon (50% hydrous, 100 mg), and the mixture was stirred at room temperature for 3 hr under 2 atm of hydrogen atmosphere. The catalyst was removed by filtration, and the filtrate was concentrated to give 6-amino-3-ethyl-1-(2-methoxyethyl)-1H-quinazoline-2,4-dione (321 mg, 91.61%) as a yellow solid.

MS(API): 264 (M+H)

(Step 3)

To a solution of the compound obtained in Step 1 of Reference Example 1 (319 mg, 1.14 mmol) in ethyl acetate (100 mL) were added DIEA (369 mg, 2.85 mmol), T3P (50% ethyl acetate solution, 906 mg, 2.85 mmol) and the compound obtained in Step 2 (300 mg, 1.14 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (200 mg, 33.36%) as a grayish white solid.

MS(API): 526 (M+H)

¹H-NMR (400 MHz, DMSO-d₆): δ1.00 (d, 3H, J=6.36 Hz), 1.15 (t, 3H, J=6.96 Hz), 2.29-2.50 (m, 5H), 3.25 (s, 3H), 3.60 (t, 2H, J=5.72 Hz), 3.97-3.99 (m, 2H), 4.26 (t, 2H, J=5.72 Hz), 7.46 (d, 1H, J=9.20 Hz), 7.57 (dd, 1H, J=8.64 Hz, 1.80 Hz), 7.83 (d, 1H, J=8.60 Hz), 7.88 (dd, 1H, J=9.06 Hz, 2.40 Hz), 8.02 (d, 1H, J=1.76 Hz), 8.32 (d, 1H, J=2.36 Hz), 10.18 (s, 1H), 10.59 (s, 1H).

purification condition by preparative HPLC
    instrument: Waters Semi-Preparative HPLC instrument
    column: Prep Scalar 10 μm C18 (250×30 mm)
    solvent: A=5 mM aqueous ammonium acetate solution, B=acetonitrile
    solvent gradient: 70% A/B(0 min)→50% A/B(60 min)→5% A/B(61 min)→5% A/B(70 min)→70% A/B(71 min)
    flow rate: 30 mL/min
    temperature: room temperature

Example 106

N-(3-chloro-4-cyanophenyl)-N'-(3-ethyl-1-(3-methoxypropyl)-2,4-dioxo-1,2,3,4-tetrahydroquinazolin-6-yl)-3-methylpentanediamide (Step 1)

To a solution of the compound obtained in Step 2 of Example 103 (400 mg, 1.70 mmol) in DMF (40 mL) were added sodium hydride (60% oil, 170.21 mg, 3.4 mmol) and 1-bromo-3-methoxypropane (0.39 mL, 3.40 mmol) at 0° C., and the mixture was stirred at room temperature for 20 hr. To the reaction mixture was added ice water, and the mixture was extracted with ethyl acetate. The organic layer was washed with saturated brine, and dried over sodium sulfate, and the solvent was evaporated under reduced pressure. The obtained residue was washed with ethyl acetate-hexane (2:98) to give 3-ethyl-1-(3-methoxypropyl)-6-nitro-1H-quinazoline-2,4-dione (265 mg, 50.66%) as a brown solid.

MS(API): 308 (M+H)

(Step 2)

To a solution of the compound obtained in Step 1 (150 mg, 0.49 mmol) in ethyl acetate (30 mL) was added 10% palladium on carbon (50% hydrous, 80 mg), and the mixture was stirred at room temperature for 3 hr under 2 atm of hydrogen atmosphere. The catalyst was removed by filtration, and the filtrate was concentrated to give 6-amino-3-ethyl-1-(3-methoxy-propyl)-1H-quinazoline-2,4-dione (130 mg, 96.29%) as a yellow solid.

MS(API): 278 (M+H)

(Step 3)

To a solution of the compound obtained in Step 1 of Reference Example 1 (196 mg, 0.70 mmol) in ethyl acetate (100 mL) were added DIEA (226 mg, 1.753 mmol), T3P (50% ethyl acetate solution, 556 mg, 1.75 mmol) and the compound obtained in Step 2 (194 mg, 0.70 mmol), and the mixture was refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (200 mg, 33.36%) as a grayish white solid.

MS(API): 540 (M+H)

¹H-NMR (400 MHz, DMSO-d₆): δ1.00 (d, 3H, J=6.40 Hz), 1.15 (t, 3H, J=6.92 Hz), 1.84 (t, 2H, J=6.44 Hz), 2.29-2.50 (m, 5H), 3.23 (s, 3H), 3.40 (t, 2H, J=5.96 Hz), 3.96-3.98 (m, 2H), 4.12 (t, 2H, J=7.20 Hz), 7.40 (d, 1H, J=9.16 Hz), 7.57 (dd, 1H, J=8.70 Hz, 1.76 Hz), 7.84 (d, 1H, J=8.56 Hz), 7.89 (dd, 1H, J=9.04 Hz, 2.32 Hz), 8.02 (d, 1H, J=1.60 Hz), 8.34 (d, 1H, J=2.48 Hz), 10.14 (s, 1H), 10.52 (s, 1H).

purification condition by preparative HPLC
    instrument: Waters Semi-Preparative HPLC instrument
    column: Prep Scalar 10 μm C18 (250×30 mm)

solvent: A=5 mM aqueous ammonium acetate solution, B=acetonitrile solvent gradient: 70% A/B(0 min)→50% A/B(60 min)→5% A/B(61 min)→5% A/B(70 min)→70% A/B(71 min)

flow rate: 30 mL/min temperature: room temperature

Example 107

N-(3-chloro-4-cyanophenyl)-N'-(3-ethyl-1-(2-hydroxyethyl)-2,4-dioxo-1,2,3, 4-tetrahydroquinazolin-6-yl)-3-methylpentanediamide The title compound (55 mg, 41.66%) was obtained as a grayish white solid using the compound of Example 105 (136 mg, 0.258 mmol) by the reaction and purification in the same manner as in Example 33.

MS(API): 512 (M+H)

Example 108

N-(3-chloro-4-cyanophenyl)-N'-(3-ethyl-1-(3-hydroxypropyl)-2,4-dioxo-1,2,3,4-tetrahydroquinazolin-6-yl)-3-methylpentanediamide The title compound (60 mg, 61.47%) was obtained as a grayish white solid using the compound of Example 106 (100 mg, 0.186 mmol) by the reaction and purification in the same manner as in Example 33.

MS(API): 524 (M−H)

Example 109

N-(4-cyano-2-thienyl)-N'-(1,3-diethyl-2,4-dioxo-1,2,3,4-tetrahydroquinazolin-6-yl)-3-methylpentanediamide The title compound (0.065 g, 16.73%) was obtained as a grayish white solid using 5-aminothiophene-3-carbonitrile (0.103 g, 0.83 mmol) by the reaction and purification in the same manner as in Example 95.

MS(API): 468 (M+H)

purification condition by preparative HPLC instrument: Waters Semi-Preparative HPLC instrument column: Prep Scalar 10 μm C18 (250×30 mm)

solvent: A=5 mM aqueous ammonium acetate solution, B=acetonitrile solvent gradient: 70% A/B(0 min)→50% A/B(60 min)→5% A/B(61 min)→5% A/B(70 min)→70% A/B(71 min)

flow rate: 30 mL/min temperature: room temperature

Example 110

3-chloro-4-cyano-N-((3S)-1-((1,3-diethyl-2,4-dioxo-1,2,3,4-tetrahydroquinazolin-6-yl)amino)-4-methyl-1-oxopentan-3-yl)benzamide (Step 1)

tert-Butyl (S)-(1-((1,3-diethyl-2,4-dioxo-1,2,3,4-tetrahydroquinazolin-6-yl)amino)-4-methyl-1-oxopentan-3-yl)carbamate (228 mg, 0.511 mmol, 79%) was obtained as a colorless solid using (S)-3-((tert-butoxycarbonyl)amino)-4-methylpentanoic acid (149 mg, 0.64 mmol) by the reaction and purification in the same manner as in Step 2 of Example 62.

MS(API): 447 (M+H)

(Step 2)

(S)-3-Amino-N-(1,3-diethyl-2,4-dioxo-1,2,3,4-tetrahydroquinazolin-6-yl)-4-methylpentanamide (160 mg, 0.462 mmol, 90%) was obtained as a colorless oil using the compound obtained in Step 1 (228 mg, 0.51 mmol) by the reaction and purification in the same manner as in Step 2 of Example 61.

MS(API): 347 (M+H)

(Step 3)

The title compound (80 mg, 0.157 mmol, 34%) was obtained as a colorless solid using the compound obtained in Step 2 (160 mg, 0.46 mmol) by the reaction and purification in the same manner as in Step 2 of Example 101.

MS(API): 510 (M+H)

Example 111

N-(4-((3-chloro-4-cyanophenyl)amino)-2-methyl-4-oxobutyl)-1,3-diethyl-2,4-dioxo-1,2,3,4-tetrahydropyrido[3,4-d]pyrimidine-6-carboxamide (Step 1)

1,3-Diethyl-6-methyl-1H-pyrimidine-2,4-dione (7.0 g, 38.46 mmol) was dissolved in a mixed solvent of 1,4-dioxane-acetic acid (11:1, 84 mL), selenium dioxide (12.80 g, 115.38 mmol) was added thereto, and the mixture was refluxed for 5 hr. The reaction mixture was concentrated under reduced pressure, and the solvent was completely evaporated by azeotropy with toluene to give 1,3-diethyl-2,6-dioxo-1,2,3,6-tetrahydropyrimidine-4-carbaldehyde (5.5 g) as a viscous solid.

$^1$H-NMR (400 MHz, DMSO-d$_6$): δ1.11 (t, 3H, J=7.04 Hz), 1.18 (t, 3H, J=6.92 Hz), 3.87 (q, 2H, J=7.04 Hz), 4.07 (q, 2H, J=6.96 Hz), 6.45 (s, 1H), 9.61 (s, 1H).

(Step 2)

To a solution of the compound obtained in Step 1 (5.5 g, 28.06 mmol) in DMF (75 mL) was added N,N-dimethylhydrazine (32 mL, 420.92 mmol), and the mixture was sealed, and stirred at 90° C. for 16 hr. The reaction mixture was filtered through Celite, and the filtrate was concentrated under reduced pressure. The residue was triturated with hexane-diethyl ether (50:50) to give 6-(dimethylhydrazonomethyl)-1,3-diethyl-1H-pyrimidine-2,4-dione (2.3 g) as a brown solid.

MS(API): 239 (M+H)

(Step 3)

To a solution of the compound obtained in Step 2 (11.5 g, 48.3 mmol) in acetonitrile (220 mL) was added methyl acrylate (5.25 mL, 57.98 mmol), and the mixture was degassed by nitrogen-bubbling for 15 min. Palladium acetate (13.02 g, 57.98 mmol) was added thereto, and the mixture was refluxed for 1 hr. The reaction mixture was filtered through Celite, and the filtrate was concentrated under reduced pressure. The obtained residue was purified by silica gel column chromatography (eluting solvent; 1% methanol/dichloromethane) to give methyl (E)-3-[6-(dimethylhydrazonomethyl)-1,3-diethyl-2,4-dioxo-1,2,3,4-tetrahydropyrimidin-5-yl]-acrylate (4.2 g, 32.86%) as a yellow white solid.

MS(API): 323 (M+H)

(Step 4)

The compound obtained in Step 3 (4.20 g, 13.04 mmol) was dissolved in a mixed solvent of chlorobenzene-acetic acid (5:1, 86.4 mL), and the mixture was stirred at 130° C. for 3 hr. The reaction mixture was concentrated under reduced pressure, and the solvent was completely evaporated by azeotropy with toluene. The residue was crystallized from ethyl acetate to give methyl 1,3-diethyl-2,4-dioxo-1,2,3,4-tetrahydropyrido[3,4-d]pyrimidine-6-carboxylate (3.0 g, 82.95%) as colorless crystals.

MS(API): 278 (M+H)

(Step 5)

The compound obtained in Step 4 (1.50 g, 5.42 mmol) was dissolved in a mixed solvent of THF-water (4:1; 50 mL), and lithium hydroxide monohydrate (340 mg, 8.12 mmol) was added thereto at 0° C. The reaction mixture was stirred at 0° C. for 30 min, and the pH of the mixture was adjusted to 4-6 with aqueous citric acid solution. THF was evaporated under reduced pressure, to the residue was added water, and the mixture was extracted with 10% methanol/dichloromethane. The organic layer was washed with saturated brine, and dried over sodium sulfate, and the solvent was evaporated under reduced pressure. The obtained residue was washed with 50% ethyl acetate/hexane to give 1,3-diethyl-2,4-dioxo-1,2,3,4-tetrahydropyrido[3,4-d]pyrimidine-6-carboxylic acid (800 mg, 56.12%) as a white solid.

MS(API): 262 (M−H)

(Step 6)

To a solution of the compound obtained in Step 5 (188 mg, 0.715 mmol), DIEA (0.45 mL, 3.57 mmol) and T3P (50% ethyl acetate solution, 1.137 mL, 0.357 mmol) in ethyl acetate (10 mL) was added dropwise a solution of the compound obtained in Step 3 of Example 3 (215.3 mg, 0.858 mmol) in ethyl acetate (10 mL) at room temperature, and the mixture was stirred at 90° C. for 5 hr. To the reaction mixture was added ice water, and the mixture was extracted with ethyl acetate. The organic layer was washed with saturated brine, and dried over sodium sulfate, and the solvent was evaporated under reduced pressure. The obtained residue was purified by preparative HPLC to give the title compound (70 mg, 19.71%) as a grayish white solid.

MS(API): 495 (M−H)

$^1$H-NMR (400 MHz, DMSO-d$_6$): δ0.95 (d, 3H, J=6.44 Hz), 1.19 (t, 3H, J=7.00 Hz), 1.25 (t, 3H, J=6.90 Hz), 2.23-2.50 (m, 3H), 3.23-3.38 (m, 2H), 3.99 (q, 2H, J=6.88 Hz), 4.24 (q, 2H, J=6.96 Hz), 7.45 (dd, 1H, J=8.68 Hz, 1.76 Hz), 7.73 (d, 1H, J=8.64 Hz), 7.83 (d, 1H, J=1.72 Hz), 8.31 (s, 1H), 8.65 (t, 1H, J=5.84 Hz), 8.80 (s, 1H), 10.45 (s, 1H).

purification condition by preparative HPLC instrument: Waters auto purification instrument column: Gemini-NX 5 μm C18 110 A (100×30 mm)

solvent: A=5 mM aqueous ammonium acetate solution, B=acetonitrile solvent gradient: 90% A/B(0 min)→5% A/B(1 min)→25% A/B(15 min)→5% A/B(16 min)→5% A/B(18 min)→90% A/B(19 min)

flow rate: 30 mL/min temperature: room temperature

Example 112

N-(4-((3-chloro-4-cyanophenyl)amino)-2-methyl-4-oxobutyl)-1,3-bis(cyclopropylmethyl)-2,4-dioxo-1,2,3,4-tetrahydropyrido[3,4-d]pyrimidine-6-carboxamide (Step 1)

To a solution of 6-methyluracil (8.0 g, 63.43 mmol) in DMF (290 mL) was added potassium carbonate (43.77 g, 317.16 mmol), and the mixture was stirred at room temperature for 30 min. To the reaction mixture was added bromocyclopropylmethane (25.69 g, 18.45 mL, 190.29 mmol), and the mixture was stirred at room temperature for 16 hr. The reaction mixture was filtered through Celite, and the filtrate was concentrated under reduced pressure. The obtained residue was purified by silica gel column chromatography (solvent gradient; 0.5% methanol/dichloromethane) to give 1,3-bis(cyclopropylmethyl)-6-methyl-1H-pyrimidine-2,4-dione (7.70 g, 51.81%) as a grayish white solid.

MS(API): 235 (M+H)

(Step 2)

The compound obtained in Step 1 (7.70 g, 32.91 mmol) was dissolved in a mixed solvent of 1,4-dioxane-acetic acid (11:1, 92.4 mL), selenium dioxide (10.95 g, 98.72 mmol) was added thereto, and the mixture was refluxed for 5 hr. The reaction mixture was concentrated under reduced pressure, and the solvent was completely evaporated by azeotropy with toluene to give 1,3-bis(cyclopropylmethyl)-2,6-dioxo-1,2,3,6-tetrahydropyrimidine-4-carbaldehyde (10.5 g) as a viscous solid.

$^1$H-NMR (400 MHz, DMSO-d): δ0.31-0.45 (m, 8H), 1.13-1.15 (m, 2H), 3.73 (d, 2H, J=7.12 Hz), 4.05 (d, 2H, J=7.00 Hz), 6.49 (s, 1H), 9.66 (s, 1H).

(Step 3)

To a solution of the compound obtained in Step 2 (3.50 g, 14.11 mmol) in DMF (60 mL) was added N,N-dimethylhydrazine (16.11 mL, 221.69 mmol), and the mixture was sealed, and stirred at 90° C. for 16 hr. The reaction mixture was filtered through Celite, and the filtrate was concentrated under reduced pressure. The residue was triturated with hexane-diethyl ether (50:50) to give 1,3-bis(cyclopropylmethyl)-6-(dimethylhydrazonomethyl)-1H-pyrimidine-2,4-dione (1.50 g) as a brown solid.

MS(API): 291 (M+H)

(Step 4)

To a solution of the compound obtained in Step 3 (4.50 g, 15.52 mmol) in acetonitrile (80 mL) was added methyl acrylate (1.60 mL, 18.62 mmol), and the mixture was degassed by nitrogen-bubbling for 15 min. Palladium acetate (4.18 g, 18.62 mmol) was added thereto, and the mixture was refluxed for 1 hr. The reaction mixture was filtered through Celite, and the filtrate was concentrated under reduced pressure. The obtained residue was purified by silica gel column chromatography (eluting solvent; 1% methanol/dichloromethane) to give methyl (E)-3-[1,3-bis(cyclopropylmethyl)-6-(dimethylhydrazonomethyl)-2,4-dioxo-1,2,3,4-tetrahydropyrimidin-5-yl]-acrylate (1.50 g, 25.82%) as a yellow white solid.

MS(API): 375 (M+H)

(Step 5)

The compound obtained in Step 4 (1.50 g, 4.01 mmol) was dissolved in a mixed solvent of chlorobenzene-acetic acid (5:1, 30.6 mL), and the solution was stirred at 130° C. for 3 hr. The reaction mixture was concentrated under reduced pressure, and the solvent was completely evaporated by azeotropy with toluene. The residue was crystallized from ethyl acetate to give methyl 1,3-bis(cyclopropylmethyl)-2,4-dioxo-1,2,3,4-tetrahydropyrido[3,4-d]pyrimidine-6-carboxylate (1.0 g, 75.7%) as brown crystals.

MS(API): 330 (M+H)

(Step 6)

The compound obtained in Step 5 (300 mg, 0.912 mmol) was dissolved in a mixed solvent of THF-water (4:1; 10 mL), and lithium hydroxide monohydrate (57.39 mg, 1.37 mmol) was added thereto at 0° C. The reaction mixture was stirred at 0° C. for 30 min, and the pH of the mixture was adjusted to 4-6 with aqueous citric acid solution. THF was evaporated under reduced pressure, to the residue was added water, and the mixture was extracted with 10% methanol/ dichloromethane. The organic layer was washed with saturated brine, and dried over sodium sulfate, and the solvent was evaporated under reduced pressure. The obtained residue was washed with 50% ethyl acetate/hexane to give 1,3-bis(cyclopropylmethyl)-2,4-dioxo-1,2,3,4-tetrahydropyrido[3,4-d]pyrimidine-6-carboxylic acid (250 mg, 86.95%) as a white solid.

MS(API): 314 (M−H)
(Step 7)

To a solution of the compound obtained in Step 6 (290 mg, 0.92 mmol), DIEA (0.58 mL, 4.603 mmol) and T3P (50% ethyl acetate solution, 1.464 mL, 4.603 mmol) in ethyl acetate (10 mL) was added dropwise a solution of the compound obtained in Step 3 of Example 3 (277.29 mg, 1.11 mmol) in ethyl acetate (10 mL) at room temperature, and the mixture was stirred at 90° C. for 5 hr. To the reaction mixture was added ice water, and the mixture was extracted with ethyl acetate. The organic layer was washed with saturated brine, and dried over sodium sulfate, and the solvent was evaporated under reduced pressure. The obtained residue was purified by preparative HPLC to give the title compound (200 mg, 39.57%) as a grayish white solid.

MS(API): 547 (M−H)
$^1$H-NMR (400 MHz, DMSO-$d_6$): δ0.37-0.53 (m, 8H), 0.95 (d, 3H, J=6.36 Hz), 1.22-1.23 (m, 2H), 2.23-2.50 (m, 3H), 3.23-3.38 (m, 2H), 3.86 (d, 2H, J=7.12 Hz), 4.18 (d, 2H, J=6.72 Hz), 7.47 (dd, 1H, J=8.68 Hz, 1.68 Hz), 7.74 (d, 1H, J=8.60 Hz), 7.84 (d, 1H, J=1.56 Hz), 8.33 (s, 1H), 8.69 (t, 1H, J=6.08 Hz), 8.90 (s, 1H), 10.46 (s, 1H).
purification condition by preparative HPLC
  instrument: Waters auto purification instrument
  column: Gemini-NX 5 μm C18 110 A (100×30 mm)
  solvent: A=5 mM aqueous ammonium acetate solution, B=acetonitrile
  solvent gradient: 90% A/B(0 min)→50% A/B(1 min)→20% A/B(15 min)→5% A/B(16 min)→5% A/B(18 min)→90% A/B(19 min)
  flow rate: 30 mL/min
  temperature: room temperature Example 113

N-(1,3-bis(cyclopropylmethyl)-2,4-dioxo-1,2,3,4-tetrahydropyrido[3,4-d]pyrimidin-6-yl)-N'-(3-chloro-4-cyanophenyl)-3-methylpentanediamide (Step 1)
To a solution of the compound obtained in Step 6 of Example 112 (400 mg, 1.27 mmol) in tert-butanol (8 mL) were added TEA (0.177 mL, 1.27 mmol) and DPPA (0.328 mL, 1.52 mmol), and the mixture was refluxed for 7 hr. The reaction mixture was concentrated under reduced pressure, the residue was dissolved in dichloromethane (50 mL), and the solution was washed with water and saturated brine. The organic layer was dried over sodium sulfate, and the solvent was evaporated under reduced pressure. The obtained residue was purified by preparative TLC (mobile phase; 2% methanol/dichloromethane) to give tert-butyl (1,3-bis(cyclopropylmethyl)-2,4-dioxo-1,2,3,4-tetrahydropyrido[3,4-d]pyrimidin-6-yl)-carbamate (210 mg, 42.90%) as a grayish white solid.

MS(API): 387 (M+H)
(Step 2)
To a solution of the compound obtained in Step 1 (210 mg, 0.544 mmol) in dichloromethane was added trifluoroacetic acid (2.5 mL, 114.2 mmol) at 0° C. The reaction mixture was stirred at room temperature for 3 hr, and concentrated under reduced pressure to give 6-amino-1,3-bis(cyclopropylmethyl)-1H-pyrido[3,4-d]pyrimidine-2,4-dione (154 mg, 99.20%) as a viscous solid.

MS(API): 287 (M+H)
(Step 3)

To a solution of the compound obtained in Step 3 of Reference Example 1 (211.47 mg, 0.755 mmoL), DIEA (0.749 mL, 4.403 mmoL) and T3P (50% ethyl acetate solution, 0.907 mL, 3.147 mmol) in ethyl acetate (2.5 mL) was added dropwise a solution of the compound obtained in Step 2 (180 mg, 0.63 mmol) in ethyl acetate (2.5 mL) at room temperature, and the mixture was refluxed for 16 hr. DIEA (0.535 mL, 3.15 mmoL) and T3P (50% ethyl acetate solution, 0.907 mL, 3.15 mmol) were added thereto again, and the mixture was refluxed for 20 hr. To the reaction mixture was added ice water, and the mixture was extracted with ethyl acetate. The organic layer was washed with water, and dried over sodium sulfate, and the solvent was evaporated under reduced pressure. The obtained residue was purified by preparative HPLC to give the title compound (20 mg, 5.79%) as a grayish white solid.

MS(API): 547 (M−H)
$^1$H-NMR (400 MHz, DMSO-$d_6$): δ0.36-0.50 (m, 8H), 0.99 (d, 3H, J=6.20 Hz), 1.19-1.23 (m, 2H), 2.32-2.50 (m, 5H), 3.85 (d, 2H, J=7.12 Hz), 4.11 (d, 2H, J=6.88 Hz), 7.55 (d, 1H, J=8.60 Hz), 7.84 (d, 1H, J=8.60 Hz), 8.01 (brs, H), 8.62 (s, 1H), 8.74 (s, 1H), 10.52 (s, 1H), 10.73 (s, 1H).
purification condition by preparative HPLC
  instrument: Waters auto purification instrument
  column: Zorbax SB C18 Prep HT(250×21.2 mm) 7 μm
  solvent: A=0.05% formic acid aqueous solution, B=acetonitrile
  solvent gradient: 50% A/B(0 min)→50% A/B(40 min)→10% A/B(45 min)→10% A/B(46 min)→50% A/B(47 min)
  flow rate: 16 mL/min
  temperature: room temperature Example 114

N-(1,3-diethyl-2,4-dioxo-1,2,3,4-tetrahydroquinazolin-6-yl)-3-methyl-N'-(3-methyl-2-oxo-2,3-dihydro-1,3-benzoxazol-6-yl)pentanediamide The title compound (0.1 g, 23.49%) was obtained as a grayish white solid using 6-amino-3-methyl-3H-benzoxazol-2-one (0.113 g, 0.69 mmol) by the reaction and purification in the same manner as in Example 95.

MS(API): 508 (M+H)
purification condition by preparative HPLC
  instrument: Waters auto purification instrument
  column: Gemini-NX 5 μm C18 110 A (100×30 mm)
  solvent: A=5 mM aqueous ammonium acetate solution, B=acetonitrile
  solvent gradient: 90% A/B(0 min)→75% A/B(1 min)→55% A/B(15 min)→5% A/B(16 min)→5% A/B(18 min)→90% A/B(19 min)
  flow rate: 30 mL/min
  temperature: room temperature Example 115

N-(1,3-diethyl-2,4-dioxo-1,2,3,4-tetrahydroquinazolin-6-yl)-3-methyl-N'-(pyridin-4-yl)pentanediamide (Step 1)
To a solution of 3-methylglutaric anhydride (0.748 g, 5.85 mmol) in dichloromethane (10 mL) were added 4-aminopyridine (0.5 g, 5.32 mmol) and TEA (1.44 mL, 10.64 mmol), and the mixture was stirred at room temperature for 3 hr. The reaction mixture was concentrated under reduced pressure to give 3-methyl-4-(pyridin-4-ylcarbamoyl)-butyric acid (0.5 g, 42.3%) as a white solid.
MS(API): 223 (M+H)
(Step 2)
To a solution of the compound obtained in Step 1 (0.23 g, 1.039 mmol) and the compound obtained in Step 3 of Example 1 (0.161 g, 0.693 mmol) in DMF (5 mL) were added DIEA (0.59 mL, 3.378 mmol) and HATU (0.316 g, 0.831 mmol), and the mixture was stirred overnight at room temperature. The reaction mixture was diluted with ethyl acetate (25 mL), and washed with water and saturated brine. The organic layer was dried over sodium sulfate, and the solvent was evaporated under reduced pressure. The obtained residue was purified by preparative HPLC to give the title compound (17 mg, 5.51%) as a grayish white solid.
MS(API): 438 (M+H)
purification condition by preparative HPLC
  instrument: Waters auto purification instrument
  column: XTerra RP18(250×19 mm) 10 μm
  solvent: A=5 mM aqueous ammonium acetate solution, B=acetonitrile
  solvent gradient: 90% A/B(0 min)→65% A/B(3 min)→65% A/B(20 min)→63% A/B(25 min)→0% A/B(26 min)→0% A/B(28 min)→90% A/B(29 min)
  flow rate: 14 mL/min
  temperature: room temperature Example 116

N-(3-chloro-4-(cyanomethoxy)phenyl)-N'-(1,3-diethyl-2,4-dioxo-1,2,3,4-tetrahydroquinazolin-6-yl)-3-methylpentanediamide The title compound (0.07 g, 16.01%) was obtained as a grayish white solid using (4-amino-2-chlorophenoxy)acetonitrile (0.151 g, 0.83 mmol) by the reaction and purification in the same manner as in Example 95.
MS(API): 526 (M+H)
purification condition by preparative HPLC
  instrument: Waters auto purification instrument
  column: Gemini-NX 5 μm C18 110 A (100×30 mm)
  solvent: A=5 mM aqueous ammonium acetate solution, B=acetonitrile
  solvent gradient: 90% A/B(0 min)→70% A/B(1 min)→35% A/B(15 min)→5% A/B(16 min)→5% A/B(18 min)→90% A/B(19 min)
  flow rate: 30 mL/min
  temperature: room temperature Example 117

N-(3-chloro-4-cyanophenyl)-N'-(1,3-diethyl-2,4-dioxo-1,2,3,4-tetrahydropyrido[2,3-d]pyrimidin-6-yl)-3-methylpentanediamide (Step 1)
To a solution of ethyl 2,4-dioxo-1,2,3,4-tetrahydropyrido[2,3-d]pyrimidine-6-carboxylate (1.2 g, 5.11 mmol) in DMF (45 mL) were added potassium carbonate (2.11 g, 15.32 mmol) and iodoethane (3.19 mL, 20.43 mmol) at room temperature, and the mixture was stirred at 100° C. for 16 hr. To the reaction mixture was added water, and the mixture was extracted with ethyl acetate. The organic layer was washed with water and saturated brine, and dried over sodium sulfate, and the solvent was evaporated under reduced pressure. The obtained residue was purified by silica gel column chromatography (eluting solvent; 10% ethyl acetate/hexane) to give ethyl 1,3-diethyl-2,4-dioxo-1,2,3,4-tetrahydropyrido[2,3-d]pyrimidine-6-carboxylate (0.7 g, 47.06%) as a grayish white solid.
MS(API): 292 (M+H)
(Step 2)
The compound obtained in Step 1 (1.1 g, 3.78 mmol) was dissolved in a mixed solvent of THF (88 mL)/water (22 mL), and lithium hydroxide was added thereto at 0° C. The reaction mixture was stirred at room temperature for 1 hr, and concentrated under reduced pressure while keeping 25° C. or below. The residue was diluted with water (25 mL), and the mixture was washed with ethyl acetate. The pH of the aqueous layer was adjusted to 5 with 1N hydrochloric acid, and the mixture was extracted with ethyl acetate. The organic layer was washed with saturated brine, and dried over sodium sulfate, and the solvent was evaporated under reduced pressure to give 1,3-diethyl-2,4-dioxo-1,2,3,4-tetrahydropyrido[2,3-d]pyrimidine-6-carboxylic acid (0.75 g, 75.37%) as a grayish white solid.
MS(API): 264 (M+H)
(Step 3)
To a solution of the compound obtained in Step 2 (0.5 g, 1.86 mmol) in tert-butyl alcohol (4 mL) were added DPPA (0.49 mL, 2.28 mmol) and TEA (0.25 mL, 1.90 mmol), and the mixture was refluxed for 16 hr. The reaction mixture was concentrated under reduced pressure, to the residue was added 1 mol/L aqueous sodium hydroxide solution, and the mixture was extracted with dichloromethane. The organic layer was washed with saturated brine, and dried over sodium sulfate, and the solvent was evaporated under reduced pressure. The obtained residue was dissolved in dichloromethane (5 mL), trifluoroacetic acid (5 mL) was added thereto, and the mixture was stirred at room temperature for 1 hr. The reaction mixture was concentrated under reduced pressure, the residue was basified with 1N aqueous sodium hydroxide solution, and the mixture was extracted with dichloromethane. The organic layer was washed with saturated brine, and dried over sodium sulfate, and the solvent was evaporated under reduced pressure. The obtained residue was purified by silica gel column chromatography (solvent gradient; 30% ethyl acetate/hexane) to give 6-amino-1,3-diethyl-1H-pyrido[2,3-d]pyrimidine-2,4-dione (0.14 g, 31.44%) as a yellow solid.
MS(API): 335 (M+H)
(Step 4)
To a solution of the compound obtained in Step 3 of Reference Example 1 (0.201 g, 0.72 mmoL) and the compound obtained in Step 3 (0.12 g, 0.513 mmol) in ethyl acetate (8 mL) were added DIEA (0.36 mL, 2.02 mmoL) and T3P (50% ethyl acetate solution, 0.74 mL, 1.28 mmol) at room temperature, and the mixture was refluxed for 16 hr. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (28 mg, 10.99%) as a grayish white solid.
MS(API): 497 (M+H)
$^1$H-NMR (400 MHz, DMSO-d$_6$): δ1.01 (d, 3H, J=6.52 Hz), 1.14-1.22 (m, 6H), 2.32-2.44 (m, 5H), 3.97 (q, 2H, J=7.16 Hz), 4.24 (q, 2H, J=7.04 Hz), 7.55 (d, 1H, J=8.60

Hz), 7.83 (d, 1H, J=8.60 Hz), 8.00 (d, 1H, J=1.68 Hz), 8.67 (d, 1H, J=2.52 Hz), 8.77 (d, 1H, J=2.56 Hz), 10.35 (s, 1H), 10.52 (s, 1H).

purification condition by preparative HPLC
  instrument: Waters auto purification instrument
  column: X Terra RP18(250×19 mm) 10 μm
  solvent: A=5 mM aqueous ammonium acetate solution, B=acetonitrile
  solvent gradient: 90% A/B(0 min)→55% A/B(2 min)→55% A/B(12 min)→50% A/B(24 min)→0% A/B(25 min)→0% A/B(27 min)→90% A/B(28 min)
  flow rate: 14 mL/min
  temperature: room temperature Example 118

N-(1,3-bis(cyclopropylmethyl)-2,4-dioxo-1,2,3,4-tetrahydropyrido[2,3-d]pyrimidin-6-yl)-N'-(3-chloro-4-cyanophenyl)-3-methylpentanediamide (Step 1)

To a solution of ethyl 2,4-dioxo-1,2,3,4-tetrahydropyrido[2,3-d]pyrimidine-6-carboxylate (1.3 g, 5.53 mmol) in DMF (38 mL) were added potassium carbonate (2.3 g, 16.6 mmol) and cyclopropylmethyl bromide (2.2 mL, 2.13 mmol) at room temperature, and the mixture was stirred at 100° C. for 16 hr. To the reaction mixture was added water, and the mixture was extracted with ethyl acetate. The organic layer was washed with water and saturated brine, and dried over sodium sulfate, and the solvent was evaporated under reduced pressure. The obtained residue was purified by silica gel column chromatography (eluting solvent; 10% ethyl acetate/hexane) to give ethyl 1,3-bis(cyclopropylmethyl)-2,4-dioxo-1,2,3,4-tetrahydropyrido[2,3-d]pyrimidine-6-carboxylate (0.9 g, 47.38%) as a grayish white solid.

MS(API): 344 (M+H)

(Step 2)

The compound obtained in Step 1 (0.2 g, 0.687 mmol) was dissolved in a mixed solvent of THF (88 mL)/water (2 mL), and lithium hydroxide monohydrate (0.086 g, 2.06 mmol) was added thereto at 0° C. The reaction mixture was stirred at room temperature for 1 hr, and concentrated under reduced pressure while keeping 25° C. or below. The residue was diluted with water (25 mL), and the mixture was washed with ethyl acetate. The pH of the aqueous layer was adjusted to 5 with 1N hydrochloric acid, and the mixture was extracted with ethyl acetate. The organic layer was washed with saturated brine, and dried over sodium sulfate, and the solvent was evaporated under reduced pressure to give 1,3-bis(cyclopropylmethyl)-2,4-dioxo-1,2,3,4-tetrahydropyrido[2,3-d]pyrimidine-6-carboxylic acid (0.14 g, 64.6%) as a grayish white solid.

MS(API): 314 (M−H)

(Step 3)

To a solution of the compound obtained in Step 2 (0.4 g, 1.27 mmol) in tert-butyl alcohol (4 mL) were added DPPA (0.33 mL, 1.524 mmol) and TEA (0.173 mL, 1.27 mmol), and the mixture was refluxed for 16 hr. The reaction mixture was concentrated under reduced pressure, to the residue was added 1 mol/L aqueous sodium hydroxide solution, and the mixture was extracted with dichloromethane. The organic layer was washed with saturated brine, and dried over sodium sulfate, and the solvent was evaporated under reduced pressure. The obtained residue was dissolved in dichloromethane (5 mL), trifluoroacetic acid (5 mL) was added thereto, and the mixture was stirred at room temperature for 1 hr. The reaction mixture was concentrated under reduced pressure, the residue was basified with 1N aqueous sodium hydroxide solution, and the mixture was extracted with dichloromethane. The organic layer was washed with saturated brine, and dried over sodium sulfate, and the solvent was evaporated under reduced pressure. The obtained residue was purified by silica gel column chromatography (eluting solvent; 30% ethyl acetate/hexane) to give 6-amino-1,3-bis(cyclopropylmethyl)-1H-pyrido[2,3-d]pyrimidine-2,4-dione (0.15 g, 37.46%).

MS(API): 287 (M+H)

(Step 4)

To a solution of the compound obtained in Step 3 of Reference Example 1 (0.191 g, 0.86 mmoL) and the compound obtained in Step 3 (0.14 g, 0.49 mmol) in ethyl acetate (8 mL) were added DIEA (0.34 mL, 1.96 mmoL) and T3P (50% ethyl acetate solution, 0.73 mL, 1.224 mmol) at room temperature, and the mixture was refluxed for 16 hr. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (48 mg, 17.86%) as a pink solid.

MS(API): 549 (M+H)

$^1$H-NMR (400 MHz, DMSO-d): δ0.36-0.45 (m, 8H), 1.01 (d, 3H, J=6.48 Hz), 1.18-1.27 (m, 2H), 2.32-2.45 (m, 4H), 2.50-2.54 (m, 1H), 3.84 (d, 2H, J=7.00 Hz), 4.12 (d, 2H, J=7.00 Hz), 7.55 (d, H, J=8.64 Hz), 7.83 (d, 1H, J=8.64 Hz), 8.00 (s, 1H), 8.70 (d, 1H, J=2.40 Hz), 8.77 (d, 1H, J=2.40 Hz), 10.37 (s, 1H), 10.52 (s, 1H).

purification condition by preparative HPLC
  instrument: Waters auto purification instrument
  column: Gemini-NX 5 μm C18 110 A (100×30 mm)
  solvent: A=5 mM aqueous ammonium acetate solution, B=acetonitrile
  solvent gradient: 90% A/B(0 min)→50% A/B(1 min)→30% A/B(15 min)→5% A/B(16 min)→5% A/B(18 min)→90% A/B(19 min) flow rate: 30 mL/min
  temperature: room temperature Example 119

N-(4-((3-chloro-4-cyanophenyl)amino)-2-methyl-4-oxobutyl)-1,3-bis(cyclopropylmethyl)-2,4-dioxo-1,2,3,4-tetrahydropyrido[2,3-d]pyrimidine-6-carboxamide To a solution of the compound obtained in Step 2 of Example 118 (0.16 g, 0.51 mmoL) and the compound obtained in Step 3 of Example 3 (0.127 g, 0.51 mmol) in ethyl acetate (6 mL) were added DIEA (0.35 mL, 2.03 mmoL) and T3P (50% ethyl acetate solution, 0.76 mL, 1.27 mmol) at room temperature, and the mixture was refluxed for 16 hr. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (63 mg, 22.59%) as a pink solid.

MS(API): 549 (M+H)

$^1$H-NMR (400 MHz, DMSO-d$_6$): δ0.39-0.47 (m, 8H), 0.97 (d, 3H, J=6.16 Hz), 1.21-1.26 (m, 2H), 2.25-2.49 (m, 3H), 3.22 (m, 1H), 3.36 (m, 1H), 3.86 (d, 2H, J=7.04 Hz), 4.15 (d, 2H, J=7.04 Hz), 7.45 (dd, 1H, J=1.76 Hz, 8.64 Hz), 7.75 (d, 1H, J=8.6 Hz), 7.99 (d, 1H, J=1.72 Hz), 8.78 (d, 1H, J=2.24 Hz), 8.84 (m, 1H), 9.03 (d, 1H, J=2.24 Hz), 10.46 (s, 1H).

purification condition by preparative HPLC
    instrument: Waters auto purification instrument
    column: Gemini-NX 5 μm C18 110 A (100×30 mm)
    solvent: A=5 mM aqueous ammonium acetate solution, B=acetonitrile
    solvent gradient: 90% A/B(0 min)→50% A/B(1 min)→30% A/B(15 min)→5% A/B(16 min)→5% A/B(18 min)→90% A/B(19 min)
    flow rate: 30 mL/min
    temperature: room temperature

Example 120

2-(2-((3-chloro-4-cyanophenyl)amino)-2-oxoethoxy)-N-(1,3-diethyl-2,4-dioxo-1,2,3,4-tetrahydroquinazolin-6-yl)acetamide (Step 1)

A solution of 4-amino-2-chlorobenzonitrile (3.05 g, 20 mmol) and 1,4-dioxane-2,6-dione (2.321 g, 20 mmol) in THF (30 mL) was refluxed for 5 hr. The reaction mixture was diluted with water (100 mL), and the resulting crystals were collected by filtration. The obtained crystals were washed successively with water, isopropanol and diethyl ether to give 2-(2-((3-chloro-4-cyanophenyl)amino)-2-oxoethoxy)acetic acid (4.69 g, 17.46 mmol, 87%) as colorless crystals.

MS(API): 267 (M−H)

(Step 2)

To a solution of the compound obtained in Step 1 (173 mg, 0.64 mmol), the compound obtained in Step 3 of Example 1 (150 mg, 0.64 mmol) and DIEA (0.56 mL, 3.22 mmol) in ethyl acetate (4 mL) was added T3P (50% ethyl acetate solution, 0.57 mL, 0.97 mmol) at room temperature. The reaction mixture was stirred at 60° C. for 15 hr, and poured into aqueous sodium hydrogencarbonate solution (80 mL), and the mixture was extracted with a mixed solvent of ethyl acetate/THF (3:1). The organic layer was washed with water and saturated brine, and dried over magnesium sulfate, and the solvent was evaporated under reduced pressure. The obtained crystals were washed with a mixed solvent of ethyl acetate-diethyl ether to give the title compound (235 mg, 75%) as colorless crystals.

MS(API): 484 (M+H)

$^1$H-NMR (300 MHz, DMSO-d$_6$): δ1.16 (3H, t, J=7.0 Hz), 1.22 (3H, t, J=7.0 Hz), 3.99 (2H, q, J=7.2 Hz), 4.13 (2H, q, J=6.8 Hz), 4.30 (2H, s), 4.34 (2H, s), 7.51 (1H, d, J=9.4 Hz), 7.76 (1H, dd, J=8.7, 1.9 Hz), 7.94 (1H, d, J=8.3 Hz), 8.02 (1H, dd, J=9.1, 2.3 Hz), 8.12 (1H, d, J=1.9 Hz), 8.42 (1H, d, J=2.6 Hz), 10.20 (1H, s), 10.59 (1H, s).

Example 121

N-(4-((3-chloro-4-cyanophenyl)amino)-2-methyl-4-oxobutyl)-1,3-diethyl-2,4-dioxo-1,2,3,4-tetrahydropyrido[2,3-d]pyrimidine-6-carboxamide To a solution of the compound obtained in Step 2 of Example 117 (0.2 g, 0.76 mmoL) and the compound obtained in Step 3 of Example 3 (0.19 g, 0.76 mmoL) in ethyl acetate (6 mL) were added DIEA (0.53 mL, 3.04 mmoL) and T3P (50% ethyl acetate solution, 1.14 mL, 1.901 mmoL) at room temperature, and the mixture was refluxed for 16 hr. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (72 mg, 19.05%) as a pink solid.

MS(API): 497 (M+H)

$^1$H-NMR (400 MHz, DMSO-d$_6$): δ1 12 (d, 3H, J=4.20 Hz), 1.28-1.35 (m, 6H), 2.36-2.41 (m, 3H), 3.49-3.57 (m, 2H), 4.16 (q, 2H, J=6.72 Hz), 4.44 (q, 2H, J=6.48 Hz), 6.75 (brs, 1H), 7.55 (d, H, J=8.56 Hz), 7.64 (d, H, J=8.44 Hz), 7.98 (d, 1H, J=1.76 Hz), 8.73 (d, 1H, J=2.44 Hz), 9.15 (d, 1H, J=2.40 Hz), 9.78 (brs, 1H).

purification condition by preparative HPLC
    instrument: Waters auto purification instrument
    column: Gemini-NX 5 μm C18 110 A (100×30 mm)
    solvent: A=5 mM aqueous ammonium acetate solution, B=acetonitrile
    solvent gradient: 90% A/B(0 min)→65% A/B(1 min)→25% A/B(15 min)→5% A/B(16 min)→5% A/B(18 min)→90% A/B(19 min)
    flow rate: 30 mL/min
    temperature: room temperature

Example 122

3-chloro-4-cyano-N-(4-((1,3-diethyl-2,4-dioxo-1,2,3,4-tetrahydroquinazolin-6-yl)amino)-2-isopropyl-4-oxobutyl)benzamide (Step 1)

A solution of the compound obtained in Step 3 of Example 1 (500 mg, 2.14 mmol), 4-methyl-2-pentenoic acid (0.283 mL, 2.36 mmoL), DIEA (0.412 mL, 2.36 mmoL) and T3P (50% ethyl acetate solution, 1.387 mL, 2.36 mmol) in DMF (5 mL) was stirred overnight at 60° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure to give (E)-N-(1,3-diethyl-2,4-dioxo-1,2,3,4-tetrahydroquinazolin-6-yl)-4-methylpent-2-enamide (quantitative).

$^1$H-NMR (300 MHz, CDCl$_3$): δ1.11 (6H, d, J=6.8 Hz), 1.20-1.45 (6H, m), 2.38-2.62 (1H, m), 4.03-4.33 (4H, m), 5.90 (1H, dd, J=15.3, 1.3 Hz), 6.92-7.10 (2H, m), 7.20 (1H, d, J=9.1 Hz), 7.95 (1H, d, J=2.6 Hz), 8.41 (1H, d, J=8.3 Hz).

(Step 2)

A mixture of the compound obtained in Step 1 (705 mg, 2.14 mmoL), nitromethane (1.31 mL, 24.4 mmol) and DBU (0.645 mL, 4.28 mmol) was stirred overnight at 50° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→50% ethyl acetate/hexane) to give N-(1,3-diethyl-2,4-dioxo-1,2,3,4-tetrahydroquinazolin-6-yl)-4-methyl-3-(nitromethyl)pentanamide (314 mg, 37.6%) as a colorless oil. $^1$H-NMR (300 MHz, CDCl$_3$): δ1.01 (6H, dd, J=6.8, 4.5 Hz), 1.16-1.48 (6H, m), 2.63 (2H, d, J=12.5 Hz), 3.94-4.32 (6H, m), 4.57 (2H, dd, J=12.8, 5.7 Hz), 7.19 (1H, d, J=9.1 Hz), 7.73 (1H, s), 8.00 (1H, d, J=2.6 Hz), 8.22 (1H, dd, J=9.1, 2.6 Hz).

(Step 3)

A mixture of the compound obtained in Step 2 (314 mg, 0.80 mmol), 10% palladium on carbon (50% hydrous, 86 mg, 0.80 mmol) and ethanol (10 mL) was stirred at room temperature for 5 hr. The reaction mixture was filtered through Celite, and the filtrate was concentrated under reduced pressure to give 3-(aminomethyl)-N-(1,3-diethyl-2,4-dioxo-1,2,3,4-tetrahydroquinazolin-6-yl)-4-methylpentanamide (79 mg, 27.3%) as a colorless oil.

MS(API): 361 (M+H)

(Step 4)

A solution of the compound obtained in Step 3 (80 mg, 0.22 mmol), the compound obtained in Step 4 of Example 61 (44.3 mg, 0.24 mmol), DIEA (0.043 mL, 0.24 mmol) and T3P (50% ethyl acetate solution, 0.144 mL, 0.24 mmol) in ethyl acetate (5 mL) was stirred overnight at 70° C. The reaction mixture was allowed to be cooled to room temperature, saturated brine was added thereto, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) to give the title compound (17 mg, 14.62%) as a colorless solid.

MS(API): 525 (M+H)

$^1$H-NMR (300 MHz, CDCl$_3$): δ0.94 (6H, dd, J=6.8, 4.9 Hz), 1.15-1.54 (7H, m), 2.12-2.49 (2H, m), 2.50-2.71 (1H, m), 3.31-3.71 (2H, m), 4.16 (4H, dt, J=13.7, 6.9 Hz), 7.14 (1H, d, J=9.1 Hz), 7.63 (1H, d, J=8.3 Hz), 7.68-7.84 (2H, m), 7.89 (1H, d, J=1.5 Hz), 7.99-8.16 (2H, m), 8.65 (1H, s).

Example 123

N-(3-chloro-4-cyanophenyl)-N'-(1,3-diethyl-2,4-dioxo-1,2,3,4-tetrahydroquinazolin-6-yl)-3, 3-dimethylpentanediamide (Step 1)

5-((3-Chloro-4-cyanophenyl)amino)-3,3-dimethyl-5-oxopentanoic acid (510 mg, 66.8%) was obtained using 4,4-dimethyldihydro-2H-pyran-2,6(3H)-dione (368 mg, 2.59 mmol) by the reaction in the same manner as in Step 1 of Example 120.

(Step 2)

The title compound (13 mg, 3.76%) was obtained as a colorless foam using the compound obtained in Step 1 (200 mg, 0.68 mmol) by the reaction in the same manner as in Step 2 of Example 120.

MS(API): 510 (M+H)

$^1$H-NMR (300 MHz, CDCl$_3$): δ1.20 (6H, s), 1.22-1.42 (6H, m), 2.48 (4H, d, J=15.5 Hz), 3.91-4.39 (4H, m), 7.23 (1H, s), 7.57 (2H, d, J=1.1 Hz), 7.95 (1H, s), 8.12 (1H, dd, J=9.1, 2.6 Hz), 8.20 (1H, d, J=2.3 Hz), 8.30 (1H, s), 10.29 (1H, s).

The compounds described in Examples 1 to 123 are below (Table 1-1-Table 1-9).

TABLE 1-1

| Example No. | 1 | 2 |
|---|---|---|
| Structure | 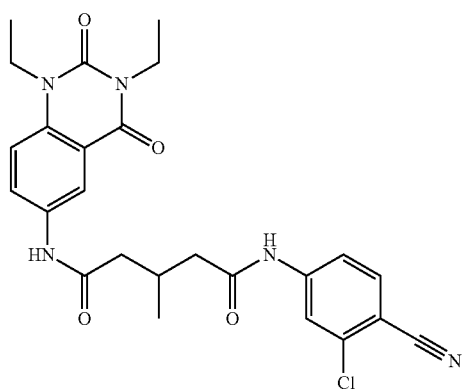 [SMILES: CCn1c(=O)c2cc(NC(=O)CC(C)CC(=O)Nc3ccc(C#N)c(Cl)c3)ccc2n(CC)c1=O] | 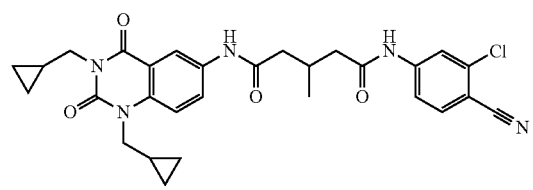 [SMILES: CC(CC(=O)Nc1ccc(C#N)c(Cl)c1)CC(=O)Nc1ccc2c(c1)c(=O)n(CC1CC1)c(=O)n2CC1CC1] |
| Example No. | 3 | 4 |
| Structure | 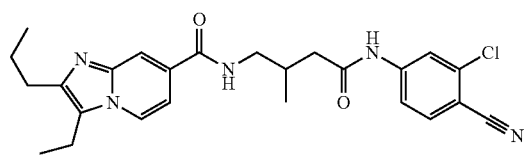 [SMILES: CCCc1nc2cc(C(=O)NCC(C)CC(=O)Nc3ccc(C#N)c(Cl)c3)ccn2c1CC] | 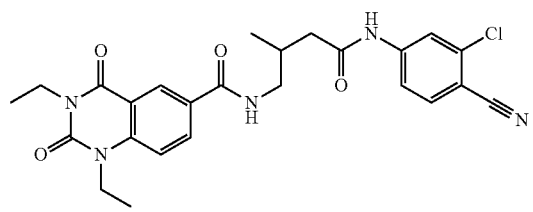 [SMILES: CCn1c(=O)c2cc(C(=O)NCC(C)CC(=O)Nc3ccc(C#N)c(Cl)c3)ccc2n(CC)c1=O] |

TABLE 1-1-continued
| Example No. | 5 | 6 |
|---|---|---|
| Structure | 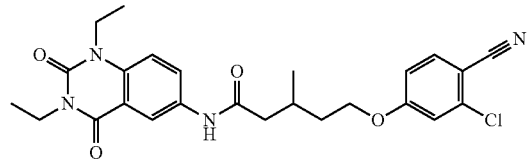 [SMILES: CCn1c(=O)c2cc(NC(=O)CC(C)CCOc3ccc(C#N)c(Cl)c3)ccc2n(CC)c1=O] | 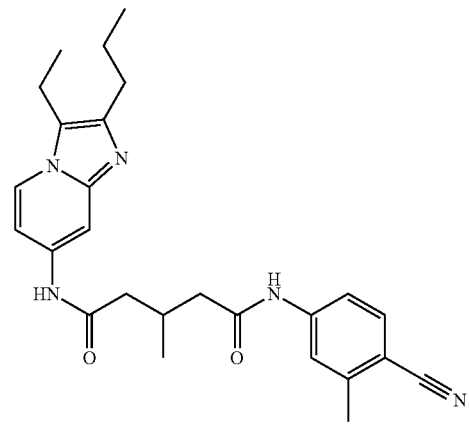 [SMILES: CCCc1nc2cc(NC(=O)CC(C)CC(=O)Nc3ccc(C#N)c(C)c3)ccn2c1CC] |
| Example No. | 7 | 8 |
|---|---|---|
| Structure | 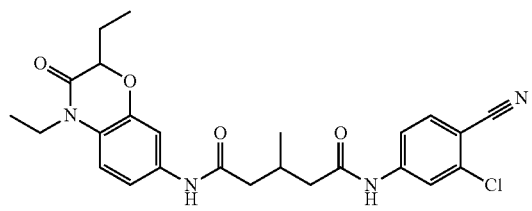 [SMILES: CCC1Oc2cc(NC(=O)CC(C)CC(=O)Nc3ccc(C#N)c(Cl)c3)ccc2N(CC)C1=O] | 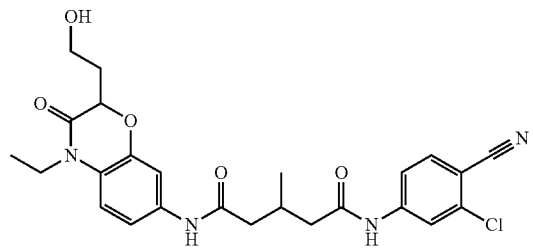 [SMILES: CCN1C(=O)C(CCO)Oc2cc(NC(=O)CC(C)CC(=O)Nc3ccc(C#N)c(Cl)c3)ccc21] |
| Example No. | 9 | 10 |
|---|---|---|
| Structure | 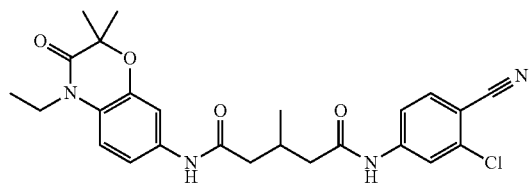 [SMILES: CCN1C(=O)C(C)(C)Oc2cc(NC(=O)CC(C)CC(=O)Nc3ccc(C#N)c(Cl)c3)ccc21] | 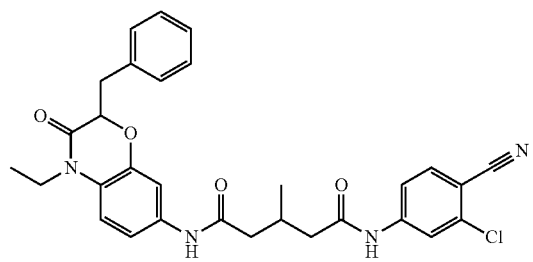 [SMILES: CCN1C(=O)C(Cc2ccccc2)Oc2cc(NC(=O)CC(C)CC(=O)Nc3ccc(C#N)c(Cl)c3)ccc21] |
| Example No. | 11 | 12 |
|---|---|---|
| Structure | 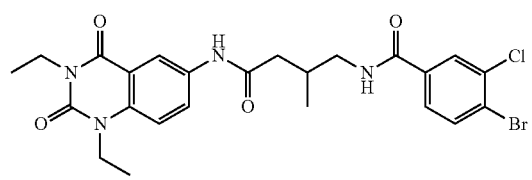 [SMILES: CCn1c(=O)c2cc(NC(=O)CC(C)CNC(=O)c3ccc(Br)c(Cl)c3)ccc2n(CC)c1=O] | 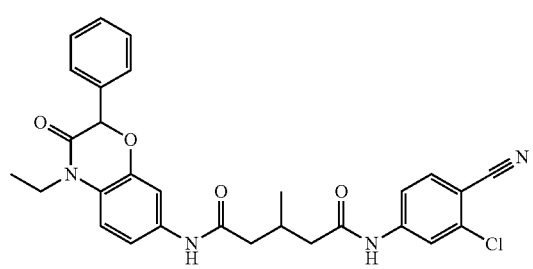 [SMILES: CCN1C(=O)C(c2ccccc2)Oc2cc(NC(=O)CC(C)CC(=O)Nc3ccc(C#N)c(Cl)c3)ccc21] |

TABLE 1-1-continued
| Example No. | 13 | 14 |
|---|---|---|
| Structure | 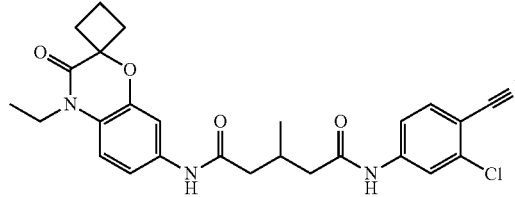 | 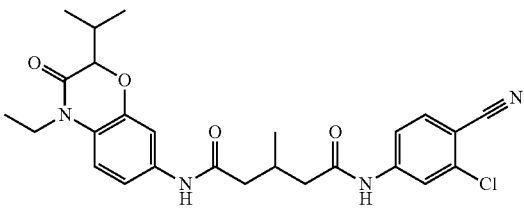 [SMILES: CCN1C(=O)C(C(C)C)Oc2cc(NC(=O)CC(C)CC(=O)Nc3ccc(C#N)c(Cl)c3)ccc21] |
| Example No. | 15 |
|---|---|
| Structure | 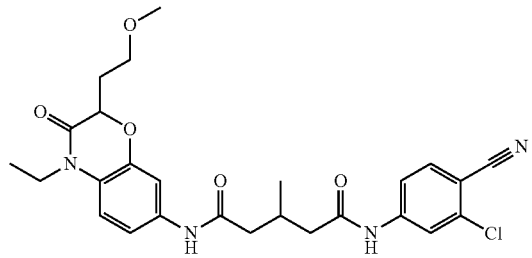 [SMILES: CCN1C(=O)C(CCOC)Oc2cc(NC(=O)CC(C)CC(=O)Nc3ccc(C#N)c(Cl)c3)ccc21] |
TABLE 1-2
| Example No. | 16 | 17 |
|---|---|---|
| Structure | 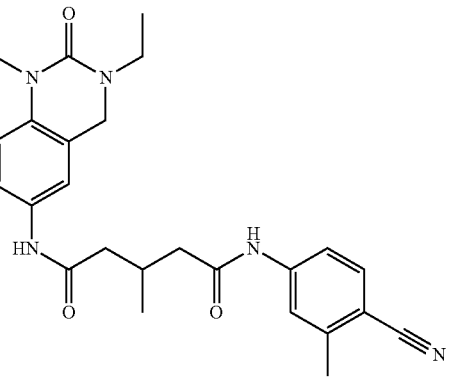 | 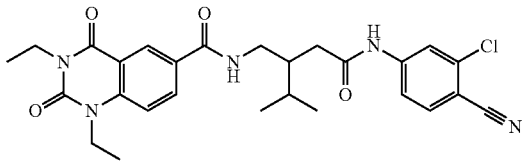 [SMILES: CCn1c(=O)c2cc(C(=O)NCC(CC(=O)Nc3ccc(C#N)c(Cl)c3)C(C)C)ccc2n(CC)c1=O] |
| Example No. | 18 | 19 |
|---|---|---|
| Structure | 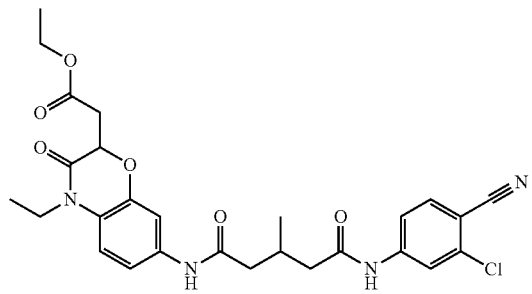 [SMILES: CCOC(=O)CC1Oc2cc(NC(=O)CC(C)CC(=O)Nc3ccc(C#N)c(Cl)c3)ccc2N(CC)C1=O] | 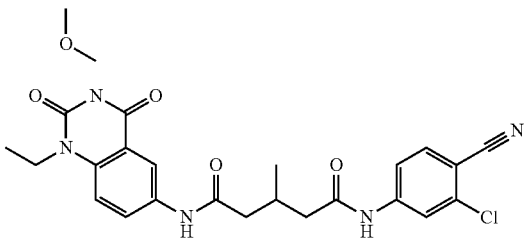 |

TABLE 1-2-continued

| Example No. | 20 | 21 |
|---|---|---|
| Structure | (structure) | (structure) |

| Example No. | 22 | 23 |
|---|---|---|
| Structure | (structure) | (structure) |

| Example No. | 24 | 25 |
|---|---|---|
| Structure | (structure) | (structure) |

| Example No. | 26 | 27 |
|---|---|---|
| Structure | (structure) | (structure) |

TABLE 1-2-continued

| Example No. | 28 | 29 |
|---|---|---|
| Structure | (structure) | (structure) |

| Example No. | 30 |
|---|---|
| Structure | (structure) |

TABLE 1-3

| Example No. | 31 | 32 |
|---|---|---|
| Structure | (structure) | (structure) |

| Example No. | 33 | 34 |
|---|---|---|
| Structure | (structure) | (structure) |

| Example No. | 35 | 36 |
|---|---|---|
| Structure | (structure) | (structure) |

TABLE 1-3-continued
| Example No. | 37 | 38 |
|---|---|---|
| Structure | 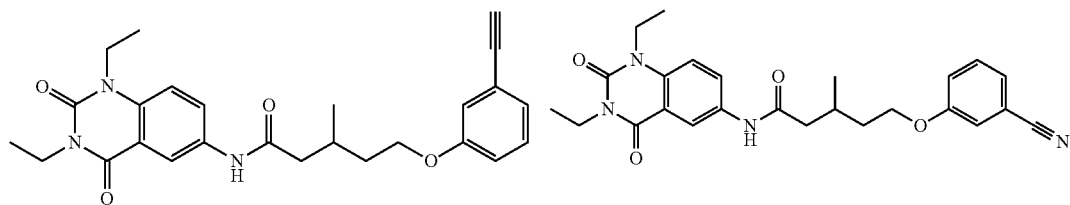 | |
| Example No. | 39 | 40 |
|---|---|---|
| Structure | 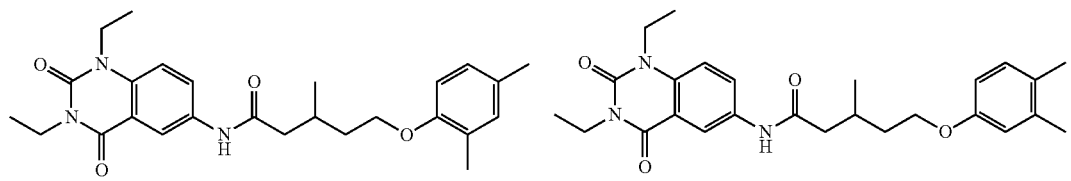 | |
| Example No. | 41 | 42 |
|---|---|---|
| Structure | 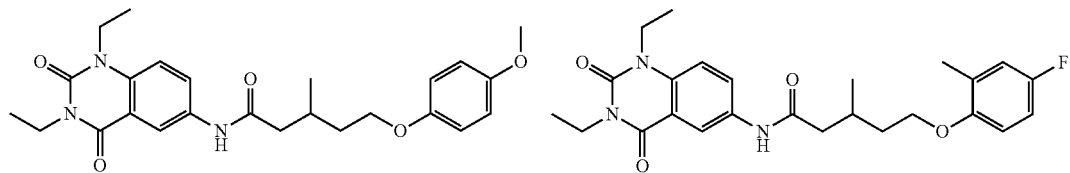 | |
| Example No. | 43 | 44 |
|---|---|---|
| Structure | 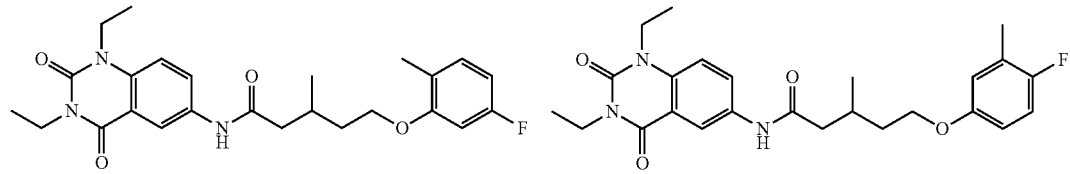 | |
| Example No. | 45 | |
|---|---|---|
| Structure | 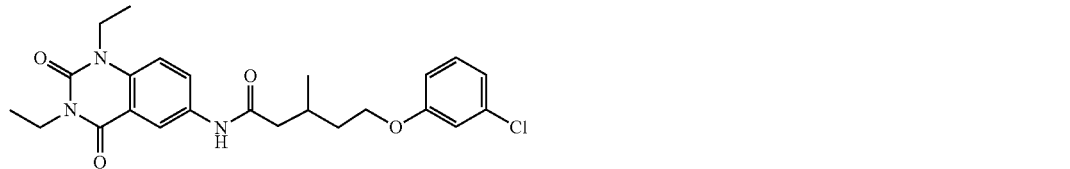 [SMILES: CCn1c(=O)c2cc(NC(=O)CC(C)CCOc3cccc(Cl)c3)ccc2n(CC)c1=O] | |
TABLE 1-4
| Example No. | 46 | 47 |
|---|---|---|
| Structure | 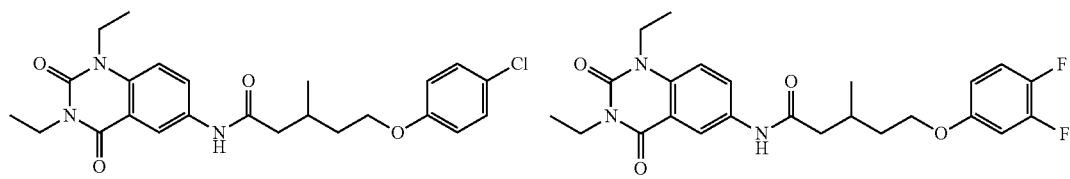 | |

TABLE 1-4-continued
| Example No. | 48 | 49 |
|---|---|---|
| Structure | 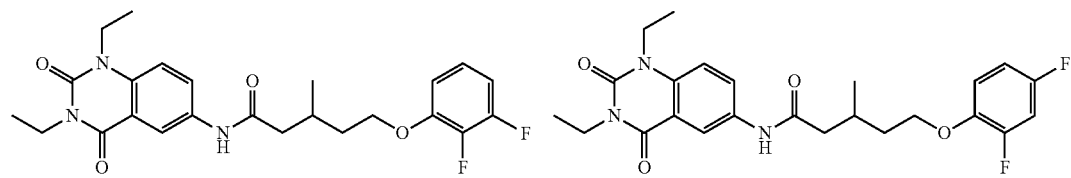 | |
| Example No. | 50 | 51 |
|---|---|---|
| Structure | 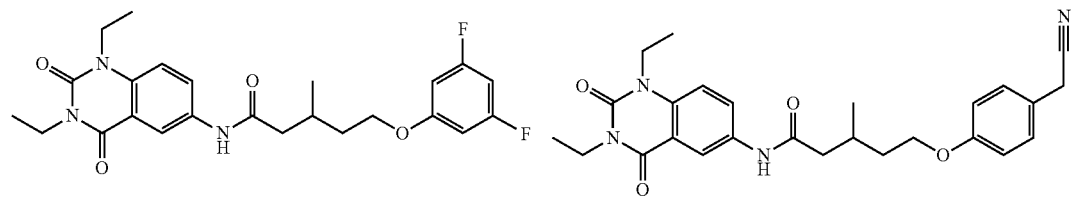 | |
| Example No. | 52 | 53 |
|---|---|---|
| Structure | 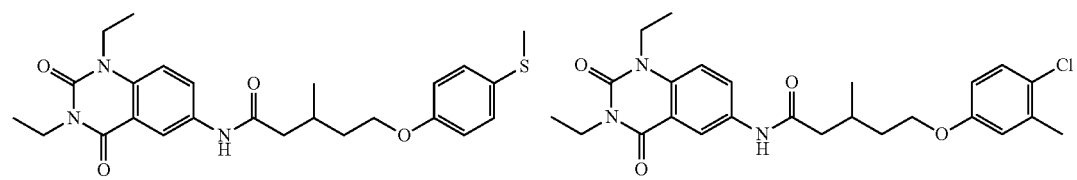 | |
| Example No. | 54 | 55 |
|---|---|---|
| Structure | 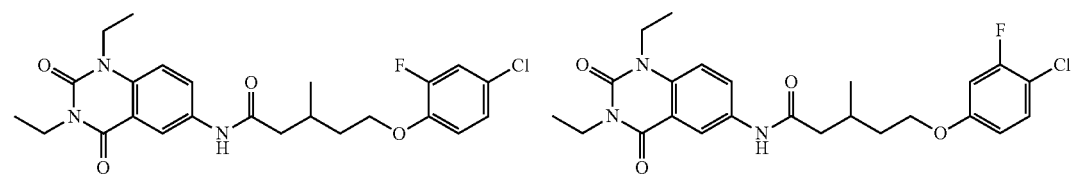 | |
| Example No. | 56 | 57 |
|---|---|---|
| Structure | 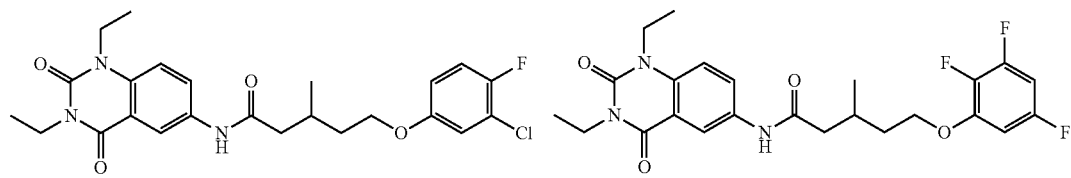 | |
| Example No. | 58 | 59 |
|---|---|---|
| Structure | 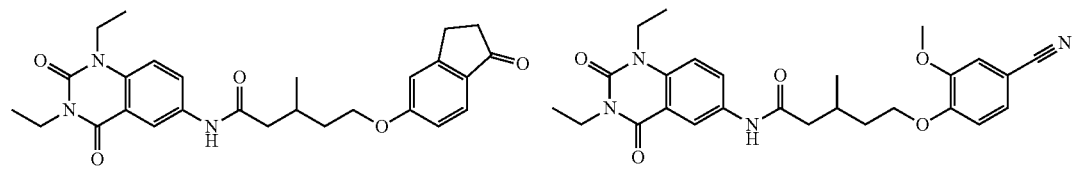 | |

TABLE 1-4-continued

| Example No. | 60 |
|---|---|
| Structure | (chemical structure) |

TABLE 1-5

| Example No. | 61 | 62 |
|---|---|---|
| Structure | (chemical structure) | (chemical structure) |

| Example No. | 63 | 64 |
|---|---|---|
| Structure | (chemical structure) | (chemical structure) |

| Example No. | 65 | 66 |
|---|---|---|
| Structure | (chemical structure) | (chemical structure) |

| Example No. | 67 | 68 |
|---|---|---|
| Structure | (chemical structure) | (chemical structure) |

TABLE 1-5-continued

| Example No. | 69 | 70 |
|---|---|---|
| Structure | (structure) | (structure) |

| Example No. | 71 | 72 |
|---|---|---|
| Structure | (structure) | (structure) |

| Example No. | 73 | 74 |
|---|---|---|
| Structure | (structure) | (structure) |

| Example No. | 75 | |
|---|---|---|
| Structure | (structure) | |

TABLE 1-6

| Example No. | 76 | 77 |
|---|---|---|
| Structure | (structure) | (structure) |

| Example No. | 78 | 79 |
|---|---|---|
| Structure | (structure) | (structure) |

TABLE 1-6-continued
| Example No. | 80 | 81 |
|---|---|---|
| Structure | 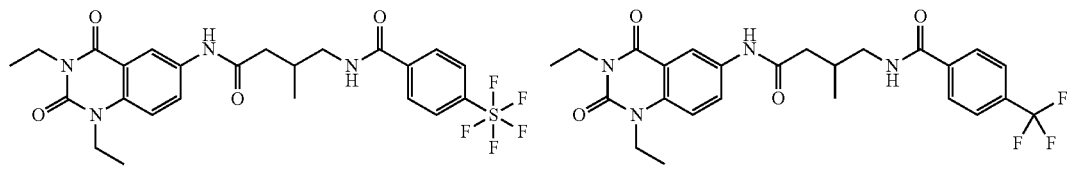 | |
| Example No. | 82 | 83 |
|---|---|---|
| Structure | 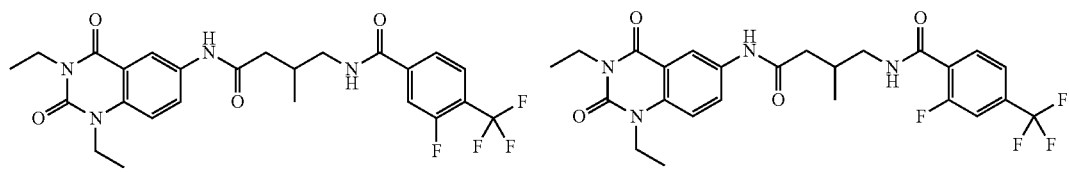 | |
| Example No. | 84 | 85 |
|---|---|---|
| Structure | 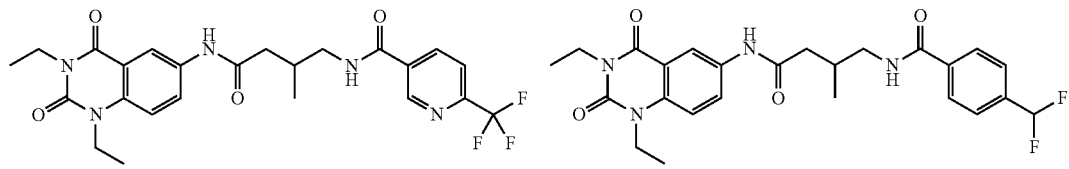 | |
| Example No. | 86 | 87 |
|---|---|---|
| Structure | 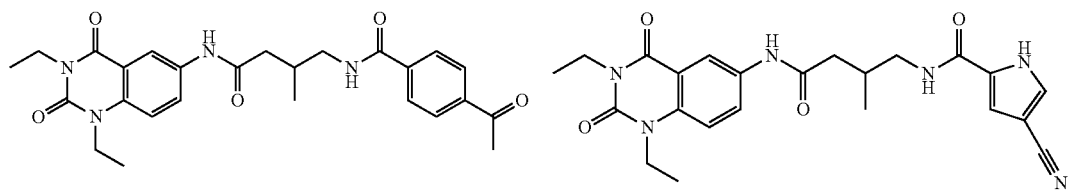 | |
| Example No. | 88 | 89 |
|---|---|---|
| Structure | 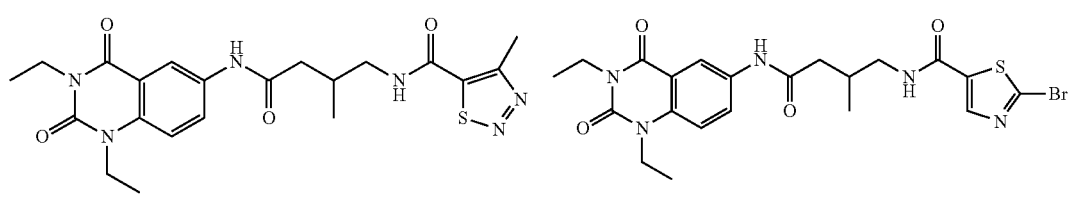 | |
| Example No. | 90 |
|---|---|
| Structure | 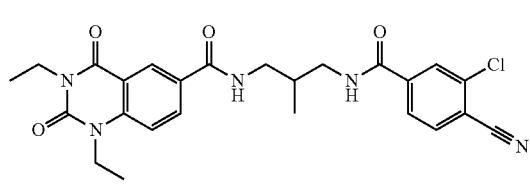 [SMILES: CCn1c(=O)c2cc(C(=O)NCC(C)CNC(=O)c3ccc(C#N)c(Cl)c3)ccc2n(CC)c1=O] |

TABLE 1-7

| Example No. | 91 | 92 |
|---|---|---|
| Structure | | |

| Example No. | 93 | 94 |
|---|---|---|
| Structure | | |

| Example No. | 95 | 96 |
|---|---|---|
| Structure | | |

| Example No. | 97 | 98 |
|---|---|---|
| Structure | | |

| Example No. | 99 | 100 |
|---|---|---|
| Structure | | |

TABLE 1-7-continued
| Example No. | 101 | 102 |
|---|---|---|
| Structure | 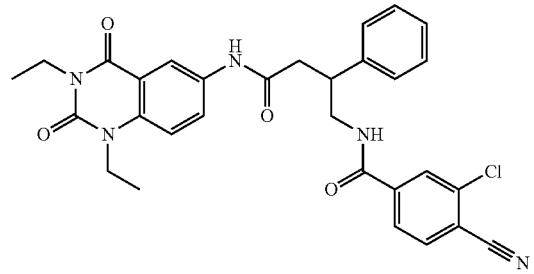 [SMILES: CCn1c(=O)c2cc(NC(=O)CC(CNC(=O)c3ccc(C#N)c(Cl)c3)c3ccccc3)ccc2n(CC)c1=O] | |
| Example No. | 103 | 104 |
|---|---|---|
| Structure | 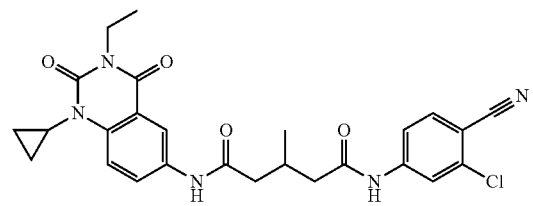 [SMILES: CCn1c(=O)c2cc(NC(=O)CC(C)CC(=O)Nc3ccc(C#N)c(Cl)c3)ccc2n(C2CC2)c1=O] | |
| Example No. | 105 | |
|---|---|---|
| Structure | 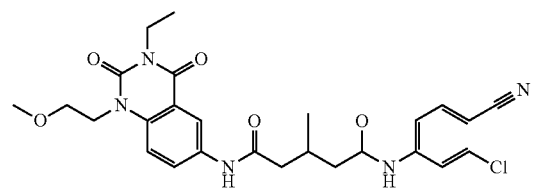 [SMILES: CCn1c(=O)c2cc(NC(=O)CC(C)CC(O)NC(/C=C/Cl)=C/C=C/C#N)ccc2n(CCOC)c1=O] | |
TABLE 1-8
| Example No. | 106 | 107 |
|---|---|---|
| Structure | 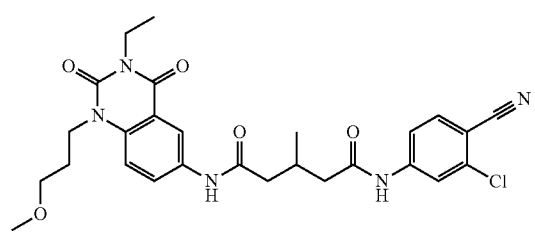 [SMILES: CCn1c(=O)c2cc(NC(=O)CC(C)CC(=O)Nc3ccc(C#N)c(Cl)c3)ccc2n(CCCOC)c1=O] | |
| Example No. | 108 | 109 |
|---|---|---|
| Structure | 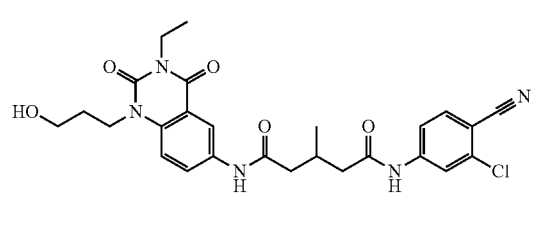 [SMILES: CCn1c(=O)c2cc(NC(=O)CC(C)CC(=O)Nc3ccc(C#N)c(Cl)c3)ccc2n(CCCO)c1=O] | |

TABLE 1-8-continued
| Example No. | 110 | 111 |
|---|---|---|
| Structure | 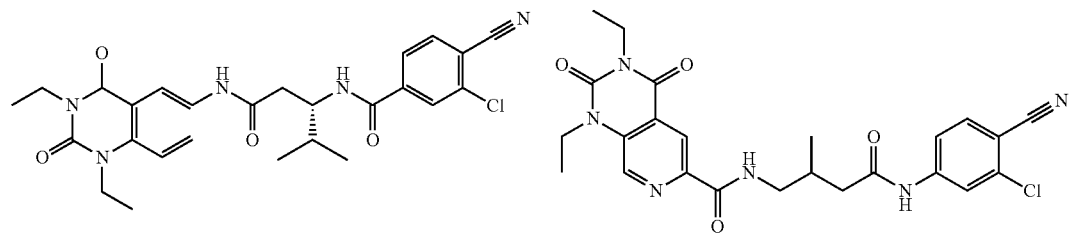 | |
| Example No. | 112 | 113 |
|---|---|---|
| Structure | 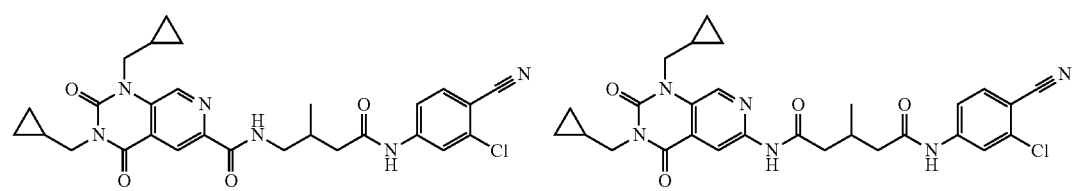 | |
| Example No. | 114 | 115 |
|---|---|---|
| Structure | 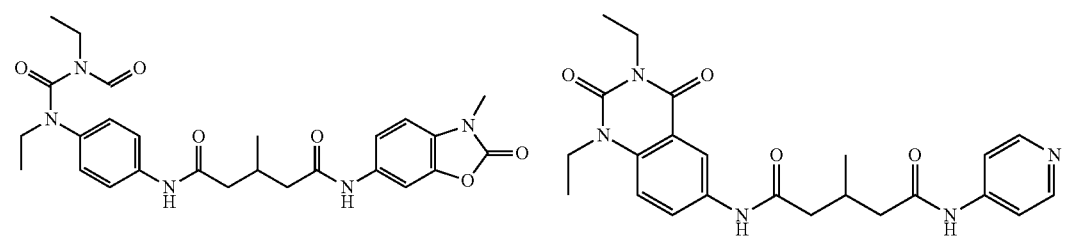 | |
| Example No. | 116 | 117 |
|---|---|---|
| Structure | 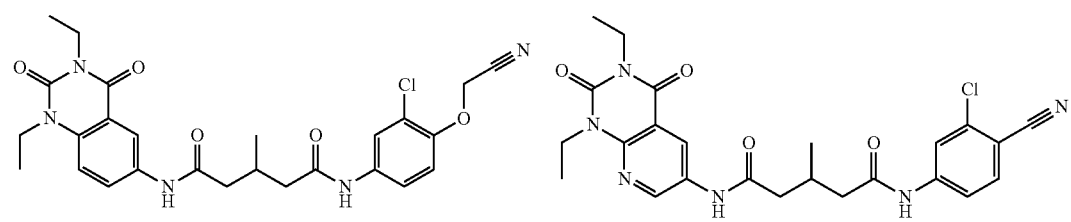 | |
| Example No. | 118 | 119 |
|---|---|---|
| Structure | 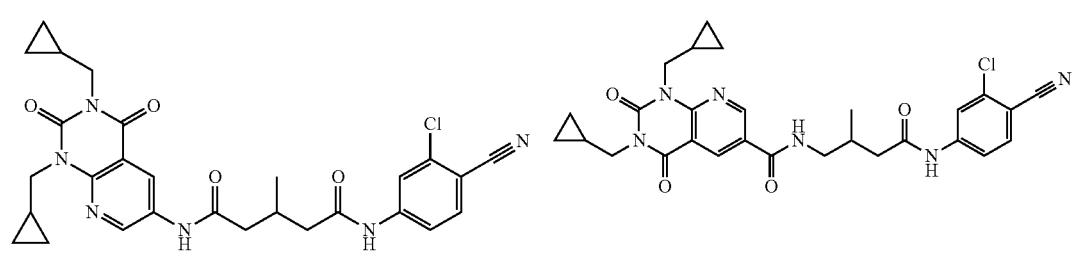 | |

TABLE 1-8-continued

| Example No. | 120 |
|---|---|
| Structure | (structure of N,N-diethyl quinazolinedione linked via -NHC(O)CH2OCH2C(O)NH- to 3-chloro-4-cyanophenyl) |

TABLE 1-9

| Example No. | 121 | 122 |
|---|---|---|
| Structure | (1,3-diethyl-2,4-dioxo-pyrido[3,4-d]pyrimidine-7-carboxamide linked via -NH-CH2-CH(CH3)-CH2-C(O)-NH- to 3-chloro-4-cyanophenyl) | (1,3-diethyl-2,4-dioxo-quinazoline-6-yl)-NHC(O)-CH2-CH(iPr)-CH2-NH-C(O)-(3-chloro-4-cyanophenyl) |

| Example No. | 123 |
|---|---|
| Structure | (1,3-diethyl-2,4-dioxo-quinazolin-6-yl)-NHC(O)-CH2-C(CH3)2-CH2-C(O)-NH-(3-chloro-4-cyanophenyl) |

Example 124

N-(3-chloro-4-cyanophenyl)-N'-(1,3-diethyl-2,4-dioxo-1,2,3,4-tetrahydropyrido[3,4-d]pyrimidin-6-yl)-3-methylpentanediamide (Step 1)

A mixture of 1,3-diethyl-2,4-dioxo-1,2,3,4-tetrahydropyrido[3,4-d]pyrimidine-6-carboxylic acid (1.7 g, 6.46 mmol), DPPA (1.68 mL, 7.76 mmol) and TEA (1.08 mL, 7.76 mmoL) in tert-butanol (25 mL) was stirred at 110° C. for 7 hr. The reaction mixture was concentrated under reduced pressure, and the residue was dissolved in dichloromethane. The organic layer was washed with saturated brine, and dried over sodium sulfate, and the solvent was evaporated under reduced pressure. The obtained residue was purified by silica gel column chromatography (solvent; 1% methanol/dichloromethane) to give tert-butyl 1,3-diethyl-2,4-dioxo-1,2,3,4-tetrahydro-pyrido[3,4-d]pyrimidin-6-yl)-carbamate (700 mg, 32%) as a white solid.

$^{1}$H-NMR (400 MHz, DMSO-$d_6$): δ1.16 (t, 3H, J=6.96 Hz), 1.22 (t, 3H, J=6.92 Hz), 1.49 (s, 9H), 3.98 (q, 2H, J=7.04 Hz), 4.17 (q, 2H, J=6.78 Hz), 8.33 (s, 1H), 8.61 (s, 1H), 10.03 (s, 1H).

(Step 2)

To a solution of tert-butyl 1,3-diethyl-2,4-dioxo-1,2,3,4-tetrahydro-pyrido[3,4-d]pyrimidin-6-yl)-carbamate (400 mg, 1.19 mmol) in dichloromethane (12 mL) was added trifluoroacetic acid (4.59 mL, 59.88 mmoL) at room temperature, and the mixture was stirred at room temperature for 3 hr. The reaction mixture was concentrated under reduced pressure to give crude 6-amino-1,3-diethyl-1H-pyrido[3,4-d]pyrimidine-2,4-dione (278 mg, 99%) as an oil.

$^{1}$H-NMR (400 MHz, DMSO-$d_6$): δ1.13-1.20 (m, 6H), 3.95 (q, 2H, J=6.98 Hz), 4.06 (q, 2H, J=7.0 Hz), 5.86 (brs, 2H), 7.28 (s, 1H), 8.27 (s, 1H).

(Step 3)

To a mixture of 4-(3-chloro-4-cyanophenylcarbamoyl)-3-methylbutyric acid (345 mg, 1.23 mmoL), DIEA (3.22 mL, 18.48 mmol) and T3P (50% ethyl acetate solution, 2.84 mL, 9.85 mmol) in ethyl acetate (5 mL) was added dropwise a solution of the crude 6-amino-1,3-diethyl-1H-pyrido[3,4-d]pyrimidine-2,4-dione (230 mg, 0.98 mmol) in ethyl acetate (2.5 mL) at room temperature. The mixture was heated under reflux for 5 hr, and the reaction mixture was poured into ice water. The organic layer was washed with saturated brine, and dried over sodium sulfate, and the solvent was evaporated under reduced pressure. The obtained residue was purified by preparative TLC (developing solvent; 70% ethyl acetate/hexane) to give the title compound (15 mg, 2.5%) as a white solid.

MS(API): 497 (M+H)

$^{1}$H-NMR (400 MHz, MeOD): δ1.12 (d, 3H, J=6.72 Hz), 1.24-1.35 (m, 6H), 2.43-2.48 (m, 4H), 2.64-2.68 (m, 1H), 4.10 (q, 2H, J=7.02 Hz), 4.23 (q, 2H, J=7.17 Hz), 7.51 (d, H, J=8.48 Hz), 7.61 (d, 1H, J=8.64 Hz), 7.93 (d, 1H, J=1.80 Hz), 8.53 (s, 1H), 8.64 (s, 1H).

Example 125

N-(3-chloro-4-cyanophenyl)-N'-(3-ethyl-2,4-dioxo-1-(prop-2-yn-1-yl)-1,2,3,4-tetrahydroquinazolin-6-yl)-3-methylpentanediamide (Step 1)
To a solution of 3-(1-ethyl-6-nitro-2,4-dioxo-1,4-dihydro-2H-quinazolin-3-yl)-propionitrile (400 mg, 1.70 mmol) in DMF (20 mL) were added sodium hydride (60% oil, 82.0 mg, 3.40 mmol) and 3-bromopropyne (0.607 mL, 5.11 mmol) at room temperature, and the mixture was stirred at room temperature for 16 hr. To the reaction mixture was added ice water, and the mixture was extracted with ethyl acetate (×4). The organic layer was washed with saturated brine, and dried over sodium sulfate, and the solvent was evaporated under reduced pressure. The obtained residue was purified by silica gel column chromatography (solvent; 2% ethyl acetate/hexane) to give 3-ethyl-6-nitro-1-(propa-2-ynyl)-1H-quinazoline-2,4-dione (150 mg, 32%) as a yellow solid.

$^1$H-NMR (400 MHz, DMSO-$d_6$): δ1.13 (t, 3H, J=3.32 Hz), 3.93-3.99 (m, 2H), 4.86 (d, 2H, J=2.16 Hz), 5.34 (brs, 1H), 7.03-7.06 (m, 1H), 7.21-7.25 (m, 2H).

(Step 2)
To a solution of 3-ethyl-6-nitro-1-(propa-2-ynyl)-1H-quinazoline-2,4-dione (50 mg, 0.18 mmol) in ethanol (100 mL) was added tin(II) chloride (104 mg, 0.55 mmol), and the mixture was heated under reflux for 2 hr. The reaction mixture was concentrated under reduced pressure, water was added thereto, and the pH of the mixture was adjusted to 8 with saturated aqueous sodium hydrogencarbonate solution. Then, the mixture was extracted with ethyl acetate (×4). The organic layer was washed with water, and dried over sodium sulfate, and the solvent was evaporated under reduced pressure to give 6-amino-3-ethyl-1-(propa-2-ynyl)-1H-quinazoline-2,4-dione (30 mg, 67.4%) as a pale yellow solid.

(Step 3)
To a solution of 4-(3-chloro-4-cyanophenylcarbamoyl)-3-methylbutyric acid (110 mg, 0.39 mmol) in ethyl acetate (25 mL) were added DIEA (139 μL, 0.82 mmol), T3P (50% ethyl acetate solution, 480 μL, 0.82 mmol) and 6-amino-3-ethyl-1-(propa-2-ynyl)-1H-quinazoline-2,4-dione (80 mg, 0.33 mmol) at room temperature, and the mixture was heated under reflux for 5 hr. The reaction mixture was allowed to be cooled to room temperature, water was added thereto, and the mixture was extracted with ethyl acetate (×3). The organic layer was washed with water and saturated brine, and dried over sodium sulfate, and the solvent was evaporated under reduced pressure. The obtained residue was purified by preparative HPLC to give the title compound (35 mg, 21%) as a white solid.

MS(API): 504 (M−H)

$^1$H-NMR (400 MHz, DMSO-$d_6$): δ1.00 (d, 3H, J=6.36 Hz), 1.16 (t, 3H, J=6.92 Hz), 1.88 (s, 1H), 2.28-2.50 (m, 5H), 3.98 (q, 2H, J=6.76 Hz), 4.92 (s, 2H), 7.45 (d, H, J=9.08 Hz), 7.57 (dd, 1H, J=6.88, 1.72 Hz), 7.84 (d, 1H, J=8.64 Hz), 7.93 (dd, 1H, J=2.36, 6.72 Hz), 8.02 (d, 1H, J=1.68 Hz), 8.35 (d, 1H, J=2.36 Hz), 10.21 (s, 1H), 10.56 (s, 1H).

purification condition by preparative HPLC
  instrument: Waters auto purification instrument
  column: Gemini-NX 5 μm C18 110 A (100×30 mm)
  solvent: A=5 mM aqueous ammonium acetate solution, B=acetonitrile
  solvent gradient: 90% A/B(0 min)→65% A/B(1 min)→25% A/B(15 min)→5% A/B(16 min)→5% A/B(17 min)→90% A/B(16 min)
  flow rate: 30 mL/min
  temperature: room temperature

Example 126

N-(3-chloro-4-cyanophenyl)-N'-(3-ethyl-2,4-dioxo-1-((trimethylsilyl)methyl)-1,2,3,4-tetrahydroquinazolin-6-yl)-3-methylpentanediamide (Step 1)
To a solution of 3-ethyl-6-nitro-1H-quinazoline-2,4-dione (300 mg, 1.28 mmol) in DMF (20 mL) was added potassium carbonate (353 mg, 2.55 mmol) at room temperature under nitrogen gas atmosphere, and the mixture was stirred for 5 min. Chloromethyltrimethylsilane (0.64 mL, 3.83 mmol) was added thereto at room temperature, and the mixture was stirred at 80° C. for 5 hr. To the reaction mixture was added ice water, and the mixture was extracted with ethyl acetate (×4). The organic layer was washed with water, and dried over sodium sulfate, and the solvent was evaporated under reduced pressure. The obtained residue was purified by preparative TLC (mobile phase; 40% ethyl acetate/hexane) to give 3-ethyl-6-nitro-1-trimethylsilanylmethyl-1H-quinazoline-2,4-dione (350 mg, 85%) as a yellow solid.

$^1$H-NMR (400 MHz, DMSO-$d_6$): δ0.09 (s, 9H), 1.17 (t, 3H, J=2.24 Hz), 3.79 (s, 2H), 3.98-4.05 (m, 2H), 7.69 (d, 1H, J=9.32 Hz), 8.51 (dd, 1H, J=6.48, 2.80 Hz), 8.73 (d, 1H, J=2.72 Hz)

(Step 2)
A solution of 3-ethyl-6-nitro-1-trimethylsilanylmethyl-1H-quinazoline-2,4-dione (350 mg, 1.09 mmol) and 10% palladium on carbon (50% hydrous, 50 mg) in ethyl acetate (25 mL) was stirred at room temperature for 3 hr under hydrogen gas atmosphere (30 psi). The reaction mixture was filtered through Celite, and the filtrate was concentrated under reduced pressure to give 6-amino-3-ethyl-1-trimethylsilanylmethyl-1H-quinazoline-2,4-dione (250 mg, 79%) as a yellow solid.

$^1$H-NMR (400 MHz, DMSO-$d_6$): δ0.02 (s, 9H), 1.12 (t, 3H, J=7.00 Hz), 3.62 (s, 2H), 3.96 (q, 2H, J=6.96 Hz), 5.26 (s, 2H), 7.01 (dd, 1H, J=6.20, 2.72 Hz), 7.17 (d, H, J=8.92 Hz), 7.24 (d, H, J=2.64 Hz)

(Step 3)
To a solution of 4-(3-chloro-4-cyanophenylcarbamoyl)-3-methylbutyric acid (288 mg, 1.03 mmol) in ethyl acetate (130 mL) were added DIEA (0.277 mL, 2.15 mmol), T3P (50% ethyl acetate solution, 0.682 mL, 2.15 mmol) and 6-amino-3-ethyl-1-trimethylsilanylmethyl-1H-quinazoline-2,4-dione (250 mg, 0.86 mmol) at room temperature, and the mixture was heated under reflux for 5 hr. To the reaction mixture was added ice water, and the mixture was extracted with ethyl acetate (×3). The organic layer was washed with water and saturated brine, and dried over sodium sulfate, and the solvent was evaporated under reduced pressure. The obtained residue was purified by preparative HPLC to give the title compound (140 mg, 29%) as a white solid.

MS(API): 552 (M−H)

$^1$H-NMR (400 MHz, DMSO-$d_6$): δ0.03 (s, 9H), 1.00 (d, 3H, J=6.32 Hz), 1.14 (t, 3H, J=6.76 Hz), 2.31-2.54 (m, 5H), 3.68 (s, 2H), 3.98-3.99 (m, 2H), 7.41 (d, 1H, J=9.12 Hz), 7.57 (dd, 1H, J=7.04, 1.60 Hz), 7.85 (d, 1H, J=8.60 Hz), 7.90 (dd, H, J=6.72, 2.28 Hz), 8.03 (d, 1H, J=1.52 Hz), 8.33 (d, 1H, J=2.32 Hz), 10.12 (s, 1H), 10.51 (s, 1H).

purification condition by preparative HPLC
  instrument: Waters Semi-Preparative HPLC instrument
  column: Prep Scalar 10 μm C18(250×30 mm)

Example 127

N-(3-chloro-4-cyanophenyl)-3-((1,3-diethyl-2,4-dioxo-1,2,3, 4-tetrahydroquinazolin-6-yl)sulfamoyl)propanamide (Step 1)

Ethyl 3-(chlorosulfonyl)propanoate (502 mg, 2.50 mmol) was added to a solution of 6-amino-1,3-diethylquinazoline-2,4(1H,3H)-dione (583 mg, 2.5 mmol), pyridine (243 μL, 3.00 mmol) and DMAP (153 mg, 1.25 mmol) in THF (5 mL) at room temperature, and the mixture was stirred for 15 hr. The reaction mixture was poured into 0.1N hydrochloric acid, and the mixture was extracted with ethyl acetate (×3). The organic layer was washed with water and saturated brine, and dried over sodium sulfate, and the solvent was evaporated under reduced pressure to give a solid. The obtained solid was washed with IPE-hexane to give ethyl 3-(N-(1,3-diethyl-2,4-dioxo-1,2,3,4-tetrahydroquinazolin-6-yl)sulfamoyl)propanoate (755 mg, 1.90 mmol, 76%) as a pale yellow solid.

$^1$H-NMR (300 MHz, CDCl$_3$): δ1.22-1.33 (6H, m), 1.36 (3H, t, J=7.2 Hz), 2.88 (2H, t, J=7.2 Hz), 3.41 (2H, t, J=7.4 Hz), 4.12-4.24 (6H, m), 7.23 (1H, d, J=9.1 Hz), 7.46 (1H, s), 7.81 (1H, dd, J=9.1, 2.6 Hz), 8.14 (1H, d, J=2.6 Hz).

(Step 2)

To a solution of ethyl 3-(N-(1,3-diethyl-2,4-dioxo-1,2,3,4-tetrahydroquinazolin-6-yl)sulfamoyl)propanoate (755 mg, 1.90 mmol) in DMF (5 mL) was added sodium hydride (60% oil, 1.99 mmol) at room temperature, and the mixture was stirred for 30 min. To the reaction mixture was added 1-(chloromethyl)-4-methoxybenzene (283 μL, 2.09 mmol) at room temperature, and the mixture was stirred for 15 hr. Water was poured into the reaction mixture, and the mixture was extracted with ethyl acetate (×3). The organic layer was washed with water and saturated brine, and dried over magnesium sulfate, and the solvent was evaporated under reduced pressure. The obtained residue was purified by silica gel column chromatography (solvent gradient; 8→50% ethyl acetate/hexane) to give ethyl 3-(N-(1,3-diethyl-2,4-dioxo-1,2,3,4-tetrahydroquinazolin-6-yl)-N-(4-methoxybenzyl)sulfamoyl)propanoate (808 mg, 1.561 mmol, 82%) as a pale yellow oil.

$^1$H-NMR (300 MHz, CDCl$_3$): δ1.23-1.34 (9H, m), 2.86 (2H, t, J=7.6 Hz), 3.40 (2H, t, J=7.6 Hz), 3.75 (3H, s), 4.08-4.17 (6H, m), 4.82 (2H, s), 6.78 (2H, d, J=8.7 Hz), 7.07 (1H, d, J=8.7 Hz), 7.16 (2H, d, J=8.7 Hz), 7.44 (1H, dd, J=9.1, 2.6 Hz), 8.14 (1H, d, J=2.3 Hz).

(Step 3)

To a solution of ethyl 3-(N-(1,3-diethyl-2,4-dioxo-1,2,3,4-tetrahydroquinazolin-6-yl)-N-(4-methoxybenzyl)sulfamoyl)propanoate (803 mg, 1.55 mmol) in a mixed solvent of THF (6 mL) and ethanol (6 mL) was added 2N aqueous lithium hydroxide solution (7.76 mL, 15.5 mmol) at room temperature, and the mixture was stirred for 1 hr. Water (80 mL) was poured into the reaction mixture, and the mixture was extracted with a mixed solvent of diethyl ether and ethyl acetate (3:1, v/v) (×3). The pH of the aqueous layer was adjusted to 4 with 2N hydrochloric acid, and the mixture was extracted with a mixed solvent of diethyl ether and ethyl acetate (3:1, v/v) (×3). The organic layer was washed with water and saturated brine, and dried over magnesium sulfate, and the solvent was evaporated under reduced pressure to give 3-(N-(1,3-diethyl-2,4-dioxo-1,2,3,4-tetrahydroquinazolin-6-yl)-N-(4-methoxybenzyl)sulfamoyl)propanoic acid (117 mg, 0.239 mmol, 15%) as a pale yellow oil.

(Step 4)

To a solution of 3-(N-(1,3-diethyl-2,4-dioxo-1,2,3,4-tetrahydroquinazolin-6-yl)-N-(4-methoxybenzyl)sulfamoyl) propanoic acid (113 mg, 0.23 mmol), 4-amino-2-chlorobenzonitrile (38.7 mg, 0.25 mmol) and DIEA (201 μL, 1.15 mmol) in ethyl acetate (3 mL) was added T3P (50% ethyl acetate solution, 206 μL, 0.35 mmol) at room temperature, and the mixture was stirred at 60° C. for 3 days. The reaction mixture was added to aqueous sodium hydrogencarbonate solution, and the mixture was extracted with ethyl acetate (×3). The organic layer was washed with water and saturated brine, and dried over magnesium sulfate, and the solvent was evaporated under reduced pressure. The obtained residue was purified by silica gel column chromatography (solvent gradient; 10→60% ethyl acetate/hexane) to give N-(3-chloro-4-cyanophenyl)-3-(N-(1,3-diethyl-2,4-dioxo-1,2,3,4-tetrahydroquinazolin-6-yl)-N-(4-methoxybenzyl)sulfamoyl)propanamide (47 mg, 0.075 mmol, 33%) as a pale yellow oil.

$^1$H-NMR (300 MHz, CDCl$_3$): δ1.23-1.34 (6H, m), 2.93 (2H, t, J=7.2 Hz), 3.51 (2H, t, J=7.0 Hz), 3.75 (3H, s), 4.13 (4H, qd, J=7.1, 2.1 Hz), 4.81 (2H, s), 6.78 (2H, d, J=8.7 Hz), 7.09 (1H, d, J=9.1 Hz), 7.14 (2H, d, J=8.7 Hz), 7.44 (1H, dd, J=8.7, 2.6 Hz), 7.48 (1H, dd, J=8.5, 2.1 Hz), 7.59 (1H, d), 7.85 (1H, d, J=1.9 Hz), 8.10 (1H, s), 8.14 (1H, d, J=2.6 Hz).

(Step 5)

A solution of N-(3-chloro-4-cyanophenyl)-3-(N-(1,3-diethyl-2,4-dioxo-1,2,3,4-tetrahydroquinazolin-6-yl)-N-(4-methoxybenzyl)sulfamoyl)propanamide (46 mg, 0.07 mmol) in TFA (1 mL) was stirred at room temperature for 40 min. The reaction mixture was poured into saturated aqueous sodium hydrogencarbonate solution, and the mixture was extracted with ethyl acetate (×3). The organic layer was washed with water and saturated brine, and dried over magnesium sulfate, and the solvent was evaporated under reduced pressure. The obtained crude crystals were washed with ethyl acetate/IPE to give the title compound (23.8 mg, 0.047 mmol, 64%) as a pale yellow powder.

MS(API): 502 (M−H)

$^1$H-NMR (400 MHz, DMSO-d$_6$): δ1.14 (3H, t, J=7.2 Hz), 1.20 (3H, m), 2.83 (2H, t, J=7.0 Hz), 3.47 (2H, t, J=7.0 Hz), 3.95 (2H, q, J=6.8 Hz), 4.09 (2H, q, J=6.8 Hz), 7.44-7.50 (2H, m), 7.60 (1H, m), 7.82-7.91 (3H, m), 10.08 (1H, s), 10.57 (1H, s).

Example 128

N-(4-((3-chloro-4-cyanophenyl)amino)-2-methyl-4-oxobutyl)-1,3-dicyclopropyl-2,4-dioxo-1,2,3,4-tetrahydropyrido[2,3-d]pyrimidine-6-carboxamide (Step 1)

To a solution of benzyl isocyanate (25.0 g, 187.97 mmol) in THF (900 mL) was added benzylamine (22.55 mL, 206.77 mmol) at room temperature, and the mixture was stirred for 16 hr. The reaction mixture was concentrated under reduced pressure to give 1,3-dibenzyl urea (45 g, 100%) as a white solid.

$^1$H-NMR (400 MHz, DMSO-d$_6$): δ4.24 (d, 4H, J=6.00 Hz), 6.44 (t, 2H, J=5.88 Hz), 7.20-7.33 (m, 10H)

(Step 2)

To a solution of 1,3-dibenzyl urea (23 g, 95.83 mmol) in acetic anhydride (230 mL) was added cyanoacetic acid (8.96 g, 105.42 mmol) at room temperature, and the mixture was stirred at 70° C. for 16 hr. The reaction mixture was concentrated under reduced pressure, and to the residue was added ethanol (30 mL). The pH of the mixture was adjusted to >10 with 5% aqueous sodium hydroxide solution at 0° C. Then, the mixture was extracted with ethyl acetate. The organic layer was washed with water and saturated brine, and dried over sodium sulfate, and the solvent was evaporated under reduced pressure to give crude 6-amino-1,3-dibenzyl-1H-pyrimidine-2,4-dione (23 g, 78%) as a yellow solid.

(Step 3)

To a solution of the crude 6-amino-1,3-dibenzyl-1H-pyrimidine-2,4-dione (20 g, 65.15 mmol) in methanol (200 mL) was added N,N-dimethylformamide dimethyl acetal (17.42 mL, 130.29 mmol) at room temperature, and the mixture was stirred for 48 hr. The reaction mixture was concentrated under reduced pressure to give crude N'-(1,3-dibenzyl-2,6-dioxo-1,2,3,6-tetrahydropyrimidin-4-yl)-N,N-dimethylformamidine (20 g, 85%) as a pale yellow oil.

(Step 4)

To a solution of the crude N'-(1,3-dibenzyl-2,6-dioxo-1,2,3,6-tetrahydropyrimidin-4-yl)-N,N-dimethylformamidine (48 g, 132.60 mmol) in dichloromethane (1.92 L) was added N-iodosuccinimide (35.80 g, 159.12 mmol) at room temperature, and the mixture was heated under reflux for 1 hr. The reaction mixture was washed with water and saturated brine, and dried over sodium sulfate, and the solvent was evaporated under reduced pressure to give crude N'-(1,3-dibenzyl-5-iodo-2,6-dioxo-1,2,3,6-tetrahydropyrimidin-4-yl)-N,N-dimethylformamidine (60 g, 93%) as a brownish-red solid.

(Step 5)

To a solution of the crude N'-(1,3-dibenzyl-5-iodo-2,6-dioxo-1,2,3,6-tetrahydropyrimidin-4-yl)-N,N-dimethylformamidine (23 g, 47.13 mmol) in DMF (800 mL) were added palladium acetate (0.529 g, 2.36 mmol), copper iodide(I) (0.275 g, 1.41 mmol) and potassium carbonate (9.44 g, 68.34 mmol) at room temperature, and the mixture was degassed under argon gas. To the mixture was added ethyl acrylate (7.53 mL, 70.70 mmol) at room temperature, and the mixture was stirred at 100° C. for 6 hr. To the reaction mixture was added ethyl acetate, and the mixture was washed with water and saturated brine, and dried over sodium sulfate, and the solvent was evaporated under reduced pressure. The obtained residue was purified by silica gel column chromatography (solvent; 10% ethyl acetate/hexane) to give ethyl 1,3-dibenzyl-2,4-dioxo-1,2,3,4-tetrahydro-pyrido[2,3-d]pyrimidine-6-carboxylate (12.16 g, 62%) as a white solid.

$^1$H-NMR (400 MHz, DMSO-d$_6$): δ1.34 (t, 3H, J=7.08 Hz), 4.36 (q, 2H, J=7.12 Hz), 5.14 (s, 2H), 5.48 (s, 2H), 7.21-7.36 (m, 10H), 8.75 (d, 1H, J=2.20 Hz), 9.16 (d, 1H, J=2.16 Hz).

(Step 6)

To a solution of ethyl 1,3-dibenzyl-2,4-dioxo-1,2,3,4-tetrahydro-pyrido[2,3-d]pyrimidine-6-carboxylate (0.2 g, 0.48 mmol) in methanol (8 mL) were added 20% palladium hydroxide carbon (0.338 g, 0.48 mmol) and ammonium formate (0.607 g, 9.64 mmol) at room temperature, and the mixture was heated under reflux for 1 hr. The reaction mixture was filtered through Celite, and the filtrate was concentrated under reduced pressure. The obtained residue was purified by silica gel column chromatography (solvent; 10% methanol/dichloromethane) to give ethyl 2,4-dioxo-1,2,3,4-tetrahydro-pyrido[2,3-d]pyrimidine-6-carboxylate (0.083 g, 74%) as a grayish white solid.

$^1$H-NMR (400 MHz, DMSO-d$_6$): δ1.34 (t, 3H, J=7.00 Hz), 4.35 (q, 2H, J=7.08 Hz), 8.58 (d, 1H, J=2.12 Hz), 9.05 (d, 1H, J=2.20 Hz), 11.69 (brs, 1H), 12.06 (brs, 1H).

(Step 7)

To a solution of ethyl 2,4-dioxo-1,2,3,4-tetrahydro-pyrido[2,3-d]pyrimidine-6-carboxylate (2 g, 8.51 mmol) in dichloroethane (160 mL) were added sodium carbonate (2.704 g, 25.53 mmol), cyclopropylboronic acid (2.19 g, 25.53 mmol), copper(II) acetate (3.08 g, 17.02 mmol) and 2,2'-bipyridine (2.65 g, 17.02 mmol) at room temperature, and the mixture was heated at 80° C. under oxygen gas atmosphere. The reaction mixture was concentrated under reduced pressure, and to the residue was added ethyl acetate. The organic layer was washed with water and saturated brine, and dried over sodium sulfate, and the solvent was evaporated under reduced pressure. The obtained residue was purified by silica gel column chromatography (solvent; 15% ethyl acetate/hexane) to give ethyl 1,3-dicyclopropyl-2,4-dioxo-1,2,3,4-tetrahydro-Jo pyrido[2,3-d]pyrimidine-6-carboxylate (0.7 g, 26%) as a grayish white solid.

$^1$H-NMR (400 MHz, DMSO-d$_6$): δ0.73-0.80 (m, 4H), 1.00-1.16 (m, 4H), 1.35 (t, 3H, J=7.08 Hz), 2.65-2.69 (m, 1H), 2.86-2.89 (m, 1H), 4.36 (q, 2H, J=7.04 Hz), 8.63 (d, 1H, J=2.24 Hz), 9.14 (d, 1H, J=2.08 Hz).

(Step 8)

To a solution of ethyl 1,3-dicyclopropyl-2,4-dioxo-1,2,3,4-tetrahydro-pyrido[2,3-d]pyrimidine-6-carboxylate (0.75 g, 2.38 mmol) in dichloromethane (14 mL) was added boron tribromide (1.15 mL, 11.9 mmol) at −78° C., and the mixture was stirred at −78° C. for 1 hr, and then at room temperature for 5 hr. The reaction mixture was cooled to 0° C., water was added thereto, and the mixture was extracted with dichloromethane. The organic layer was washed with water and saturated brine, and dried over sodium sulfate, and the solvent was evaporated under reduced pressure. The obtained residue was purified by silica gel column chromatography (solvent; 10% methanol/dichloromethane) to give 1,3-dicyclopropyl-2,4-dioxo-1,2,3,4-tetrahydro-pyrido[2,3-d]pyrimidine-6-carboxylic acid (0.185 g, 27%) as a grayish white solid.

$^1$H-NMR (400 MHz, DMSO-d$_6$): δ0.70-0.80 (m, 4H), 0.99-1.17 (m, 4H), 2.63-2.69 (m, 1H), 2.84-2.89 (m, 1H), 8.63 (d, 1H, J=1.88 Hz), 9.11 (d, 1H, J=1.96 Hz). (the peak of CO$_2$H was not observed)

(Step 9)

To a solution of 1,3-dicyclopropyl-2,4-dioxo-1,2,3,4-tetrahydro-pyrido[2,3-d]pyrimidine-6-carboxylic acid (0.08 g, 0.30 mmol) and 4-amino-N-(3-chloro-4-cyanophenyl)-3-methylbutanamide (0.076 g, 0.30 mmol) in ethyl acetate (5 mL) were added DIEA (0.21 mL, 1.22 mmol) and T3P (50% ethyl acetate solution, 0.44 mL, 0.76 mmol) at room temperature, and the mixture was heated under reflux for 16 hr. To the reaction mixture was added water, and the mixture was extracted with ethyl acetate. The organic layer was washed with water and saturated brine, and dried over sodium sulfate, and the solvent was evaporated under reduced pressure. The obtained residue was purified by preparative HPLC to give the title compound (0.012 g, 7.6%) as a grayish white solid.

MS(API): 521 (M+H)

$^1$H-NMR (300 MHz, CDCl$_3$): δ0.81-0.86 (m, 4H), 1.13 (d, 3H, J=6.04 Hz), 1.19-1.33 (m, 4H), 2.32-2.36 (m, 3H), 2.80-2.82 (m, 1H), 2.95-2.98 (m, 1H), 3.50-3.59 (m, 2H), 6.71 (m, 1H), 7.56 (d, 1H, J=8.56 Hz), 7.64 (dd, 1H, J=1.92, 8.44 Hz), 7.99 (d, 1H, J=1.76 Hz), 8.69 (d, 1H, J=2.44 Hz), 9.17 (d, 1H, J=2.40), 9.79 (s, 1H).

purification condition by preparative HPLC
    instrument: Waters auto purification instrument
    column: X Bridge C18 (250×19 mm) 5 μm
    solvent: A=5 mM aqueous ammonium acetate solution, B=acetonitrile
    solvent gradient: 90% A/B(0 min)→65% A/B(1 min)→65% A/B(10 min)→55% A/B(26 min)→0% A/B(27 min)→0% A/B(30 min)→90% A/B(30 min)→90% A/B(16 min)
    flow rate: 14 mL/min
    temperature: room temperature Example 129

N-(3-chloro-4-cyanophenyl)-N'-(1,3-diethyl-8-fluoro-2,4-dioxo-1,2,3,4-tetrahydroquinazolin-6-yl)-3-methylpentanediamide (Step 1)

To a solution of 2-amino-5-bromo-3-fluorobenzoic acid (3.0 g, 12.8 mmol) in DMF (60 mL) were added HATU (6.34 g, 16.67 mmol) and DIEA (23.6 mL, 128.2 mmol) at 0° C., and the mixture was stirred at 0° C. for 15 min. To the reaction mixture was added ethylamine solution (2 mol/L, THF solution, 19 mL, 38 mmol) at room temperature, and the mixture was stirred for 24 hr. The solvent was evaporated under reduced pressure, and to the residue was added ethyl acetate. The organic layer was washed with aqueous sodium carbonate solution, aqueous ammonium chloride solution, water and saturated brine, and dried over sodium sulfate, and the solvent was evaporated under reduced pressure. The obtained residue was purified by silica gel column chromatography (solvent; 20% ethyl acetate/hexane) to give 2-amino-5-bromo-N-ethyl-3-fluorobenzamide (2.1 g, 63%) as a grayish white solid.

$^1$H-NMR (300 MHz, CDCl$_3$): δ1.24 (3H, t, J=7.2 Hz), 3.40-3.47 (2H, m), 5.58 (2H, brs), 5.96 (1H, brs), 7.16-7.25 (2H, m).

(Step 2)

To a solution of 2-amino-5-bromo-N-ethyl-3-fluorobenzamide (1.5 g, 5.74 mmol) in THF (20 mL) were added TEA (2.45 mL, 17.24 mmol) and 20% phosgene toluene solution (5.65 mL, 11.49 mmol) at 0° C., and the mixture was heated under reflux for 16 hr. The reaction mixture was concentrated under reduced pressure, and to the residue were added ice water and ethyl acetate. The organic layer was washed with water, and dried over sodium sulfate, and the solvent was evaporated under reduced pressure. The obtained residue was purified by silica gel column chromatography (solvent gradient; 10→20% ethyl acetate/hexane) to give 6-bromo-3-ethyl-8-fluoro-1H-quinazoline-2,4-dione (1.2 g, 72%) as a grayish white solid.

$^1$H-NMR (300 MHz, CDCl$_3$): δ1.27 (3H, t, J=7.2 Hz), 4.10 (2H, q, J=7.1 Hz), 7.51 (1H, dd, J=1.9, 9.2 Hz), 8.06 (1H, s), 8.23 (1H, brs).

(Step 3)

To a solution of 6-bromo-3-ethyl-8-fluoro-1H-quinazoline-2,4-dione (1.5 g, 5.23 mmol) in DMF (15 mL) were added potassium carbonate (1.08 g, 7.84 mmol) and ethyl iodide (1.1 mL, 13.1 mmol) at room temperature, and the mixture was heated under reflux for 4 hr. The reaction mixture was concentrated under reduced pressure, and to the residue were added ice water and ethyl acetate. The organic layer was washed with water, and dried over sodium sulfate, and the solvent was evaporated under reduced pressure. The obtained residue was purified by silica gel column chromatography (solvent; 6% ethyl acetate/hexane) to give 6-bromo-1,3-diethyl-8-fluoro-1H-quinazoline-2,4-dione (1.1 g, 76%) as a yellow solid.

$^1$H-NMR (400 MHz, DMSO-d$_6$): δ1.16 (3H, t, J=7.0 Hz), 1.27 (3H, t, J=6.8 Hz), 3.95 (2H, q, J=9.6 Hz), 4.14 (2H, q, J=3.3 Hz), 7.98-8.04 (2H, m).

(Step 4)

To a solution of 6-bromo-1,3-diethyl-8-fluoro-1H-quinazoline-2,4-dione (300 mg, 1.73 mmol) and benzophenonimine (344 mg, 1.90 mmol) in DMF (10 mL) were added Pd$_2$(dba)$_3$ (43 mg, 0.048 mmol), XPhos (55 mg, 0.095 mmol) and cesium carbonate (773 mg, 4.43 mmol) at room temperature, and the mixture was stirred at 120° C. for 16 hr. The reaction mixture was allowed to be cooled to room temperature, and ethyl acetate was added thereto. The organic layer was washed with saturated brine, and dried over sodium sulfate, and the solvent was evaporated under reduced pressure to give crude 6-(benzhydrylidenamino)-1,3-diethyl-8-fluoro-1H-quinazoline-2,4-dione (390 mg, 100%) as a brownish-red oil.

(Step 5)

To a solution of the crude 6-(benzhydrylidenamino)-1,3-diethyl-8-fluoro-1H-quinazoline-2,4-dione (500 mg, 1.2 mmol) in THF (10 mL) was added 2N hydrochloric acid (10 mL) at room temperature, and the mixture was stirred for 1 hr. To the reaction mixture was added ice water, and the mixture was basified with aqueous sodium carbonate solution. Ethyl acetate was added thereto, the organic layer was dried over sodium sulfate, and the solvent was evaporated under reduced pressure. The obtained residue was purified by silica gel column chromatography (solvent; 20% ethyl acetate/hexane) to give 6-amino-1,3-diethyl-8-fluoro-1H-quinazoline-2,4-dione (140 mg, 76%) as a yellow solid.

$^1$H-NMR (400 MHz, DMSO-d$_6$): δ1.13 (3H, t, J=7.0 Hz), 1.22 (3H, t, J=6.6 Hz), 3.95 (2H, q, J=7.0 Hz), 4.09 (2H, q, J=2.8 Hz), 5.56 (2H, s), 6.83 (1H, dd, J=2.6, 16.7 Hz), 7.13 (1H, d, J=2.6 Hz).

(Step 6)

To a solution of 6-amino-1,3-diethyl-8-fluoro-1H-quinazoline-2,4-dione (130 mg, 0.51 mmol) in ethyl acetate (10 mL) were added 4-(3-chloro-4-cyanophenylcarbamoyl)-3-methylbutyric acid (174 mg, 0.62 mmol), DIEA (0.32 mL, 1.81 mmol) and T3P (50% ethyl acetate solution, 0.41 mL, 1.29 mmol) at room temperature, and the mixture was heated under reflux for 16 hr. To the reaction mixture was added ethyl acetate. The organic layer was washed with water, and dried over sodium sulfate, and the solvent was evaporated under reduced pressure. The obtained residue was purified by silica gel column chromatography (solvent; 40% ethyl acetate/hexane) to give the title compound (60 mg, 22%) as a grayish white solid.

MS(API): 512 (M−H)

$^1$H-NMR (400 MHz, DMSO-d$_6$): δ1.00 (3H, d, J=6.5 Hz), 1.16 (3H, t, J=6.8 Hz), 1.27 (3H, t, J=6.6 Hz), 2.29-2.50 (5H, m), 3.96 (2H, q, J=6.9 Hz), 4.13-4.16 (2H, m), 7.55 (1H, dd, J=1.8, 8.7 Hz), 7.83 (1H, d, J=8.7 Hz), 7.93-7.96 (1H, m), 8.00 (1H, d, J=1.6 Hz), 8.04 (1H, s), 10.28 (1H, s), 10.49 (1H, s).

Example 130

N-(3-chloro-4-cyanophenyl)-N'-(1,3-diethyl-7-fluoro-2,4-dioxo-1,2,3,4-tetrahydroquinazolin-6-yl)-3-methylpentanediamide (Step 1)

To a solution of 2-amino-5-bromo-4-fluorobenzoic acid (3.0 g, 12.8 mmol) in DMF (60 mL) were added HATU (6.34 g, 16.67 mmol) and DIEA (23.6 mL, 128.2 mmol) at 0° C., and the mixture was stirred at 0° C. for 15 min. To the reaction mixture was added ethylamine solution (2 mol/L, THF solution, 19 mL, 38 mmol) at room temperature, and the mixture was stirred for 24 hr. The solvent was evaporated under reduced pressure, and to the residue was added ethyl acetate. The organic layer was washed with aqueous sodium carbonate solution, aqueous ammonium chloride solution, water and saturated brine, and dried over sodium sulfate, and the solvent was evaporated under reduced pressure. The obtained residue was purified by silica gel column chromatography (solvent; 20% ethyl acetate/hexane) to give 2-amino-5-bromo-N-ethyl-4-fluorobenzamide (2.7 g, 80%) as a white solid.

(Step 2)

To a solution of 2-amino-5-bromo-N-ethyl-4-fluorobenzamide (2.0 g, 7.66 mmol) in THF (20 mL) was added TEA (3.19 mL, 22.99 mmol) and 20% phosgene toluene solution (7 mL, 13.79 mmol) at 0° C., and the mixture was heated under reflux for 16 hr. The reaction mixture was concentrated under reduced pressure, and to the residue were added ice water and ethyl acetate. The organic layer was washed with water, and dried over sodium sulfate, and the solvent was evaporated under reduced pressure. The obtained residue was purified by silica gel column chromatography (solvent gradient; 10→20% ethyl acetate/hexane) to give 6-bromo-3-ethyl-7-fluoroquinazoline-2,4(1H,3H)-dione (500 mg, 23%) as a pale yellow solid.

$^1$H-NMR (400 MHz, DMSO-$d_6$): δ1.14 (3H, t, J=6.9 Hz), 3.90 (2H, q, J=7.04 Hz), 7.05 (1H, d, J=9.4 Hz), 8.14 (1H, d, J=7.4 Hz), 11.64 (1H, brs)

(Step 3)

To a solution of 6-bromo-3-ethyl-7-fluoroquinazoline-2,4(1H,3H)-dione (1.5 g, 5.23 mmol) in DMF (15 mL) were added potassium carbonate (1.08 g, 7.84 mmol) and ethyl iodide (1.1 mL, 13.1 mmol) at room temperature, and the mixture was heated under reflux for 4 hr. The reaction mixture was concentrated under reduced pressure, and to the residue were added ice water and ethyl acetate. The organic layer was washed with water, and dried over sodium sulfate, and the solvent was evaporated under reduced pressure. The obtained residue was purified by silica gel column chromatography (solvent; 6% ethyl acetate/hexane) to give 6-bromo-1,3-diethyl-7-fluoroquinazoline-2,4(1H,3H)-dione (650 mg, 40%) as a yellow solid.

$^1$H-NMR (400 MHz, DMSO-$d_6$): δ1.13-1.20 (6H, m), 3.95 (2H, q, J=7.0 Hz), 4.10 (2H, q, J=7.0 Hz), 7.66 (H, d, J=11.04 Hz), 8.24 (1H, d, J=7.7 Hz).

(Step 4)

To a solution of 6-bromo-1,3-diethyl-7-fluoroquinazoline-2,4(1H,3H)-dione (300 mg, 1.73 mmol) and benzophenonimine (344 mg, 1.90 mmol) in DMF (10 mL) were added Pd$_2$(dba)$_3$ (43 mg, 0.048 mmol), XPhos (55 mg, 0.095 mmol) and cesium carbonate (773 mg, 4.43 mmol) at room temperature, and the mixture was stirred at 110° C. for 16 hr. The reaction mixture was allowed to be cooled to room temperature, and ethyl acetate was added thereto. The organic layer was washed with saturated brine, and dried over sodium sulfate, and the solvent was evaporated under reduced pressure to give crude 6-((diphenylmethylene)amino)-1,3-diethyl-7-fluoroquinazoline-2,4(1H,3H)-dione (250 mg, 63%) as a green oil.

(Step 5)

To a solution of the crude 6-((diphenylmethylene)amino)-1,3-diethyl-7-fluoroquinazoline-2,4(1H,3H)-dione (250 mg, 0.60 mmol) in THF (5 mL) was added 2N hydrochloric acid (10 ml) at room temperature, and the mixture was stirred for 1 hr. To the reaction mixture was added ice water, and the mixture was basified with aqueous sodium carbonate solution. Ethyl acetate was added thereto, the organic layer was dried over sodium sulfate, and the solvent was evaporated under reduced pressure. The obtained residue was purified by silica gel column chromatography (solvent; 10% ethyl acetate/hexane) to give 6-amino-1,3-diethyl-7-fluoroquinazoline-2,4(1H,3H)-dione (100 mg, 66%) as a brown solid.

$^1$H-NMR (400 MHz, DMSO-$d_6$): δ1.11-1.23 (6H, m), 3.94 (2H, q, J=7.0 Hz), 4.04 (2H, q, J=7.00 Hz), 5.33 (2H, s), 7.30 (1H, d, J=13.0 Hz), 7.46 (1H, d, J=9.7 Hz).

(Step 6)

To a solution of 6-amino-1,3-diethyl-7-fluoroquinazoline-2,4(1H,3H)-dione (501 mg, 1.79 mmol) in ethyl acetate (15 mL) were added 4-(3-chloro-4-cyanophenylcarbamoyl)-3-methyl-butyric acid (300 mg, 1.19 mmol), DIEA (0.74 mL, 4.18 mmol) and T3P (50% ethyl acetate solution, 1.03 mL, 2.98 mmol) at room temperature, and the mixture was heated under reflux for 16 hr. To the reaction mixture was added ethyl acetate. The organic layer was washed with water, and dried over sodium sulfate, and the solvent was evaporated under reduced pressure. The obtained residue was purified by silica gel column chromatography (solvent; 60% ethyl acetate/hexane) to give the title compound (162 mg, 26%) as a grayish white solid.

MS(API): 512 (M−H)

$^1$H-NMR (400 MHz, DMSO-$d_6$): δ1.00 (3H, d, J=6.0 Hz), 1.13-1.20 (6H, m), 2.33-2.50 (5H, m), 3.96 (2H, q, J=6.9 Hz), 4.09 (2H, q, J=6.8 Hz), 7.49 (1H, d, J=12.7 Hz), 7.57 (1H, dd, J=1.8, 8.6 Hz), 7.84 (1H, d, J=8.6 Hz), 8.02 (1H, d, J=1.8 Hz), 8.52 (1H, d, J=8.6 Hz), 9.84 (1H, s), 10.51 (1H, s).

Example 131

N-(5-cyano-1-methyl-1H-pyrrol-2-yl)-N'-(1,3-diethyl-2,4-dioxo-1,2,3,4-tetrahydroquinazolin-6-yl)-3-methylpentanediamide (Step 1)

To a solution of 1-methyl-1H-pyrrole-2-carbaldehyde (5.0 g, 45.82 mmol) in pyridine (34.5 mL) was added hydroxylamine hydrochloride (6.368 g, 91.63 mmol) at room temperature, and the mixture was stirred at 95° C. for 10 min. Then, acetic anhydride (27.5 mL) was added thereto, and the mixture was stirred at 95° C. for 2 hr. To the reaction mixture was added water, and the precipitate was collected by filtration. The obtained crude product was purified by silica gel column chromatography (solvent; 5% ethyl acetate/hexane) to give 1-methyl-1H-pyrrole-2-carbonitrile (3.2 g, 65.81%) as a colorless oil.

$^1$H-NMR (400 MHz, DMSO-$d_6$): δ3.76 (s, 3H), 6.14 (dd, 1H, J=2.84, 3.56 Hz), 6.75-6.78 (m, 2H).

(Step 2)

To a solution of 1-methyl-1H-pyrrole-2-carbonitrile (2.5 g, 23.585 mmol) in acetic anhydride (25 mL) was added a solution of fuming nitric acid (1.5 mL) in acetic anhydride (25 mL) at −10° C., and the mixture was stirred at −10° C.

for 30 min. The reaction mixture was poured into ice water, and the precipitate was collected by filtration. The obtained crude product was purified by silica gel column chromatography (solvent gradient; 5→10% ethyl acetate/hexane) to give 1-methyl-5-nitro-1H-pyrrole-2-carbonitrile (0.250 g, 7.0%) as a grayish white solid.

$^1$H-NMR (300 MHz, CDCl$_3$): δ3.86 (s, 3H), 7.30 (d, 1H, J=1.56 Hz), 7.63 (s, 1H).

(Step 3)

To a solution of 1-methyl-5-nitro-1H-pyrrole-2-carbonitrile (0.3 g, 1.987 mmol) in a mixed solvent of ethyl acetate (10 mL) and 1,4-dioxane (0.5 mL) was added 10% palladium on carbon (50% hydrous, 0.211 g), and the mixture was stirred at room temperature for 16 hr under 1 atm of under hydrogen atmosphere. The catalyst was removed by filtration, and the filtrate was concentrated under reduced pressure to give 5-amino-1-methyl-1H-pyrrole-2-carbonitrile (0.22 g, 91%) as a grayish white solid.

$^1$H-NMR (400 MHz, DMSO-d$_6$): δ3.37 (s, 3H), 5.16 (d, 1H, J=4.00 Hz), 5.49 (brs, 2H), 6.67 (d, 1H, J=4.04 Hz).

(Step 4)

To a solution of 5-amino-1-methyl-1H-pyrrole-2-carbonitrile (0.108 g, 0.90 mmol) and 4-(1,3-diethyl-2,4-dioxo-1,2,3,4-tetrahydroquinazolin-6-ylcarbamoyl)-3-methylbutyric acid (0.25 g, 0.69 mmol) in ethyl acetate (6 mL) were added DIEA (0.36 mL, 2.08 mmol) and T3P (50% ethyl acetate solution, 1.03 mL, 1.731 mmol) at room temperature, and the mixture was heated under refluxed for 16 hr. The reaction mixture was diluted with ethyl acetate (25 mL), and washed with water and saturated brine. The organic layer was dried over sodium sulfate, and the solvent was evaporated under reduced pressure. The obtained residue was purified by preparative HPLC to give the title compound (0.16 g, 50%) as a grayish white solid.

MS(API): 463 (M−H)

$^1$H-NMR (400 MHz, DMSO-d$_6$): δ1.00 (d, 3H, J=6.16 Hz), 1.15 (t, 3H, J=7.00 Hz), 1.20 (t, 3H, J=7.08 Hz), 2.28-2.46 (m, 5H), 3.52 (s, 3H), 3.98 (q, 2H, J=6.96 Hz), 4.12 (q, 2H, J=6.64 Hz), 6.10 (d, 1H, J=4.16 Hz), 6.88 (d, 1H, J=4.20 Hz), 7.94 (d, 1H, J=8.76 Hz), 8.36 (d, 1H, J=1.80 Hz), 9.91 (s, 1H), 10.14 (s, 1H).

purification condition by preparative HPLC
  instrument: Waters auto purification instrument
  column: X Bridge Prep C18 OBD (250×19 mm) 5 mμ
  solvent: A=5 mM aqueous ammonium acetate solution, B=acetonitrile
  solvent gradient: 90% A/B(0 min)→75% A/B(3 min)→35% A/B(22 min)→0% A/B(23 min)→0% A/B(25 min)→90% A/B(26 min)
  flow rate: 14 mL/min
  temperature: room temperature Example 132

N-(3-chloro-4-cyanophenyl)-N'-(1-(cyanomethyl)-3-ethyl-2,4-dioxo-1,2,3,4-tetrahydroquinazolin-6-yl)-3-methylpentanediamide (Step 1)

To a solution of 1-ethyl-6-nitro-1H-quinazoline-2,4-dione (400 mg, 1.70 mmol) in DMF (5 mL) were added sodium hydride (60% oil, 82.0 mg, 3.40 mmol) and bromoacetonitrile (0.35 mL, 4.25 mmol) at 0° C., and the mixture was stirred at room temperature for 5 hr. To the reaction mixture was added water, and the mixture was extracted with ethyl acetate. The organic layer was washed with saturated brine, and dried over sodium sulfate, and the solvent was evapo-rated under reduced pressure. The obtained crude crystals were washed with 2% ethyl acetate/hexane to give (3-ethyl-6-nitro-2,4-dioxo-3,4-dihydro-2H-quinazolin-1-yl)acetonitrile (385 mg, 83%) as a grayish white solid.

$^1$H-NMR (400 MHz, DMSO-d$_6$): δ1.19 (t, 3H, J=7.0 Hz), 3.99 (q, 2H, J=7.0 Hz), 5.39 (s, 2H), 7.81 (d, 1H, J=9.24 Hz), 8.63 (dd, 1H, J=6.48, 2.64 Hz), 8.74 (d, 1H, J=2.60 Hz).

(Step 2)

To a solution of (3-ethyl-6-nitro-2,4-dioxo-3,4-dihydro-2H-quinazolin-1-yl)acetonitrile (385 mg, 1.40 mmol) in ethanol (100 mL) was added tin(II) chloride (799 mg, 4.21 mmol) at room temperature, and the mixture was heated under reflux for 2 hr. The reaction mixture was concentrated under reduced pressure, and to the residue was added water. The pH of the mixture was adjusted to 8 or more with saturated aqueous sodium carbonate solution, and the mixture was extracted with ethyl acetate. The organic layer was washed with water, and dried over sodium sulfate, and the solvent was evaporated under reduced pressure to give (6-amino-3-ethyl-2,4-dioxo-3,4-dihydro-2H-quinazolin-1-yl)acetonitrile (300 mg, 87%) as a pale yellow solid.

$^1$H-NMR (400 MHz, DMSO-d$_6$): δ1.14 (t, 3H, J=4.08), 3.93-3.99 (m, 2H), 5.20 (s, 2H), 5.40 (s, 2H), 7.06 (dd, 1H, J=9.24, 2.04 Hz), 7.28 (d, 1H, J=2.32 Hz), 7.30 (s, 1H).

(Step 3)

To a solution of 4-(3-chloro-4-cyanophenylcarbamoyl)-3-methylbutyric acid (345 mg, 1.23 mmol) in ethyl acetate (125 mL) were added DIEA (536 μL, 3.07 mmol), T3P (50% ethyl acetate solution, 922 μL, 3.07 mmol) and (6-amino-3-ethyl-2,4-dioxo-3,4-dihydro-2H-quinazolin-1-yl)acetonitrile (300 mg, 1.23 mmol) at room temperature, and the mixture was heated under refluxed for 5 hr. To the reaction mixture was added water, and the mixture was extracted with ethyl acetate. The organic layer was washed with saturated brine, and dried over sodium sulfate, and the solvent was evaporated under reduced pressure. The obtained residue was purified by preparative HPLC to give the title compound (65 mg, 10%) as a grayish white solid.

MS(API): 505 (M−H)

$^1$H-NMR (400 MHz, DMSO-d$_6$): δ1.00 (d, 3H, J=6.40 Hz), 1.17 (t, 3H, J=7.04 Hz), 2.29-2.67 (m, 5H), 3.97 (q, 2H, J=6.96 Hz), 5.27 (s, 2H), 7.53 (d, 1H, J=9.12 Hz), 7.57 (dd, 1H, J=6.88, 1.76 Hz), 7.85 (d, 1H, J=8.64 Hz), 7.96 (dd, 1H, J=6.60, 2.32 Hz), 8.02 (d, 1H, J=1.80 Hz), 8.38 (d, 1H, J=2.36 Hz), 10.21 (s, 1H), 10.52 (s, 1H)

purification condition by preparative HPLC
  instrument: Waters Semi-Preparative HPLC instrument
  column: Prep Scalar 10 μm C18(250×30 mm)
  solvent: A=5 mM aqueous ammonium acetate solution, B=acetonitrile
  solvent gradient: 90% A/B(0 min)→70% A/B(15 min)→30% A/B(60 min)→5% A/B(61 min)→5% A/B(70 min)→90% A/B(71 min)
  flow rate: 30 mL/min
  temperature: room temperature Example 133

N-(3-chloro-4-cyanophenyl)-N'-(1-(2-cyanoethyl)-3-ethyl-2,4-dioxo-1,2,3,4-tetrahydroquinazolin-6-yl)-3-methylpentanediamide (Step 1)

A solution of methyl 2-fluoro-5-nitrobenzoate (800 mg, 4.02 mmol), potassium carbonate (833 mg, 6.03 mmol) and 1-bromo-3-methoxypropane (0.879 mL, 12.05 mmol) in THF (10 mL) was sealed at 0° C., and the mixture was stirred at 70° C. for 5 hr. To the reaction mixture was added ice water, and the mixture was extracted with ethyl acetate (×4). The organic layer was washed with saturated brine, and dried over sodium sulfate, and the solvent was evaporated under reduced pressure to give methyl 2-(2-cyanoethyl-amino)-5-nitrobenzoate (959 mg, 96%) as a yellow solid.
(Step 2)

To a solution of methyl 2-(2-cyanoethylamino)-5-nitrobenzoate (500 mg, 2.02 mmol) in a mixed solvent of THF and water (4:1, v/v, 20 mL) was added lithium hydroxide hydrate (169 mg, 4.03 mmol) at 0° C., and the mixture was stirred at room temperature for 3 hr. The reaction mixture was concentrated under reduced pressure, and to the obtained residue was added ice water, and the pH of the mixture was adjusted to 4 to 5 with 50% hydrochloric acid. The mixture was extracted with 10% methanol/dichloromethane (×6), the organic layer was washed with saturated brine, and dried over sodium sulfate, and the solvent was evaporated under reduced pressure to give 2-(2-cyanoethyl-amino)-5-nitrobenzoic acid (400 mg, 84%) as a grayish white solid.

$^1$H-NMR (400 MHz, DMSO-d$_6$): δ2.87 (t, 2H, J=6.60 Hz), 3.71 (q, 2H, J=6.56 Hz), 7.07 (d, H, J=9.52 Hz), 8.19 (dd, 1H, J=6.68, 2.76 Hz), 8.66 (d, 1H, J=2.72 Hz), 8.93 (t, 1H, J=6.24 Hz), 13.59 (brs, 1H).
(Step 3)

To a solution of 2-(2-cyanoethylamino)-5-nitrobenzoic acid (400 mg, 1.70 mmol) in DMF (5 mL) were added ethylamine (2 mol/L, THF solution, 2.68 mL, 5.11 mmol), DIEA (869 μL, 5.11 mmol) and HATU (776.17 mg, 2.04 mmol) at 0° C., and the mixture was stirred at room temperature for 20 hr. To the reaction mixture was added ice water, and the mixture was extracted with ethyl acetate (×3). The organic layer was washed with water, and dried over sodium sulfate, and the solvent was evaporated under reduced pressure. The obtained residue was purified by silica gel column chromatography (solvent; 30% ethyl acetate/hexane) to give 2-(2-cyanoethylamino)-N-ethyl-5-nitrobenzamide (200 mg, 45%) as a yellow solid.

$^1$H-NMR (400 MHz, DMSO-d$_6$): δ1.14 (t, 3H, J=7.20 Hz), 2.84 (t, 2H, J=6.64 Hz), 3.29 (m, 2H), 3.63 (q, 2H, J=6.52 Hz), 6.97 (d, 1H, J=9.40 Hz), 8.13 (dd, H, J=6.86, 2.52 Hz), 8.53 (d, 1H, J=2.52 Hz), 8.84 (t, 1H), 9.09 (t, 1H)
(Step 4)

To a solution of 2-(2-cyanoethylamino)-N-ethyl-5-nitrobenzamide (700 mg, 3.40 mmol) in THF (30 mL) were added triphosgene (1.74 g, 5.88 mmol) and TEA (1.49 mL, 10.69 mmol) at 0° C., and the mixture was heated under reflux for 24 hr. The reaction mixture was concentrated under reduced pressure, to the obtained residue was added ice water, and the mixture was extracted with ethyl acetate (×4). The organic layer was washed with water, and dried over sodium sulfate, and the solvent was evaporated under reduced pressure. The obtained residue was purified by silica gel column chromatography (solvent; 30% ethyl acetate/hexane) to give 3-(3-ethyl-6-nitro-2,4-dioxo-3,4-dihydro-2H-quinazolin-1-yl)propionitrile (400 mg, 52%) as a yellow solid.

$^1$H-NMR (400 MHz, DMSO-d$_6$): δ1.19 (t, 3H, J=7.00 Hz), 2.95 (t, 2H, J=6.68 Hz), 3.99 (t, 2H, J=7.04 Hz), 4.48 (t, 2H, J=6.76 Hz), 7.89 (d, 1H, J=9.32 Hz), 8.52 (dd, 1H, J=6.72, 2.48 Hz), 8.75 (d, 1H, J=2.44 Hz).
(Step 5)

To a solution of 3-(3-ethyl-6-nitro-2,4-dioxo-3,4-dihydro-2H-quinazolin-1-yl)propionitrile (250 mg, 0.867 mmol) in ethanol was added (90 mL) tin(II) chloride (493 mg, 2.602 mmol), and the mixture was heated under reflux for 2 hr. The reaction mixture was concentrated under reduced pressure, and to the residue was added water. The pH of the mixture was adjusted to 8 with saturated aqueous sodium carbonate solution, and the mixture was extracted with ethyl acetate (×4). The organic layer was washed with water, and dried over sodium sulfate, and the solvent was evaporated under reduced pressure to give 3-(6-amino-3-ethyl-2,4-dioxo-3,4-dihydro-2H-quinazolin-1-yl)propionitrile (200 mg, 89%) as a yellow solid.

$^1$H-NMR (400 MHz, DMSO-d$_6$): δ1.13 (t, 3H, J=3.56 Hz), 2.89 (t, 2H, J=6.72 Hz), 4.01-3.93 (m, 2H), 4.33 (t, 2H, J=6.76 Hz), 5.54 (s, 2H), 7.01 (dd, 1H, J=6.20, 2.68 Hz), 7.25 (brs, 1H), 7.32 (d, 1H, J=8.92 Hz).
(Step 6)

To a solution of 4-(3-chloro-4-cyanophenylcarbamoyl)-3-methylbutyric acid (272 mg, 0.97 mmol) in ethyl acetate (150 mL) were added DIEA (0.423 mL, 2.42 mmol), T3P (50% ethyl acetate solution, 0.73 mL, 2.42 mmol) and 3-(6-amino-3-ethyl-2,4-dioxo-3,4-dihydro-2H-quinazolin-1-yl)propionitrile (250 mg, 0.97 mmol) at room temperature, and the mixture was heated under reflux for 5 hr. To the reaction mixture was added water, and the mixture was extracted with ethyl acetate (×3). The organic layer was washed with saturated brine, and dried over sodium sulfate, and the solvent was evaporated under reduced pressure. The obtained residue was purified by preparative HPLC to give the title compound (70 mg, 14%) as a grayish white solid.

MS(API): 519 (M−H)

$^1$H-NMR (400 MHz, DMSO-d$_6$): δ0.99 (d, 3H, J=6.28 Hz), 1.16 (t, 3H, J=6.96 Hz), 2.28-2.50 (m, 5H), 2.92 (t, 2H, J=6.68 Hz), 3.98 (q, 2H, J 6.76 Hz), 4.38 (t, 2H, J=6.72 Hz), 7.56 (d, 2H, J=8.68 Hz), 7.85 (d, 1H, J=8.60 Hz), 7.91 (dd, 1H, J=6.80, 2.24 Hz), 8.03 (d, 1H, J=1.44 Hz), 8.35 (d, 1H, J=2.24 Hz), 10.16 (s, 1H), 10.52 (s, 1H).

purification condition by preparative HPLC
   instrument: Waters Semi-Preparative HPLC instrument
   column: Prep Scalar 10 μm C18(250×30 mm)
   solvent: A=5 mM aqueous ammonium acetate solution, B=acetonitrile
   solvent gradient: 90% A/B(0 min)→70% A/B(15 min)→30% A/B(60 min)→5% A/B(61 min)→5% A/B(70 min)→90% A/B(71 min)
   flow rate: 30 mL/min
   temperature: room temperature Example 134

N-(5-chloro-6-cyanopyridin-3-yl)-N'-(1,3-diethyl-2,4-dioxo-1,2,3,4-tetrahydroquinazolin-6-yl)-3-methylpentanediamide (Step 1)

To a solution of 2,3-dichloro-5-nitropyridine (1.0 g, 5.181 mmol) in acetic acid (12 mL) was added potassium iodide (3.01 mg, 18.13 mmol) at room temperature, and the mixture was stirred at 100° C. for 3 hr. The reaction mixture was concentrated under reduced pressure, and to the residue was added ethyl acetate. The organic layer was washed with water and saturated brine, and dried over sodium sulfate, and the solvent was evaporated under reduced pressure. The obtained residue was purified by silica gel column chromatography (solvent; 20% ethyl acetate/hexane) to give crude 3-chloro-2-iodo-5-nitropyridine (1.6 g) as a brown solid.
(Step 2)

To a solution of the crude 3-chloro-2-iodo-5-nitropyridine (1.6 g, 5.63 mmol) in acetonitrile (45 mL) was added copper(I) cyanide (1.937 g, 22.53 mmol) at room temperature, and the mixture was heated under reflux for 5 hr. To the reaction mixture was added ethyl acetate, the organic layer was washed with water and saturated brine, and dried over sodium sulfate, and the solvent was evaporated under reduced pressure. The obtained residue was purified by silica gel column chromatography (solvent; 10% ethyl acetate/hexane) to give 3-chloro-5-nitropyridine-2-carbonitrile (0.2 g, 21%, Step 1 and 2) as a grayish white solid.

$^1$H-NMR (400 MHz, DMSO-$d_6$): δ9.17 (d, 1H, J=2.20 Hz), 9.46 (d, 1H, J=2.04 Hz).

(Step 3)

To a solution of 3-chloro-5-nitropyridine-2-carbonitrile (0.18 g, 0.984 mmol) in ethanol (6.0 mL) was added tin(II) chloride (0.929 g, 4.918 mmol), and the mixture was heated under refluxed for 2 hr. The reaction mixture was allowed to be cooled to room temperature, and the pH of the mixture was adjusted to 7 with saturated aqueous sodium hydrogencarbonate solution. The mixture was extracted with ethyl acetate (×3), the organic layer was washed with water and saturated brine, and dried over sodium sulfate, and the solvent was evaporated under reduced pressure to give 5-amino-3-chloropyridine-2-carbonitrile (0.13 g, 87%) as a grayish white solid.

$^1$H-NMR (400 MHz, DMSO-$d_6$): δ6.77 (brs, 2H), 7.05 (d, 1H, J=2.32 Hz), 7.94 (d, 1H, J=2.28 Hz).

(Step 4)

To a solution of 5-amino-3-chloropyridine-2-carbonitrile (0.126 g, 0.69 mmol) and 4-(1,3-diethyl-2,4-dioxo-1,2,3,4-tetrahydroquinazolin-6-ylcarbamoyl)-3-methylbutyric acid (0.25 g, 0.69 mmol) in ethyl acetate (4 mL) were added DIEA (0.36 mL, 2.08 mmol) and T3P (50% ethyl acetate solution, 1.0 mL, 1.731 mmol) at room temperature, and the mixture was heated under reflux for 16 hr. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative HPLC to give the title compound (0.035 g, 10%) as a grayish white solid.

MS(API): 495 (M−H)

$^1$H-NMR (400 MHz, DMSO-$d_6$): δ1.01 (d, 3H, J=6.20 Hz), 1.15 (t, 3H, J=7.00 Hz), 1.20 (t, 3H, J=7.04 Hz), 2.32-2.41 (m, 4H), 2.54 (m, 1H), 3.97 (q, 2H, J=7.00 Hz), 4.11 (q, 2H, J=7.08 Hz), 7.43 (d, 1H, J=9.08 Hz), 7.88 (d, 1H, J=8.56 Hz), 8.31 (s, 1H), 8.42 (s, 1H), 8.64 (s, 1H), 10.14 (s, 1H), 10.80 (s, 1H).

purification condition by preparative HPLC
   instrument: Waters auto purification instrument
   column: X Terra Prep RP18 OBD (250×19 mm) 10 mμ
   solvent: A=5 mM aqueous ammonium acetate solution, B=acetonitrile
   solvent gradient: 90% A/B(0 min)→60% A/B(3 min)→55% A/B(10 min)→50% A/B(26 min)→0% A/B(27 min)→0% A/B(29 min)→90% A/B(30 min)
   flow rate: 14 mL/min
   temperature: room temperature Example 135

N-(3-chloro-4-cyanophenyl)-N'-(1,3-diethyl-2,4-dioxo-1,2,3,4-tetrahydropyrido[3,2-d]pyrimidin-6-yl)-3-methylpentanediamide (Step 1)

To a solution of 3-aminopyridine-2-carboxylic acid (20 g, 144.9 mmol) in methanol (300 mL) was added conc. sulfuric acid (5.4 mL), and the mixture was heated under reflux for 5 days. The reaction mixture was concentrated under reduced pressure, water was added thereto, and sodium carbonate was added thereto until the complete of foaming. The mixture was extracted with dichloromethane (×3), the organic layer was dried over sodium sulfate, and the solvent was evaporated under reduced pressure to give methyl 3-aminopyridine-2-carboxylate (17.0 g, 77%) as a pale yellow solid.

$^1$H-NMR (300 MHz, CDCl$_3$): δ3.95 (3H, s), 5.72 (2H, brs), 7.03 (1H, dd, J=0.99, 8.35 Hz), 7.18-7.21 (1H, m), 8.05 (1H, dd, J=0.96, 4.04 Hz).

(Step 2)

To a mixture of methyl 3-aminopyridine-2-carboxylate (17 g, 111.8 mmol) in a mixed solvent of water (288 mL) and 2M sulfuric acid (58 mL) was added a solution of bromine (5.76 mL, 111.8 mmol) in acetic acid (43 mL) at room temperature, and the mixture was stirred at room temperature for 4 hr. The pH of the mixture was adjusted to 6 with 2N aqueous sodium hydroxide solution. The mixture was extracted with ethyl acetate (×2), the organic layer was dried over sodium sulfate, and the solvent was evaporated under reduced pressure. The obtained residue was purified by silica gel column chromatography (solvent; dichloromethane) to give methyl 3-amino-6-bromopyridine-2-carboxylate (19.2 g, 74%) as a white solid.

$^1$H-NMR (300 MHz, CDCl$_3$): δ3.94 (3H, s), 5.81 (2H, brs), 6.93 (1H, d, J=8.72 Hz), 7.32 (1H, d, J=8.71 Hz).

(Step 3)

To a solution of methyl 3-amino-6-bromopyridine-2-carboxylate (10 g, 43.28 mmol) in a mixed solvent of THF and methanol (2:1, v/v, 142 mL) was added 1M aqueous lithium hydroxide solution (71 mL) at room temperature, and the mixture was stirred at room temperature for 16 hr. To the reaction mixture was added 1N hydrochloric acid (71 mL), and the mixture was concentrated under reduced pressure. The precipitate was collected by filtration, and the crude crystals were washed with water to give to 3-amino-6-bromopyridine-2-carboxylic acid (9.0 g, 96%) as a grayish white solid.

$^1$H-NMR (400 MHz, DMSO-$d_6$): δ6.50-7.05 (1H, brs), 7.18 (1H, d, J=8.76 Hz), 7.42 (1H, d, J=8.76 Hz), 11.20-13.80 (1H, brs). (the peak of CO$_2$H was not observed)

(Step 4)

To a solution of 3-amino-6-bromopyridine-2-carboxylic acid (12 g, 55.29 mmol) in DMF (30 mL) were added HATU (27.33 g, 71.88 mmol) and DIEA (96.3 mL, 552 mmol) at room temperature, and the mixture was stirred at room temperature for 15 min. Ethylamine (2 mol/L, THF solution, 82.94 mL, 165.88 mmol) was added thereto at 5° C., and the mixture was stirred at room temperature for 16 hr. The reaction mixture was concentrated under reduced pressure, ice water was added thereto, and the precipitate was collected by filtration. The crude crystals were washed with water to give 3-amino-6-bromopyridine-2-carboxylic acid ethylamide (12.0 g, 89%) as a brown solid.

$^1$H-NMR (400 MHz, CDCl$_3$): δ1.25 (3H, t, J=7.32 Hz), 3.42 (2H, q, J=7.12 Hz), 6.01 (2H, brs), 6.88 (1H, d, J=8.64 Hz), 7.25 (1H, d, J=8.52 Hz), 7.79 (1H, brs).

(Step 5)

To a solution of 3-amino-6-bromopyridine-2-carboxylic acid ethylamide (2 g, 8.19 mmol) in THF (40 mL) were added CDI (19.936 g, 122.9 mmol) and DBU (6.1 mL, 40.93 mmol) at room temperature, and the mixture was stirred at room temperature for 2 days. To the reaction mixture was added water, and the mixture was extracted with ethyl acetate (×2). The organic layer was washed with water and saturated brine, and dried over magnesium sulfate, and the solvent was evaporated under reduced pressure. The obtained residue was purified by silica gel column chromatography (solvent; 50% ethyl acetate/hexane) to give 6-bromo-3-ethyl-1H-pyrido[3,2-d]pyrimidine-2,4-dione (1.2 g, 54%) as a grayish white solid.

$^1$H-NMR (400 MHz, DMSO-d$_6$): δ1.14 (3H, t, J=7.00 Hz), 3.91 (2H, q, J=7.00 Hz), 7.52 (1H, d, J=8.68 Hz), 7.83 (1H, d, J=8.52 Hz), 11.62 (1H, brs).

(Step 6)

To a solution of 6-bromo-3-ethyl-1H-pyrido[3,2-d]pyrimidine-2,4-dione (4.3 g, 15.93 mmol) in DMF (45 mL) were added potassium carbonate (6.59 g, 47.77 mmol) and ethyl iodide (2.58 mL, 31.85 mmol) at room temperature, and the mixture was stirred at 90° C. for 16 hr. The reaction mixture was concentrated under reduced pressure, to the residue was added water, and the precipitate was collected by filtration. The crude crystals were washed with water to give 6-bromo-1,3-diethyl-1H-pyrido[3,2-d]pyrimidine-2,4-dione (3.3 g, 69%) as a grayish white solid.

$^1$H-NMR (400 MHz, CDCl$_3$): δ1.24-1.35 (6H, m), 4.12-4.19 (4H, m), 7.45 (1H, d, J=8.80 Hz), 7.71 (1H, d, J=8.80 Hz).

(Step 7)

A solution of 6-bromo-1,3-diethyl-1H-pyrido[3,2-d]pyrimidine-2,4-dione (2.7 g, 9.06 mmol), copper(II) oxide (259.29 mg, 1.81 mmol) and aqueous ammonia (20 mL) in NMP (4 mL) was sealed, and the mixture was stirred at 90° C. for 16 hr. The reaction mixture was concentrated under reduced pressure, and the obtained residue was extracted with ethyl acetate. The organic layer was washed with water and saturated brine, and dried over magnesium sulfate, and the solvent was evaporated under reduced pressure. The obtained residue was purified by NH-silica gel column chromatography (solvent; 90% ethyl acetate/hexane) to give 6-amino-1,3-diethyl-1H-pyrido[3,2-d]pyrimidine-2,4-dione (640 mg, 30%) as a yellow solid.

$^1$H-NMR (400 MHz, DMSO-d$_6$): δ1.11-1.23 (6H, m), 3.95 (2H, q, J=7.0 Hz), 4.04 (2H, q, J=6.88 Hz), 6.27 (2H, brs), 6.89 (1H, d, J=9.16 Hz), 7.69 (1H, d, J=9.12 Hz).

(Step 8)

To a solution of 4-(3-chloro-4-cyanophenylcarbamoyl)-3-methylbutyric acid (233.73 mg, 0.83 mmol) in ethyl acetate were added 6-amino-1,3-diethyl-1H-pyrido[3,2-d]pyrimidine-2,4-dione (150 mg, 0.64 mmol), T3P (50% ethyl acetate solution, 1.2 mL, 1.91 mmol) and DIEA (0.5 mL, 2.56 mmol) at room temperature, and the mixture was heated under reflux for 16 hr. To the reaction mixture was added ethyl acetate, the organic layer was washed with water and saturated brine, and dried over sodium sulfate, and the solvent was evaporated under reduced pressure. The obtained residue was purified by silica gel column chromatography (solvent; 80% ethyl acetate/hexane) to give the title compound (35 mg, 11%) as a yellow solid.

MS(API): 497 (M+H)

$^1$H-NMR (400 MHz, DMSO-d$_6$): δ0.90-1.00 (3H, m), 1.17-1.25 (6H, m), 2.28-2.33 (1H, m), 2.37-2.44 (4H, m), 3.98 (2H, q, J=6.84 Hz), 4.11 (2H, q, J=6.80 Hz), 7.56 (1H, dd, J=1.68, 8.56 Hz), 7.84 (1H, d, J=8.56 Hz), 8.01-8.03 (2H, m), 8.43 (1H, d, J=9.20 Hz), 10.49 (1H, brs), 10.97 (1H, brs).

Example 136

N-(3-chloro-4-cyanophenyl)-N'-(1-ethyl-3-(oxetan-3-ylmethyl)-2,4-dioxo-1,2,3,4-tetrahydroquinazolin-6-yl)-3-methylpentanediamide (Step 1)

To a solution of 2-amino-5-nitrobenzoic acid (1.045 g, 5.74 mmol), 3-aminomethyloxetane (500 mg, 5.74 mmol) and DIEA (3.51 mL, 20.09 mmol) in DMF (10 mL) was added T3P (50% ethyl acetate solution, 3.88 mL, 6.60 mmol) at room temperature, and the mixture was stirred at room temperature for 3 days. To the reaction mixture was added water, and the mixture was extracted with ethyl acetate. The organic layer was washed with water and saturated brine, and dried over magnesium sulfate, and the solvent was evaporated under reduced pressure. The obtained residue was crystallized from ethyl acetate/hexane to give 2-amino-5-nitro-N-(oxetan-3-ylmethyl)benzamide (1.010 g, 4.02 mmol, 70.0%) as a yellow solid.

$^1$H-NMR (300 MHz, DMSO-d$_6$): δ3.05-3.26 (1H, m), 3.52 (2H, dd, J=7.0, 5.9 Hz), 4.34 (2H, t, J=6.1 Hz), 4.64 (2H, dd, J=8.0, 6.1 Hz), 6.80 (1H, d, J=9.1 Hz), 7.75 (2H, brs), 8.02 (1H, dd, J=9.3, 2.5 Hz), 8.49 (1H, d, J=2.7 Hz), 8.81 (1H, t, J=5.3 Hz).

(Step 2)

To a solution of 2-amino-5-nitro-N-(oxetan-3-ylmethyl)benzamide (1.01 g, 4.02 mmol) in THF (15 mL) was added CDI (1.304 g, 8.04 mmol) at room temperature, and the mixture was heated under reflux for 12 hr. Then, CDI (1.304 g, 8.04 mmol) was added thereto four time, and the mixture was heated under reflux for 12 hr. The reaction mixture was allowed to be cooled to room temperature, and water was added thereto. The precipitate was collected by filtration to give 6-nitro-3-(oxetan-3-ylmethyl)quinazoline-2,4(1H,3H)-dione (0.906 g, 3.27 mmol, 81%) as a yellow solid.

$^1$H-NMR (300 MHz, CDCl$_3$): δ3.36-3.61 (1H, m), 4.44 (2H, d, J=6.8 Hz), 4.66 (2H, t, J=6.4 Hz), 4.81 (2H, dd, J=7.9, 6.4 Hz), 7.14-7.26 (1H, m), 8.49 (1H, dd, J=9.1, 2.6 Hz), 9.03 (1H, d, J=2.6 Hz), 9.72 (1H, brs).

(Step 3)

A solution of 6-nitro-3-(oxetan-3-ylmethyl)quinazoline-2,4(1H,3H)-dione (895 mg, 3.23 mmol), potassium carbonate (2231 mg, 16.14 mmol) and ethyl iodide (0.387 mL, 4.84 mmol) in DMF (12 mL) was stirred overnight at 60° C. The reaction mixture was allowed to be cooled to room temperature, water was added thereto, and the mixture was extracted with ethyl acetate. The organic layer was washed with water and saturated brine, and dried over magnesium sulfate, and the solvent was evaporated under reduced pressure. The residue was crystallized from ethyl acetate/hexane to give 1-ethyl-6-nitro-3-(oxetan-3-ylmethyl)quinazoline-2,4(1H,3H)-dione (809 mg, 2.65 mmol, 82%) as a grayish white solid.

$^1$H-NMR (300 MHz, CDCl$_3$): δ1.39 (3H, t, J=7.2 Hz), 3.34-3.55 (1H, m), 4.25 (2H, q, J=7.2 Hz), 4.43 (2H, d, J=6.8 Hz), 4.57-4.70 (2H, m), 4.77 (2H, dd, J=7.9, 6.4 Hz), 7.33 (1H, d, J=9.4 Hz), 8.51 (1H, dd, J=9.1, 2.6 Hz), 9.08 (1H, d, J=2.6 Hz).

(Step 4)

A solution of 1-ethyl-6-nitro-3-(oxetan-3-ylmethyl)quinazoline-2,4(1H,3H)-dione (800 mg, 2.62 mmol) and 10% palladium on carbon (50% hydrous, 10 mg, 4.70 μmol) in methanol (12 mL) was stirred overnight at room temperature under 1 atm of under hydrogen atmosphere. The catalyst was removed by filtration, and the filtrate was concentrated under reduced pressure to give 6-amino-1-ethyl-3-(oxetan-3-ylmethyl)quinazoline-2,4(1H,3H)-dione (774 mg, 2.81 mmol, 107%) as a grayish solid.

$^1$H-NMR (300 MHz, DMSO-d$_6$): δ1.17 (3H, t, J=7.00 Hz), 3.19-3.29 (1H, m), 3.94-4.14 (2H, m), 4.23 (2H, d, J=6.8 Hz), 4.42 (2H, t, J=6.2 Hz), 4.58 (2H, dd, J=7.9, 6.0 Hz), 5.28 (2H, s), 7.04 (1H, dd, J=8.7, 2.6 Hz), 7.16-7.29 (2H, m).

(Step 5)

To a solution of 6-amino-1-ethyl-3-(oxetan-3-ylmethyl)quinazoline-2,4(1H,3H)-dione (100 mg, 0.36 mmol), 4-(3-chloro-4-cyanophenylcarbamoyl)-3-methylbutyric acid (102 mg, 0.36 mmol) and DIEA (0.317 mL, 1.82 mmol) in ethyl acetate (6 mL) was added T3P (50% ethyl acetate solution, 0.321 mL, 0.54 mmol) at room temperature, and the mixture was stirred at 80° C. for 1 hr. To the reaction mixture was added water, and the mixture was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane) to give the title compound (106 mg, 0.196 mmol, 54%) as a colorless amorphous solid.

MS(API): 536 (M−H)

$^1$H-NMR (300 MHz, DMSO-d$_6$): δ1.01 (3H, d, J=6.0 Hz), 1.19 (3H, q, J=6.8 Hz), 2.19-2.48 (5H, m), 3.20-3.42 (1H, m), 3.93-4.18 (2H, m), 4.25 (2H, d, J=6.8 Hz), 4.44 (2H, t, J=6.2 Hz), 4.60 (2H, dd, J=7.9, 6.0 Hz), 7.44 (1H, d, J=9.4 Hz), 7.58 (1H, dd, J=8.7, 1.5 Hz), 7.78-7.97 (2H, m), 8.02 (1H, d, J=1.9 Hz), 835 (1H, d, J=2.3 Hz), 10.13 (1H, s), 10.52 (1H, s).

Example 137

N-(3-chloro-4-cyanophenyl)-N'-(1,3-diethyl-2,4-dioxo-1,2,3,4-tetrahydropteridin-6-yl)-3-methylpentanediamide (Step 1)

To a solution of 4-amino-2-chlorobenzonitrile (300 mg, 1.97 mmol) and potassium carbonate (80 mg, 0.295 mmol) in DMSO (1 mL) was added 30% aqueous hydrogen peroxide at 0° C., and the mixture was stirred at 0° C. for 10 min, and then at room temperature for 1.5 hr. To the reaction mixture was added ethyl acetate, the organic layer was washed with water and saturated brine, and dried over sodium sulfate, and the solvent was evaporated under reduced pressure. The obtained crude crystals were washed with a mixed solvent of 50% diethyl ether/hexane to give 4-amino-2-chloro-benzamide (250 mg, 75%) as a brown solid.

$^1$H-NMR (400 MHz, DMSO-d$_6$): δ5.67 (s, 2H), 6.47 (dd, 1H, J=6.32, 2.06 Hz), 6.57 (d, 1H, J=2.00 Hz), 7.16 (brs, 1H), 7.22 (d, 1H, J=8.36 Hz), 7.40 (brs, 1H).

(Step 2)

To a solution of 3-amino-6-bromopyrazine-2-carboxylic acid (10 g, 45.87 mmol) in DMF (50 mL) were added HATU (26.16 g, 68.8 mmol) and DIEA (80.1 mL, 458.7 mmol) at room temperature. Ethylamine (2 mol/L, THF solution, 114.65 mL, 229.3 mmol) was added thereto at room temperature, and the mixture was stirred at room temperature for 20 hr. The reaction mixture was concentrated under reduced pressure, to the residue was added ethyl acetate, and the solution was washed with water. The aqueous layer was extracted with ethyl acetate (×3). The organic layer was washed with water and saturated brine, and dried over sodium sulfate, and the solvent was evaporated under reduced pressure. The obtained residue was purified by silica gel column chromatography (solvent; 15% ethyl acetate/hexane) to give 3-amino-6-bromopyrazine-2-carboxylic acid ethylamide (6.60 g, 59%) as a pale yellow solid.

$^1$H-NMR (400 MHz, DMSO-d$_6$): δ1.10 (t, 3H, J=7.20 Hz), 3.24-3.30 (m, 2H), 7.69 (brs, 2H), 8.33 (s, 1H), 8.60 (t-like, 1H, J=5.44 Hz).

(Step 3)

To a solution of 3-amino-6-bromopyrazine-2-carboxylic acid ethylamide (2 g, 8.163 mmol) and TEA (5.68 mL, 40.81 mmol) in THF (50 mL) was added triphosgene (3.6 g, 12.24 mmol) at 0° C., and the mixture was stirred at 0° C. for 3 hr. To the reaction mixture were added ice water and aqueous sodium hydrogencarbonate solution, and the mixture was extracted with 5% methanol/dichloromethane (×3). The organic layer was washed with water and saturated brine, and dried over sodium sulfate, and the solvent was evaporated under reduced pressure to give crude 6-bromo-3-ethyl-1H-pteridine-2,4-dione (1.9 g) as a brown solid.

(Step 4)

A solution of the crude 6-bromo-3-ethyl-1H-pteridine-2,4-dione (1.9 g, 17.01 mmol), iodoethane (5.6 mL, 70.11 mmol) and potassium carbonate (3.87 g, 28.04 mmol) in DMF (40 mL) was sealed, and the mixture was stirred at 80° C. for 16 hr. The reaction mixture was concentrated under reduced pressure, and to the obtained residue was added ethyl acetate. The mixture was washed with water and saturated brine, and dried over sodium sulfate, and the solvent was evaporated under reduced pressure. The obtained residue was purified by silica gel column chromatography (solvent; 10% ethyl acetate/hexane) to give 6-bromo-1,3-diethyl-1H-pteridine-2,4-dione (700 mg, 22%, Step 1 and 2) as a yellow solid.

$^1$H-NMR (400 MHz, DMSO-d$_6$): δ1.16-1.22 (m, 6H), 3.98 (q, 2H, J=7.04 Hz), 4.19 (q, 2H, J=6.96 Hz), 8.97 (s, 1H).

(Step 5)

A solution of 6-bromo-1,3-diethyl-1H-pteridine-2,4-dione (1 g, 3.344 mmol), copper(II) oxide (96 mg, 0.669 mmol) and aqueous ammonia (50 mL) in NMP (0.7 mL) was sealed, and the mixture was stirred at 90° C. for 6 hr. To the reaction mixture was added water, and the mixture was extracted with 5% methanol/dichloromethane. The organic layer was washed with water and saturated brine, and dried over magnesium sulfate, and the solvent was evaporated under reduced pressure. The obtained crude crystals were washed with 5% methanol/hexane to give 6-amino-1,3-diethyl-1H-pteridine-2,4-dione (500 mg, 63%) as a pale yellow solid.

$^1$H-NMR (400 MHz, DMSO-d$_6$): δ1.13-1.19 (m, 6H), 3.96 (q, 2H, J=6.96 Hz), 4.16 (q, 2H, J=6.96 Hz), 6.74 (s, 2H), 8.11 (s, 1H).

(Step 6)

A solution of 6-amino-1,3-diethyl-1H-pteridine-2,4-dione (200 mg, 0.851 mmol) and 3-methylglutaric anhydride (218 mg, 1.70 mmol) in toluene (12 mL) was heated under reflux for 16 hr. The reaction mixture was concentrated under reduced pressure, and the obtained crude crystals were washed with 10% diethyl ether/hexane to give 4-(1,3-diethyl-2,4-dioxo-1,2,3,4-tetrahydropteridin-6-ylcarbamoyl)-3-methylbutyric acid (125 mg, 65%) as a grayish white solid.

$^1$H-NMR (400 MHz, DMSO-d$_6$): δ0.96 (d, 3H, J=5.56 Hz), 1.16-1.23 (m, 6H), 2.12 (m, 1H), 2.30-2.50 (m, 4H), 3.99 (q, 2H, J=6.40 Hz), 4.23 (q, 2H, J=7.04 Hz), 9.43 (s, 1H), 1.25 (brs, 1H), 12.09 (brs, 1H).

(Step 7)

To a solution of 4-amino-2-chlorobenzamide (117 mg, 0.689 mmol) and 4-(1,3-diethyl-2,4-dioxo-1,2,3,4-tetrahydropteridin-6-ylcarbamoyl)-3-methylbutyric acid (100 mg, 0.275 mmol) in a mixed solvent of DMF (0.3 mL) and ethyl acetate (3 mL) were added DIEA (0.12 mL, 0.689 mmol) and T3P (50% ethyl acetate solution, 0.2 mL, 0.689 mmol) at room temperature, and the mixture was stirred at room temperature for 6 hr. To the reaction mixture were added DIEA (0.12 mL, 0.689 mmol) and T3P (50% ethyl acetate solution, 0.2 mL, 0.689 mmol), and the mixture was stirred at room temperature for 14 hr. To the reaction mixture was added ethyl acetate, the organic layer was washed with water and saturated brine, and dried over sodium sulfate, and the solvent was evaporated under reduced pressure to give crude 3-methylpentanedicarboxylic acid (4-carbamoyl-3-chlorophenyl)amide(1,3-diethyl-2,4-dioxo-1,2,3,4-tetrahydropteridin-6-yl)amide.

(Step 8)

To a solution of the crude 3-methylpentanedicarboxylic acid (4-carbamoyl-3-chloro-phenyl)amide(1,3-diethyl-2,4-dioxo-1,2,3,4-tetrahydropteridin-6-yl)amide (105 mg, 0.203 mmol) in ethyl acetate (10 mL) were added DIEA (0.14 mL, 0.815 mmol) and T3P (50% ethyl acetate solution, 0.24 mL, 0.815 mmol) at room temperature, and the mixture was heated under reflux for 6 hr. The reaction mixture was allowed to be cooled to room temperature, diluted with ethyl acetate (25 mL), and washed with water and saturated brine. The organic layer was dried over sodium sulfate, and the solvent was evaporated under reduced pressure. The obtained residue was purified by preparative TLC (mobile phase; 70% ethyl acetate/hexane) to give the title compound (32 mg, 32%) as a grayish white solid.

MS(API): 498 (M+H)

$^1$H-NMR (400 MHz, DMSO-$d_6$): δ0.99 (d, 3H, J=6.28 Hz), 1.16-1.23 (m, 6H), 2.32-2.50 (m, 5H), 3.99 (q, 2H, J=6.96 Hz), 4.22 (q, 2H, J=6.90 Hz), 7.56 (dd, 1H, J=8.68, 1.88 Hz), 7.84 (d, 1H, J=8.64 Hz), 8.00 (d, 1H, J=1.84 Hz), 9.40 (s, 1H), 10.51 (s, 1H), 11.26 (s, 1H).

Example 138

(2R)—$N^1$-(3-chloro-4-cyanophenyl)-$N^5$-(3-(cyclopropylmethyl)-1-ethyl-2,4-dioxo-1,2,3,4-tetrahydroquinazolin-6-yl)-2-hydroxypentanediamide (Step 1)

A solution of 4-amino-2-chlorobenzonitrile (1.00 g, 6.55 mmol), (S)-5-oxotetrahydrofuran-2-carboxylic acid (0.853 g, 6.55 mmol), T3P (50% ethyl acetate solution, 11.6 mL, 19.7 mmol) and DIEA (5.1 mL, 32.8 mmol) in ethyl acetate (20 mL) was stirred at 60° C. for 16 hr. The reaction mixture was allowed to be cooled to room temperature, water was added thereto, and the mixture was extracted with ethyl acetate. The organic layer was washed with 1N hydrochloric acid, aqueous sodium carbonate solution and saturated brine, and dried over sodium sulfate, and the solvent was evaporated under reduced pressure. The obtained residue was purified by silica gel column chromatography (solvent gradient; 20→70% ethyl acetate/hexane) to give (S)—N-(3-chloro-4-cyanophenyl)-5-oxotetrahydrofuran-2-carboxamide (1.08 g, 62%) as a yellow solid.

$^1$H-NMR (300 MHz, DMSO-$d_6$): δ2.23-2.29 (1H, m), 2.54-2.59 (3H, m), 5.07-5.11 (1H, m), 7.70 (1H, dd, J=8.7, 1.8 Hz), 7.94 (1H, d, J=8.7 Hz), 8.07 (1H, d, J=1.8 Hz), 10.80 (1H, brs).
(Step 2)

A solution of 4-amino-2-chlorobenzonitrile (1.00 g, 6.55 mmol), (R)-5-oxotetrahydrofuran-2-carboxylic acid (0.853 g, 6.55 mmol), T3P (50% ethyl acetate solution, 11.6 mL, 19.7 mmol) and DIEA (5.1 mL, 32.8 mmol) in ethyl acetate (20 mL) was stirred at 60° C. for 16 hr. The reaction mixture was allowed to be cooled to room temperature, water was added thereto, and the mixture was extracted with ethyl acetate. The organic layer was washed with 1N hydrochloric acid, aqueous sodium carbonate solution and saturated brine, and dried over sodium sulfate, and the solvent was evaporated under reduced pressure. The obtained residue was purified by silica gel column chromatography (solvent gradient; 20→70% ethyl acetate/hexane) to give (R)—N-(3-chloro-4-cyanophenyl)-5-oxotetrahydrofuran-2-carboxamide (1.23 g, 71%) as a brown solid.

$^1$H-NMR (300 MHz, DMSO-$d_6$): δ2.23-2.29 (1H, m), 2.54-2.59 (3H, m), 5.07-5.11 (1H, m), 7.70 (1H, dd, J=8.7, 1.8 Hz), 7.94 (1H, d, J=8.7 Hz), 8.07 (1H, d, J=1.8 Hz), 10.80 (1H, brs).

(Step 3)

A solution of the mixture of (1:1, mol/mol, 1.00 g, 3.78 mmol) (S)—N-(3-chloro-4-cyanophenyl)-5-oxotetrahydrofuran-2-carboxamide and (R)—N-(3-chloro-4-cyanophenyl)-5-oxotetrahydrofuran-2-carboxamide, 6-amino-1-cyclopropylmethyl-3-ethyl-1H-quinazoline-2,4-dione (980 mg, 3.78 mmol) and potassium carbonate (574 mg, 4.16 mmol) in DMA (20 mL) was stirred at 80° C. for 14 hr. The reaction mixture was allowed to be cooled to room temperature, dilute hydrochloric acid was added thereto, and the mixture was extracted with ethyl acetate. The organic layer was washed with brine, and dried over sodium sulfate, and the solvent was evaporated under reduced pressure. The obtained residue was purified by silica gel column chromatography (solvent gradient; 5→100% ethyl acetate/hexane) to give $N^1$-(3-chloro-4-cyanophenyl)-$N^5$-(3-(cyclopropylmethyl)-1-ethyl-2,4-dioxo-1,2,3,4-tetrahydroquinazolin-6-yl)-2-hydroxypentanediamide (70 mg, 7%) as a pale brown powder.

(Step 4)

$N^1$-(3-Chloro-4-cyanophenyl)-$N^5$-(3-(cyclopropylmethyl)-1-ethyl-2,4-dioxo-1,2,3,4-tetrahydroquinazolin-6-yl)-2-hydroxypentanediamide (70 mg) was subjected to optical resolution by chiral column chromatography. The preparative fraction having a longer retention time was concentrated to give the title compound (33.0 mg, 98.2% ee).

purification condition by chiral column chromatography condition column: CHIRALPAK IA 4.6 mmID×250 mmL
mobile phase: hexane/2-propanol=400/600 (v/v)
flow rate: 1.0 mL/min
temperature: 30° C.
detection method: UV 220 nm
MS(API): 522 (M−H)

$^1$H-NMR (300 MHz, CDCl$_3$): δ0.41-0.52 (4H, m), 1.23-1.38 (4H, m), 2.18-2.29 (1H, m), 2.34-2.45 (1H, m), 2.76-2.82 (2H, m), 3.98 (2H, d, J=7.2 Hz), 4.20 (2H, q, J=7.2 Hz), 4.32-4.38 (1H, m), 6.32 (1H, d, J=3.0 Hz), 7.21 (1H, d, J=9.3 Hz), 7.54 (1H, dd, J=8.7, 1.8 Hz), 7.61 (1H, d, J=8.4 Hz), 7.93-8.03 (3H, m), 8.15 (1H, d, J=2.7 Hz), 9.26 (1H, brs).

Example 139

(2S)—$N^1$-(3-chloro-4-cyanophenyl)-$N^5$-(3-(cyclopropylmethyl)-1-ethyl-2,4-dioxo-1,2,3,4-tetrahydroquinazolin-6-yl)-2-hydroxypentanediamide $N^1$-(3-Chloro-4-cyanophenyl)-$N^5$-(3-(cyclopropylmethyl)-1-ethyl-2,4-dioxo-1,2,3,4-tetrahydroquinazolin-6-yl)-2-hydroxypentanediamide (70 mg) was subjected to optical resolution by chiral column chromatography. The preparative fraction having a shorter retention time was concentrated to give the title compound (30.8 mg, 100% ee).

purification condition by chiral column chromatography condition column: CHIRALPAK IA 4.6 mmID×250 mmL
mobile phase: hexane/2-propanol=400/600 (v/v)
flow rate: 1.0 mL/min
temperature: 30° C.
detection method: UV 220 nm
MS(API): 522 (M−H)

¹H-NMR (300 MHz, CDCl₃): δ0.41-0.52 (4H, m), 1.23-1.38 (4H, m), 2.18-2.29 (1H, m), 2.34-2.45 (1H, m), 2.76-2.82 (2H, m), 3.98 (2H, d, J=7.2 Hz), 4.20 (2H, q, J=7.2 Hz), 4.32-4.38 (1H, m), 6.32 (1H, d, J=3.0 Hz), 7.21 (1H, d, J=9.3 Hz), 7.54 (1H, dd, J=8.7, 1.8 Hz), 7.61 (1H, d, J=8.4 Hz), 7.93-8.03 (3H, m), 8.15 (1H, d, J=2.7 Hz), 9.26 (1H, brs).

Example 140

(2R)—N⁵-(3-chloro-4-cyanophenyl)-N¹-(3-(cyclopropylmethyl)-1-ethyl-2,4-dioxo-1,2,3,4-tetrahydroquinazolin-6-yl)-2-hydroxypentanediamide (Step 1)
A solution of 6-amino-1-(cyclopropylmethyl)-3-ethyl-1H-quinazoline-2,4-dione (1.00 g, 3.86 mmol), (R)-5-oxotetrahydrofuran-2-carboxylic acid (0.50 g, 3.86 mmol), DIEA (3.36 mL, 19.3 mmol) and T3P (50% ethyl acetate solution, 6.8 mL, 11.6 mmol) in ethyl acetate (20 mL) was stirred at 60° C. for 16 hr. The reaction mixture was allowed to be cooled to room temperature, water was added thereto, and the mixture was extracted with ethyl acetate. The organic layer was washed with 1N hydrochloric acid, aqueous sodium carbonate solution and saturated brine, and dried over sodium sulfate, and the solvent was evaporated under reduced pressure. The obtained residue was purified by silica gel column chromatography (solvent; ethyl acetate) to give (R)—N-(3-(cyclopropylmethyl)-1-ethyl-2,4-dioxo-1,2,3,4-tetrahydroquinazolin-6-yl)-5-oxotetrahydrofuran-2-carboxamide (1.08 g, 75%) as a brown solid.
¹H-NMR (300 MHz, DMSO-d₆): δ0.33-0.46 (4H, m), 1.15-1.24 (4H, m), 2.21-2.33 (1H, m), 2.53-2.61 (3H, m), 3.85 (2H, d, J=6.9 Hz), 4.14 (2H, q, J=7.2 Hz), 5.04-5.08 (1H, m), 7.52 (1H, d, J=9.0 Hz), 7.99 (1H, dd, J=9.0, 2.7 Hz), 8.40 (1H, d, J=2.4 Hz), 10.47 (1H, brs).
(Step 2)
To a solution of sodium hydride (60% oil, 23.7 mg, 0.59 mmol) in DMF (3.0 mL) was slowly added 4-amino-2-chlorobenzonitrile (82.0 mg, 0.54 mmol) at room temperature, and the mixture was stirred at room temperature for 20 min. To the reaction mixture was added (R)—N-(3-(cyclopropylmethyl)-1-ethyl-2,4-dioxo-1,2,3,4-tetrahydroquinazolin-6-yl)-5-oxotetrahydrofuran-2-carboxamide (200 mg, 0.54 mmol) at room temperature, and the mixture was stirred at room temperature for 3 hr. To the reaction mixture was added 0.1N hydrochloric acid, and the mixture was extracted with ethyl acetate. The organic layer was washed with saturated brine, and dried over sodium sulfate, and the solvent was evaporated under reduced pressure. The obtained residue was purified by silica gel column chromatography (solvent gradient; 20→100% ethyl acetate/hexane) to give the title compound (10.0 mg, 4%) as a colorless powder.
MS(API): 522 (M–H)
¹H-NMR (300 MHz, CDCl₃): δ0.38-0.51 (4H, m), 1.24-1.36 (4H, m), 2.20-2.41 (2H, m), 2.80 (2H, t, J=6.3 Hz), 3.96 (2H, d, J=2.1 Hz), 4.11-4.20 (2H, m), 4.38-4.45 (1H, m), 5.65 (1H, brs), 7.17 (1H, d, J=9.3 Hz), 7.49-7.55 (2H, m), 7.81-7.85 (2H, m), 8.40 (1H, d, J=2.7 Hz), 9.18 (1H, brs), 9.34 (H, brs)

Example 141

(2S)—N⁵-(3-chloro-4-cyanophenyl)-N¹-(3-(cyclopropylmethyl)-1-ethyl-2,4-dioxo-1,2,3,4-tetrahydroquinazolin-6-yl)-2-hydroxypentanediamide (Step 1)
A solution of 6-amino-1-(cyclopropylmethyl)-3-ethyl-1H-quinazoline-2,4-dione (1.00 g, 3.86 mmol), (S)-5-oxotetrahydrofuran-2-carboxylic acid (0.50 g, 3.86 mmol), DIEA (3.36 mL, 19.3 mmol) and T3P (50% ethyl acetate solution, 6.8 mL, 11.6 mmol) in ethyl acetate (20 mL) was stirred at 60° C. for 16 hr. The reaction mixture was allowed to be cooled to room temperature, water was added thereto, and the mixture was extracted with ethyl acetate. The organic layer was washed with 1N hydrochloric acid, aqueous sodium carbonate solution and saturated brine, and dried over sodium sulfate, and the solvent was evaporated under reduced pressure. The obtained residue was purified by silica gel column chromatography (solvent; ethyl acetate) to give (S)—N-(3-(cyclopropylmethyl)-1-ethyl-2,4-dioxo-1,2,3,4-tetrahydroquinazolin-6-yl)-5-oxotetrahydrofuran-2-carboxamide (0.96 g, 67%) as a pale brown solid.
¹H-NMR (300 MHz, DMSO-d₆): δ0.33-0.46 (4H, m), 1.15-1.24 (4H, m), 2.21-2.33 (1H, m), 2.53-2.61 (3H, m), 3.85 (2H, d, J=6.9 Hz), 4.14 (2H, q, J=7.2 Hz), 5.04-5.08 (1H, m), 7.52 (1H, d, J=9.0 Hz), 7.99 (1H, dd, J=9.0, 2.7 Hz), 8.40 (1H, d, J=2.4 Hz), 10.47 (1H, brs).
(Step 2)
To a solution of sodium hydride (60% oil, 23.7 mg, 0.59 mmol) in DMF (3.0 mL) was slowly added 4-amino-2-chlorobenzonitrile (82.0 mg, 0.54 mmol) at room temperature, and the mixture was stirred at room temperature for 20 min. To the reaction mixture was added (S)—N-(3-(cyclopropylmethyl)-1-ethyl-2,4-dioxo-1,2,3,4-tetrahydroquinazolin-6-yl)-5-oxotetrahydrofuran-2-carboxamide (200 mg, 0.54 mmol) at room temperature, and the mixture was stirred at room temperature for 3 hr. To the reaction mixture was added 0.1N hydrochloric acid, and the mixture was extracted with ethyl acetate. The organic layer was washed with saturated brine, and dried over sodium sulfate, and the solvent was evaporated under reduced pressure. The obtained residue was purified by silica gel column chromatography (solvent gradient; 20→100% ethyl acetate/hexane), and purified by NH-silica gel column chromatography (solvent gradient; 0→20% methanol/ethyl acetate) to give the title compound (24.2 mg, 8%) as a colorless amorphous solid.
MS(API): 522 (M–H)
¹H-NMR (300 MHz, CDCl₃): δ0.38-0.51 (4H, m), 1.24-1.36 (4H, m), 2.20-2.41 (2H, m), 2.80 (2H, t, J=6.3 Hz), 3.96 (2H, d, J=2.1 Hz), 4.11-4.20 (2H, m), 4.38-4.45 (1H, m), 5.65 (1H, brs), 7.17 (1H, d, J=9.3 Hz), 7.49-7.55 (2H, m), 7.81-7.85 (2H, m), 8.40 (1H, d, J=2.7 Hz), 9.18 (1H, brs), 9.34 (1H, brs).

Example 142

N-(3-chloro-4-cyanophenyl)-N'-(3-(cyclopropylmethyl)-1-isopropyl-2,4-dioxo-1,2,3,4-tetrahydroquinazolin-6-yl)-3-hydroxy-3-methylpentanediamide (Step 1)
To a solution of 2-amino-5-nitrobenzoic acid (10 g, 54.90 mmol), aminomethylcyclopropane (4.76 mL, 54.90 mmol) and DIEA (33.6 mL, 192.17 mmol) in DMF (50 mL) was added T3P (50% ethyl acetate solution, 37.1 mL, 63.14 mmol) at room temperature, and the mixture was stirred at room temperature for 3 hr. To the reaction mixture was added water, and the mixture was extracted with ethyl acetate. The organic layer was washed with water and saturated brine, and dried over magnesium sulfate, and the solvent was evaporated under reduced pressure. The residue was crystallized from ethyl acetate/hexane to give 2-amino-N-(cyclopropylmethyl)-5-nitrobenzamide (11.10 g, 47.2 mmol, 86%) as a yellow solid.
¹H-NMR (300 MHz, CDCl₃): δ0.22-0.40 (2H, m), 0.52-0.68 (2H, m), 0.98-1.20 (1H, m), 3.29 (2H, dd, J=7.2, 5.3

Hz), 6.36 (1H, brs), 6.53 (2H, brs), 6.65 (1H, d, J=9.1 Hz), 8.09 (1H, dd, J=9.1, 2.3 Hz), 8.36 (1H, d, J=2.3 Hz).
(Step 2)

To a solution of 2-amino-N-(cyclopropylmethyl)-5-nitrobenzamide (11.1 g, 47.19 mmol) in THF (60 mL) was added CDI (8.42 g, 51.90 mmol) at room temperature, and the mixture was stirred at 50° C. for 12 hr. To the reaction mixture was added CDI (11.48 g, 70.78 mmol), and the mixture was heated under reflux for 2 hr. Then, CDI (7.65 g, 47.19 mmol) was added thereto, and the mixture was heated under reflux for 2 hr. Then, CDI (7.65 g, 47.19 mmol) was added thereto, and the mixture was heated under reflux for 1 hr. The reaction mixture was allowed to be cooled to room temperature, and water was added thereto. The precipitate was collected by filtration, and the crude crystals were washed with ethyl acetate/hexane (1:3, v/v) to give 3-(cyclopropylmethyl)-6-nitroquinazoline-2,4(1H,3H)-dione (10.70 g, 41.0 mmol, 87%) as a pale yellow solid.

$^1$H-NMR (300 MHz, DMSO-$d_6$): δ0.23-0.60 (4H, m), 1.06-1.37 (1H, m), 3.80 (2H, d, J=7.2 Hz), 7.35 (1H, d, J=9.1 Hz), 8.48 (1H, dd, J=9.1, 2.6 Hz), 8.65 (1H, d, J=2.6 Hz), 12.07 (1H, brs).
(Step 3)

2-Iodopropane (1.146 mL, 11.48 mmol) was added to a solution of 3-(cyclopropylmethyl)-6-nitroquinazoline-2,4 (1H,3H)-dione (1.00 g, 3.83 mmol) and cesium carbonate (1.871 g, 5.74 mmol) in DMF (22 mL) at room temperature, and the mixture was stirred at 50° C. for 2 hr. Then, 2-iodopropane (1.146 mL, 11.48 mmol) and cesium carbonate (1.871 g, 5.74 mmol) were added thereto, and the mixture was stirred at 65° C. for 18 hr. To the reaction mixture was added water, and the mixture was extracted with ethyl acetate (×3). The organic layer was washed with water and saturated brine, and dried over magnesium sulfate, and the solvent was evaporated under reduced pressure. The obtained residue was purified by silica gel column chromatography (solvent gradient; 2-20% ethyl acetate/hexane) to give 3-(cyclopropylmethyl)-2-isopropoxy-6-nitroquinazolin-4 (3H)-one (518 mg, 1.708 mmol, 44.6%) (less polar) as a white powder, and 3-(cyclopropylmethyl)-1-isopropyl-6-nitroquinazoline-2,4(1H,3H)-dione (447 mg, 1.474 mmol, 38.5%) (more polar) as a white powder, respectively. spectrum data of 3-(cyclopropylmethyl)-2-isopropoxy-6-nitroquinazolin-4(3H)-one $^1$H-NMR (300 MHz, CDCl$_3$): δ0.42-0.57 (4H, m), 1.17-1.32 (1H, m), 1.47 (6H, d, J=6.0 Hz), 3.99 (2H, d, J=7.2 Hz), 5.59 (1H, spt, J=6.2 Hz), 7.52 (1H, d, J=8.7 Hz), 8.42 (1H, dd, J=9.1, 2.6 Hz), 9.06 (1H, d, J=2.6 Hz).
spectrum data of 3-(cyclopropylmethyl)-1-isopropyl-6-nitroquinazoline-2,4(1H,3H)-dione $^1$H-NMR (300 MHz, CDCl$_3$): δ0.42-0.55 (4H, m), 1.24-1.36 (1H, m), 1.65 (6H, d, J=6.8 Hz), 3.98 (2H, d, J=7.2 Hz), 5.12 (1H, brs), 7.48 (1H, d, J=9.1 Hz), 8.45 (1H, dd, J=9.3, 2.8 Hz), 9.10 (1H, d, J=2.6 Hz).
(Step 4)

Isopropylamine (32.4 mL, 377.53 mmol) was added to a solution of methyl 2-fluoro-5-nitrobenzoate (25.06 g, 125.84 mmol) in acetonitrile (250 mL) at 0° C., and the mixture was stirred at room temperature for 1 hr. To the reaction mixture was added water (800 mL), and the mixture was stirred for 10 min. The precipitate was collected by filtration, and the crude crystals were washed successively with water, 2-propanol and IPE to give methyl 2-(isopropylamino)-5-nitrobenzoate (28.64 g, 120 mmol, 96%) as a pale yellow solid.

$^1$H-NMR (300 MHz, CDCl$_3$): δ1.33 (6H, d, J=6.4 Hz), 3.81 (1H, septet, J=7.5 Hz), 3.91 (3H, s), 6.69 (1H, d, J=9.4 Hz), 8.19 (1H, dd, J=9.4, 2.3 Hz), 8.56 (1H, brs), 8.87 (1H, d, J=2.6 Hz).
(Step 5)

2N Aqueous sodium hydroxide solution (174 mL, 347.30 mmol) was added to a solution of methyl 2-(isopropylamino)-5-nitrobenzoate (27.58 g, 115.77 mmol) in ethanol (120 mL) and THF (120 mL) at room temperature, and the mixture was stirred at 75° C. for 2.5 hr. To the reaction mixture was added ice water (600 mL), and the pH of the mixture was adjusted to <3 with conc. hydrochloric acid. The mixture was extracted with a mixed solvent of ethyl acetate/THF (3:1, v/v) (×3). The organic layer was washed with water and saturated brine, and dried over magnesium sulfate, and the solvent was evaporated under reduced pressure to give 2-(isopropylamino)-5-nitrobenzoic acid (25.32 g, 113 mmol, 98%) as a pale yellow solid.

$^1$H-NMR (300 MHz, CDCl$_3$): δ1.36 (6H, d, J=6.4 Hz), 3.84 (1H, septet, J=6.0 Hz), 6.73 (1H, d, J=9.4 Hz), 8.24 (1H, dd, J=9.4, 2.6 Hz), 8.35 (1H, d, J=6.8 Hz), 8.95 (1H, d, J=2.6 Hz), 11.04 (1H, brs).
(Step 6)

WSC (24.81 mL, 135.51 mmol) was added to a solution of 2-(isopropylamino)-5-nitrobenzoic acid (25.32 g, 112.93 mmol), cyclopropylmethanamine (8.83 g, 124.22 mmol) and HOBt (16.79 g, 124.22 mmol) in DMF (300 mL) at 0° C., and the mixture was stirred at room temperature for 18 hr. The reaction mixture was poured into 50% aqueous sodium hydrogencarbonate solution (1200 mL), and the mixture was extracted with a mixed solvent of ethyl acetate/THF (3:1, v/v) (×3). The organic layer was washed with water and saturated brine, and dried over magnesium sulfate, and the solvent was evaporated under reduced pressure to give N-(cyclopropylmethyl)-2-(isopropylamino)-5-nitrobenzamide (28.68 g, 103 mmol, 92%) as a pale yellow solid.

$^1$H-NMR (300 MHz, CDCl$_3$): δ0.26-0.33 (2H, m), 0.57-0.65 (2H, m), 1.03-1.14 (1H, m), 1.30 (6H, d, J=6.4 Hz), 3.27 (2H, dd, J=7.2, 5.3 Hz), 3.77 (1H, sxt, J=6.5 Hz), 6.32 (1H, brs), 6.65 (1H, d, J=9.4 Hz), 8.16 (1H, dd, J=9.1, 2.3 Hz), 8.36 (1H, d, J=2.6 Hz), 8.75 (1H, d, J=7.2 Hz).
(Step 7)

Triphosgene (20.56 g, 69.29 mmol) was added to a solution of N-(cyclopropylmethyl)-2-(isopropylamino)-5-nitrobenzamide (28.68 g, 103.42 mmol) and TEA (31.7 mL, 227.52 mmol) in THF (280 mL) at 0° C., and the mixture was stirred at 0° C. for 15 min, and then at 65° C. for 4.5 hr. The reaction mixture was poured into 50% aqueous sodium hydrogencarbonate solution (700 mL), and the mixture was extracted with a mixed solvent of ethyl acetate/THF (3:1, v/v) (×3). The organic layer was washed with water and saturated brine, and dried over magnesium sulfate, and the solvent was evaporated under reduced pressure. The obtained residue was dissolved in THF (280 mL), and TEA (23.78 mL, 170.64 mmol) and triphosgene (15.34 g, 51.71 mmol) were added thereto at 0° C. The mixture was stirred at 0° C. for 15 min, and then at 65° C. for 4.5 hr. The reaction mixture was poured into 50% aqueous sodium hydrogencarbonate solution (700 mL), and the mixture was extracted with a mixed solvent of ethyl acetate/THF (3:1, v/v) (×3). The organic layer was washed with water and saturated brine, and dried over magnesium sulfate, and the solvent was evaporated under reduced pressure. The obtained residue was purified by silica gel column chromatography (solvent gradient; 5→20% ethyl acetate/hexane), and the obtained precipitate was collected by filtration with hexane to give 3-(cyclopropylmethyl)-1-isopropyl-6-nitroquinazoline-2,4(1H,3H)-dione (18.62 g, 61.4 mmol, 59%) as a pale yellow solid.

$^1$H-NMR (300 MHz, CDCl$_3$): δ0.42-0.54 (4H, m), 1.24-1.37 (1H, m), 1.65 (6H, d, J=6.8 Hz), 3.98 (2H, d, J=7.2 Hz), 5.11 (1H, brs), 7.48 (1H, d, J=9.1 Hz), 8.46 (1H, dd, J=9.4, 3.0 Hz), 9.10 (1H, d, J=3.0 Hz).

(Step 8)

A solution of 3-(cyclopropylmethyl)-1-isopropyl-6-nitroquinazoline-2,4(1H,3H)-dione (442 mg, 1.46 mmol) and 10% palladium on carbon (50% hydrous, 150 mg, 1.27 mmol) in a mixed solvent of methanol (7 mL) and THF (3.5 mL) was stirred at room temperature for 2 hr under 1 atm of under hydrogen atmosphere. The catalyst was removed by filtration, and the filtrate was concentrated under reduced pressure. The obtained residue was purified by silica gel column chromatography (solvent gradient; 10→50% ethyl acetate/hexane), and the obtained precipitate was collected by filtration with a mixed solvent of hexane/IPE to give 6-amino-3-(cyclopropylmethyl)-1-isopropylquinazoline-2,4(1H,3H)-dione (318 mg, 1.163 mmol, 80%) as a pale yellow solid.

$^1$H-NMR (300 MHz, CDCl$_3$): δ0.42-0.48 (4H, m), 1.23-1.36 (1H, m), 1.59 (6H, d, J=7.2 Hz), 3.73 (2H, brs), 3.96 (2H, d, J=7.2 Hz), 5.01 (1H, brs), 6.99 (1H, dd, J=8.9, 2.8 Hz), 7.20 (1H, d, J=9.1 Hz), 7.51 (1H, d, J=3.0 Hz).

(Step 9)

T3P (50% ethyl acetate solution, 268 μl, 0.45 mmol) was added to a solution of 6-amino-3-(cyclopropylmethyl)-1-isopropylquinazoline-2,4(1H,3H)-dione (82 mg, 0.3 mmol), 5-((3-chloro-4-cyanophenyl)amino)-3-hydroxy-3-methyl-5-oxopentanoic acid (89 mg, 0.30 mmol) and DIEA (261 μl, 1.50 mmol) in ethyl acetate (2.5 mL) at room temperature, and the mixture was stirred at 65° C. for 15 hr. Water (60 mL) was poured into the reaction mixture, and the mixture was extracted with ethyl acetate (×3). The organic layer was washed with water and saturated brine, and dried over magnesium sulfate, and the solvent was evaporated under reduced pressure. The obtained residue was purified by silica gel column chromatography (solvent gradient; 30→100% ethyl acetate/hexane) to give the title compound (84.5 mg, 0.153 mmol, 51%) as a yellow amorphous solid.

MS(API): 550 (M−H)

$^1$H-NMR (300 MHz, CDCl$_3$): δ0.40-0.49 (4H, m), 1.23-1.32 (1H, m), 1.44 (3H, s), 1.62 (6H, d, J=7.2 Hz), 2.69 (2H, s), 2.72 (2H, d, J=5.3 Hz), 3.96 (2H, d, J=6.8 Hz), 5.06 (1H, brs), 5.35 (1H, s), 7.38 (1H, d, J=9.4 Hz), 7.51 (1H, m), 7.59 (1H, m), 7.90 (1H, d, J=1.9 Hz), 7.99 (1H, dd, J=9.4, 2.6 Hz), 8.20 (1H, d, J=2.6 Hz), 8.70 (1H, s), 9.49 (1H, s).

Example 143

N-(3-chloro-4-cyanophenyl)-N'-(2-(cyclopropylmethyl)-4-ethyl-3-methoxy-1-oxo-1,2,3,4-tetrahydroisoquinolin-7-yl)-3-methylpentanediamide (Step 1)

To α-cyano-o-tolunitrile (1.5 g, 10.55 mmol) and benzyltributylammonium bromide (0.150 g, 0.42 mmol) in 8N aqueous sodium hydroxide solution (26.4 mL, 211.03 mmol) was added ethyl iodide (2.126 mL, 26.38 mmol) at room temperature, and the mixture was stirred overnight at room temperature. To the reaction mixture was added water, and the mixture was extracted with ethyl acetate. The organic layer was washed with saturated brine, and dried over magnesium sulfate, and the solvent was evaporated under reduced pressure to give crude 2-(1-cyanopropyl)benzonitrile (2.040 g, 11.99 mmol, 114%) as a brown oil.

$^1$H-NMR (300 MHz, CDCl$_3$): δ1.14 (3H, t, J=7.5 Hz), 1.90-2.12 (2H, m), 4.20 (1H, dd, J=8.1, 6.4 Hz), 7.38-7.57 (1H, m), 7.65-7.73 (3H, m).

(Step 2)

A solution of the crude 2-(1-cyanopropyl)benzonitrile (2.00 g, 11.75 mmol) in conc. sulfuric acid (15 mL) was stirred overnight at 60° C. The reaction mixture was cooled, and poured into ice water, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane⇒ 0→15% methanol/ethyl acetate) to give 4-ethylisoquinoline-1,3(2H,4H)-dione (0.463 g, 2.446 mmol, 20.82%) as a pale yellow solid.

$^1$H-NMR (300 MHz, DMSO-d$_6$): δ0.75 (3H, t, J=7.2 Hz), 1.47-1.71 (1H, m), 1.85-2.08 (1H, m), 3.70 (1H, dd, J=8.1, 7.0 Hz), 6.85 (1H, brs), 7.32-7.44 (1H, m), 7.50 (1H, brs), 7.64 (1H, brs), 8.08 (1H, brs).

(Step 3)

To a solution of 4-ethylisoquinoline-1,3(2H,4H)-dione (460 mg, 2.43 mmol) in conc. sulfuric acid (8 mL) was added 69% nitric acid (8 mL) at 0° C., and the mixture was stirred at 0° C. for 1 hr. The reaction mixture was poured into ice water, and the precipitate was collected by filtration. The crude crystals were washed with water to give 4-ethyl-7-nitroisoquinoline-1,3(2H,4H)-dione (50 mg) as a brown solid. The filtrate was extracted with ethyl acetate. The organic layer was washed with water and saturated brine, and dried over magnesium sulfate, and the solvent was evaporated under reduced pressure. The obtained residue was purified by silica gel column chromatography (solvent gradient; 10→100% ethyl acetate/hexane) to give 4-ethyl-7-nitroisoquinoline-1,3(2H,4H)-dione (111 mg).

$^1$H-NMR (300 MHz, DMSO-d$_6$): δ0.66-0.91 (3H, m), 1.66 (1H, double quintet, J=13.9, 7.1 Hz), 1.87-2.11 (1H, m), 3.86 (1H, t, J=7.6 Hz), 7.74 (1H, d, J=8.7 Hz), 8.10-8.23 (1H, m), 8.23-8.38 (2H, m).

(Step 4)

To a solution of 4-ethyl-7-nitroisoquinoline-1,3(2H,4H)-dione (100 mg, 0.43 mmol) in DMF (4 mL) was added sodium hydride (60% oil, 41.0 mg, 0.85 mmol) at room temperature, and the mixture was stirred at room temperature for 10 min. To the reaction mixture was added (bromomethyl)cyclopropane (0.083 mL, 0.85 mmol) at 0° C., and the mixture was stirred overnight at room temperature. Water was poured into the reaction mixture, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5→75% ethyl acetate/hexane) to give 2-(cyclopropylmethyl)-4-ethyl-7-nitroisoquinoline-1,3(2H,4H)-dione (42.9 mg, 0.149 mmol, 34.9%) as a brown amorphous solid.

$^1$H-NMR (300 MHz, CDCl$_3$) δ0.33-0.61 (4H, m), 0.80-0.94 (3H, m), 1.16-1.37 (2H, m), 1.77-2.02 (1H, m), 3.84-4.04 (2H, m), 4.04-4.25 (1H, m), 7.92 (1H, d, J=8.3 Hz), 8.43-8.60 (1H, m), 8.99 (1H, d, J=2.6 Hz)

(Step 5)

A solution of 2-(cyclopropylmethyl)-4-ethyl-7-nitroisoquinoline-1,3(2H,4H)-dione (40 mg, 0.14 mmol) and 10% palladium on carbon (50% hydrous, 5 mg) in methanol (4 mL) was stirred overnight at room temperature under 1 atm of under hydrogen atmosphere. The catalyst was removed by filtration, and the filtrate was concentrated under reduced pressure to give crude 7-amino-2-(cyclopropylmethyl)-4-ethyl-3-methoxy-3,4-dihydroisoquinolin-1(2H)-one (28.3 mg, 0.103 mmol, 74%) as a pale yellow amorphous solid.
(Step 6)

To a solution of the crude 7-amino-2-(cyclopropylmethyl)-4-ethyl-3-methoxy-3,4-dihydroisoquinolin-1(2H)-one (28 mg, 0.10 mmol), 4-(3-chloro-4-cyanophenylcarbamoyl)-3-methylbutyric acid (28.6 mg, 0.10 mmol), DIEA (0.267 mL, 1.53 mmol) and DMAP (12.47 mg, 0.10 mmol) in ethyl acetate (4 mL) was added T3P (50% ethyl acetate solution, 0.300 mL, 0.51 mmol) at room temperature, and the mixture was stirred overnight at room temperature. Water was poured into the reaction mixture, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane), and purified by NH-silica gel column chromatography (solvent gradient; 10→100% ethyl acetate/hexane) to give the title compound (34.8 mg, 0.065 mmol, 64%) as a white solid.

$^1$H-NMR (300 MHz, CDCl$_3$): δ0.29-0.59 (4H, m), 0.72-0.93 (3H, m), 1.19 (3H, d, J=4.9 Hz), 1.65 (5H, s), 1.78-1.98 (1H, m), 2.33-2.67 (4H, m), 3.70 (1H, s), 3.76-4.03 (2H, m), 7.46-7.63 (2H, m), 7.68 (1H, d, J=8.3 Hz), 7.89-8.09 (3H, m), 8.19 (1H, dd, J=3.8, 2.3 Hz), 9.25 (1H, brs). (The two exchangeable protons were not observed)

Example 144

N-(3-chloro-4-cyanophenyl)-N'-(3-(cyclopropylmethyl)-1-isopropyl-2,4-dioxo-1,2,3,4-tetrahydroquinazolin-6-yl)-3-methylpentanediamide A solution of 4-(3-chloro-4-cyanophenylcarbamoyl)-3-methylbutyric acid (123 mg, 0.44 mmol), 6-amino-3-(cyclopropylmethyl)-1-isopropylquinazoline-2,4(1H,3H)-dione (100 mg, 0.37 mmol), T3P (50% ethyl acetate solution, 0.646 mL, 1.10 mmol), DIEA (0.319 mL, 1.83 mmol) and DMAP (49.2 mg, 0.40 mmol) in DMF (3 mL) was stirred overnight at room temperature. To the reaction mixture was added water, and the mixture was extracted with ethyl acetate. The organic layer was washed with water and saturated brine, and dried over sodium sulfate, and the solvent was evaporated under reduced pressure. The obtained residue was purified by silica gel column chromatography (solvent gradient; 5→80% ethyl acetate/hexane) to give the title compound (118 mg, 0.221 mmol, 60%) as a colorless amorphous solid.

MS(API): 534 (M−H)

$^1$H-NMR (300 MHz, CDCl$_3$): δ0.38-0.52 (4H, m), 1.07-1.23 (3H, m), 1.24-1.38 (1H, m), 1.56-1.71 (8H, m), 2.39-2.64 (4H, m), 3.97 (2H, d, J=7.2 Hz), 5.07 (1H, brs), 7.33-7.44 (1H, m), 7.53-7.58 (1H, m), 7.92 (1H, d, J=1.1 Hz), 8.01-8.21 (3H, m), 9.48 (1H, s).

Example 145

N-(3-chloro-4-cyanophenyl)-N'-(2'-(cyclopropylmethyl)-1',3'-dioxo-2',3'-dihydro-1'H-spiro[cyclopentane-1,4'-isoquinoline]-7'-yl)-3-methylpentanediamide (Step 1)

To α-cyano-o-tolunitrile (1.5 g, 10.55 mmol) and benzyltributylammonium bromide (0.150 g, 0.42 mmol) in 8N aqueous sodium hydroxide solution (26.4 mL, 211.03 mmol) was added 1,4-butylene bromide (1.449 mL, 12.13 mmol) at room temperature, and the mixture was stirred overnight at room temperature. To the reaction mixture was added water, and the mixture was extracted with ethyl acetate. The organic layer was washed with saturated brine, and dried over magnesium sulfate, and the solvent was evaporated under reduced pressure to give crude 2-(1-cyanocyclopentyl)benzonitrile (2.69 g, 13.71 mmol, 130%) as a brown oil.

$^1$H-NMR (300 MHz, CDCl$_3$): δ1.98-2.18 (4H, m), 2.26-2.44 (2H, m), 2.59-2.79 (2H, m), 7.38-7.50 (1H, m), 7.62 (1H, td, J=7.8, 1.5 Hz), 7.67-7.83 (2H, m).

(Step 2)

A solution of the crude 2-(1-cyanopropyl)benzonitrile (2.00 g, 10.19 mmol) in conc. sulfuric acid (15 mL) was stirred overnight at 60° C. The reaction mixture was cooled, and poured into ice water, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→75% ethyl acetate/hexane) to give 1'H-spiro[cyclopentane-1,4'-isoquinoline]-1',3'(2'H)-dione (0.937 g, 4.35 mmol, 42.7%) as a white solid.

$^1$H-NMR (300 MHz, CDCl$_3$): δ1.77-2.06 (6H, m), 2.21-2.47 (2H, m), 7.33-7.60 (2H, m), 7.64-7.84 (1H, m), 8.01 (1H, dd, J=7.9, 1.5 Hz), 11.29 (1H, brs).

(Step 3)

To a solution of 1'H-spiro[cyclopentane-1,4'-isoquinoline]-1',3' (2'H)-dione (920 mg, 4.27 mmol) in conc. sulfuric acid (15 mL) was added 69% nitric acid (15 mL) at 0° C., and the mixture was stirred at 0° C. for 1 hr. The reaction mixture was poured into ice water, and the precipitate was collected by filtration. The crude crystals were washed with water to give 7'-nitro-1'H-spiro[cyclopentane-1,4'-isoquinoline]-1',3' (2'H)-dione (1050 mg, 4.03 mmol, 94%) as a white solid.

$^1$H-NMR (300 MHz, DMSO-d$_6$): δ1.83-2.10 (6H, m), 2.32-2.48 (2H, m), 7.83 (1H, d, J=8.7 Hz), 8.47 (1H, dd, J=8.7, 2.6 Hz), 8.66 (1H, d, J=2.6 Hz), 11.65 (1H, s).

(Step 4)

To a solution of 7'-nitro-1'H-spiro[cyclopentane-1,4'-isoquinoline]-1',3' (2'H)-dione (100 mg, 0.38 mmol) in acetonitrile (4 mL) was added potassium carbonate (531 mg, 3.84 mmol) at room temperature, and the mixture was stirred at room temperature for 10 min. To the reaction mixture was added (bromomethyl)cyclopropane (0.186 mL, 1.92 mmol) at room temperature, and the mixture was stirred overnight at room temperature. Water was poured into the reaction mixture, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 5→50% ethyl acetate/hexane) to give 2'-(cyclopropylmethyl)-7'-nitro-1'H-spiro[cyclopentane-1,4'-isoquinoline]-1',3'(2'H)-dione (121 mg, 0.383 mmol, 100%) as a colorless amorphous solid.

$^1$H-NMR (300 MHz, CDCl$_3$): δ0.31-0.56 (4H, m), 1.14-1.37 (1H, m), 1.89-2.29 (6H, m), 2.45-2.76 (2H, m), 3.92 (2H, d, J=7.2 Hz), 7.50-7.68 (1H, m), 8.43 (1H, dd, J=8.7, 2.6 Hz), 9.03 (1H, d, J=2.3 Hz).

(Step 5)

A solution of 2'-(cyclopropylmethyl)-7'-nitro-1'H-spiro[cyclopentane-1,4'-isoquinoline]-1',3' (2'H)-dione (115 mg, 0.37 mmol) and 10% palladium on carbon (50% hydrous, 5 mg) in methanol (4 mL) was stirred overnight at room temperature under 1 atm of under hydrogen atmosphere. The catalyst was removed by filtration, and the filtrate was concentrated under reduced pressure to give 7'-amino-2'-

(cyclopropylmethyl)-1'H-spiro[cyclopentane-1,4'-isoquinoline]-1',3' (2'H)-dione (100 mg, 0.352 mmol, 96%) as a colorless amorphous solid.

$^1$H-NMR (300 MHz, CDCl$_3$): δ0.24-0.51 (4H, m), 1.08-1.34 (1H, m), 1.78-2.17 (6H, m), 2.33-2.58 (2H, m), 3.86 (2H, d, J=7.2 Hz), 4.91 (2H, brs), 7.08-7.30 (2H, m), 7.66 (1H, brs).

(Step 6)

To a solution of 7'-amino-2'-(cyclopropylmethyl)-1'H-spiro[cyclopentane-1,4'-isoquinoline]-1',3'(2'H)-dione (100 mg, 0.35 mmol), 4-(3-chloro-4-cyanophenylcarbamoyl)-3-methylbutyric acid (99 mg, 0.35 mmol), DIEA (0.921 mL, 5.28 mmol) and DMAP (43.0 mg, 0.35 mmol) in ethyl acetate (4 mL) was added T3P (50% ethyl acetate solution, 1.034 mL, 1.76 mmol) at room temperature, and the mixture was stirred at room temperature for 2 hr. Water was poured into the reaction mixture, and the mixture was extracted with ethyl acetate. The organic layer was washed with saturated brine, and dried over magnesium sulfate, and the solvent was evaporated under reduced pressure. The obtained residue was purified by silica gel column chromatography (solvent gradient; 10→100% ethyl acetate/hexane) to give the title compound (135 mg, 0.246 mmol, 70%) as a colorless amorphous solid.

MS(API): 545 (M−H)

$^1$H-NMR (300 MHz, DMSO-d$_6$): δ0.31 (2H, brs), 0.36-0.56 (2H, m), 1.00 (3H, d, J=5.3 Hz), 1.07-1.34 (2H, m), 1.80-2.09 (6H, m), 2.36 (4H, d, J=6.4 Hz), 2.40-2.48 (2H, m), 3.77 (2H (2H, d, J=6.4 Hz), 7.46 (1H, d, J=8.3 Hz), 7.58 (1H, d, J=8.3 Hz), 7.87 (2H, t, J=7.9 Hz), 8.04 (1H, brs), 8.32 (1H, brs), 10.18 (1H, brs), 10.53 (1H, brs).

The compounds described in Examples 124 to 145 are below (Table 1-10-Table 1-12).

TABLE 1-10

| Example No. | 124 | 125 |
|---|---|---|
| Structure | | |

| Example No. | 126 | 127 |
|---|---|---|
| Structure | | |

| Example No. | 128 | 129 |
|---|---|---|
| Structure | | |

TABLE 1-10-continued

| Example No. | 130 | 131 |
|---|---|---|
| Structure | (chemical structure) | (chemical structure) |

| Example No. | 132 | 133 |
|---|---|---|
| Structure | (chemical structure) | (chemical structure) |

TABLE 1-11

| Example No. | 134 | 135 |
|---|---|---|
| Structure | (chemical structure) | (chemical structure) |

| Example No. | 136 | 137 |
|---|---|---|
| Structure | (chemical structure) | (chemical structure) |

| Example No. | 138 | 139 |
|---|---|---|
| Structure | (chemical structure) | (chemical structure) |

TABLE 1-11-continued

| Example No. | 140 | 141 |
|---|---|---|
| Structure | 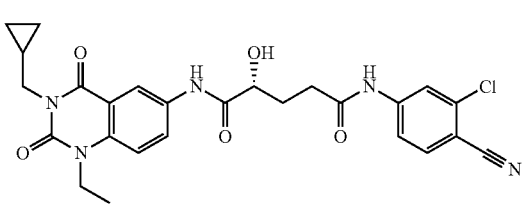 [SMILES: CCn1c(=O)n(CC2CC2)c(=O)c2cc(NC(=O)[C@H](O)CCC(=O)Nc3ccc(C#N)c(Cl)c3)ccc21] | |

| Example No. | 142 | 143 |
|---|---|---|
| Structure | 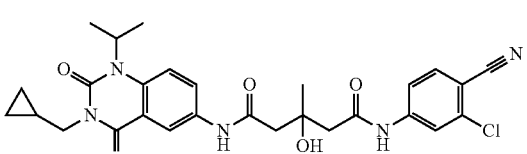 | |

TABLE 1-12

| Example No. | 144 | 145 |
|---|---|---|
| Structure | 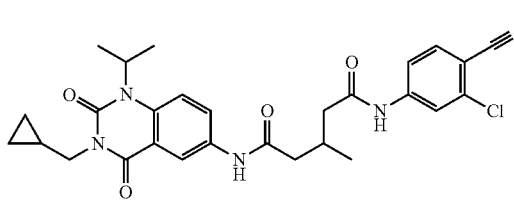 | |

Experimental Example 1

RORγt Binding Test

The binding activity of the test compound to RORγt was measured by a time resolved fluorescence resonance energy transfer method (TR-FRET) utilizing histidine-tagged RORγt, fluorescent-labeled cholesterol (BODIPY-cholesterol, AVIVA) and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 μL each. Then, RORγt diluted with an assay buffer to 240 nM was added by 3 μL each, after which fluorescent-labeled cholesterol diluted with the assay buffer to 12 μM was added by 3 μL each, and the mixture was stood at room temperature for 20 min. Thereafter, a terbium-labeled anti-histidine tag antibody diluted with the assay buffer to 8 nM was added by 3 μL each. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled cholesterol to RORγt at test compound 1 μM) measured by the above-mentioned method are shown in Table 2.

TABLE 2

| Test Compound (Example No.) | binding inhibitory rate (%) |
|---|---|
| 1 | 101.0 |
| 2 | 99.4 |

TABLE 2-continued

| Test Compound (Example No.) | binding inhibitory rate (%) |
|---|---|
| 4 | 96.7 |
| 7 | 88.0 |
| 12 | 98.3 |
| 16 | 92.8 |
| 17 | 101.0 |
| 19 | 99.6 |
| 20 | 101.0 |
| 21 | 103.0 |
| 23 | 97.3 |
| 27 | 99.5 |
| 28 | 99.3 |
| 32 | 98.5 |
| 35 | 102.0 |
| 60 | 102.0 |
| 65 | 100.0 |
| 98 | 101.0 |
| 99 | 95.6 |
| 102 | 103.0 |
| 112 | 96.6 |
| 113 | 103.0 |
| 126 | 103.0 |
| 129 | 100.0 |
| 130 | 101.0 |
| 138 | 104.0 |
| 139 | 102.0 |
| 141 | 102.0 |

Experimental Example 2

Cofactor Recruitment Test

Cofactor recruitment test was performed by Alpha Screen (Histidine Detection Kit, PerkinElmer) method. First, a test compound diluted with an assay buffer (50 mM Tris-HCl (pH 7.5), 50 mM KCl, 1 mM DTT, 0.1% BSA) was added to a 384 well plate by 5 μL each. Then, RORγt diluted with an assay buffer to 125 nM was added by 10 μL each, after which solutions of 25 nM biotinylated SRC-1 peptide (biotin-CLTARHKILHRLLQEGSPSD), 12.5 μg/mL acceptor beads and 12.5 g/mL donor beads, which was prepared with the assay buffer, were added by 10 μL each. The mixture was stood in a dark place for 1 hr, and the signal value was measured by Envision (PerkinElmer).

The results (signal value inhibitory rate at test compound 1 μM) measured by the above-mentioned method are shown in Table 3.

TABLE 3

| Test Compound (Example No.) | signal value inhibitory rate (%) |
|---|---|
| 1 | 102.0 |
| 2 | 106.0 |
| 4 | 105.0 |
| 7 | 105.0 |
| 12 | 104.0 |
| 16 | 104.0 |
| 17 | 103.0 |
| 19 | 104.0 |
| 20 | 105.0 |
| 21 | 104.0 |
| 23 | 104.0 |
| 27 | 105.0 |
| 28 | 105.0 |
| 32 | 103.0 |
| 35 | 105.0 |
| 60 | 103.0 |
| 65 | 102.0 |
| 98 | 104.0 |
| 99 | 103.0 |
| 102 | 104.0 |
| 112 | 100.0 |
| 113 | 102.0 |
| 124 | 101.0 |
| 126 | 100.0 |
| 129 | 100.0 |
| 130 | 102.0 |
| 138 | 100.0 |
| 139 | 102.0 |
| 141 | 102.0 |
| 142 | 103.0 |
| 144 | 102.0 |
| 145 | 103.0 |

Experimental Example 3

Jurkat Reporter Test

The Jurkat cells used for the reporter test were cultured in a culture medium (RPMI (Invitrogen), 10% FCS (AusGeneX), 100 U/mL penicillin, 100 μg/mL streptomycin). On the day of the test, $4 \times 10^7$ cells were recovered by a centrifugal operation (1000 rpm, 5 min.) and suspended in PBS (phosphate buffered saline) (Invitrogen). Thereafter, the cells were recovered again by a centrifugal operation, and suspended in 2 mL of R buffer (NEON transfection kit, Invitrogen). Then, a reporter vector (53 μg) wherein a human IL-17 ROR response element was inserted into the upstream of luciferase of pGL 4.28 (Promega), and a vector (27 μg) wherein RORγt sequence was inserted into the downstream of CMV promoter were added to the cell suspension. Gene transfer was performed by Electroporation apparatus (NEON, Invitrogen) under the conditions of pulse voltage 1350 V, interval 10 milliseconds, number of times 3. The cells after gene transfer were suspended in 40 mL of a reaction medium (RPMI, 10% Lipid reduced FCS (HyClone), 10 mM HEPES (pH 7.5), 100 U/mL penicillin, 100 μg/mL streptomycin, 5 μM lovastatin), and plated in a 96 well plate by 90 μL each. A test compound diluted with the reaction medium was added by 10 μL each, and the cells were cultured overnight in an incubator. Bright-Glo (Promega) was added by 100 μL each, and the mixture was stirred at room temperature for 10 min, and the luminescence level was measured by Envision (PerkinElmer).

The results (luminescence level inhibitory rate at test compound 3 μM) measured by the above-mentioned method are shown in Table 4.

TABLE 4

| Test Compound (Example No.) | luminescence level inhibitory rate (%) |
|---|---|
| 1 | 104.0 |
| 2 | 115.0 |
| 4 | 116.0 |
| 7 | 116.0 |
| 12 | 120.0 |
| 16 | 117.0 |
| 17 | 121.0 |
| 19 | 115.0 |
| 20 | 116.0 |
| 21 | 118.0 |
| 23 | 115.0 |
| 27 | 117.0 |
| 28 | 115.0 |
| 32 | 114.0 |
| 35 | 122.0 |
| 60 | 122.0 |
| 65 | 102.0 |
| 98 | 103.0 |
| 99 | 102.0 |
| 102 | 104.0 |
| 112 | 97.7 |
| 113 | 96.5 |
| 124 | 100.0 |
| 126 | 102.0 |
| 129 | 102.0 |
| 130 | 101.0 |
| 138 | 104.0 |
| 139 | 104.0 |
| 141 | 103.0 |
| 142 | 103.0 |
| 144 | 103.0 |
| 145 | 103.0 |

Experimental Example 4

Mouse Th17 Cell Differentiation Test

CD4 positive naive T cells were collected from the spleen cells of Balb/c mice (female, 8-11w) using CD4+CD62L+ T Cell Isolation kit II (Miltenyi Biotec). The CD4 positive naive T cells was plated in a 96 well plate ($3 \times 10^5$ cells/well), and stimulated (37° C. for culture) with anti-mouse CD3ε antibody (10 μg/mL, solid phase) and anti-CD28 antibody (5 μg/mL) for 4 days in the presence of anti-IFN-γ antibody, anti-IL-4 antibody, anti-IL-2 antibody, IL-6, TGF-β and IL-23 to differentiate into Th17 cells. The compound was dissolved in DMSO and then added thereto. The cells were cultured under these conditions for 4 days, and differentiation of the Th17 cells was evaluated by using the concentration of IL-17A, which was measured by ELISA, in the culture supernatant obtained by centrifugation.

The results (inhibitory rate at 10 μM of test compound) evaluated by the above-mentioned method are shown in Table 5.

TABLE 5

| Test Compound (Example No.) | inhibitory rate(%) |
|---|---|
| 2 | 97 |
| 12 | 97 |
| 23 | 94 |

Experimental Example 5
Human Th17 Cell Differentiation Test

CD4 positive naive T cells are isolated from peripheral blood mononuclear cells (PBMC) collected from human peripheral blood by a density gradient centrifugation method. The CD4 positive naive T cells are plated in a 96 well plate ($2\times10^4$ cells/well), and stimulated (37° C. for culture) with anti-CD3/28Ab Dynabeads for 6 days in the presence of IL-1β, IL-6, IL-23, TGFβ, anti-IFNγ Ab and anti-IL-4 Ab to differentiate into Th17 cells. The compound is dissolved in DMSO and then added thereto. After culture for 6 days, the concentration of IL-17A in the culture supernatant obtained by centrifugation is measured by ELISA to evaluate differentiation of the Th17 cells.

Experimental Example 6
IL17 Production Test in Human PBMC

Peripheral blood mononuclear cells (PBMC) collected from human peripheral blood by a density gradient centrifugation method were stimulated by Dynabeads (registered trade mark; anti-CD3/CD28 antibody) and cultured at 37° C. for 3 days. The test compound was dissolved in DMSO and then added thereto. After culture for 3 days under such conditions, the concentration of IL-17A in the culture supernatant obtained by centrifugation was measured by ELISA to evaluate the effect of the compound on IL-17 production.

The results (inhibitory rate at 10 μM of test compound) evaluated by the above-mentioned method are shown in Table 6.

TABLE 6

| Test Compound (Example No.) | inhibitory rate (%) |
|---|---|
| 2 | 96 |
| 4 | 97 |
| 7 | 100 |
| 12 | 97 |
| 17 | 84 |

Formulation Example 1

| (1) the compound of Example 1 | 10.0 g |
| (2) lactose | 70.0 g |
| (3) cornstarch | 50.0 g |
| (4) soluble starch | 7.0 g |
| (5) magnesium stearate | 3.0 g |

Compound of Example 1 (10.0 g) and magnesium stearate (3.0 g) are granulated in aqueous solution (70 mL) of soluble starch (7.0 g as soluble starch) and then dried, the resulting mixture is mixed with lactose (70.0 g) and cornstarch (50.0 g) (lactose, cornstarch, soluble starch and magnesium stearate are all products in compliance with Japanese Pharmacopoeia 14$^{th}$ Edition). The mixture compressed to give tablets.

INDUSTRIAL APPLICABILITY

The compound of the present invention has a superior RORγt inhibitory action, and useful as an agent for the prophylaxis or treatment of inflammatory bowel disease (IBD), Crohn's disease (CD), rheumatoid arthritis, multiple sclerosis, psoriasis and the like.

This application is based on patent application No. 051867/2013 filed in Japan, the contents of which are encompassed in full herein.

The invention claimed is:
1. A compound represented by the formula (I):

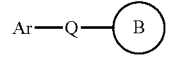

(I)

wherein
Ar is
the partial structure (1):

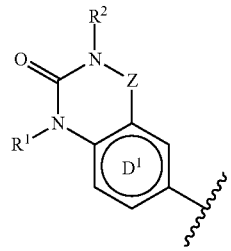

(1)

wherein in the partial structure (1),
Z is a carbonyl group or a methylene group,
$R^1$ is a $C_{2-12}$ alkyl group, a substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group (excluding a $C_{1-12}$ alkyl group, a $C_{2-12}$ alkenyl group or a $C_{2-12}$ alkynyl group, each substituted by optionally substituted

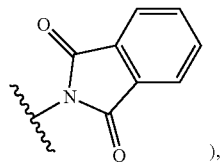 [SMILES: *N1C(=O)c2ccccc2C1=O]

), $R^2$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group, and $D^1$ is an optionally further substituted 6-membered aromatic ring, Q is a bivalent group (Ia):

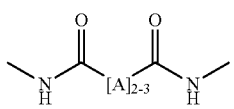

wherein

[A] are each a methylene group optionally substituted by substituent(s) selected from the group consisting of a hydroxy group and a $C_{1-6}$ alkyl group, and B is a $C_{6-14}$ aryl group substituted by cyano group(s) wherein the aryl group is optionally further substituted, or a salt thereof.

2. The compound or salt of claim 1, wherein $R^1$ is a $C_{2-6}$ alkyl group or a substituted $C_{1-12}$ alkyl group.

3. N-[1,3-Bis(cyclopropylmethyl)-2,4-dioxo-1,2,3,4-tetrahydroquinazolin-6-yl]-N'-(3-chloro-4-cyanophenyl)-3-methylpentanediamide.

4. N-(3-Chloro-4-cyanophenyl)-N'-[3-(cyclopropylmethyl)-1-isopropyl-2,4-dioxo-1,2,3,4-tetrahydroquinazolin-6-yl]-3-hydroxy-3-methylpentanediamide or a salt thereof.

5. N-(3-Chloro-4-cyanophenyl)-N'-[3-(cyclopropylmethyl)-1-isopropyl-2,4-dioxo-1,2,3,4-tetrahydroquinazolin-6-yl]-3-methylpentanediamide.

6. N-(3-Chloro-4-cyanophenyl)-N'-[2'-(cyclopropylmethyl)-1',3'-dioxo-2',3'-dihydro-1'H-spiro(cyclopentane-1,4'-isoquinoline)-7'-yl]-3-methylpentanediamide.

7. A medicament comprising the compound or salt of claim 1.

8. The medicament of claim 7, which is a RORγt inhibitor.

9. The medicament of claim 8, which is an agent for the treatment of inflammatory disease or autoimmune disease.

10. The medicament of claim 8, which is an agent for the treatment of inflammatory bowel disease (IBD), ulcerative colitis (UC), Crohn's disease (CD), rheumatoid arthritis, multiple sclerosis, psoriasis, bronchial asthma, chronic obstructive pulmonary diseases, ankylopoietic spondylarthritis, Sjogren's syndrome nephritis, systemic lupus erythematosus, Behcet's disease, scleroderma, idiopathic interstitial pneumonia, type I diabetes, atopic dermatitis, graft versus host disease, uveitis, cystic fibrosis or non-alcoholic steatohepatitis.

11. A method of inhibiting RORγt, which comprises administering an effective amount of the compound or salt of claim 1 to a mammal.

12. A method for the treatment of inflammatory disease or autoimmune disease, which comprises administering an effective amount of the compound or salt of claim 1 to a mammal.

13. A compound represented by the formula (I):

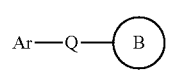

(I)

wherein

Ar is the partial structure (1):

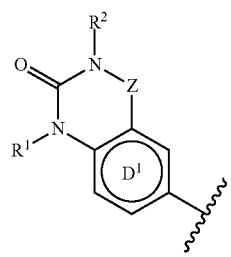

(1)

wherein in the partial structure (1),

Z is a carbonyl group or a methylene group, $R^1$ is a $C_{2-6}$ alkyl group or a substituted $C_{1-12}$ alkyl group (excluding a $C_{1-12}$ alkyl group substituted by optionally substituted

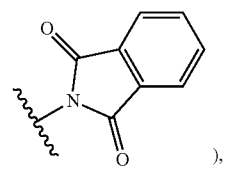

), $R^2$ is an optionally substituted $C_{1-12}$ alkyl group, an optionally substituted $C_{2-12}$ alkenyl group, an optionally substituted $C_{2-12}$ alkynyl group, an optionally substituted $C_{3-12}$ cycloalkyl group, an optionally substituted $C_{3-12}$ cycloalkenyl group, an optionally substituted $C_{6-14}$ aryl group, an optionally substituted $C_{7-16}$ aralkyl group, an acyl group or a cyano group; and $D^1$ is an optionally further substituted 6-membered aromatic ring;

Q is a bivalent group (Ia)

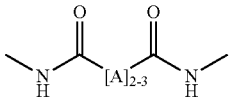

(Ia)

wherein
[A] are each a methylene group optionally substituted by substituent(s) selected from a hydroxy group and a $C_{1-6}$ alkyl group; and B is a $C_{6-14}$ aryl group substituted by cyano group(s) wherein the aryl group is optionally further substituted.

14. N-(3-chloro-4-cyanophenyl)-N'-(1-ethyl-3-(3-methoxypropyl)-2,4-dioxo-1,2,3,4-tetrahydroquinazolin-6-yl)-3-methylpentanediamide.

15. N-(3-chloro-4-cyanophenyl)-N'-(3-(cyclopropylmethyl)-1-ethyl-2,4-dioxo-1,2,3,4-tetrahydroquinazolin-6-yl)-3-methylpentanediamide.

* * * * *